(12) United States Patent
 Sato

(10) Patent No.: US 11,180,539 B2
(45) Date of Patent: Nov. 23, 2021

(54) PHARMACEUTICAL COMPOSITION OR FOOD COMPOSITION, AND METHOD FOR ASSESSING EFFECT OF ACTIVE INGREDIENT IN VIVO

(71) Applicant: KARYDO THERAPEUTIX, INC., Tokyo (JP)

(72) Inventor: Narutoku Sato, Kyoto (JP)

(73) Assignee: KARYDO THERAPEUTIX, INC., Tokyo (JP)

( * ) Notice: Subject to any disclaimer, the term of this patent is extended or adjusted under 35 U.S.C. 154(b) by 10 days.

(21) Appl. No.: 16/089,648

(22) PCT Filed: Mar. 29, 2017

(86) PCT No.: PCT/JP2017/013124
§ 371 (c)(1),
(2) Date: Mar. 7, 2019

(87) PCT Pub. No.: WO2017/170803
PCT Pub. Date: Oct. 5, 2017

(65) Prior Publication Data
US 2019/0382464 A1    Dec. 19, 2019

(30) Foreign Application Priority Data

Mar. 29, 2016 (JP) .............................. JP2016-066684
Jan. 31, 2017 (JP) .............................. JP2017-015821

(51) Int. Cl.
| | | |
|---|---|---|
| C07K 14/705 | (2006.01) | |
| A61P 13/12 | (2006.01) | |
| A61K 38/00 | (2006.01) | |
| C12N 9/22 | (2006.01) | |
| C12N 15/11 | (2006.01) | |

(52) U.S. Cl.
CPC ........ *C07K 14/70503* (2013.01); *A61P 13/12* (2018.01); *C12N 9/22* (2013.01); *C12N 15/11* (2013.01); *A61K 38/00* (2013.01); *C07K 2319/30* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| 9,970,946 | B2 | 5/2018 | Uchiyama et al. |
|---|---|---|---|
| 2003/0017481 | A1 | 1/2003 | Golub et al. |
| 2004/0091498 | A1 | 5/2004 | Zhang et al. |
| 2004/0185503 | A1 | 9/2004 | Yamanouchi et al. |
| 2005/0079514 | A1 | 4/2005 | Liew |
| 2005/0112701 | A1 | 5/2005 | Arndt et al. |
| 2005/0159896 | A1 | 7/2005 | Ishikawa et al. |
| 2006/0008804 | A1 | 1/2006 | Chibout et al. |
| 2006/0088876 | A1 | 4/2006 | Bauer |
| 2007/0161125 | A1 | 7/2007 | Rosenfeld et al. |
| 2009/0061454 | A1 | 3/2009 | Brody et al. |
| 2009/0291434 | A1 | 11/2009 | Cowens et al. |
| 2010/0322850 | A1 | 12/2010 | Eizirik et al. |
| 2013/0023054 | A1 | 1/2013 | Meikle et al. |
| 2013/0045494 | A1 | 2/2013 | Anderberg et al. |
| 2013/0045873 | A1 | 2/2013 | Hood et al. |
| 2013/0157883 | A1 | 6/2013 | Keller et al. |
| 2013/0230871 | A1 | 9/2013 | Anderberg et al. |
| 2013/0259879 | A1 | 10/2013 | Baumhof et al. |
| 2014/0056918 | A1* | 2/2014 | Guo ................... C07K 16/2803 424/172.1 |
| 2014/0100125 | A1 | 4/2014 | Vanburen et al. |

(Continued)

FOREIGN PATENT DOCUMENTS

| CN | 101611319 | 12/2009 |
|---|---|---|
| CN | 102558336 | 7/2012 |

(Continued)

OTHER PUBLICATIONS

Imel et al., J Am Soc Nephrol 16: 2565-2575, 2005.*
Extended European Search Report dated Jul. 16, 2019 in European Application No. 16814543.1.
Tothill et al., "An Expression-Based Site of Origin Diagnostic Method Designed for Clinical Application to Cancer of Unknown Origin", Cancer Res., vol. 65, No. 10, May 15, 2005, pp. 4031-4040.
Talantov et al., "A Quantitative Reverse Transcriptase-Polymerase Chain Reaction Assay to Identify Metastatic Carcinoma Tissue of Origin", Journal of Molecular Diagnostics, vol. 8, No. 3, Jul. 2006, pp. 320-329.

(Continued)

*Primary Examiner* — Marianne P Allen
(74) *Attorney, Agent, or Firm* — Wenderoth, Lind & Ponack, L.L.P.

(57) ABSTRACT

An object of the present invention is to provide a pharmaceutical composition or food or drink composition comprising an active ingredient that suppresses functional expression of Oscar protein. Another object of the present invention is to provide a pharmaceutical composition or food composition for preventing or treating kidney disease. A further object of the present invention is to provide a pharmaceutical composition or food or drink composition that suppresses functional expression of Oscar in a living organism in order to suppress functional expression of FGF23. A still further object of the present invention is to provide a method for evaluating an effect, in the body, of an active ingredient that suppresses functional expression of Oscar protein. The above objects are achieved by at least one member selected from the group consisting of antagonists of the Oscar protein; genome editing systems that target Oscar gene; at least one RNA molecule selected from the group consisting of siRNA, shRNA, and miRNA that target Oscar mRNA, or vectors capable of expressing the RNA molecule; and antibodies that specifically bind to the Oscar protein and suppress function of the Oscar.

1 Claim, 53 Drawing Sheets

Specification includes a Sequence Listing.

(56) References Cited

U.S. PATENT DOCUMENTS

| | | | |
|---|---|---|---|
| 2014/0170677 | A1 | 6/2014 | Klinguer-Hamour et al. |
| 2014/0286953 | A1 | 9/2014 | Sasu et al. |
| 2015/0285821 | A1 | 10/2015 | Uchiyama et al. |
| 2019/0250170 | A1 | 8/2019 | Anderberg et al. |

FOREIGN PATENT DOCUMENTS

| | | |
|---|---|---|
| CN | 102884205 | 1/2013 |
| CN | 103717620 | 4/2014 |
| CN | 105004864 | 10/2015 |
| DE | 44 00 745 | 7/1995 |
| EP | 1 124 572 | 8/2001 |
| EP | 1 466 925 | 10/2004 |
| EP | 2 479 572 | 7/2012 |
| EP | 3 316 159 | 5/2018 |
| EP | 3 438 282 | 2/2019 |
| JP | 2001-17171 | 1/2001 |
| JP | 2001-37486 | 2/2001 |
| JP | 2002-516107 | 6/2002 |
| JP | 2004-187620 | 7/2004 |
| JP | 2005-500803 | 1/2005 |
| JP | 2005-508505 | 3/2005 |
| JP | 2005-510240 | 4/2005 |
| JP | 2005-518810 | 6/2005 |
| JP | 2005-229834 | 9/2005 |
| JP | 2005-323573 | 11/2005 |
| JP | 2007-521799 | 8/2007 |
| JP | 2008-512104 | 4/2008 |
| JP | 2008-518626 | 6/2008 |
| JP | 2011-50250 | 3/2011 |
| JP | 2012-507012 | 3/2012 |
| JP | 2013-126427 | 6/2013 |
| JP | 2013-215201 | 10/2013 |
| JP | 2013-538565 | 10/2013 |
| JP | 2013-541323 | 11/2013 |
| JP | 2014-122170 | 7/2014 |
| WO | 99/61622 | 12/1999 |
| WO | 00/23100 | 4/2000 |
| WO | 02/20718 | 3/2002 |
| WO | 03/040404 | 5/2003 |
| WO | 03/046180 | 6/2003 |
| WO | 03/057874 | 7/2003 |
| WO | 03/074731 | 9/2003 |
| WO | 03/085548 | 10/2003 |
| WO | 2004/005934 | 1/2004 |
| WO | 2005/045044 | 5/2005 |
| WO | 2005/106493 | 11/2005 |
| WO | 2005/114207 | 12/2005 |
| WO | 2006/027265 | 3/2006 |
| WO | 2007/011412 | 1/2007 |
| WO | 2008/008430 | 1/2008 |
| WO | 2010/048670 | 5/2010 |
| WO | 2010/100633 | 9/2010 |
| WO | 2012/012693 | 1/2012 |
| WO | 2012/012725 | 1/2012 |
| WO | 2013/011059 | 1/2013 |
| WO | 2013/011063 | 1/2013 |
| WO | 2014/093622 | 6/2014 |
| WO | 2015/069900 | 5/2015 |
| WO | 2015/184011 | 12/2015 |

OTHER PUBLICATIONS

Greene et al., "Understanding multicellular function and disease with human tissue-specific networks", Nat Genet., vol. 47, No. 6, Jun. 2015, pp. 569-576.
Manconi et al., "The intriguing heterogeneity of human salivary proline-rich proteins; Short title: Salivary proline-rich protein species", Journal of Proteomics, 2015, vol. 134, pp. 47-56.
International Preliminary Report on Patentability dated Jun. 5, 2017 in International (PCT) Application No. PCT/JP2017/069564 With English translation.
Partial Supplementary European Search Report dated Dec. 12, 2019 in European Patent Application No. 17775147.6.
Extended European Search Report dated Jan. 7, 2020 in corresponding European Patent Application No. 17775337.3.
Han et al., "Apelin: A novel inhibitor of vascular calcification in chronic kidney disease", Atherosclerosis, 2015, vol. 244, pp. 1-8.
Sagiroglu et al., "Effects of apelin and leptin on renal functions following renal ischemia/reperfusion: An experimental study", Experimental and Therapeutic Medicine, 2012, vol. 3, No. 5, pp. 908-914.
Chen et al., "Apelin protects against acute renal injury by inhibiting TGF-β1", Biochimica et Biophysica Acta, 2015, vol. 1852, No. 7, pp. 1278-1287.
Clarkson et al., "Serum and Urinary Fibrin/Fibrinogen Degradation Products in Glomerulonephritis", British Medical Journal, 1971, vol. 3, pp. 447-451.
Crotti et al., "Osteoimmunology: Major and Costimulatory Pathway Expression Associated with Chronic Inflammatory Induced Bone Loss", Journal of Immunology Research, 2015, vol. 2015, pp. 1-13.
Goettsch et al., "The Osteoclast-Associated Receptor (OSCAR) Is a Novel Receptor Regulated by Oxidized Low-Density Lipoprotein in Human Endothelial Cells", Endocrinology, 2011, vol. 152, No. 12, pp. 4915-4926.
Ndongo-Thiam et al., "Levels of soluble osteoclast-associated receptor (sOSCAR) in rheumatoid arthritis: link to disease severity and cardiovascular risk", Annals of the Rheumatic Diseases, 2014, vol. 73, No. 6, pp. 1276-1277.
Partial Supplementary European Search Report dated Mar. 13, 2019 in European Application No. 16814543.1.
Keen et al., "The Genotype-Tissue Expression (GTEx) Project: Linking Clinical Data with Molecular Analysis to Advance Personalized Medicine", Journal of Personalized Medicine, 2015, vol. 5, No. 1, pp. 22-29.
Uhlén et al., "Tissue-based map of the human proteome", Science, Jan. 2015, vol. 347, Issue No. 6220, pp. 1260419-1 to 1260419-9.
Kim et al., "A draft map of the human proteome", vol. 509, No. 7502, Nature, May 2014, pp. 575-581.
Uhlén et al., "Transcriptomics resources of human tissues and organs", Molecular Systems Biology, 2016, vol. 12:862, No. 4, pp. 1-12.
Kozawa et al., "The Body-wide Transcriptome Landscape of Disease Models", iScience, vol. 2, 2018, pp. 238-268.
Supplementary Extended European Search Report dated Apr. 6, 2020 in European Patent Application No. 17775147.6.
Eulitz et al., "Inhibition of deoxyribonuclease I by actin is to protect cells from premature cell death", Apoptosis, 2007, vol. 12, No. 8, pp. 1511-1521.
Isern et al., "Functional analysis and androgen-regulated expression of mouse organic anion transporting polypeptide 1 (Oatp 1) in the kidney", Biochimica et Biophysica Acta, 2001, vol. 1518, No. 1-2, pp. 73-78.
Saraheimo et al., "Increased levels of α-defensin (-1, -2 and -3) in type 1 diabetic patients with nephropathy", Nephrology Dialysis Transplantation, 2008, vol. 23, No. 3, pp. 914-918.
Young et al., "Hepcidin for Clinicians", Clinical Journal of the American Society of Nephrology, 2009, vol. 4, No. 8, pp. 1384-1387.
Ruchala et al., "The pathophysiology and pharmacology of hepcidin", Trends in Pharmacological Sciences, 2014, vol. 35, No. 3, pp. 155-161.
International Search Report dated Sep. 27, 2016 in International (PCT) Application No. PCT/JP2016/069564.
Takeda, "Senescence-Accelerated Mouse (SAM): With Special Reference to Age-associated Pathologies and Their Modulation", vol. 51, Jpn. J. Hyp., 1996, pp. 569-578, with English abstract.
International Search Report dated Mar. 21, 2017 in International (PCT) Application No. PCT/JP2017/002406.
Oh et al., "Profile of Human β-Defensins 1,2 and Proinflammatory Cytokines (TNF-α, IL-6) in Patients with Chronic Kidney Disease", Kidney & Blood Pressure Research, vol. 37, 2013, pp. 602-610.
Koike et al., "Identification of α-HNP-3 defensin in diabetes mellitus patient's urine—Potential marker for early diagnosis of diabetic nephropathy-", Journal of Analytical Bio-science, vol. 30, No. 4, 2007, pp. 334-339, with English summary, cited in DC.

(56) References Cited

OTHER PUBLICATIONS

Orita, "Recent progress in protein restriction therapy for chronic renal insufficiency", Journal of Clinical and Experimental Medicine, vol. 171, No. 6, 1994, pp. 607-610, cited in DC.

Mikiko Funakoshi et al., "Proline-rich Protein (PRP) Levels in Inflammatory Diseases", The Journal Japan Atherosclerosis Society, vol. 14, No. 6, 1987, pp. 1249-1250, with English summary, cited in DC.

Lu et al., "Inductively coupled mass spectrometry analysis of biometals in conditional Hamp1 and Hamp1 and Hamp2 transgenic mouse models", Transgenic Res., vol. 24, 2015, pp. 765-773.

Lysaght, "Maintenance Dialysis Population Dynamics: Current Trends and Long-Term Implications", J Am Soc Nephrol, vol. 13, 2002, pp. S37-S40.

Sata et al., "New protein in human blood plasma, rich in proline, with lipid-binding properties", Proc. Nat. Acad. Sci. USA, vol. 73, No. 4, Apr. 1976, pp. 1063-1067.

Matsuguch et al., "Molecular Cloning of the cDNA Coding for Proline-Rich Protein (PRP): Identity of PRP as C4b-Binding Protein", Biochemical and Biophysical Research Communications, vol. 165, No. 1, Nov. 30, 1989, pp. 138-144.

International Search Report dated Jul. 4, 2017 in International (PCT) Application No. PCT/JP2017/012761.

Husain-Syed et al., "Cardio-Pulmonary-Renal Interactions", Journal of the American College of Cardiology, 2015, vol. 65, No. 22, pp. 2433-2448.

White et al., "Inflammatory Mechanisms of Organ Crosstalk during Ischemic Acute Kidney Injury", International Journal of Nephrology, 2012, Article ID 505197, pp. 1-8.

Zoccali et al., "Chronic Kidney Disease (CKD) as a Systemic Disease: Whole Body Autoregulation and Inter-Organ Cross-Talk", Kidney & Blood Pressure Research, 2014, vol. 39, pp. 134-141.

White et al., "Surgical Sepsis and Organ Crosstalk: The Role of the Kidney", Journal of Surgical Research, 2011, vol. 167, pp. 306-315.

Lysaght, "Maintenance Dialysis Population Dynamics: Current Trends and Long-Term Implications", Journal of the American Society of Nephrology, 2002, vol. 13, pp. S37-S40.

Hu et al., "Klotho Deficiency Causes Vascular Calcification in Chronic Kidney Disease", Journal of the American Society of Nephrology, 2011, vol. 22, pp. 124-136.

International Search Report dated May 9, 2017 in International (PCT) Application No. PCT/JP2017/013124.

Manconi et al., "The intriguing heterogeneity of human salivary proline-rich proteins; Short title: Salivary proline-rich protein species", Journal of Proteomics, 2015, vol. 134, p. 47-56.

Hoffmann et al., "Fibrinogen Excretion in the Urine and Immunoreactivity in the Kidney Serves as a Translational Biomarker for Acute Kidney Injury", The American Journal of Pathology, 2012, vol. 181, No. 3, pp. 818-828.

Prinsen et al., "Increased albumin and fibrinogen synthesis rate in patients with chronic renal failure", Kidney International, 2003, vol. 64, pp. 1495-1504.

Zhang et al., "Urinary biomarkers track the progression of nephropathy in hypertensive and obese rats", Biomarkers in Medicine, 2014, vol. 8, No. 1, pp. 85-94.

Craciun et al., "Pharmacological and genetic depletion of fibrinogen protects from kidney fibrosis", American Journal of Physiology, 2014, vol. 307, pp. F471-F484.

International Preliminary Report on Patentability dated Apr. 6, 2017 in International (PCT) Application No. PCT/JP2017/002406, with English translation.

International Preliminary Report on Patentability dated Jun. 5, 2017 in International (PCT) Application No. PCT/JP2016/069564 with English translation.

Qisheng et al., "Gene Editing Tools Mediated by CRISPR-Cas", Biotechnology Bulletin, 2014, Issue No. 7, pp. 37-43.

Bing et al., "Significance of change of renal tubule markers before and after treatment in chronic glomerulonephritis", Lab Med Clin, 2012, vol. 9, No. 19, pp. 2436-2439.

Notice of First Office Action dated Sep. 3, 2020 in corresponding Chinese Patent Application No. 201780032992.8, with English Translation.

Karn et al., "Shared and Unique Proteins in Human, Mouse and Rat Saliva Proteomes: Footprints of Functional Adaptation", Proteomes, 2013, vol. 1, pp. 275-289.

Abstract of Isemura et al., "Tissue distribution and nucleotide sequence of bovine mRNA for salivary proline-rich protein P—B", Archives of Oral Biology, 2004, vol. 49, No. 11, pp. 881-887.

Hao et al., "Effects of Valsartan on Ventricular Hypertrophy and Expression of Proline-rich Tyrosine Kinase 2 in Myocardium of Re-novascular Hypertensive Rats", Chin J Hypertension, 2008, vol. 16, No. 3, pp. 249-252, with Abstract.

Machine translation of reference CN 102558336 submitted with the IDS filed on Apr. 7, 2021.

Office Action dated May 25, 2021 in corresponding Chinese Patent Application No. 201680049081.1, with English Machine Translation.

Tsuchiya, K, et al., Hepcidin is a Potential Regulator of Iron Status in Chronic Kidney Disease, Therapeutic Apheresis and Dialysis, 2013, vol. 17, No. 1, pp. 1-8.

Srai, S.K., et al., "Erythropoietin regulates intestinal iron absorption in a rat model of chronic renal failure", Kidney International, 2010, vol. 78, pp. 660-667.

\* cited by examiner

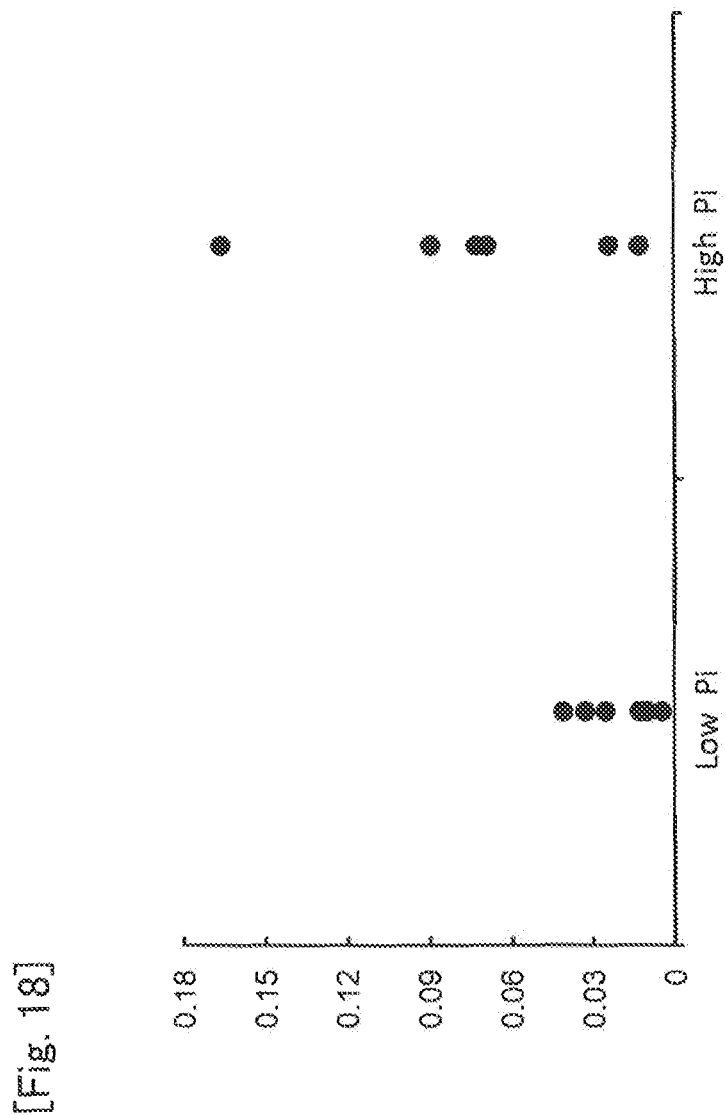
[Fig. 18]

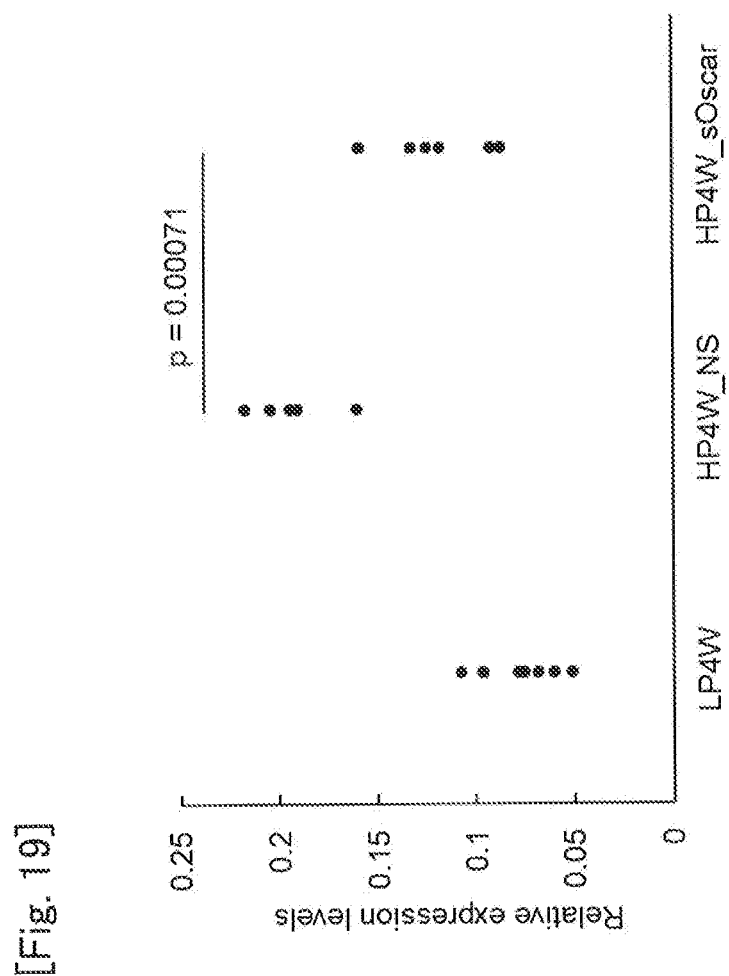
[Fig. 19]

[Fig. 20-1]

| Variant No./ Exon (E) or Intron (I) No. | Score | Sequence | SEQ ID: |
|---|---|---|---|
| V7/I1 | 94 | CAACACAAATTAGCCGGGCGTGG | 35 |
| | 93 | AGCTCAACATCGGCTCGTCCTGG | 36 |
| | 92 | GTCACTCCGGAGCGACTTCTAGG | 37 |
| | 91 | CCACGCAGGTCCGCAAAGTCAGG | 38 |
| | 91 | GGACTATTTTGTTCCGCCTTAGG | 39 |
| | 91 | GTCTCGAACTTCCCGACCTCAGG | 40 |
| | 91 | GCGAGGGTCTGGCACGTAATAGG | 41 |
| | 90 | CGCCTTAGGTGGGTCGCAGCAGG | 42 |
| | 90 | ACCTCGTGATCCGCCCGCCTCGG | 43 |
| | 90 | AATCGCTTGAACTCGGGAGTCGG | 44 |
| | 90 | TCTTGGTCTTTCAGTCGGACTGG | 45 |
| | 89 | CCTGACTTTGCGGACCTGCGTGG | 46 |
| | 89 | TCTCAGCCTAGAAGTCGCTCCGG | 47 |
| | 89 | CGCTTGAACTCGGGAGTCGGAGG | 48 |
| | 89 | GGAGTGCAATGGCGCGATCTCGG | 49 |
| | 88 | ATGTTGAGCTGAGACCTCGAAGG | 50 |
| | 88 | ACAACCGCGCCCGGCCTAGAGGG | 51 |
| | 87 | AGACTAAGGAGATTCCACGCAGG | 52 |
| | 87 | AACAACCGCGCCCGGCCTAGAGG | 53 |
| | 86 | GGATGAGACCTAGCGCTTCCAGG | 54 |
| | 85 | CAACCGCGCCCGGCCTAGAGGGG | 55 |
| | 84 | TATTTTGTTCCGCCTTAGGTGGG | 56 |
| | 84 | GAGAATGGCGTGAACCCGGGAGG | 57 |
| | 83 | AATGACTAACCTGTCCTTCGAGG | 58 |
| | 83 | TAGCCCCTCTAGGCCGGGCGCGG | 59 |
| | 82 | GGCGGGCGGATCACGAGGTCAGG | 60 |
| | 82 | CGCTAGGTCTCATCCCAGATGGG | 61 |
| | 81 | CTGCTGCGACCCACCTAAGGCGG | 62 |
| | 81 | CGGCTCGTCCTGGAAGCGCTAGG | 63 |
| | 81 | CAGAAAGCTCCTAACCCATCTGG | 64 |
| | 81 | GGGGGTTCAGTCATAACCTGTGG | 65 |
| | 80 | CTATTTTGTTCCGCCTTAGGTGG | 66 |
| | 80 | AGCAGGAGGACTAGTCACTCCGG | 67 |
| | 80 | GAGCTGAGACCTCGAAGGACAGG | 68 |
| | 80 | CACAAATTAGCCGGGCGTGGTGG | 69 |
| | 78 | GCGCCCGTAGTCCCAGCTACTGG | 70 |
| | 78 | CTGCCAACATGGCACAGCGAGGG | 71 |
| | 78 | AACATGGCACAGCGAGGGTCTGG | 72 |
| | 77 | TCGAGGTCTCAGCTCAACATCGG | 73 |
| | 77 | GCGCTAGGTCTCATCCCAGATGG | 74 |
| | 77 | GCAGGAGAATGGCGTGAACCCGG | 75 |
| | 77 | AAAATTAGCCCCTCTAGGCCGGG | 76 |
| | 76 | GGTCTCATCCCAGATGGGTTAGG | 77 |
| | 76 | AATGGCGTGAACCCGGGAGGCGG | 78 |
| | 76 | GAAAAATTAGCCGGCTGTGGAGG | 79 |
| | 76 | CAGGAGAATCGCTTGAACTCGGG | 80 |
| | 75 | CGACTTCTAGGCTGAGACTAAGG | 81 |
| | 75 | AGAAAGCTCCTAACCCATCTGGG | 82 |
| | 75 | AGTGATCTGAGCTATAATGGCGG | 83 |
| | 75 | CAGGAGAATGGCGTGAACCCGGG | 84 |
| | 75 | AAAGAAAAATTAGCCGGCTGTGG | 85 |
| | 75 | AAAAATTAGCCCCTCTAGGCCGG | 86 |
| | 74 | CTCCTGCTGCGACCCACCTAAGG | 87 |
| | 74 | TCAGGAGATCTAGACCATCCTGG | 88 |
| | 74 | CAAGGCGGGTGGATCACCTGAGG | 89 |
| | 74 | CCTCGCTGTGCCATGTTGGCAGG | 90 |

[Fig. 20-2]

| | | |
|---|---|---|
| 74 | GTCATAGCCCTATGGCACTGTGG | 91 |
| 73 | AATTAGCCGGGCGTGGTGGTGGG | 92 |
| 73 | AGACGGGGTTTCTCCATGTTGG | 93 |
| 73 | CAGGCGCGCGCCTCCACAGCCGG | 94 |
| 71 | ATGGGTTAGGAGCTTTCTGCGGG | 95 |
| 71 | TCGATCAATTAATCACAGCAAGG | 96 |
| 70 | GAACAAAGATGGAGCCGTGGAGG | 97 |
| 70 | TTAAGTGATCTGAGCTATAATGG | 98 |
| 70 | CCCTTGCTGTGATTGATTGATGG | 99 |
| 69 | CTTAGGTGGGTCGCAGCAGGAGG | 100 |
| 69 | ACAGTATCACACCAAGAGCCTGG | 101 |
| 69 | AGACCCTCGCTGTGCCATGTTGG | 102 |
| 69 | CCTGCCAACATGGCACAGCGAGG | 103 |
| 68 | GATCACTTAAGAAACTGACCTGG | 104 |
| 68 | CTTAAGAAACTGACCTGGTCTGG | 105 |
| 67 | CCGACTGAAAGACCAAGACCAGG | 106 |
| 67 | TCTAGAAACAAATACTAGTCAGG | 107 |
| 66 | ATTAGCACCTGTTAAGTGCCAGG | 108 |
| 66 | GGCACTGTGGAAAAATTAGCAGG | 109 |
| 65 | AAACTGACCTGGTCTGGGCCAGG | 110 |
| 65 | GCCTTAGCCTCCCCAGTAGCTGG | 111 |
| 65 | TCCATCAATCAATCACAGCAAGG | 112 |
| 64 | CGATCAATTAATCACAGCAAGGG | 113 |
| 64 | CCTGGTCTTGGTCTTTCAGTCGG | 114 |
| 64 | CTGCTGCTTGAGAGCAGTAACGG | 115 |
| 64 | TTTCAATCACAGCAAGGGCCTGG | 116 |
| 64 | CAGGCTGCTCTTGAACTCTTGGG | 117 |
| 63 | AGATGGAGCCGTGGAGGTAAAGG | 118 |
| 63 | GCTACTGGGGAGGCTAAGGCAGG | 119 |
| 63 | AAATTAGCCGGGCGTGGTGGTGG | 120 |
| 63 | GCCTCAGCCTCCTGAATAGCTGG | 121 |
| 63 | AATCAATCACAGCAAGGGCCTGG | 122 |
| 62 | GATGGGTTAGGAGCTTTCTGCGG | 123 |
| 62 | TTCTTTTTTAGGAGAGACGGGGG | 124 |
| 62 | GCACTGTGGAAAAATTAGCAGGG | 125 |
| 62 | AGAAACAAATACTAGTCAGGAGG | 126 |
| 61 | CGTAGTCCCAGCTACTGGGGAGG | 127 |
| 61 | AACAAATACTAGTCAGGAGGTGG | 128 |
| 60 | TTAAGAAACTGACCTGGTCTGGG | 129 |
| 60 | CCTTAGCCTCCCCAGTAGCTGGG | 130 |
| 60 | AGATAAAAATTAGCCCCTCTAGG | 131 |
| 60 | CCATCAATCAATCACAGCAAGGG | 132 |
| 59 | GAGGTAAAGGAAGTGGTGTCAGG | 133 |
| 59 | CACTGCAAGCTCCGCCTCCCGGG | 134 |
| 59 | TAATTGATCGATTGATAGATTGG | 135 |
| 58 | AAATACAACACAAATTAGCCGGG | 136 |
| 58 | TCCCTCTGTGCCTGCCAACATGG | 137 |
| 58 | GTTAAATAAATGAACACCACAGG | 138 |
| 57 | GTTAGTCATTCACCTTCTCCCGG | 139 |
| 57 | CACCGCGCCTGGCCCAGACCAGG | 140 |
| 57 | GTTAGTCATTCACCTTCTCCCGG | 141 |
| 57 | AAAAGAAACTGACCTGGTCTTGG | 142 |
| 57 | GCAAGAGTCTGGCACATAATAGG | 143 |
| 56 | AAGAAACTGAGCCCGGGAGAAGG | 144 |
| 56 | CAAGCGCAAGCCTGACTTTGCGG | 145 |
| 56 | CTGGTCTGGGCCAGGCGCGGTGG | 146 |
| 56 | AATCAATGACAGCAAGAGTCTGG | 147 |
| 56 | CCAGGCTGCTCTTGAACTCTTGG | 148 |
| 55 | TTAGTCATTCACCTTCTCCCGGG | 149 |

[Fig. 20-3]

| | | |
|---|---|---|
| 55 | TCACTGCAAGCTCCGCCTCCCGG | 150 |
| 55 | AAATACTAGTCAGGAGGTGGAGG | 151 |
| 54 | CTATCTTTCAATCACAGCAAGGG | 152 |
| 54 | CAAGAGTTCAAGAGCAGCCTGGG | 153 |
| 53 | GCCATGTTGGCAGGCACAGAGGG | 154 |
| 53 | TGCCATGTTGGCAGGCACAGAGG | 155 |
| 52 | ACAGACGAAGAAACTGAGCCCGG | 156 |
| 52 | TCTATCTTTCAATCACAGCAAGG | 157 |
| 52 | CCAAGAGTTCAAGAGCAGCCTGG | 158 |
| 51 | CCCAGCTACTGGGGAGGCTAAGG | 159 |
| 51 | TTTCTTTTTTAGGAGAGACGGGG | 160 |
| 51 | ACTGTGGAAAAATTAGCAGGGGG | 161 |
| 50 | TGTAATCCCAGCTATTCAGGAGG | 162 |
| 49 | CACCACTTCCTTTACCTCCACGG | 163 |
| 49 | CGCCCGTAGTCCCAGCTACTGGG | 164 |
| 49 | CACTGTGGAAAAATTAGCAGGGG | 165 |
| 48 | CCAAGAGCCTGGCACATAATAGG | 166 |
| 47 | GCCGAGGCGGGCGGATCACGAGG | 167 |
| 47 | CAGGCGTGAACAACCGCGCCCGG | 168 |
| 45 | ATTAACACCAATTATGTGCCAGG | 169 |
| 45 | GCAAGGGCCTGGCACATAATTGG | 170 |
| 43 | CCTCAGCCTCCTGAATAGCTGGG | 171 |
| 43 | ATGGTCTCACTCTATCACCCAGG | 172 |
| 42 | AGCCGTGGAGGTAAAGGAAGTGG | 173 |
| 42 | GCCTGTAATCCCAGCTATTCAGG | 174 |
| 42 | GCAAGGGCCTGGCACTTAACAGG | 175 |
| 42 | GCAGGAGAATCGCTTGAACTCGG | 176 |
| 40 | GACCTGGTCTGGGCCAGGCGCGG | 177 |
| 40 | CTAGACCATCCTGGCTAACATGG | 178 |
| 40 | GTGATTGAAAGATAGATAGATGG | 179 |
| 39 | CAGACGAAGAAACTGAGCCCGGG | 180 |
| 39 | AAAATACAACACAAATTAGCCGG | 181 |
| 39 | GCGGGTGGATCACCTGAGGTCGG | 182 |
| 39 | CCTATTATGTGCCAGGCTCTTGG | 183 |
| 38 | TCCTGAATAGCTGGGATTACAGG | 184 |
| 37 | GCCCGTAGTCCCAGCTACTGGGG | 185 |
| 37 | CTCAGGTGATCCACCCGCCTTGG | 186 |
| 37 | AATTAATCACAGCAAGGGCCTGG | 187 |
| 36 | TTTTCTTTTTTAGGAGAGACGGG | 188 |
| 36 | TAATTTTTCCACAGTGCCATAGG | 189 |
| 35 | TTGTATTTTTAAGTAGAGACAGG | 190 |
| 35 | AATTTTTCCACAGTGCCATAGGG | 191 |
| 33 | CGGGTGGATCACCTGAGGTCGGG | 192 |
| 33 | ACTAGTCAGGAGGTGGAGGCAGG | 193 |
| 31 | TTCATACATAAACTATAAAATGG | 194 |
| 30 | GGGAGGCTAAGGCAGGAGAATGG | 195 |
| 30 | TGAGTCTAGCTCTGTCGCCCAGG | 196 |
| 29 | CTTTGGGAGGCCGAGGCGGGCGG | 197 |
| 29 | CAAAAAAAAAGAAACTGACCTGG | 198 |
| 29 | CGGGCGCCCACCACCACGCCCGG | 199 |
| 29 | CCGGCTAATTTTTCTTTTTTAGG | 200 |
| 28 | TCATACATAAACTATAAAATGGG | 201 |
| 28 | TTGAAAGATAGATAGATGGATGG | 202 |
| 27 | CCCAGCTATTCAGGAGGCTGAGG | 203 |
| 26 | TGTATTTTTAAGTAGAGACAGGG | 204 |
| 26 | CCTAAAAAAGAAAATTAGCCGG | 205 |
| 25 | CATACATAAACTATAAAATGGGG | 206 |
| 25 | ATTTGCACCTATTATGTGCCAGG | 207 |
| 24 | AGTTCTTCGTCTGTAAAATGGG | 208 |

[Fig. 20-4]

|       | 24 | CGCGCCATTGCACTCCAGCCTGG | 209 |
|-------|----|-------------------------|-----|
|       | 24 | GCGCCATTGCACTCCAGCCTGGG | 210 |
|       | 23 | CTTTGGGAGGCCAAGGCGGGTGG | 211 |
|       | 21 | GCTATTCAGGAGGCTGAGGCAGG | 212 |
|       | 21 | TTTTTCTTTTTTAGGAGAGACGG | 213 |
|       | 21 | AAGATAGATAGATGGATGGATGG | 214 |
|       | 21 | TATTTATTTATTTTTTAGACAGG | 215 |
|       | 19 | AGGGTTTCACCATGTTAGCCAGG | 216 |
|       | 19 | CTCCCCAGTAGCTGGGACTACGG | 217 |
|       | 18 | GCACTTTGGGAGGCCGAGGCGGG | 218 |
|       | 18 | GGAGTGCAGTGGTGTGATCTCGG | 219 |
|       | 17 | CAGTTTCTTCGTCTGTAAAATGG | 220 |
|       | 17 | TCCCCAGTAGCTGGGACTACGGG | 221 |
|       | 16 | TTTCACCATGTTAGCCAGGATGG | 222 |
|       | 16 | GGGGTTTCTCCATGTTGGTCAGG | 223 |
|       | 16 | AGTCAGGAGGTGGAGGCAGGAGG | 224 |
|       | 15 | AGCACTTTGGGAGGCCGAGGCGG | 225 |
|       | 15 | TCTAGCTCTGTCGCCCAGGCTGG | 226 |
|       | 14 | AGGGTCTCGCTCTGTTGCCCAGG | 227 |
|       | 13 | ATTTATTTATTTTTTAGACAGGG | 228 |
|       | 12 | TGTGCCACTGCACTCCAGCCTGG | 229 |
|       | 11 | GGAGTCTCGCTCTGTCGCCCAGG | 230 |
|       | 11 | CACACCACTGCACTCCAGCCTGG | 231 |
|       | 11 | TTTCTCCATGTTGGTCAGGCTGG | 232 |
|       | 11 | TCTCACTCTATCACCCAGGCTGG | 233 |
|       | 10 | CCCAGCACTTTGGGAGGCCGAGG | 234 |
|       | 10 | CAGTTTCTTTTTTTTTGAGACGG | 235 |
|       | 10 | CGAGACCAGCCTGACCAACATGG | 236 |
|       | 10 | TCGCCCAGGCTGGAGTGCAATGG | 237 |
|       | 9  | GCCTCGGCCTCCCAAAGTGCTGG | 238 |
|       | 9  | TCTCGCTCTGTCGCCCAGGCTGG | 239 |
|       | 9  | ACACCACTGCACTCCAGCCTGGG | 240 |
|       | 9  | GTGCCACTGCACTCCAGCCTGGG | 241 |
|       | 7  | CCTCGGCCTCCCAAAGTGCTGGG | 242 |
|       | 7  | GCACTTTGGGAGGCCAAGGCGGG | 243 |
|       | 6  | CCCAGCACTTTGGGAGGCCAAGG | 244 |
|       | 5  | TCGCCCAGGCTGGAGTGCAGTGG | 245 |
|       | 5  | AGCACTTTGGGAGGCCAAGGCGG | 246 |
|       | 5  | GCCTTGGCCTCCCAAAGTGCTGG | 247 |
|       | 5  | ATTAGCACCTATTATGTGCCAGG | 248 |
|       | 4  | CGCCTGTAATCCCAGCACTTTGG | 249 |
|       | 4  | CCTTGGCCTCCCAAAGTGCTGGG | 250 |
|       | 4  | CGCCTGTAATCCCAGCACTTTGG | 251 |
|       | 4  | TCACCCAGGCTGGAGTGCAGTGG | 252 |
|       | 3  | TGTAATCCCAGCACTTTGGGAGG | 253 |
|       | 3  | GCCTGTAATCCCAGCACTTTGGG | 254 |
|       | 3  | TGTAATCCCAGCACTTTGGGAGG | 255 |
|       | 3  | GCCTGTAATCCCAGCACTTTGGG | 256 |
|       | 2  | CAGGCGTGAGCCACCGCGCCTGG | 257 |
|       | 2  | TCCCAAAGTGCTGGGATTACAGG | 258 |
| V7/E2 | 91 | ATTTACGGAAGAGAGTATCGAGG | 259 |
|       | 89 | TACGGAAGAGAGTATCGAGGTGG | 260 |
|       | 89 | GGGCAGATACCCGCTAGAGCTGG | 261 |
|       | 87 | CGGAAGAGAGTATCGAGGTGGGG | 262 |
|       | 86 | TAGCGGGTATCTGCCCACCATGG | 263 |
|       | 85 | ACGGAAGAGAGTATCGAGGTGGG | 264 |
|       | 83 | GATACTCTCTTCCGTAAATGAGG | 265 |
|       | 82 | TCTTCCGTAAATGAGGATCTGGG | 266 |
|       | 79 | CTCTTCCGTAAATGAGGATCTGG | 267 |

[Fig. 20-5]

|  | | | |
|---|---|---|---|
| | 76 | CGTAAATGAGGATCTGGGTCTGG | 268 |
| | 75 | GTGACTGTGTCATAGCCCTATGG | 269 |
| | 74 | GTATCGAGGTGGGGGCCTGTGGG | 270 |
| | 74 | GTCATAGCCCTATGGCACTGTGG | 271 |
| | 73 | GCTATGACACAGTCACCCACAGG | 272 |
| | 70 | GAGAGGGTGCGACCAAGCCCTGG | 273 |
| | 66 | GGCACTGTGGAAAAATTAGCAGG | 274 |
| | 66 | GGAAGAGAGTATCGAGGTGGGGG | 275 |
| | 66 | TACCCGCTAGAGCTGGAGCCAGG | 276 |
| | 65 | CAGACCCAGATCCTCATTTACGG | 277 |
| | 63 | AGTATCGAGGTGGGGGCCTGTGG | 278 |
| | 62 | GCACTGTGGAAAAATTAGCAGGG | 279 |
| | 54 | CAGCTGGAGGATCAGCACCAGGG | 280 |
| | 54 | GCAGCTGGAGGATCAGCACCAGG | 281 |
| | 54 | ACTCACAGAGGGTCAGCAGCTGG | 282 |
| | 54 | AAGAAAGGGGTGACTCACAGAGG | 283 |
| | 53 | GTATCTGCCCACCATGGCCCTGG | 284 |
| | 52 | TGTTGCCTCATTTCCTGGGAGGG | 285 |
| | 52 | ATGTTGCCTCATTTCCTGGGAGG | 286 |
| | 51 | ACTGTGGAAAAATTAGCAGGGGG | 287 |
| | 51 | CTGATGTTGCCTCATTTCCTGGG | 288 |
| | 51 | AGCCCTGGCTCCAGCTCTAGCGG | 289 |
| | 51 | ATCAGCACCAGGGCCATGGTGGG | 290 |
| | 49 | ACCCGCTAGAGCTGGAGCCAGGG | 291 |
| | 49 | CACTGTGGAAAAATTAGCAGGGG | 292 |
| | 48 | TCTGATGTTGCCTCATTTCCTGG | 293 |
| | 47 | AGAAAGGGGTGACTCACAGAGGG | 294 |
| | 45 | GTTGCCTCATTTCCTGGGAGGGG | 295 |
| | 42 | CTCTCCCCTCCCAGGAAATGAGG | 296 |
| | 38 | GAGGATCAGCACCAGGGCCATGG | 297 |
| | 38 | CACAGAGGGTCAGCAGCTGGAGG | 298 |
| | 36 | TAATTTTTCCACAGTGCCATAGG | 299 |
| | 35 | AATTTTTCCACAGTGCCATAGGG | 300 |
| | 31 | GCCCTGGCTCCAGCTCTAGCGGG | 301 |
| | 30 | CTCATTTCCTGGGAGGGGAGAGG | 302 |
| | 30 | GATCAGCACCAGGGCCATGGTGG | 303 |
| | 28 | TCATTTCCTGGGAGGGGAGAGGG | 304 |
| | 28 | CTAGAGCTGGAGCCAGGGCTTGG | 305 |
| | 28 | GTCGCACCCTCTCCCCTCCCAGG | 306 |
| V1/E3 | 78 | CACACAGACATCACTCCGTCTGG | 307 |
| V6/E3 | 76 | CTAGTCCCTCAACCTCCTACAGG | 308 |
| | 71 | TAGTCCCTCAACCTCCTACAGGG | 309 |
| | 70 | TGGGGTGGCTACTCACCAGACGG | 310 |
| | 60 | AGAGGCCCTGTAGGAGGTTGAGG | 311 |
| | 57 | TGACACAGAGGCCCTGTAGGAGG | 312 |
| | 56 | GAGGCCCTGTAGGAGGTTGAGGG | 313 |
| | 51 | GTGATGTCTGTGTGACACAGAGG | 314 |
| | 50 | GTGTGACACAGAGGCCCTGTAGG | 315 |
| V1/E4 | 83 | CTCACCTATAATGGCCACTAAGG | 316 |
| V3/E4 | 82 | CACCTATAATGGCCACTAAGGGG | 317 |
| | 81 | TCACCTATAATGGCCACTAAGGG | 318 |
| | 79 | TTCCCCTTAGTGGCCATTATAGG | 319 |
| | 71 | TCTTCAGTACTCACCTATAATGG | 320 |
| | 62 | ATAGGTGAGTACTGAAGACCAGG | 321 |
| | 49 | TCTTTTCTCATTCCCCTTAGTGG | 322 |
| V5/I2 | 92 | TGCGTTCAGACTTCTTCGGTAGG | 323 |
| V6/I2 | 91 | TTCAGACTTCTTCGGTAGGTGGG | 324 |
| V7/I2 | 91 | TACTTGAACCCTAGAGTCGGAGG | 325 |
| | 90 | GTTTCTCCTCTCACGAGTTCAGG | 326 |

[Fig. 20-6]

| | | |
|---|---|---|
| 90 | GTTCAGACTTCTTCGGTAGGTGG | 327 |
| 90 | GAGCATTCGCTATATTGCCCAGG | 328 |
| 89 | GCGGTCTCCCTATGTTGAGCAGG | 329 |
| 87 | AACTGCAGCCTCCGACTCTAGGG | 330 |
| 86 | GCCTCAGCCTCCGTAGTAGCTGG | 331 |
| 86 | CAGATTCCTGAACTCGTGAGAGG | 332 |
| 85 | CAAGCTAGCACTACCACGCCTGG | 333 |
| 84 | TGTAGTCCCAGCTACTACGGAGG | 334 |
| 84 | GAACTCGCTGTTGGGCGCAGCGG | 335 |
| 84 | CTTCTTCGGTAGGTGGGCAATGG | 336 |
| 84 | AGAGAGGGGTTTCGCCATGTTGG | 337 |
| 83 | GGGGTTTCACCACATTAGCCAGG | 338 |
| 83 | CTCACCTATAATGGCCACTAAGG | 339 |
| 83 | AGGTCAGATCGAGATCATCCTGG | 340 |
| 82 | TAACTGCAGCCTCCGACTCTAGG | 341 |
| 82 | CACCTATAATGGCCACTAAGGGG | 342 |
| 81 | TCACCTATAATGGCCACTAAGGG | 343 |
| 81 | TAAAAATAAGGGTCGGGTGAGGG | 344 |
| 81 | CCCCCTCCCATATAAGAATCTGG | 345 |
| 80 | CCTCAGCCTCCGTAGTAGCTGGG | 346 |
| 80 | CCCCATCTCATTGGTAACCCAGG | 347 |
| 79 | TTCCCCTTAGTGGCCATTATAGG | 348 |
| 79 | GCAGGTTGGTCTTAAACTACTGG | 349 |
| 79 | CCCAGATTCTTATATGGGAGGGG | 350 |
| 78 | GGACTCCCAGATTCTTATATGGG | 351 |
| 78 | CTCTCACGAGTTCAGGAATCTGG | 352 |
| 78 | CTCCCAGATTCTTATATGGGAGG | 353 |
| 78 | CCCCTCCCATATAAGAATCTGGG | 354 |
| 78 | CACACAGACATCACTCCGTCTGG | 355 |
| 78 | AGGAAGGCTGTTGGGTCCGGTGG | 356 |
| 78 | ACTCTACGATCATTGTTCCCTGG | 357 |
| 77 | TTTGAAAAGAACTCGCTGTTGGG | 358 |
| 77 | TCTCCCTATGTTGAGCAGGTTGG | 359 |
| 77 | TCTCACGAGTTCAGGAATCTGGG | 360 |
| 77 | GGATCTTGGGCTGGGCGCAATGG | 361 |
| 77 | GCAGAGGCGGGCGGATCACAAGG | 362 |
| 77 | GAGCCGAGGCCCAGCACTTTGGG | 363 |
| 77 | CGAGATCATCCTGGCTAATGTGG | 364 |
| 76 | TTTTGAAAAGAACTCGCTGTTGG | 365 |
| 76 | GGTCTGCGTTCAGACTTCTTCGG | 366 |
| 76 | GCCTGGGCAACCAAGAGTTCAGG | 367 |
| 76 | CTAGTCCCTCAACCTCCTACAGG | 368 |
| 76 | CACAGGGTCTTTAATTAATCTGG | 369 |
| 76 | CAAAAATTATCCGGGCATTGTGG | 370 |
| 76 | AGTCTGAACGCAGACCCCTCTGG | 371 |
| 76 | AGACCAACCTGCTCAACATAGGG | 372 |
| 76 | AATTACTTGAACCCTAGAGTCGG | 373 |
| 75 | CTCCATGGTGGCATGCACTTTGG | 374 |
| 75 | AGAACACAGATTCCCGAAAGAGG | 375 |
| 75 | AAAAATAAGGGTCGGGTGAGGGG | 376 |
| 74 | TCCCAGATTCTTATATGGGAGGG | 377 |
| 74 | TCCATGGTGGCATGCACTTTGGG | 378 |
| 74 | CTGAATAAACGGGGCTGCCTGGG | 379 |
| 74 | CAGACCAGCCTGACCAACATGGG | 380 |
| 74 | ATAAAAATAAGGGTCGGGTGAGG | 381 |
| 73 | AGGACTCCCAGATTCTTATATGG | 382 |
| 73 | ACGATCATTGTTCCCTGGAAAGG | 383 |
| 72 | GTTCTCTTGCTTTAGGACCCAGG | 384 |
| 72 | CTGCCCCTCTGATTTGCACCTGG | 385 |

[Fig. 20-7]

| | | |
|---|---|---|
| 72 | ATTAGAGTTCTGGCTGGGCGTGG | 386 |
| 72 | AAGACCAACCTGCTCAACATAGG | 387 |
| 71 | TCTTCAGTACTCACCTATAATGG | 388 |
| 71 | TCCTGGGTTACCAATGAGATGGG | 389 |
| 71 | TAGTCCCTCAACCTCCTACAGGG | 390 |
| 71 | CTTAAGCCCTGTACTGTGCCAGG | 391 |
| 71 | CCTGGGTTACCAATGAGATGGGG | 392 |
| 71 | AAAGGGGCAGTAATTGTCCAAGG | 393 |
| 70 | TGTTTGAGCCCAAGAGATTGAGG | 394 |
| 70 | TGGGGTGGCTACTCACCAGACGG | 395 |
| 70 | TGAATACGATGGTGAAACTGAGG | 396 |
| 70 | TCTCATTGTGTCACCCGGGCTGG | 397 |
| 70 | GCTTGTAGTTCCAGCTGTTTGGG | 398 |
| 70 | ATACAAAGATTAGCCTGGTGTGG | 399 |
| 70 | AGCTTGTAGTTCCAGCTGTTTGG | 400 |
| 70 | ACAGGTATCTCTGGTTCTTGAGG | 401 |
| 69 | TCCCAAAGTGCATGCCACCATGG | 402 |
| 69 | CAGGCTACTCTTGAACTCTTGGG | 403 |
| 69 | AATCAAGCCTTGTTAAAACCAGG | 404 |
| 68 | TGCTTTAGGACCCAGGGGTCTGG | 405 |
| 68 | TCACCCGGGCTGGAGTACGGTGG | 406 |
| 68 | GGGCTTAAGAAATAGGATCTTGG | 407 |
| 68 | AGCTTGTAAACTTAGCACTTTGG | 408 |
| 68 | AGAGCCACCGTACTCCAGCCCGG | 409 |
| 68 | AAATTTCTGCCTACTGAGACAGG | 410 |
| 67 | TTCCTGGGTTACCAATGAGATGG | 411 |
| 67 | TGAAACTGAGGTCCTAGCTTAGG | 412 |
| 67 | TCACATATAAATGAATACGATGG | 413 |
| 67 | GATTTGATGAGATCTCACAGCGG | 414 |
| 67 | GAGGTGGGGACAGGTATCTCTGG | 415 |
| 67 | CCTGGAAGGTGGAGTTCAAGGG | 416 |
| 67 | CCATGTTGGTCAGGCTGGTCTGG | 417 |
| 67 | ATGGTGGCATGCACTTTGGGAGG | 418 |
| 67 | AGTTGCCAAAACTTGCTATTTGG | 419 |
| 67 | AGTTCAAGGGCCTGAACTCTTGG | 420 |
| 67 | AGCAAGCTGTGACTTGTTCTAGG | 421 |
| 66 | TGTGGCCAGCCCCATCTCATTGG | 422 |
| 66 | GGCTTAAGAAATAGGATCTTGGG | 423 |
| 66 | CCAGTTTCTCTCTGTCGCCCAGG | 424 |
| 65 | CCAGATTCTTATATGGGAGGGGG | 425 |
| 65 | ATCACACAAATTAAGAGTACAGG | 426 |
| 65 | ACTGAATAAACGGGGCTGCCTGG | 427 |
| 64 | TAAGAAATAGGATCTTGGGCTGG | 428 |
| 64 | GGTTACCAATGAGATGGGGCTGG | 429 |
| 64 | GCGCAGCGGCTCATGCCTGTGGG | 430 |
| 64 | GAACGCAGACCCCTCTGGCCTGG | 431 |
| 64 | CTGAGGCAGAGGCCTAAGCTAGG | 432 |
| 64 | CAGTACAGGGCTTAAGAAATAGG | 433 |
| 64 | CACTGCAGCCTCAATCTCTTGGG | 434 |
| 64 | CAAGAGTTCAAGAGTAGCCTGGG | 435 |
| 64 | AAAATAAGGGTCGGGTGAGGGGG | 436 |
| 63 | TACAGGAAGGCTGTTGGGTCCGG | 437 |
| 63 | GTATCTCTGGTTCTTGAGGCAGG | 438 |
| 63 | CCCAGCTACTACGGAGGCTGAGG | 439 |
| 63 | CAAGTGCCCGCCACCACACCAGG | 440 |
| 63 | ACAGAAAAATTAGCCAGGCGTGG | 441 |
| 62 | GGTCTTGAACTCCTGTCCTCAGG | 442 |
| 62 | GCAACCACCTCCTGGGTTCAAGG | 443 |
| 62 | GATTAGCCTGGTGTGGTGGCGGG | 444 |

[Fig. 20-8]

| | | |
|---|---|---|
| 62 | CCAAGAGTTCAAGAGTAGCCTGG | 445 |
| 62 | CAAGGTGGGTGCATCACCTGAGG | 446 |
| 62 | ATAGGTGAGTACTGAAGACCAGG | 447 |
| 62 | AGACACCCTGCAGGGGGACCAGG | 448 |
| 62 | ACAGAGTGAGAACTCCATGGTGG | 449 |
| 61 | TAAAACCAGGTGCAAATCAGAGG | 450 |
| 61 | GGTCTTGAACTCCTGACCTCAGG | 451 |
| 61 | GCTTGTAAACTTAGCACTTTGGG | 452 |
| 61 | GAGATGGGGCTGGCCACAAAGGG | 453 |
| 61 | CTGGAGGATTGTCTGAGCCCAGG | 454 |
| 61 | CCCCCTTTTCCCAGGGAATCAGG | 455 |
| 61 | CAGGCACATGCCACTACACCAGG | 456 |
| 61 | AAAAAATTAGCCTGGTGTAGTGG | 457 |
| 60 | TTCTCTTGCTTTAGGACCCAGGG | 458 |
| 60 | TGAGATGGGGCTGGCCACAAAGG | 459 |
| 60 | TCTCTTGCTTTAGGACCCAGGGG | 460 |
| 60 | TCACTGCAGCTTTGAATTCCTGG | 461 |
| 60 | TACTCAGCATCCCAAACAGCTGG | 462 |
| 60 | GGCTCACTGCAACCACCTCCTGG | 463 |
| 60 | GGCAGCAGGTTTGGGATTCTAGG | 464 |
| 60 | GCTCATGCCTGTGGGAGCCGAGG | 465 |
| 60 | CCTTGAACTCCACCTTTCCAGGG | 466 |
| 60 | CCGAGGCCCAGCACTTTGGGAGG | 467 |
| 60 | CACAAATTAAGAGTACAGGAAGG | 468 |
| 60 | AGCGGCCCATTTTACAGAGAAGG | 469 |
| 60 | AGAGGCCCTGTAGGAGGTTGAGG | 470 |
| 60 | AAGGATATCTGGGATGGGATTGG | 471 |
| 59 | TGGGGTCTCATTGTGTCACCCGG | 472 |
| 59 | GGAGCCGAGGCCCAGCACTTTGG | 473 |
| 59 | CTCTCCCTGATTTTACAAACAGG | 474 |
| 59 | CACAGATTCCCGAAAGAGGAAGG | 475 |
| 59 | CAAAGATTAGCCTGGTGTGGTGG | 476 |
| 59 | AAGAGTACAGGAAGGCTGTTGGG | 477 |
| 58 | TTTAAAATTAGAGTTCTGGCTGG | 478 |
| 58 | TGGGTGCATCACCTGAGGTCAGG | 479 |
| 58 | GTTCAAATAAAGAACAGGGCTGG | 480 |
| 58 | GCCTGTGGTCCCAGGTACTCAGG | 481 |
| 58 | GAAACTGTGTTTACAAACTGTGG | 482 |
| 58 | AGGATATCTGGGATGGGATTGGG | 483 |
| 58 | AGCTGGGGGGACTGAATAAACGG | 484 |
| 57 | TTAAAATTAGAGTTCTGGCTGGG | 485 |
| 57 | TGTCTCAGTAGGCAGAAATTTGG | 486 |
| 57 | TGACACAGAGGCCCTGTAGGAGG | 487 |
| 57 | GCAACAGAGTGAGAACTCCATGG | 488 |
| 57 | GAGCTGGGAACTCAGATTCCTGG | 489 |
| 57 | CCCTTGAACTCCACCTTTCCAGG | 490 |
| 57 | CATGTGCAAAACCCTGAGCCTGG | 491 |
| 57 | CACTGCAGCTTTGAATTCCTGGG | 492 |
| 57 | ATTTGCACCTGGTTTTAACAAGG | 493 |
| 57 | AGCTGTTTGGGATGCTGAGTAGG | 494 |
| 56 | TGGTCCCCCTGCAGGGTGTCTGG | 495 |
| 56 | TCTTGGTTGCCCAGGCCAGAGGG | 496 |
| 56 | GGTCCCCCTGCAGGGTGTCTGGG | 497 |
| 56 | GGGATTTTACCATGTTGGTCAGG | 498 |
| 56 | GAGGCCCTGTAGGAGGTTGAGGG | 499 |
| 56 | CCTGGGCGACAGAGAGAAACTGG | 500 |
| 56 | CCCTGGAAAGGTGGAGTTCAAGG | 501 |
| 56 | CCCTGAGCCTGGCACAGTACAGG | 502 |
| 56 | AGAATCCCAAACCTGCTGCCTGG | 503 |

[Fig. 20-9]

| | | |
|---|---|---|
| 56 | AACGCAGACCCCTCTGGCCTGGG | 504 |
| 55 | TTTCTGCCTACTGAGACAGGAGG | 505 |
| 55 | TCTAGGTTCAAATAAAGAACAGG | 506 |
| 55 | TAAGAGTACAGGAAGGCTGTTGG | 507 |
| 55 | GTGACTTGTTCTAGGTCATATGG | 508 |
| 55 | GGGAGGAAAATAAGGATATCTGG | 509 |
| 55 | GCTTTAGGACCCAGGGGTCTGGG | 510 |
| 55 | AGCTGGGAACTCAGATTCCTGGG | 511 |
| 55 | AAGAAATAGGATCTTGGGCTGGG | 512 |
| 54 | TTGGGAAATGGTATGAGGTAGGG | 513 |
| 54 | TGTAAACTTAGCACTTTGGGAGG | 514 |
| 54 | GGTGTAGTGGCATGTGCCTGTGG | 515 |
| 54 | CAGGTGCAAATCAGAGGGGCAGG | 516 |
| 54 | ACTCACAGAGGGTCAGCAGCTGG | 517 |
| 54 | AAGAAAGGGGTGACTCACAGAGG | 518 |
| 53 | TTCCCAGCTCCTATCTCCTCTGG | 519 |
| 53 | TGGAGACCCAGACACCCTGCAGG | 520 |
| 53 | GAGCCACCGTACTCCAGCCCGGG | 521 |
| 53 | CCTGGGTCCTCGGGCCTCCTGGG | 522 |
| 53 | AGATTAGCCTGGTGTGGTGGCGG | 523 |
| 53 | AGAGTTCTGGCTGGGCGTGGTGG | 524 |
| 52 | TGTTTGTAATCCCAACACTTTGG | 525 |
| 52 | TGCTGGGCCTCGGCTCCCACAGG | 526 |
| 52 | TCCTGAGTACCTGGGACCACAGG | 527 |
| 52 | GTTCTTTTCAAAACCCTTTGTGG | 528 |
| 52 | GGGAAGGAGGAAAATCACCTTGG | 529 |
| 52 | GCTCACTGCAACCACCTCCTGGG | 530 |
| 52 | GCTACTACGGAGGCTGAGGCAGG | 531 |
| 52 | CTTGGTTGCCCAGGCCAGAGGGG | 532 |
| 52 | CTGAAGACCAGGAACTTCTGAGG | 533 |
| 52 | CGGGTGGATCACCTGAGGACAGG | 534 |
| 51 | TTTGGGAAATGGTATGAGGTAGG | 535 |
| 51 | TCCCAGAGGAGATAGGAGCTGGG | 536 |
| 51 | GTGATGTCTGTGTGACACAGAGG | 537 |
| 51 | GGAGGAAAATAAGGATATCTGGG | 538 |
| 51 | CTTTTCCAAATAGCAAGTTTTGG | 539 |
| 51 | ATTCCCTGGGAAAAGGGGGCTGG | 540 |
| 51 | AGCCAGGACTCCTGATTCCCTGG | 541 |
| 51 | AAAATAAGGATATCTGGGATGGG | 542 |
| 50 | TCAAATAAAGAACAGGGCTGGGG | 543 |
| 50 | GTGTGACACAGAGGCCCTGTAGG | 544 |
| 50 | GGTCTGGAACTCCTGACCTCAGG | 545 |
| 50 | CTGCTGCCTGGTCCCCCTGCAGG | 546 |
| 50 | CGAGGCGGGTGGATCACCTGAGG | 547 |
| 50 | AAACCAGGTGCAAATCAGAGGGG | 548 |
| 50 | AAACACAGTTTCAAAAGGTCAGG | 549 |
| 49 | TTTCATCTTCTGGGGCTCCCAGG | 550 |
| 49 | TTCCCAGAGGAGATAGGAGCTGG | 551 |
| 49 | TGGGAGCCCCAGAAGATGAAAGG | 552 |
| 49 | TCTTTTCTCATTCCCCTTAGTGG | 553 |
| 49 | TATTTGTCTTGGGGTAAGGAAGG | 554 |
| 49 | GTTTGTAATCCCAACACTTTGGG | 555 |
| 49 | GCCTGGGTCCTCGGGCCTCCTGG | 556 |
| 49 | CAGGTGCGTCCCACCACACCCGG | 557 |
| 49 | ATCATTGTTCCCTGGAAAGGTGG | 558 |
| 49 | AATGAATAAAAATAAGGGTCGGG | 559 |
| 49 | AAAACCAGGTGCAAATCAGAGGG | 560 |
| 48 | TTTAAGTAATGAGATGGGAGGGG | 561 |
| 48 | TTCAAATAAAGAACAGGGCTGGG | 562 |

[Fig. 20-10]

| | | |
|---|---|---|
| 48 | TGAGGCAGAGGGATCACCTGAGG | 563 |
| 48 | TCACTGCAGCCTCAATCTCTTGG | 564 |
| 48 | GAGACCCAGACACCCTGCAGGGG | 565 |
| 48 | GAAAATAAGGATATCTGGGATGG | 566 |
| 48 | CTGCCTACTGAGACAGGAGGAGG | 567 |
| 48 | CCTGAGCCTGGCACAGTACAGGG | 568 |
| 48 | CAGGAGAATCACTTGAACCTGGG | 569 |
| 48 | ACCTCAGCCTCCTGAGTACCTGG | 570 |
| 48 | AATATATTTGTCTTGGGGTAAGG | 571 |
| 47 | TCTTGAGGCAGGAAGAGGTCAGG | 572 |
| 47 | TCCCAGGGAATCAGGAGTCCTGG | 573 |
| 47 | GTGTCACCCGGGCTGGAGTACGG | 574 |
| 47 | GGGAGCCCCAGAAGATGAAAGGG | 575 |
| 47 | GCCTCTGCCTCAGAAGTTCCTGG | 576 |
| 47 | CTCTTGGTTGCCCAGGCCAGAGG | 577 |
| 47 | CTCTTAGCTCCTGAGAGAAGAGG | 578 |
| 47 | CTCCCTCCTCCTGTCTCAGTAGG | 579 |
| 47 | CTCAGGTGATGCACCCACCTTGG | 580 |
| 47 | CCTCCCAAAGTGCTGGGCCTCGG | 581 |
| 47 | CCCAGGAGGCCCGAGGACCCAGG | 582 |
| 47 | CCAGGCTACTCTTGAACTCTTGG | 583 |
| 47 | CAGGCACACACCACAATGCCCGG | 584 |
| 47 | CAACAAAAGGAGAGTGGATGGGG | 585 |
| 47 | ATTCTTATATGGGAGGGGGATGG | 586 |
| 47 | AGAAAGGGGTGACTCACAGAGGG | 587 |
| 46 | TTTTTAAGTAATGAGATGGGAGG | 588 |
| 46 | TGCCTACTGAGACAGGAGGAGGG | 589 |
| 46 | TCTCATTTCCCAGAGGAGATAGG | 590 |
| 46 | GGGGGACCAGGCAGCAGGTTTGG | 591 |
| 46 | GCTATTTAAAATTAGAGTTCTGG | 592 |
| 46 | CCTGATTCCCTGGGAAAAGGGGG | 593 |
| 46 | CAGGAGAATCCCTTGAACCCAGG | 594 |
| 46 | CAGAGGGATCACCTGAGGTCAGG | 595 |
| 46 | AGATTCCCGAAAGAGGAAGGAGG | 596 |
| 45 | CTTAGCACTTTGGGAGGCCGAGG | 597 |
| 45 | ACCAGGAACTTCTGAGGCAGAGG | 598 |
| 44 | TCCTGATTCCCTGGGAAAAGGGG | 599 |
| 44 | TCCCAGCTCCTATCTCCTCTGGG | 600 |
| 44 | GCCAGGACTCCTGATTCCCTGGG | 601 |
| 44 | CATCTTCTGGGGCTCCCAGGAGG | 602 |
| 44 | AAAAATTAGCCGGGTGTGGTGGG | 603 |
| 43 | TTGTTTTGGGAAATGGTATGAGG | 604 |
| 43 | TTCCCTGGGAAAAGGGGGCTGGG | 605 |
| 43 | TGCTGCCTGGTCCCCCTGCAGGG | 606 |
| 43 | TCCCGAAAGAGGAAGGAGGTGGG | 607 |
| 43 | GCCTGAACTCTTGGTTGCCCAGG | 608 |
| 43 | ATTAATCTGGAAGTTGTTTTGGG | 609 |
| 43 | ATGCTAAAAGACAAAACTAGAGG | 610 |
| 43 | ACTCCTGATTCCCTGGGAAAAGG | 611 |
| 43 | ACGGGGCTGCCTGGGTCCTCGGG | 612 |
| 43 | AATTAATCTGGAAGTTGTTTTGG | 613 |
| 42 | TTAAGTAATGAGATGGGAGGGGG | 614 |
| 42 | GAGATGGGATTTTACCATGTTGG | 615 |
| 42 | CTCCTGATTCCCTGGGAAAAGGG | 616 |
| 42 | CAACCACCTCCTGGGTTCAAGGG | 617 |
| 42 | AGTTTCCTGTTTGTAAAATCAGG | 618 |
| 42 | AAAAAAAAATTAGCCGGGTGTGG | 619 |
| 41 | TGGGGCTCCCAGGAGGCCCGAGG | 620 |
| 41 | TCTTAGCTCCTGAGAGAAGAGGG | 621 |

[Fig. 20-11]

| | | |
|---|---|---|
| 41 | TAGAGGACAAATGATAGTACTGG | 622 |
| 41 | TAATAAAATTACAGAGTTCTGGG | 623 |
| 41 | GCATGCACTTTGGGAGGCTGAGG | 624 |
| 41 | GAGACAGGGTTTCCCCATGTTGG | 625 |
| 41 | CGAGGTGGGAGGATTGCTTGAGG | 626 |
| 41 | ATAAGATTCTCATTTCCCAGAGG | 627 |
| 41 | AACGGGGCTGCCTGGGTCCTCGG | 628 |
| 41 | AAAAAATTAGCCGGGTGTGGTGG | 629 |
| 40 | GGAGACCCAGACACCCTGCAGGG | 630 |
| 40 | GCACCACTGCACTCCGGCCTGGG | 631 |
| 40 | CCAACTTCCCTTTCATCTTCTGG | 632 |
| 40 | ATGGGAGGGGGATGGAAGCCAGG | 633 |
| 40 | AGTCACCCCTTTCTTCTCCCTGG | 634 |
| 40 | AATCTGTGTTCTCTTGCTTTAGG | 635 |
| 40 | AACTTCCCTTTCATCTTCTGGGG | 636 |
| 39 | TGTCAGCAACAAAAGGAGAGTGG | 637 |
| 39 | GTTCCCAGCCCCCTTTTCCCAGG | 638 |
| 39 | GGAGTGCAGTGGTGCAATCTCGG | 639 |
| 39 | CTAGGTTCAAATAAAGAACAGGG | 640 |
| 39 | ATACTATATTGCAAATATTCTGG | 641 |
| 39 | AGACCCAGACACCCTGCAGGGGG | 642 |
| 39 | AAAGGGGTGTCAGCAACAAAAGG | 643 |
| 38 | TTGCTCAGGCAGGAGTGCAGTGG | 644 |
| 38 | TAAAAATACAAAGATTAGCCTGG | 645 |
| 38 | GGGGACCAGGCAGCAGGTTTGGG | 646 |
| 38 | GCAGGAAGAGGTCAGGAGACAGG | 647 |
| 38 | GAGAATCACTTGAACCTGGGAGG | 648 |
| 38 | CTGGTTCTTGAGGCAGGAAGAGG | 649 |
| 38 | CACAGAGGGTCAGCAGCTGGAGG | 650 |
| 38 | CAACTTCCCTTTCATCTTCTGGG | 651 |
| 38 | AAAATCTGAGTAATTGGAAAAGG | 652 |
| 37 | TTCCCAGCCCCCTTTTCCCAGGG | 653 |
| 37 | TGGCATGTGCCTGTGGTCCCAGG | 654 |
| 37 | GGGGTCTCATTGTGTCACCCGGG | 655 |
| 37 | GGGCTGGGGCCCAGACCCCTGGG | 656 |
| 37 | CTCAGGTGATCCACCCGCCTCGG | 657 |
| 37 | CAGAAGATGAAAGGGAAGTTGGG | 658 |
| 37 | CACTTGAACCTGGGAGGCAGAGG | 659 |
| 37 | CAAAATAAAATCTGAGTAATTGG | 660 |
| 36 | TGGGTTCCTGGCTGGGGTTGGGG | 661 |
| 36 | GCCTCAGCCTCCCAAAGTGTTGG | 662 |
| 36 | CTGGAAGTTGTTTTGGGAAATGG | 663 |
| 36 | CCCGAAAGAGGAAGGAGGTGGGG | 664 |
| 36 | CAAAAGGAGAGTGGATGGGGTGG | 665 |
| 36 | ATAATAAAATTACAGAGTTCTGG | 666 |
| 36 | AGCAACAAAAGGAGAGTGGATGG | 667 |
| 35 | TCCCCACCTCCTTCCTCTTTCGG | 668 |
| 35 | GCAACAAAAGGAGAGTGGATGGG | 669 |
| 35 | CTTCTCCCTGGGTTCCTGGCTGG | 670 |
| 35 | AGGGTTTCCCCATGTTGGTCAGG | 671 |
| 35 | AGGGCTGGGGCCCAGACCCCTGG | 672 |
| 34 | TTGTAAAATCAGGGAGAGACTGG | 673 |
| 34 | GTTTCCTGTTTGTAAAATCAGGG | 674 |
| 34 | CTTTCTTCTCCCTGGGTTCCTGG | 675 |
| 34 | CTGCAGGGGACCAGGCAGCAGG | 676 |
| 34 | CAAGAGAATCGCTTGAACCCAGG | 677 |
| 34 | ACAACTTAAGAAATTTGAAGTGG | 678 |
| 34 | AAAAAAAAGTCTGGGTGTGGTGG | 679 |
| 33 | TTTGTAAACACAGTTTCAAAAGG | 680 |

[Fig. 20-12]

| | | |
|---|---|---|
| 33 | TCCTGAGAGAAGAGGGAAATGGG | 681 |
| 33 | GGGAAAAGGGGGCTGGGAACAGG | 682 |
| 33 | GGCGCAGCGGCTCATGCCTGTGG | 683 |
| 33 | GGAAACTGAGGCTAAGAAAGGGG | 684 |
| 33 | GCCTCAGCCTCCTGAGTAGCTGG | 685 |
| 33 | GATGAAAGGGAAGTTGGGGAAGG | 686 |
| 33 | AGTAATGAGATGGGAGGGGGCGG | 687 |
| 32 | TTATTTTTAAGTAATGAGATGGG | 688 |
| 32 | TACTGCAACCTCTGCCTCCTGGG | 689 |
| 32 | CCCCATTTCCCTCTTCTCTCAGG | 690 |
| 32 | CAACCCCAGCCAGGAACCCAGGG | 691 |
| 32 | AGGAAACTGAGGCTAAGAAAGGG | 692 |
| 32 | AATCCCTTGAACCCAGGAGGTGG | 693 |
| 32 | AAATCTGAGTAATTGGAAAAGGG | 694 |
| 32 | AAAAGTATTCAAAAAACTATAGG | 695 |
| 31 | TCCTGAGTAGCTGGGATTACAGG | 696 |
| 31 | GCCTCTGCCTCCCAAAGTGCTGG | 697 |
| 31 | CCTGAGAGAAGAGGGAAATGGGG | 698 |
| 31 | CCCTGTACTGTGCCAGGCTCAGG | 699 |
| 30 | CTTTGGGAGGCAGAGGCGGGCGG | 700 |
| 30 | CTACTGAGACAGGAGGAGGGAGG | 701 |
| 30 | CCAGAAGATGAAAGGGAAGTTGG | 702 |
| 30 | CAGGAAGAGGTCAGGAGACAGGG | 703 |
| 30 | ATAGGAAAATATATTTGTCTTGG | 704 |
| 30 | AGGAAAATATATTTGTCTTGGGG | 705 |
| 29 | TTCTCCCTGGGTTCCTGGCTGGG | 706 |
| 29 | TAGGAAAATATATTTGTCTTGGG | 707 |
| 29 | GGAAAAGGGGGCTGGGAACAGGG | 708 |
| 29 | CTTTGGGAGGCCGAGGCGGGTGG | 709 |
| 29 | CCTCAGCCTCCTGAGTACCTGGG | 710 |
| 29 | CCTCAGCCTCCCAAAGTGTTGGG | 711 |
| 29 | CCAACCCCAGCCAGGAACCCAGG | 712 |
| 29 | CAGGAACCCAGGGAGAAGAAAGG | 713 |
| 29 | CAGGAAACTGAGGCTAAGAAAGG | 714 |
| 29 | CACACCACTACACTCCAGCCTGG | 715 |
| 29 | ATTATTTTTAAGTAATGAGATGG | 716 |
| 28 | TTTTAAGTAATGAGATGGGAGGG | 717 |
| 28 | TTCCCGAAAGAGGAAGGAGGTGG | 718 |
| 28 | TGCACCACTGCACTCCGGCCTGG | 719 |
| 28 | GAGAATCGCTTGAACCCAGGAGG | 720 |
| 28 | GAAGAGGTCAGGAGACAGGGAGG | 721 |
| 28 | ATATAAAATAAAAAGTTGTATGG | 722 |
| 28 | AGAAGATGAAAGGGAAGTTGGGG | 723 |
| 27 | TTTCTCTCTGTCGCCCAGGCCGG | 724 |
| 27 | TTACTGCAACCTCTGCCTCCTGG | 725 |
| 27 | GTCACCCCTTTCTTCTCCCTGGG | 726 |
| 27 | GGGGTTTCGCCATGTTGGTCAGG | 727 |
| 27 | GAGAATCCCTTGAACCCAGGAGG | 728 |
| 27 | CTCCTGAGAGAAGAGGGAAATGG | 729 |
| 27 | CTAAGGGGAATGAGAAAAGAAGG | 730 |
| 26 | TTTCTGTTTTTAGTAGAGATGGG | 731 |
| 26 | TCGCCCAGGCTGGAGTGTAGTGG | 732 |
| 26 | GGGTTCCTGGCTGGGGTTGGGGG | 733 |
| 26 | GCACTTTGGGAGGCAGAGGCGGG | 734 |
| 26 | CCCCACCTCCTTCCTCTTTCGGG | 735 |
| 26 | CAATTACTCAGATTTTATTTTGG | 736 |
| 26 | ATTTTACAAACAGGAAACTGAGG | 737 |
| 26 | ACTTGTAGTCCCAGCTACTACGG | 738 |
| 26 | AAAAAAAAAAAGTCTGGGTGTGG | 739 |

[ Fig. 20-13]

| | | |
|---|---|---|
| 25 | TGTAATCCCAGCTACTCAGGAGG | 740 |
| 25 | TGGAGGGAGGGAGGAAAATAAGG | 741 |
| 25 | TAAAAATACAAAAATTATCCGGG | 742 |
| 25 | GGGGAATGAGAAAAGAAGGAAGG | 743 |
| 25 | AGGAACCCAGGGAGAAGAAAGGG | 744 |
| 25 | ACACCACTACACTCCAGCCTGGG | 745 |
| 24 | TTTTATTCATTTTTAGAGATGGG | 746 |
| 24 | TCTCCCTGGGTTCCTGGCTGGGG | 747 |
| 24 | TACTGAGACAGGAGGAGGGAGGG | 748 |
| 24 | CACTGCAACCTCTGCCTCCCAGG | 749 |
| 24 | AGCACTTTGGGAGGCAGAGGCGG | 750 |
| 24 | AAATGAATAAAAATAAGGGTCGG | 751 |
| 23 | TCCTGAGTAGCTGGGACTACAGG | 752 |
| 23 | CCCAGCACTTTGGGAGGCAGAGG | 753 |
| 22 | TTTATTCATTTTTAGAGATGGGG | 754 |
| 22 | GGAACCCAGGGAGAAGAAAGGGG | 755 |
| 22 | GCAGGAGAATCACTTGAACCTGG | 756 |
| 22 | GAGATTGCACCACTGCACTCCGG | 757 |
| 22 | CTTTGGGAGGCTGAGGCAGAGGG | 758 |
| 22 | AAGAGGAAGGAGGTGGGGACAGG | 759 |
| 21 | CTGGGTTCCTGGCTGGGGTTGGG | 760 |
| 21 | CCTGGGTTCCTGGCTGGGGTTGG | 761 |
| 20 | TATTTGGAAAAGAAAAATGTTGG | 762 |
| 20 | TAAAAACAGAAAAATTAGCCAGG | 763 |
| 20 | CTTTGGGAGGCCGAGGTGGGAGG | 764 |
| 20 | CTCAAGCAATCCTCCCACCTCGG | 765 |
| 19 | TTTTACCATGTTGGTCAGGCTGG | 766 |
| 19 | TCGCCCAGGCCGGAGTGCAGTGG | 767 |
| 19 | CTAAAAATACAAAAATTATCCGG | 768 |
| 19 | CCCAGGTACTCAGGAGGCTGAGG | 769 |
| 19 | CATTTCCTTCTCTGTAAAATGGG | 770 |
| 19 | AGGTACTCAGGAGGCTGAGGTGG | 771 |
| 19 | AAGAAGGAAGGAATGGAGGGAGG | 772 |
| 18 | TACTCAGGAGGCTGAGGTGGAGG | 773 |
| 18 | GTTTAAAAAAAAAGAAACACAGG | 774 |
| 18 | GCACTTTGGGAGGCCGAGGCGGG | 775 |
| 18 | CTTTGGGAGGCTGAGGCTGGAGG | 776 |
| 18 | CCTCTGCCTCCCAAAGTGCTGGG | 777 |
| 18 | AGTGCTGGGATTACAGACGTTGG | 778 |
| 17 | TTTTTATTCATTTTTAGAGATGG | 779 |
| 17 | GGGGGCAGAGAGAGAGGCAATGG | 780 |
| 17 | GCGCCACTGCACTCCAGCCTGGG | 781 |
| 17 | CGCGCCACTGCACTCCAGCCTGG | 782 |
| 17 | CCCAACACTTTGGGAGGCTGAGG | 783 |
| 17 | AGAAAAGAAGGAAGGAATGGAGG | 784 |
| 17 | ACTTTGGGAGGCTGAGGCAGAGG | 785 |
| 17 | ACCTCGGCCTCCCAAAGTGCTGG | 786 |
| 16 | TTTCCCCATGTTGGTCAGGCTGG | 787 |
| 16 | GGATTACAGCTGTGAGCCACCGG | 788 |
| 16 | GGAGTCTTGCACTGTCACCCAGG | 789 |
| 16 | GAAAGGGAAGTTGGGGAAGGAGG | 790 |
| 16 | CCATTTTACAGAGAAGGAAATGG | 791 |
| 16 | CCATTTCCTTCTCTGTAAAATGG | 792 |
| 16 | CCAGACCAGCCTGACCAACATGG | 793 |
| 16 | AGGGTCTTGCTCTGTTGCTCAGG | 794 |
| 15 | TCTAAAAATGAATAAAAATAAGG | 795 |
| 15 | GCTACTCAGGAGGCTGAGGCAGG | 796 |
| 15 | CGCTTGAACCCAGGAGGCAGAGG | 797 |
| 15 | CCCAGCTACTCAGGAGGCTGAGG | 798 |

[Fig. 20-14]

| | | |
|---|---|---|
| 15 | CAAGACCAGCCTGACCAACATGG | 799 |
| 15 | AGCACTTTGGGAGGCCGAGGTGG | 800 |
| 15 | AGCACTTTGGGAGGCCGAGGCGG | 801 |
| 14 | TTTTTTTTTTAGTAGAGACGGGG | 802 |
| 14 | TCTTGCACTGTCACCCAGGCTGG | 803 |
| 14 | CCTCAGCCTCCTGAGTAGCTGGG | 804 |
| 14 | ACCTGTAATCCCAGCTACTCAGG | 805 |
| 14 | ACAAACAAAAAAAACTCTTTTGG | 806 |
| 13 | TTTCGCCATGTTGGTCAGGCTGG | 807 |
| 13 | TCTTTGTATTTTTAGTAGAGAGG | 808 |
| 13 | GGGGTTGGGGGCAGAGAGAGAGG | 809 |
| 13 | CAGCTGTAATCCCAGCACTTTGG | 810 |
| 13 | ATGAGAAAAGAAGGAAGGAATGG | 811 |
| 13 | AGACCAGCCTGACCAACATGGGG | 812 |
| 12 | TTTTTTTTTTTAGTAGAGACGGG | 813 |
| 12 | GCCTGTAGTCCCAGCTACTCAGG | 814 |
| 12 | GCACTTTGGGAGGCTGAGGCTGG | 815 |
| 12 | GCACTTTGGGAGGCCAAGGTGGG | 816 |
| 12 | GAAAAGAAGGAAGGAATGGAGGG | 817 |
| 12 | CTCTGCCCCAACCCCAGCCAGG | 818 |
| 11 | CGTCTGTAATCCCAGCACTTTGG | 819 |
| 10 | TTTTCTGTTTTTAGTAGAGATGG | 820 |
| 10 | TTTAAAAAAAAAGAAACACAGGG | 821 |
| 10 | TGTAATCCCAACACTTTGGGAGG | 822 |
| 10 | TCTTGCTCTGTTGCTCAGGCAGG | 823 |
| 10 | CTAAAAATGAATAAAAATAAGGG | 824 |
| 10 | CCCAGCACTTTGGGAGGCCGAGG | 825 |
| 10 | AGAGTCTCACTCTGTCGCCCAGG | 826 |
| 10 | AGAAGGAAGGAATGGAGGGAGGG | 827 |
| 9 | TGTGGTCCCAGGTACTCAGGAGG | 828 |
| 9 | GCCTCGGCCTCCCAAAGTGCTGG | 829 |
| 9 | CATGCCACTGCACTCCAGCCTGG | 830 |
| 9 | AGCTGTAATCCCAGCACTTTGGG | 831 |
| 7 | TAAAAAAAAAAAAATTAGCCTGG | 832 |
| 7 | CCTTTTTTTTTTTTTGTCTGAGG | 833 |
| 7 | CCTCGGCCTCCCAAAGTGCTGGG | 834 |
| 7 | ATGCCACTGCACTCCAGCCTGGG | 835 |
| 7 | ACCTTGGCCTCCCAAAGTGCTGG | 836 |
| 6 | TTTGTATTTTTAGTAGAGAGGGG | 837 |
| 6 | GTCTGTAATCCCAGCACTTTGGG | 838 |
| 6 | CCCAGCACTTTGGGAGGCCAAGG | 839 |
| 6 | CACCTGTAATCCCAGCACTTTGG | 840 |
| 5 | TTGTTTGTTTGTTTTTGAAGTGG | 841 |
| 5 | TTGCCCAGGCTGGAGTGCAGTGG | 842 |
| 5 | TCTCACTCTGTCGCCCAGGCTGG | 843 |
| 5 | AGCACTTTGGGAGGCCAAGGTGG | 844 |
| 4 | TTTTTTTTTTTAGTAGAGACGG | 845 |
| 4 | TTGTATTTTTAGTAGAGACAGGG | 846 |
| 4 | TGTAGTCCCAGCTACTCAGGAGG | 847 |
| 4 | TCACCCAGGCTGGAGTGCAGTGG | 848 |
| 4 | CCTTGGCCTCCCAAAGTGCTGGG | 849 |
| 4 | CCTCAGACAAAAAAAAAAAAAGG | 850 |
| 4 | AGGAAGGAATGGAGGGAGGGAGG | 851 |
| 4 | AATAAATAAATAAAATAAATAGG | 852 |
| 4 | AAAAAAAAAAAAAATTAGCCGGG | 853 |
| 3 | TGTAATCCCAGCACTTTGGGAGG | 854 |
| 3 | TCTCACTCTGTTGCCCAGGCTGG | 855 |
| 3 | ACCTGTAATCCCAGCACTTTGGG | 856 |
| 3 | AAAAAAAAAAAAAAATTAGCCGG | 857 |

[Fig. 20-15]

| | | | |
|---|---|---|---|
| | 2 | TTTGTATTTTTAGTAGAGACAGG | 858 |
| | 2 | TCCCAAAGTGCTGGGATTACAGG | 859 |
| | 2 | CTTTGTATTTTTAGTAGAGAGGG | 860 |
| | 1 | TTTTTTTTTTTTTTGAGGCAGG | 861 |
| | 1 | TTTTTTTTTTTTTTGAGGCAGGG | 862 |
| | 0 | TTTTTTTTTTTTTTTTTTTGAGG | 863 |
| | 0 | AAAAAAAAAAAAAAAAGTCTGGG | 864 |
| | 0 | AAAAAAAAAAAAAAAAAGTCTGG | 865 |
| V1/I3 | 83 | CTCACCTATAATGGCCACTAAGG | 866 |
| V3/I3 | 82 | CACCTATAATGGCCACTAAGGGG | 867 |
| | 81 | TCACCTATAATGGCCACTAAGGG | 868 |
| | 79 | TTCCCCTTAGTGGCCATTATAGG | 869 |
| | 78 | CACACAGACATCACTCCGTCTGG | 870 |
| | 71 | TCTTCAGTACTCACCTATAATGG | 871 |
| | 70 | TGGGGTGGCTACTCACCAGACGG | 872 |
| | 70 | TGAATACGATGGTGAAACTGAGG | 873 |
| | 67 | TGAAACTGAGGTCCTAGCTTAGG | 874 |
| | 67 | TCACATATAAATGAATACGATGG | 875 |
| | 67 | AGCAAGCTGTGACTTGTTCTAGG | 876 |
| | 64 | CTGAGGCAGAGGCCTAAGCTAGG | 877 |
| | 62 | ATAGGTGAGTACTGAAGACCAGG | 878 |
| | 60 | AAGGATATCTGGGATGGGATTGG | 879 |
| | 58 | AGGATATCTGGGATGGGATTGGG | 880 |
| | 55 | GTGACTTGTTCTAGGTCATATGG | 881 |
| | 55 | GGGAGGAAAATAAGGATATCTGG | 882 |
| | 52 | CTGAAGACCAGGAACTTCTGAGG | 883 |
| | 51 | AAAATAAGGATATCTGGGATGGG | 884 |
| | 51 | GGAGGAAAATAAGGATATCTGGG | 885 |
| | 49 | TCTTTTCTCATTCCCCTTAGTGG | 886 |
| | 48 | GAAAATAAGGATATCTGGGATGG | 887 |
| | 47 | CAACAAAAGGAGAGTGGATGGGG | 888 |
| | 47 | GCCTCTGCCTCAGAAGTTCCTGG | 889 |
| | 45 | ACCAGGAACTTCTGAGGCAGAGG | 890 |
| | 39 | TGTCAGCAACAAAAGGAGAGTGG | 891 |
| | 39 | AAAGGGTGTCAGCAACAAAAGG | 892 |
| | 38 | AAAATCTGAGTAATTGGAAAAGG | 893 |
| | 37 | CAAAATAAAATCTGAGTAATTGG | 894 |
| | 36 | AGCAACAAAAGGAGAGTGGATGG | 895 |
| | 36 | CAAAAGGAGAGTGGATGGGGTGG | 896 |
| | 35 | GCAACAAAAGGAGAGTGGATGGG | 897 |
| | 32 | AAATCTGAGTAATTGGAAAAGGG | 898 |
| | 27 | CTAAGGGGAATGAGAAAAGAAGG | 899 |
| | 26 | CAATTACTCAGATTTTATTTTGG | 900 |
| | 25 | TGGAGGGAGGGAGGAAAATAAGG | 901 |
| | 25 | GGGGAATGAGAAAAGAAGGAAGG | 902 |
| | 19 | AAGAAGGAAGGAATGGAGGGAGG | 903 |
| | 17 | AGAAAAGAAGGAAGGAATGGAGG | 904 |
| | 13 | ATGAGAAAAGAAGGAAGGAATGG | 905 |
| | 12 | GAAAAGAAGGAAGGAATGGAGGG | 906 |
| | 10 | AGAAGGAAGGAATGGAGGGAGGG | 907 |
| | 4 | AGGAAGGAATGGAGGGAGGGAGG | 908 |
| V1/I4 | 91 | TACTTGAACCCTAGAGTCGGAGG | 909 |
| V3/I4 | 90 | GAGCATTCGCTATATTGCCCAGG | 910 |
| V4/I3 | 89 | GCGGTCTCCCTATGTTGAGCAGG | 911 |
| V6/I3 | 87 | AACTGCAGCCTCCGACTCTAGGG | 912 |
| | 85 | CAAGCTAGCACTACCACGCCTGG | 913 |
| | 83 | CTCACCTATAATGGCCACTAAGG | 914 |
| | 83 | GGGGTTTCACCACATTAGCCAGG | 915 |
| | 83 | AGGTCAGATCGAGATCATCCTGG | 916 |

[Fig. 20-16]

| | | |
|---|---|---|
| 83 | CTCACCTATAATGGCCACTAAGG | 917 |
| 82 | CACCTATAATGGCCACTAAGGGG | 918 |
| 82 | TAACTGCAGCCTCCGACTCTAGG | 919 |
| 81 | TCACCTATAATGGCCACTAAGGG | 920 |
| 81 | TAAAAATAAGGGTCGGGTGAGGG | 921 |
| 79 | TTCCCCTTAGTGGCCATTATAGG | 922 |
| 79 | GCAGGTTGGTCTTAAACTACTGG | 923 |
| 78 | AGGAAGGCTGTTGGGTCCGGTGG | 924 |
| 77 | TCTCCCTATGTTGAGCAGGTTGG | 925 |
| 77 | CGAGATCATCCTGGCTAATGTGG | 926 |
| 77 | GGATCTTGGGCTGGGCGCAATGG | 927 |
| 77 | GCAGAGGCGGGCGGATCACAAGG | 928 |
| 76 | AGACCAACCTGCTCAACATAGGG | 929 |
| 76 | CAAAAATTATCCGGGCATTGTGG | 930 |
| 76 | AATTACTTGAACCCTAGAGTCGG | 931 |
| 76 | CACAGGGTCTTTAATTAATCTGG | 932 |
| 75 | CTCCATGGTGGCATGCACTTTGG | 933 |
| 75 | AAAAATAAGGGTCGGGTGAGGGG | 934 |
| 74 | CTGAATAAACGGGGCTGCCTGGG | 935 |
| 74 | TCCATGGTGGCATGCACTTTGGG | 936 |
| 74 | ATAAAAATAAGGGTCGGGTGAGG | 937 |
| 74 | CAGACCAGCCTGACCAACATGGG | 938 |
| 72 | AAGACCAACCTGCTCAACATAGG | 939 |
| 72 | CTGCCCCTCTGATTTGCACCTGG | 940 |
| 72 | ATTAGAGTTCTGGCTGGGCGTGG | 941 |
| 71 | TCTTCAGTACTCACCTATAATGG | 942 |
| 71 | AAAGGGGCAGTAATTGTCCAAGG | 943 |
| 71 | CTTAAGCCCTGTACTGTGCCAGG | 944 |
| 71 | TCTTCAGTACTCACCTATAATGG | 945 |
| 70 | TGTTTGAGCCCAAGAGATTGAGG | 946 |
| 70 | TGAATACGATGGTGAAACTGAGG | 947 |
| 70 | TCTCATTGTGTCACCCGGGCTGG | 948 |
| 70 | GCTTGTAGTTCCAGCTGTTTGGG | 949 |
| 70 | AGCTTGTAGTTCCAGCTGTTTGG | 950 |
| 69 | CAGGCTACTCTTGAACTCTTGGG | 951 |
| 69 | AATCAAGCCTTGTTAAAACCAGG | 952 |
| 69 | TCCCAAAGTGCATGCCACCATGG | 953 |
| 68 | AGCTTGTAAACTTAGCACTTTGG | 954 |
| 68 | GGGCTTAAGAAATAGGATCTTGG | 955 |
| 68 | AGAGCCACCGTACTCCAGCCCGG | 956 |
| 68 | TCACCCGGGCTGGAGTACGGTGG | 957 |
| 67 | GATTTGATGAGATCTCACAGCGG | 958 |
| 67 | TGAAACTGAGGTCCTAGCTTAGG | 959 |
| 67 | TCACATATAAATGAATACGATGG | 960 |
| 67 | AGCAAGCTGTGACTTGTTCTAGG | 961 |
| 67 | ATGGTGGCATGCACTTTGGGAGG | 962 |
| 67 | CCATGTTGGTCAGGCTGGTCTGG | 963 |
| 67 | AGTTGCCAAAACTTGCTATTTGG | 964 |
| 66 | GGCTTAAGAAATAGGATCTTGGG | 965 |
| 66 | CCAGTTTCTCTCTGTCGCCCAGG | 966 |
| 65 | ACTGAATAAACGGGGCTGCCTGG | 967 |
| 65 | ATCACACAAATTAAGAGTACAGG | 968 |
| 64 | CAAGAGTTCAAGAGTAGCCTGGG | 969 |
| 64 | CACTGCAGCCTCAATCTCTTGGG | 970 |
| 64 | TAAGAAATAGGATCTTGGGCTGG | 971 |
| 64 | CAGTACAGGGCTTAAGAAATAGG | 972 |
| 64 | CTGAGGCAGAGGCCTAAGCTAGG | 973 |
| 64 | AAAATAAGGGTCGGGTGAGGGGG | 974 |
| 63 | TACAGGAAGGCTGTTGGGTCCGG | 975 |

[Fig. 20-17]

| | | |
|---|---|---|
| 63 | ACAGAAAAATTAGCCAGGCGTGG | 976 |
| 62 | ATAGGTGAGTACTGAAGACCAGG | 977 |
| 62 | CCAAGAGTTCAAGAGTAGCCTGG | 978 |
| 62 | ACAGAGTGAGAACTCCATGGTGG | 979 |
| 62 | GCAACCACCTCCTGGGTTCAAGG | 980 |
| 62 | CAAGGTGGGTGCATCACCTGAGG | 981 |
| 61 | AAAAAATTAGCCTGGTGTAGTGG | 982 |
| 61 | CAGGCACATGCCACTACACCAGG | 983 |
| 61 | GCTTGTAAACTTAGCACTTTGGG | 984 |
| 61 | TAAAACCAGGTGCAAATCAGAGG | 985 |
| 61 | CTGGAGGATTGTCTGAGCCCAGG | 986 |
| 61 | GGTCTTGAACTCCTGACCTCAGG | 987 |
| 60 | AGCGGCCCATTTTACAGAGAAGG | 988 |
| 60 | TCACTGCAGCTTTGAATTCCTGG | 989 |
| 60 | GGCTCACTGCAACCACCTCCTGG | 990 |
| 60 | CACAAATTAAGAGTACAGGAAGG | 991 |
| 60 | TACTCAGCATCCCAAACAGCTGG | 992 |
| 59 | CTCTCCCTGATTTTACAAACAGG | 993 |
| 59 | TGGGGTCTCATTGTGTCACCCGG | 994 |
| 59 | AAGAGTACAGGAAGGCTGTTGGG | 995 |
| 58 | GCCTGTGGTCCCAGGTACTCAGG | 996 |
| 58 | GAAACTGTGTTTACAAACTGTGG | 997 |
| 58 | AGCTGGGGGACTGAATAAACGG | 998 |
| 58 | TGGGTGCATCACCTGAGGTCAGG | 999 |
| 58 | TTTAAAATTAGAGTTCTGGCTGG | 1000 |
| 57 | ATTTGCACCTGGTTTTAACAAGG | 1001 |
| 57 | CATGTGCAAAACCCTGAGCCTGG | 1002 |
| 57 | GCAACAGAGTGAGAACTCCATGG | 1003 |
| 57 | CACTGCAGCTTTGAATTCCTGGG | 1004 |
| 57 | AGCTGTTTGGGATGCTGAGTAGG | 1005 |
| 57 | TTAAAATTAGAGTTCTGGCTGGG | 1006 |
| 56 | CCCTGAGCCTGGCACAGTACAGG | 1007 |
| 56 | CCTGGGCGACAGAGAGAAACTGG | 1008 |
| 56 | GGGATTTTACCATGTTGGTCAGG | 1009 |
| 55 | GTGACTTGTTCTAGGTCATATGG | 1010 |
| 55 | AAGAAATAGGATCTTGGGCTGGG | 1011 |
| 55 | TAAGAGTACAGGAAGGCTGTTGG | 1012 |
| 54 | GGTGTAGTGGCATGTGCCTGTGG | 1013 |
| 54 | TGTAAACTTAGCACTTTGGGAGG | 1014 |
| 54 | CAGGTGCAAATCAGAGGGGCAGG | 1015 |
| 54 | TTGGGAAATGGTATGAGGTAGGG | 1016 |
| 53 | CCTGGGTCCTCGGGCCTCCTGGG | 1017 |
| 53 | GAGCCACCGTACTCCAGCCCGGG | 1018 |
| 53 | AGAGTTCTGGCTGGGCGTGGTGG | 1019 |
| 52 | CTGAAGACCAGGAACTTCTGAGG | 1020 |
| 52 | TCCTGAGTACCTGGGACCACAGG | 1021 |
| 52 | GGGAAGGAGGAAAATCACCTTGG | 1022 |
| 52 | TGTTTGTAATCCCAACACTTTGG | 1023 |
| 52 | GCTCACTGCAACCACCTCCTGGG | 1024 |
| 51 | TTTGGGAAATGGTATGAGGTAGG | 1025 |
| 51 | CTTTTCCAAATAGCAAGTTTTGG | 1026 |
| 50 | AAACACAGTTTCAAAAGGTCAGG | 1027 |
| 50 | AAACCAGGTGCAAATCAGAGGGG | 1028 |
| 50 | GGTCTGGAACTCCTGACCTCAGG | 1029 |
| 49 | AAAACCAGGTGCAAATCAGAGGG | 1030 |
| 49 | TGGGAGCCCAGAAGATGAAAGG | 1031 |
| 49 | TTTCATCTTCTGGGGCTCCCAGG | 1032 |
| 49 | GCCTGGGTCCTCGGGCCTCCTGG | 1033 |
| 49 | CAGGTGCGTCCCACCACACCCGG | 1034 |

[ Fig. 20-18]

| | | |
|---|---|---|
| 49 | GTTTGTAATCCCAACACTTTGGG | 1035 |
| 49 | AATGAATAAAAATAAGGGTCGGG | 1036 |
| 49 | TATTTGTCTTGGGGTAAGGAAGG | 1037 |
| 48 | ACCTCAGCCTCCTGAGTACCTGG | 1038 |
| 48 | TCACTGCAGCCTCAATCTCTTGG | 1039 |
| 48 | TTTAAGTAATGAGATGGGAGGGG | 1040 |
| 48 | CCTGAGCCTGGCACAGTACAGGG | 1041 |
| 48 | TGAGGCAGAGGGATCACCTGAGG | 1042 |
| 48 | AATATATTTGTCTTGGGGTAAGG | 1043 |
| 47 | GCCTCTGCCTCAGAAGTTCCTGG | 1044 |
| 47 | CCAGGCTACTCTTGAACTCTTGG | 1045 |
| 47 | CCCAGGAGGCCCGAGGACCCAGG | 1046 |
| 47 | GGGAGCCCCAGAAGATGAAAGGG | 1047 |
| 47 | GTGTCACCCGGGCTGGAGTACGG | 1048 |
| 47 | CAGGCACACACCACAATGCCCGG | 1049 |
| 47 | CTCAGGTGATGCACCCACCTTGG | 1050 |
| 46 | TTTTTAAGTAATGAGATGGGAGG | 1051 |
| 46 | CAGAGGGATCACCTGAGGTCAGG | 1052 |
| 46 | CAGGAGAATCCCTTGAACCCAGG | 1053 |
| 46 | GCTATTTAAAATTAGAGTTCTGG | 1054 |
| 45 | ACCAGGAACTTCTGAGGCAGAGG | 1055 |
| 45 | CTTAGCACTTTGGGAGGCCGAGG | 1056 |
| 44 | CATCTTCTGGGGCTCCCAGGAGG | 1057 |
| 44 | AAAAATTAGCCGGGTGTGGTGGG | 1058 |
| 43 | ACGGGGCTGCCTGGGTCCTCGGG | 1059 |
| 43 | ATGCTAAAAGACAAAACTAGAGG | 1060 |
| 43 | AATTAATCTGGAAGTTGTTTTGG | 1061 |
| 43 | TTGTTTTGGGAAATGGTATGAGG | 1062 |
| 43 | ATTAATCTGGAAGTTGTTTTGGG | 1063 |
| 42 | TTAAGTAATGAGATGGGAGGGGG | 1064 |
| 42 | AGTTTCCTGTTTGTAAATCAGG | 1065 |
| 42 | AAAAAAAATTAGCCGGGTGTGG | 1066 |
| 42 | CAACCACCTCCTGGGTTCAAGGG | 1067 |
| 42 | GAGATGGGATTTTACCATGTTGG | 1068 |
| 41 | TAATAAAATTACAGAGTTCTGGG | 1069 |
| 41 | CGAGGTGGGAGGATTGCTTGAGG | 1070 |
| 41 | AACGGGGCTGCCTGGGTCCTCGG | 1071 |
| 41 | TGGGGCTCCCAGGAGGCCCGAGG | 1072 |
| 41 | AAAAAATTAGCCGGGTGTGGTGG | 1073 |
| 41 | GCATGCACTTTGGGAGGCTGAGG | 1074 |
| 41 | GAGACAGGGTTTCCCCATGTTGG | 1075 |
| 41 | TAGAGGACAAATGATAGTACTGG | 1076 |
| 40 | AACTTCCCTTTCATCTTCTGGGG | 1077 |
| 40 | CCAACTTCCCTTTCATCTTCTGG | 1078 |
| 40 | GCACCACTGCACTCCGGCCTGGG | 1079 |
| 39 | GGAGTGCAGTGGTGCAATCTCGG | 1080 |
| 39 | ATACTATATTGCAAATATTCTGG | 1081 |
| 38 | TTGCTCAGGCAGGAGTGCAGTGG | 1082 |
| 38 | CAACTTCCCTTTCATCTTCTGGG | 1083 |
| 37 | TGGCATGTGCCTGTGGTCCCAGG | 1084 |
| 37 | CAGAAGATGAAAGGGAAGTTGGG | 1085 |
| 37 | GGGGTCTCATTGTGTCACCCGGG | 1086 |
| 36 | ATAATAAAATTACAGAGTTCTGG | 1087 |
| 36 | GCCTCAGCCTCCCAAAGTGTTGG | 1088 |
| 36 | CTGGAAGTTGTTTTGGGAAATGG | 1089 |
| 35 | AGGGTTTCCCCATGTTGGTCAGG | 1090 |
| 34 | AAAAAAAAGTCTGGGTGTGGTGG | 1091 |
| 34 | GTTTCCTGTTTGTAAAATCAGGG | 1092 |
| 34 | TTGTAAAATCAGGGAGAGACTGG | 1093 |

[Fig. 20-19]

| | | |
|---|---|---|
| 34 | CAAGAGAATCGCTTGAACCCAGG | 1094 |
| 34 | ACAACTTAAGAAATTTGAAGTGG | 1095 |
| 33 | AGTAATGAGATGGGAGGGGCGG | 1096 |
| 33 | TTTGTAAACACAGTTTCAAAAGG | 1097 |
| 33 | GATGAAAGGGAAGTTGGGGAAGG | 1098 |
| 33 | GGAAACTGAGGCTAAGAAAGGGG | 1099 |
| 33 | GCCTCAGCCTCCTGAGTAGCTGG | 1100 |
| 32 | TTATTTTTAAGTAATGAGATGGG | 1101 |
| 32 | AGGAAACTGAGGCTAAGAAAGGG | 1102 |
| 32 | TACTGCAACCTCTGCCTCCTGGG | 1103 |
| 32 | AATCCCTTGAACCCAGGAGGTGG | 1104 |
| 32 | AAAAGTATTCAAAAAACTATAGG | 1105 |
| 31 | TCCTGAGTAGCTGGGATTACAGG | 1106 |
| 31 | CCCTGTACTGTGCCAGGCTCAGG | 1107 |
| 31 | GCCTCTGCCTCCCAAAGTGCTGG | 1108 |
| 30 | CCAGAAGATGAAAGGGAAGTTGG | 1109 |
| 30 | CTTTGGGAGGCAGAGGCGGGCGG | 1110 |
| 30 | ATAGGAAAATATATTTGTCTTGG | 1111 |
| 30 | AGGAAAATATATTTGTCTTGGGG | 1112 |
| 29 | CCTCAGCCTCCTGAGTACCTGGG | 1113 |
| 29 | ATTATTTTTAAGTAATGAGATGG | 1114 |
| 29 | CAGGAAACTGAGGCTAAGAAAGG | 1115 |
| 29 | CCTCAGCCTCCCAAAGTGTTGGG | 1116 |
| 29 | TAGGAAAATATATTTGTCTTGGG | 1117 |
| 28 | TTTTAAGTAATGAGATGGGAGGG | 1118 |
| 28 | AGAAGATGAAAGGGAAGTTGGGG | 1119 |
| 28 | GAGAATCGCTTGAACCCAGGAGG | 1120 |
| 28 | TGCACCACTGCACTCCGGCCTGG | 1121 |
| 28 | ATATAAAATAAAAAGTTGTATGG | 1122 |
| 27 | TTACTGCAACCTCTGCCTCCTGG | 1123 |
| 27 | GAGAATCCCTTGAACCCAGGAGG | 1124 |
| 27 | TTTCTCTCTGTCGCCCAGGCCGG | 1125 |
| 26 | AAAAAAAAAAAGTCTGGGTGTGG | 1126 |
| 26 | ATTTTACAAACAGGAAACTGAGG | 1127 |
| 26 | GCACTTTGGGAGGCAGAGGCGGG | 1128 |
| 26 | TTTCTGTTTTTAGTAGAGATGGG | 1129 |
| 25 | TGTAATCCCAGCTACTCAGGAGG | 1130 |
| 25 | TAAAAATACAAAAATTATCCGGG | 1131 |
| 24 | AGCACTTTGGGAGGCAGAGGCGG | 1132 |
| 24 | TTTTATTCATTTTTAGAGATGGG | 1133 |
| 24 | AAATGAATAAAAATAAGGGTCGG | 1134 |
| 23 | CCCAGCACTTTGGGAGGCAGAGG | 1135 |
| 23 | TCCTGAGTAGCTGGGACTACAGG | 1136 |
| 22 | TTTATTCATTTTTAGAGATGGGG | 1137 |
| 22 | CTTTGGGAGGCTGAGGCAGAGGG | 1138 |
| 22 | GAGATTGCACCACTGCACTCCGG | 1139 |
| 20 | CTTTGGGAGGCCGAGGTGGGAGG | 1140 |
| 20 | CTCAAGCAATCCTCCCACCTCGG | 1141 |
| 20 | CTTTGGGAGGCCGAGGTGGGAGG | 1142 |
| 20 | CTCAAGCAATCCTCCCACCTCGG | 1143 |
| 20 | TAAAAACAGAAAAATTAGCCAGG | 1144 |
| 20 | TATTTGGAAAAGAAAAATGTTGG | 1145 |
| 19 | AGGTACTCAGGAGGCTGAGGTGG | 1146 |
| 19 | CCCAGGTACTCAGGAGGCTGAGG | 1147 |
| 19 | CATTTCCTTCTCTGTAAAATGGG | 1148 |
| 19 | CTAAAAATACAAAAATTATCCGG | 1149 |
| 19 | TCGCCCAGGCCGGAGTGCAGTGG | 1150 |
| 19 | TTTTACCATGTTGGTCAGGCTGG | 1151 |
| 18 | TACTCAGGAGGCTGAGGTGGAGG | 1152 |

[Fig. 20-20]

| | | |
|---|---|---|
| 18 | AGTGCTGGGATTACAGACGTTGG | 1153 |
| 18 | CCTCTGCCTCCCAAAGTGCTGGG | 1154 |
| 18 | CTTTGGGAGGCTGAGGCTGGAGG | 1155 |
| 18 | GTTTAAAAAAAAAGAAACACAGG | 1156 |
| 17 | GCGCCACTGCACTCCAGCCTGGG | 1157 |
| 17 | CGCGCCACTGCACTCCAGCCTGG | 1158 |
| 17 | TTTTTATTCATTTTTAGAGATGG | 1159 |
| 17 | ACTTTGGGAGGCTGAGGCAGAGG | 1160 |
| 17 | CCCAACACTTTGGGAGGCTGAGG | 1161 |
| 17 | ACCTCGGCCTCCCAAAGTGCTGG | 1162 |
| 16 | AGGGTCTTGCTCTGTTGCTCAGG | 1163 |
| 16 | GAAAGGGAAGTTGGGGAAGGAGG | 1164 |
| 16 | GGAGTCTTGCACTGTCACCCAGG | 1165 |
| 16 | CCATTTCCTTCTCTGTAAAATGG | 1166 |
| 16 | CCATTTTACAGAGAAGGAAATGG | 1167 |
| 16 | CCAGACCAGCCTGACCAACATGG | 1168 |
| 16 | TTTCCCCATGTTGGTCAGGCTGG | 1169 |
| 16 | GGATTACAGCTGTGAGCCACCGG | 1170 |
| 15 | AGCACTTTGGGAGGCCGAGGTGG | 1171 |
| 15 | CGCTTGAACCCAGGAGGCAGAGG | 1172 |
| 15 | CCCAGCTACTCAGGAGGCTGAGG | 1173 |
| 15 | TCTAAAAATGAATAAAAATAAGG | 1174 |
| 15 | GCTACTCAGGAGGCTGAGGCAGG | 1175 |
| 15 | CAAGACCAGCCTGACCAACATGG | 1176 |
| 14 | ACAAACAAAAAAAACTCTTTTGG | 1177 |
| 14 | CCTCAGCCTCCTGAGTAGCTGGG | 1178 |
| 14 | ACCTGTAATCCCAGCTACTCAGG | 1179 |
| 14 | TCTTGCACTGTCACCCAGGCTGG | 1180 |
| 14 | TTTTTTTTTTAGTAGAGACGGGG | 1181 |
| 14 | CCTCAGCCTCCTGAGTAGCTGGG | 1182 |
| 13 | AGACCAGCCTGACCAACATGGGG | 1183 |
| 13 | CAGCTGTAATCCCAGCACTTTGG | 1184 |
| 12 | TTTTTTTTTTAGTAGAGACGGG | 1185 |
| 12 | GCACTTTGGGAGGCTGAGGCTGG | 1186 |
| 12 | GCCTGTAGTCCCAGCTACTCAGG | 1187 |
| 12 | GCACTTTGGGAGGCCAAGGTGGG | 1188 |
| 11 | CGTCTGTAATCCCAGCACTTTGG | 1189 |
| 10 | TCTTGCTCTGTTGCTCAGGCAGG | 1190 |
| 10 | TGTAATCCCAACACTTTGGGAGG | 1191 |
| 10 | CTAAAAATGAATAAAAATAAGGG | 1192 |
| 10 | TTTTCTGTTTTTAGTAGAGATGG | 1193 |
| 10 | CCCAGCACTTTGGGAGGCCGAGG | 1194 |
| 10 | TTTAAAAAAAAAGAAACACAGGG | 1195 |
| 9 | TGTGGTCCCAGGTACTCAGGAGG | 1196 |
| 9 | AGCTGTAATCCCAGCACTTTGGG | 1197 |
| 9 | CATGCCACTGCACTCCAGCCTGG | 1198 |
| 7 | TAAAAAAAAAAAAATTAGCCTGG | 1199 |
| 7 | ATGCCACTGCACTCCAGCCTGGG | 1200 |
| 7 | ACCTTGGCCTCCCAAAGTGCTGG | 1201 |
| 7 | CCTCGGCCTCCCAAAGTGCTGGG | 1202 |
| 6 | GTCTGTAATCCCAGCACTTTGGG | 1203 |
| 6 | CCCAGCACTTTGGGAGGCCAAGG | 1204 |
| 6 | CACCTGTAATCCCAGCACTTTGG | 1205 |
| 5 | TTGTTTGTTTGTTTTTGAAGTGG | 1206 |
| 5 | TTGCCCAGGCTGGAGTGCAGTGG | 1207 |
| 5 | AGCACTTTGGGAGGCCAAGGTGG | 1208 |
| 4 | AAAAAAAAAAAAAATTAGCCGGG | 1209 |
| 4 | TCACCCAGGCTGGAGTGCAGTGG | 1210 |
| 4 | TTTTTTTTTTTTTAGTAGAGACGG | 1211 |

[Fig. 20-21]

|   |   |   |   |
|---|---|---|---|
|   | 4 | TTGTATTTTTAGTAGAGACAGGG | 1212 |
|   | 4 | AATAAATAAATAAAATAAATAGG | 1213 |
|   | 4 | TGTAGTCCCAGCTACTCAGGAGG | 1214 |
|   | 4 | CCTTGGCCTCCCAAAGTGCTGGG | 1215 |
|   | 3 | AAAAAAAAAAAAAAATTAGCCGG | 1216 |
|   | 3 | TCTCACTCTGTTGCCCAGGCTGG | 1217 |
|   | 3 | ACCTGTAATCCCAGCACTTTGGG | 1218 |
|   | 3 | TGTAATCCCAGCACTTTGGGAGG | 1219 |
|   | 2 | TTTGTATTTTTAGTAGAGACAGG | 1220 |
|   | 2 | TCCCAAAGTGCTGGGATTACAGG | 1221 |
|   | 1 | TTTTTTTTTTTTTTGAGGCAGGG | 1222 |
|   | 1 | TTTTTTTTTTTTTTTGAGGCAGG | 1223 |
|   | 0 | AAAAAAAAAAAAAAAAGTCTGGG | 1224 |
|   | 0 | AAAAAAAAAAAAAAAAAGTCTGG | 1225 |
|   | 0 | TTTTTTTTTTTTTTTTTTTGAGG | 1226 |
| V1/E5 | 93 | TCCAAATCTCCAAGCGGGTTGGG | 1227 |
| V3/E5 | 89 | CCAAATCTCCAAGCGGGTTGGGG | 1228 |
| V4/E4 | 87 | GTCCAAATCTCCAAGCGGGTTGG | 1229 |
| V5/E3 | 86 | CCGGCTACAGTTGTGACCCCTGG | 1230 |
| V6/E4 | 85 | CCCCAACCCGCTTGGAGATTTGG | 1231 |
| V7/E3 | 84 | GCCGGGCACCCCAACCCGCTTGG | 1232 |
|   | 84 | CGGCTACAGTTGTGACCCCTGGG | 1233 |
|   | 83 | CTCAAGGTCACGTTGACCCCAGG | 1234 |
|   | 83 | CCGGGATGTGTCCTCCGAGCTGG | 1235 |
|   | 80 | TTGGGGTGCCCGGCATCTCAAGG | 1236 |
|   | 80 | AAAGAATTCTGCCAGCTCGGAGG | 1237 |
|   | 80 | AGCAGCTCCAGGACATCGCTGGG | 1238 |
|   | 79 | TCAACGTGACCTTGAGATGCCGG | 1239 |
|   | 78 | GCTTAGGGTGGTATGAAGCTGGG | 1240 |
|   | 78 | CTTCATACCACCCTAAGCCATGG | 1241 |
|   | 78 | CCAGGGGTCACAACTGTAGCCGG | 1242 |
|   | 78 | GCTGCTACCGAAGGCCAGACTGG | 1243 |
|   | 78 | CTGCTACCGAAGGCCAGACTGGG | 1244 |
|   | 76 | TCAAGGTCACGTTGACCCCAGGG | 1245 |
|   | 75 | GGCTTAGGGTGGTATGAAGCTGG | 1246 |
|   | 75 | AGAAGGGGAGCGATCTCTCCAGG | 1247 |
|   | 75 | GTCCCAGCCCAGCGATGTCCTGG | 1248 |
|   | 74 | ATACCACCCTAAGCCATGGCTGG | 1249 |
|   | 73 | CAACGTGACCTTGAGATGCCGGG | 1250 |
|   | 71 | GAGCTCCCAGCCATGGCTTAGGG | 1251 |
|   | 71 | TGCTACCGAAGGCCAGACTGGGG | 1252 |
|   | 71 | GCTACCGAAGGCCAGACTGGGGG | 1253 |
|   | 70 | CAAGGTCACGTTGACCCCAGGGG | 1254 |
|   | 70 | TACCACCCTAAGCCATGGCTGGG | 1255 |
|   | 70 | TCCAAGCGGGTTGGGGTGCCCGG | 1256 |
|   | 70 | GCTCCAGGACATCGCTGGGCTGG | 1257 |
|   | 69 | CTTAGGGTGGTATGAAGCTGGGG | 1258 |
|   | 68 | GGCTACAGTTGTGACCCCTGGGG | 1259 |
|   | 67 | CCAGCTCGGAGGACACATCCCGG | 1260 |
|   | 66 | AGATCGCTCCCCTTCTCTTCCGG | 1261 |
|   | 66 | TGAGCTCCCAGCCATGGCTTAGG | 1262 |
|   | 66 | CAGCAGCTCCAGGACATCGCTGG | 1263 |
|   | 65 | AGATTTGGACTTTTCAAGCCTGG | 1264 |
|   | 65 | AGGACACATCCGGAAGAGAAGG | 1265 |
|   | 65 | CAGACTGGGGGCCGGGTGTCTGG | 1266 |
|   | 65 | ACTGAATAAACGGGGCTGCCTGG | 1267 |
|   | 64 | GGACACATCCCGGAAGAGAAGGG | 1268 |
|   | 63 | CTCCCAGCCATGGCTTAGGGTGG | 1269 |
|   | 62 | CGAGCTGGCAGAATTCTTTCTGG | 1270 |

[Fig. 20-22]

| | | | |
|---|---|---|---|
| | 62 | AGGAGGTGACTCCAGCCCAAGGG | 1271 |
| | 62 | CAGACACCCGGCCCCCAGTCTGG | 1272 |
| | 61 | TAGGGTGGTATGAAGCTGGGGGG | 1273 |
| | 60 | TTAGGGTGGTATGAAGCTGGGGG | 1274 |
| | 60 | AGCAGCGGTAACTTCCCCCTTGG | 1275 |
| | 59 | CTGGCCTTCGGTAGCAGCAGCGG | 1276 |
| | 58 | GAAAAGTCCAAATCTCCAAGCGG | 1277 |
| | 58 | AGCTGGGGGGACTGAATAAACGG | 1278 |
| | 58 | GCAGCGGTAACTTCCCCCTTGGG | 1279 |
| | 58 | AGCTGGGGGGACTGAATAAACGG | 1280 |
| | 57 | AAAAGTCCAAATCTCCAAGCGGG | 1281 |
| | 56 | CTCCAGGACATCGCTGGGCTGGG | 1282 |
| | 56 | CCGGCCCCCAGTCTGGCCTTCGG | 1283 |
| | 55 | GACACATCCCGGAAGAGAAGGGG | 1284 |
| | 54 | GGAGGTGACTCCAGCCCAAGGGG | 1285 |
| | 54 | CGGTAACTTCCCCCTTGGGCTGG | 1286 |
| | 53 | CAGAAAGAATTCTGCCAGCTCGG | 1287 |
| | 52 | GATCGCTCCCCTTCTCTTCCGGG | 1288 |
| | 52 | TGGTGACAGGTGAGGTCCTGGGG | 1289 |
| | 51 | CTGGTGACAGGTGAGGTCCTGGG | 1290 |
| | 51 | CAGCGATGTCCTGGAGCTGCTGG | 1291 |
| | 51 | CTGGTGACAGGTGAGGTCCTGGG | 1292 |
| | 50 | GAGGTGACTCCAGCCCAAGGGGG | 1293 |
| | 50 | GCTGGTGACAGGTGAGGTCCTGG | 1294 |
| | 50 | CTGGGCTGGGACCAGACACCCGG | 1295 |
| | 50 | CCGAAGGCCAGACTGGGGGCCGG | 1296 |
| | 49 | CAGGTGAGGTCCTGGGGTCGGGG | 1297 |
| | 48 | GCTGGCAGAATTCTTTCTGGAGG | 1298 |
| | 47 | GCCATGGCTGGGAGCTCAGCCGG | 1299 |
| | 47 | GGCAGAATTCTTTCTGGAGGAGG | 1300 |
| | 47 | GTTACCGCTGCTGCTACCGAAGG | 1301 |
| | 46 | CGAAGGCCAGACTGGGGGCCGGG | 1302 |
| | 44 | GCCGGCTGAGCTCCCAGCCATGG | 1303 |
| | 44 | ACAGGTGAGGTCCTGGGGTCGGG | 1304 |
| | 38 | GAGGAGGTGACTCCAGCCCAAGG | 1305 |
| | 38 | GGAGCTGCTGGTGACAGGTGAGG | 1306 |
| | 37 | GTCCTGGAGCTGCTGGTGACAGG | 1307 |
| | 17 | CACCTGTCACCAGCAGCTCCAGG | 1308 |
| V1/I5 | 92 | GCGAGCGGAAGACGCTCACGCGG | 1309 |
| V3/I5 | 88 | GGAAGACGCTCACGCGGCCCCGG | 1310 |
| V4/I4 | 77 | AGAGACGGGGTGAGAGTCCGGGG | 1311 |
| V5/I3 | 66 | AGAGAGAGAGGTACAGTGCGGGG | 1312 |
| V6/I4 | 64 | AGAGAGAGGTACAGTGCGGGGGG | 1313 |
| V7/I3 | 64 | CAGAGACGGGGTGAGAGTCCGGG | 1314 |
| | 61 | AAACAGAGCGAGCGAGCGAGCGG | 1315 |
| | 59 | GTGGGTGGAACAAGGGAGTTGGG | 1316 |
| | 59 | GACAGATACAGAGACACTAGGGG | 1317 |
| | 59 | GAGAGAGAGGTACAGTGCGGGGG | 1318 |
| | 57 | GCAGCTCCTCTGCAGAGACGGGG | 1319 |
| | 56 | ACAGATACAGAGACACTAGGGGG | 1320 |
| | 54 | AGTGGGTGGAACAAGGGAGTTGG | 1321 |
| | 52 | TGGTGACAGGTGAGGTCCTGGGG | 1322 |
| | 52 | TGGGTGGAACAAGGGAGTTGGGG | 1323 |
| | 52 | TCTCTGCAGAGGAGCTGCCGCGG | 1324 |
| | 51 | CTGGTGACAGGTGAGGTCCTGGG | 1325 |
| | 51 | GAGAGAGAGGTACAGTGCGGG | 1326 |
| | 50 | GCTGGTGACAGGTGAGGTCCTGG | 1327 |
| | 50 | GCAGAGACGGGGTGAGAGTCCGG | 1328 |
| | 49 | CAGGTGAGGTCCTGGGGTCGGGG | 1329 |

[Fig. 20-23]

| | | | |
|---|---|---|---|
| | 48 | CTCTCACCCCGTCTCTGCAGAGG | 1330 |
| | 45 | AGAGAGAGAGAGGTACAGTGCGG | 1331 |
| | 44 | ACAGGTGAGGTCCTGGGGTCGGG | 1332 |
| | 44 | GGGTGGAACAAGGGAGTTGGGGG | 1333 |
| | 43 | GGCAGCTCCTCTGCAGAGACGGG | 1334 |
| | 42 | GAGGAGAAGTGGGTGGAACAAGG | 1335 |
| | 41 | CACTTCTCCTCCCCGACCCCAGG | 1336 |
| | 40 | GGGAGGGACAGAGAGATATAGGG | 1337 |
| | 40 | GGGGAGGGACAGAGAGATATAGG | 1338 |
| | 39 | GACAGGTGAGGTCCTGGGGTCGG | 1339 |
| | 38 | GTGAGGTCCTGGGGTCGGGGAGG | 1340 |
| | 38 | GGAGCTGCTGGTGACAGGTGAGG | 1341 |
| | 38 | TGGGGTCGGGGAGGAGAAGTGGG | 1342 |
| | 37 | GTCCTGGAGCTGCTGGTGACAGG | 1343 |
| | 36 | TGGAACAAGGGAGTTGGGGGAGG | 1344 |
| | 36 | CGGCAGCTCCTCTGCAGAGACGG | 1345 |
| | 35 | AAAGAGAGACAGAGCGAGGCGGG | 1346 |
| | 31 | GGAACAAGGGAGTTGGGGGAGGG | 1347 |
| | 31 | GAAAGAGAGACAGAGCGAGGCGG | 1348 |
| | 29 | AGGGAAAGAGAGACAGAGCGAGG | 1349 |
| | 28 | GGTCGGGGAGGAGAAGTGGGTGG | 1350 |
| | 27 | CTGGGGTCGGGGAGGAGAAGTGG | 1351 |
| | 25 | AGGAGAAGTGGGTGGAACAAGGG | 1352 |
| | 25 | AAGACAGATACAGAGACACTAGG | 1353 |
| | 22 | ACAGAGAAAGCGAGAGACAGAGG | 1354 |
| | 21 | AGAGGCAGAAGGAGAAAGGGAGG | 1355 |
| | 21 | AAAGCGAGAGACAGAGGAGAAGG | 1356 |
| | 18 | CTAGGGGAGAGAGAGAGACAGG | 1357 |
| | 17 | CACCTGTCACCAGCAGCTCCAGG | 1358 |
| | 15 | AGGGAGGCAGAGAGAGAGAGGCAGG | 1359 |
| | 15 | AGAGAGGCAGGCAGAGAGAGAGG | 1360 |
| | 15 | AGAAAGAGGCAGAAGGAGAAAGG | 1361 |
| | 15 | AGGGAGGCAGAGAGAGAGGCAGG | 1362 |
| | 13 | AGAGGGAGGCAGAGAGAGGGAGG | 1363 |
| | 13 | AGGCAGGCAGAGAGAGAGGCAGG | 1364 |
| | 12 | GAAAGAGGCAGAAGGAGAAAGGG | 1365 |
| | 12 | AGGCAGGCAGAGAGAGAGGGAGG | 1366 |
| | 11 | AGACAGGCAGAGAGAAAGAGAGG | 1367 |
| | 10 | TAGGGGGAGAGAGAGAGACAGGG | 1368 |
| | 10 | AGGGGGAGAGAGAGAGACAGGGG | 1369 |
| | 10 | AGGGGAGCAGAGAGAGAGAGAGG | 1370 |
| | 10 | GAGAGGCAGGCAGAGAGAGAGGG | 1371 |
| | 10 | AGAAAGGGAGGCAGAGAGAGAGG | 1372 |
| | 10 | AGGCAGACAGAGAGAGAGACAGG | 1373 |
| | 9 | AGAGAGAGGGAGGCAGAGAGAGG | 1374 |
| | 8 | AGGGAGGCAGAGAGAGAGGGAGG | 1375 |
| | 8 | AGAGAGGGAGGCAGAGAGAGAGG | 1376 |
| | 7 | GAAAGGGAGGCAGAGAGAGAGGG | 1377 |
| | 7 | GAGAGAGAGAAAGAGGCAGAAGG | 1378 |
| | 6 | GAGAGAGGGAGGCAGAGAGAGGG | 1379 |
| | 6 | GGGGGGAGAGAGAGAGAAAGAGG | 1380 |
| | 5 | GAGAGGGAGGCAGAGAGAGAGGG | 1381 |
| | 5 | AGAGGCAGAAAGAGAGAGAGAGG | 1382 |
| V1/E6 | 95 | GAGCTTCGTGCTGTACCGCGAGG | 1383 |
| V3/E6 | 95 | CGGGGGAACCTAGTCCGCCTGGG | 1384 |
| V4/E5 | 94 | GGGGTCTAAGGACCGTTCCGCGG | 1385 |
| V5/E4 | 93 | GTTCCCCGGGTGTAGTCGGAGG | 1386 |
| V6/E5 | 93 | GGGGGAACCTAGTCCGCCTGGGG | 1387 |
| V7/F4 | 92 | AGCTTCGTGCTGTACCGCGAGGG | 1388 |

[ Fig. 20-24]

| | | |
|---|---|---|
| 92 | CGTGCTGTACCGCGAGGGCGTGG | 1389 |
| 92 | CTGCGCTGCGACAGCACGTAGGG | 1390 |
| 92 | TAGGTTCCCCCGGGTGTAGTCGG | 1391 |
| 92 | AAAAGTGACCAGCGCGCCCAGGG | 1392 |
| 92 | GCGCGCTGGTCACTTTTGACTGG | 1393 |
| 91 | GCACGAAGCTCATGTTCCGCAGG | 1394 |
| 91 | GACAGCACGTAGGGCGCGGAGGG | 1395 |
| 91 | TGAAAGGAAGACGCGATTAGTGG | 1396 |
| 90 | TGGGCCGACTTCACGCTGCTGGG | 1397 |
| 90 | AGCAGCGTGAAGTCGGCCCAGGG | 1398 |
| 90 | GCTCAGGGGCGGATACCAGCAGG | 1399 |
| 90 | CAAAAGTGACCAGCGCGCCCAGG | 1400 |
| 90 | GGAATAAAAGCTGGCGAGCGCGG | 1401 |
| 89 | CGCGCAGCGCAGGCTCACGTTGG | 1402 |
| 89 | AGCGCCACCAGCGACGGCCGCGG | 1403 |
| 89 | CTGCGACAGCACGTAGGGCGCGG | 1404 |
| 89 | CCGGGGGAACCTAGTCCGCCTGG | 1405 |
| 89 | CAATCAGCAGGACACGGGCGGGG | 1406 |
| 89 | CCATTTTACAGAGCGCTGATTGG | 1407 |
| 88 | AACGTGAGCCTGCGCTGCGCGGG | 1408 |
| 87 | CAACGTGAGCCTGCGCTGCGCGG | 1409 |
| 87 | GCTGCGCTGCGACAGCACGTAGG | 1410 |
| 86 | CGACAGCACGTAGGGCGCGGAGG | 1411 |
| 86 | CGTGCTGTCGCAGCGCAGCGAGG | 1412 |
| 86 | CTGGGCCGACTTCACGCTGCTGG | 1413 |
| 86 | CAGCAGCGTGAAGTCGGCCCAGG | 1414 |
| 86 | GCTCCTCCGACTACACCCGGGGG | 1415 |
| 86 | GCTGGCTGAGCTCCGCGGAACGG | 1416 |
| 85 | GCTGTACCGCGAGGGCGTGGCGG | 1417 |
| 85 | CGAAGCTCATGTTCCGCAGGCGG | 1418 |
| 85 | GGCTCCTCCGACTACACCCGGGG | 1419 |
| 84 | AGAGTCTGCTTCCACGTTGTGGG | 1420 |
| 83 | CTGGCTCCTCCGACTACACCCGG | 1421 |
| 83 | CAAAGTTGAGGGGGAGTCGATGG | 1422 |
| 83 | CAGGCGGACTAGGTTCCCCCGGG | 1423 |
| 82 | GGACACGGGCGGGGACAATAAGG | 1424 |
| 81 | CGGAGTGGCGGTACTGCAGCGGG | 1425 |
| 81 | GGAGTGGCGGTACTGCAGCGGGG | 1426 |
| 81 | AGTCAGAACCGCGCTCCTGCTGG | 1427 |
| 81 | CCAGGCGGACTAGGTTCCCCCGG | 1428 |
| 81 | CCTCATCTCCCTGGGCGCGCTGG | 1429 |
| 80 | GCGGAGTGGCGGTACTGCAGCGG | 1430 |
| 80 | TGGCTCCTCCGACTACACCCGGG | 1431 |
| 80 | TCGATGGAGGCTTCAACTCCTGG | 1432 |
| 80 | GAACCTAGTCCGCCTGGGGCTGG | 1433 |
| 79 | TTGGCGCCAGGACCCACCACCGG | 1434 |
| 79 | CGTGTGATAGTAGCAGCTGTAGG | 1435 |
| 79 | GTCGCAGCGCAGCGAGGTGCTGG | 1436 |
| 79 | CCAATCAGCAGGACACGGGCGGG | 1437 |
| 79 | AGAACAAAGCTCCCACAACGTGG | 1438 |
| 79 | CAGAGTCTGCTTCCACGTTGTGG | 1439 |
| 79 | CCAATCAGCGCTCTGTAAAATGG | 1440 |
| 79 | GACACGGGCGGGGACAATAAGGG | 1441 |
| 78 | CCGGGCAGCGCCACCAGCGACGG | 1442 |
| 78 | GCTGCCGCGGCCGTCGCTGGTGG | 1443 |
| 78 | CGATGGAGGCTTCAACTCCTGGG | 1444 |
| 78 | AGCTTCTCCGCCACTCAGGTTGG | 1445 |
| 78 | CCCGAGACTTCAACCTGAGTGGG | 1446 |
| 77 | GGCGCCCAGCAGCGTGAAGTCGG | 1447 |

[Fig. 20-25]

| | | |
|---|---|---|
| 77 | GACTAGACTCCTGGATCTGAGGG | 1448 |
| 77 | CGGCCAGCCCCAGGCGGACTAGG | 1449 |
| 76 | GATTCGAACCCTCTGTCTTCTGG | 1450 |
| 76 | CACAACGTGGAAGCAGACTCTGG | 1451 |
| 75 | GTAGCAGCTGTAGGTGCCGGGGG | 1452 |
| 75 | GCGAGGTGCTGGTCATCAGCTGG | 1453 |
| 75 | ATAGTAGCAGCTGTAGGTGCCGG | 1454 |
| 75 | GAGCTGGAGGACTAGACTCCTGG | 1455 |
| 75 | GGCTGCAGGACTAGACCCCTGGG | 1456 |
| 75 | AGTTGAGGGGGAGTCGATGGAGG | 1457 |
| 75 | ACAGGGCACAGCGGGGTCTAAGG | 1458 |
| 75 | CTACTACTACAGTGAGTAGACGG | 1459 |
| 75 | ACCAATCAGCAGGACACGGGCGG | 1460 |
| 74 | GCTCCCGGACCCCAAAGTCTGGG | 1461 |
| 74 | CCACTCAGGTTGGAAGTCTCGGG | 1462 |
| 74 | GCCACTCAGGTTGGAAGTCTCGG | 1463 |
| 73 | ACGTGGAAGCAGACTCTGGTGGG | 1464 |
| 72 | GGAGCTGCCGCGGCCGTCGCTGG | 1465 |
| 72 | AGTAGCAGCTGTAGGTGCCGGGG | 1466 |
| 72 | AGCTCCCGGACCCCAAAGTCTGG | 1467 |
| 72 | CAGTGAGTAGACGGCAGTGCTGG | 1468 |
| 72 | CCATCTTACAGAGTGCTGATTGG | 1469 |
| 71 | GCGCTGCCCGGGCCGGTGGTGGG | 1470 |
| 71 | CCAATCAGCACTCTGTAAGATGG | 1471 |
| 70 | TAGTAGCAGCTGTAGGTGCCGGG | 1472 |
| 70 | CGAGGTGCTGGTCATCAGCTGGG | 1473 |
| 70 | GGGCTGCAGGACTAGACCCCTGG | 1474 |
| 70 | GGTCCCTAAGTCCACCCCAGGGG | 1475 |
| 70 | GAGACTTCCAACCTGAGTGGCGG | 1476 |
| 70 | TTCAACCCAGGAAGTCCAGCTGG | 1477 |
| 70 | TAGTGAGACGTGAAGCCAGCTGG | 1478 |
| 70 | AGTGAGTAGACGGCAGTGCTGGG | 1479 |
| 70 | TGTAAAATGGACCAATCAGCAGG | 1480 |
| 69 | TGCGCTGCGCGGGCCGCCTGCGG | 1481 |
| 69 | GCAGGCGGCCCGCGCAGCGCAGG | 1482 |
| 69 | AACTTTGAGACTGTAGAGTCAGG | 1483 |
| 69 | CAGCCCCTGGGGTGGACTTAGGG | 1484 |
| 69 | ACTCTACAGTCTCAAAGTTGAGG | 1485 |
| 69 | GGCGGATACCAGCAGGAGCGCGG | 1486 |
| 69 | AACCTGAGTGGCGGAGAAGCTGG | 1487 |
| 69 | TGGACTTCCTGGGTTGAATGGGG | 1488 |
| 68 | GGACTAGACTCCTGGATCTGAGG | 1489 |
| 68 | TCCAGGTCCCCATTCAACCCAGG | 1490 |
| 67 | GCGGGGCCGCCACGCCCTCGCGG | 1491 |
| 67 | GCCAGGACCCACCACCGGCCCGG | 1492 |
| 67 | GACTAGACCCCTGGGTCTGAAGG | 1493 |
| 67 | GTACTGGGGCCGGGAATCCTGG | 1494 |
| 67 | CCGGCTCCGCCCGCAGACTCTGG | 1495 |
| 67 | CCAGAGTCTGCGGGCGGAGCCGG | 1496 |
| 66 | GTCTCGGGCTGCAGTGCTCCTGG | 1497 |
| 66 | ACCTGAGTGGCGGAGAAGCTGGG | 1498 |
| 65 | CTACAGTCTCAAAGTTGAGGGGG | 1499 |
| 65 | GAGTTCAGGGCCCAGACTTTGGG | 1500 |
| 65 | GCTGGACTTCCTGGGTTGAATGG | 1501 |
| 65 | CTGGACTTCCTGGGTTGAATGGG | 1502 |
| 65 | TGGACCAATCAGCAGGACACGGG | 1503 |
| 64 | ACCGCCACTCCGCGCAGCCCTGG | 1504 |
| 64 | TACTGGGGCCCGGGAATCCTGGG | 1505 |
| 64 | CAGGTCCCTAAGTCCACCCCAGG | 1506 |

[Fig. 20-26]

| | | |
|---|---|---|
| 64 | TTCCGCGGAGCTCAGCCAGCAGG | 1507 |
| 64 | CGTGGAAGCAGACTCTGGTGGGG | 1508 |
| 64 | AACGTGGAAGCAGACTCTGGTGG | 1509 |
| 63 | CGTCGCTGGTGGCGCTGCCCGGG | 1510 |
| 63 | CCGTCGCTGGTGGCGCTGCCCGG | 1511 |
| 63 | CCTGGACTGCTGGATCAGGAAGG | 1512 |
| 62 | CCCGGGCCGGTGGTGGGTCCTGG | 1513 |
| 62 | GCTGTAGGTGCCGGGGGCGCGGG | 1514 |
| 62 | GGTCTGAGGGCGGAGGTCCTGGG | 1515 |
| 62 | AGGTCCCTAAGTCCACCCCAGGG | 1516 |
| 62 | CAGAGTCTGCGGGCGGAGCCGGG | 1517 |
| 62 | TCTCGGGCTGCAGTGCTCCTGGG | 1518 |
| 61 | GAAGTCGGCCCAGGGCTGCGCGG | 1519 |
| 61 | CCCGGGAATCCTGGGTCTGAGGG | 1520 |
| 61 | TCGGAGGAGCCAGAGTCTGCGGG | 1521 |
| 61 | TCTACAGTCTCAAAGTTGAGGGG | 1522 |
| 61 | CTCTACAGTCTCAAAGTTGAGGG | 1523 |
| 61 | AGTTCAGGGCCCAGACTTTGGGG | 1524 |
| 61 | TGAAGCCAGCTGGACTTCCTGGG | 1525 |
| 61 | CTGGAAAGAAGCTACAGCACAGG | 1526 |
| 60 | TAGACTCCTGGATCTGAGGGAGG | 1527 |
| 60 | AAGTCTGGGCCCTGAACTCCAGG | 1528 |
| 60 | ATGGACCAATCAGCAGGACACGG | 1529 |
| 59 | CCGCCACTCCGCGCAGCCCTGGG | 1530 |
| 59 | AGCTGTAGGTGCCGGGGGCGCGG | 1531 |
| 59 | CCTTCCTGATCCAGCAGTCCAGG | 1532 |
| 58 | CTGCATTCCTGGGGCGGAGGAGG | 1533 |
| 58 | TAGACCCCTGGGTCTGAAGGAGG | 1534 |
| 58 | TCCCAGCTTCTCCGCCACTCAGG | 1535 |
| 58 | TTTCCCAAGGAGTAGCTGAAAGG | 1536 |
| 58 | GAACCCTCTGTCTTCTGGCTTGG | 1537 |
| 58 | CTTACAAGAGGATTGTAAAATGG | 1538 |
| 57 | GCAGCTCCTCTGCAGAGACGGGG | 1539 |
| 57 | CTCCTCCGCCCCAGGAATGCAGG | 1540 |
| 57 | GGTATCCGCCCCTGAGCCCCAGG | 1541 |
| 57 | TAGTAGTAGCAGCTACAGAAAGG | 1542 |
| 57 | TTTCAGCTACTCCTTGGGAAAGG | 1543 |
| 56 | GGTGGCGCTGCCCGGGCCGGTGG | 1544 |
| 56 | CCAGGACCCACCACCGGCCCGGG | 1545 |
| 56 | CCCAGGAATCCTGGGTCTGAGGG | 1546 |
| 56 | GGGGCCTGGACTGCTGGATCAGG | 1547 |
| 56 | CCAGCCCCTGGGGTGGACTTAGG | 1548 |
| 56 | TAGTCCGCCTGGGGCTGGCCGGG | 1549 |
| 56 | CGGGCTGGTCCTCATCTCCCTGG | 1550 |
| 56 | CTAGTCCGCCTGGGGCTGGCCGG | 1551 |
| 56 | CTTCCTTTCAGCTACTCCTTGGG | 1552 |
| 56 | GTAAGACAGAAAAGTTCTCCAGG | 1553 |
| 55 | CGGCCCAGGGCTGCGCGGAGTGG | 1554 |
| 55 | CTGCTGGGCGCCCGCGCCCCCGG | 1555 |
| 55 | GGCCTGCATTCCTGGGGCGGAGG | 1556 |
| 55 | CTCGGGCTGCAGTGCTCCTGGGG | 1557 |
| 55 | AGCTCAGCCAGCAGGACTGTGGG | 1558 |
| 55 | GAACTTTCTGTCTTACAAGAGG | 1559 |
| 54 | GGCGCTGCCCGGGCCGGTGGTGG | 1560 |
| 54 | GTCTGAGGGCGGAGGTCCTGGGG | 1561 |
| 53 | GGGTCTGAGGGCGGAGGTCCTGG | 1562 |
| 53 | CCCAGGGCTGCGCGGAGTGGCGG | 1563 |
| 53 | AGGAGGCGGGCCGGGCCTCAGGG | 1564 |
| 53 | CCTAAGTCCACCCCAGGGGCTGG | 1565 |

[Fig. 20-27]

| | | |
|---|---|---|
| 53 | GCTACTCCTTGGGAAAGGCCTGG | 1566 |
| 52 | TCTCTGCAGAGGAGCTGCCGCGG | 1567 |
| 52 | GTGCTGGTCATCAGCTGGGAAGG | 1568 |
| 52 | GGCTGGAAACCTGGAGTTCAGGG | 1569 |
| 52 | AGGGCCCAGACTTTGGGGTCCGG | 1570 |
| 52 | AGCTGATGGCCCCTCTCTCCCGG | 1571 |
| 52 | CCAGCGCGCCCAGGGAGATGAGG | 1572 |
| 52 | CTACAGCACAGGGCACAGCGGGG | 1573 |
| 51 | GGAGTTCAGGGCCCAGACTTTGG | 1574 |
| 51 | AGAGAGGGGCCATCAGCTCCCGG | 1575 |
| 50 | GCTGGTGGCGCTGCCCGGGCCGG | 1576 |
| 50 | GGCTGGGTCCCAGGAATCCTGGG | 1577 |
| 50 | GAGGAGCCAGAGTCTGCGGGCGG | 1578 |
| 50 | GCGGGCGGAGCCGGGAGAGAGGG | 1579 |
| 49 | GGTCCTGGGGCCTGCATTCCTGG | 1580 |
| 49 | GGTCATCAGCTGGGAAGGTGAGG | 1581 |
| 49 | GCCTGGAGTCCTGGGTCTGAGGG | 1582 |
| 49 | GGTCTGAGGGAGGAGGTACTGGG | 1583 |
| 49 | GTCGGAGGAGCCAGAGTCTGCGG | 1584 |
| 49 | CTGTGCTGTAGCTTCTTTCCAGG | 1585 |
| 49 | TCCTGGGTTGAATGGGGACCTGG | 1586 |
| 49 | GACAATAAGGGAATAAAAGCTGG | 1587 |
| 48 | CTCTCACCCCGTCTCTGCAGAGG | 1588 |
| 48 | GGGCCCAGACTTTGGGGTCCGGG | 1589 |
| 48 | TGGAAAGAAGCTACAGCACAGGG | 1590 |
| 46 | GTCCTGGGGCCTGCATTCCTGGG | 1591 |
| 46 | CCCTCAGACCCAGGATTCCCGGG | 1592 |
| 46 | GCTCAGCCAGCAGGACTGTGGGG | 1593 |
| 45 | GGACCTCCGCCCTCAGACCCAGG | 1594 |
| 45 | AGGAATCCTGGGTCTGAGGGAGG | 1595 |
| 45 | CCTCTCCTCCTTCAGACCCAGGG | 1596 |
| 45 | TCCCAGGAATCCTGGGTCTGAGG | 1597 |
| 45 | AACTCCAGGTTTCCAGCCCCTGG | 1598 |
| 45 | TGCAGTGCTCCTGGGGCTCAGGG | 1599 |
| 45 | AGGAAAGGACAGTCCAGCCCAGG | 1600 |
| 45 | CCCGCCCGTGTCCTGCTGATTGG | 1601 |
| 44 | GCTCCTGGGTCTGAGGGCGGAGG | 1602 |
| 44 | CTTCCTGGACCCAGGACTCCAGG | 1603 |
| 44 | GTCTGAGGGAGGAGGTACTGGGG | 1604 |
| 44 | CACCCCAGGGGCTGGAAACCTGG | 1605 |
| 44 | GGACTGCTGGATCAGGAAGGAGG | 1606 |
| 44 | CTTTGGGGTCCGGGAGCTGATGG | 1607 |
| 44 | CTGCAGCCCCACAGTCCTGCTGG | 1608 |
| 44 | GGCGGAGAAGCTGGGACCCTGGG | 1609 |
| 43 | GGCAGCTCCTCTGCAGAGACGGG | 1610 |
| 43 | GCCCGGGAATCCTGGGTCTGAGG | 1611 |
| 43 | GACTGCTGGATCAGGAAGGAGGG | 1612 |
| 43 | ACTCCTGGGTCCAGGAAGAAGGG | 1613 |
| 43 | ACTTCCAAGCCAGAAGACAGAGG | 1614 |
| 42 | ATTCCTGGGGCGGAGGAGGCGGG | 1615 |
| 42 | GCCCCAGGAATGCAGGCCCCAGG | 1616 |
| 42 | TCCCTCAGACCCAGGATTCCCGG | 1617 |
| 42 | TCCCTCAGACCCAGGATTCCTGG | 1618 |
| 42 | GGGCTGGGTCCCAGGAATCCTGG | 1619 |
| 42 | GCCTCTCCTCCTTCAGACCCAGG | 1620 |
| 42 | GGGTCTGAGGGAGGAGGTACTGG | 1621 |
| 42 | GAGCTCAGCCAGCAGGACTGTGG | 1622 |
| 41 | GCCTGGGCTCCTGGGTCTGAGGG | 1623 |
| 41 | GAGGAGGCGGGCCGGGCCTCAGG | 1624 |

[ Fig. 20-28]

| | | |
|---|---|---|
| 41 | CCCTCAGACCCAGGATTCCTGGG | 1625 |
| 41 | CTGGAGTCCTGGGTCCAGGAAGG | 1626 |
| 41 | CTCTCCTCCTTCAGACCCAGGGG | 1627 |
| 41 | GGGAATCCTGGGTCTGAGGGAGG | 1628 |
| 41 | CAGGTTTCCAGCCCCTGGGGTGG | 1629 |
| 41 | CAGGGAGATGAGGACCAGCCCGG | 1630 |
| 41 | AGCTACAGCACAGGGCACAGCGG | 1631 |
| 41 | CTTCCAAGCCAGAAGACAGAGGG | 1632 |
| 40 | CGGCCCGCCTCCTCCGCCCCAGG | 1633 |
| 40 | TGGAGTCCTGGGTCTGAGGGAGG | 1634 |
| 40 | GGGCTGGAAACCTGGAGTTCAGG | 1635 |
| 40 | TGCGGGCGGAGCCGGGAGAGAGG | 1636 |
| 40 | CTCCAGGTTTCCAGCCCCTGGGG | 1637 |
| 39 | TGGCGGAGAAGCTGGGACCCTGG | 1638 |
| 39 | CCGCCTGGGGCTGGCCGGGCTGG | 1639 |
| 38 | AACTCCTGGGTCCAGGAAGAAGG | 1640 |
| 38 | CGGGCGGAGCCGGGAGAGAGGGG | 1641 |
| 38 | GCAGTGCTCCTGGGGCTCAGGGG | 1642 |
| 38 | GCTACAGCACAGGGCACAGCGGG | 1643 |
| 37 | TGGGGCGGAGGAGGCGGGCCGGG | 1644 |
| 37 | ACTCCTGGATCTGAGGGAGGAGG | 1645 |
| 37 | TCCCTCAGACCCAGGACTCCAGG | 1646 |
| 37 | AGCCCCTTCTTCCTGGACCCAGG | 1647 |
| 37 | CTGCAGTGCTCCTGGGGCTCAGG | 1648 |
| 37 | GTCCTGCTGGCTGAGCTCCGCGG | 1649 |
| 36 | CGGCAGCTCCTCTGCAGAGACGG | 1650 |
| 36 | GCCCCTCCTCCCTCAGATCCAGG | 1651 |
| 36 | ACTGCTGGATCAGGAAGGAGGGG | 1652 |
| 36 | AGGCTTCAACTCCTGGGTCCAGG | 1653 |
| 35 | TCCTGGGGCCTGCATTCCTGGGG | 1654 |
| 35 | TGGGCTCCTGGGTCTGAGGGCGG | 1655 |
| 35 | GTACCTCCTCCCTCAGACCCAGG | 1656 |
| 35 | GGGCTGGTCCTCATCTCCCTGGG | 1657 |
| 34 | CATTCCTGGGGCGGAGGAGGCGG | 1658 |
| 34 | CTCCTGGATCTGAGGGAGGAGGG | 1659 |
| 34 | TGGGTCCAGGAAGAAGGGGCTGG | 1660 |
| 34 | CTGGATCAGGAAGGAGGGGCTGG | 1661 |
| 34 | CTCCTGGGTCCAGGAAGAAGGGG | 1662 |
| 34 | GGACCAGCCCGGCCAGCCCCAGG | 1663 |
| 34 | TTCTTTCCAGGCCTTTCCCAAGG | 1664 |
| 33 | CGCAGGCTCACGTTGGCGCCAGG | 1665 |
| 33 | GTCATCAGCTGGGAAGGTGAGGG | 1666 |
| 33 | CTGGGGCGGAGGAGGCGGGCCGG | 1667 |
| 33 | AGGGAGGAGGTACTGGGGCCCGG | 1668 |
| 33 | ACTCCAGGTTTCCAGCCCCTGGG | 1669 |
| 32 | CAGCAGGACTGTGGGGCTGCAGG | 1670 |
| 32 | GGACTGTGGGGCTGCAGGAAAGG | 1671 |
| 31 | GCCCTCAGACCCAGGAGCCCAGG | 1672 |
| 31 | GGGAGGAGGTACTGGGGCCCGGG | 1673 |
| 31 | AGTCCTGGGTCCAGGAAGGAGGG | 1674 |
| 31 | CCCTGGGTCTGAAGGAGGAGAGG | 1675 |
| 31 | TGGATCAGGAAGGAGGGGCTGGG | 1676 |
| 31 | GGAAAGGACAGTCCAGCCCAGGG | 1677 |
| 30 | AAGGTGAGGGCCCTGAGGCCCGG | 1678 |
| 30 | AGCCCCTCCTTCCTGGACCCAGG | 1679 |
| 30 | ATCCTGGGTCTGAGGGAGGAGGG | 1680 |
| 30 | AATCCTGGGTCTGAGGGAGGAGG | 1681 |
| 29 | GTCCTGGGTCCAGGAAGGAGGGG | 1682 |
| 29 | GGTCTGAAGGAGGAGAGGCTGGG | 1683 |

[Fig. 20-29]

| | | | |
|---|---|---|---|
| | 29 | GGGTCCAGGAAGAAGGGGCTGGG | 1684 |
| | 28 | AGGCCCCAGCCCCTTCTTCCTGG | 1685 |
| | 28 | TCTTCCTTTCAGCTACTCCTTGG | 1686 |
| | 27 | GGCTGGGGGCCTGGAGTCCTGGG | 1687 |
| | 27 | GGCCTGGAGTCCTGGGTCTGAGG | 1688 |
| | 27 | AGTCCTGGGTCTGAGGGAGGAGG | 1689 |
| | 27 | GTGAAGCCAGCTGGACTTCCTGG | 1690 |
| | 26 | GGCCTGGGCTCCTGGGTCTGAGG | 1691 |
| | 26 | TGGGGCCTGCATTCCTGGGGCGG | 1692 |
| | 26 | GGGCTGGGGGCCTGGAGTCCTGG | 1693 |
| | 26 | TGGGTCCAGGAAGGAGGGGCTGG | 1694 |
| | 26 | GGTCCAGGAAGAAGGGGCTGGGG | 1695 |
| | 25 | TCTGAAGGAGGAGAGGCTGGGGG | 1696 |
| | 25 | GATCTGAGGGAGGAGGGGCTGGG | 1697 |
| | 25 | GGGGCTGGGGCCTGGACTGCTGG | 1698 |
| | 25 | GTGCTCCTGGGGCTCAGGGGCGG | 1699 |
| | 24 | GGCTGGGGGCCTGGGCTCCTGGG | 1700 |
| | 24 | GAGTCCTGGGTCCAGGAAGGAGG | 1701 |
| | 24 | GGGCCTGGAGTCCTGGGTCCAGG | 1702 |
| | 24 | GTCTGAAGGAGGAGAGGCTGGGG | 1703 |
| | 24 | GGGTCTGAAGGAGGAGAGGCTGG | 1704 |
| | 23 | TCCTGGATCTGAGGGAGGAGGGG | 1705 |
| | 23 | GGGAGGAGGGGCTGGGTCCAGG | 1706 |
| | 23 | GGGTCCAGGAAGGAGGGGCTGGG | 1707 |
| | 22 | TCTGAGGGAGGAGGGGCTGCAGG | 1708 |
| | 22 | GGAGGAGAGGCTGGGGGCCTGGG | 1709 |
| | 22 | GATCAGGAAGGAGGGGCTGGGGG | 1710 |
| | 21 | CTGGGAAGGTGAGGGCCCTGAGG | 1711 |
| | 21 | AGGAGGAGAGGCTGGGGGCCTGG | 1712 |
| | 20 | AGGCTGGGGGCCTGGGCTCCTGG | 1713 |
| | 20 | GGTCCAGGAAGGAGGGGCTGGGG | 1714 |
| | 20 | GAGAAGCTGGGACCCTGGGCTGG | 1715 |
| | 20 | CCAGCCCGGCCAGCCCCAGGCGG | 1716 |
| | 19 | GCTCCTCCTCCCTCAGACCCAGG | 1717 |
| | 19 | GGCCCCAGCCCCTCCTTCCTGG | 1718 |
| | 19 | GTCCAGGAAGGAGGGGCTGGGGG | 1719 |
| | 18 | GCCCCTCCTCCCTCAGACCCAGG | 1720 |
| | 18 | GGAAGGAGGGGCTGGGGGCCTGG | 1721 |
| | 18 | TCTGAGGGAGGAGGAGCTGGAGG | 1722 |
| | 18 | GGATCAGGAAGGAGGGGCTGGGG | 1723 |
| | 17 | TCCTGGGTCTGAGGGAGGAGGGG | 1724 |
| | 15 | GGGTCTGAGGGAGGAGGAGCTGG | 1725 |
| | 14 | GGATCTGAGGGAGGAGGGGCTGG | 1726 |
| | 14 | AGGAAGAAGGGGCTGGGGCCTGG | 1727 |
| V3/E7 | 95 | CGGGGGAACCTAGTCCGCCTGGG | 1728 |
| V4/E6 | 94 | GGGGTCTAAGGACCGTTCCGCGG | 1729 |
| V5/E5 | 93 | GTTCCCCCGGGTGTAGTCGGAGG | 1730 |
| | 93 | GGGGGAACCTAGTCCGCCTGGGG | 1731 |
| | 92 | TAGGTTCCCCCGGGTGTAGTCGG | 1732 |
| | 92 | AAAAGTGACCAGCGCGCCCAGGG | 1733 |
| | 92 | GCGCGCTGGTCACTTTTGACTGG | 1734 |
| | 91 | TGAAAGGAAGACGCGATTAGTGG | 1735 |
| | 90 | GCTCAGGGGCGGATACCAGCAGG | 1736 |
| | 90 | CAAAAGTGACCAGCGCGCCCAGG | 1737 |
| | 90 | GGAATAAAAGCTGGCGAGCGCGG | 1738 |
| | 89 | CCGGGGGAACCTAGTCCGCCTGG | 1739 |
| | 89 | CAATCAGCAGGACACGGGCGGGG | 1740 |
| | 89 | CCATTTTACAGAGCGCTGATTGG | 1741 |
| | 86 | GCTCCTCCGACTACACCCGGGGG | 1742 |

[Fig. 20-30]

| | | |
|---|---|---|
| 86 | GCTGGCTGAGCTCCGCGGAACGG | 1743 |
| 85 | GGCTCCTCCGACTACACCCGGGG | 1744 |
| 84 | AGAGTCTGCTTCCACGTTGTGGG | 1745 |
| 83 | CAGGCGGACTAGGTTCCCCCGGG | 1746 |
| 83 | CTGGCTCCTCCGACTACACCCGG | 1747 |
| 82 | GGACACGGGCGGGGACAATAAGG | 1748 |
| 81 | AGTCAGAACCGCGCTCCTGCTGG | 1749 |
| 81 | CCAGGCGGACTAGGTTCCCCCGG | 1750 |
| 81 | CCTCATCTCCCTGGGCGCGCTGG | 1751 |
| 80 | TGGCTCCTCCGACTACACCCGGG | 1752 |
| 80 | GAACCTAGTCCGCCTGGGGCTGG | 1753 |
| 79 | CCAATCAGCAGGACACGGGCGGG | 1754 |
| 79 | AGAACAAAGCTCCCACAACGTGG | 1755 |
| 79 | CAGAGTCTGCTTCCACGTTGTGG | 1756 |
| 79 | CCAATCAGCGCTCTGTAAAATGG | 1757 |
| 79 | GACACGGGCGGGGACAATAAGGG | 1758 |
| 78 | AGCTTCTCCGCCACTCAGGTTGG | 1759 |
| 78 | CCCGAGACTTCCAACCTGAGTGG | 1760 |
| 77 | CGGCCAGCCCCAGGCGGACTAGG | 1761 |
| 76 | GATTCGAACCCTCTGTCTTCTGG | 1762 |
| 76 | CACAACGTGGAAGCAGACTCTGG | 1763 |
| 75 | ACAGGGCACAGCGGGGTCTAAGG | 1764 |
| 75 | CTACTACTACAGTGAGTAGACGG | 1765 |
| 75 | ACCAATCAGCAGGACACGGGCGG | 1766 |
| 74 | CCACTCAGGTTGGAAGTCTCGGG | 1767 |
| 74 | GCCACTCAGGTTGGAAGTCTCGG | 1768 |
| 73 | ACGTGGAAGCAGACTCTGGTGGG | 1769 |
| 72 | CAGTGAGTAGACGGCAGTGCTGG | 1770 |
| 72 | CCATCTTACAGAGTGCTGATTGG | 1771 |
| 71 | CCAATCAGCACTCTGTAAGATGG | 1772 |
| 70 | GAGACTTCCAACCTGAGTGGCGG | 1773 |
| 70 | TAGTGAGACGTGAAGCCAGCTGG | 1774 |
| 70 | AGTGAGTAGACGGCAGTGCTGGG | 1775 |
| 70 | TGTAAAATGGACCAATCAGCAGG | 1776 |
| 69 | GGCGGATACCAGCAGGAGCGCGG | 1777 |
| 69 | AACCTGAGTGGCGGAGAAGCTGG | 1778 |
| 69 | TGGACTTCCTGGGTTGAATGGGG | 1779 |
| 68 | TCCAGGTCCCCATTCAACCCAGG | 1780 |
| 67 | CCGGCTCCGCCCGCAGACTCTGG | 1781 |
| 67 | CCAGAGTCTGCGGGCGGAGCCGG | 1782 |
| 66 | GTCTCGGGCTGCAGTGCTCCTGG | 1783 |
| 66 | ACCTGAGTGGCGGAGAAGCTGGG | 1784 |
| 65 | GCTGGACTTCCTGGGTTGAATGG | 1785 |
| 65 | TGGACCAATCAGCAGGACACGGG | 1786 |
| 65 | CTGGACTTCCTGGGTTGAATGGG | 1787 |
| 64 | TTCCGCGGAGCTCAGCCAGCAGG | 1788 |
| 64 | CGTGGAAGCAGACTCTGGTGGGG | 1789 |
| 64 | AACGTGGAAGCAGACTCTGGTGG | 1790 |
| 62 | CAGAGTCTGCGGGCGGAGCCGGG | 1791 |
| 62 | TCTCGGGCTGCAGTGCTCCTGGG | 1792 |
| 61 | TCGGAGGAGCCAGAGTCTGCGGG | 1793 |
| 61 | TGAAGCCAGCTGGACTTCCTGGG | 1794 |
| 61 | CTGGAAAGAAGCTACAGCACAGG | 1795 |
| 60 | ATGGACCAATCAGCAGGACACGG | 1796 |
| 58 | TCCCAGCTTCTCCGCCACTCAGG | 1797 |
| 58 | TTTCCCAAGGAGTAGCTGAAAGG | 1798 |
| 58 | GAACCCTCTGTCTTCTGGCTTGG | 1799 |
| 58 | CTTACAAGAGGATTGTAAAATGG | 1800 |
| 57 | GGTATCCGCCCCTGAGCCCCAGG | 1801 |

[Fig. 20-31]

|  | | | |
|---|---|---|---|
| | 57 | TAGTAGTAGCAGCTACAGAAAGG | 1802 |
| | 57 | TTTCAGCTACTCCTTGGGAAAGG | 1803 |
| | 56 | TAGTCCGCCTGGGGCTGGCCGGG | 1804 |
| | 56 | CGGGCTGGTCCTCATCTCCCTGG | 1805 |
| | 56 | CTAGTCCGCCTGGGGCTGGCCGG | 1806 |
| | 56 | CTTCCTTTCAGCTACTCCTTGGG | 1807 |
| | 56 | GTAAGACAGAAAAGTTCTCCAGG | 1808 |
| | 55 | CTCGGGCTGCAGTGCTCCTGGGG | 1809 |
| | 55 | AGCTCAGCCAGCAGGACTGTGGG | 1810 |
| | 55 | GAACTTTTCTGTCTTACAAGAGG | 1811 |
| | 53 | GCTACTCCTTGGGAAAGGCCTGG | 1812 |
| | 52 | CCAGCGCGCCCAGGGAGATGAGG | 1813 |
| | 52 | CTACAGCACAGGGCACAGCGGGG | 1814 |
| | 50 | GAGGAGCCAGAGTCTGCGGGCGG | 1815 |
| | 49 | GTCGGAGGAGCCAGAGTCTGCGG | 1816 |
| | 49 | CTGTGCTGTAGCTTCTTTCCAGG | 1817 |
| | 49 | GACAATAAGGGAATAAAAGCTGG | 1818 |
| | 49 | TCCTGGGTTGAATGGGGACCTGG | 1819 |
| | 48 | TGGAAAGAAGCTACAGCACAGGG | 1820 |
| | 46 | GCTCAGCCAGCAGGACTGTGGGG | 1821 |
| | 45 | TGCAGTGCTCCTGGGGCTCAGGG | 1822 |
| | 45 | AGGAAAGGACAGTCCAGCCCAGG | 1823 |
| | 45 | CCCGCCCGTGTCCTGCTGATTGG | 1824 |
| | 44 | GGCGGAGAAGCTGGGACCCTGGG | 1825 |
| | 44 | CTGCAGCCCCACAGTCCTGCTGG | 1826 |
| | 43 | ACTTCCAAGCCAGAAGACAGAGG | 1827 |
| | 42 | GAGCTCAGCCAGCAGGACTGTGG | 1828 |
| | 41 | CAGGGAGATGAGGACCAGCCCGG | 1829 |
| | 41 | AGCTACAGCACAGGGCACAGCGG | 1830 |
| | 41 | CTTCCAAGCCAGAAGACAGAGGG | 1831 |
| | 39 | TGGCGGAGAAGCTGGGACCCTGG | 1832 |
| | 39 | CCGCCTGGGGCTGGCCGGGCTGG | 1833 |
| | 38 | GCAGTGCTCCTGGGGCTCAGGGG | 1834 |
| | 38 | GCTACAGCACAGGGCACAGCGGG | 1835 |
| | 37 | CTGCAGTGCTCCTGGGGCTCAGG | 1836 |
| | 37 | GTCCTGCTGGCTGAGCTCCGCGG | 1837 |
| | 35 | GGGCTGGTCCTCATCTCCCTGGG | 1838 |
| | 34 | GGACCAGCCCGGCCAGCCCCAGG | 1839 |
| | 34 | TTCTTTCCAGGCCTTTCCCAAGG | 1840 |
| | 32 | GGACTGTGGGGCTGCAGGAAAGG | 1841 |
| | 32 | CAGCAGGACTGTGGGGCTGCAGG | 1842 |
| | 31 | GGAAAGGACAGTCCAGCCCAGGG | 1843 |
| | 28 | TCTTCCTTTCAGCTACTCCTTGG | 1844 |
| | 27 | GTGAAGCCAGCTGGACTTCCTGG | 1845 |
| | 25 | GTGCTCCTGGGGCTCAGGGGCGG | 1846 |
| | 20 | GAGAAGCTGGGACCCTGGGCTGG | 1847 |
| | 20 | CCAGCCCGGCCAGCCCCAGGCGG | 1848 |
| V3/I6 | 83 | CAAAGTTGAGGGGAGTCGATGG | 1849 |
| V4/I5 | 80 | TCGATGGAGGCTTCAACTCCTGG | 1850 |
| V5/I4 | 78 | CGATGGAGGCTTCAACTCCTGGG | 1851 |
| | 77 | GACTAGACTCCTGGATCTGAGGG | 1852 |
| | 75 | GGCTGCAGGACTAGACCCCTGGG | 1853 |
| | 75 | GAGCTGGAGGACTAGACTCCTGG | 1854 |
| | 75 | AGTTGAGGGGGAGTCGATGGAGG | 1855 |
| | 74 | GCTCCCGGACCCCAAAGTCTGGG | 1856 |
| | 72 | AGCTCCCGGACCCCAAAGTCTGG | 1857 |
| | 70 | GGTCCCTAAGTCCACCCCAGGGG | 1858 |
| | 70 | GGGCTGCAGGACTAGACCCCTGG | 1859 |
| | 69 | CAGCCCCTGGGGTGGACTTAGGG | 1860 |

[Fig. 20-32]

| | | |
|---|---|---|
| 69 | ACTCTACAGTCTCAAAGTTGAGG | 1861 |
| 69 | AACTTTGAGACTGTAGAGTCAGG | 1862 |
| 68 | GGACTAGACTCCTGGATCTGAGG | 1863 |
| 67 | GTACTGGGGCCCGGGAATCCTGG | 1864 |
| 67 | GACTAGACCCCTGGGTCTGAAGG | 1865 |
| 67 | CCGGCTCCGCCCGCAGACTCTGG | 1866 |
| 67 | CCAGAGTCTGCGGGCGGAGCCGG | 1867 |
| 65 | GAGTTCAGGGCCCAGACTTTGGG | 1868 |
| 65 | CTACAGTCTCAAAGTTGAGGGGG | 1869 |
| 64 | TACTGGGGCCCGGGAATCCTGGG | 1870 |
| 64 | CAGGTCCCTAAGTCCACCCCAGG | 1871 |
| 63 | CCTGGACTGCTGGATCAGGAAGG | 1872 |
| 62 | GGTCTGAGGGCGGAGGTCCTGGG | 1873 |
| 62 | CAGAGTCTGCGGGCGGAGCCGGG | 1874 |
| 62 | AGGTCCCTAAGTCCACCCCAGGG | 1875 |
| 61 | TCTACAGTCTCAAAGTTGAGGGG | 1876 |
| 61 | TCGGAGGAGCCAGAGTCTGCGGG | 1877 |
| 61 | CTCTACAGTCTCAAAGTTGAGGG | 1878 |
| 61 | CCCGGGAATCCTGGGTCTGAGGG | 1879 |
| 61 | AGTTCAGGGCCCAGACTTTGGGG | 1880 |
| 60 | TAGACTCCTGGATCTGAGGGAGG | 1881 |
| 60 | AAGTCTGGGCCCTGAACTCCAGG | 1882 |
| 59 | CCTTCCTGATCCAGCAGTCCAGG | 1883 |
| 58 | TAGACCCCTGGGTCTGAAGGAGG | 1884 |
| 58 | CTGCATTCCTGGGGCGGAGGAGG | 1885 |
| 57 | CTCCTCCGCCCCAGGAATGCAGG | 1886 |
| 56 | GGGGCCTGGACTGCTGGATCAGG | 1887 |
| 56 | CCCAGGAATCCTGGGTCTGAGGG | 1888 |
| 56 | CCAGCCCCTGGGGTGGACTTAGG | 1889 |
| 55 | GGCCTGCATTCCTGGGGCGGAGG | 1890 |
| 54 | GTCTGAGGGCGGAGGTCCTGGGG | 1891 |
| 53 | GGGTCTGAGGGCGGAGGTCCTGG | 1892 |
| 53 | CCTAAGTCCACCCCAGGGGCTGG | 1893 |
| 53 | AGGAGGCGGGCCGGGCCTCAGGG | 1894 |
| 52 | GTGCTGGTCATCAGCTGGGAAGG | 1895 |
| 52 | GGCTGGAAACCTGGAGTTCAGGG | 1896 |
| 52 | AGGGCCCAGACTTTGGGGTCCGG | 1897 |
| 52 | AGCTGATGGCCCCTCTCTCCCGG | 1898 |
| 51 | GGAGTTCAGGGCCCAGACTTTGG | 1899 |
| 51 | AGAGAGGGGCCATCAGCTCCCGG | 1900 |
| 50 | GGCTGGGTCCCAGGAATCCTGGG | 1901 |
| 50 | GCGGGCGGAGCCGGGAGAGAGGG | 1902 |
| 50 | GAGGAGCCAGAGTCTGCGGGCGG | 1903 |
| 49 | GTCGGAGGAGCCAGAGTCTGCGG | 1904 |
| 49 | GGTCTGAGGGAGGAGGTACTGGG | 1905 |
| 49 | GGTCCTGGGGCCTGCATTCCTGG | 1906 |
| 49 | GGTCATCAGCTGGGAAGGTGAGG | 1907 |
| 49 | GCCTGGAGTCCTGGGTCTGAGGG | 1908 |
| 48 | GGGCCCAGACTTTGGGGTCCGGG | 1909 |
| 46 | GTCCTGGGGCCTGCATTCCTGGG | 1910 |
| 46 | CCCTCAGACCCAGGATTCCCGGG | 1911 |
| 45 | TCCCAGGAATCCTGGGTCTGAGG | 1912 |
| 45 | GGACCTCCGCCCTCAGACCCAGG | 1913 |
| 45 | CCTCTCCTCCTTCAGACCCAGGG | 1914 |
| 45 | AGGAATCCTGGGTCTGAGGGAGG | 1915 |
| 45 | AACTCCAGGTTTCCAGCCCCTGG | 1916 |
| 44 | GTCTGAGGGAGGAGGTACTGGGG | 1917 |
| 44 | GGACTGCTGGATCAGGAAGGAGG | 1918 |
| 44 | GCTCCTGGGTCTGAGGGCGGAGG | 1919 |

[ Fig. 20-33]

| | | |
|---|---|---|
| 44 | CTTTGGGGTCCGGGAGCTGATGG | 1920 |
| 44 | CTTCCTGGACCCAGGACTCCAGG | 1921 |
| 44 | CACCCCAGGGGCTGGAAACCTGG | 1922 |
| 43 | GCCCGGGAATCCTGGGTCTGAGG | 1923 |
| 43 | GACTGCTGGATCAGGAAGGAGGG | 1924 |
| 43 | ACTCCTGGGTCCAGGAAGAAGGG | 1925 |
| 42 | TCCCTCAGACCCAGGATTCCTGG | 1926 |
| 42 | TCCCTCAGACCCAGGATTCCCGG | 1927 |
| 42 | GGGTCTGAGGGAGGAGGTACTGG | 1928 |
| 42 | GGGCTGGGTCCAGGAATCCTGG | 1929 |
| 42 | GCCTCTCCTCCTTCAGACCCAGG | 1930 |
| 42 | GCCCCAGGAATGCAGGCCCCAGG | 1931 |
| 42 | ATTCCTGGGGCGGAGGAGGCGGG | 1932 |
| 41 | GGGAATCCTGGGTCTGAGGGAGG | 1933 |
| 41 | GCCTGGGCTCCTGGGTCTGAGGG | 1934 |
| 41 | GAGGAGGCGGGCCGGGCCTCAGG | 1935 |
| 41 | CTGGAGTCCTGGGTCCAGGAAGG | 1936 |
| 41 | CTCTCCTCCTTCAGACCCAGGGG | 1937 |
| 41 | CCCTCAGACCCAGGATTCCTGGG | 1938 |
| 41 | CAGGTTTCCAGCCCCTGGGGTGG | 1939 |
| 40 | TGGAGTCCTGGGTCTGAGGGAGG | 1940 |
| 40 | TGCGGGCGGAGCCGGGAGAGAGG | 1941 |
| 40 | GGGCTGGAAACCTGGAGTTCAGG | 1942 |
| 40 | CTCCAGGTTTCCAGCCCCTGGGG | 1943 |
| 40 | CGGCCCGCCTCCTCCGCCCCAGG | 1944 |
| 38 | CGGGCGGAGCCGGGAGAGAGGGG | 1945 |
| 38 | AACTCCTGGGTCCAGGAAGAAGG | 1946 |
| 37 | TGGGGCGGAGGAGGCGGGCCGGG | 1947 |
| 37 | TCCCTCAGACCCAGGACTCCAGG | 1948 |
| 37 | AGCCCCTTCTTCCTGGACCCAGG | 1949 |
| 37 | ACTCCTGGATCTGAGGGAGGAGG | 1950 |
| 36 | GCCCCTCCTCCCTCAGATCCAGG | 1951 |
| 36 | AGGCTTCAACTCCTGGGTCCAGG | 1952 |
| 36 | ACTGCTGGATCAGGAAGGAGGGG | 1953 |
| 35 | TGGGCTCCTGGGTCTGAGGGCGG | 1954 |
| 35 | TCCTGGGGCCTGCATTCCTGGGG | 1955 |
| 35 | GTACCTCCTCCCTCAGACCCAGG | 1956 |
| 34 | TGGGTCCAGGAAGAAGGGGCTGG | 1957 |
| 34 | CTGGATCAGGAAGGAGGGGCTGG | 1958 |
| 34 | CTCCTGGGTCCAGGAAGAAGGGG | 1959 |
| 34 | CTCCTGGATCTGAGGGAGGAGGG | 1960 |
| 34 | CATTCCTGGGGCGGAGGAGGCGG | 1961 |
| 33 | GTCATCAGCTGGGAAGGTGAGGG | 1962 |
| 33 | CTGGGGCGGAGGAGGCGGGCCGG | 1963 |
| 33 | AGGGAGGAGGTACTGGGGCCCGG | 1964 |
| 33 | ACTCCAGGTTTCCAGCCCCTGGG | 1965 |
| 31 | TGGATCAGGAAGGAGGGGCTGGG | 1966 |
| 31 | GGGAGGAGGTACTGGGGCCCGGG | 1967 |
| 31 | GCCCTCAGACCCAGGAGCCCAGG | 1968 |
| 31 | CCCTGGGTCTGAAGGAGGAGAGG | 1969 |
| 31 | AGTCCTGGGTCCAGGAAGGAGGG | 1970 |
| 30 | ATCCTGGGTCTGAGGGAGGAGGG | 1971 |
| 30 | AGCCCCTCCTTCCTGGACCCAGG | 1972 |
| 30 | AATCCTGGGTCTGAGGGAGGAGG | 1973 |
| 30 | AAGGTGAGGGCCCTGAGGCCCGG | 1974 |
| 29 | GTCCTGGGTCCAGGAAGGAGGGG | 1975 |
| 29 | GGTCTGAAGGAGGAGAGGCTGGG | 1976 |
| 29 | GGGTCCAGGAAGAAGGGGCTGGG | 1977 |
| 28 | AGGCCCCAGCCCCTTCTTCCTGG | 1978 |

[ Fig. 20-34]

| 27 | GGCTGGGGGCCTGGAGTCCTGGG | 1979 |
|---|---|---|
| 27 | GGCCTGGAGTCCTGGGTCTGAGG | 1980 |
| 27 | AGTCCTGGGTCTGAGGGAGGAGG | 1981 |
| 26 | TGGGTCCAGGAAGGAGGGGCTGG | 1982 |
| 26 | TGGGGCCTGCATTCCTGGGGCGG | 1983 |
| 26 | GGTCCAGGAAGAAGGGGCTGGGG | 1984 |
| 26 | GGGCTGGGGGCCTGGAGTCCTGG | 1985 |
| 26 | GGCCTGGGCTCCTGGGTCTGAGG | 1986 |
| 25 | TCTGAAGGAGGAGAGGCTGGGGG | 1987 |
| 25 | GGGGCTGGGGCCTGGACTGCTGG | 1988 |
| 25 | GATCTGAGGGAGGAGGGGCTGGG | 1989 |
| 24 | GTCTGAAGGAGGAGAGGCTGGGG | 1990 |
| 24 | GGGTCTGAAGGAGGAGAGGCTGG | 1991 |
| 24 | GGGCCTGGAGTCCTGGGTCCAGG | 1992 |
| 24 | GGCTGGGGGCCTGGGCTCCTGGG | 1993 |
| 24 | GAGTCCTGGGTCCAGGAAGGAGG | 1994 |
| 23 | TCCTGGATCTGAGGGAGGAGGGG | 1995 |
| 23 | GGGTCCAGGAAGGAGGGGCTGGG | 1996 |
| 23 | GGGAGGAGGGGCTGGGTCCCAGG | 1997 |
| 22 | TCTGAGGGAGGAGGGGCTGCAGG | 1998 |
| 22 | GGAGGAGAGGCTGGGGGCCTGGG | 1999 |
| 22 | GATCAGGAAGGAGGGGCTGGGGG | 2000 |
| 21 | CTGGGAAGGTGAGGGCCCTGAGG | 2001 |
| 21 | AGGAGGAGAGGCTGGGGGCCTGG | 2002 |
| 20 | GGTCCAGGAAGGAGGGGCTGGGG | 2003 |
| 20 | AGGCTGGGGGCCTGGGCTCCTGG | 2004 |
| 19 | GTCCAGGAAGGAGGGGCTGGGGG | 2005 |
| 19 | GGCCCCAGCCCCTCCTTCCTGG | 2006 |
| 19 | GCTCCTCCTCCCTCAGACCCAGG | 2007 |
| 18 | TCTGAGGGAGGAGGAGCTGGAGG | 2008 |
| 18 | GGATCAGGAAGGAGGGGCTGGGG | 2009 |
| 18 | GGAAGGAGGGGCTGGGGGCCTGG | 2010 |
| 18 | GCCCCTCCTCCCTCAGACCCAGG | 2011 |
| 17 | TCCTGGGTCTGAGGGAGGAGGGG | 2012 |
| 15 | GGGTCTGAGGGAGGAGGAGCTGG | 2013 |
| 14 | GGATCTGAGGGAGGAGGGGCTGG | 2014 |
| 14 | AGGAAGAAGGGGCTGGGGCCTGG | 2015 |

SEQUENCE LISTING

```
<160> NUMBER OF SEQ ID NOS: 2028

<210> SEQ ID NO 1
<211> LENGTH: 286
<212> TYPE: PRT
<213> ORGANISM: Homo sapiens

<400> SEQUENCE: 1

Met Ala Leu Val Leu Ile Leu Gln Leu Leu Thr Leu Trp Pro Leu Cys
1               5                   10                  15

His Thr Asp Ile Thr Pro Ser Val Ala Ile Ile Val Pro Pro Ala Ser
            20                  25                  30

Tyr His Pro Lys Pro Trp Leu Gly Ala Gln Pro Ala Thr Val Val Thr
        35                  40                  45

Pro Gly Val Asn Val Thr Leu Arg Cys Arg Ala Pro Gln Pro Ala Trp
    50                  55                  60

Arg Phe Gly Leu Phe Lys Pro Gly Glu Ile Ala Pro Leu Leu Phe Arg
65                  70                  75                  80

Asp Val Ser Ser Glu Leu Ala Glu Phe Phe Leu Glu Glu Val Thr Pro
                85                  90                  95

Ala Gln Gly Gly Ser Tyr Arg Cys Cys Tyr Arg Arg Pro Asp Trp Gly
            100                 105                 110

Pro Gly Val Trp Ser Gln Pro Ser Asp Val Leu Glu Leu Leu Val Thr
        115                 120                 125

Glu Glu Leu Pro Arg Pro Ser Leu Val Ala Leu Pro Gly Pro Val Val
    130                 135                 140
```

Gly Pro Gly Ala Asn Val Ser Leu Arg Cys Ala Gly Arg Leu Arg Asn
145                 150                 155                 160

Met Ser Phe Val Leu Tyr Arg Glu Gly Val Ala Ala Pro Leu Gln Tyr
                165                 170                 175

Arg His Ser Ala Gln Pro Trp Ala Asp Phe Thr Leu Leu Gly Ala Arg
            180                 185                 190

Ala Pro Gly Thr Tyr Ser Cys Tyr Tyr His Thr Pro Ser Ala Pro Tyr
        195                 200                 205

Val Leu Ser Gln Arg Ser Glu Val Leu Val Ile Ser Trp Glu Gly Glu
    210                 215                 220

Gly Pro Glu Ala Arg Pro Ala Ser Ser Ala Pro Gly Met Gln Ala Pro
225                 230                 235                 240

Gly Pro Pro Pro Ser Asp Pro Gly Ala Gln Ala Pro Ser Leu Ser Ser
                245                 250                 255

Phe Arg Pro Arg Gly Leu Val Leu Gln Pro Leu Leu Pro Gln Thr Gln
                260                 265                 270

Asp Ser Trp Asp Pro Ala Pro Pro Ser Asp Pro Gly Val
                275                 280                 285

<210> SEQ ID NO 2
<211> LENGTH: 459
<212> TYPE: PRT
<213> ORGANISM: Artificial Sequence
<220> FEATURE:
<223> OTHER INFORMATION: Oscar-Fc fusion

<400> SEQUENCE: 2

Met Ala Leu Val Leu Ile Leu Gln Leu Leu Thr Leu Trp Pro Leu Cys
1               5                   10                  15

His Thr Asp Ile Thr Pro Ser Val Ala Ile Ile Val Pro Pro Ala Ser
                20                  25                  30

Tyr His Pro Lys Pro Trp Leu Gly Ala Gln Pro Ala Thr Val Val Thr
            35                  40                  45

Pro Gly Val Asn Val Thr Leu Arg Cys Arg Ala Pro Gln Pro Ala Trp
    50                  55                  60

Arg Phe Gly Leu Phe Lys Pro Gly Glu Ile Ala Pro Leu Leu Phe Arg
65                  70                  75                  80

Asp Val Ser Ser Glu Leu Ala Glu Phe Phe Leu Glu Glu Val Thr Pro
                85                  90                  95

Ala Gln Gly Gly Ser Tyr Arg Cys Cys Tyr Arg Arg Pro Asp Trp Gly
            100                 105                 110

Pro Gly Val Trp Ser Gln Pro Ser Asp Val Leu Glu Leu Leu Val Thr
        115                 120                 125

Glu Glu Leu Pro Arg Pro Ser Leu Val Ala Leu Pro Gly Pro Val Val
    130                 135                 140

Gly Pro Gly Ala Asn Val Ser Leu Arg Cys Ala Gly Arg Leu Arg Asn
145                 150                 155                 160

Met Ser Phe Val Leu Tyr Arg Glu Gly Val Ala Ala Pro Leu Gln Tyr
                165                 170                 175

Arg His Ser Ala Gln Pro Trp Ala Asp Phe Thr Leu Leu Gly Ala Arg
            180                 185                 190

Ala Pro Gly Thr Tyr Ser Cys Tyr Tyr His Thr Pro Ser Ala Pro Tyr
        195                 200                 205

Val Leu Ser Gln Arg Ser Glu Val Leu Val Ile Ser Trp Glu Gly Glu
    210                 215                 220

Gly Pro Glu Ala Arg Pro Ala Ser Asp Lys Thr His Thr Cys Pro Pro
225                 230                 235                 240

Cys Pro Ala Pro Glu Leu Leu Gly Gly Pro Ser Val Phe Leu Phe Pro
            245                 250                 255

Pro Lys Pro Lys Asp Thr Leu Met Ile Ser Arg Thr Pro Glu Val Thr
        260                 265                 270

Cys Val Val Val Asp Val Ser His Glu Asp Pro Glu Val Lys Phe Asn
    275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Ser Arg Glu
        355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
450                 455

<210> SEQ ID NO 3
<211> LENGTH: 271
<212> TYPE: PRT
<213> ORGANISM: Mus musculus

<400> SEQUENCE: 3

Met Val Leu Ser Leu Ile Leu Gln Leu Ser Thr Leu Cys Glu Leu Ser
1               5                   10                  15

Leu Pro Trp Pro Ala Cys Arg Ala Asp Phe Thr Pro Thr Ala Pro Leu
            20                  25                  30

Ala Ser Tyr Pro Gln Pro Trp Leu Gly Ala His Pro Ala Ala Val Val
        35                  40                  45

Thr Pro Gly Ile Asn Val Thr Leu Thr Cys Arg Ala Pro Gln Ser Ala
    50                  55                  60

Trp Arg Phe Ala Leu Phe Lys Ser Gly Leu Val Thr Pro Leu Leu Leu
65                  70                  75                  80

Arg Asp Val Ser Val Glu Leu Ala Glu Phe Phe Leu Glu Glu Val Thr
                85                  90                  95

Pro Ala Gln Gly Gly Ser Tyr His Cys Arg Tyr Arg Lys Thr Asp Trp
            100                 105                 110

Gly Pro Gly Val Trp Ser Gln Pro Ser Asn Val Leu Glu Leu Leu Val
        115                 120                 125

Thr Asp Gln Leu Pro Arg Pro Ser Leu Val Ala Leu Pro Gly Pro Val
    130                 135                 140

```
Val Ala Pro Gly Ala Asn Val Ser Leu Arg Cys Ala Gly Arg Ile Pro
145                 150                 155                 160

Gly Met Ser Phe Ala Leu Tyr Arg Val Gly Val Ala Thr Pro Leu Gln
                165                 170                 175

Tyr Ile Asp Ser Val Gln Pro Trp Ala Asp Phe Leu Leu Ile Gly Thr
            180                 185                 190

His Thr Pro Gly Thr Tyr Cys Cys Tyr Tyr His Thr Pro Ser Ala Pro
        195                 200                 205

Tyr Val Leu Ser Gln Arg Ser Gln Pro Leu Val Ile Ser Phe Glu Gly
    210                 215                 220

Ser Gly Ser Leu Asp Tyr Thr Gln Gly Asn Leu Ile Arg Leu Gly Leu
225                 230                 235                 240

Ala Gly Met Val Leu Ile Cys Leu Gly Ile Ile Val Thr Cys Asp Trp
                245                 250                 255

His Ser Arg Ser Ser Ala Phe Asp Gly Leu Leu Pro Gln Gln Asn
            260                 265                 270
```

<210> SEQ ID NO 4
<211> LENGTH: 462
<212> TYPE: PRT
<213> ORGANISM: Artificial Sequence
<220> FEATURE:
<223> OTHER INFORMATION: Oscar-Fc fusion

<400> SEQUENCE: 4

```
Met Val Leu Ser Leu Ile Leu Gln Leu Ser Thr Leu Cys Glu Leu Ser
1               5                   10                  15

Leu Pro Trp Pro Ala Cys Arg Ala Asp Phe Thr Pro Thr Ala Pro Leu
                20                  25                  30

Ala Ser Tyr Pro Gln Pro Trp Leu Gly Ala His Pro Ala Ala Val Val
            35                  40                  45

Thr Pro Gly Ile Asn Val Thr Leu Thr Cys Arg Ala Pro Gln Ser Ala
        50                  55                  60

Trp Arg Phe Ala Leu Phe Lys Ser Gly Leu Val Thr Pro Leu Leu Leu
65                  70                  75                  80

Arg Asp Val Ser Val Glu Leu Ala Glu Phe Phe Leu Glu Glu Val Thr
                85                  90                  95

Pro Ala Gln Gly Gly Ser Tyr His Cys Arg Tyr Arg Lys Thr Asp Trp
            100                 105                 110

Gly Pro Gly Val Trp Ser Gln Pro Ser Asn Val Leu Glu Leu Leu Val
        115                 120                 125

Thr Asp Gln Leu Pro Arg Pro Ser Leu Val Ala Leu Pro Gly Pro Val
130                 135                 140

Val Ala Pro Gly Ala Asn Val Ser Leu Arg Cys Ala Gly Arg Ile Pro
145                 150                 155                 160

Gly Met Ser Phe Ala Leu Tyr Arg Val Gly Val Ala Thr Pro Leu Gln
                165                 170                 175

Tyr Ile Asp Ser Val Gln Pro Trp Ala Asp Phe Leu Leu Ile Gly Thr
            180                 185                 190

His Thr Pro Gly Thr Tyr Cys Cys Tyr Tyr His Thr Pro Ser Ala Pro
        195                 200                 205

Tyr Val Leu Ser Gln Arg Ser Gln Pro Leu Val Ile Ser Phe Glu Gly
    210                 215                 220

Ser Gly Ser Leu Asp Tyr Thr Gln Gly Asn Leu Asp Lys Thr His Thr
225                 230                 235                 240
```

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 5
<211> LENGTH: 1601
<212> TYPE: DNA
<213> ORGANISM: Artificial Sequence
<220> FEATURE:
<223> OTHER INFORMATION: Oscar-Fc

<400> SEQUENCE: 5
aagcttgcca ccatggccct cgtgcttatc ctccaacttc tcacgctttg gcctctgtgc    60
cacaccgaca ttactccgtc tgttgcgata attgtccctc cgcctcttat tcaccctaaa    120
ccttggctgg gcgcacagcc agctactgtg gttactcctg gggtgaacgt aacactgcgc    180
tgccgtgctc ctcagcccgc ctggagattt gggttgttta agcccggaga gatagcacca    240
ctgctgtttc gggatgtgtc ctcagagctg gctgagttct tcctggaaga ggtcactcct    300
gcccaaggag gcagctatcg gtgctgttat aggcggccgg attggggacc cggcgtttgg    360
tcccaaccat ctgatgtgct cgaactgctt gtgacagaag agctgcccag acctagcttg    420
gtagccttgc ccggtcctgt cgtcggacct ggtgccaatg tttctcttcg atgtgccgga    480
aggctgcgca atatgtcctt tgtactgtat agggagggag tagccgcacc tctgcagtat    540
aggcatagcg ctcagccctg gcggattttt actctgcttg tgccagagc acccgggacc    600 tattcctgct actaccacac tccttccgca ccctacgtcc tgtcacagag atcagaagtg    660
ctcgtgatct cctgggaggg agaaggccca gaagccgaca aaactcacac atgcccaccg    720
tgcccaggta agccagccca ggcctcgccc tccagctcaa ggcgggacag gtgccctaga    780

```
gtagcctgca tccagggaca ggccccagcc gggtgctgac acgtccacct ccatctcttc    840
ctcagcacct gaactcctgg ggggaccgtc agtcttcctc ttcccccaa  acccaagga     900 caccctcatg atctcccgga cccctgaggt cacatgcgtg gtggtggacg tgagccacga    960
agaccctgag gtcaagttca actggtacgt ggacggcgtg gaggtgcata atgccaagac   1020
aaagccgcgg gaggagcagt acaacagcac gtaccgtgtg gtcagcgtcc tcaccgtcct   1080
gcaccaggac tggctgaatg gcaaggagta caagtgcaag gtctccaaca aagccctccc   1140
agcccccatc gagaaaacca tctccaaagc caaaggtggg acccgtgggg tgcgagggcc   1200
acatggacag aggccggctc ggcccaccct ctgccctgag agtgactgct gtaccaacct   1260
ctgtccctac agggcagccc cgagaaccac aggtgtacac cctgccccca tcccgggatg   1320
agctgaccaa gaaccaggtc agcctgacct gcctggtcaa aggcttctat cccagcgaca   1380
tcgccgtgga gtgggagagc aatgggcagc cggagaacaa ctacaagacc acgcctcccg   1440
tgctggactc cgacggctcc ttcttcctct acagcaagct caccgtggac aagagcaggt   1500
ggcagcaggg gaacgtcttc tcatgctccg tgatgcatga ggctctgcac aaccactaca   1560
cgcagaagag cctctccctg tctccgggta aatgatctag a                       1601
```

```
<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
aagaccttga gtagttgccc a                                               21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
tgctcgatcc tacgtttgca g                                               21

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
aggagccatg actcgaaggt                                                 20

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
gctcaccagg tagtgatgct t                                               21

<210> SEQ ID NO 10
<211> LENGTH: 20
```

```
<212> TYPE: DNA
<213> ORGANISM: Artificial Sequence
<220> FEATURE:
<223> OTHER INFORMATION: primer

<400> SEQUENCE: 10
accccagcat ggaaacaaag                                              20

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
aagaatggta ttgaagtcat ctgtc                                        25

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
accccgtgaa gaaaatcaga a                                            21

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
taacaggcgg tcttggttgg                                              20

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
tggtggtcct gtttacagtg g                                            21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ttctgaagtt cttcacgggg t                                            21

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
```
cctacgaaga ctcaaattct cagc                                              24

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
gaggaccatg gtggtgtcc                                                    19

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
gctcggtgac cctggtcttt                                                   20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
aatgtgaggc gggtggaact                                                   20

<210> SEQ ID NO 20
<211> LENGTH: 20
<212> TYPE: DNA
<213> ORGANISM: Mus musculus

<400> SEQUENCE: 20
acagctggag tatcagcgac                                                   20

<210> SEQ ID NO 21
<211> LENGTH: 20
<212> TYPE: DNA
<213> ORGANISM: Mus musculus

<400> SEQUENCE: 21
gctcacagag agtcgacagc                                                   20

<210> SEQ ID NO 22
<211> LENGTH: 146
<212> TYPE: DNA
<213> ORGANISM: Artificial Sequence
<220> FEATURE:
<223> OTHER INFORMATION: ssODN

<400> SEQUENCE: 22
gccaaggatc cacacacagg ggagggacag ctcacagaga gtcgacagct ggagtatcag        60
cctcagaaga actcgtcaag aagtcacgac aggaccatgg tgggcactct ccgtggagct       120
gaggaaaagg ttgaccctgc ctttttt                                           146

<210> SEQ ID NO 23
<211> LENGTH: 146
<212> TYPE: DNA
<213> ORGANISM: Artificial Sequence
<220> FEATURE:
<223> OTHER INFORMATION: ssODN

<400> SEQUENCE: 23
atagccctca gcccagccaa ggatccacac acaggggagg gacagctcac agagagtcga    60
cctcagaaga actcgtcaag aagtcacagc tggagtatca gcgacaggac catggtgggc    120
actctccgtg gagctgagga aaaggt    146

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctacttagcg acaacgtcct    20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gccttggggt ttgaaggttt    20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
cagaggctat gactgttcca    20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ggcagggtca accttttcct    20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
agggacagct cacagagagt    20

<210> SEQ ID NO 29
<211> LENGTH: 20
<212> TYPE: DNA
<213> ORGANISM: Artificial Sequence
<220> FEATURE:
<223> OTHER INFORMATION: primer -continued

<400> SEQUENCE: 29
gctcggtgac cctggtctttt                                              20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
aatgtgaggc gggtggaact                                               20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
cgggcatgag ttttgcactg                                               20

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tgggtatagt ccaaggagcc a                                             21

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
aggagccatg actcgaaggt                                               20

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
gctcaccagg tagtgatgct t                                             21

<210> SEQ ID NO 35
<211> LENGTH: 23
<212> TYPE: DNA
<213> ORGANISM: Homo sapiens

<400> SEQUENCE: 35
caacacaaat tagccgggcg tgg                                           23

<210> SEQ ID NO 36
<211> LENGTH: 23
<212> TYPE: DNA
<213> ORGANISM: Homo sapiens

```
<400> SEQUENCE: 36
agctcaacat cggctcgtcc tgg                                          23

<210> SEQ ID NO 37
<211> LENGTH: 23
<212> TYPE: DNA
<213> ORGANISM: Homo sapiens

<400> SEQUENCE: 37
gtcactccgg agcgacttct agg                                          23

<210> SEQ ID NO 38
<211> LENGTH: 23
<212> TYPE: DNA
<213> ORGANISM: Homo sapiens

<400> SEQUENCE: 38
ccacgcaggt ccgcaaagtc agg                                          23

<210> SEQ ID NO 39
<211> LENGTH: 23
<212> TYPE: DNA
<213> ORGANISM: Homo sapiens

<400> SEQUENCE: 39
ggactatttt gttccgcctt agg                                          23

<210> SEQ ID NO 40
<211> LENGTH: 23
<212> TYPE: DNA
<213> ORGANISM: Homo sapiens

<400> SEQUENCE: 40
gtctcgaact tcccgacctc agg                                          23

<210> SEQ ID NO 41
<211> LENGTH: 23
<212> TYPE: DNA
<213> ORGANISM: Homo sapiens

<400> SEQUENCE: 41
gcgagggtct ggcacgtaat agg                                          23

<210> SEQ ID NO 42
<211> LENGTH: 23
<212> TYPE: DNA
<213> ORGANISM: Homo sapiens

<400> SEQUENCE: 42
cgccttaggt gggtcgcagc agg                                          23

<210> SEQ ID NO 43
<211> LENGTH: 23
<212> TYPE: DNA
<213> ORGANISM: Homo sapiens

<400> SEQUENCE: 43
acctcgtgat ccgcccgcct cgg                                          23

<210> SEQ ID NO 44
<211> LENGTH: 23
<212> TYPE: DNA
```

```
<213> ORGANISM: Homo sapiens

<400> SEQUENCE: 44
aatcgcttga actcgggagt cgg                                              23

<210> SEQ ID NO 45
<211> LENGTH: 23
<212> TYPE: DNA
<213> ORGANISM: Homo sapiens

<400> SEQUENCE: 45
tcttggtctt tcagtcggac tgg                                              23

<210> SEQ ID NO 46
<211> LENGTH: 23
<212> TYPE: DNA
<213> ORGANISM: Homo sapiens

<400> SEQUENCE: 46
cctgactttg cggacctgcg tgg                                              23

<210> SEQ ID NO 47
<211> LENGTH: 23
<212> TYPE: DNA
<213> ORGANISM: Homo sapiens

<400> SEQUENCE: 47
tctcagccta gaagtcgctc cgg                                              23

<210> SEQ ID NO 48
<211> LENGTH: 23
<212> TYPE: DNA
<213> ORGANISM: Homo sapiens

<400> SEQUENCE: 48
cgcttgaact cgggagtcgg agg                                              23

<210> SEQ ID NO 49
<211> LENGTH: 23
<212> TYPE: DNA
<213> ORGANISM: Homo sapiens

<400> SEQUENCE: 49
ggagtgcaat ggcgcgatct cgg                                              23

<210> SEQ ID NO 50
<211> LENGTH: 23
<212> TYPE: DNA
<213> ORGANISM: Homo sapiens

<400> SEQUENCE: 50
atgttgagct gagacctcga agg                                              23

<210> SEQ ID NO 51
<211> LENGTH: 23
<212> TYPE: DNA
<213> ORGANISM: Homo sapiens

<400> SEQUENCE: 51
acaaccgcgc ccggcctaga ggg                                              23

<210> SEQ ID NO 52
<211> LENGTH: 23
```

```
<212> TYPE: DNA
<213> ORGANISM: Homo sapiens

<400> SEQUENCE: 52
agactaagga gattccacgc agg                                              23

<210> SEQ ID NO 53
<211> LENGTH: 23
<212> TYPE: DNA
<213> ORGANISM: Homo sapiens

<400> SEQUENCE: 53
aacaaccgcg cccggcctag agg                                              23

<210> SEQ ID NO 54
<211> LENGTH: 23
<212> TYPE: DNA
<213> ORGANISM: Homo sapiens

<400> SEQUENCE: 54
ggatgagacc tagcgcttcc agg                                              23

<210> SEQ ID NO 55
<211> LENGTH: 23
<212> TYPE: DNA
<213> ORGANISM: Homo sapiens

<400> SEQUENCE: 55
caaccgcgcc cggcctagag ggg                                              23

<210> SEQ ID NO 56
<211> LENGTH: 23
<212> TYPE: DNA
<213> ORGANISM: Homo sapiens

<400> SEQUENCE: 56
tattttgttc cgccttaggt ggg                                              23

<210> SEQ ID NO 57
<211> LENGTH: 23
<212> TYPE: DNA
<213> ORGANISM: Homo sapiens

<400> SEQUENCE: 57
gagaatggcg tgaacccggg agg                                              23

<210> SEQ ID NO 58
<211> LENGTH: 23
<212> TYPE: DNA
<213> ORGANISM: Homo sapiens

<400> SEQUENCE: 58
aatgactaac ctgtccttcg agg                                              23

<210> SEQ ID NO 59
<211> LENGTH: 23
<212> TYPE: DNA
<213> ORGANISM: Homo sapiens

<400> SEQUENCE: 59
tagcccctct aggccgggcg cgg                                              23

<210> SEQ ID NO 60
```

```
<211> LENGTH: 23
<212> TYPE: DNA
<213> ORGANISM: Homo sapiens

<400> SEQUENCE: 60
ggcgggcgga tcacgaggtc agg                                              23

<210> SEQ ID NO 61
<211> LENGTH: 23
<212> TYPE: DNA
<213> ORGANISM: Homo sapiens

<400> SEQUENCE: 61
cgctaggtct catcccagat ggg                                              23

<210> SEQ ID NO 62
<211> LENGTH: 23
<212> TYPE: DNA
<213> ORGANISM: Homo sapiens

<400> SEQUENCE: 62
ctgctgcgac ccacctaagg cgg                                              23

<210> SEQ ID NO 63
<211> LENGTH: 23
<212> TYPE: DNA
<213> ORGANISM: Homo sapiens

<400> SEQUENCE: 63
cggctcgtcc tggaagcgct agg                                              23

<210> SEQ ID NO 64
<211> LENGTH: 23
<212> TYPE: DNA
<213> ORGANISM: Homo sapiens

<400> SEQUENCE: 64
cagaaagctc ctaacccatc tgg                                              23

<210> SEQ ID NO 65
<211> LENGTH: 23
<212> TYPE: DNA
<213> ORGANISM: Homo sapiens

<400> SEQUENCE: 65
gggggttcag tcataacctg tgg                                              23

<210> SEQ ID NO 66
<211> LENGTH: 23
<212> TYPE: DNA
<213> ORGANISM: Homo sapiens

<400> SEQUENCE: 66
ctattttgtt ccgccttagg tgg                                              23

<210> SEQ ID NO 67
<211> LENGTH: 23
<212> TYPE: DNA
<213> ORGANISM: Homo sapiens

<400> SEQUENCE: 67
agcaggagga ctagtcactc cgg                                              23
```

```
<210> SEQ ID NO 68
<211> LENGTH: 23
<212> TYPE: DNA
<213> ORGANISM: Homo sapiens

<400> SEQUENCE: 68
gagctgagac ctcgaaggac agg                                              23

<210> SEQ ID NO 69
<211> LENGTH: 23
<212> TYPE: DNA
<213> ORGANISM: Homo sapiens

<400> SEQUENCE: 69
cacaaattag ccgggcgtgg tgg                                              23

<210> SEQ ID NO 70
<211> LENGTH: 23
<212> TYPE: DNA
<213> ORGANISM: Homo sapiens

<400> SEQUENCE: 70
gcgcccgtag tcccagctac tgg                                              23

<210> SEQ ID NO 71
<211> LENGTH: 23
<212> TYPE: DNA
<213> ORGANISM: Homo sapiens

<400> SEQUENCE: 71
ctgccaacat ggcacagcga ggg                                              23

<210> SEQ ID NO 72
<211> LENGTH: 23
<212> TYPE: DNA
<213> ORGANISM: Homo sapiens

<400> SEQUENCE: 72
aacatggcac agcgagggtc tgg                                              23

<210> SEQ ID NO 73
<211> LENGTH: 23
<212> TYPE: DNA
<213> ORGANISM: Homo sapiens

<400> SEQUENCE: 73
tcgaggtctc agctcaacat cgg                                              23

<210> SEQ ID NO 74
<211> LENGTH: 23
<212> TYPE: DNA
<213> ORGANISM: Homo sapiens

<400> SEQUENCE: 74
gcgctaggtc tcatcccaga tgg                                              23

<210> SEQ ID NO 75
<211> LENGTH: 23
<212> TYPE: DNA
<213> ORGANISM: Homo sapiens

<400> SEQUENCE: 75
gcaggagaat ggcgtgaacc cgg                                              23
```

```
<210> SEQ ID NO 76
<211> LENGTH: 23
<212> TYPE: DNA
<213> ORGANISM: Homo sapiens

<400> SEQUENCE: 76
aaaattagcc cctctaggcc ggg                                              23

<210> SEQ ID NO 77
<211> LENGTH: 23
<212> TYPE: DNA
<213> ORGANISM: Homo sapiens

<400> SEQUENCE: 77
ggtctcatcc cagatgggtt agg                                              23

<210> SEQ ID NO 78
<211> LENGTH: 23
<212> TYPE: DNA
<213> ORGANISM: Homo sapiens

<400> SEQUENCE: 78
aatggcgtga acccgggagg cgg                                              23

<210> SEQ ID NO 79
<211> LENGTH: 23
<212> TYPE: DNA
<213> ORGANISM: Homo sapiens

<400> SEQUENCE: 79
gaaaaattag ccggctgtgg agg                                              23

<210> SEQ ID NO 80
<211> LENGTH: 23
<212> TYPE: DNA
<213> ORGANISM: Homo sapiens

<400> SEQUENCE: 80
caggagaatc gcttgaactc ggg                                              23

<210> SEQ ID NO 81
<211> LENGTH: 23
<212> TYPE: DNA
<213> ORGANISM: Homo sapiens

<400> SEQUENCE: 81
cgacttctag gctgagacta agg                                              23

<210> SEQ ID NO 82
<211> LENGTH: 23
<212> TYPE: DNA
<213> ORGANISM: Homo sapiens

<400> SEQUENCE: 82
agaaagctcc taacccatct ggg                                              23

<210> SEQ ID NO 83
<211> LENGTH: 23
<212> TYPE: DNA
<213> ORGANISM: Homo sapiens

<400> SEQUENCE: 83
agtgatctga gctataatgg cgg                                              23
```

```
<210> SEQ ID NO 84
<211> LENGTH: 23
<212> TYPE: DNA
<213> ORGANISM: Homo sapiens

<400> SEQUENCE: 84
caggagaatg gcgtgaaccc ggg                                          23

<210> SEQ ID NO 85
<211> LENGTH: 23
<212> TYPE: DNA
<213> ORGANISM: Homo sapiens

<400> SEQUENCE: 85
aaagaaaaat tagccggctg tgg                                          23

<210> SEQ ID NO 86
<211> LENGTH: 23
<212> TYPE: DNA
<213> ORGANISM: Homo sapiens

<400> SEQUENCE: 86
aaaaattagc ccctctaggc cgg                                          23

<210> SEQ ID NO 87
<211> LENGTH: 23
<212> TYPE: DNA
<213> ORGANISM: Homo sapiens

<400> SEQUENCE: 87
ctcctgctgc gacccaccta agg                                          23

<210> SEQ ID NO 88
<211> LENGTH: 23
<212> TYPE: DNA
<213> ORGANISM: Homo sapiens

<400> SEQUENCE: 88
tcaggagatc tagaccatcc tgg                                          23

<210> SEQ ID NO 89
<211> LENGTH: 23
<212> TYPE: DNA
<213> ORGANISM: Homo sapiens

<400> SEQUENCE: 89
caaggcgggt ggatcacctg agg                                          23

<210> SEQ ID NO 90
<211> LENGTH: 23
<212> TYPE: DNA
<213> ORGANISM: Homo sapiens

<400> SEQUENCE: 90
cctcgctgtg ccatgttggc agg                                          23

<210> SEQ ID NO 91
<211> LENGTH: 23
<212> TYPE: DNA
<213> ORGANISM: Homo sapiens

<400> SEQUENCE: 91
```
gtcatagccc tatggcactg tgg                                                         23

<210> SEQ ID NO 92
<211> LENGTH: 23
<212> TYPE: DNA
<213> ORGANISM: Homo sapiens

<400> SEQUENCE: 92
aattagccgg gcgtggtggt ggg                                                         23

<210> SEQ ID NO 93
<211> LENGTH: 23
<212> TYPE: DNA
<213> ORGANISM: Homo sapiens

<400> SEQUENCE: 93
agacgggggt ttctccatgt tgg                                                         23

<210> SEQ ID NO 94
<211> LENGTH: 23
<212> TYPE: DNA
<213> ORGANISM: Homo sapiens

<400> SEQUENCE: 94
caggcgcgcg cctccacagc cgg                                                         23

<210> SEQ ID NO 95
<211> LENGTH: 23
<212> TYPE: DNA
<213> ORGANISM: Homo sapiens

<400> SEQUENCE: 95
atgggttagg agctttctgc ggg                                                         23

<210> SEQ ID NO 96
<211> LENGTH: 23
<212> TYPE: DNA
<213> ORGANISM: Homo sapiens

<400> SEQUENCE: 96
tcgatcaatt aatcacagca agg                                                         23

<210> SEQ ID NO 97
<211> LENGTH: 23
<212> TYPE: DNA
<213> ORGANISM: Homo sapiens

<400> SEQUENCE: 97
gaacaaagat ggagccgtgg agg                                                         23

<210> SEQ ID NO 98
<211> LENGTH: 23
<212> TYPE: DNA
<213> ORGANISM: Homo sapiens

<400> SEQUENCE: 98
ttaagtgatc tgagctataa tgg                                                         23

<210> SEQ ID NO 99
<211> LENGTH: 23
<212> TYPE: DNA
<213> ORGANISM: Homo sapiens

<400> SEQUENCE: 99

```
cccttgctgt gattgattga tgg                                              23

<210> SEQ ID NO 100
<211> LENGTH: 23
<212> TYPE: DNA
<213> ORGANISM: Homo sapiens

<400> SEQUENCE: 100
cttaggtggg tcgcagcagg agg                                              23

<210> SEQ ID NO 101
<211> LENGTH: 23
<212> TYPE: DNA
<213> ORGANISM: Homo sapiens

<400> SEQUENCE: 101
acagtatcac accaagagcc tgg                                              23

<210> SEQ ID NO 102
<211> LENGTH: 23
<212> TYPE: DNA
<213> ORGANISM: Homo sapiens

<400> SEQUENCE: 102
agaccctcgc tgtgccatgt tgg                                              23

<210> SEQ ID NO 103
<211> LENGTH: 23
<212> TYPE: DNA
<213> ORGANISM: Homo sapiens

<400> SEQUENCE: 103
cctgccaaca tggcacagcg agg                                              23

<210> SEQ ID NO 104
<211> LENGTH: 23
<212> TYPE: DNA
<213> ORGANISM: Homo sapiens

<400> SEQUENCE: 104
gatcacttaa gaaactgacc tgg                                              23

<210> SEQ ID NO 105
<211> LENGTH: 23
<212> TYPE: DNA
<213> ORGANISM: Homo sapiens

<400> SEQUENCE: 105
cttaagaaac tgacctggtc tgg                                              23

<210> SEQ ID NO 106
<211> LENGTH: 23
<212> TYPE: DNA
<213> ORGANISM: Homo sapiens

<400> SEQUENCE: 106
ccgactgaaa gaccaagacc agg                                              23

<210> SEQ ID NO 107
<211> LENGTH: 23
<212> TYPE: DNA
<213> ORGANISM: Homo sapiens
```

```
<400> SEQUENCE: 107
tctagaaaca aatactagtc agg                                        23

<210> SEQ ID NO 108
<211> LENGTH: 23
<212> TYPE: DNA
<213> ORGANISM: Homo sapiens

<400> SEQUENCE: 108
attagcacct gttaagtgcc agg                                        23

<210> SEQ ID NO 109
<211> LENGTH: 23
<212> TYPE: DNA
<213> ORGANISM: Homo sapiens

<400> SEQUENCE: 109
ggcactgtgg aaaaattagc agg                                        23

<210> SEQ ID NO 110
<211> LENGTH: 23
<212> TYPE: DNA
<213> ORGANISM: Homo sapiens

<400> SEQUENCE: 110
aaactgacct ggtctgggcc agg                                        23

<210> SEQ ID NO 111
<211> LENGTH: 23
<212> TYPE: DNA
<213> ORGANISM: Homo sapiens

<400> SEQUENCE: 111
gccttagcct ccccagtagc tgg                                        23

<210> SEQ ID NO 112
<211> LENGTH: 23
<212> TYPE: DNA
<213> ORGANISM: Homo sapiens

<400> SEQUENCE: 112
tccatcaatc aatcacagca agg                                        23

<210> SEQ ID NO 113
<211> LENGTH: 23
<212> TYPE: DNA
<213> ORGANISM: Homo sapiens

<400> SEQUENCE: 113
cgatcaatta atcacagcaa ggg                                        23

<210> SEQ ID NO 114
<211> LENGTH: 23
<212> TYPE: DNA
<213> ORGANISM: Homo sapiens

<400> SEQUENCE: 114
cctggtcttg gtctttcagt cgg                                        23

<210> SEQ ID NO 115
<211> LENGTH: 23
<212> TYPE: DNA
<213> ORGANISM: Homo sapiens
```

```
<400> SEQUENCE: 115
ctgctgcttg agagcagtaa cgg                                        23

<210> SEQ ID NO 116
<211> LENGTH: 23
<212> TYPE: DNA
<213> ORGANISM: Homo sapiens

<400> SEQUENCE: 116
tttcaatcac agcaagggcc tgg                                        23

<210> SEQ ID NO 117
<211> LENGTH: 23
<212> TYPE: DNA
<213> ORGANISM: Homo sapiens

<400> SEQUENCE: 117
caggctgctc ttgaactctt ggg                                        23

<210> SEQ ID NO 118
<211> LENGTH: 23
<212> TYPE: DNA
<213> ORGANISM: Homo sapiens

<400> SEQUENCE: 118
agatggagcc gtggaggtaa agg                                        23

<210> SEQ ID NO 119
<211> LENGTH: 23
<212> TYPE: DNA
<213> ORGANISM: Homo sapiens

<400> SEQUENCE: 119
gctactgggg aggctaaggc agg                                        23

<210> SEQ ID NO 120
<211> LENGTH: 23
<212> TYPE: DNA
<213> ORGANISM: Homo sapiens

<400> SEQUENCE: 120
aaattagccg ggcgtggtgg tgg                                        23

<210> SEQ ID NO 121
<211> LENGTH: 23
<212> TYPE: DNA
<213> ORGANISM: Homo sapiens

<400> SEQUENCE: 121
gcctcagcct cctgaatagc tgg                                        23

<210> SEQ ID NO 122
<211> LENGTH: 23
<212> TYPE: DNA
<213> ORGANISM: Homo sapiens

<400> SEQUENCE: 122
aatcaatcac agcaagggcc tgg                                        23

<210> SEQ ID NO 123
<211> LENGTH: 23
<212> TYPE: DNA
```

<213> ORGANISM: Homo sapiens

<400> SEQUENCE: 123
gatgggttag gagctttctg cgg                                          23

<210> SEQ ID NO 124
<211> LENGTH: 23
<212> TYPE: DNA
<213> ORGANISM: Homo sapiens

<400> SEQUENCE: 124 ttcttttta ggagagacgg ggg                                           23

<210> SEQ ID NO 125
<211> LENGTH: 23
<212> TYPE: DNA
<213> ORGANISM: Homo sapiens

<400> SEQUENCE: 125
gcactgtgga aaaattagca ggg                                          23

<210> SEQ ID NO 126
<211> LENGTH: 23
<212> TYPE: DNA
<213> ORGANISM: Homo sapiens

<400> SEQUENCE: 126
agaaacaaat actagtcagg agg                                          23

<210> SEQ ID NO 127
<211> LENGTH: 23
<212> TYPE: DNA
<213> ORGANISM: Homo sapiens

<400> SEQUENCE: 127
cgtagtccca gctactgggg agg                                          23

<210> SEQ ID NO 128
<211> LENGTH: 23
<212> TYPE: DNA
<213> ORGANISM: Homo sapiens

<400> SEQUENCE: 128
aacaaatact agtcaggagg tgg                                          23

<210> SEQ ID NO 129
<211> LENGTH: 23
<212> TYPE: DNA
<213> ORGANISM: Homo sapiens

<400> SEQUENCE: 129
ttaagaaact gacctggtct ggg                                          23

<210> SEQ ID NO 130
<211> LENGTH: 23
<212> TYPE: DNA
<213> ORGANISM: Homo sapiens

<400> SEQUENCE: 130
ccttagcctc cccagtagct ggg                                          23

<210> SEQ ID NO 131
<211> LENGTH: 23

<212> TYPE: DNA
<213> ORGANISM: Homo sapiens

<400> SEQUENCE: 131
agataaaaat tagcccctct agg                                              23

<210> SEQ ID NO 132
<211> LENGTH: 23
<212> TYPE: DNA
<213> ORGANISM: Homo sapiens

<400> SEQUENCE: 132
ccatcaatca atcacagcaa ggg                                              23

<210> SEQ ID NO 133
<211> LENGTH: 23
<212> TYPE: DNA
<213> ORGANISM: Homo sapiens

<400> SEQUENCE: 133
gaggtaaagg aagtggtgtc agg                                              23

<210> SEQ ID NO 134
<211> LENGTH: 23
<212> TYPE: DNA
<213> ORGANISM: Homo sapiens

<400> SEQUENCE: 134
cactgcaagc tccgcctccc ggg                                              23

<210> SEQ ID NO 135
<211> LENGTH: 23
<212> TYPE: DNA
<213> ORGANISM: Homo sapiens

<400> SEQUENCE: 135
taattgatcg attgatagat tgg                                              23

<210> SEQ ID NO 136
<211> LENGTH: 23
<212> TYPE: DNA
<213> ORGANISM: Homo sapiens

<400> SEQUENCE: 136
aaatacaaca caaattagcc ggg                                              23

<210> SEQ ID NO 137
<211> LENGTH: 23
<212> TYPE: DNA
<213> ORGANISM: Homo sapiens

<400> SEQUENCE: 137
tccctctgtg cctgccaaca tgg                                              23

<210> SEQ ID NO 138
<211> LENGTH: 23
<212> TYPE: DNA
<213> ORGANISM: Homo sapiens

<400> SEQUENCE: 138
gttaaataaa tgaacaccac agg                                              23

<210> SEQ ID NO 139

-continued

```
<211> LENGTH: 23
<212> TYPE: DNA
<213> ORGANISM: Homo sapiens

<400> SEQUENCE: 139
gttagtcatt caccttctcc cgg                                              23

<210> SEQ ID NO 140
<211> LENGTH: 23
<212> TYPE: DNA
<213> ORGANISM: Homo sapiens

<400> SEQUENCE: 140
caccgcgcct ggcccagacc agg                                              23

<210> SEQ ID NO 141
<211> LENGTH: 23
<212> TYPE: DNA
<213> ORGANISM: Homo sapiens

<400> SEQUENCE: 141
gttagtcatt caccttctcc cgg                                              23

<210> SEQ ID NO 142
<211> LENGTH: 23
<212> TYPE: DNA
<213> ORGANISM: Homo sapiens

<400> SEQUENCE: 142
aaaagaaact gacctggtct tgg                                              23

<210> SEQ ID NO 143
<211> LENGTH: 23
<212> TYPE: DNA
<213> ORGANISM: Homo sapiens

<400> SEQUENCE: 143
gcaagagtct ggcacataat agg                                              23

<210> SEQ ID NO 144
<211> LENGTH: 23
<212> TYPE: DNA
<213> ORGANISM: Homo sapiens

<400> SEQUENCE: 144
aagaaactga gcccgggaga agg                                              23

<210> SEQ ID NO 145
<211> LENGTH: 23
<212> TYPE: DNA
<213> ORGANISM: Homo sapiens

<400> SEQUENCE: 145
caagcgcaag cctgactttg cgg                                              23

<210> SEQ ID NO 146
<211> LENGTH: 23
<212> TYPE: DNA
<213> ORGANISM: Homo sapiens

<400> SEQUENCE: 146
ctggtctggg ccaggcgcgg tgg                                              23
```

```
<210> SEQ ID NO 147
<211> LENGTH: 23
<212> TYPE: DNA
<213> ORGANISM: Homo sapiens

<400> SEQUENCE: 147
aatcaatgac agcaagagtc tgg                                              23

<210> SEQ ID NO 148
<211> LENGTH: 23
<212> TYPE: DNA
<213> ORGANISM: Homo sapiens

<400> SEQUENCE: 148
ccaggctgct cttgaactct tgg                                              23

<210> SEQ ID NO 149
<211> LENGTH: 23
<212> TYPE: DNA
<213> ORGANISM: Homo sapiens

<400> SEQUENCE: 149
ttagtcattc accttctccc ggg                                              23

<210> SEQ ID NO 150
<211> LENGTH: 23
<212> TYPE: DNA
<213> ORGANISM: Homo sapiens

<400> SEQUENCE: 150
tcactgcaag ctccgcctcc cgg                                              23

<210> SEQ ID NO 151
<211> LENGTH: 23
<212> TYPE: DNA
<213> ORGANISM: Homo sapiens

<400> SEQUENCE: 151
aaatactagt caggaggtgg agg                                              23

<210> SEQ ID NO 152
<211> LENGTH: 23
<212> TYPE: DNA
<213> ORGANISM: Homo sapiens

<400> SEQUENCE: 152
ctatctttca atcacagcaa ggg                                              23

<210> SEQ ID NO 153
<211> LENGTH: 23
<212> TYPE: DNA
<213> ORGANISM: Homo sapiens

<400> SEQUENCE: 153
caagagttca agagcagcct ggg                                              23

<210> SEQ ID NO 154
<211> LENGTH: 23
<212> TYPE: DNA
<213> ORGANISM: Homo sapiens

<400> SEQUENCE: 154
gccatgttgg caggcacaga ggg                                              23
```

```
<210> SEQ ID NO 155
<211> LENGTH: 23
<212> TYPE: DNA
<213> ORGANISM: Homo sapiens

<400> SEQUENCE: 155
tgccatgttg gcaggcacag agg                                              23

<210> SEQ ID NO 156
<211> LENGTH: 23
<212> TYPE: DNA
<213> ORGANISM: Homo sapiens

<400> SEQUENCE: 156
acagacgaag aaactgagcc cgg                                              23

<210> SEQ ID NO 157
<211> LENGTH: 23
<212> TYPE: DNA
<213> ORGANISM: Homo sapiens

<400> SEQUENCE: 157
tctatctttc aatcacagca agg                                              23

<210> SEQ ID NO 158
<211> LENGTH: 23
<212> TYPE: DNA
<213> ORGANISM: Homo sapiens

<400> SEQUENCE: 158
ccaagagttc aagagcagcc tgg                                              23

<210> SEQ ID NO 159
<211> LENGTH: 23
<212> TYPE: DNA
<213> ORGANISM: Homo sapiens

<400> SEQUENCE: 159
cccagctact ggggaggcta agg                                              23

<210> SEQ ID NO 160
<211> LENGTH: 23
<212> TYPE: DNA
<213> ORGANISM: Homo sapiens

<400> SEQUENCE: 160
tttctttttt aggagagacg ggg                                              23

<210> SEQ ID NO 161
<211> LENGTH: 23
<212> TYPE: DNA
<213> ORGANISM: Homo sapiens

<400> SEQUENCE: 161
actgtggaaa aattagcagg ggg                                              23

<210> SEQ ID NO 162
<211> LENGTH: 23
<212> TYPE: DNA
<213> ORGANISM: Homo sapiens

<400> SEQUENCE: 162
tgtaatccca gctattcagg agg                                              23
```

<210> SEQ ID NO 163
<211> LENGTH: 23
<212> TYPE: DNA
<213> ORGANISM: Homo sapiens

<400> SEQUENCE: 163
caccacttcc tttacctcca cgg					23

<210> SEQ ID NO 164
<211> LENGTH: 23
<212> TYPE: DNA
<213> ORGANISM: Homo sapiens

<400> SEQUENCE: 164
cgcccgtagt cccagctact ggg					23

<210> SEQ ID NO 165
<211> LENGTH: 23
<212> TYPE: DNA
<213> ORGANISM: Homo sapiens

<400> SEQUENCE: 165
cactgtggaa aaattagcag ggg					23

<210> SEQ ID NO 166
<211> LENGTH: 23
<212> TYPE: DNA
<213> ORGANISM: Homo sapiens

<400> SEQUENCE: 166
ccaagagcct ggcacataat agg					23

<210> SEQ ID NO 167
<211> LENGTH: 23
<212> TYPE: DNA
<213> ORGANISM: Homo sapiens

<400> SEQUENCE: 167
gccgaggcgg gcggatcacg agg					23

<210> SEQ ID NO 168
<211> LENGTH: 23
<212> TYPE: DNA
<213> ORGANISM: Homo sapiens

<400> SEQUENCE: 168
caggcgtgaa caaccgcgcc cgg					23

<210> SEQ ID NO 169
<211> LENGTH: 23
<212> TYPE: DNA
<213> ORGANISM: Homo sapiens

<400> SEQUENCE: 169
attaacacca attatgtgcc agg					23

<210> SEQ ID NO 170
<211> LENGTH: 23
<212> TYPE: DNA
<213> ORGANISM: Homo sapiens

<400> SEQUENCE: 170
gcaagggcct ggcacataat tgg                                       23

<210> SEQ ID NO 171
<211> LENGTH: 23
<212> TYPE: DNA
<213> ORGANISM: Homo sapiens

<400> SEQUENCE: 171
cctcagcctc ctgaatagct ggg                                       23

<210> SEQ ID NO 172
<211> LENGTH: 23
<212> TYPE: DNA
<213> ORGANISM: Homo sapiens

<400> SEQUENCE: 172
atggtctcac tctatcaccc agg                                       23

<210> SEQ ID NO 173
<211> LENGTH: 23
<212> TYPE: DNA
<213> ORGANISM: Homo sapiens

<400> SEQUENCE: 173
agccgtggag gtaaaggaag tgg                                       23

<210> SEQ ID NO 174
<211> LENGTH: 23
<212> TYPE: DNA
<213> ORGANISM: Homo sapiens

<400> SEQUENCE: 174
gcctgtaatc ccagctattc agg                                       23

<210> SEQ ID NO 175
<211> LENGTH: 23
<212> TYPE: DNA
<213> ORGANISM: Homo sapiens

<400> SEQUENCE: 175
gcaagggcct ggcacttaac agg                                       23

<210> SEQ ID NO 176
<211> LENGTH: 23
<212> TYPE: DNA
<213> ORGANISM: Homo sapiens

<400> SEQUENCE: 176
gcaggagaat cgcttgaact cgg                                       23

<210> SEQ ID NO 177
<211> LENGTH: 23
<212> TYPE: DNA
<213> ORGANISM: Homo sapiens

<400> SEQUENCE: 177
gacctggtct gggccaggcg cgg                                       23

<210> SEQ ID NO 178
<211> LENGTH: 23
<212> TYPE: DNA
<213> ORGANISM: Homo sapiens

<400> SEQUENCE: 178
ctagaccatc ctggctaaca tgg                                          23

<210> SEQ ID NO 179
<211> LENGTH: 23
<212> TYPE: DNA
<213> ORGANISM: Homo sapiens

<400> SEQUENCE: 179
gtgattgaaa gatagataga tgg                                          23

<210> SEQ ID NO 180
<211> LENGTH: 23
<212> TYPE: DNA
<213> ORGANISM: Homo sapiens

<400> SEQUENCE: 180
cagacgaaga aactgagccc ggg                                          23

<210> SEQ ID NO 181
<211> LENGTH: 23
<212> TYPE: DNA
<213> ORGANISM: Homo sapiens

<400> SEQUENCE: 181
aaaatacaac acaaattagc cgg                                          23

<210> SEQ ID NO 182
<211> LENGTH: 23
<212> TYPE: DNA
<213> ORGANISM: Homo sapiens

<400> SEQUENCE: 182
gcgggtggat cacctgaggt cgg                                          23

<210> SEQ ID NO 183
<211> LENGTH: 23
<212> TYPE: DNA
<213> ORGANISM: Homo sapiens

<400> SEQUENCE: 183
cctattatgt gccaggctct tgg                                          23

<210> SEQ ID NO 184
<211> LENGTH: 23
<212> TYPE: DNA
<213> ORGANISM: Homo sapiens

<400> SEQUENCE: 184
tcctgaatag ctgggattac agg                                          23

<210> SEQ ID NO 185
<211> LENGTH: 23
<212> TYPE: DNA
<213> ORGANISM: Homo sapiens

<400> SEQUENCE: 185
gcccgtagtc ccagctactg ggg                                          23

<210> SEQ ID NO 186
<211> LENGTH: 23
<212> TYPE: DNA
<213> ORGANISM: Homo sapiens

```
<400> SEQUENCE: 186
ctcaggtgat ccacccgcct tgg                                          23

<210> SEQ ID NO 187
<211> LENGTH: 23
<212> TYPE: DNA
<213> ORGANISM: Homo sapiens

<400> SEQUENCE: 187
aattaatcac agcaagggcc tgg                                          23

<210> SEQ ID NO 188
<211> LENGTH: 23
<212> TYPE: DNA
<213> ORGANISM: Homo sapiens

<400> SEQUENCE: 188
ttttcttttt taggagagac ggg                                          23

<210> SEQ ID NO 189
<211> LENGTH: 23
<212> TYPE: DNA
<213> ORGANISM: Homo sapiens

<400> SEQUENCE: 189 taattttttcc acagtgccat agg                                         23

<210> SEQ ID NO 190
<211> LENGTH: 23
<212> TYPE: DNA
<213> ORGANISM: Homo sapiens

<400> SEQUENCE: 190
ttgtattttt aagtagagac agg                                          23

<210> SEQ ID NO 191
<211> LENGTH: 23
<212> TYPE: DNA
<213> ORGANISM: Homo sapiens

<400> SEQUENCE: 191 aattttttcca cagtgccata ggg                                         23

<210> SEQ ID NO 192
<211> LENGTH: 23
<212> TYPE: DNA
<213> ORGANISM: Homo sapiens

<400> SEQUENCE: 192
cgggtggatc acctgaggtc ggg                                          23

<210> SEQ ID NO 193
<211> LENGTH: 23
<212> TYPE: DNA
<213> ORGANISM: Homo sapiens

<400> SEQUENCE: 193
actagtcagg aggtggaggc agg                                          23

<210> SEQ ID NO 194
<211> LENGTH: 23
<212> TYPE: DNA
<213> ORGANISM: Homo sapiens
```

```
-continued

<400> SEQUENCE: 194
ttcatacata aactataaaa tgg                                          23

<210> SEQ ID NO 195
<211> LENGTH: 23
<212> TYPE: DNA
<213> ORGANISM: Homo sapiens

<400> SEQUENCE: 195
gggaggctaa ggcaggagaa tgg                                          23

<210> SEQ ID NO 196
<211> LENGTH: 23
<212> TYPE: DNA
<213> ORGANISM: Homo sapiens

<400> SEQUENCE: 196
tgagtctagc tctgtcgccc agg                                          23

<210> SEQ ID NO 197
<211> LENGTH: 23
<212> TYPE: DNA
<213> ORGANISM: Homo sapiens

<400> SEQUENCE: 197
ctttgggagg ccgaggcggg cgg                                          23

<210> SEQ ID NO 198
<211> LENGTH: 23
<212> TYPE: DNA
<213> ORGANISM: Homo sapiens

<400> SEQUENCE: 198
caaaaaaaaa gaaactgacc tgg                                          23

<210> SEQ ID NO 199
<211> LENGTH: 23
<212> TYPE: DNA
<213> ORGANISM: Homo sapiens

<400> SEQUENCE: 199
cgggcgccca ccaccacgcc cgg                                          23

<210> SEQ ID NO 200
<211> LENGTH: 23
<212> TYPE: DNA
<213> ORGANISM: Homo sapiens

<400> SEQUENCE: 200
ccggctaatt tttcttttt agg                                           23

<210> SEQ ID NO 201
<211> LENGTH: 23
<212> TYPE: DNA
<213> ORGANISM: Homo sapiens

<400> SEQUENCE: 201
tcatacataa actataaaat ggg                                          23

<210> SEQ ID NO 202
<211> LENGTH: 23
<212> TYPE: DNA
```

<213> ORGANISM: Homo sapiens

<400> SEQUENCE: 202
ttgaaagata gatagatgga tgg                                                23

<210> SEQ ID NO 203
<211> LENGTH: 23
<212> TYPE: DNA
<213> ORGANISM: Homo sapiens

<400> SEQUENCE: 203
cccagctatt caggaggctg agg                                                23

<210> SEQ ID NO 204
<211> LENGTH: 23
<212> TYPE: DNA
<213> ORGANISM: Homo sapiens

<400> SEQUENCE: 204
tgtattttta agtagagaca ggg                                                23

<210> SEQ ID NO 205
<211> LENGTH: 23
<212> TYPE: DNA
<213> ORGANISM: Homo sapiens

<400> SEQUENCE: 205
cctaaaaaag aaaaattagc cgg                                                23

<210> SEQ ID NO 206
<211> LENGTH: 23
<212> TYPE: DNA
<213> ORGANISM: Homo sapiens

<400> SEQUENCE: 206
catacataaa ctataaaatg ggg                                                23

<210> SEQ ID NO 207
<211> LENGTH: 23
<212> TYPE: DNA
<213> ORGANISM: Homo sapiens

<400> SEQUENCE: 207
atttgcacct attatgtgcc agg                                                23

<210> SEQ ID NO 208
<211> LENGTH: 23
<212> TYPE: DNA
<213> ORGANISM: Homo sapiens

<400> SEQUENCE: 208
agtttcttcg tctgtaaaat ggg                                                23

<210> SEQ ID NO 209
<211> LENGTH: 23
<212> TYPE: DNA
<213> ORGANISM: Homo sapiens

<400> SEQUENCE: 209
cgcgccattg cactccagcc tgg                                                23

<210> SEQ ID NO 210
<211> LENGTH: 23

```
<212> TYPE: DNA
<213> ORGANISM: Homo sapiens

<400> SEQUENCE: 210
gcgccattgc actccagcct ggg                                              23

<210> SEQ ID NO 211
<211> LENGTH: 23
<212> TYPE: DNA
<213> ORGANISM: Homo sapiens

<400> SEQUENCE: 211
ctttgggagg ccaaggcggg tgg                                              23

<210> SEQ ID NO 212
<211> LENGTH: 23
<212> TYPE: DNA
<213> ORGANISM: Homo sapiens

<400> SEQUENCE: 212
gctattcagg aggctgaggc agg                                              23

<210> SEQ ID NO 213
<211> LENGTH: 23
<212> TYPE: DNA
<213> ORGANISM: Homo sapiens

<400> SEQUENCE: 213
tttttctttt ttaggagaga cgg                                              23

<210> SEQ ID NO 214
<211> LENGTH: 23
<212> TYPE: DNA
<213> ORGANISM: Homo sapiens

<400> SEQUENCE: 214
aagatagata gatggatgga tgg                                              23

<210> SEQ ID NO 215
<211> LENGTH: 23
<212> TYPE: DNA
<213> ORGANISM: Homo sapiens

<400> SEQUENCE: 215
tatttattta tttttagac agg                                               23

<210> SEQ ID NO 216
<211> LENGTH: 23
<212> TYPE: DNA
<213> ORGANISM: Homo sapiens

<400> SEQUENCE: 216
agggtttcac catgttagcc agg                                              23

<210> SEQ ID NO 217
<211> LENGTH: 23
<212> TYPE: DNA
<213> ORGANISM: Homo sapiens

<400> SEQUENCE: 217
ctccccagta gctgggacta cgg                                              23

<210> SEQ ID NO 218
```

```
<211> LENGTH: 23
<212> TYPE: DNA
<213> ORGANISM: Homo sapiens

<400> SEQUENCE: 218
gcactttggg aggccgaggc ggg                                              23

<210> SEQ ID NO 219
<211> LENGTH: 23
<212> TYPE: DNA
<213> ORGANISM: Homo sapiens

<400> SEQUENCE: 219
ggagtgcagt ggtgtgatct cgg                                              23

<210> SEQ ID NO 220
<211> LENGTH: 23
<212> TYPE: DNA
<213> ORGANISM: Homo sapiens

<400> SEQUENCE: 220
cagtttcttc gtctgtaaaa tgg                                              23

<210> SEQ ID NO 221
<211> LENGTH: 23
<212> TYPE: DNA
<213> ORGANISM: Homo sapiens

<400> SEQUENCE: 221
tccccagtag ctgggactac ggg                                              23

<210> SEQ ID NO 222
<211> LENGTH: 23
<212> TYPE: DNA
<213> ORGANISM: Homo sapiens

<400> SEQUENCE: 222
tttcaccatg ttagccagga tgg                                              23

<210> SEQ ID NO 223
<211> LENGTH: 23
<212> TYPE: DNA
<213> ORGANISM: Homo sapiens

<400> SEQUENCE: 223
ggggtttctc catgttggtc agg                                              23

<210> SEQ ID NO 224
<211> LENGTH: 23
<212> TYPE: DNA
<213> ORGANISM: Homo sapiens

<400> SEQUENCE: 224
agtcaggagg tggaggcagg agg                                              23

<210> SEQ ID NO 225
<211> LENGTH: 23
<212> TYPE: DNA
<213> ORGANISM: Homo sapiens

<400> SEQUENCE: 225
agcactttgg gaggccgagg cgg                                              23
```

```
<210> SEQ ID NO 226
<211> LENGTH: 23
<212> TYPE: DNA
<213> ORGANISM: Homo sapiens

<400> SEQUENCE: 226
tctagctctg tcgcccaggc tgg                                              23

<210> SEQ ID NO 227
<211> LENGTH: 23
<212> TYPE: DNA
<213> ORGANISM: Homo sapiens

<400> SEQUENCE: 227
agggtctcgc tctgttgccc agg                                              23

<210> SEQ ID NO 228
<211> LENGTH: 23
<212> TYPE: DNA
<213> ORGANISM: Homo sapiens

<400> SEQUENCE: 228
atttatttat tttttagaca ggg                                              23

<210> SEQ ID NO 229
<211> LENGTH: 23
<212> TYPE: DNA
<213> ORGANISM: Homo sapiens

<400> SEQUENCE: 229
tgtgccactg cactccagcc tgg                                              23

<210> SEQ ID NO 230
<211> LENGTH: 23
<212> TYPE: DNA
<213> ORGANISM: Homo sapiens

<400> SEQUENCE: 230
ggagtctcgc tctgtcgccc agg                                              23

<210> SEQ ID NO 231
<211> LENGTH: 23
<212> TYPE: DNA
<213> ORGANISM: Homo sapiens

<400> SEQUENCE: 231
cacaccactg cactccagcc tgg                                              23

<210> SEQ ID NO 232
<211> LENGTH: 23
<212> TYPE: DNA
<213> ORGANISM: Homo sapiens

<400> SEQUENCE: 232
tttctccatg ttggtcaggc tgg                                              23

<210> SEQ ID NO 233
<211> LENGTH: 23
<212> TYPE: DNA
<213> ORGANISM: Homo sapiens

<400> SEQUENCE: 233
tctcactcta tcacccaggc tgg                                              23
```

```
<210> SEQ ID NO 234
<211> LENGTH: 23
<212> TYPE: DNA
<213> ORGANISM: Homo sapiens

<400> SEQUENCE: 234
cccagcactt tgggaggccg agg                                          23

<210> SEQ ID NO 235
<211> LENGTH: 23
<212> TYPE: DNA
<213> ORGANISM: Homo sapiens

<400> SEQUENCE: 235
cagtttcttt tttttttgaga cgg                                         23

<210> SEQ ID NO 236
<211> LENGTH: 23
<212> TYPE: DNA
<213> ORGANISM: Homo sapiens

<400> SEQUENCE: 236
cgagaccagc ctgaccaaca tgg                                          23

<210> SEQ ID NO 237
<211> LENGTH: 23
<212> TYPE: DNA
<213> ORGANISM: Homo sapiens

<400> SEQUENCE: 237
tcgcccaggc tggagtgcaa tgg                                          23

<210> SEQ ID NO 238
<211> LENGTH: 23
<212> TYPE: DNA
<213> ORGANISM: Homo sapiens

<400> SEQUENCE: 238
gcctcggcct cccaaagtgc tgg                                          23

<210> SEQ ID NO 239
<211> LENGTH: 23
<212> TYPE: DNA
<213> ORGANISM: Homo sapiens

<400> SEQUENCE: 239
tctcgctctg tcgcccaggc tgg                                          23

<210> SEQ ID NO 240
<211> LENGTH: 23
<212> TYPE: DNA
<213> ORGANISM: Homo sapiens

<400> SEQUENCE: 240
acaccactgc actccagcct ggg                                          23

<210> SEQ ID NO 241
<211> LENGTH: 23
<212> TYPE: DNA
<213> ORGANISM: Homo sapiens

<400> SEQUENCE: 241
gtgccactgc actccagcct ggg                                          23
```

<210> SEQ ID NO 242
<211> LENGTH: 23
<212> TYPE: DNA
<213> ORGANISM: Homo sapiens

<400> SEQUENCE: 242
cctcggcctc ccaaagtgct ggg                                           23

<210> SEQ ID NO 243
<211> LENGTH: 23
<212> TYPE: DNA
<213> ORGANISM: Homo sapiens

<400> SEQUENCE: 243
gcactttggg aggccaaggc ggg                                           23

<210> SEQ ID NO 244
<211> LENGTH: 23
<212> TYPE: DNA
<213> ORGANISM: Homo sapiens

<400> SEQUENCE: 244
cccagcactt tgggaggcca agg                                           23

<210> SEQ ID NO 245
<211> LENGTH: 23
<212> TYPE: DNA
<213> ORGANISM: Homo sapiens

<400> SEQUENCE: 245
tcgcccaggc tggagtgcag tgg                                           23

<210> SEQ ID NO 246
<211> LENGTH: 23
<212> TYPE: DNA
<213> ORGANISM: Homo sapiens

<400> SEQUENCE: 246
agcactttgg gaggccaagg cgg                                           23

<210> SEQ ID NO 247
<211> LENGTH: 23
<212> TYPE: DNA
<213> ORGANISM: Homo sapiens

<400> SEQUENCE: 247
gccttggcct cccaaagtgc tgg                                           23

<210> SEQ ID NO 248
<211> LENGTH: 23
<212> TYPE: DNA
<213> ORGANISM: Homo sapiens

<400> SEQUENCE: 248
attagcacct attatgtgcc agg                                           23

<210> SEQ ID NO 249
<211> LENGTH: 23
<212> TYPE: DNA
<213> ORGANISM: Homo sapiens

<400> SEQUENCE: 249

-continued cgcctgtaat cccagcactt tgg                                          23

<210> SEQ ID NO 250
<211> LENGTH: 23
<212> TYPE: DNA
<213> ORGANISM: Homo sapiens

<400> SEQUENCE: 250
ccttggcctc ccaaagtgct ggg                                          23

<210> SEQ ID NO 251
<211> LENGTH: 23
<212> TYPE: DNA
<213> ORGANISM: Homo sapiens

<400> SEQUENCE: 251
cgcctgtaat cccagcactt tgg                                          23

<210> SEQ ID NO 252
<211> LENGTH: 23
<212> TYPE: DNA
<213> ORGANISM: Homo sapiens

<400> SEQUENCE: 252
tcacccaggc tggagtgcag tgg                                          23

<210> SEQ ID NO 253
<211> LENGTH: 23
<212> TYPE: DNA
<213> ORGANISM: Homo sapiens

<400> SEQUENCE: 253
tgtaatccca gcactttggg agg                                          23

<210> SEQ ID NO 254
<211> LENGTH: 23
<212> TYPE: DNA
<213> ORGANISM: Homo sapiens

<400> SEQUENCE: 254
gcctgtaatc ccagcacttt ggg                                          23

<210> SEQ ID NO 255
<211> LENGTH: 23
<212> TYPE: DNA
<213> ORGANISM: Homo sapiens

<400> SEQUENCE: 255
tgtaatccca gcactttggg agg                                          23

<210> SEQ ID NO 256
<211> LENGTH: 23
<212> TYPE: DNA
<213> ORGANISM: Homo sapiens

<400> SEQUENCE: 256
gcctgtaatc ccagcacttt ggg                                          23

<210> SEQ ID NO 257
<211> LENGTH: 23
<212> TYPE: DNA
<213> ORGANISM: Homo sapiens

<400> SEQUENCE: 257
caggcgtgag ccaccgcgcc tgg                                            23

<210> SEQ ID NO 258
<211> LENGTH: 23
<212> TYPE: DNA
<213> ORGANISM: Homo sapiens

<400> SEQUENCE: 258
tcccaaagtg ctgggattac agg                                            23

<210> SEQ ID NO 259
<211> LENGTH: 23
<212> TYPE: DNA
<213> ORGANISM: Homo sapiens

<400> SEQUENCE: 259
atttacggaa gagagtatcg agg                                            23

<210> SEQ ID NO 260
<211> LENGTH: 23
<212> TYPE: DNA
<213> ORGANISM: Homo sapiens

<400> SEQUENCE: 260
tacggaagag agtatcgagg tgg                                            23

<210> SEQ ID NO 261
<211> LENGTH: 23
<212> TYPE: DNA
<213> ORGANISM: Homo sapiens

<400> SEQUENCE: 261
gggcagatac ccgctagagc tgg                                            23

<210> SEQ ID NO 262
<211> LENGTH: 23
<212> TYPE: DNA
<213> ORGANISM: Homo sapiens

<400> SEQUENCE: 262
cggaagagag tatcgaggtg ggg                                            23

<210> SEQ ID NO 263
<211> LENGTH: 23
<212> TYPE: DNA
<213> ORGANISM: Homo sapiens

<400> SEQUENCE: 263
tagcgggtat ctgcccacca tgg                                            23

<210> SEQ ID NO 264
<211> LENGTH: 23
<212> TYPE: DNA
<213> ORGANISM: Homo sapiens

<400> SEQUENCE: 264
acggaagaga gtatcgaggt ggg                                            23

<210> SEQ ID NO 265
<211> LENGTH: 23
<212> TYPE: DNA
<213> ORGANISM: Homo sapiens

<400> SEQUENCE: 265
gatactctct tccgtaaatg agg                                              23

<210> SEQ ID NO 266
<211> LENGTH: 23
<212> TYPE: DNA
<213> ORGANISM: Homo sapiens

<400> SEQUENCE: 266
tcttccgtaa atgaggatct ggg                                              23

<210> SEQ ID NO 267
<211> LENGTH: 23
<212> TYPE: DNA
<213> ORGANISM: Homo sapiens

<400> SEQUENCE: 267
ctcttccgta aatgaggatc tgg                                              23

<210> SEQ ID NO 268
<211> LENGTH: 23
<212> TYPE: DNA
<213> ORGANISM: Homo sapiens

<400> SEQUENCE: 268
cgtaaatgag gatctgggtc tgg                                              23

<210> SEQ ID NO 269
<211> LENGTH: 23
<212> TYPE: DNA
<213> ORGANISM: Homo sapiens

<400> SEQUENCE: 269
gtgactgtgt catagcccta tgg                                              23

<210> SEQ ID NO 270
<211> LENGTH: 23
<212> TYPE: DNA
<213> ORGANISM: Homo sapiens

<400> SEQUENCE: 270
gtatcgaggt gggggcctgt ggg                                              23

<210> SEQ ID NO 271
<211> LENGTH: 23
<212> TYPE: DNA
<213> ORGANISM: Homo sapiens

<400> SEQUENCE: 271
gtcatagccc tatggcactg tgg                                              23

<210> SEQ ID NO 272
<211> LENGTH: 23
<212> TYPE: DNA
<213> ORGANISM: Homo sapiens

<400> SEQUENCE: 272
gctatgacac agtcacccac agg                                              23

<210> SEQ ID NO 273
<211> LENGTH: 23
<212> TYPE: DNA
<213> ORGANISM: Homo sapiens

<400> SEQUENCE: 273
gagagggtgc gaccaagccc tgg				23

<210> SEQ ID NO 274
<211> LENGTH: 23
<212> TYPE: DNA
<213> ORGANISM: Homo sapiens

<400> SEQUENCE: 274
ggcactgtgg aaaaattagc agg				23

<210> SEQ ID NO 275
<211> LENGTH: 23
<212> TYPE: DNA
<213> ORGANISM: Homo sapiens

<400> SEQUENCE: 275
ggaagagagt atcgaggtgg ggg				23

<210> SEQ ID NO 276
<211> LENGTH: 23
<212> TYPE: DNA
<213> ORGANISM: Homo sapiens

<400> SEQUENCE: 276
tacccgctag agctggagcc agg				23

<210> SEQ ID NO 277
<211> LENGTH: 23
<212> TYPE: DNA
<213> ORGANISM: Homo sapiens

<400> SEQUENCE: 277
cagacccaga tcctcattta cgg				23

<210> SEQ ID NO 278
<211> LENGTH: 23
<212> TYPE: DNA
<213> ORGANISM: Homo sapiens

<400> SEQUENCE: 278
agtatcgagg tgggggcctg tgg				23

<210> SEQ ID NO 279
<211> LENGTH: 23
<212> TYPE: DNA
<213> ORGANISM: Homo sapiens

<400> SEQUENCE: 279
gcactgtgga aaaattagca ggg				23

<210> SEQ ID NO 280
<211> LENGTH: 23
<212> TYPE: DNA
<213> ORGANISM: Homo sapiens

<400> SEQUENCE: 280
cagctggagg atcagcacca ggg				23

<210> SEQ ID NO 281
<211> LENGTH: 23
<212> TYPE: DNA

<213> ORGANISM: Homo sapiens

<400> SEQUENCE: 281
gcagctggag gatcagcacc agg                                              23

<210> SEQ ID NO 282
<211> LENGTH: 23
<212> TYPE: DNA
<213> ORGANISM: Homo sapiens

<400> SEQUENCE: 282
actcacagag ggtcagcagc tgg                                              23

<210> SEQ ID NO 283
<211> LENGTH: 23
<212> TYPE: DNA
<213> ORGANISM: Homo sapiens

<400> SEQUENCE: 283
aagaaagggg tgactcacag agg                                              23

<210> SEQ ID NO 284
<211> LENGTH: 23
<212> TYPE: DNA
<213> ORGANISM: Homo sapiens

<400> SEQUENCE: 284
gtatctgccc accatggccc tgg                                              23

<210> SEQ ID NO 285
<211> LENGTH: 23
<212> TYPE: DNA
<213> ORGANISM: Homo sapiens

<400> SEQUENCE: 285
tgttgcctca tttcctggga ggg                                              23

<210> SEQ ID NO 286
<211> LENGTH: 23
<212> TYPE: DNA
<213> ORGANISM: Homo sapiens

<400> SEQUENCE: 286
atgttgcctc atttcctggg agg                                              23

<210> SEQ ID NO 287
<211> LENGTH: 23
<212> TYPE: DNA
<213> ORGANISM: Homo sapiens

<400> SEQUENCE: 287
actgtggaaa aattagcagg ggg                                              23

<210> SEQ ID NO 288
<211> LENGTH: 23
<212> TYPE: DNA
<213> ORGANISM: Homo sapiens

<400> SEQUENCE: 288
ctgatgttgc ctcatttcct ggg                                              23

<210> SEQ ID NO 289
<211> LENGTH: 23

<212> TYPE: DNA
<213> ORGANISM: Homo sapiens

<400> SEQUENCE: 289
agccctggct ccagctctag cgg                                          23

<210> SEQ ID NO 290
<211> LENGTH: 23
<212> TYPE: DNA
<213> ORGANISM: Homo sapiens

<400> SEQUENCE: 290
atcagcacca gggccatggt ggg                                          23

<210> SEQ ID NO 291
<211> LENGTH: 23
<212> TYPE: DNA
<213> ORGANISM: Homo sapiens

<400> SEQUENCE: 291
acccgctaga gctggagcca ggg                                          23

<210> SEQ ID NO 292
<211> LENGTH: 23
<212> TYPE: DNA
<213> ORGANISM: Homo sapiens

<400> SEQUENCE: 292
cactgtggaa aaattagcag ggg                                          23

<210> SEQ ID NO 293
<211> LENGTH: 23
<212> TYPE: DNA
<213> ORGANISM: Homo sapiens

<400> SEQUENCE: 293
tctgatgttg cctcatttcc tgg                                          23

<210> SEQ ID NO 294
<211> LENGTH: 23
<212> TYPE: DNA
<213> ORGANISM: Homo sapiens

<400> SEQUENCE: 294
agaaaggggt gactcacaga ggg                                          23

<210> SEQ ID NO 295
<211> LENGTH: 23
<212> TYPE: DNA
<213> ORGANISM: Homo sapiens

<400> SEQUENCE: 295
gttgcctcat ttcctgggag ggg                                          23

<210> SEQ ID NO 296
<211> LENGTH: 23
<212> TYPE: DNA
<213> ORGANISM: Homo sapiens

<400> SEQUENCE: 296
ctctcccctc ccaggaaatg agg                                          23

<210> SEQ ID NO 297

```
<211> LENGTH: 23
<212> TYPE: DNA
<213> ORGANISM: Homo sapiens

<400> SEQUENCE: 297
gaggatcagc accagggcca tgg                                              23

<210> SEQ ID NO 298
<211> LENGTH: 23
<212> TYPE: DNA
<213> ORGANISM: Homo sapiens

<400> SEQUENCE: 298
cacagagggt cagcagctgg agg                                              23

<210> SEQ ID NO 299
<211> LENGTH: 23
<212> TYPE: DNA
<213> ORGANISM: Homo sapiens

<400> SEQUENCE: 299 taattttttcc acagtgccat agg                                             23

<210> SEQ ID NO 300
<211> LENGTH: 23
<212> TYPE: DNA
<213> ORGANISM: Homo sapiens

<400> SEQUENCE: 300 aattttttcca cagtgccata ggg                                             23

<210> SEQ ID NO 301
<211> LENGTH: 23
<212> TYPE: DNA
<213> ORGANISM: Homo sapiens

<400> SEQUENCE: 301
gccctggctc cagctctagc ggg                                              23

<210> SEQ ID NO 302
<211> LENGTH: 23
<212> TYPE: DNA
<213> ORGANISM: Homo sapiens

<400> SEQUENCE: 302
ctcatttcct gggaggggag agg                                              23

<210> SEQ ID NO 303
<211> LENGTH: 23
<212> TYPE: DNA
<213> ORGANISM: Homo sapiens

<400> SEQUENCE: 303
gatcagcacc agggccatgg tgg                                              23

<210> SEQ ID NO 304
<211> LENGTH: 23
<212> TYPE: DNA
<213> ORGANISM: Homo sapiens

<400> SEQUENCE: 304
tcatttcctg ggaggggaga ggg                                              23
```

```
<210> SEQ ID NO 305
<211> LENGTH: 23
<212> TYPE: DNA
<213> ORGANISM: Homo sapiens

<400> SEQUENCE: 305
ctagagctgg agccagggct tgg                                             23

<210> SEQ ID NO 306
<211> LENGTH: 23
<212> TYPE: DNA
<213> ORGANISM: Homo sapiens

<400> SEQUENCE: 306
gtcgcaccct ctccctccc agg                                              23

<210> SEQ ID NO 307
<211> LENGTH: 23
<212> TYPE: DNA
<213> ORGANISM: Homo sapiens

<400> SEQUENCE: 307
cacacagaca tcactccgtc tgg                                             23

<210> SEQ ID NO 308
<211> LENGTH: 23
<212> TYPE: DNA
<213> ORGANISM: Homo sapiens

<400> SEQUENCE: 308
ctagtccctc aacctcctac agg                                             23

<210> SEQ ID NO 309
<211> LENGTH: 23
<212> TYPE: DNA
<213> ORGANISM: Homo sapiens

<400> SEQUENCE: 309
tagtccctca acctcctaca ggg                                             23

<210> SEQ ID NO 310
<211> LENGTH: 23
<212> TYPE: DNA
<213> ORGANISM: Homo sapiens

<400> SEQUENCE: 310
tggggtggct actcaccaga cgg                                             23

<210> SEQ ID NO 311
<211> LENGTH: 23
<212> TYPE: DNA
<213> ORGANISM: Homo sapiens

<400> SEQUENCE: 311
agaggccctg taggaggttg agg                                             23

<210> SEQ ID NO 312
<211> LENGTH: 23
<212> TYPE: DNA
<213> ORGANISM: Homo sapiens

<400> SEQUENCE: 312
tgacacagag gccctgtagg agg                                             23
```

```
<210> SEQ ID NO 313
<211> LENGTH: 23
<212> TYPE: DNA
<213> ORGANISM: Homo sapiens

<400> SEQUENCE: 313
gaggccctgt aggaggttga ggg                                              23

<210> SEQ ID NO 314
<211> LENGTH: 23
<212> TYPE: DNA
<213> ORGANISM: Homo sapiens

<400> SEQUENCE: 314
gtgatgtctg tgtgacacag agg                                              23

<210> SEQ ID NO 315
<211> LENGTH: 23
<212> TYPE: DNA
<213> ORGANISM: Homo sapiens

<400> SEQUENCE: 315
gtgtgacaca gaggccctgt agg                                              23

<210> SEQ ID NO 316
<211> LENGTH: 23
<212> TYPE: DNA
<213> ORGANISM: Homo sapiens

<400> SEQUENCE: 316
ctcacctata atggccacta agg                                              23

<210> SEQ ID NO 317
<211> LENGTH: 23
<212> TYPE: DNA
<213> ORGANISM: Homo sapiens

<400> SEQUENCE: 317
cacctataat ggccactaag ggg                                              23

<210> SEQ ID NO 318
<211> LENGTH: 23
<212> TYPE: DNA
<213> ORGANISM: Homo sapiens

<400> SEQUENCE: 318
tcacctataa tggccactaa ggg                                              23

<210> SEQ ID NO 319
<211> LENGTH: 23
<212> TYPE: DNA
<213> ORGANISM: Homo sapiens

<400> SEQUENCE: 319
ttccccttag tggccattat agg                                              23

<210> SEQ ID NO 320
<211> LENGTH: 23
<212> TYPE: DNA
<213> ORGANISM: Homo sapiens

<400> SEQUENCE: 320
tcttcagtac tcacctataa tgg                                              23
```

```
<210> SEQ ID NO 321
<211> LENGTH: 23
<212> TYPE: DNA
<213> ORGANISM: Homo sapiens

<400> SEQUENCE: 321
ataggtgagt actgaagacc agg                                              23

<210> SEQ ID NO 322
<211> LENGTH: 23
<212> TYPE: DNA
<213> ORGANISM: Homo sapiens

<400> SEQUENCE: 322
tcttttctca ttccccttag tgg                                              23

<210> SEQ ID NO 323
<211> LENGTH: 23
<212> TYPE: DNA
<213> ORGANISM: Homo sapiens

<400> SEQUENCE: 323
tgcgttcaga cttcttcggt agg                                              23

<210> SEQ ID NO 324
<211> LENGTH: 23
<212> TYPE: DNA
<213> ORGANISM: Homo sapiens

<400> SEQUENCE: 324
ttcagacttc ttcggtaggt ggg                                              23

<210> SEQ ID NO 325
<211> LENGTH: 23
<212> TYPE: DNA
<213> ORGANISM: Homo sapiens

<400> SEQUENCE: 325
tacttgaacc ctagagtcgg agg                                              23

<210> SEQ ID NO 326
<211> LENGTH: 23
<212> TYPE: DNA
<213> ORGANISM: Homo sapiens

<400> SEQUENCE: 326
gtttctcctc tcacgagttc agg                                              23

<210> SEQ ID NO 327
<211> LENGTH: 23
<212> TYPE: DNA
<213> ORGANISM: Homo sapiens

<400> SEQUENCE: 327
gttcagactt cttcggtagg tgg                                              23

<210> SEQ ID NO 328
<211> LENGTH: 23
<212> TYPE: DNA
<213> ORGANISM: Homo sapiens

<400> SEQUENCE: 328
```

```
gagcattcgc tatattgccc agg                                              23

<210> SEQ ID NO 329
<211> LENGTH: 23
<212> TYPE: DNA
<213> ORGANISM: Homo sapiens

<400> SEQUENCE: 329
gcggtctccc tatgttgagc agg                                              23

<210> SEQ ID NO 330
<211> LENGTH: 23
<212> TYPE: DNA
<213> ORGANISM: Homo sapiens

<400> SEQUENCE: 330
aactgcagcc tccgactcta ggg                                              23

<210> SEQ ID NO 331
<211> LENGTH: 23
<212> TYPE: DNA
<213> ORGANISM: Homo sapiens

<400> SEQUENCE: 331
gcctcagcct ccgtagtagc tgg                                              23

<210> SEQ ID NO 332
<211> LENGTH: 23
<212> TYPE: DNA
<213> ORGANISM: Homo sapiens

<400> SEQUENCE: 332
cagattcctg aactcgtgag agg                                              23

<210> SEQ ID NO 333
<211> LENGTH: 23
<212> TYPE: DNA
<213> ORGANISM: Homo sapiens

<400> SEQUENCE: 333
caagctagca ctaccacgcc tgg                                              23

<210> SEQ ID NO 334
<211> LENGTH: 23
<212> TYPE: DNA
<213> ORGANISM: Homo sapiens

<400> SEQUENCE: 334
tgtagtccca gctactacgg agg                                              23

<210> SEQ ID NO 335
<211> LENGTH: 23
<212> TYPE: DNA
<213> ORGANISM: Homo sapiens

<400> SEQUENCE: 335
gaactcgctg ttgggcgcag cgg                                              23

<210> SEQ ID NO 336
<211> LENGTH: 23
<212> TYPE: DNA
<213> ORGANISM: Homo sapiens

<400> SEQUENCE: 336
```
cttcttcggt aggtgggcaa tgg					23

<210> SEQ ID NO 337
<211> LENGTH: 23
<212> TYPE: DNA
<213> ORGANISM: Homo sapiens

<400> SEQUENCE: 337
agagaggggt ttcgccatgt tgg					23

<210> SEQ ID NO 338
<211> LENGTH: 23
<212> TYPE: DNA
<213> ORGANISM: Homo sapiens

<400> SEQUENCE: 338
ggggtttcac cacattagcc agg					23

<210> SEQ ID NO 339
<211> LENGTH: 23
<212> TYPE: DNA
<213> ORGANISM: Homo sapiens

<400> SEQUENCE: 339
ctcacctata atggccacta agg					23

<210> SEQ ID NO 340
<211> LENGTH: 23
<212> TYPE: DNA
<213> ORGANISM: Homo sapiens

<400> SEQUENCE: 340
aggtcagatc gagatcatcc tgg					23

<210> SEQ ID NO 341
<211> LENGTH: 23
<212> TYPE: DNA
<213> ORGANISM: Homo sapiens

<400> SEQUENCE: 341
taactgcagc ctccgactct agg					23

<210> SEQ ID NO 342
<211> LENGTH: 23
<212> TYPE: DNA
<213> ORGANISM: Homo sapiens

<400> SEQUENCE: 342
cacctataat ggccactaag ggg					23

<210> SEQ ID NO 343
<211> LENGTH: 23
<212> TYPE: DNA
<213> ORGANISM: Homo sapiens

<400> SEQUENCE: 343
tcacctataa tggccactaa ggg					23

<210> SEQ ID NO 344
<211> LENGTH: 23
<212> TYPE: DNA
<213> ORGANISM: Homo sapiens

<400> SEQUENCE: 344
taaaaataag ggtcgggtga ggg                                          23

<210> SEQ ID NO 345
<211> LENGTH: 23
<212> TYPE: DNA
<213> ORGANISM: Homo sapiens

<400> SEQUENCE: 345
cccctcccca tataagaatc tgg                                          23

<210> SEQ ID NO 346
<211> LENGTH: 23
<212> TYPE: DNA
<213> ORGANISM: Homo sapiens

<400> SEQUENCE: 346
cctcagcctc cgtagtagct ggg                                          23

<210> SEQ ID NO 347
<211> LENGTH: 23
<212> TYPE: DNA
<213> ORGANISM: Homo sapiens

<400> SEQUENCE: 347
ccccatctca ttggtaaccc agg                                          23

<210> SEQ ID NO 348
<211> LENGTH: 23
<212> TYPE: DNA
<213> ORGANISM: Homo sapiens

<400> SEQUENCE: 348 ttcccttag tggccattat agg                                           23

<210> SEQ ID NO 349
<211> LENGTH: 23
<212> TYPE: DNA
<213> ORGANISM: Homo sapiens

<400> SEQUENCE: 349
gcaggttggt cttaaactac tgg                                          23

<210> SEQ ID NO 350
<211> LENGTH: 23
<212> TYPE: DNA
<213> ORGANISM: Homo sapiens

<400> SEQUENCE: 350
cccagattct tatatgggag ggg                                          23

<210> SEQ ID NO 351
<211> LENGTH: 23
<212> TYPE: DNA
<213> ORGANISM: Homo sapiens

<400> SEQUENCE: 351
ggactcccag attcttatat ggg                                          23

<210> SEQ ID NO 352
<211> LENGTH: 23
<212> TYPE: DNA
<213> ORGANISM: Homo sapiens

```
<400> SEQUENCE: 352
ctctcacgag ttcaggaatc tgg                                          23

<210> SEQ ID NO 353
<211> LENGTH: 23
<212> TYPE: DNA
<213> ORGANISM: Homo sapiens

<400> SEQUENCE: 353
ctcccagatt cttatatggg agg                                          23

<210> SEQ ID NO 354
<211> LENGTH: 23
<212> TYPE: DNA
<213> ORGANISM: Homo sapiens

<400> SEQUENCE: 354
cccctcccat ataagaatct ggg                                          23

<210> SEQ ID NO 355
<211> LENGTH: 23
<212> TYPE: DNA
<213> ORGANISM: Homo sapiens

<400> SEQUENCE: 355
cacacagaca tcactccgtc tgg                                          23

<210> SEQ ID NO 356
<211> LENGTH: 23
<212> TYPE: DNA
<213> ORGANISM: Homo sapiens

<400> SEQUENCE: 356
aggaaggctg ttgggtccgg tgg                                          23

<210> SEQ ID NO 357
<211> LENGTH: 23
<212> TYPE: DNA
<213> ORGANISM: Homo sapiens

<400> SEQUENCE: 357
actctacgat cattgttccc tgg                                          23

<210> SEQ ID NO 358
<211> LENGTH: 23
<212> TYPE: DNA
<213> ORGANISM: Homo sapiens

<400> SEQUENCE: 358
tttgaaaaga actcgctgtt ggg                                          23

<210> SEQ ID NO 359
<211> LENGTH: 23
<212> TYPE: DNA
<213> ORGANISM: Homo sapiens

<400> SEQUENCE: 359
tctccctatg ttgagcaggt tgg                                          23

<210> SEQ ID NO 360
<211> LENGTH: 23
<212> TYPE: DNA
```

<213> ORGANISM: Homo sapiens

<400> SEQUENCE: 360
tctcacgagt tcaggaatct ggg 23

<210> SEQ ID NO 361
<211> LENGTH: 23
<212> TYPE: DNA
<213> ORGANISM: Homo sapiens

<400> SEQUENCE: 361
ggatcttggg ctgggcgcaa tgg 23

<210> SEQ ID NO 362
<211> LENGTH: 23
<212> TYPE: DNA
<213> ORGANISM: Homo sapiens

<400> SEQUENCE: 362
gcagaggcgg gcggatcaca agg 23

<210> SEQ ID NO 363
<211> LENGTH: 23
<212> TYPE: DNA
<213> ORGANISM: Homo sapiens

<400> SEQUENCE: 363
gagccgaggc ccagcacttt ggg 23

<210> SEQ ID NO 364
<211> LENGTH: 23
<212> TYPE: DNA
<213> ORGANISM: Homo sapiens

<400> SEQUENCE: 364
cgagatcatc ctggctaatg tgg 23

<210> SEQ ID NO 365
<211> LENGTH: 23
<212> TYPE: DNA
<213> ORGANISM: Homo sapiens

<400> SEQUENCE: 365
ttttgaaaag aactcgctgt tgg 23

<210> SEQ ID NO 366
<211> LENGTH: 23
<212> TYPE: DNA
<213> ORGANISM: Homo sapiens

<400> SEQUENCE: 366
ggtctgcgtt cagacttctt cgg 23

<210> SEQ ID NO 367
<211> LENGTH: 23
<212> TYPE: DNA
<213> ORGANISM: Homo sapiens

<400> SEQUENCE: 367
gcctgggcaa ccaagagttc agg 23

<210> SEQ ID NO 368
<211> LENGTH: 23

<212> TYPE: DNA
<213> ORGANISM: Homo sapiens

<400> SEQUENCE: 368
ctagtccctc aacctcctac agg                                            23

<210> SEQ ID NO 369
<211> LENGTH: 23
<212> TYPE: DNA
<213> ORGANISM: Homo sapiens

<400> SEQUENCE: 369
cacagggtct ttaattaatc tgg                                            23

<210> SEQ ID NO 370
<211> LENGTH: 23
<212> TYPE: DNA
<213> ORGANISM: Homo sapiens

<400> SEQUENCE: 370
caaaaattat ccgggcattg tgg                                            23

<210> SEQ ID NO 371
<211> LENGTH: 23
<212> TYPE: DNA
<213> ORGANISM: Homo sapiens

<400> SEQUENCE: 371
agtctgaacg cagacccctc tgg                                            23

<210> SEQ ID NO 372
<211> LENGTH: 23
<212> TYPE: DNA
<213> ORGANISM: Homo sapiens

<400> SEQUENCE: 372
agaccaacct gctcaacata ggg                                            23

<210> SEQ ID NO 373
<211> LENGTH: 23
<212> TYPE: DNA
<213> ORGANISM: Homo sapiens

<400> SEQUENCE: 373
aattacttga accctagagt cgg                                            23

<210> SEQ ID NO 374
<211> LENGTH: 23
<212> TYPE: DNA
<213> ORGANISM: Homo sapiens

<400> SEQUENCE: 374
ctccatggtg gcatgcactt tgg                                            23

<210> SEQ ID NO 375
<211> LENGTH: 23
<212> TYPE: DNA
<213> ORGANISM: Homo sapiens

<400> SEQUENCE: 375
agaacacaga ttcccgaaag agg                                            23

<210> SEQ ID NO 376

```
<211> LENGTH: 23
<212> TYPE: DNA
<213> ORGANISM: Homo sapiens

<400> SEQUENCE: 376
aaaaataagg gtcgggtgag ggg                                              23

<210> SEQ ID NO 377
<211> LENGTH: 23
<212> TYPE: DNA
<213> ORGANISM: Homo sapiens

<400> SEQUENCE: 377
tcccagattc ttatatggga ggg                                              23

<210> SEQ ID NO 378
<211> LENGTH: 23
<212> TYPE: DNA
<213> ORGANISM: Homo sapiens

<400> SEQUENCE: 378
tccatggtgg catgcacttt ggg                                              23

<210> SEQ ID NO 379
<211> LENGTH: 23
<212> TYPE: DNA
<213> ORGANISM: Homo sapiens

<400> SEQUENCE: 379
ctgaataaac ggggctgcct ggg                                              23

<210> SEQ ID NO 380
<211> LENGTH: 23
<212> TYPE: DNA
<213> ORGANISM: Homo sapiens

<400> SEQUENCE: 380
cagaccagcc tgaccaacat ggg                                              23

<210> SEQ ID NO 381
<211> LENGTH: 23
<212> TYPE: DNA
<213> ORGANISM: Homo sapiens

<400> SEQUENCE: 381
ataaaaataa gggtcgggtg agg                                              23

<210> SEQ ID NO 382
<211> LENGTH: 23
<212> TYPE: DNA
<213> ORGANISM: Homo sapiens

<400> SEQUENCE: 382
aggactccca gattcttata tgg                                              23

<210> SEQ ID NO 383
<211> LENGTH: 23
<212> TYPE: DNA
<213> ORGANISM: Homo sapiens

<400> SEQUENCE: 383
acgatcattg ttccctggaa agg                                              23
```

```
<210> SEQ ID NO 384
<211> LENGTH: 23
<212> TYPE: DNA
<213> ORGANISM: Homo sapiens

<400> SEQUENCE: 384
gttctcttgc tttaggaccc agg                                              23

<210> SEQ ID NO 385
<211> LENGTH: 23
<212> TYPE: DNA
<213> ORGANISM: Homo sapiens

<400> SEQUENCE: 385
ctgcccctct gatttgcacc tgg                                              23

<210> SEQ ID NO 386
<211> LENGTH: 23
<212> TYPE: DNA
<213> ORGANISM: Homo sapiens

<400> SEQUENCE: 386
attagagttc tggctgggcg tgg                                              23

<210> SEQ ID NO 387
<211> LENGTH: 23
<212> TYPE: DNA
<213> ORGANISM: Homo sapiens

<400> SEQUENCE: 387
aagaccaacc tgctcaacat agg                                              23

<210> SEQ ID NO 388
<211> LENGTH: 23
<212> TYPE: DNA
<213> ORGANISM: Homo sapiens

<400> SEQUENCE: 388
tcttcagtac tcacctataa tgg                                              23

<210> SEQ ID NO 389
<211> LENGTH: 23
<212> TYPE: DNA
<213> ORGANISM: Homo sapiens

<400> SEQUENCE: 389
tcctgggtta ccaatgagat ggg                                              23

<210> SEQ ID NO 390
<211> LENGTH: 23
<212> TYPE: DNA
<213> ORGANISM: Homo sapiens

<400> SEQUENCE: 390
tagtccctca acctcctaca ggg                                              23

<210> SEQ ID NO 391
<211> LENGTH: 23
<212> TYPE: DNA
<213> ORGANISM: Homo sapiens

<400> SEQUENCE: 391
cttaagccct gtactgtgcc agg                                              23
```

```
<210> SEQ ID NO 392
<211> LENGTH: 23
<212> TYPE: DNA
<213> ORGANISM: Homo sapiens

<400> SEQUENCE: 392
cctgggttac caatgagatg ggg                                             23

<210> SEQ ID NO 393
<211> LENGTH: 23
<212> TYPE: DNA
<213> ORGANISM: Homo sapiens

<400> SEQUENCE: 393 aaagggcag taattgtcca agg                                              23

<210> SEQ ID NO 394
<211> LENGTH: 23
<212> TYPE: DNA
<213> ORGANISM: Homo sapiens

<400> SEQUENCE: 394
tgtttgagcc caagagattg agg                                             23

<210> SEQ ID NO 395
<211> LENGTH: 23
<212> TYPE: DNA
<213> ORGANISM: Homo sapiens

<400> SEQUENCE: 395
tggggtggct actcaccaga cgg                                             23

<210> SEQ ID NO 396
<211> LENGTH: 23
<212> TYPE: DNA
<213> ORGANISM: Homo sapiens

<400> SEQUENCE: 396
tgaatacgat ggtgaaactg agg                                             23

<210> SEQ ID NO 397
<211> LENGTH: 23
<212> TYPE: DNA
<213> ORGANISM: Homo sapiens

<400> SEQUENCE: 397
tctcattgtg tcacccgggc tgg                                             23

<210> SEQ ID NO 398
<211> LENGTH: 23
<212> TYPE: DNA
<213> ORGANISM: Homo sapiens

<400> SEQUENCE: 398
gcttgtagtt ccagctgttt ggg                                             23

<210> SEQ ID NO 399
<211> LENGTH: 23
<212> TYPE: DNA
<213> ORGANISM: Homo sapiens

<400> SEQUENCE: 399
atacaaagat tagcctggtg tgg                                             23
```

<210> SEQ ID NO 400
<211> LENGTH: 23
<212> TYPE: DNA
<213> ORGANISM: Homo sapiens

<400> SEQUENCE: 400
agcttgtagt tccagctgtt tgg                                              23

<210> SEQ ID NO 401
<211> LENGTH: 23
<212> TYPE: DNA
<213> ORGANISM: Homo sapiens

<400> SEQUENCE: 401
acaggtatct ctggttcttg agg                                              23

<210> SEQ ID NO 402
<211> LENGTH: 23
<212> TYPE: DNA
<213> ORGANISM: Homo sapiens

<400> SEQUENCE: 402
tcccaaagtg catgccacca tgg                                              23

<210> SEQ ID NO 403
<211> LENGTH: 23
<212> TYPE: DNA
<213> ORGANISM: Homo sapiens

<400> SEQUENCE: 403
caggctactc ttgaactctt ggg                                              23

<210> SEQ ID NO 404
<211> LENGTH: 23
<212> TYPE: DNA
<213> ORGANISM: Homo sapiens

<400> SEQUENCE: 404
aatcaagcct tgttaaaacc agg                                              23

<210> SEQ ID NO 405
<211> LENGTH: 23
<212> TYPE: DNA
<213> ORGANISM: Homo sapiens

<400> SEQUENCE: 405
tgctttagga cccaggggtc tgg                                              23

<210> SEQ ID NO 406
<211> LENGTH: 23
<212> TYPE: DNA
<213> ORGANISM: Homo sapiens

<400> SEQUENCE: 406
tcacccgggc tggagtacgg tgg                                              23

<210> SEQ ID NO 407
<211> LENGTH: 23
<212> TYPE: DNA
<213> ORGANISM: Homo sapiens

<400> SEQUENCE: 407
gggcttaaga ataggatct tgg                                               23

<210> SEQ ID NO 408
<211> LENGTH: 23
<212> TYPE: DNA
<213> ORGANISM: Homo sapiens

<400> SEQUENCE: 408
agcttgtaaa cttagcactt tgg                                              23

<210> SEQ ID NO 409
<211> LENGTH: 23
<212> TYPE: DNA
<213> ORGANISM: Homo sapiens

<400> SEQUENCE: 409
agagccaccg tactccagcc cgg                                              23

<210> SEQ ID NO 410
<211> LENGTH: 23
<212> TYPE: DNA
<213> ORGANISM: Homo sapiens

<400> SEQUENCE: 410
aaatttctgc ctactgagac agg                                              23

<210> SEQ ID NO 411
<211> LENGTH: 23
<212> TYPE: DNA
<213> ORGANISM: Homo sapiens

<400> SEQUENCE: 411
ttcctgggtt accaatgaga tgg                                              23

<210> SEQ ID NO 412
<211> LENGTH: 23
<212> TYPE: DNA
<213> ORGANISM: Homo sapiens

<400> SEQUENCE: 412
tgaaactgag gtcctagctt agg                                              23

<210> SEQ ID NO 413
<211> LENGTH: 23
<212> TYPE: DNA
<213> ORGANISM: Homo sapiens

<400> SEQUENCE: 413
tcacatataa atgaatacga tgg                                              23

<210> SEQ ID NO 414
<211> LENGTH: 23
<212> TYPE: DNA
<213> ORGANISM: Homo sapiens

<400> SEQUENCE: 414
gatttgatga gatctcacag cgg                                              23

<210> SEQ ID NO 415
<211> LENGTH: 23
<212> TYPE: DNA
<213> ORGANISM: Homo sapiens

<400> SEQUENCE: 415

```
gaggtgggga caggtatctc tgg                                                    23

<210> SEQ ID NO 416
<211> LENGTH: 23
<212> TYPE: DNA
<213> ORGANISM: Homo sapiens

<400> SEQUENCE: 416
cctggaaagg tggagttcaa ggg                                                    23

<210> SEQ ID NO 417
<211> LENGTH: 23
<212> TYPE: DNA
<213> ORGANISM: Homo sapiens

<400> SEQUENCE: 417
ccatgttggt caggctggtc tgg                                                    23

<210> SEQ ID NO 418
<211> LENGTH: 23
<212> TYPE: DNA
<213> ORGANISM: Homo sapiens

<400> SEQUENCE: 418
atggtggcat gcactttggg agg                                                    23

<210> SEQ ID NO 419
<211> LENGTH: 23
<212> TYPE: DNA
<213> ORGANISM: Homo sapiens

<400> SEQUENCE: 419
agttgccaaa acttgctatt tgg                                                    23

<210> SEQ ID NO 420
<211> LENGTH: 23
<212> TYPE: DNA
<213> ORGANISM: Homo sapiens

<400> SEQUENCE: 420
agttcaaggg cctgaactct tgg                                                    23

<210> SEQ ID NO 421
<211> LENGTH: 23
<212> TYPE: DNA
<213> ORGANISM: Homo sapiens

<400> SEQUENCE: 421
agcaagctgt gacttgttct agg                                                    23

<210> SEQ ID NO 422
<211> LENGTH: 23
<212> TYPE: DNA
<213> ORGANISM: Homo sapiens

<400> SEQUENCE: 422
tgtggccagc cccatctcat tgg                                                    23

<210> SEQ ID NO 423
<211> LENGTH: 23
<212> TYPE: DNA
<213> ORGANISM: Homo sapiens
```

```
<400> SEQUENCE: 423
ggcttaagaa ataggatctt ggg                                          23

<210> SEQ ID NO 424
<211> LENGTH: 23
<212> TYPE: DNA
<213> ORGANISM: Homo sapiens

<400> SEQUENCE: 424
ccagtttctc tctgtcgccc agg                                          23

<210> SEQ ID NO 425
<211> LENGTH: 23
<212> TYPE: DNA
<213> ORGANISM: Homo sapiens

<400> SEQUENCE: 425
ccagattctt atatgggagg ggg                                          23

<210> SEQ ID NO 426
<211> LENGTH: 23
<212> TYPE: DNA
<213> ORGANISM: Homo sapiens

<400> SEQUENCE: 426
atcacacaaa ttaagagtac agg                                          23

<210> SEQ ID NO 427
<211> LENGTH: 23
<212> TYPE: DNA
<213> ORGANISM: Homo sapiens

<400> SEQUENCE: 427
actgaataaa cggggctgcc tgg                                          23

<210> SEQ ID NO 428
<211> LENGTH: 23
<212> TYPE: DNA
<213> ORGANISM: Homo sapiens

<400> SEQUENCE: 428
taagaaatag gatctgggc tgg                                           23

<210> SEQ ID NO 429
<211> LENGTH: 23
<212> TYPE: DNA
<213> ORGANISM: Homo sapiens

<400> SEQUENCE: 429
ggttaccaat gagatggggc tgg                                          23

<210> SEQ ID NO 430
<211> LENGTH: 23
<212> TYPE: DNA
<213> ORGANISM: Homo sapiens

<400> SEQUENCE: 430
gcgcagcggc tcatgcctgt ggg                                          23

<210> SEQ ID NO 431
<211> LENGTH: 23
<212> TYPE: DNA
<213> ORGANISM: Homo sapiens
```

-continued

```
<400> SEQUENCE: 431
gaacgcagac ccctctggcc tgg                                            23

<210> SEQ ID NO 432
<211> LENGTH: 23
<212> TYPE: DNA
<213> ORGANISM: Homo sapiens

<400> SEQUENCE: 432
ctgaggcaga ggcctaagct agg                                            23

<210> SEQ ID NO 433
<211> LENGTH: 23
<212> TYPE: DNA
<213> ORGANISM: Homo sapiens

<400> SEQUENCE: 433
cagtacaggg cttaagaaat agg                                            23

<210> SEQ ID NO 434
<211> LENGTH: 23
<212> TYPE: DNA
<213> ORGANISM: Homo sapiens

<400> SEQUENCE: 434
cactgcagcc tcaatctctt ggg                                            23

<210> SEQ ID NO 435
<211> LENGTH: 23
<212> TYPE: DNA
<213> ORGANISM: Homo sapiens

<400> SEQUENCE: 435
caagagttca agagtagcct ggg                                            23

<210> SEQ ID NO 436
<211> LENGTH: 23
<212> TYPE: DNA
<213> ORGANISM: Homo sapiens

<400> SEQUENCE: 436
aaaataaggg tcgggtgagg ggg                                            23

<210> SEQ ID NO 437
<211> LENGTH: 23
<212> TYPE: DNA
<213> ORGANISM: Homo sapiens

<400> SEQUENCE: 437
tacaggaagg ctgttgggtc cgg                                            23

<210> SEQ ID NO 438
<211> LENGTH: 23
<212> TYPE: DNA
<213> ORGANISM: Homo sapiens

<400> SEQUENCE: 438
gtatctctgg ttcttgaggc agg                                            23

<210> SEQ ID NO 439
<211> LENGTH: 23
<212> TYPE: DNA
```

<213> ORGANISM: Homo sapiens

<400> SEQUENCE: 439
cccagctact acggaggctg agg                                           23

<210> SEQ ID NO 440
<211> LENGTH: 23
<212> TYPE: DNA
<213> ORGANISM: Homo sapiens

<400> SEQUENCE: 440
caagtgcccg ccaccacacc agg                                           23

<210> SEQ ID NO 441
<211> LENGTH: 23
<212> TYPE: DNA
<213> ORGANISM: Homo sapiens

<400> SEQUENCE: 441
acagaaaaat tagccaggcg tgg                                           23

<210> SEQ ID NO 442
<211> LENGTH: 23
<212> TYPE: DNA
<213> ORGANISM: Homo sapiens

<400> SEQUENCE: 442
ggtcttgaac tcctgtcctc agg                                           23

<210> SEQ ID NO 443
<211> LENGTH: 23
<212> TYPE: DNA
<213> ORGANISM: Homo sapiens

<400> SEQUENCE: 443
gcaaccacct cctgggttca agg                                           23

<210> SEQ ID NO 444
<211> LENGTH: 23
<212> TYPE: DNA
<213> ORGANISM: Homo sapiens

<400> SEQUENCE: 444
gattagcctg gtgtggtggc ggg                                           23

<210> SEQ ID NO 445
<211> LENGTH: 23
<212> TYPE: DNA
<213> ORGANISM: Homo sapiens

<400> SEQUENCE: 445
ccaagagttc aagagtagcc tgg                                           23

<210> SEQ ID NO 446
<211> LENGTH: 23
<212> TYPE: DNA
<213> ORGANISM: Homo sapiens

<400> SEQUENCE: 446
caaggtgggt gcatcacctg agg                                           23

<210> SEQ ID NO 447
<211> LENGTH: 23

<212> TYPE: DNA
<213> ORGANISM: Homo sapiens

<400> SEQUENCE: 447
ataggtgagt actgaagacc agg    23

<210> SEQ ID NO 448
<211> LENGTH: 23
<212> TYPE: DNA
<213> ORGANISM: Homo sapiens

<400> SEQUENCE: 448
agacaccctg caggggacc agg    23

<210> SEQ ID NO 449
<211> LENGTH: 23
<212> TYPE: DNA
<213> ORGANISM: Homo sapiens

<400> SEQUENCE: 449
acagagtgag aactccatgg tgg    23

<210> SEQ ID NO 450
<211> LENGTH: 23
<212> TYPE: DNA
<213> ORGANISM: Homo sapiens

<400> SEQUENCE: 450
taaaaccagg tgcaaatcag agg    23

<210> SEQ ID NO 451
<211> LENGTH: 23
<212> TYPE: DNA
<213> ORGANISM: Homo sapiens

<400> SEQUENCE: 451
ggtcttgaac tcctgacctc agg    23

<210> SEQ ID NO 452
<211> LENGTH: 23
<212> TYPE: DNA
<213> ORGANISM: Homo sapiens

<400> SEQUENCE: 452
gcttgtaaac ttagcacttt ggg    23

<210> SEQ ID NO 453
<211> LENGTH: 23
<212> TYPE: DNA
<213> ORGANISM: Homo sapiens

<400> SEQUENCE: 453
gagatggggc tggccacaaa ggg    23

<210> SEQ ID NO 454
<211> LENGTH: 23
<212> TYPE: DNA
<213> ORGANISM: Homo sapiens

<400> SEQUENCE: 454
ctggaggatt gtctgagccc agg    23

<210> SEQ ID NO 455

-continued

```
<211> LENGTH: 23
<212> TYPE: DNA
<213> ORGANISM: Homo sapiens

<400> SEQUENCE: 455
cccccttttc ccagggaatc agg                                              23

<210> SEQ ID NO 456
<211> LENGTH: 23
<212> TYPE: DNA
<213> ORGANISM: Homo sapiens

<400> SEQUENCE: 456
caggcacatg ccactacacc agg                                              23

<210> SEQ ID NO 457
<211> LENGTH: 23
<212> TYPE: DNA
<213> ORGANISM: Homo sapiens

<400> SEQUENCE: 457
aaaaaattag cctggtgtag tgg                                              23

<210> SEQ ID NO 458
<211> LENGTH: 23
<212> TYPE: DNA
<213> ORGANISM: Homo sapiens

<400> SEQUENCE: 458
ttctcttgct ttaggaccca ggg                                              23

<210> SEQ ID NO 459
<211> LENGTH: 23
<212> TYPE: DNA
<213> ORGANISM: Homo sapiens

<400> SEQUENCE: 459
tgagatgggg ctggccacaa agg                                              23

<210> SEQ ID NO 460
<211> LENGTH: 23
<212> TYPE: DNA
<213> ORGANISM: Homo sapiens

<400> SEQUENCE: 460
tctcttgctt taggacccag ggg                                              23

<210> SEQ ID NO 461
<211> LENGTH: 23
<212> TYPE: DNA
<213> ORGANISM: Homo sapiens

<400> SEQUENCE: 461
tcactgcagc tttgaattcc tgg                                              23

<210> SEQ ID NO 462
<211> LENGTH: 23
<212> TYPE: DNA
<213> ORGANISM: Homo sapiens

<400> SEQUENCE: 462
tactcagcat cccaaacagc tgg                                              23
```

```
<210> SEQ ID NO 463
<211> LENGTH: 23
<212> TYPE: DNA
<213> ORGANISM: Homo sapiens

<400> SEQUENCE: 463
ggctcactgc aaccacctcc tgg                                           23

<210> SEQ ID NO 464
<211> LENGTH: 23
<212> TYPE: DNA
<213> ORGANISM: Homo sapiens

<400> SEQUENCE: 464
ggcagcaggt ttgggattct agg                                           23

<210> SEQ ID NO 465
<211> LENGTH: 23
<212> TYPE: DNA
<213> ORGANISM: Homo sapiens

<400> SEQUENCE: 465
gctcatgcct gtgggagccg agg                                           23

<210> SEQ ID NO 466
<211> LENGTH: 23
<212> TYPE: DNA
<213> ORGANISM: Homo sapiens

<400> SEQUENCE: 466
ccttgaactc cacctttcca ggg                                           23

<210> SEQ ID NO 467
<211> LENGTH: 23
<212> TYPE: DNA
<213> ORGANISM: Homo sapiens

<400> SEQUENCE: 467
ccgaggccca gcactttggg agg                                           23

<210> SEQ ID NO 468
<211> LENGTH: 23
<212> TYPE: DNA
<213> ORGANISM: Homo sapiens

<400> SEQUENCE: 468
cacaaattaa gagtacagga agg                                           23

<210> SEQ ID NO 469
<211> LENGTH: 23
<212> TYPE: DNA
<213> ORGANISM: Homo sapiens

<400> SEQUENCE: 469
agcggcccat tttacagaga agg                                           23

<210> SEQ ID NO 470
<211> LENGTH: 23
<212> TYPE: DNA
<213> ORGANISM: Homo sapiens

<400> SEQUENCE: 470
agaggccctg taggaggttg agg                                           23
```

```
<210> SEQ ID NO 471
<211> LENGTH: 23
<212> TYPE: DNA
<213> ORGANISM: Homo sapiens

<400> SEQUENCE: 471
aaggatatct gggatgggat tgg                                              23

<210> SEQ ID NO 472
<211> LENGTH: 23
<212> TYPE: DNA
<213> ORGANISM: Homo sapiens

<400> SEQUENCE: 472
tggggtctca ttgtgtcacc cgg                                              23

<210> SEQ ID NO 473
<211> LENGTH: 23
<212> TYPE: DNA
<213> ORGANISM: Homo sapiens

<400> SEQUENCE: 473
ggagccgagg cccagcactt tgg                                              23

<210> SEQ ID NO 474
<211> LENGTH: 23
<212> TYPE: DNA
<213> ORGANISM: Homo sapiens

<400> SEQUENCE: 474
ctctccctga ttttacaaac agg                                              23

<210> SEQ ID NO 475
<211> LENGTH: 23
<212> TYPE: DNA
<213> ORGANISM: Homo sapiens

<400> SEQUENCE: 475
cacagattcc cgaaagagga agg                                              23

<210> SEQ ID NO 476
<211> LENGTH: 23
<212> TYPE: DNA
<213> ORGANISM: Homo sapiens

<400> SEQUENCE: 476
caaagattag cctggtgtgg tgg                                              23

<210> SEQ ID NO 477
<211> LENGTH: 23
<212> TYPE: DNA
<213> ORGANISM: Homo sapiens

<400> SEQUENCE: 477
aagagtacag gaaggctgtt ggg                                              23

<210> SEQ ID NO 478
<211> LENGTH: 23
<212> TYPE: DNA
<213> ORGANISM: Homo sapiens

<400> SEQUENCE: 478
tttaaaatta gagttctggc tgg                                              23
```

<210> SEQ ID NO 479
<211> LENGTH: 23
<212> TYPE: DNA
<213> ORGANISM: Homo sapiens

<400> SEQUENCE: 479
tgggtgcatc acctgaggtc agg                                              23

<210> SEQ ID NO 480
<211> LENGTH: 23
<212> TYPE: DNA
<213> ORGANISM: Homo sapiens

<400> SEQUENCE: 480
gttcaaataa agaacagggc tgg                                              23

<210> SEQ ID NO 481
<211> LENGTH: 23
<212> TYPE: DNA
<213> ORGANISM: Homo sapiens

<400> SEQUENCE: 481
gcctgtggtc ccaggtactc agg                                              23

<210> SEQ ID NO 482
<211> LENGTH: 23
<212> TYPE: DNA
<213> ORGANISM: Homo sapiens

<400> SEQUENCE: 482
gaaactgtgt ttacaaactg tgg                                              23

<210> SEQ ID NO 483
<211> LENGTH: 23
<212> TYPE: DNA
<213> ORGANISM: Homo sapiens

<400> SEQUENCE: 483
aggatatctg ggatgggatt ggg                                              23

<210> SEQ ID NO 484
<211> LENGTH: 23
<212> TYPE: DNA
<213> ORGANISM: Homo sapiens

<400> SEQUENCE: 484 agctggggggg actgaataaa cgg                                             23

<210> SEQ ID NO 485
<211> LENGTH: 23
<212> TYPE: DNA
<213> ORGANISM: Homo sapiens

<400> SEQUENCE: 485
ttaaaattag agttctggct ggg                                              23

<210> SEQ ID NO 486
<211> LENGTH: 23
<212> TYPE: DNA
<213> ORGANISM: Homo sapiens

<400> SEQUENCE: 486
tgtctcagta ggcagaaatt tgg                                                23

<210> SEQ ID NO 487
<211> LENGTH: 23
<212> TYPE: DNA
<213> ORGANISM: Homo sapiens

<400> SEQUENCE: 487
tgacacagag gccctgtagg agg                                                23

<210> SEQ ID NO 488
<211> LENGTH: 23
<212> TYPE: DNA
<213> ORGANISM: Homo sapiens

<400> SEQUENCE: 488
gcaacagagt gagaactcca tgg                                                23

<210> SEQ ID NO 489
<211> LENGTH: 23
<212> TYPE: DNA
<213> ORGANISM: Homo sapiens

<400> SEQUENCE: 489
gagctgggaa ctcagattcc tgg                                                23

<210> SEQ ID NO 490
<211> LENGTH: 23
<212> TYPE: DNA
<213> ORGANISM: Homo sapiens

<400> SEQUENCE: 490
cccttgaact ccacctttcc agg                                                23

<210> SEQ ID NO 491
<211> LENGTH: 23
<212> TYPE: DNA
<213> ORGANISM: Homo sapiens

<400> SEQUENCE: 491
catgtgcaaa accctgagcc tgg                                                23

<210> SEQ ID NO 492
<211> LENGTH: 23
<212> TYPE: DNA
<213> ORGANISM: Homo sapiens

<400> SEQUENCE: 492
cactgcagct ttgaattcct ggg                                                23

<210> SEQ ID NO 493
<211> LENGTH: 23
<212> TYPE: DNA
<213> ORGANISM: Homo sapiens

<400> SEQUENCE: 493
atttgcacct ggttttaaca agg                                                23

<210> SEQ ID NO 494
<211> LENGTH: 23
<212> TYPE: DNA
<213> ORGANISM: Homo sapiens

<400> SEQUENCE: 494

```
agctgtttgg gatgctgagt agg                                               23

<210> SEQ ID NO 495
<211> LENGTH: 23
<212> TYPE: DNA
<213> ORGANISM: Homo sapiens

<400> SEQUENCE: 495
tggtccccct gcagggtgtc tgg                                               23

<210> SEQ ID NO 496
<211> LENGTH: 23
<212> TYPE: DNA
<213> ORGANISM: Homo sapiens

<400> SEQUENCE: 496
tcttggttgc ccaggccaga ggg                                               23

<210> SEQ ID NO 497
<211> LENGTH: 23
<212> TYPE: DNA
<213> ORGANISM: Homo sapiens

<400> SEQUENCE: 497 ggtcccctg cagggtgtct ggg                                                23

<210> SEQ ID NO 498
<211> LENGTH: 23
<212> TYPE: DNA
<213> ORGANISM: Homo sapiens

<400> SEQUENCE: 498
gggattttac catgttggtc agg                                               23

<210> SEQ ID NO 499
<211> LENGTH: 23
<212> TYPE: DNA
<213> ORGANISM: Homo sapiens

<400> SEQUENCE: 499
gaggccctgt aggaggttga ggg                                               23

<210> SEQ ID NO 500
<211> LENGTH: 23
<212> TYPE: DNA
<213> ORGANISM: Homo sapiens

<400> SEQUENCE: 500
cctgggcgac agagagaaac tgg                                               23

<210> SEQ ID NO 501
<211> LENGTH: 23
<212> TYPE: DNA
<213> ORGANISM: Homo sapiens

<400> SEQUENCE: 501
ccctggaaag gtggagttca agg                                               23

<210> SEQ ID NO 502
<211> LENGTH: 23
<212> TYPE: DNA
<213> ORGANISM: Homo sapiens
```

<400> SEQUENCE: 502
ccctgagcct ggcacagtac agg                                   23

<210> SEQ ID NO 503
<211> LENGTH: 23
<212> TYPE: DNA
<213> ORGANISM: Homo sapiens

<400> SEQUENCE: 503
agaatcccaa acctgctgcc tgg                                   23

<210> SEQ ID NO 504
<211> LENGTH: 23
<212> TYPE: DNA
<213> ORGANISM: Homo sapiens

<400> SEQUENCE: 504
aacgcagacc cctctggcct ggg                                   23

<210> SEQ ID NO 505
<211> LENGTH: 23
<212> TYPE: DNA
<213> ORGANISM: Homo sapiens

<400> SEQUENCE: 505
tttctgccta ctgagacagg agg                                   23

<210> SEQ ID NO 506
<211> LENGTH: 23
<212> TYPE: DNA
<213> ORGANISM: Homo sapiens

<400> SEQUENCE: 506
tctaggttca aataaagaac agg                                   23

<210> SEQ ID NO 507
<211> LENGTH: 23
<212> TYPE: DNA
<213> ORGANISM: Homo sapiens

<400> SEQUENCE: 507
taagagtaca ggaaggctgt tgg                                   23

<210> SEQ ID NO 508
<211> LENGTH: 23
<212> TYPE: DNA
<213> ORGANISM: Homo sapiens

<400> SEQUENCE: 508
gtgacttgtt ctaggtcata tgg                                   23

<210> SEQ ID NO 509
<211> LENGTH: 23
<212> TYPE: DNA
<213> ORGANISM: Homo sapiens

<400> SEQUENCE: 509
gggaggaaaa taaggatatc tgg                                   23

<210> SEQ ID NO 510
<211> LENGTH: 23
<212> TYPE: DNA
<213> ORGANISM: Homo sapiens

<400> SEQUENCE: 510
gctttaggac ccagggtct ggg                                              23

<210> SEQ ID NO 511
<211> LENGTH: 23
<212> TYPE: DNA
<213> ORGANISM: Homo sapiens

<400> SEQUENCE: 511
agctgggaac tcagattcct ggg                                             23

<210> SEQ ID NO 512
<211> LENGTH: 23
<212> TYPE: DNA
<213> ORGANISM: Homo sapiens

<400> SEQUENCE: 512
aagaaatagg atcttgggct ggg                                             23

<210> SEQ ID NO 513
<211> LENGTH: 23
<212> TYPE: DNA
<213> ORGANISM: Homo sapiens

<400> SEQUENCE: 513
ttgggaaatg gtatgaggta ggg                                             23

<210> SEQ ID NO 514
<211> LENGTH: 23
<212> TYPE: DNA
<213> ORGANISM: Homo sapiens

<400> SEQUENCE: 514
tgtaaactta gcactttggg agg                                             23

<210> SEQ ID NO 515
<211> LENGTH: 23
<212> TYPE: DNA
<213> ORGANISM: Homo sapiens

<400> SEQUENCE: 515
ggtgtagtgg catgtgcctg tgg                                             23

<210> SEQ ID NO 516
<211> LENGTH: 23
<212> TYPE: DNA
<213> ORGANISM: Homo sapiens

<400> SEQUENCE: 516
caggtgcaaa tcagaggggc agg                                             23

<210> SEQ ID NO 517
<211> LENGTH: 23
<212> TYPE: DNA
<213> ORGANISM: Homo sapiens

<400> SEQUENCE: 517
actcacagag ggtcagcagc tgg                                             23

<210> SEQ ID NO 518
<211> LENGTH: 23
<212> TYPE: DNA

<213> ORGANISM: Homo sapiens

<400> SEQUENCE: 518
aagaaagggg tgactcacag agg                                    23

<210> SEQ ID NO 519
<211> LENGTH: 23
<212> TYPE: DNA
<213> ORGANISM: Homo sapiens

<400> SEQUENCE: 519
ttcccagctc ctatctcctc tgg                                    23

<210> SEQ ID NO 520
<211> LENGTH: 23
<212> TYPE: DNA
<213> ORGANISM: Homo sapiens

<400> SEQUENCE: 520
tggagaccca gacaccctgc agg                                    23

<210> SEQ ID NO 521
<211> LENGTH: 23
<212> TYPE: DNA
<213> ORGANISM: Homo sapiens

<400> SEQUENCE: 521
gagccaccgt actccagccc ggg                                    23

<210> SEQ ID NO 522
<211> LENGTH: 23
<212> TYPE: DNA
<213> ORGANISM: Homo sapiens

<400> SEQUENCE: 522
cctgggtcct cgggcctcct ggg                                    23

<210> SEQ ID NO 523
<211> LENGTH: 23
<212> TYPE: DNA
<213> ORGANISM: Homo sapiens

<400> SEQUENCE: 523
agattagcct ggtgtggtgg cgg                                    23

<210> SEQ ID NO 524
<211> LENGTH: 23
<212> TYPE: DNA
<213> ORGANISM: Homo sapiens

<400> SEQUENCE: 524
agagttctgg ctgggcgtgg tgg                                    23

<210> SEQ ID NO 525
<211> LENGTH: 23
<212> TYPE: DNA
<213> ORGANISM: Homo sapiens

<400> SEQUENCE: 525
tgtttgtaat cccaacactt tgg                                    23

<210> SEQ ID NO 526
<211> LENGTH: 23

<212> TYPE: DNA
<213> ORGANISM: Homo sapiens

<400> SEQUENCE: 526
tgctgggcct cggctcccac agg						23

<210> SEQ ID NO 527
<211> LENGTH: 23
<212> TYPE: DNA
<213> ORGANISM: Homo sapiens

<400> SEQUENCE: 527
tcctgagtac ctgggaccac agg						23

<210> SEQ ID NO 528
<211> LENGTH: 23
<212> TYPE: DNA
<213> ORGANISM: Homo sapiens

<400> SEQUENCE: 528
gttcttttca aaacccttg tgg						23

<210> SEQ ID NO 529
<211> LENGTH: 23
<212> TYPE: DNA
<213> ORGANISM: Homo sapiens

<400> SEQUENCE: 529
gggaaggagg aaaatcacct tgg						23

<210> SEQ ID NO 530
<211> LENGTH: 23
<212> TYPE: DNA
<213> ORGANISM: Homo sapiens

<400> SEQUENCE: 530
gctcactgca accacctcct ggg						23

<210> SEQ ID NO 531
<211> LENGTH: 23
<212> TYPE: DNA
<213> ORGANISM: Homo sapiens

<400> SEQUENCE: 531
gctactacgg aggctgaggc agg						23

<210> SEQ ID NO 532
<211> LENGTH: 23
<212> TYPE: DNA
<213> ORGANISM: Homo sapiens

<400> SEQUENCE: 532
cttggttgcc caggccagag ggg						23

<210> SEQ ID NO 533
<211> LENGTH: 23
<212> TYPE: DNA
<213> ORGANISM: Homo sapiens

<400> SEQUENCE: 533
ctgaagacca ggaacttctg agg						23

<210> SEQ ID NO 534

```
<211> LENGTH: 23
<212> TYPE: DNA
<213> ORGANISM: Homo sapiens

<400> SEQUENCE: 534
cgggtggatc acctgaggac agg                                              23

<210> SEQ ID NO 535
<211> LENGTH: 23
<212> TYPE: DNA
<213> ORGANISM: Homo sapiens

<400> SEQUENCE: 535
tttgggaaat ggtatgaggt agg                                              23

<210> SEQ ID NO 536
<211> LENGTH: 23
<212> TYPE: DNA
<213> ORGANISM: Homo sapiens

<400> SEQUENCE: 536
tcccagagga gataggagct ggg                                              23

<210> SEQ ID NO 537
<211> LENGTH: 23
<212> TYPE: DNA
<213> ORGANISM: Homo sapiens

<400> SEQUENCE: 537
gtgatgtctg tgtgacacag agg                                              23

<210> SEQ ID NO 538
<211> LENGTH: 23
<212> TYPE: DNA
<213> ORGANISM: Homo sapiens

<400> SEQUENCE: 538
ggaggaaaat aaggatatct ggg                                              23

<210> SEQ ID NO 539
<211> LENGTH: 23
<212> TYPE: DNA
<213> ORGANISM: Homo sapiens

<400> SEQUENCE: 539
cttttccaaa tagcaagttt tgg                                              23

<210> SEQ ID NO 540
<211> LENGTH: 23
<212> TYPE: DNA
<213> ORGANISM: Homo sapiens

<400> SEQUENCE: 540
attccctggg aaaaggggc tgg                                               23

<210> SEQ ID NO 541
<211> LENGTH: 23
<212> TYPE: DNA
<213> ORGANISM: Homo sapiens

<400> SEQUENCE: 541
agccaggact cctgattccc tgg                                              23
```

-continued

```
<210> SEQ ID NO 542
<211> LENGTH: 23
<212> TYPE: DNA
<213> ORGANISM: Homo sapiens

<400> SEQUENCE: 542
aaaataagga tatctgggat ggg                                             23

<210> SEQ ID NO 543
<211> LENGTH: 23
<212> TYPE: DNA
<213> ORGANISM: Homo sapiens

<400> SEQUENCE: 543
tcaaataaag aacagggctg ggg                                             23

<210> SEQ ID NO 544
<211> LENGTH: 23
<212> TYPE: DNA
<213> ORGANISM: Homo sapiens

<400> SEQUENCE: 544
gtgtgacaca gaggccctgt agg                                             23

<210> SEQ ID NO 545
<211> LENGTH: 23
<212> TYPE: DNA
<213> ORGANISM: Homo sapiens

<400> SEQUENCE: 545
ggtctggaac tcctgacctc agg                                             23

<210> SEQ ID NO 546
<211> LENGTH: 23
<212> TYPE: DNA
<213> ORGANISM: Homo sapiens

<400> SEQUENCE: 546
ctgctgcctg gtccccctgc agg                                             23

<210> SEQ ID NO 547
<211> LENGTH: 23
<212> TYPE: DNA
<213> ORGANISM: Homo sapiens

<400> SEQUENCE: 547
cgaggcgggt ggatcacctg agg                                             23

<210> SEQ ID NO 548
<211> LENGTH: 23
<212> TYPE: DNA
<213> ORGANISM: Homo sapiens

<400> SEQUENCE: 548
aaaccaggtg caaatcagag ggg                                             23

<210> SEQ ID NO 549
<211> LENGTH: 23
<212> TYPE: DNA
<213> ORGANISM: Homo sapiens

<400> SEQUENCE: 549
aaacacagtt tcaaaaggtc agg                                             23
```

```
<210> SEQ ID NO 550
<211> LENGTH: 23
<212> TYPE: DNA
<213> ORGANISM: Homo sapiens

<400> SEQUENCE: 550
tttcatcttc tggggctccc agg                                              23

<210> SEQ ID NO 551
<211> LENGTH: 23
<212> TYPE: DNA
<213> ORGANISM: Homo sapiens

<400> SEQUENCE: 551
ttcccagagg agataggagc tgg                                              23

<210> SEQ ID NO 552
<211> LENGTH: 23
<212> TYPE: DNA
<213> ORGANISM: Homo sapiens

<400> SEQUENCE: 552
tgggagcccc agaagatgaa agg                                              23

<210> SEQ ID NO 553
<211> LENGTH: 23
<212> TYPE: DNA
<213> ORGANISM: Homo sapiens

<400> SEQUENCE: 553
tcttttctca ttccccttag tgg                                              23

<210> SEQ ID NO 554
<211> LENGTH: 23
<212> TYPE: DNA
<213> ORGANISM: Homo sapiens

<400> SEQUENCE: 554
tatttgtctt ggggtaagga agg                                              23

<210> SEQ ID NO 555
<211> LENGTH: 23
<212> TYPE: DNA
<213> ORGANISM: Homo sapiens

<400> SEQUENCE: 555
gtttgtaatc ccaacacttt ggg                                              23

<210> SEQ ID NO 556
<211> LENGTH: 23
<212> TYPE: DNA
<213> ORGANISM: Homo sapiens

<400> SEQUENCE: 556
gcctgggtcc tcgggcctcc tgg                                              23

<210> SEQ ID NO 557
<211> LENGTH: 23
<212> TYPE: DNA
<213> ORGANISM: Homo sapiens

<400> SEQUENCE: 557
caggtgcgtc ccaccacacc cgg                                              23
```

<210> SEQ ID NO 558
<211> LENGTH: 23
<212> TYPE: DNA
<213> ORGANISM: Homo sapiens

<400> SEQUENCE: 558
atcattgttc cctggaaagg tgg                                          23

<210> SEQ ID NO 559
<211> LENGTH: 23
<212> TYPE: DNA
<213> ORGANISM: Homo sapiens

<400> SEQUENCE: 559
aatgaataaa aataagggtc ggg                                          23

<210> SEQ ID NO 560
<211> LENGTH: 23
<212> TYPE: DNA
<213> ORGANISM: Homo sapiens

<400> SEQUENCE: 560
aaaaccaggt gcaaatcaga ggg                                          23

<210> SEQ ID NO 561
<211> LENGTH: 23
<212> TYPE: DNA
<213> ORGANISM: Homo sapiens

<400> SEQUENCE: 561
tttaagtaat gagatgggag ggg                                          23

<210> SEQ ID NO 562
<211> LENGTH: 23
<212> TYPE: DNA
<213> ORGANISM: Homo sapiens

<400> SEQUENCE: 562
ttcaaataaa gaacagggct ggg                                          23

<210> SEQ ID NO 563
<211> LENGTH: 23
<212> TYPE: DNA
<213> ORGANISM: Homo sapiens

<400> SEQUENCE: 563
tgaggcagag ggatcacctg agg                                          23

<210> SEQ ID NO 564
<211> LENGTH: 23
<212> TYPE: DNA
<213> ORGANISM: Homo sapiens

<400> SEQUENCE: 564
tcactgcagc ctcaatctct tgg                                          23

<210> SEQ ID NO 565
<211> LENGTH: 23
<212> TYPE: DNA
<213> ORGANISM: Homo sapiens

<400> SEQUENCE: 565
gagacccaga caccctgcag ggg                                              23

<210> SEQ ID NO 566
<211> LENGTH: 23
<212> TYPE: DNA
<213> ORGANISM: Homo sapiens

<400> SEQUENCE: 566
gaaaataagg atatctggga tgg                                              23

<210> SEQ ID NO 567
<211> LENGTH: 23
<212> TYPE: DNA
<213> ORGANISM: Homo sapiens

<400> SEQUENCE: 567
ctgcctactg agacaggagg agg                                              23

<210> SEQ ID NO 568
<211> LENGTH: 23
<212> TYPE: DNA
<213> ORGANISM: Homo sapiens

<400> SEQUENCE: 568
cctgagcctg gcacagtaca ggg                                              23

<210> SEQ ID NO 569
<211> LENGTH: 23
<212> TYPE: DNA
<213> ORGANISM: Homo sapiens

<400> SEQUENCE: 569
caggagaatc acttgaacct ggg                                              23

<210> SEQ ID NO 570
<211> LENGTH: 23
<212> TYPE: DNA
<213> ORGANISM: Homo sapiens

<400> SEQUENCE: 570
acctcagcct cctgagtacc tgg                                              23

<210> SEQ ID NO 571
<211> LENGTH: 23
<212> TYPE: DNA
<213> ORGANISM: Homo sapiens

<400> SEQUENCE: 571
aatatatttg tcttggggta agg                                              23

<210> SEQ ID NO 572
<211> LENGTH: 23
<212> TYPE: DNA
<213> ORGANISM: Homo sapiens

<400> SEQUENCE: 572
tcttgaggca ggaagaggtc agg                                              23

<210> SEQ ID NO 573
<211> LENGTH: 23
<212> TYPE: DNA
<213> ORGANISM: Homo sapiens

<400> SEQUENCE: 573
tcccagggaa tcaggagtcc tgg								23

<210> SEQ ID NO 574
<211> LENGTH: 23
<212> TYPE: DNA
<213> ORGANISM: Homo sapiens

<400> SEQUENCE: 574
gtgtcacccg ggctggagta cgg								23

<210> SEQ ID NO 575
<211> LENGTH: 23
<212> TYPE: DNA
<213> ORGANISM: Homo sapiens

<400> SEQUENCE: 575
gggagcccca gaagatgaaa ggg								23

<210> SEQ ID NO 576
<211> LENGTH: 23
<212> TYPE: DNA
<213> ORGANISM: Homo sapiens

<400> SEQUENCE: 576
gcctctgcct cagaagttcc tgg								23

<210> SEQ ID NO 577
<211> LENGTH: 23
<212> TYPE: DNA
<213> ORGANISM: Homo sapiens

<400> SEQUENCE: 577
ctcttggttg cccaggccag agg								23

<210> SEQ ID NO 578
<211> LENGTH: 23
<212> TYPE: DNA
<213> ORGANISM: Homo sapiens

<400> SEQUENCE: 578
ctcttagctc ctgagagaag agg								23

<210> SEQ ID NO 579
<211> LENGTH: 23
<212> TYPE: DNA
<213> ORGANISM: Homo sapiens

<400> SEQUENCE: 579
ctccctcctc ctgtctcagt agg								23

<210> SEQ ID NO 580
<211> LENGTH: 23
<212> TYPE: DNA
<213> ORGANISM: Homo sapiens

<400> SEQUENCE: 580
ctcaggtgat gcacccacct tgg								23

<210> SEQ ID NO 581
<211> LENGTH: 23
<212> TYPE: DNA
<213> ORGANISM: Homo sapiens

```
<400> SEQUENCE: 581
cctcccaaag tgctgggcct cgg                                              23

<210> SEQ ID NO 582
<211> LENGTH: 23
<212> TYPE: DNA
<213> ORGANISM: Homo sapiens

<400> SEQUENCE: 582
cccaggaggc ccgaggaccc agg                                              23

<210> SEQ ID NO 583
<211> LENGTH: 23
<212> TYPE: DNA
<213> ORGANISM: Homo sapiens

<400> SEQUENCE: 583
ccaggctact cttgaactct tgg                                              23

<210> SEQ ID NO 584
<211> LENGTH: 23
<212> TYPE: DNA
<213> ORGANISM: Homo sapiens

<400> SEQUENCE: 584
caggcacaca ccacaatgcc cgg                                              23

<210> SEQ ID NO 585
<211> LENGTH: 23
<212> TYPE: DNA
<213> ORGANISM: Homo sapiens

<400> SEQUENCE: 585
caacaaaagg agagtggatg ggg                                              23

<210> SEQ ID NO 586
<211> LENGTH: 23
<212> TYPE: DNA
<213> ORGANISM: Homo sapiens

<400> SEQUENCE: 586
attcttatat gggaggggga tgg                                              23

<210> SEQ ID NO 587
<211> LENGTH: 23
<212> TYPE: DNA
<213> ORGANISM: Homo sapiens

<400> SEQUENCE: 587 agaaagggt gactcacaga ggg                                               23

<210> SEQ ID NO 588
<211> LENGTH: 23
<212> TYPE: DNA
<213> ORGANISM: Homo sapiens

<400> SEQUENCE: 588
tttttaagta atgagatggg agg                                              23

<210> SEQ ID NO 589
<211> LENGTH: 23
<212> TYPE: DNA
```

```
<400> SEQUENCE: 589
tgcctactga gacaggagga ggg                                          23

<210> SEQ ID NO 590
<211> LENGTH: 23
<212> TYPE: DNA
<213> ORGANISM: Homo sapiens

<400> SEQUENCE: 590
tctcatttcc cagaggagat agg                                          23

<210> SEQ ID NO 591
<211> LENGTH: 23
<212> TYPE: DNA
<213> ORGANISM: Homo sapiens

<400> SEQUENCE: 591
gggggaccag gcagcaggtt tgg                                          23

<210> SEQ ID NO 592
<211> LENGTH: 23
<212> TYPE: DNA
<213> ORGANISM: Homo sapiens

<400> SEQUENCE: 592
gctatttaaa attagagttc tgg                                          23

<210> SEQ ID NO 593
<211> LENGTH: 23
<212> TYPE: DNA
<213> ORGANISM: Homo sapiens

<400> SEQUENCE: 593
cctgattccc tgggaaaagg ggg                                          23

<210> SEQ ID NO 594
<211> LENGTH: 23
<212> TYPE: DNA
<213> ORGANISM: Homo sapiens

<400> SEQUENCE: 594
caggagaatc ccttgaaccc agg                                          23

<210> SEQ ID NO 595
<211> LENGTH: 23
<212> TYPE: DNA
<213> ORGANISM: Homo sapiens

<400> SEQUENCE: 595
cagagggatc acctgaggtc agg                                          23

<210> SEQ ID NO 596
<211> LENGTH: 23
<212> TYPE: DNA
<213> ORGANISM: Homo sapiens

<400> SEQUENCE: 596
agattcccga aagaggaagg agg                                          23

<210> SEQ ID NO 597
<211> LENGTH: 23
<212> TYPE: DNA
```

<213> ORGANISM: Homo sapiens

<400> SEQUENCE: 597
cttagcactt tgggaggccg agg                                              23

<210> SEQ ID NO 598
<211> LENGTH: 23
<212> TYPE: DNA
<213> ORGANISM: Homo sapiens

<400> SEQUENCE: 598
accaggaact tctgaggcag agg                                              23

<210> SEQ ID NO 599
<211> LENGTH: 23
<212> TYPE: DNA
<213> ORGANISM: Homo sapiens

<400> SEQUENCE: 599
tcctgattcc ctgggaaaag ggg                                              23

<210> SEQ ID NO 600
<211> LENGTH: 23
<212> TYPE: DNA
<213> ORGANISM: Homo sapiens

<400> SEQUENCE: 600
tcccagctcc tatctcctct ggg                                              23

<210> SEQ ID NO 601
<211> LENGTH: 23
<212> TYPE: DNA
<213> ORGANISM: Homo sapiens

<400> SEQUENCE: 601
gccaggactc ctgattccct ggg                                              23

<210> SEQ ID NO 602
<211> LENGTH: 23
<212> TYPE: DNA
<213> ORGANISM: Homo sapiens

<400> SEQUENCE: 602
catcttctgg ggctcccagg agg                                              23

<210> SEQ ID NO 603
<211> LENGTH: 23
<212> TYPE: DNA
<213> ORGANISM: Homo sapiens

<400> SEQUENCE: 603
aaaaattagc cgggtgtggt ggg                                              23

<210> SEQ ID NO 604
<211> LENGTH: 23
<212> TYPE: DNA
<213> ORGANISM: Homo sapiens

<400> SEQUENCE: 604
ttgttttggg aaatggtatg agg                                              23

<210> SEQ ID NO 605
<211> LENGTH: 23

```
<212> TYPE: DNA
<213> ORGANISM: Homo sapiens

<400> SEQUENCE: 605
ttccctggga aaggggggct ggg                                          23

<210> SEQ ID NO 606
<211> LENGTH: 23
<212> TYPE: DNA
<213> ORGANISM: Homo sapiens

<400> SEQUENCE: 606
tgctgcctgg tccccctgca ggg                                          23

<210> SEQ ID NO 607
<211> LENGTH: 23
<212> TYPE: DNA
<213> ORGANISM: Homo sapiens

<400> SEQUENCE: 607
tcccgaaaga ggaaggaggt ggg                                          23

<210> SEQ ID NO 608
<211> LENGTH: 23
<212> TYPE: DNA
<213> ORGANISM: Homo sapiens

<400> SEQUENCE: 608
gcctgaactc ttggttgccc agg                                          23

<210> SEQ ID NO 609
<211> LENGTH: 23
<212> TYPE: DNA
<213> ORGANISM: Homo sapiens

<400> SEQUENCE: 609
attaatctgg aagttgtttt ggg                                          23

<210> SEQ ID NO 610
<211> LENGTH: 23
<212> TYPE: DNA
<213> ORGANISM: Homo sapiens

<400> SEQUENCE: 610
atgctaaaag acaaaactag agg                                          23

<210> SEQ ID NO 611
<211> LENGTH: 23
<212> TYPE: DNA
<213> ORGANISM: Homo sapiens

<400> SEQUENCE: 611
actcctgatt ccctgggaaa agg                                          23

<210> SEQ ID NO 612
<211> LENGTH: 23
<212> TYPE: DNA
<213> ORGANISM: Homo sapiens

<400> SEQUENCE: 612
acggggctgc ctgggtcctc ggg                                          23

<210> SEQ ID NO 613
```

```
<211> LENGTH: 23
<212> TYPE: DNA
<213> ORGANISM: Homo sapiens

<400> SEQUENCE: 613
aattaatctg gaagttgttt tgg                                              23

<210> SEQ ID NO 614
<211> LENGTH: 23
<212> TYPE: DNA
<213> ORGANISM: Homo sapiens

<400> SEQUENCE: 614
ttaagtaatg agatgggagg ggg                                              23

<210> SEQ ID NO 615
<211> LENGTH: 23
<212> TYPE: DNA
<213> ORGANISM: Homo sapiens

<400> SEQUENCE: 615
gagatgggat tttaccatgt tgg                                              23

<210> SEQ ID NO 616
<211> LENGTH: 23
<212> TYPE: DNA
<213> ORGANISM: Homo sapiens

<400> SEQUENCE: 616
ctcctgattc cctgggaaaa ggg                                              23

<210> SEQ ID NO 617
<211> LENGTH: 23
<212> TYPE: DNA
<213> ORGANISM: Homo sapiens

<400> SEQUENCE: 617
caaccacctc ctgggttcaa ggg                                              23

<210> SEQ ID NO 618
<211> LENGTH: 23
<212> TYPE: DNA
<213> ORGANISM: Homo sapiens

<400> SEQUENCE: 618
agtttcctgt ttgtaaaatc agg                                              23

<210> SEQ ID NO 619
<211> LENGTH: 23
<212> TYPE: DNA
<213> ORGANISM: Homo sapiens

<400> SEQUENCE: 619
aaaaaaaaat tagccgggtg tgg                                              23

<210> SEQ ID NO 620
<211> LENGTH: 23
<212> TYPE: DNA
<213> ORGANISM: Homo sapiens

<400> SEQUENCE: 620
tggggctccc aggaggcccg agg                                              23
```

```
<210> SEQ ID NO 621
<211> LENGTH: 23
<212> TYPE: DNA
<213> ORGANISM: Homo sapiens

<400> SEQUENCE: 621
tcttagctcc tgagagaaga ggg                                              23

<210> SEQ ID NO 622
<211> LENGTH: 23
<212> TYPE: DNA
<213> ORGANISM: Homo sapiens

<400> SEQUENCE: 622
tagaggacaa atgatagtac tgg                                              23

<210> SEQ ID NO 623
<211> LENGTH: 23
<212> TYPE: DNA
<213> ORGANISM: Homo sapiens

<400> SEQUENCE: 623
taataaaatt acagagttct ggg                                              23

<210> SEQ ID NO 624
<211> LENGTH: 23
<212> TYPE: DNA
<213> ORGANISM: Homo sapiens

<400> SEQUENCE: 624
gcatgcactt tgggaggctg agg                                              23

<210> SEQ ID NO 625
<211> LENGTH: 23
<212> TYPE: DNA
<213> ORGANISM: Homo sapiens

<400> SEQUENCE: 625
gagacagggt ttccccatgt tgg                                              23

<210> SEQ ID NO 626
<211> LENGTH: 23
<212> TYPE: DNA
<213> ORGANISM: Homo sapiens

<400> SEQUENCE: 626
cgaggtggga ggattgcttg agg                                              23

<210> SEQ ID NO 627
<211> LENGTH: 23
<212> TYPE: DNA
<213> ORGANISM: Homo sapiens

<400> SEQUENCE: 627
ataagattct catttcccag agg                                              23

<210> SEQ ID NO 628
<211> LENGTH: 23
<212> TYPE: DNA
<213> ORGANISM: Homo sapiens

<400> SEQUENCE: 628
aacggggctg cctgggtcct cgg                                              23
```

```
<210> SEQ ID NO 629
<211> LENGTH: 23
<212> TYPE: DNA
<213> ORGANISM: Homo sapiens

<400> SEQUENCE: 629
aaaaaattag ccgggtgtgg tgg                                            23

<210> SEQ ID NO 630
<211> LENGTH: 23
<212> TYPE: DNA
<213> ORGANISM: Homo sapiens

<400> SEQUENCE: 630
ggagacccag acaccctgca ggg                                            23

<210> SEQ ID NO 631
<211> LENGTH: 23
<212> TYPE: DNA
<213> ORGANISM: Homo sapiens

<400> SEQUENCE: 631
gcaccactgc actccggcct ggg                                            23

<210> SEQ ID NO 632
<211> LENGTH: 23
<212> TYPE: DNA
<213> ORGANISM: Homo sapiens

<400> SEQUENCE: 632
ccaacttccc tttcatcttc tgg                                            23

<210> SEQ ID NO 633
<211> LENGTH: 23
<212> TYPE: DNA
<213> ORGANISM: Homo sapiens

<400> SEQUENCE: 633
atgggagggg gatggaagcc agg                                            23

<210> SEQ ID NO 634
<211> LENGTH: 23
<212> TYPE: DNA
<213> ORGANISM: Homo sapiens

<400> SEQUENCE: 634
agtcacccct ttcttctccc tgg                                            23

<210> SEQ ID NO 635
<211> LENGTH: 23
<212> TYPE: DNA
<213> ORGANISM: Homo sapiens

<400> SEQUENCE: 635
aatctgtgtt ctcttgcttt agg                                            23

<210> SEQ ID NO 636
<211> LENGTH: 23
<212> TYPE: DNA
<213> ORGANISM: Homo sapiens

<400> SEQUENCE: 636
aacttccctt tcatcttctg ggg                                            23
```

```
<210> SEQ ID NO 637
<211> LENGTH: 23
<212> TYPE: DNA
<213> ORGANISM: Homo sapiens

<400> SEQUENCE: 637
tgtcagcaac aaaaggagag tgg                                              23

<210> SEQ ID NO 638
<211> LENGTH: 23
<212> TYPE: DNA
<213> ORGANISM: Homo sapiens

<400> SEQUENCE: 638
gttcccagcc cccttttccc agg                                              23

<210> SEQ ID NO 639
<211> LENGTH: 23
<212> TYPE: DNA
<213> ORGANISM: Homo sapiens

<400> SEQUENCE: 639
ggagtgcagt ggtgcaatct cgg                                              23

<210> SEQ ID NO 640
<211> LENGTH: 23
<212> TYPE: DNA
<213> ORGANISM: Homo sapiens

<400> SEQUENCE: 640
ctaggttcaa ataaagaaca ggg                                              23

<210> SEQ ID NO 641
<211> LENGTH: 23
<212> TYPE: DNA
<213> ORGANISM: Homo sapiens

<400> SEQUENCE: 641
atactatatt gcaaatattc tgg                                              23

<210> SEQ ID NO 642
<211> LENGTH: 23
<212> TYPE: DNA
<213> ORGANISM: Homo sapiens

<400> SEQUENCE: 642
agacccagac accctgcagg ggg                                              23

<210> SEQ ID NO 643
<211> LENGTH: 23
<212> TYPE: DNA
<213> ORGANISM: Homo sapiens

<400> SEQUENCE: 643 aaagggtgt cagcaacaaa agg                                               23

<210> SEQ ID NO 644
<211> LENGTH: 23
<212> TYPE: DNA
<213> ORGANISM: Homo sapiens

<400> SEQUENCE: 644
```
ttgctcaggc aggagtgcag tgg                                          23

<210> SEQ ID NO 645
<211> LENGTH: 23
<212> TYPE: DNA
<213> ORGANISM: Homo sapiens

<400> SEQUENCE: 645
taaaaataca aagattagcc tgg                                          23

<210> SEQ ID NO 646
<211> LENGTH: 23
<212> TYPE: DNA
<213> ORGANISM: Homo sapiens

<400> SEQUENCE: 646
ggggaccagg cagcaggttt ggg                                          23

<210> SEQ ID NO 647
<211> LENGTH: 23
<212> TYPE: DNA
<213> ORGANISM: Homo sapiens

<400> SEQUENCE: 647
gcaggaagag gtcaggagac agg                                          23

<210> SEQ ID NO 648
<211> LENGTH: 23
<212> TYPE: DNA
<213> ORGANISM: Homo sapiens

<400> SEQUENCE: 648
gagaatcact tgaacctggg agg                                          23

<210> SEQ ID NO 649
<211> LENGTH: 23
<212> TYPE: DNA
<213> ORGANISM: Homo sapiens

<400> SEQUENCE: 649
ctggttcttg aggcaggaag agg                                          23

<210> SEQ ID NO 650
<211> LENGTH: 23
<212> TYPE: DNA
<213> ORGANISM: Homo sapiens

<400> SEQUENCE: 650
cacagagggt cagcagctgg agg                                          23

<210> SEQ ID NO 651
<211> LENGTH: 23
<212> TYPE: DNA
<213> ORGANISM: Homo sapiens

<400> SEQUENCE: 651
caacttccct ttcatcttct ggg                                          23

<210> SEQ ID NO 652
<211> LENGTH: 23
<212> TYPE: DNA
<213> ORGANISM: Homo sapiens

<400> SEQUENCE: 652

```
aaaatctgag taattggaaa agg                                              23

<210> SEQ ID NO 653
<211> LENGTH: 23
<212> TYPE: DNA
<213> ORGANISM: Homo sapiens

<400> SEQUENCE: 653
ttcccagccc cctttccca ggg                                               23

<210> SEQ ID NO 654
<211> LENGTH: 23
<212> TYPE: DNA
<213> ORGANISM: Homo sapiens

<400> SEQUENCE: 654
tggcatgtgc ctgtggtccc agg                                              23

<210> SEQ ID NO 655
<211> LENGTH: 23
<212> TYPE: DNA
<213> ORGANISM: Homo sapiens

<400> SEQUENCE: 655
ggggtctcat tgtgtcaccc ggg                                              23

<210> SEQ ID NO 656
<211> LENGTH: 23
<212> TYPE: DNA
<213> ORGANISM: Homo sapiens

<400> SEQUENCE: 656
gggctggggc ccagacccct ggg                                              23

<210> SEQ ID NO 657
<211> LENGTH: 23
<212> TYPE: DNA
<213> ORGANISM: Homo sapiens

<400> SEQUENCE: 657
ctcaggtgat ccacccgcct cgg                                              23

<210> SEQ ID NO 658
<211> LENGTH: 23
<212> TYPE: DNA
<213> ORGANISM: Homo sapiens

<400> SEQUENCE: 658
cagaagatga aagggaagtt ggg                                              23

<210> SEQ ID NO 659
<211> LENGTH: 23
<212> TYPE: DNA
<213> ORGANISM: Homo sapiens

<400> SEQUENCE: 659
cacttgaacc tgggaggcag agg                                              23

<210> SEQ ID NO 660
<211> LENGTH: 23
<212> TYPE: DNA
<213> ORGANISM: Homo sapiens
```

<400> SEQUENCE: 660
caaaataaaa tctgagtaat tgg                                            23

<210> SEQ ID NO 661
<211> LENGTH: 23
<212> TYPE: DNA
<213> ORGANISM: Homo sapiens

<400> SEQUENCE: 661
tgggttcctg gctggggttg ggg                                            23

<210> SEQ ID NO 662
<211> LENGTH: 23
<212> TYPE: DNA
<213> ORGANISM: Homo sapiens

<400> SEQUENCE: 662
gcctcagcct cccaaagtgt tgg                                            23

<210> SEQ ID NO 663
<211> LENGTH: 23
<212> TYPE: DNA
<213> ORGANISM: Homo sapiens

<400> SEQUENCE: 663
ctggaagttg ttttgggaaa tgg                                            23

<210> SEQ ID NO 664
<211> LENGTH: 23
<212> TYPE: DNA
<213> ORGANISM: Homo sapiens

<400> SEQUENCE: 664
cccgaaagag gaaggaggtg ggg                                            23

<210> SEQ ID NO 665
<211> LENGTH: 23
<212> TYPE: DNA
<213> ORGANISM: Homo sapiens

<400> SEQUENCE: 665
caaaaggaga gtggatgggg tgg                                            23

<210> SEQ ID NO 666
<211> LENGTH: 23
<212> TYPE: DNA
<213> ORGANISM: Homo sapiens

<400> SEQUENCE: 666
ataataaaat tacagagttc tgg                                            23

<210> SEQ ID NO 667
<211> LENGTH: 23
<212> TYPE: DNA
<213> ORGANISM: Homo sapiens

<400> SEQUENCE: 667
agcaacaaaa ggagagtgga tgg                                            23

<210> SEQ ID NO 668
<211> LENGTH: 23
<212> TYPE: DNA
<213> ORGANISM: Homo sapiens

```
<400> SEQUENCE: 668
tccccacctc cttcctcttt cgg                                              23

<210> SEQ ID NO 669
<211> LENGTH: 23
<212> TYPE: DNA
<213> ORGANISM: Homo sapiens

<400> SEQUENCE: 669
gcaacaaaag gagagtggat ggg                                              23

<210> SEQ ID NO 670
<211> LENGTH: 23
<212> TYPE: DNA
<213> ORGANISM: Homo sapiens

<400> SEQUENCE: 670
cttctccctg ggttcctggc tgg                                              23

<210> SEQ ID NO 671
<211> LENGTH: 23
<212> TYPE: DNA
<213> ORGANISM: Homo sapiens

<400> SEQUENCE: 671
agggtttccc catgttggtc agg                                              23

<210> SEQ ID NO 672
<211> LENGTH: 23
<212> TYPE: DNA
<213> ORGANISM: Homo sapiens

<400> SEQUENCE: 672
agggctgggg cccagacccc tgg                                              23

<210> SEQ ID NO 673
<211> LENGTH: 23
<212> TYPE: DNA
<213> ORGANISM: Homo sapiens

<400> SEQUENCE: 673
ttgtaaaatc agggagagac tgg                                              23

<210> SEQ ID NO 674
<211> LENGTH: 23
<212> TYPE: DNA
<213> ORGANISM: Homo sapiens

<400> SEQUENCE: 674
gtttcctgtt tgtaaaatca ggg                                              23

<210> SEQ ID NO 675
<211> LENGTH: 23
<212> TYPE: DNA
<213> ORGANISM: Homo sapiens

<400> SEQUENCE: 675
ctttcttctc cctgggttcc tgg                                              23

<210> SEQ ID NO 676
<211> LENGTH: 23
<212> TYPE: DNA
```

```
<213> ORGANISM: Homo sapiens

<400> SEQUENCE: 676
ctgcaggggg accaggcagc agg                                            23

<210> SEQ ID NO 677
<211> LENGTH: 23
<212> TYPE: DNA
<213> ORGANISM: Homo sapiens

<400> SEQUENCE: 677
caagagaatc gcttgaaccc agg                                            23

<210> SEQ ID NO 678
<211> LENGTH: 23
<212> TYPE: DNA
<213> ORGANISM: Homo sapiens

<400> SEQUENCE: 678
acaacttaag aaatttgaag tgg                                            23

<210> SEQ ID NO 679
<211> LENGTH: 23
<212> TYPE: DNA
<213> ORGANISM: Homo sapiens

<400> SEQUENCE: 679
aaaaaaaagt ctgggtgtgg tgg                                            23

<210> SEQ ID NO 680
<211> LENGTH: 23
<212> TYPE: DNA
<213> ORGANISM: Homo sapiens

<400> SEQUENCE: 680
tttgtaaaca cagtttcaaa agg                                            23

<210> SEQ ID NO 681
<211> LENGTH: 23
<212> TYPE: DNA
<213> ORGANISM: Homo sapiens

<400> SEQUENCE: 681
tcctgagaga agagggaaat ggg                                            23

<210> SEQ ID NO 682
<211> LENGTH: 23
<212> TYPE: DNA
<213> ORGANISM: Homo sapiens

<400> SEQUENCE: 682
gggaaaaggg ggctgggaac agg                                            23

<210> SEQ ID NO 683
<211> LENGTH: 23
<212> TYPE: DNA
<213> ORGANISM: Homo sapiens

<400> SEQUENCE: 683
ggcgcagcgg ctcatgcctg tgg                                            23

<210> SEQ ID NO 684
<211> LENGTH: 23
```

```
<212> TYPE: DNA
<213> ORGANISM: Homo sapiens

<400> SEQUENCE: 684
ggaaactgag gctaagaaag ggg                                            23

<210> SEQ ID NO 685
<211> LENGTH: 23
<212> TYPE: DNA
<213> ORGANISM: Homo sapiens

<400> SEQUENCE: 685
gcctcagcct cctgagtagc tgg                                            23

<210> SEQ ID NO 686
<211> LENGTH: 23
<212> TYPE: DNA
<213> ORGANISM: Homo sapiens

<400> SEQUENCE: 686
gatgaaaggg aagttgggga agg                                            23

<210> SEQ ID NO 687
<211> LENGTH: 23
<212> TYPE: DNA
<213> ORGANISM: Homo sapiens

<400> SEQUENCE: 687
agtaatgaga tgggaggggg cgg                                            23

<210> SEQ ID NO 688
<211> LENGTH: 23
<212> TYPE: DNA
<213> ORGANISM: Homo sapiens

<400> SEQUENCE: 688
ttatttttaa gtaatgagat ggg                                            23

<210> SEQ ID NO 689
<211> LENGTH: 23
<212> TYPE: DNA
<213> ORGANISM: Homo sapiens

<400> SEQUENCE: 689
tactgcaacc tctgcctcct ggg                                            23

<210> SEQ ID NO 690
<211> LENGTH: 23
<212> TYPE: DNA
<213> ORGANISM: Homo sapiens

<400> SEQUENCE: 690
ccccatttcc ctcttctctc agg                                            23

<210> SEQ ID NO 691
<211> LENGTH: 23
<212> TYPE: DNA
<213> ORGANISM: Homo sapiens

<400> SEQUENCE: 691
caaccccagc caggaaccca ggg                                            23

<210> SEQ ID NO 692
```

```
<211> LENGTH: 23
<212> TYPE: DNA
<213> ORGANISM: Homo sapiens

<400> SEQUENCE: 692
aggaaactga ggctaagaaa ggg                                              23

<210> SEQ ID NO 693
<211> LENGTH: 23
<212> TYPE: DNA
<213> ORGANISM: Homo sapiens

<400> SEQUENCE: 693
aatcccttga acccaggagg tgg                                              23

<210> SEQ ID NO 694
<211> LENGTH: 23
<212> TYPE: DNA
<213> ORGANISM: Homo sapiens

<400> SEQUENCE: 694
aaatctgagt aattggaaaa ggg                                              23

<210> SEQ ID NO 695
<211> LENGTH: 23
<212> TYPE: DNA
<213> ORGANISM: Homo sapiens

<400> SEQUENCE: 695
aaaagtattc aaaaaactat agg                                              23

<210> SEQ ID NO 696
<211> LENGTH: 23
<212> TYPE: DNA
<213> ORGANISM: Homo sapiens

<400> SEQUENCE: 696
tcctgagtag ctgggattac agg                                              23

<210> SEQ ID NO 697
<211> LENGTH: 23
<212> TYPE: DNA
<213> ORGANISM: Homo sapiens

<400> SEQUENCE: 697
gcctctgcct cccaaagtgc tgg                                              23

<210> SEQ ID NO 698
<211> LENGTH: 23
<212> TYPE: DNA
<213> ORGANISM: Homo sapiens

<400> SEQUENCE: 698
cctgagagaa gagggaaatg ggg                                              23

<210> SEQ ID NO 699
<211> LENGTH: 23
<212> TYPE: DNA
<213> ORGANISM: Homo sapiens

<400> SEQUENCE: 699
ccctgtactg tgccaggctc agg                                              23
```

```
<210> SEQ ID NO 700
<211> LENGTH: 23
<212> TYPE: DNA
<213> ORGANISM: Homo sapiens

<400> SEQUENCE: 700
ctttgggagg cagaggcggg cgg                                              23

<210> SEQ ID NO 701
<211> LENGTH: 23
<212> TYPE: DNA
<213> ORGANISM: Homo sapiens

<400> SEQUENCE: 701
ctactgagac aggaggaggg agg                                              23

<210> SEQ ID NO 702
<211> LENGTH: 23
<212> TYPE: DNA
<213> ORGANISM: Homo sapiens

<400> SEQUENCE: 702
ccagaagatg aaagggaagt tgg                                              23

<210> SEQ ID NO 703
<211> LENGTH: 23
<212> TYPE: DNA
<213> ORGANISM: Homo sapiens

<400> SEQUENCE: 703
caggaagagg tcaggagaca ggg                                              23

<210> SEQ ID NO 704
<211> LENGTH: 23
<212> TYPE: DNA
<213> ORGANISM: Homo sapiens

<400> SEQUENCE: 704
ataggaaaat atatttgtct tgg                                              23

<210> SEQ ID NO 705
<211> LENGTH: 23
<212> TYPE: DNA
<213> ORGANISM: Homo sapiens

<400> SEQUENCE: 705
aggaaaatat atttgtcttg ggg                                              23

<210> SEQ ID NO 706
<211> LENGTH: 23
<212> TYPE: DNA
<213> ORGANISM: Homo sapiens

<400> SEQUENCE: 706
ttctccctgg gttcctggct ggg                                              23

<210> SEQ ID NO 707
<211> LENGTH: 23
<212> TYPE: DNA
<213> ORGANISM: Homo sapiens

<400> SEQUENCE: 707
taggaaaata tatttgtctt ggg                                              23
```

```
<210> SEQ ID NO 708
<211> LENGTH: 23
<212> TYPE: DNA
<213> ORGANISM: Homo sapiens

<400> SEQUENCE: 708
ggaaaagggg gctgggaaca ggg                                   23

<210> SEQ ID NO 709
<211> LENGTH: 23
<212> TYPE: DNA
<213> ORGANISM: Homo sapiens

<400> SEQUENCE: 709
ctttgggagg ccgaggcggg tgg                                   23

<210> SEQ ID NO 710
<211> LENGTH: 23
<212> TYPE: DNA
<213> ORGANISM: Homo sapiens

<400> SEQUENCE: 710
cctcagcctc ctgagtacct ggg                                   23

<210> SEQ ID NO 711
<211> LENGTH: 23
<212> TYPE: DNA
<213> ORGANISM: Homo sapiens

<400> SEQUENCE: 711
cctcagcctc ccaaagtgtt ggg                                   23

<210> SEQ ID NO 712
<211> LENGTH: 23
<212> TYPE: DNA
<213> ORGANISM: Homo sapiens

<400> SEQUENCE: 712
ccaaccccag ccaggaaccc agg                                   23

<210> SEQ ID NO 713
<211> LENGTH: 23
<212> TYPE: DNA
<213> ORGANISM: Homo sapiens

<400> SEQUENCE: 713
caggaaccca gggagaagaa agg                                   23

<210> SEQ ID NO 714
<211> LENGTH: 23
<212> TYPE: DNA
<213> ORGANISM: Homo sapiens

<400> SEQUENCE: 714
caggaaactg aggctaagaa agg                                   23

<210> SEQ ID NO 715
<211> LENGTH: 23
<212> TYPE: DNA
<213> ORGANISM: Homo sapiens

<400> SEQUENCE: 715
cacaccacta cactccagcc tgg                                   23
```

```
<210> SEQ ID NO 716
<211> LENGTH: 23
<212> TYPE: DNA
<213> ORGANISM: Homo sapiens

<400> SEQUENCE: 716
attattttta agtaatgaga tgg                                              23

<210> SEQ ID NO 717
<211> LENGTH: 23
<212> TYPE: DNA
<213> ORGANISM: Homo sapiens

<400> SEQUENCE: 717
ttttaagtaa tgagatggga ggg                                              23

<210> SEQ ID NO 718
<211> LENGTH: 23
<212> TYPE: DNA
<213> ORGANISM: Homo sapiens

<400> SEQUENCE: 718
ttcccgaaag aggaaggagg tgg                                              23

<210> SEQ ID NO 719
<211> LENGTH: 23
<212> TYPE: DNA
<213> ORGANISM: Homo sapiens

<400> SEQUENCE: 719
tgcaccactg cactccggcc tgg                                              23

<210> SEQ ID NO 720
<211> LENGTH: 23
<212> TYPE: DNA
<213> ORGANISM: Homo sapiens

<400> SEQUENCE: 720
gagaatcgct tgaacccagg agg                                              23

<210> SEQ ID NO 721
<211> LENGTH: 23
<212> TYPE: DNA
<213> ORGANISM: Homo sapiens

<400> SEQUENCE: 721
gaagaggtca ggagacaggg agg                                              23

<210> SEQ ID NO 722
<211> LENGTH: 23
<212> TYPE: DNA
<213> ORGANISM: Homo sapiens

<400> SEQUENCE: 722
atataaaata aaaagttgta tgg                                              23

<210> SEQ ID NO 723
<211> LENGTH: 23
<212> TYPE: DNA
<213> ORGANISM: Homo sapiens

<400> SEQUENCE: 723
```
agaagatgaa agggaagttg ggg                                              23

<210> SEQ ID NO 724
<211> LENGTH: 23
<212> TYPE: DNA
<213> ORGANISM: Homo sapiens

<400> SEQUENCE: 724
tttctctctg tcgcccaggc cgg                                              23

<210> SEQ ID NO 725
<211> LENGTH: 23
<212> TYPE: DNA
<213> ORGANISM: Homo sapiens

<400> SEQUENCE: 725
ttactgcaac ctctgcctcc tgg                                              23

<210> SEQ ID NO 726
<211> LENGTH: 23
<212> TYPE: DNA
<213> ORGANISM: Homo sapiens

<400> SEQUENCE: 726 gtcaccccctt tcttctccct ggg                                             23

<210> SEQ ID NO 727
<211> LENGTH: 23
<212> TYPE: DNA
<213> ORGANISM: Homo sapiens

<400> SEQUENCE: 727
ggggtttcgc catgttggtc agg                                              23

<210> SEQ ID NO 728
<211> LENGTH: 23
<212> TYPE: DNA
<213> ORGANISM: Homo sapiens

<400> SEQUENCE: 728
gagaatccct tgaacccagg agg                                              23

<210> SEQ ID NO 729
<211> LENGTH: 23
<212> TYPE: DNA
<213> ORGANISM: Homo sapiens

<400> SEQUENCE: 729
ctcctgagag aagagggaaa tgg                                              23

<210> SEQ ID NO 730
<211> LENGTH: 23
<212> TYPE: DNA
<213> ORGANISM: Homo sapiens

<400> SEQUENCE: 730
ctaaggggaa tgagaaaaga agg                                              23

<210> SEQ ID NO 731
<211> LENGTH: 23
<212> TYPE: DNA
<213> ORGANISM: Homo sapiens

<400> SEQUENCE: 731 tttctgttttt tagtagagat ggg                                          23

<210> SEQ ID NO 732
<211> LENGTH: 23
<212> TYPE: DNA
<213> ORGANISM: Homo sapiens

<400> SEQUENCE: 732
tcgcccaggc tggagtgtag tgg                                           23

<210> SEQ ID NO 733
<211> LENGTH: 23
<212> TYPE: DNA
<213> ORGANISM: Homo sapiens

<400> SEQUENCE: 733
gggttcctgg ctggggttgg ggg                                           23

<210> SEQ ID NO 734
<211> LENGTH: 23
<212> TYPE: DNA
<213> ORGANISM: Homo sapiens

<400> SEQUENCE: 734
gcactttggg aggcagaggc ggg                                           23

<210> SEQ ID NO 735
<211> LENGTH: 23
<212> TYPE: DNA
<213> ORGANISM: Homo sapiens

<400> SEQUENCE: 735
ccccacctcc ttcctctttc ggg                                           23

<210> SEQ ID NO 736
<211> LENGTH: 23
<212> TYPE: DNA
<213> ORGANISM: Homo sapiens

<400> SEQUENCE: 736
caattactca gattttattt tgg                                           23

<210> SEQ ID NO 737
<211> LENGTH: 23
<212> TYPE: DNA
<213> ORGANISM: Homo sapiens

<400> SEQUENCE: 737
attttacaaa caggaaactg agg                                           23

<210> SEQ ID NO 738
<211> LENGTH: 23
<212> TYPE: DNA
<213> ORGANISM: Homo sapiens

<400> SEQUENCE: 738
acttgtagtc ccagctacta cgg                                           23

<210> SEQ ID NO 739
<211> LENGTH: 23
<212> TYPE: DNA
<213> ORGANISM: Homo sapiens

```
<400> SEQUENCE: 739
aaaaaaaaaa agtctgggtg tgg                                            23

<210> SEQ ID NO 740
<211> LENGTH: 23
<212> TYPE: DNA
<213> ORGANISM: Homo sapiens

<400> SEQUENCE: 740
tgtaatccca gctactcagg agg                                            23

<210> SEQ ID NO 741
<211> LENGTH: 23
<212> TYPE: DNA
<213> ORGANISM: Homo sapiens

<400> SEQUENCE: 741
tggagggagg gaggaaaata agg                                            23

<210> SEQ ID NO 742
<211> LENGTH: 23
<212> TYPE: DNA
<213> ORGANISM: Homo sapiens

<400> SEQUENCE: 742
taaaaataca aaaattatcc ggg                                            23

<210> SEQ ID NO 743
<211> LENGTH: 23
<212> TYPE: DNA
<213> ORGANISM: Homo sapiens

<400> SEQUENCE: 743
ggggaatgag aaaagaagga agg                                            23

<210> SEQ ID NO 744
<211> LENGTH: 23
<212> TYPE: DNA
<213> ORGANISM: Homo sapiens

<400> SEQUENCE: 744
aggaacccag ggagaagaaa ggg                                            23

<210> SEQ ID NO 745
<211> LENGTH: 23
<212> TYPE: DNA
<213> ORGANISM: Homo sapiens

<400> SEQUENCE: 745
acaccactac actccagcct ggg                                            23

<210> SEQ ID NO 746
<211> LENGTH: 23
<212> TYPE: DNA
<213> ORGANISM: Homo sapiens

<400> SEQUENCE: 746
ttttattcat ttttagagat ggg                                            23

<210> SEQ ID NO 747
<211> LENGTH: 23
<212> TYPE: DNA
<213> ORGANISM: Homo sapiens
```

```
<400> SEQUENCE: 747
tctccctggg ttcctggctg ggg                                         23

<210> SEQ ID NO 748
<211> LENGTH: 23
<212> TYPE: DNA
<213> ORGANISM: Homo sapiens

<400> SEQUENCE: 748
tactgagaca ggaggaggga ggg                                         23

<210> SEQ ID NO 749
<211> LENGTH: 23
<212> TYPE: DNA
<213> ORGANISM: Homo sapiens

<400> SEQUENCE: 749
cactgcaacc tctgcctccc agg                                         23

<210> SEQ ID NO 750
<211> LENGTH: 23
<212> TYPE: DNA
<213> ORGANISM: Homo sapiens

<400> SEQUENCE: 750
agcactttgg gaggcagagg cgg                                         23

<210> SEQ ID NO 751
<211> LENGTH: 23
<212> TYPE: DNA
<213> ORGANISM: Homo sapiens

<400> SEQUENCE: 751
aaatgaataa aaataagggt cgg                                         23

<210> SEQ ID NO 752
<211> LENGTH: 23
<212> TYPE: DNA
<213> ORGANISM: Homo sapiens

<400> SEQUENCE: 752
tcctgagtag ctgggactac agg                                         23

<210> SEQ ID NO 753
<211> LENGTH: 23
<212> TYPE: DNA
<213> ORGANISM: Homo sapiens

<400> SEQUENCE: 753
cccagcactt tgggaggcag agg                                         23

<210> SEQ ID NO 754
<211> LENGTH: 23
<212> TYPE: DNA
<213> ORGANISM: Homo sapiens

<400> SEQUENCE: 754
tttattcatt tttagagatg ggg                                         23

<210> SEQ ID NO 755
<211> LENGTH: 23
<212> TYPE: DNA
```

<213> ORGANISM: Homo sapiens

<400> SEQUENCE: 755
ggaacccagg gagaagaaag ggg            23

<210> SEQ ID NO 756
<211> LENGTH: 23
<212> TYPE: DNA
<213> ORGANISM: Homo sapiens

<400> SEQUENCE: 756
gcaggagaat cacttgaacc tgg            23

<210> SEQ ID NO 757
<211> LENGTH: 23
<212> TYPE: DNA
<213> ORGANISM: Homo sapiens

<400> SEQUENCE: 757
gagattgcac cactgcactc cgg            23

<210> SEQ ID NO 758
<211> LENGTH: 23
<212> TYPE: DNA
<213> ORGANISM: Homo sapiens

<400> SEQUENCE: 758
ctttgggagg ctgaggcaga ggg            23

<210> SEQ ID NO 759
<211> LENGTH: 23
<212> TYPE: DNA
<213> ORGANISM: Homo sapiens

<400> SEQUENCE: 759
aagaggaagg aggtggggac agg            23

<210> SEQ ID NO 760
<211> LENGTH: 23
<212> TYPE: DNA
<213> ORGANISM: Homo sapiens

<400> SEQUENCE: 760
ctgggttcct ggctggggtt ggg            23

<210> SEQ ID NO 761
<211> LENGTH: 23
<212> TYPE: DNA
<213> ORGANISM: Homo sapiens

<400> SEQUENCE: 761
cctgggttcc tggctggggt tgg            23

<210> SEQ ID NO 762
<211> LENGTH: 23
<212> TYPE: DNA
<213> ORGANISM: Homo sapiens

<400> SEQUENCE: 762
tatttggaaa agaaaaatgt tgg            23

<210> SEQ ID NO 763
<211> LENGTH: 23

<212> TYPE: DNA
<213> ORGANISM: Homo sapiens

<400> SEQUENCE: 763
taaaaacaga aaaattagcc agg                                              23

<210> SEQ ID NO 764
<211> LENGTH: 23
<212> TYPE: DNA
<213> ORGANISM: Homo sapiens

<400> SEQUENCE: 764
ctttgggagg ccgaggtggg agg                                              23

<210> SEQ ID NO 765
<211> LENGTH: 23
<212> TYPE: DNA
<213> ORGANISM: Homo sapiens

<400> SEQUENCE: 765
ctcaagcaat cctcccacct cgg                                              23

<210> SEQ ID NO 766
<211> LENGTH: 23
<212> TYPE: DNA
<213> ORGANISM: Homo sapiens

<400> SEQUENCE: 766
ttttaccatg ttggtcaggc tgg                                              23

<210> SEQ ID NO 767
<211> LENGTH: 23
<212> TYPE: DNA
<213> ORGANISM: Homo sapiens

<400> SEQUENCE: 767
tcgcccaggc cggagtgcag tgg                                              23

<210> SEQ ID NO 768
<211> LENGTH: 23
<212> TYPE: DNA
<213> ORGANISM: Homo sapiens

<400> SEQUENCE: 768
ctaaaaatac aaaaattatc cgg                                              23

<210> SEQ ID NO 769
<211> LENGTH: 23
<212> TYPE: DNA
<213> ORGANISM: Homo sapiens

<400> SEQUENCE: 769
cccaggtact caggaggctg agg                                              23

<210> SEQ ID NO 770
<211> LENGTH: 23
<212> TYPE: DNA
<213> ORGANISM: Homo sapiens

<400> SEQUENCE: 770
catttccttc tctgtaaaat ggg                                              23

<210> SEQ ID NO 771

```
<211> LENGTH: 23
<212> TYPE: DNA
<213> ORGANISM: Homo sapiens

<400> SEQUENCE: 771
aggtactcag gaggctgagg tgg                                              23

<210> SEQ ID NO 772
<211> LENGTH: 23
<212> TYPE: DNA
<213> ORGANISM: Homo sapiens

<400> SEQUENCE: 772
aagaaggaag gaatggaggg agg                                              23

<210> SEQ ID NO 773
<211> LENGTH: 23
<212> TYPE: DNA
<213> ORGANISM: Homo sapiens

<400> SEQUENCE: 773
tactcaggag gctgaggtgg agg                                              23

<210> SEQ ID NO 774
<211> LENGTH: 23
<212> TYPE: DNA
<213> ORGANISM: Homo sapiens

<400> SEQUENCE: 774
gtttaaaaaa aaagaaacac agg                                              23

<210> SEQ ID NO 775
<211> LENGTH: 23
<212> TYPE: DNA
<213> ORGANISM: Homo sapiens

<400> SEQUENCE: 775
gcactttggg aggccgaggc ggg                                              23

<210> SEQ ID NO 776
<211> LENGTH: 23
<212> TYPE: DNA
<213> ORGANISM: Homo sapiens

<400> SEQUENCE: 776
ctttgggagg ctgaggctgg agg                                              23

<210> SEQ ID NO 777
<211> LENGTH: 23
<212> TYPE: DNA
<213> ORGANISM: Homo sapiens

<400> SEQUENCE: 777
cctctgcctc ccaaagtgct ggg                                              23

<210> SEQ ID NO 778
<211> LENGTH: 23
<212> TYPE: DNA
<213> ORGANISM: Homo sapiens

<400> SEQUENCE: 778
agtgctggga ttacagacgt tgg                                              23
```

```
<210> SEQ ID NO 779
<211> LENGTH: 23
<212> TYPE: DNA
<213> ORGANISM: Homo sapiens

<400> SEQUENCE: 779
tttttattca tttttagaga tgg                                              23

<210> SEQ ID NO 780
<211> LENGTH: 23
<212> TYPE: DNA
<213> ORGANISM: Homo sapiens

<400> SEQUENCE: 780
gggggcagag agagaggcaa tgg                                              23

<210> SEQ ID NO 781
<211> LENGTH: 23
<212> TYPE: DNA
<213> ORGANISM: Homo sapiens

<400> SEQUENCE: 781
gcgccactgc actccagcct ggg                                              23

<210> SEQ ID NO 782
<211> LENGTH: 23
<212> TYPE: DNA
<213> ORGANISM: Homo sapiens

<400> SEQUENCE: 782
cgcgccactg cactccagcc tgg                                              23

<210> SEQ ID NO 783
<211> LENGTH: 23
<212> TYPE: DNA
<213> ORGANISM: Homo sapiens

<400> SEQUENCE: 783
cccaacactt tgggaggctg agg                                              23

<210> SEQ ID NO 784
<211> LENGTH: 23
<212> TYPE: DNA
<213> ORGANISM: Homo sapiens

<400> SEQUENCE: 784
agaaaagaag gaaggaatgg agg                                              23

<210> SEQ ID NO 785
<211> LENGTH: 23
<212> TYPE: DNA
<213> ORGANISM: Homo sapiens

<400> SEQUENCE: 785
actttgggag gctgaggcag agg                                              23

<210> SEQ ID NO 786
<211> LENGTH: 23
<212> TYPE: DNA
<213> ORGANISM: Homo sapiens

<400> SEQUENCE: 786
acctcggcct cccaaagtgc tgg                                              23
```

```
<210> SEQ ID NO 787
<211> LENGTH: 23
<212> TYPE: DNA
<213> ORGANISM: Homo sapiens

<400> SEQUENCE: 787
tttccccatg ttggtcaggc tgg                                            23

<210> SEQ ID NO 788
<211> LENGTH: 23
<212> TYPE: DNA
<213> ORGANISM: Homo sapiens

<400> SEQUENCE: 788
ggattacagc tgtgagccac cgg                                            23

<210> SEQ ID NO 789
<211> LENGTH: 23
<212> TYPE: DNA
<213> ORGANISM: Homo sapiens

<400> SEQUENCE: 789
ggagtcttgc actgtcaccc agg                                            23

<210> SEQ ID NO 790
<211> LENGTH: 23
<212> TYPE: DNA
<213> ORGANISM: Homo sapiens

<400> SEQUENCE: 790
gaaagggaag ttggggaagg agg                                            23

<210> SEQ ID NO 791
<211> LENGTH: 23
<212> TYPE: DNA
<213> ORGANISM: Homo sapiens

<400> SEQUENCE: 791
ccattttaca gagaaggaaa tgg                                            23

<210> SEQ ID NO 792
<211> LENGTH: 23
<212> TYPE: DNA
<213> ORGANISM: Homo sapiens

<400> SEQUENCE: 792
ccatttcctt ctctgtaaaa tgg                                            23

<210> SEQ ID NO 793
<211> LENGTH: 23
<212> TYPE: DNA
<213> ORGANISM: Homo sapiens

<400> SEQUENCE: 793
ccagaccagc ctgaccaaca tgg                                            23

<210> SEQ ID NO 794
<211> LENGTH: 23
<212> TYPE: DNA
<213> ORGANISM: Homo sapiens

<400> SEQUENCE: 794
agggtcttgc tctgttgctc agg                                            23
```

<210> SEQ ID NO 795
<211> LENGTH: 23
<212> TYPE: DNA
<213> ORGANISM: Homo sapiens

<400> SEQUENCE: 795
tctaaaaatg aataaaaata agg                                              23

<210> SEQ ID NO 796
<211> LENGTH: 23
<212> TYPE: DNA
<213> ORGANISM: Homo sapiens

<400> SEQUENCE: 796
gctactcagg aggctgaggc agg                                              23

<210> SEQ ID NO 797
<211> LENGTH: 23
<212> TYPE: DNA
<213> ORGANISM: Homo sapiens

<400> SEQUENCE: 797
cgcttgaacc caggaggcag agg                                              23

<210> SEQ ID NO 798
<211> LENGTH: 23
<212> TYPE: DNA
<213> ORGANISM: Homo sapiens

<400> SEQUENCE: 798
cccagctact caggaggctg agg                                              23

<210> SEQ ID NO 799
<211> LENGTH: 23
<212> TYPE: DNA
<213> ORGANISM: Homo sapiens

<400> SEQUENCE: 799
caagaccagc ctgaccaaca tgg                                              23

<210> SEQ ID NO 800
<211> LENGTH: 23
<212> TYPE: DNA
<213> ORGANISM: Homo sapiens

<400> SEQUENCE: 800
agcactttgg gaggccgagg tgg                                              23

<210> SEQ ID NO 801
<211> LENGTH: 23
<212> TYPE: DNA
<213> ORGANISM: Homo sapiens

<400> SEQUENCE: 801
agcactttgg gaggccgagg cgg                                              23

<210> SEQ ID NO 802
<211> LENGTH: 23
<212> TYPE: DNA
<213> ORGANISM: Homo sapiens

<400> SEQUENCE: 802
tttttttttt agtagagacg ggg                                      23

<210> SEQ ID NO 803
<211> LENGTH: 23
<212> TYPE: DNA
<213> ORGANISM: Homo sapiens

<400> SEQUENCE: 803
tcttgcactg tcacccaggc tgg                                      23

<210> SEQ ID NO 804
<211> LENGTH: 23
<212> TYPE: DNA
<213> ORGANISM: Homo sapiens

<400> SEQUENCE: 804
cctcagcctc ctgagtagct ggg                                      23

<210> SEQ ID NO 805
<211> LENGTH: 23
<212> TYPE: DNA
<213> ORGANISM: Homo sapiens

<400> SEQUENCE: 805
acctgtaatc ccagctactc agg                                      23

<210> SEQ ID NO 806
<211> LENGTH: 23
<212> TYPE: DNA
<213> ORGANISM: Homo sapiens

<400> SEQUENCE: 806
acaaacaaaa aaaactcttt tgg                                      23

<210> SEQ ID NO 807
<211> LENGTH: 23
<212> TYPE: DNA
<213> ORGANISM: Homo sapiens

<400> SEQUENCE: 807
tttcgccatg ttggtcaggc tgg                                      23

<210> SEQ ID NO 808
<211> LENGTH: 23
<212> TYPE: DNA
<213> ORGANISM: Homo sapiens

<400> SEQUENCE: 808
tctttgtatt tttagtagag agg                                      23

<210> SEQ ID NO 809
<211> LENGTH: 23
<212> TYPE: DNA
<213> ORGANISM: Homo sapiens

<400> SEQUENCE: 809 gggggttgggg gcagagagag agg                                     23

<210> SEQ ID NO 810
<211> LENGTH: 23
<212> TYPE: DNA
<213> ORGANISM: Homo sapiens

<400> SEQUENCE: 810
cagctgtaat cccagcactt tgg                                               23

<210> SEQ ID NO 811
<211> LENGTH: 23
<212> TYPE: DNA
<213> ORGANISM: Homo sapiens

<400> SEQUENCE: 811
atgagaaaag aaggaaggaa tgg                                               23

<210> SEQ ID NO 812
<211> LENGTH: 23
<212> TYPE: DNA
<213> ORGANISM: Homo sapiens

<400> SEQUENCE: 812
agaccagcct gaccaacatg ggg                                               23

<210> SEQ ID NO 813
<211> LENGTH: 23
<212> TYPE: DNA
<213> ORGANISM: Homo sapiens

<400> SEQUENCE: 813
tttttttttt tagtagagac ggg                                               23

<210> SEQ ID NO 814
<211> LENGTH: 23
<212> TYPE: DNA
<213> ORGANISM: Homo sapiens

<400> SEQUENCE: 814
gcctgtagtc ccagctactc agg                                               23

<210> SEQ ID NO 815
<211> LENGTH: 23
<212> TYPE: DNA
<213> ORGANISM: Homo sapiens

<400> SEQUENCE: 815
gcactttggg aggctgaggc tgg                                               23

<210> SEQ ID NO 816
<211> LENGTH: 23
<212> TYPE: DNA
<213> ORGANISM: Homo sapiens

<400> SEQUENCE: 816
gcactttggg aggccaaggt ggg                                               23

<210> SEQ ID NO 817
<211> LENGTH: 23
<212> TYPE: DNA
<213> ORGANISM: Homo sapiens

<400> SEQUENCE: 817
gaaaagaagg aaggaatgga ggg                                               23

<210> SEQ ID NO 818
<211> LENGTH: 23
<212> TYPE: DNA
<213> ORGANISM: Homo sapiens

```
<400> SEQUENCE: 818
ctctgccccc aacccagcc agg                                              23

<210> SEQ ID NO 819
<211> LENGTH: 23
<212> TYPE: DNA
<213> ORGANISM: Homo sapiens

<400> SEQUENCE: 819
cgtctgtaat cccagcactt tgg                                             23

<210> SEQ ID NO 820
<211> LENGTH: 23
<212> TYPE: DNA
<213> ORGANISM: Homo sapiens

<400> SEQUENCE: 820
ttttctgttt ttagtagaga tgg                                             23

<210> SEQ ID NO 821
<211> LENGTH: 23
<212> TYPE: DNA
<213> ORGANISM: Homo sapiens

<400> SEQUENCE: 821
tttaaaaaaa aagaaacaca ggg                                             23

<210> SEQ ID NO 822
<211> LENGTH: 23
<212> TYPE: DNA
<213> ORGANISM: Homo sapiens

<400> SEQUENCE: 822
tgtaatccca cactttggg agg                                              23

<210> SEQ ID NO 823
<211> LENGTH: 23
<212> TYPE: DNA
<213> ORGANISM: Homo sapiens

<400> SEQUENCE: 823
tcttgctctg ttgctcaggc agg                                             23

<210> SEQ ID NO 824
<211> LENGTH: 23
<212> TYPE: DNA
<213> ORGANISM: Homo sapiens

<400> SEQUENCE: 824
ctaaaaatga ataaaaataa ggg                                             23

<210> SEQ ID NO 825
<211> LENGTH: 23
<212> TYPE: DNA
<213> ORGANISM: Homo sapiens

<400> SEQUENCE: 825
cccagcactt tgggaggccg agg                                             23

<210> SEQ ID NO 826
<211> LENGTH: 23
<212> TYPE: DNA
<213> ORGANISM: Homo sapiens
```

```
<400> SEQUENCE: 826
agagtctcac tctgtcgccc agg                                           23

<210> SEQ ID NO 827
<211> LENGTH: 23
<212> TYPE: DNA
<213> ORGANISM: Homo sapiens

<400> SEQUENCE: 827
agaaggaagg aatggaggga ggg                                           23

<210> SEQ ID NO 828
<211> LENGTH: 23
<212> TYPE: DNA
<213> ORGANISM: Homo sapiens

<400> SEQUENCE: 828
tgtggtccca ggtactcagg agg                                           23

<210> SEQ ID NO 829
<211> LENGTH: 23
<212> TYPE: DNA
<213> ORGANISM: Homo sapiens

<400> SEQUENCE: 829
gcctcggcct cccaaagtgc tgg                                           23

<210> SEQ ID NO 830
<211> LENGTH: 23
<212> TYPE: DNA
<213> ORGANISM: Homo sapiens

<400> SEQUENCE: 830
catgccactg cactccagcc tgg                                           23

<210> SEQ ID NO 831
<211> LENGTH: 23
<212> TYPE: DNA
<213> ORGANISM: Homo sapiens

<400> SEQUENCE: 831
agctgtaatc ccagcacttt ggg                                           23

<210> SEQ ID NO 832
<211> LENGTH: 23
<212> TYPE: DNA
<213> ORGANISM: Homo sapiens

<400> SEQUENCE: 832
taaaaaaaaa aaaattagcc tgg                                           23

<210> SEQ ID NO 833
<211> LENGTH: 23
<212> TYPE: DNA
<213> ORGANISM: Homo sapiens

<400> SEQUENCE: 833
cctttttttt ttttgtctg agg                                            23

<210> SEQ ID NO 834
<211> LENGTH: 23
<212> TYPE: DNA
```

<213> ORGANISM: Homo sapiens

<400> SEQUENCE: 834
cctcggcctc ccaaagtgct ggg                                              23

<210> SEQ ID NO 835
<211> LENGTH: 23
<212> TYPE: DNA
<213> ORGANISM: Homo sapiens

<400> SEQUENCE: 835
atgccactgc actccagcct ggg                                              23

<210> SEQ ID NO 836
<211> LENGTH: 23
<212> TYPE: DNA
<213> ORGANISM: Homo sapiens

<400> SEQUENCE: 836
accttggcct cccaaagtgc tgg                                              23

<210> SEQ ID NO 837
<211> LENGTH: 23
<212> TYPE: DNA
<213> ORGANISM: Homo sapiens

<400> SEQUENCE: 837
tttgtatttt tagtagagag ggg                                              23

<210> SEQ ID NO 838
<211> LENGTH: 23
<212> TYPE: DNA
<213> ORGANISM: Homo sapiens

<400> SEQUENCE: 838
gtctgtaatc ccagcacttt ggg                                              23

<210> SEQ ID NO 839
<211> LENGTH: 23
<212> TYPE: DNA
<213> ORGANISM: Homo sapiens

<400> SEQUENCE: 839
cccagcactt tgggaggcca agg                                              23

<210> SEQ ID NO 840
<211> LENGTH: 23
<212> TYPE: DNA
<213> ORGANISM: Homo sapiens

<400> SEQUENCE: 840
cacctgtaat cccagcactt tgg                                              23

<210> SEQ ID NO 841
<211> LENGTH: 23
<212> TYPE: DNA
<213> ORGANISM: Homo sapiens

<400> SEQUENCE: 841
ttgtttgttt gttttttgaag tgg                                             23

<210> SEQ ID NO 842
<211> LENGTH: 23

<212> TYPE: DNA
<213> ORGANISM: Homo sapiens

<400> SEQUENCE: 842
ttgcccaggc tggagtgcag tgg					23

<210> SEQ ID NO 843
<211> LENGTH: 23
<212> TYPE: DNA
<213> ORGANISM: Homo sapiens

<400> SEQUENCE: 843
tctcactctg tcgcccaggc tgg					23

<210> SEQ ID NO 844
<211> LENGTH: 23
<212> TYPE: DNA
<213> ORGANISM: Homo sapiens

<400> SEQUENCE: 844
agcactttgg gaggccaagg tgg					23

<210> SEQ ID NO 845
<211> LENGTH: 23
<212> TYPE: DNA
<213> ORGANISM: Homo sapiens

<400> SEQUENCE: 845
tttttttttt ttagtagaga cgg					23

<210> SEQ ID NO 846
<211> LENGTH: 23
<212> TYPE: DNA
<213> ORGANISM: Homo sapiens

<400> SEQUENCE: 846
ttgtattttt agtagagaca ggg					23

<210> SEQ ID NO 847
<211> LENGTH: 23
<212> TYPE: DNA
<213> ORGANISM: Homo sapiens

<400> SEQUENCE: 847
tgtagtccca gctactcagg agg					23

<210> SEQ ID NO 848
<211> LENGTH: 23
<212> TYPE: DNA
<213> ORGANISM: Homo sapiens

<400> SEQUENCE: 848
tcacccaggc tggagtgcag tgg					23

<210> SEQ ID NO 849
<211> LENGTH: 23
<212> TYPE: DNA
<213> ORGANISM: Homo sapiens

<400> SEQUENCE: 849
ccttggcctc ccaaagtgct ggg					23

<210> SEQ ID NO 850

```
<211> LENGTH: 23
<212> TYPE: DNA
<213> ORGANISM: Homo sapiens

<400> SEQUENCE: 850
cctcagacaa aaaaaaaaa agg                                              23

<210> SEQ ID NO 851
<211> LENGTH: 23
<212> TYPE: DNA
<213> ORGANISM: Homo sapiens

<400> SEQUENCE: 851
aggaaggaat ggagggaggg agg                                             23

<210> SEQ ID NO 852
<211> LENGTH: 23
<212> TYPE: DNA
<213> ORGANISM: Homo sapiens

<400> SEQUENCE: 852
aataaataaa taaataaat agg                                              23

<210> SEQ ID NO 853
<211> LENGTH: 23
<212> TYPE: DNA
<213> ORGANISM: Homo sapiens

<400> SEQUENCE: 853
aaaaaaaaaa aaaattagcc ggg                                             23

<210> SEQ ID NO 854
<211> LENGTH: 23
<212> TYPE: DNA
<213> ORGANISM: Homo sapiens

<400> SEQUENCE: 854
tgtaatccca gcactttggg agg                                             23

<210> SEQ ID NO 855
<211> LENGTH: 23
<212> TYPE: DNA
<213> ORGANISM: Homo sapiens

<400> SEQUENCE: 855
tctcactctg ttgcccaggc tgg                                             23

<210> SEQ ID NO 856
<211> LENGTH: 23
<212> TYPE: DNA
<213> ORGANISM: Homo sapiens

<400> SEQUENCE: 856
acctgtaatc ccagcacttt ggg                                             23

<210> SEQ ID NO 857
<211> LENGTH: 23
<212> TYPE: DNA
<213> ORGANISM: Homo sapiens

<400> SEQUENCE: 857
aaaaaaaaaa aaaaattagc cgg                                             23
```

```
<210> SEQ ID NO 858
<211> LENGTH: 23
<212> TYPE: DNA
<213> ORGANISM: Homo sapiens

<400> SEQUENCE: 858
tttgtatttt tagtagagac agg                                             23

<210> SEQ ID NO 859
<211> LENGTH: 23
<212> TYPE: DNA
<213> ORGANISM: Homo sapiens

<400> SEQUENCE: 859
tcccaaagtg ctgggattac agg                                             23

<210> SEQ ID NO 860
<211> LENGTH: 23
<212> TYPE: DNA
<213> ORGANISM: Homo sapiens

<400> SEQUENCE: 860
ctttgtattt ttagtagaga ggg                                             23

<210> SEQ ID NO 861
<211> LENGTH: 23
<212> TYPE: DNA
<213> ORGANISM: Homo sapiens

<400> SEQUENCE: 861
tttttttttt tttttgaggc agg                                             23

<210> SEQ ID NO 862
<211> LENGTH: 23
<212> TYPE: DNA
<213> ORGANISM: Homo sapiens

<400> SEQUENCE: 862
tttttttttt ttttgaggca ggg                                             23

<210> SEQ ID NO 863
<211> LENGTH: 23
<212> TYPE: DNA
<213> ORGANISM: Homo sapiens

<400> SEQUENCE: 863
tttttttttt ttttttttttg agg                                            23

<210> SEQ ID NO 864
<211> LENGTH: 23
<212> TYPE: DNA
<213> ORGANISM: Homo sapiens

<400> SEQUENCE: 864
aaaaaaaaaa aaaaaagtct ggg                                             23

<210> SEQ ID NO 865
<211> LENGTH: 23
<212> TYPE: DNA
<213> ORGANISM: Homo sapiens

<400> SEQUENCE: 865
aaaaaaaaaa aaaaaagtc tgg                                              23
```

```
<210> SEQ ID NO 866
<211> LENGTH: 23
<212> TYPE: DNA
<213> ORGANISM: Homo sapiens

<400> SEQUENCE: 866
ctcacctata atggccacta agg                                              23

<210> SEQ ID NO 867
<211> LENGTH: 23
<212> TYPE: DNA
<213> ORGANISM: Homo sapiens

<400> SEQUENCE: 867
cacctataat ggccactaag ggg                                              23

<210> SEQ ID NO 868
<211> LENGTH: 23
<212> TYPE: DNA
<213> ORGANISM: Homo sapiens

<400> SEQUENCE: 868
tcacctataa tggccactaa ggg                                              23

<210> SEQ ID NO 869
<211> LENGTH: 23
<212> TYPE: DNA
<213> ORGANISM: Homo sapiens

<400> SEQUENCE: 869 ttcccctctag tggccattat agg                                             23

<210> SEQ ID NO 870
<211> LENGTH: 23
<212> TYPE: DNA
<213> ORGANISM: Homo sapiens

<400> SEQUENCE: 870
cacacagaca tcactccgtc tgg                                              23

<210> SEQ ID NO 871
<211> LENGTH: 23
<212> TYPE: DNA
<213> ORGANISM: Homo sapiens

<400> SEQUENCE: 871
tcttcagtac tcacctataa tgg                                              23

<210> SEQ ID NO 872
<211> LENGTH: 23
<212> TYPE: DNA
<213> ORGANISM: Homo sapiens

<400> SEQUENCE: 872
tggggtggct actcaccaga cgg                                              23

<210> SEQ ID NO 873
<211> LENGTH: 23
<212> TYPE: DNA
<213> ORGANISM: Homo sapiens

<400> SEQUENCE: 873
tgaatacgat ggtgaaactg agg                                              23
```

<210> SEQ ID NO 874
<211> LENGTH: 23
<212> TYPE: DNA
<213> ORGANISM: Homo sapiens

<400> SEQUENCE: 874
tgaaactgag gtcctagctt agg                                              23

<210> SEQ ID NO 875
<211> LENGTH: 23
<212> TYPE: DNA
<213> ORGANISM: Homo sapiens

<400> SEQUENCE: 875
tcacatataa atgaatacga tgg                                              23

<210> SEQ ID NO 876
<211> LENGTH: 23
<212> TYPE: DNA
<213> ORGANISM: Homo sapiens

<400> SEQUENCE: 876
agcaagctgt gacttgttct agg                                              23

<210> SEQ ID NO 877
<211> LENGTH: 23
<212> TYPE: DNA
<213> ORGANISM: Homo sapiens

<400> SEQUENCE: 877
ctgaggcaga ggcctaagct agg                                              23

<210> SEQ ID NO 878
<211> LENGTH: 23
<212> TYPE: DNA
<213> ORGANISM: Homo sapiens

<400> SEQUENCE: 878
ataggtgagt actgaagacc agg                                              23

<210> SEQ ID NO 879
<211> LENGTH: 23
<212> TYPE: DNA
<213> ORGANISM: Homo sapiens

<400> SEQUENCE: 879
aaggatatct gggatgggat tgg                                              23

<210> SEQ ID NO 880
<211> LENGTH: 23
<212> TYPE: DNA
<213> ORGANISM: Homo sapiens

<400> SEQUENCE: 880
aggatatctg ggatgggatt ggg                                              23

<210> SEQ ID NO 881
<211> LENGTH: 23
<212> TYPE: DNA
<213> ORGANISM: Homo sapiens

<400> SEQUENCE: 881

```
gtgacttgtt ctaggtcata tgg                                              23

<210> SEQ ID NO 882
<211> LENGTH: 23
<212> TYPE: DNA
<213> ORGANISM: Homo sapiens

<400> SEQUENCE: 882
gggaggaaaa taaggatatc tgg                                              23

<210> SEQ ID NO 883
<211> LENGTH: 23
<212> TYPE: DNA
<213> ORGANISM: Homo sapiens

<400> SEQUENCE: 883
ctgaagacca ggaacttctg agg                                              23

<210> SEQ ID NO 884
<211> LENGTH: 23
<212> TYPE: DNA
<213> ORGANISM: Homo sapiens

<400> SEQUENCE: 884
aaaataagga tatctgggat ggg                                              23

<210> SEQ ID NO 885
<211> LENGTH: 23
<212> TYPE: DNA
<213> ORGANISM: Homo sapiens

<400> SEQUENCE: 885
ggaggaaaat aaggatatct ggg                                              23

<210> SEQ ID NO 886
<211> LENGTH: 23
<212> TYPE: DNA
<213> ORGANISM: Homo sapiens

<400> SEQUENCE: 886
tcttttctca ttccccttag tgg                                              23

<210> SEQ ID NO 887
<211> LENGTH: 23
<212> TYPE: DNA
<213> ORGANISM: Homo sapiens

<400> SEQUENCE: 887
gaaaataagg atatctggga tgg                                              23

<210> SEQ ID NO 888
<211> LENGTH: 23
<212> TYPE: DNA
<213> ORGANISM: Homo sapiens

<400> SEQUENCE: 888
caacaaaagg agagtggatg ggg                                              23

<210> SEQ ID NO 889
<211> LENGTH: 23
<212> TYPE: DNA
<213> ORGANISM: Homo sapiens

<400> SEQUENCE: 889
```
gcctctgcct cagaagttcc tgg                                              23

<210> SEQ ID NO 890
<211> LENGTH: 23
<212> TYPE: DNA
<213> ORGANISM: Homo sapiens

<400> SEQUENCE: 890
accaggaact tctgaggcag agg                                              23

<210> SEQ ID NO 891
<211> LENGTH: 23
<212> TYPE: DNA
<213> ORGANISM: Homo sapiens

<400> SEQUENCE: 891
tgtcagcaac aaaaggagag tgg                                              23

<210> SEQ ID NO 892
<211> LENGTH: 23
<212> TYPE: DNA
<213> ORGANISM: Homo sapiens

<400> SEQUENCE: 892
aaaggggtgt cagcaacaaa agg                                              23

<210> SEQ ID NO 893
<211> LENGTH: 23
<212> TYPE: DNA
<213> ORGANISM: Homo sapiens

<400> SEQUENCE: 893
aaaatctgag taattggaaa agg                                              23

<210> SEQ ID NO 894
<211> LENGTH: 23
<212> TYPE: DNA
<213> ORGANISM: Homo sapiens

<400> SEQUENCE: 894
caaaataaaa tctgagtaat tgg                                              23

<210> SEQ ID NO 895
<211> LENGTH: 23
<212> TYPE: DNA
<213> ORGANISM: Homo sapiens

<400> SEQUENCE: 895
agcaacaaaa ggagagtgga tgg                                              23

<210> SEQ ID NO 896
<211> LENGTH: 23
<212> TYPE: DNA
<213> ORGANISM: Homo sapiens

<400> SEQUENCE: 896
caaaaggaga gtggatgggg tgg                                              23

<210> SEQ ID NO 897
<211> LENGTH: 23
<212> TYPE: DNA
<213> ORGANISM: Homo sapiens

```
<400> SEQUENCE: 897
gcaacaaaag gagagtggat ggg                                           23

<210> SEQ ID NO 898
<211> LENGTH: 23
<212> TYPE: DNA
<213> ORGANISM: Homo sapiens

<400> SEQUENCE: 898
aaatctgagt aattggaaaa ggg                                           23

<210> SEQ ID NO 899
<211> LENGTH: 23
<212> TYPE: DNA
<213> ORGANISM: Homo sapiens

<400> SEQUENCE: 899 ctaagggaa tgagaaaaga agg                                            23

<210> SEQ ID NO 900
<211> LENGTH: 23
<212> TYPE: DNA
<213> ORGANISM: Homo sapiens

<400> SEQUENCE: 900
caattactca gattttattt tgg                                           23

<210> SEQ ID NO 901
<211> LENGTH: 23
<212> TYPE: DNA
<213> ORGANISM: Homo sapiens

<400> SEQUENCE: 901
tggagggagg gaggaaaata agg                                           23

<210> SEQ ID NO 902
<211> LENGTH: 23
<212> TYPE: DNA
<213> ORGANISM: Homo sapiens

<400> SEQUENCE: 902
ggggaatgag aaaagaagga agg                                           23

<210> SEQ ID NO 903
<211> LENGTH: 23
<212> TYPE: DNA
<213> ORGANISM: Homo sapiens

<400> SEQUENCE: 903
aagaaggaag gaatggaggg agg                                           23

<210> SEQ ID NO 904
<211> LENGTH: 23
<212> TYPE: DNA
<213> ORGANISM: Homo sapiens

<400> SEQUENCE: 904
agaaaagaag gaaggaatgg agg                                           23

<210> SEQ ID NO 905
<211> LENGTH: 23
<212> TYPE: DNA
<213> ORGANISM: Homo sapiens
```

```
<400> SEQUENCE: 905
atgagaaaag aaggaaggaa tgg                                              23

<210> SEQ ID NO 906
<211> LENGTH: 23
<212> TYPE: DNA
<213> ORGANISM: Homo sapiens

<400> SEQUENCE: 906
gaaaagaagg aaggaatgga ggg                                              23

<210> SEQ ID NO 907
<211> LENGTH: 23
<212> TYPE: DNA
<213> ORGANISM: Homo sapiens

<400> SEQUENCE: 907
agaaggaagg aatggaggga ggg                                              23

<210> SEQ ID NO 908
<211> LENGTH: 23
<212> TYPE: DNA
<213> ORGANISM: Homo sapiens

<400> SEQUENCE: 908
aggaaggaat ggagggaggg agg                                              23

<210> SEQ ID NO 909
<211> LENGTH: 23
<212> TYPE: DNA
<213> ORGANISM: Homo sapiens

<400> SEQUENCE: 909
tacttgaacc ctagagtcgg agg                                              23

<210> SEQ ID NO 910
<211> LENGTH: 23
<212> TYPE: DNA
<213> ORGANISM: Homo sapiens

<400> SEQUENCE: 910
gagcattcgc tatattgccc agg                                              23

<210> SEQ ID NO 911
<211> LENGTH: 23
<212> TYPE: DNA
<213> ORGANISM: Homo sapiens

<400> SEQUENCE: 911
gcggtctccc tatgttgagc agg                                              23

<210> SEQ ID NO 912
<211> LENGTH: 23
<212> TYPE: DNA
<213> ORGANISM: Homo sapiens

<400> SEQUENCE: 912
aactgcagcc tccgactcta ggg                                              23

<210> SEQ ID NO 913
<211> LENGTH: 23
<212> TYPE: DNA
```

<213> ORGANISM: Homo sapiens

<400> SEQUENCE: 913
caagctagca ctaccacgcc tgg    23

<210> SEQ ID NO 914
<211> LENGTH: 23
<212> TYPE: DNA
<213> ORGANISM: Homo sapiens

<400> SEQUENCE: 914
ctcacctata atggccacta agg    23

<210> SEQ ID NO 915
<211> LENGTH: 23
<212> TYPE: DNA
<213> ORGANISM: Homo sapiens

<400> SEQUENCE: 915
ggggtttcac cacattagcc agg    23

<210> SEQ ID NO 916
<211> LENGTH: 23
<212> TYPE: DNA
<213> ORGANISM: Homo sapiens

<400> SEQUENCE: 916
aggtcagatc gagatcatcc tgg    23

<210> SEQ ID NO 917
<211> LENGTH: 23
<212> TYPE: DNA
<213> ORGANISM: Homo sapiens

<400> SEQUENCE: 917
ctcacctata atggccacta agg    23

<210> SEQ ID NO 918
<211> LENGTH: 23
<212> TYPE: DNA
<213> ORGANISM: Homo sapiens

<400> SEQUENCE: 918
cacctataat ggccactaag ggg    23

<210> SEQ ID NO 919
<211> LENGTH: 23
<212> TYPE: DNA
<213> ORGANISM: Homo sapiens

<400> SEQUENCE: 919
taactgcagc ctccgactct agg    23

<210> SEQ ID NO 920
<211> LENGTH: 23
<212> TYPE: DNA
<213> ORGANISM: Homo sapiens

<400> SEQUENCE: 920
tcacctataa tggccactaa ggg    23

<210> SEQ ID NO 921
<211> LENGTH: 23

<212> TYPE: DNA
<213> ORGANISM: Homo sapiens

<400> SEQUENCE: 921
taaaaataag ggtcgggtga ggg                                           23

<210> SEQ ID NO 922
<211> LENGTH: 23
<212> TYPE: DNA
<213> ORGANISM: Homo sapiens

<400> SEQUENCE: 922
ttccccttag tggccattat agg                                           23

<210> SEQ ID NO 923
<211> LENGTH: 23
<212> TYPE: DNA
<213> ORGANISM: Homo sapiens

<400> SEQUENCE: 923
gcaggttggt cttaaactac tgg                                           23

<210> SEQ ID NO 924
<211> LENGTH: 23
<212> TYPE: DNA
<213> ORGANISM: Homo sapiens

<400> SEQUENCE: 924
aggaaggctg ttgggtccgg tgg                                           23

<210> SEQ ID NO 925
<211> LENGTH: 23
<212> TYPE: DNA
<213> ORGANISM: Homo sapiens

<400> SEQUENCE: 925
tctccctatg ttgagcaggt tgg                                           23

<210> SEQ ID NO 926
<211> LENGTH: 23
<212> TYPE: DNA
<213> ORGANISM: Homo sapiens

<400> SEQUENCE: 926
cgagatcatc ctggctaatg tgg                                           23

<210> SEQ ID NO 927
<211> LENGTH: 23
<212> TYPE: DNA
<213> ORGANISM: Homo sapiens

<400> SEQUENCE: 927
ggatcttggg ctgggcgcaa tgg                                           23

<210> SEQ ID NO 928
<211> LENGTH: 23
<212> TYPE: DNA
<213> ORGANISM: Homo sapiens

<400> SEQUENCE: 928
gcagaggcgg gcggatcaca agg                                           23

<210> SEQ ID NO 929

```
<211> LENGTH: 23
<212> TYPE: DNA
<213> ORGANISM: Homo sapiens

<400> SEQUENCE: 929
agaccaacct gctcaacata ggg                                              23

<210> SEQ ID NO 930
<211> LENGTH: 23
<212> TYPE: DNA
<213> ORGANISM: Homo sapiens

<400> SEQUENCE: 930
caaaaattat ccgggcattg tgg                                              23

<210> SEQ ID NO 931
<211> LENGTH: 23
<212> TYPE: DNA
<213> ORGANISM: Homo sapiens

<400> SEQUENCE: 931
aattacttga accctagagt cgg                                              23

<210> SEQ ID NO 932
<211> LENGTH: 23
<212> TYPE: DNA
<213> ORGANISM: Homo sapiens

<400> SEQUENCE: 932
cacagggtct ttaattaatc tgg                                              23

<210> SEQ ID NO 933
<211> LENGTH: 23
<212> TYPE: DNA
<213> ORGANISM: Homo sapiens

<400> SEQUENCE: 933
ctccatggtg gcatgcactt tgg                                              23

<210> SEQ ID NO 934
<211> LENGTH: 23
<212> TYPE: DNA
<213> ORGANISM: Homo sapiens

<400> SEQUENCE: 934
aaaaataagg gtcgggtgag ggg                                              23

<210> SEQ ID NO 935
<211> LENGTH: 23
<212> TYPE: DNA
<213> ORGANISM: Homo sapiens

<400> SEQUENCE: 935
ctgaataaac ggggctgcct ggg                                              23

<210> SEQ ID NO 936
<211> LENGTH: 23
<212> TYPE: DNA
<213> ORGANISM: Homo sapiens

<400> SEQUENCE: 936
tccatggtgg catgcacttt ggg                                              23
```

```
<210> SEQ ID NO 937
<211> LENGTH: 23
<212> TYPE: DNA
<213> ORGANISM: Homo sapiens

<400> SEQUENCE: 937
ataaaaataa gggtcgggtg agg                                              23

<210> SEQ ID NO 938
<211> LENGTH: 23
<212> TYPE: DNA
<213> ORGANISM: Homo sapiens

<400> SEQUENCE: 938
cagaccagcc tgaccaacat ggg                                              23

<210> SEQ ID NO 939
<211> LENGTH: 23
<212> TYPE: DNA
<213> ORGANISM: Homo sapiens

<400> SEQUENCE: 939
aagaccaacc tgctcaacat agg                                              23

<210> SEQ ID NO 940
<211> LENGTH: 23
<212> TYPE: DNA
<213> ORGANISM: Homo sapiens

<400> SEQUENCE: 940
ctgcccctct gatttgcacc tgg                                              23

<210> SEQ ID NO 941
<211> LENGTH: 23
<212> TYPE: DNA
<213> ORGANISM: Homo sapiens

<400> SEQUENCE: 941
attagagttc tggctgggcg tgg                                              23

<210> SEQ ID NO 942
<211> LENGTH: 23
<212> TYPE: DNA
<213> ORGANISM: Homo sapiens

<400> SEQUENCE: 942
tcttcagtac tcacctataa tgg                                              23

<210> SEQ ID NO 943
<211> LENGTH: 23
<212> TYPE: DNA
<213> ORGANISM: Homo sapiens

<400> SEQUENCE: 943
aaaggggcag taattgtcca agg                                              23

<210> SEQ ID NO 944
<211> LENGTH: 23
<212> TYPE: DNA
<213> ORGANISM: Homo sapiens

<400> SEQUENCE: 944
cttaagccct gtactgtgcc agg                                              23
```

```
<210> SEQ ID NO 945
<211> LENGTH: 23
<212> TYPE: DNA
<213> ORGANISM: Homo sapiens

<400> SEQUENCE: 945
tcttcagtac tcacctataa tgg                                           23

<210> SEQ ID NO 946
<211> LENGTH: 23
<212> TYPE: DNA
<213> ORGANISM: Homo sapiens

<400> SEQUENCE: 946
tgtttgagcc caagagattg agg                                           23

<210> SEQ ID NO 947
<211> LENGTH: 23
<212> TYPE: DNA
<213> ORGANISM: Homo sapiens

<400> SEQUENCE: 947
tgaatacgat ggtgaaactg agg                                           23

<210> SEQ ID NO 948
<211> LENGTH: 23
<212> TYPE: DNA
<213> ORGANISM: Homo sapiens

<400> SEQUENCE: 948
tctcattgtg tcacccgggc tgg                                           23

<210> SEQ ID NO 949
<211> LENGTH: 23
<212> TYPE: DNA
<213> ORGANISM: Homo sapiens

<400> SEQUENCE: 949
gcttgtagtt ccagctgttt ggg                                           23

<210> SEQ ID NO 950
<211> LENGTH: 23
<212> TYPE: DNA
<213> ORGANISM: Homo sapiens

<400> SEQUENCE: 950
agcttgtagt tccagctgtt tgg                                           23

<210> SEQ ID NO 951
<211> LENGTH: 23
<212> TYPE: DNA
<213> ORGANISM: Homo sapiens

<400> SEQUENCE: 951
caggctactc ttgaactctt ggg                                           23

<210> SEQ ID NO 952
<211> LENGTH: 23
<212> TYPE: DNA
<213> ORGANISM: Homo sapiens

<400> SEQUENCE: 952
aatcaagcct tgttaaaacc agg                                           23
```

```
<210> SEQ ID NO 953
<211> LENGTH: 23
<212> TYPE: DNA
<213> ORGANISM: Homo sapiens

<400> SEQUENCE: 953
tcccaaagtg catgccacca tgg                                          23

<210> SEQ ID NO 954
<211> LENGTH: 23
<212> TYPE: DNA
<213> ORGANISM: Homo sapiens

<400> SEQUENCE: 954
agcttgtaaa cttagcactt tgg                                          23

<210> SEQ ID NO 955
<211> LENGTH: 23
<212> TYPE: DNA
<213> ORGANISM: Homo sapiens

<400> SEQUENCE: 955
gggcttaaga aataggatct tgg                                          23

<210> SEQ ID NO 956
<211> LENGTH: 23
<212> TYPE: DNA
<213> ORGANISM: Homo sapiens

<400> SEQUENCE: 956
agagccaccg tactccagcc cgg                                          23

<210> SEQ ID NO 957
<211> LENGTH: 23
<212> TYPE: DNA
<213> ORGANISM: Homo sapiens

<400> SEQUENCE: 957
tcacccgggc tggagtacgg tgg                                          23

<210> SEQ ID NO 958
<211> LENGTH: 23
<212> TYPE: DNA
<213> ORGANISM: Homo sapiens

<400> SEQUENCE: 958
gatttgatga gatctcacag cgg                                          23

<210> SEQ ID NO 959
<211> LENGTH: 23
<212> TYPE: DNA
<213> ORGANISM: Homo sapiens

<400> SEQUENCE: 959
tgaaactgag gtcctagctt agg                                          23

<210> SEQ ID NO 960
<211> LENGTH: 23
<212> TYPE: DNA
<213> ORGANISM: Homo sapiens

<400> SEQUENCE: 960
```
tcacatataa atgaatacga tgg    23

<210> SEQ ID NO 961
<211> LENGTH: 23
<212> TYPE: DNA
<213> ORGANISM: Homo sapiens

<400> SEQUENCE: 961
agcaagctgt gacttgttct agg    23

<210> SEQ ID NO 962
<211> LENGTH: 23
<212> TYPE: DNA
<213> ORGANISM: Homo sapiens

<400> SEQUENCE: 962
atggtggcat gcactttggg agg    23

<210> SEQ ID NO 963
<211> LENGTH: 23
<212> TYPE: DNA
<213> ORGANISM: Homo sapiens

<400> SEQUENCE: 963
ccatgttggt caggctggtc tgg    23

<210> SEQ ID NO 964
<211> LENGTH: 23
<212> TYPE: DNA
<213> ORGANISM: Homo sapiens

<400> SEQUENCE: 964
agttgccaaa acttgctatt tgg    23

<210> SEQ ID NO 965
<211> LENGTH: 23
<212> TYPE: DNA
<213> ORGANISM: Homo sapiens

<400> SEQUENCE: 965
ggcttaagaa ataggatctt ggg    23

<210> SEQ ID NO 966
<211> LENGTH: 23
<212> TYPE: DNA
<213> ORGANISM: Homo sapiens

<400> SEQUENCE: 966
ccagtttctc tctgtcgccc agg    23

<210> SEQ ID NO 967
<211> LENGTH: 23
<212> TYPE: DNA
<213> ORGANISM: Homo sapiens

<400> SEQUENCE: 967
actgaataaa cggggctgcc tgg    23

<210> SEQ ID NO 968
<211> LENGTH: 23
<212> TYPE: DNA
<213> ORGANISM: Homo sapiens

<400> SEQUENCE: 968

-continued atcacacaaa ttaagagtac agg                                             23

<210> SEQ ID NO 969
<211> LENGTH: 23
<212> TYPE: DNA
<213> ORGANISM: Homo sapiens

<400> SEQUENCE: 969
caagagttca agagtagcct ggg                                             23

<210> SEQ ID NO 970
<211> LENGTH: 23
<212> TYPE: DNA
<213> ORGANISM: Homo sapiens

<400> SEQUENCE: 970
cactgcagcc tcaatctctt ggg                                             23

<210> SEQ ID NO 971
<211> LENGTH: 23
<212> TYPE: DNA
<213> ORGANISM: Homo sapiens

<400> SEQUENCE: 971
taagaaatag gatcttgggc tgg                                             23

<210> SEQ ID NO 972
<211> LENGTH: 23
<212> TYPE: DNA
<213> ORGANISM: Homo sapiens

<400> SEQUENCE: 972
cagtacaggg cttaagaaat agg                                             23

<210> SEQ ID NO 973
<211> LENGTH: 23
<212> TYPE: DNA
<213> ORGANISM: Homo sapiens

<400> SEQUENCE: 973
ctgaggcaga ggcctaagct agg                                             23

<210> SEQ ID NO 974
<211> LENGTH: 23
<212> TYPE: DNA
<213> ORGANISM: Homo sapiens

<400> SEQUENCE: 974
aaaataaggg tcgggtgagg ggg                                             23

<210> SEQ ID NO 975
<211> LENGTH: 23
<212> TYPE: DNA
<213> ORGANISM: Homo sapiens

<400> SEQUENCE: 975
tacaggaagg ctgttgggtc cgg                                             23

<210> SEQ ID NO 976
<211> LENGTH: 23
<212> TYPE: DNA
<213> ORGANISM: Homo sapiens

```
<400> SEQUENCE: 976
acagaaaaat tagccaggcg tgg                                          23

<210> SEQ ID NO 977
<211> LENGTH: 23
<212> TYPE: DNA
<213> ORGANISM: Homo sapiens

<400> SEQUENCE: 977
ataggtgagt actgaagacc agg                                          23

<210> SEQ ID NO 978
<211> LENGTH: 23
<212> TYPE: DNA
<213> ORGANISM: Homo sapiens

<400> SEQUENCE: 978
ccaagagttc aagagtagcc tgg                                          23

<210> SEQ ID NO 979
<211> LENGTH: 23
<212> TYPE: DNA
<213> ORGANISM: Homo sapiens

<400> SEQUENCE: 979
acagagtgag aactccatgg tgg                                          23

<210> SEQ ID NO 980
<211> LENGTH: 23
<212> TYPE: DNA
<213> ORGANISM: Homo sapiens

<400> SEQUENCE: 980
gcaaccacct cctgggttca agg                                          23

<210> SEQ ID NO 981
<211> LENGTH: 23
<212> TYPE: DNA
<213> ORGANISM: Homo sapiens

<400> SEQUENCE: 981
caaggtgggt gcatcacctg agg                                          23

<210> SEQ ID NO 982
<211> LENGTH: 23
<212> TYPE: DNA
<213> ORGANISM: Homo sapiens

<400> SEQUENCE: 982
aaaaaattag cctggtgtag tgg                                          23

<210> SEQ ID NO 983
<211> LENGTH: 23
<212> TYPE: DNA
<213> ORGANISM: Homo sapiens

<400> SEQUENCE: 983
caggcacatg ccactacacc agg                                          23

<210> SEQ ID NO 984
<211> LENGTH: 23
<212> TYPE: DNA
<213> ORGANISM: Homo sapiens
```

```
<400> SEQUENCE: 984
gcttgtaaac ttagcacttt ggg                                              23

<210> SEQ ID NO 985
<211> LENGTH: 23
<212> TYPE: DNA
<213> ORGANISM: Homo sapiens

<400> SEQUENCE: 985
taaaaccagg tgcaaatcag agg                                              23

<210> SEQ ID NO 986
<211> LENGTH: 23
<212> TYPE: DNA
<213> ORGANISM: Homo sapiens

<400> SEQUENCE: 986
ctggaggatt gtctgagccc agg                                              23

<210> SEQ ID NO 987
<211> LENGTH: 23
<212> TYPE: DNA
<213> ORGANISM: Homo sapiens

<400> SEQUENCE: 987
ggtcttgaac tcctgacctc agg                                              23

<210> SEQ ID NO 988
<211> LENGTH: 23
<212> TYPE: DNA
<213> ORGANISM: Homo sapiens

<400> SEQUENCE: 988
agcggcccat tttacagaga agg                                              23

<210> SEQ ID NO 989
<211> LENGTH: 23
<212> TYPE: DNA
<213> ORGANISM: Homo sapiens

<400> SEQUENCE: 989
tcactgcagc tttgaattcc tgg                                              23

<210> SEQ ID NO 990
<211> LENGTH: 23
<212> TYPE: DNA
<213> ORGANISM: Homo sapiens

<400> SEQUENCE: 990
ggctcactgc aaccacctcc tgg                                              23

<210> SEQ ID NO 991
<211> LENGTH: 23
<212> TYPE: DNA
<213> ORGANISM: Homo sapiens

<400> SEQUENCE: 991
cacaaattaa gagtacagga agg                                              23

<210> SEQ ID NO 992
<211> LENGTH: 23
<212> TYPE: DNA
```

```
<213> ORGANISM: Homo sapiens

<400> SEQUENCE: 992
tactcagcat cccaaacagc tgg                                                23

<210> SEQ ID NO 993
<211> LENGTH: 23
<212> TYPE: DNA
<213> ORGANISM: Homo sapiens

<400> SEQUENCE: 993
ctctccctga ttttacaaac agg                                                23

<210> SEQ ID NO 994
<211> LENGTH: 23
<212> TYPE: DNA
<213> ORGANISM: Homo sapiens

<400> SEQUENCE: 994
tggggtctca ttgtgtcacc cgg                                                23

<210> SEQ ID NO 995
<211> LENGTH: 23
<212> TYPE: DNA
<213> ORGANISM: Homo sapiens

<400> SEQUENCE: 995
aagagtacag gaaggctgtt ggg                                                23

<210> SEQ ID NO 996
<211> LENGTH: 23
<212> TYPE: DNA
<213> ORGANISM: Homo sapiens

<400> SEQUENCE: 996
gcctgtggtc ccaggtactc agg                                                23

<210> SEQ ID NO 997
<211> LENGTH: 23
<212> TYPE: DNA
<213> ORGANISM: Homo sapiens

<400> SEQUENCE: 997
gaaactgtgt ttacaaactg tgg                                                23

<210> SEQ ID NO 998
<211> LENGTH: 23
<212> TYPE: DNA
<213> ORGANISM: Homo sapiens

<400> SEQUENCE: 998
agctgggggg actgaataaa cgg                                                23

<210> SEQ ID NO 999
<211> LENGTH: 23
<212> TYPE: DNA
<213> ORGANISM: Homo sapiens

<400> SEQUENCE: 999
tgggtgcatc acctgaggtc agg                                                23

<210> SEQ ID NO 1000
<211> LENGTH: 23
```

```
<212> TYPE: DNA
<213> ORGANISM: Homo sapiens

<400> SEQUENCE: 1000
tttaaaatta gagttctggc tgg                                              23

<210> SEQ ID NO 1001
<211> LENGTH: 23
<212> TYPE: DNA
<213> ORGANISM: Homo sapiens

<400> SEQUENCE: 1001
atttgcacct ggttttaaca agg                                              23

<210> SEQ ID NO 1002
<211> LENGTH: 23
<212> TYPE: DNA
<213> ORGANISM: Homo sapiens

<400> SEQUENCE: 1002
catgtgcaaa accctgagcc tgg                                              23

<210> SEQ ID NO 1003
<211> LENGTH: 23
<212> TYPE: DNA
<213> ORGANISM: Homo sapiens

<400> SEQUENCE: 1003
gcaacagagt gagaactcca tgg                                              23

<210> SEQ ID NO 1004
<211> LENGTH: 23
<212> TYPE: DNA
<213> ORGANISM: Homo sapiens

<400> SEQUENCE: 1004
cactgcagct ttgaattcct ggg                                              23

<210> SEQ ID NO 1005
<211> LENGTH: 23
<212> TYPE: DNA
<213> ORGANISM: Homo sapiens

<400> SEQUENCE: 1005
agctgtttgg gatgctgagt agg                                              23

<210> SEQ ID NO 1006
<211> LENGTH: 23
<212> TYPE: DNA
<213> ORGANISM: Homo sapiens

<400> SEQUENCE: 1006
ttaaaattag agttctggct ggg                                              23

<210> SEQ ID NO 1007
<211> LENGTH: 23
<212> TYPE: DNA
<213> ORGANISM: Homo sapiens

<400> SEQUENCE: 1007
ccctgagcct ggcacagtac agg                                              23

<210> SEQ ID NO 1008
```

```
<211> LENGTH: 23
<212> TYPE: DNA
<213> ORGANISM: Homo sapiens

<400> SEQUENCE: 1008
cctgggcgac agagagaaac tgg                                              23

<210> SEQ ID NO 1009
<211> LENGTH: 23
<212> TYPE: DNA
<213> ORGANISM: Homo sapiens

<400> SEQUENCE: 1009
gggattttac catgttggtc agg                                              23

<210> SEQ ID NO 1010
<211> LENGTH: 23
<212> TYPE: DNA
<213> ORGANISM: Homo sapiens

<400> SEQUENCE: 1010
gtgacttgtt ctaggtcata tgg                                              23

<210> SEQ ID NO 1011
<211> LENGTH: 23
<212> TYPE: DNA
<213> ORGANISM: Homo sapiens

<400> SEQUENCE: 1011
aagaaatagg atcttgggct ggg                                              23

<210> SEQ ID NO 1012
<211> LENGTH: 23
<212> TYPE: DNA
<213> ORGANISM: Homo sapiens

<400> SEQUENCE: 1012
taagagtaca ggaaggctgt tgg                                              23

<210> SEQ ID NO 1013
<211> LENGTH: 23
<212> TYPE: DNA
<213> ORGANISM: Homo sapiens

<400> SEQUENCE: 1013
ggtgtagtgg catgtgcctg tgg                                              23

<210> SEQ ID NO 1014
<211> LENGTH: 23
<212> TYPE: DNA
<213> ORGANISM: Homo sapiens

<400> SEQUENCE: 1014
tgtaaactta gcactttggg agg                                              23

<210> SEQ ID NO 1015
<211> LENGTH: 23
<212> TYPE: DNA
<213> ORGANISM: Homo sapiens

<400> SEQUENCE: 1015
caggtgcaaa tcagaggggc agg                                              23
```

```
<210> SEQ ID NO 1016
<211> LENGTH: 23
<212> TYPE: DNA
<213> ORGANISM: Homo sapiens

<400> SEQUENCE: 1016
ttgggaaatg gtatgaggta ggg                                            23

<210> SEQ ID NO 1017
<211> LENGTH: 23
<212> TYPE: DNA
<213> ORGANISM: Homo sapiens

<400> SEQUENCE: 1017
cctgggtcct cgggcctcct ggg                                            23

<210> SEQ ID NO 1018
<211> LENGTH: 23
<212> TYPE: DNA
<213> ORGANISM: Homo sapiens

<400> SEQUENCE: 1018
gagccaccgt actccagccc ggg                                            23

<210> SEQ ID NO 1019
<211> LENGTH: 23
<212> TYPE: DNA
<213> ORGANISM: Homo sapiens

<400> SEQUENCE: 1019
agagttctgg ctgggcgtgg tgg                                            23

<210> SEQ ID NO 1020
<211> LENGTH: 23
<212> TYPE: DNA
<213> ORGANISM: Homo sapiens

<400> SEQUENCE: 1020
ctgaagacca ggaacttctg agg                                            23

<210> SEQ ID NO 1021
<211> LENGTH: 23
<212> TYPE: DNA
<213> ORGANISM: Homo sapiens

<400> SEQUENCE: 1021
tcctgagtac ctgggaccac agg                                            23

<210> SEQ ID NO 1022
<211> LENGTH: 23
<212> TYPE: DNA
<213> ORGANISM: Homo sapiens

<400> SEQUENCE: 1022
gggaaggagg aaaatcacct tgg                                            23

<210> SEQ ID NO 1023
<211> LENGTH: 23
<212> TYPE: DNA
<213> ORGANISM: Homo sapiens

<400> SEQUENCE: 1023
tgtttgtaat cccaacactt tgg                                            23
```

<210> SEQ ID NO 1024
<211> LENGTH: 23
<212> TYPE: DNA
<213> ORGANISM: Homo sapiens

<400> SEQUENCE: 1024
gctcactgca accacctcct ggg                                          23

<210> SEQ ID NO 1025
<211> LENGTH: 23
<212> TYPE: DNA
<213> ORGANISM: Homo sapiens

<400> SEQUENCE: 1025
tttgggaaat ggtatgaggt agg                                          23

<210> SEQ ID NO 1026
<211> LENGTH: 23
<212> TYPE: DNA
<213> ORGANISM: Homo sapiens

<400> SEQUENCE: 1026
cttttccaaa tagcaagttt tgg                                          23

<210> SEQ ID NO 1027
<211> LENGTH: 23
<212> TYPE: DNA
<213> ORGANISM: Homo sapiens

<400> SEQUENCE: 1027
aaacacagtt tcaaaaggtc agg                                          23

<210> SEQ ID NO 1028
<211> LENGTH: 23
<212> TYPE: DNA
<213> ORGANISM: Homo sapiens

<400> SEQUENCE: 1028
aaaccaggtg caaatcagag ggg                                          23

<210> SEQ ID NO 1029
<211> LENGTH: 23
<212> TYPE: DNA
<213> ORGANISM: Homo sapiens

<400> SEQUENCE: 1029
ggtctggaac tcctgacctc agg                                          23

<210> SEQ ID NO 1030
<211> LENGTH: 23
<212> TYPE: DNA
<213> ORGANISM: Homo sapiens

<400> SEQUENCE: 1030
aaaaccaggt gcaaatcaga ggg                                          23

<210> SEQ ID NO 1031
<211> LENGTH: 23
<212> TYPE: DNA
<213> ORGANISM: Homo sapiens

<400> SEQUENCE: 1031
tgggagcccc agaagatgaa agg                                          23

```
<210> SEQ ID NO 1032
<211> LENGTH: 23
<212> TYPE: DNA
<213> ORGANISM: Homo sapiens

<400> SEQUENCE: 1032
tttcatcttc tgggctccc agg                                              23

<210> SEQ ID NO 1033
<211> LENGTH: 23
<212> TYPE: DNA
<213> ORGANISM: Homo sapiens

<400> SEQUENCE: 1033
gcctgggtcc tcgggcctcc tgg                                             23

<210> SEQ ID NO 1034
<211> LENGTH: 23
<212> TYPE: DNA
<213> ORGANISM: Homo sapiens

<400> SEQUENCE: 1034
caggtgcgtc ccaccacacc cgg                                             23

<210> SEQ ID NO 1035
<211> LENGTH: 23
<212> TYPE: DNA
<213> ORGANISM: Homo sapiens

<400> SEQUENCE: 1035
gtttgtaatc ccaacacttt ggg                                             23

<210> SEQ ID NO 1036
<211> LENGTH: 23
<212> TYPE: DNA
<213> ORGANISM: Homo sapiens

<400> SEQUENCE: 1036
aatgaataaa aataagggtc ggg                                             23

<210> SEQ ID NO 1037
<211> LENGTH: 23
<212> TYPE: DNA
<213> ORGANISM: Homo sapiens

<400> SEQUENCE: 1037
tatttgtctt ggggtaagga agg                                             23

<210> SEQ ID NO 1038
<211> LENGTH: 23
<212> TYPE: DNA
<213> ORGANISM: Homo sapiens

<400> SEQUENCE: 1038
acctcagcct cctgagtacc tgg                                             23

<210> SEQ ID NO 1039
<211> LENGTH: 23
<212> TYPE: DNA
<213> ORGANISM: Homo sapiens

<400> SEQUENCE: 1039
```

| | |
|---|---|
| tcactgcagc ctcaatctct tgg | 23 |

<210> SEQ ID NO 1040
<211> LENGTH: 23
<212> TYPE: DNA
<213> ORGANISM: Homo sapiens

<400> SEQUENCE: 1040

| | |
|---|---|
| tttaagtaat gagatgggag ggg | 23 |

<210> SEQ ID NO 1041
<211> LENGTH: 23
<212> TYPE: DNA
<213> ORGANISM: Homo sapiens

<400> SEQUENCE: 1041

| | |
|---|---|
| cctgagcctg gcacagtaca ggg | 23 |

<210> SEQ ID NO 1042
<211> LENGTH: 23
<212> TYPE: DNA
<213> ORGANISM: Homo sapiens

<400> SEQUENCE: 1042

| | |
|---|---|
| tgaggcagag ggatcacctg agg | 23 |

<210> SEQ ID NO 1043
<211> LENGTH: 23
<212> TYPE: DNA
<213> ORGANISM: Homo sapiens

<400> SEQUENCE: 1043

| | |
|---|---|
| aatatatttg tcttggggta agg | 23 |

<210> SEQ ID NO 1044
<211> LENGTH: 23
<212> TYPE: DNA
<213> ORGANISM: Homo sapiens

<400> SEQUENCE: 1044

| | |
|---|---|
| gcctctgcct cagaagttcc tgg | 23 |

<210> SEQ ID NO 1045
<211> LENGTH: 23
<212> TYPE: DNA
<213> ORGANISM: Homo sapiens

<400> SEQUENCE: 1045

| | |
|---|---|
| ccaggctact cttgaactct tgg | 23 |

<210> SEQ ID NO 1046
<211> LENGTH: 23
<212> TYPE: DNA
<213> ORGANISM: Homo sapiens

<400> SEQUENCE: 1046

| | |
|---|---|
| cccaggaggc ccgaggaccc agg | 23 |

<210> SEQ ID NO 1047
<211> LENGTH: 23
<212> TYPE: DNA
<213> ORGANISM: Homo sapiens

<400> SEQUENCE: 1047
gggagcccca gaagatgaaa ggg                           23

<210> SEQ ID NO 1048
<211> LENGTH: 23
<212> TYPE: DNA
<213> ORGANISM: Homo sapiens

<400> SEQUENCE: 1048
gtgtcacccg ggctggagta cgg                           23

<210> SEQ ID NO 1049
<211> LENGTH: 23
<212> TYPE: DNA
<213> ORGANISM: Homo sapiens

<400> SEQUENCE: 1049
caggcacaca ccacaatgcc cgg                           23

<210> SEQ ID NO 1050
<211> LENGTH: 23
<212> TYPE: DNA
<213> ORGANISM: Homo sapiens

<400> SEQUENCE: 1050
ctcaggtgat gcacccacct tgg                           23

<210> SEQ ID NO 1051
<211> LENGTH: 23
<212> TYPE: DNA
<213> ORGANISM: Homo sapiens

<400> SEQUENCE: 1051
tttttaagta atgagatggg agg                           23

<210> SEQ ID NO 1052
<211> LENGTH: 23
<212> TYPE: DNA
<213> ORGANISM: Homo sapiens

<400> SEQUENCE: 1052
cagagggatc acctgaggtc agg                           23

<210> SEQ ID NO 1053
<211> LENGTH: 23
<212> TYPE: DNA
<213> ORGANISM: Homo sapiens

<400> SEQUENCE: 1053
caggagaatc ccttgaaccc agg                           23

<210> SEQ ID NO 1054
<211> LENGTH: 23
<212> TYPE: DNA
<213> ORGANISM: Homo sapiens

<400> SEQUENCE: 1054
gctatttaaa attagagttc tgg                           23

<210> SEQ ID NO 1055
<211> LENGTH: 23
<212> TYPE: DNA
<213> ORGANISM: Homo sapiens

```
<400> SEQUENCE: 1055
accaggaact tctgaggcag agg                                              23

<210> SEQ ID NO 1056
<211> LENGTH: 23
<212> TYPE: DNA
<213> ORGANISM: Homo sapiens

<400> SEQUENCE: 1056
cttagcactt tgggaggccg agg                                              23

<210> SEQ ID NO 1057
<211> LENGTH: 23
<212> TYPE: DNA
<213> ORGANISM: Homo sapiens

<400> SEQUENCE: 1057
catcttctgg ggctcccagg agg                                              23

<210> SEQ ID NO 1058
<211> LENGTH: 23
<212> TYPE: DNA
<213> ORGANISM: Homo sapiens

<400> SEQUENCE: 1058
aaaaattagc cgggtgtggt ggg                                              23

<210> SEQ ID NO 1059
<211> LENGTH: 23
<212> TYPE: DNA
<213> ORGANISM: Homo sapiens

<400> SEQUENCE: 1059
acggggctgc ctgggtcctc ggg                                              23

<210> SEQ ID NO 1060
<211> LENGTH: 23
<212> TYPE: DNA
<213> ORGANISM: Homo sapiens

<400> SEQUENCE: 1060
atgctaaaag acaaaactag agg                                              23

<210> SEQ ID NO 1061
<211> LENGTH: 23
<212> TYPE: DNA
<213> ORGANISM: Homo sapiens

<400> SEQUENCE: 1061
aattaatctg gaagttgttt tgg                                              23

<210> SEQ ID NO 1062
<211> LENGTH: 23
<212> TYPE: DNA
<213> ORGANISM: Homo sapiens

<400> SEQUENCE: 1062
ttgttttggg aaatggtatg agg                                              23

<210> SEQ ID NO 1063
<211> LENGTH: 23
<212> TYPE: DNA
<213> ORGANISM: Homo sapiens
```

<400> SEQUENCE: 1063
attaatctgg aagttgttttt ggg                                          23

<210> SEQ ID NO 1064
<211> LENGTH: 23
<212> TYPE: DNA
<213> ORGANISM: Homo sapiens

<400> SEQUENCE: 1064
ttaagtaatg agatgggagg ggg                                           23

<210> SEQ ID NO 1065
<211> LENGTH: 23
<212> TYPE: DNA
<213> ORGANISM: Homo sapiens

<400> SEQUENCE: 1065
agtttcctgt ttgtaaaatc agg                                           23

<210> SEQ ID NO 1066
<211> LENGTH: 23
<212> TYPE: DNA
<213> ORGANISM: Homo sapiens

<400> SEQUENCE: 1066
aaaaaaaaat tagccgggtg tgg                                           23

<210> SEQ ID NO 1067
<211> LENGTH: 23
<212> TYPE: DNA
<213> ORGANISM: Homo sapiens

<400> SEQUENCE: 1067
caaccacctc ctgggttcaa ggg                                           23

<210> SEQ ID NO 1068
<211> LENGTH: 23
<212> TYPE: DNA
<213> ORGANISM: Homo sapiens

<400> SEQUENCE: 1068
gagatgggat tttaccatgt tgg                                           23

<210> SEQ ID NO 1069
<211> LENGTH: 23
<212> TYPE: DNA
<213> ORGANISM: Homo sapiens

<400> SEQUENCE: 1069
taataaaatt acagagttct ggg                                           23

<210> SEQ ID NO 1070
<211> LENGTH: 23
<212> TYPE: DNA
<213> ORGANISM: Homo sapiens

<400> SEQUENCE: 1070
cgaggtggga ggattgcttg agg                                           23

<210> SEQ ID NO 1071
<211> LENGTH: 23
<212> TYPE: DNA

```
<213> ORGANISM: Homo sapiens

<400> SEQUENCE: 1071 aacgggctg cctgggtcct cgg                                        23

<210> SEQ ID NO 1072
<211> LENGTH: 23
<212> TYPE: DNA
<213> ORGANISM: Homo sapiens

<400> SEQUENCE: 1072
tggggctccc aggaggcccg agg                                       23

<210> SEQ ID NO 1073
<211> LENGTH: 23
<212> TYPE: DNA
<213> ORGANISM: Homo sapiens

<400> SEQUENCE: 1073
aaaaaattag ccgggtgtgg tgg                                       23

<210> SEQ ID NO 1074
<211> LENGTH: 23
<212> TYPE: DNA
<213> ORGANISM: Homo sapiens

<400> SEQUENCE: 1074
gcatgcactt tgggaggctg agg                                       23

<210> SEQ ID NO 1075
<211> LENGTH: 23
<212> TYPE: DNA
<213> ORGANISM: Homo sapiens

<400> SEQUENCE: 1075
gagacagggt ttccccatgt tgg                                       23

<210> SEQ ID NO 1076
<211> LENGTH: 23
<212> TYPE: DNA
<213> ORGANISM: Homo sapiens

<400> SEQUENCE: 1076
tagaggacaa atgatagtac tgg                                       23

<210> SEQ ID NO 1077
<211> LENGTH: 23
<212> TYPE: DNA
<213> ORGANISM: Homo sapiens

<400> SEQUENCE: 1077
aacttccctt tcatcttctg ggg                                       23

<210> SEQ ID NO 1078
<211> LENGTH: 23
<212> TYPE: DNA
<213> ORGANISM: Homo sapiens

<400> SEQUENCE: 1078
ccaacttccc tttcatcttc tgg                                       23

<210> SEQ ID NO 1079
<211> LENGTH: 23
```

```
<212> TYPE: DNA
<213> ORGANISM: Homo sapiens

<400> SEQUENCE: 1079
gcaccactgc actccggcct ggg                                              23

<210> SEQ ID NO 1080
<211> LENGTH: 23
<212> TYPE: DNA
<213> ORGANISM: Homo sapiens

<400> SEQUENCE: 1080
ggagtgcagt ggtgcaatct cgg                                              23

<210> SEQ ID NO 1081
<211> LENGTH: 23
<212> TYPE: DNA
<213> ORGANISM: Homo sapiens

<400> SEQUENCE: 1081
atactatatt gcaaatattc tgg                                              23

<210> SEQ ID NO 1082
<211> LENGTH: 23
<212> TYPE: DNA
<213> ORGANISM: Homo sapiens

<400> SEQUENCE: 1082
ttgctcaggc aggagtgcag tgg                                              23

<210> SEQ ID NO 1083
<211> LENGTH: 23
<212> TYPE: DNA
<213> ORGANISM: Homo sapiens

<400> SEQUENCE: 1083
caacttccct ttcatcttct ggg                                              23

<210> SEQ ID NO 1084
<211> LENGTH: 23
<212> TYPE: DNA
<213> ORGANISM: Homo sapiens

<400> SEQUENCE: 1084
tggcatgtgc ctgtggtccc agg                                              23

<210> SEQ ID NO 1085
<211> LENGTH: 23
<212> TYPE: DNA
<213> ORGANISM: Homo sapiens

<400> SEQUENCE: 1085
cagaagatga aagggaagtt ggg                                              23

<210> SEQ ID NO 1086
<211> LENGTH: 23
<212> TYPE: DNA
<213> ORGANISM: Homo sapiens

<400> SEQUENCE: 1086
ggggtctcat tgtgtcaccc ggg                                              23

<210> SEQ ID NO 1087
```

```
<211> LENGTH: 23
<212> TYPE: DNA
<213> ORGANISM: Homo sapiens

<400> SEQUENCE: 1087
ataataaaat tacagagttc tgg                                              23

<210> SEQ ID NO 1088
<211> LENGTH: 23
<212> TYPE: DNA
<213> ORGANISM: Homo sapiens

<400> SEQUENCE: 1088
gcctcagcct cccaaagtgt tgg                                              23

<210> SEQ ID NO 1089
<211> LENGTH: 23
<212> TYPE: DNA
<213> ORGANISM: Homo sapiens

<400> SEQUENCE: 1089
ctggaagttg ttttgggaaa tgg                                              23

<210> SEQ ID NO 1090
<211> LENGTH: 23
<212> TYPE: DNA
<213> ORGANISM: Homo sapiens

<400> SEQUENCE: 1090
agggtttccc catgttggtc agg                                              23

<210> SEQ ID NO 1091
<211> LENGTH: 23
<212> TYPE: DNA
<213> ORGANISM: Homo sapiens

<400> SEQUENCE: 1091
aaaaaaaagt ctgggtgtgg tgg                                              23

<210> SEQ ID NO 1092
<211> LENGTH: 23
<212> TYPE: DNA
<213> ORGANISM: Homo sapiens

<400> SEQUENCE: 1092
gtttcctgtt tgtaaaatca ggg                                              23

<210> SEQ ID NO 1093
<211> LENGTH: 23
<212> TYPE: DNA
<213> ORGANISM: Homo sapiens

<400> SEQUENCE: 1093
ttgtaaaatc agggagagac tgg                                              23

<210> SEQ ID NO 1094
<211> LENGTH: 23
<212> TYPE: DNA
<213> ORGANISM: Homo sapiens

<400> SEQUENCE: 1094
caagagaatc gcttgaaccc agg                                              23
```

```
<210> SEQ ID NO 1095
<211> LENGTH: 23
<212> TYPE: DNA
<213> ORGANISM: Homo sapiens

<400> SEQUENCE: 1095
acaacttaag aaatttgaag tgg                                              23

<210> SEQ ID NO 1096
<211> LENGTH: 23
<212> TYPE: DNA
<213> ORGANISM: Homo sapiens

<400> SEQUENCE: 1096
agtaatgaga tgggaggggg cgg                                              23

<210> SEQ ID NO 1097
<211> LENGTH: 23
<212> TYPE: DNA
<213> ORGANISM: Homo sapiens

<400> SEQUENCE: 1097
tttgtaaaca cagtttcaaa agg                                              23

<210> SEQ ID NO 1098
<211> LENGTH: 23
<212> TYPE: DNA
<213> ORGANISM: Homo sapiens

<400> SEQUENCE: 1098
gatgaaaggg aagttgggga agg                                              23

<210> SEQ ID NO 1099
<211> LENGTH: 23
<212> TYPE: DNA
<213> ORGANISM: Homo sapiens

<400> SEQUENCE: 1099
ggaaactgag gctaagaaag ggg                                              23

<210> SEQ ID NO 1100
<211> LENGTH: 23
<212> TYPE: DNA
<213> ORGANISM: Homo sapiens

<400> SEQUENCE: 1100
gcctcagcct cctgagtagc tgg                                              23

<210> SEQ ID NO 1101
<211> LENGTH: 23
<212> TYPE: DNA
<213> ORGANISM: Homo sapiens

<400> SEQUENCE: 1101
ttatttttaa gtaatgagat ggg                                              23

<210> SEQ ID NO 1102
<211> LENGTH: 23
<212> TYPE: DNA
<213> ORGANISM: Homo sapiens

<400> SEQUENCE: 1102
aggaaactga ggctaagaaa ggg                                              23
```

```
<210> SEQ ID NO 1103
<211> LENGTH: 23
<212> TYPE: DNA
<213> ORGANISM: Homo sapiens

<400> SEQUENCE: 1103
tactgcaacc tctgcctcct ggg                                              23

<210> SEQ ID NO 1104
<211> LENGTH: 23
<212> TYPE: DNA
<213> ORGANISM: Homo sapiens

<400> SEQUENCE: 1104
aatcccttga acccaggagg tgg                                              23

<210> SEQ ID NO 1105
<211> LENGTH: 23
<212> TYPE: DNA
<213> ORGANISM: Homo sapiens

<400> SEQUENCE: 1105
aaaagtattc aaaaaactat agg                                              23

<210> SEQ ID NO 1106
<211> LENGTH: 23
<212> TYPE: DNA
<213> ORGANISM: Homo sapiens

<400> SEQUENCE: 1106
tcctgagtag ctgggattac agg                                              23

<210> SEQ ID NO 1107
<211> LENGTH: 23
<212> TYPE: DNA
<213> ORGANISM: Homo sapiens

<400> SEQUENCE: 1107
ccctgtactg tgccaggctc agg                                              23

<210> SEQ ID NO 1108
<211> LENGTH: 23
<212> TYPE: DNA
<213> ORGANISM: Homo sapiens

<400> SEQUENCE: 1108
gcctctgcct cccaaagtgc tgg                                              23

<210> SEQ ID NO 1109
<211> LENGTH: 23
<212> TYPE: DNA
<213> ORGANISM: Homo sapiens

<400> SEQUENCE: 1109
ccagaagatg aaagggaagt tgg                                              23

<210> SEQ ID NO 1110
<211> LENGTH: 23
<212> TYPE: DNA
<213> ORGANISM: Homo sapiens

<400> SEQUENCE: 1110
ctttgggagg cagaggcggg cgg                                              23
```

<210> SEQ ID NO 1111
<211> LENGTH: 23
<212> TYPE: DNA
<213> ORGANISM: Homo sapiens

<400> SEQUENCE: 1111
ataggaaaat atatttgtct tgg                                             23

<210> SEQ ID NO 1112
<211> LENGTH: 23
<212> TYPE: DNA
<213> ORGANISM: Homo sapiens

<400> SEQUENCE: 1112
aggaaaatat atttgtcttg ggg                                             23

<210> SEQ ID NO 1113
<211> LENGTH: 23
<212> TYPE: DNA
<213> ORGANISM: Homo sapiens

<400> SEQUENCE: 1113
cctcagcctc ctgagtacct ggg                                             23

<210> SEQ ID NO 1114
<211> LENGTH: 23
<212> TYPE: DNA
<213> ORGANISM: Homo sapiens

<400> SEQUENCE: 1114
attattttta agtaatgaga tgg                                             23

<210> SEQ ID NO 1115
<211> LENGTH: 23
<212> TYPE: DNA
<213> ORGANISM: Homo sapiens

<400> SEQUENCE: 1115
caggaaactg aggctaagaa agg                                             23

<210> SEQ ID NO 1116
<211> LENGTH: 23
<212> TYPE: DNA
<213> ORGANISM: Homo sapiens

<400> SEQUENCE: 1116
cctcagcctc ccaaagtgtt ggg                                             23

<210> SEQ ID NO 1117
<211> LENGTH: 23
<212> TYPE: DNA
<213> ORGANISM: Homo sapiens

<400> SEQUENCE: 1117
taggaaaata tatttgtctt ggg                                             23

<210> SEQ ID NO 1118
<211> LENGTH: 23
<212> TYPE: DNA
<213> ORGANISM: Homo sapiens

<400> SEQUENCE: 1118
ttttaagtaa tgagatggga ggg                                              23

<210> SEQ ID NO 1119
<211> LENGTH: 23
<212> TYPE: DNA
<213> ORGANISM: Homo sapiens

<400> SEQUENCE: 1119
agaagatgaa agggaagttg ggg                                              23

<210> SEQ ID NO 1120
<211> LENGTH: 23
<212> TYPE: DNA
<213> ORGANISM: Homo sapiens

<400> SEQUENCE: 1120
gagaatcgct tgaacccagg agg                                              23

<210> SEQ ID NO 1121
<211> LENGTH: 23
<212> TYPE: DNA
<213> ORGANISM: Homo sapiens

<400> SEQUENCE: 1121
tgcaccactg cactccggcc tgg                                              23

<210> SEQ ID NO 1122
<211> LENGTH: 23
<212> TYPE: DNA
<213> ORGANISM: Homo sapiens

<400> SEQUENCE: 1122
atataaaata aaaagttgta tgg                                              23

<210> SEQ ID NO 1123
<211> LENGTH: 23
<212> TYPE: DNA
<213> ORGANISM: Homo sapiens

<400> SEQUENCE: 1123
ttactgcaac ctctgcctcc tgg                                              23

<210> SEQ ID NO 1124
<211> LENGTH: 23
<212> TYPE: DNA
<213> ORGANISM: Homo sapiens

<400> SEQUENCE: 1124
gagaatccct tgaacccagg agg                                              23

<210> SEQ ID NO 1125
<211> LENGTH: 23
<212> TYPE: DNA
<213> ORGANISM: Homo sapiens

<400> SEQUENCE: 1125
tttctctctg tcgcccaggc cgg                                              23

<210> SEQ ID NO 1126
<211> LENGTH: 23
<212> TYPE: DNA
<213> ORGANISM: Homo sapiens

<400> SEQUENCE: 1126
aaaaaaaaaa agtctgggtg tgg                                            23

<210> SEQ ID NO 1127
<211> LENGTH: 23
<212> TYPE: DNA
<213> ORGANISM: Homo sapiens

<400> SEQUENCE: 1127
attttacaaa caggaaactg agg                                            23

<210> SEQ ID NO 1128
<211> LENGTH: 23
<212> TYPE: DNA
<213> ORGANISM: Homo sapiens

<400> SEQUENCE: 1128
gcactttggg aggcagaggc ggg                                            23

<210> SEQ ID NO 1129
<211> LENGTH: 23
<212> TYPE: DNA
<213> ORGANISM: Homo sapiens

<400> SEQUENCE: 1129
tttctgtttt tagtagagat ggg                                            23

<210> SEQ ID NO 1130
<211> LENGTH: 23
<212> TYPE: DNA
<213> ORGANISM: Homo sapiens

<400> SEQUENCE: 1130
tgtaatccca gctactcagg agg                                            23

<210> SEQ ID NO 1131
<211> LENGTH: 23
<212> TYPE: DNA
<213> ORGANISM: Homo sapiens

<400> SEQUENCE: 1131
taaaaataca aaaattatcc ggg                                            23

<210> SEQ ID NO 1132
<211> LENGTH: 23
<212> TYPE: DNA
<213> ORGANISM: Homo sapiens

<400> SEQUENCE: 1132
agcactttgg gaggcagagg cgg                                            23

<210> SEQ ID NO 1133
<211> LENGTH: 23
<212> TYPE: DNA
<213> ORGANISM: Homo sapiens

<400> SEQUENCE: 1133
ttttattcat ttttagagat ggg                                            23

<210> SEQ ID NO 1134
<211> LENGTH: 23
<212> TYPE: DNA
<213> ORGANISM: Homo sapiens

```
<400> SEQUENCE: 1134
aaatgaataa aaataagggt cgg                                             23

<210> SEQ ID NO 1135
<211> LENGTH: 23
<212> TYPE: DNA
<213> ORGANISM: Homo sapiens

<400> SEQUENCE: 1135
cccagcactt tgggaggcag agg                                             23

<210> SEQ ID NO 1136
<211> LENGTH: 23
<212> TYPE: DNA
<213> ORGANISM: Homo sapiens

<400> SEQUENCE: 1136
tcctgagtag ctgggactac agg                                             23

<210> SEQ ID NO 1137
<211> LENGTH: 23
<212> TYPE: DNA
<213> ORGANISM: Homo sapiens

<400> SEQUENCE: 1137
tttattcatt tttagagatg ggg                                             23

<210> SEQ ID NO 1138
<211> LENGTH: 23
<212> TYPE: DNA
<213> ORGANISM: Homo sapiens

<400> SEQUENCE: 1138
ctttgggagg ctgaggcaga ggg                                             23

<210> SEQ ID NO 1139
<211> LENGTH: 23
<212> TYPE: DNA
<213> ORGANISM: Homo sapiens

<400> SEQUENCE: 1139
gagattgcac cactgcactc cgg                                             23

<210> SEQ ID NO 1140
<211> LENGTH: 23
<212> TYPE: DNA
<213> ORGANISM: Homo sapiens

<400> SEQUENCE: 1140
ctttgggagg ccgaggtggg agg                                             23

<210> SEQ ID NO 1141
<211> LENGTH: 23
<212> TYPE: DNA
<213> ORGANISM: Homo sapiens

<400> SEQUENCE: 1141
ctcaagcaat cctcccacct cgg                                             23

<210> SEQ ID NO 1142
<211> LENGTH: 23
<212> TYPE: DNA
<213> ORGANISM: Homo sapiens
```

```
<400> SEQUENCE: 1142
ctttgggagg ccgaggtggg agg                                      23

<210> SEQ ID NO 1143
<211> LENGTH: 23
<212> TYPE: DNA
<213> ORGANISM: Homo sapiens

<400> SEQUENCE: 1143
ctcaagcaat cctcccacct cgg                                      23

<210> SEQ ID NO 1144
<211> LENGTH: 23
<212> TYPE: DNA
<213> ORGANISM: Homo sapiens

<400> SEQUENCE: 1144
taaaaacaga aaaattagcc agg                                      23

<210> SEQ ID NO 1145
<211> LENGTH: 23
<212> TYPE: DNA
<213> ORGANISM: Homo sapiens

<400> SEQUENCE: 1145
tatttggaaa agaaaaatgt tgg                                      23

<210> SEQ ID NO 1146
<211> LENGTH: 23
<212> TYPE: DNA
<213> ORGANISM: Homo sapiens

<400> SEQUENCE: 1146
aggtactcag gaggctgagg tgg                                      23

<210> SEQ ID NO 1147
<211> LENGTH: 23
<212> TYPE: DNA
<213> ORGANISM: Homo sapiens

<400> SEQUENCE: 1147
cccaggtact caggaggctg agg                                      23

<210> SEQ ID NO 1148
<211> LENGTH: 23
<212> TYPE: DNA
<213> ORGANISM: Homo sapiens

<400> SEQUENCE: 1148
catttccttc tctgtaaaat ggg                                      23

<210> SEQ ID NO 1149
<211> LENGTH: 23
<212> TYPE: DNA
<213> ORGANISM: Homo sapiens

<400> SEQUENCE: 1149
ctaaaaatac aaaaattatc cgg                                      23

<210> SEQ ID NO 1150
<211> LENGTH: 23
<212> TYPE: DNA
```

```
<213> ORGANISM: Homo sapiens

<400> SEQUENCE: 1150
tcgcccaggc cggagtgcag tgg                                    23

<210> SEQ ID NO 1151
<211> LENGTH: 23
<212> TYPE: DNA
<213> ORGANISM: Homo sapiens

<400> SEQUENCE: 1151
ttttaccatg ttggtcaggc tgg                                    23

<210> SEQ ID NO 1152
<211> LENGTH: 23
<212> TYPE: DNA
<213> ORGANISM: Homo sapiens

<400> SEQUENCE: 1152
tactcaggag gctgaggtgg agg                                    23

<210> SEQ ID NO 1153
<211> LENGTH: 23
<212> TYPE: DNA
<213> ORGANISM: Homo sapiens

<400> SEQUENCE: 1153
agtgctggga ttacagacgt tgg                                    23

<210> SEQ ID NO 1154
<211> LENGTH: 23
<212> TYPE: DNA
<213> ORGANISM: Homo sapiens

<400> SEQUENCE: 1154
cctctgcctc ccaaagtgct ggg                                    23

<210> SEQ ID NO 1155
<211> LENGTH: 23
<212> TYPE: DNA
<213> ORGANISM: Homo sapiens

<400> SEQUENCE: 1155
ctttgggagg ctgaggctgg agg                                    23

<210> SEQ ID NO 1156
<211> LENGTH: 23
<212> TYPE: DNA
<213> ORGANISM: Homo sapiens

<400> SEQUENCE: 1156
gtttaaaaaa aaagaaacac agg                                    23

<210> SEQ ID NO 1157
<211> LENGTH: 23
<212> TYPE: DNA
<213> ORGANISM: Homo sapiens

<400> SEQUENCE: 1157
gcgccactgc actccagcct ggg                                    23

<210> SEQ ID NO 1158
<211> LENGTH: 23
```

```
<212> TYPE: DNA
<213> ORGANISM: Homo sapiens

<400> SEQUENCE: 1158
cgcgccactg cactccagcc tgg                                              23

<210> SEQ ID NO 1159
<211> LENGTH: 23
<212> TYPE: DNA
<213> ORGANISM: Homo sapiens

<400> SEQUENCE: 1159
tttttattca tttttagaga tgg                                              23

<210> SEQ ID NO 1160
<211> LENGTH: 23
<212> TYPE: DNA
<213> ORGANISM: Homo sapiens

<400> SEQUENCE: 1160
actttgggag gctgaggcag agg                                              23

<210> SEQ ID NO 1161
<211> LENGTH: 23
<212> TYPE: DNA
<213> ORGANISM: Homo sapiens

<400> SEQUENCE: 1161
cccaacactt tgggaggctg agg                                              23

<210> SEQ ID NO 1162
<211> LENGTH: 23
<212> TYPE: DNA
<213> ORGANISM: Homo sapiens

<400> SEQUENCE: 1162
acctcggcct cccaaagtgc tgg                                              23

<210> SEQ ID NO 1163
<211> LENGTH: 23
<212> TYPE: DNA
<213> ORGANISM: Homo sapiens

<400> SEQUENCE: 1163
agggtcttgc tctgttgctc agg                                              23

<210> SEQ ID NO 1164
<211> LENGTH: 23
<212> TYPE: DNA
<213> ORGANISM: Homo sapiens

<400> SEQUENCE: 1164
gaaagggaag ttggggaagg agg                                              23

<210> SEQ ID NO 1165
<211> LENGTH: 23
<212> TYPE: DNA
<213> ORGANISM: Homo sapiens

<400> SEQUENCE: 1165
ggagtcttgc actgtcaccc agg                                              23

<210> SEQ ID NO 1166
```

-continued

```
<211> LENGTH: 23
<212> TYPE: DNA
<213> ORGANISM: Homo sapiens

<400> SEQUENCE: 1166
ccatttcctt ctctgtaaaa tgg                                        23

<210> SEQ ID NO 1167
<211> LENGTH: 23
<212> TYPE: DNA
<213> ORGANISM: Homo sapiens

<400> SEQUENCE: 1167
ccattttaca gagaaggaaa tgg                                        23

<210> SEQ ID NO 1168
<211> LENGTH: 23
<212> TYPE: DNA
<213> ORGANISM: Homo sapiens

<400> SEQUENCE: 1168
ccagaccagc ctgaccaaca tgg                                        23

<210> SEQ ID NO 1169
<211> LENGTH: 23
<212> TYPE: DNA
<213> ORGANISM: Homo sapiens

<400> SEQUENCE: 1169
tttccccatg ttggtcaggc tgg                                        23

<210> SEQ ID NO 1170
<211> LENGTH: 23
<212> TYPE: DNA
<213> ORGANISM: Homo sapiens

<400> SEQUENCE: 1170
ggattacagc tgtgagccac cgg                                        23

<210> SEQ ID NO 1171
<211> LENGTH: 23
<212> TYPE: DNA
<213> ORGANISM: Homo sapiens

<400> SEQUENCE: 1171
agcactttgg gaggccgagg tgg                                        23

<210> SEQ ID NO 1172
<211> LENGTH: 23
<212> TYPE: DNA
<213> ORGANISM: Homo sapiens

<400> SEQUENCE: 1172
cgcttgaacc caggaggcag agg                                        23

<210> SEQ ID NO 1173
<211> LENGTH: 23
<212> TYPE: DNA
<213> ORGANISM: Homo sapiens

<400> SEQUENCE: 1173
cccagctact caggaggctg agg                                        23
```

```
<210> SEQ ID NO 1174
<211> LENGTH: 23
<212> TYPE: DNA
<213> ORGANISM: Homo sapiens

<400> SEQUENCE: 1174
tctaaaaatg aataaaaata agg                                              23

<210> SEQ ID NO 1175
<211> LENGTH: 23
<212> TYPE: DNA
<213> ORGANISM: Homo sapiens

<400> SEQUENCE: 1175
gctactcagg aggctgaggc agg                                              23

<210> SEQ ID NO 1176
<211> LENGTH: 23
<212> TYPE: DNA
<213> ORGANISM: Homo sapiens

<400> SEQUENCE: 1176
caagaccagc ctgaccaaca tgg                                              23

<210> SEQ ID NO 1177
<211> LENGTH: 23
<212> TYPE: DNA
<213> ORGANISM: Homo sapiens

<400> SEQUENCE: 1177
acaaacaaaa aaaactcttt tgg                                              23

<210> SEQ ID NO 1178
<211> LENGTH: 23
<212> TYPE: DNA
<213> ORGANISM: Homo sapiens

<400> SEQUENCE: 1178
cctcagcctc ctgagtagct ggg                                              23

<210> SEQ ID NO 1179
<211> LENGTH: 23
<212> TYPE: DNA
<213> ORGANISM: Homo sapiens

<400> SEQUENCE: 1179
acctgtaatc ccagctactc agg                                              23

<210> SEQ ID NO 1180
<211> LENGTH: 23
<212> TYPE: DNA
<213> ORGANISM: Homo sapiens

<400> SEQUENCE: 1180
tcttgcactg tcacccaggc tgg                                              23

<210> SEQ ID NO 1181
<211> LENGTH: 23
<212> TYPE: DNA
<213> ORGANISM: Homo sapiens

<400> SEQUENCE: 1181
tttttttttt agtagagacg ggg                                              23
```

<210> SEQ ID NO 1182
<211> LENGTH: 23
<212> TYPE: DNA
<213> ORGANISM: Homo sapiens

<400> SEQUENCE: 1182
cctcagcctc ctgagtagct ggg                                    23

<210> SEQ ID NO 1183
<211> LENGTH: 23
<212> TYPE: DNA
<213> ORGANISM: Homo sapiens

<400> SEQUENCE: 1183
agaccagcct gaccaacatg ggg                                    23

<210> SEQ ID NO 1184
<211> LENGTH: 23
<212> TYPE: DNA
<213> ORGANISM: Homo sapiens

<400> SEQUENCE: 1184
cagctgtaat cccagcactt tgg                                    23

<210> SEQ ID NO 1185
<211> LENGTH: 23
<212> TYPE: DNA
<213> ORGANISM: Homo sapiens

<400> SEQUENCE: 1185
tttttttttt tagtagagac ggg                                    23

<210> SEQ ID NO 1186
<211> LENGTH: 23
<212> TYPE: DNA
<213> ORGANISM: Homo sapiens

<400> SEQUENCE: 1186
gcactttggg aggctgaggc tgg                                    23

<210> SEQ ID NO 1187
<211> LENGTH: 23
<212> TYPE: DNA
<213> ORGANISM: Homo sapiens

<400> SEQUENCE: 1187
gcctgtagtc ccagctactc agg                                    23

<210> SEQ ID NO 1188
<211> LENGTH: 23
<212> TYPE: DNA
<213> ORGANISM: Homo sapiens

<400> SEQUENCE: 1188
gcactttggg aggccaaggt ggg                                    23

<210> SEQ ID NO 1189
<211> LENGTH: 23
<212> TYPE: DNA
<213> ORGANISM: Homo sapiens

<400> SEQUENCE: 1189
cgtctgtaat cccagcactt tgg                                    23

<210> SEQ ID NO 1190
<211> LENGTH: 23
<212> TYPE: DNA
<213> ORGANISM: Homo sapiens

<400> SEQUENCE: 1190
tcttgctctg ttgctcaggc agg                                          23

<210> SEQ ID NO 1191
<211> LENGTH: 23
<212> TYPE: DNA
<213> ORGANISM: Homo sapiens

<400> SEQUENCE: 1191
tgtaatccca cactttggg agg                                           23

<210> SEQ ID NO 1192
<211> LENGTH: 23
<212> TYPE: DNA
<213> ORGANISM: Homo sapiens

<400> SEQUENCE: 1192
ctaaaaatga ataaaaataa ggg                                          23

<210> SEQ ID NO 1193
<211> LENGTH: 23
<212> TYPE: DNA
<213> ORGANISM: Homo sapiens

<400> SEQUENCE: 1193
ttttctgttt ttagtagaga tgg                                          23

<210> SEQ ID NO 1194
<211> LENGTH: 23
<212> TYPE: DNA
<213> ORGANISM: Homo sapiens

<400> SEQUENCE: 1194
cccagcactt tgggaggccg agg                                          23

<210> SEQ ID NO 1195
<211> LENGTH: 23
<212> TYPE: DNA
<213> ORGANISM: Homo sapiens

<400> SEQUENCE: 1195
tttaaaaaaa aagaaacaca ggg                                          23

<210> SEQ ID NO 1196
<211> LENGTH: 23
<212> TYPE: DNA
<213> ORGANISM: Homo sapiens

<400> SEQUENCE: 1196
tgtggtccca ggtactcagg agg                                          23

<210> SEQ ID NO 1197
<211> LENGTH: 23
<212> TYPE: DNA
<213> ORGANISM: Homo sapiens

<400> SEQUENCE: 1197
agctgtaatc ccagcactttt ggg                      23

<210> SEQ ID NO 1198
<211> LENGTH: 23
<212> TYPE: DNA
<213> ORGANISM: Homo sapiens

<400> SEQUENCE: 1198
catgccactg cactccagcc tgg                       23

<210> SEQ ID NO 1199
<211> LENGTH: 23
<212> TYPE: DNA
<213> ORGANISM: Homo sapiens

<400> SEQUENCE: 1199
taaaaaaaaa aaaattagcc tgg                       23

<210> SEQ ID NO 1200
<211> LENGTH: 23
<212> TYPE: DNA
<213> ORGANISM: Homo sapiens

<400> SEQUENCE: 1200
atgccactgc actccagcct ggg                       23

<210> SEQ ID NO 1201
<211> LENGTH: 23
<212> TYPE: DNA
<213> ORGANISM: Homo sapiens

<400> SEQUENCE: 1201
accttggcct cccaaagtgc tgg                       23

<210> SEQ ID NO 1202
<211> LENGTH: 23
<212> TYPE: DNA
<213> ORGANISM: Homo sapiens

<400> SEQUENCE: 1202
cctcggcctc ccaaagtgct ggg                       23

<210> SEQ ID NO 1203
<211> LENGTH: 23
<212> TYPE: DNA
<213> ORGANISM: Homo sapiens

<400> SEQUENCE: 1203
gtctgtaatc ccagcactttt ggg                      23

<210> SEQ ID NO 1204
<211> LENGTH: 23
<212> TYPE: DNA
<213> ORGANISM: Homo sapiens

<400> SEQUENCE: 1204
cccagcactt tgggaggcca agg                       23

<210> SEQ ID NO 1205
<211> LENGTH: 23
<212> TYPE: DNA
<213> ORGANISM: Homo sapiens

<400> SEQUENCE: 1205

```
cacctgtaat cccagcactt tgg                                              23

<210> SEQ ID NO 1206
<211> LENGTH: 23
<212> TYPE: DNA
<213> ORGANISM: Homo sapiens

<400> SEQUENCE: 1206
ttgtttgttt gtttttgaag tgg                                              23

<210> SEQ ID NO 1207
<211> LENGTH: 23
<212> TYPE: DNA
<213> ORGANISM: Homo sapiens

<400> SEQUENCE: 1207
ttgcccaggc tggagtgcag tgg                                              23

<210> SEQ ID NO 1208
<211> LENGTH: 23
<212> TYPE: DNA
<213> ORGANISM: Homo sapiens

<400> SEQUENCE: 1208
agcactttgg gaggccaagg tgg                                              23

<210> SEQ ID NO 1209
<211> LENGTH: 23
<212> TYPE: DNA
<213> ORGANISM: Homo sapiens

<400> SEQUENCE: 1209
aaaaaaaaaa aaaattagcc ggg                                              23

<210> SEQ ID NO 1210
<211> LENGTH: 23
<212> TYPE: DNA
<213> ORGANISM: Homo sapiens

<400> SEQUENCE: 1210
tcacccaggc tggagtgcag tgg                                              23

<210> SEQ ID NO 1211
<211> LENGTH: 23
<212> TYPE: DNA
<213> ORGANISM: Homo sapiens

<400> SEQUENCE: 1211 ttttttttt ttagtagaga cgg                                               23

<210> SEQ ID NO 1212
<211> LENGTH: 23
<212> TYPE: DNA
<213> ORGANISM: Homo sapiens

<400> SEQUENCE: 1212
ttgtattttt agtagagaca ggg                                              23

<210> SEQ ID NO 1213
<211> LENGTH: 23
<212> TYPE: DNA
<213> ORGANISM: Homo sapiens
```

```
<400> SEQUENCE: 1213
aataaataaa taaaataaat agg                                              23

<210> SEQ ID NO 1214
<211> LENGTH: 23
<212> TYPE: DNA
<213> ORGANISM: Homo sapiens

<400> SEQUENCE: 1214
tgtagtccca gctactcagg agg                                              23

<210> SEQ ID NO 1215
<211> LENGTH: 23
<212> TYPE: DNA
<213> ORGANISM: Homo sapiens

<400> SEQUENCE: 1215
ccttggcctc ccaaagtgct ggg                                              23

<210> SEQ ID NO 1216
<211> LENGTH: 23
<212> TYPE: DNA
<213> ORGANISM: Homo sapiens

<400> SEQUENCE: 1216
aaaaaaaaaa aaaattagc cgg                                               23

<210> SEQ ID NO 1217
<211> LENGTH: 23
<212> TYPE: DNA
<213> ORGANISM: Homo sapiens

<400> SEQUENCE: 1217
tctcactctg ttgcccaggc tgg                                              23

<210> SEQ ID NO 1218
<211> LENGTH: 23
<212> TYPE: DNA
<213> ORGANISM: Homo sapiens

<400> SEQUENCE: 1218
acctgtaatc ccagcacttt ggg                                              23

<210> SEQ ID NO 1219
<211> LENGTH: 23
<212> TYPE: DNA
<213> ORGANISM: Homo sapiens

<400> SEQUENCE: 1219
tgtaatccca gcactttggg agg                                              23

<210> SEQ ID NO 1220
<211> LENGTH: 23
<212> TYPE: DNA
<213> ORGANISM: Homo sapiens

<400> SEQUENCE: 1220
tttgtatttt tagtagagac agg                                              23

<210> SEQ ID NO 1221
<211> LENGTH: 23
<212> TYPE: DNA
<213> ORGANISM: Homo sapiens
```

```
<400> SEQUENCE: 1221
tcccaaagtg ctgggattac agg                                              23

<210> SEQ ID NO 1222
<211> LENGTH: 23
<212> TYPE: DNA
<213> ORGANISM: Homo sapiens

<400> SEQUENCE: 1222
tttttttttt ttttgaggca ggg                                              23

<210> SEQ ID NO 1223
<211> LENGTH: 23
<212> TYPE: DNA
<213> ORGANISM: Homo sapiens

<400> SEQUENCE: 1223
tttttttttt tttttgaggc agg                                              23

<210> SEQ ID NO 1224
<211> LENGTH: 23
<212> TYPE: DNA
<213> ORGANISM: Homo sapiens

<400> SEQUENCE: 1224
aaaaaaaaaa aaaaaagtct ggg                                              23

<210> SEQ ID NO 1225
<211> LENGTH: 23
<212> TYPE: DNA
<213> ORGANISM: Homo sapiens

<400> SEQUENCE: 1225
aaaaaaaaaa aaaaaaagtc tgg                                              23

<210> SEQ ID NO 1226
<211> LENGTH: 23
<212> TYPE: DNA
<213> ORGANISM: Homo sapiens

<400> SEQUENCE: 1226
tttttttttt ttttttttg agg                                               23

<210> SEQ ID NO 1227
<211> LENGTH: 23
<212> TYPE: DNA
<213> ORGANISM: Homo sapiens

<400> SEQUENCE: 1227
tccaaatctc caagcgggtt ggg                                              23

<210> SEQ ID NO 1228
<211> LENGTH: 23
<212> TYPE: DNA
<213> ORGANISM: Homo sapiens

<400> SEQUENCE: 1228
ccaaatctcc aagcgggttg ggg                                              23

<210> SEQ ID NO 1229
<211> LENGTH: 23
<212> TYPE: DNA
```

<213> ORGANISM: Homo sapiens

<400> SEQUENCE: 1229
gtccaaatct ccaagcgggt tgg            23

<210> SEQ ID NO 1230
<211> LENGTH: 23
<212> TYPE: DNA
<213> ORGANISM: Homo sapiens

<400> SEQUENCE: 1230
ccggctacag ttgtgacccc tgg            23

<210> SEQ ID NO 1231
<211> LENGTH: 23
<212> TYPE: DNA
<213> ORGANISM: Homo sapiens

<400> SEQUENCE: 1231
ccccaacccg cttggagatt tgg            23

<210> SEQ ID NO 1232
<211> LENGTH: 23
<212> TYPE: DNA
<213> ORGANISM: Homo sapiens

<400> SEQUENCE: 1232
gccgggcacc ccaacccgct tgg            23

<210> SEQ ID NO 1233
<211> LENGTH: 23
<212> TYPE: DNA
<213> ORGANISM: Homo sapiens

<400> SEQUENCE: 1233
cggctacagt tgtgacccct ggg            23

<210> SEQ ID NO 1234
<211> LENGTH: 23
<212> TYPE: DNA
<213> ORGANISM: Homo sapiens

<400> SEQUENCE: 1234
ctcaaggtca cgttgacccc agg            23

<210> SEQ ID NO 1235
<211> LENGTH: 23
<212> TYPE: DNA
<213> ORGANISM: Homo sapiens

<400> SEQUENCE: 1235
ccgggatgtg tcctccgagc tgg            23

<210> SEQ ID NO 1236
<211> LENGTH: 23
<212> TYPE: DNA
<213> ORGANISM: Homo sapiens

<400> SEQUENCE: 1236
ttggggtgcc cggcatctca agg            23

<210> SEQ ID NO 1237
<211> LENGTH: 23

```
<212> TYPE: DNA
<213> ORGANISM: Homo sapiens

<400> SEQUENCE: 1237
aaagaattct gccagctcgg agg                                         23

<210> SEQ ID NO 1238
<211> LENGTH: 23
<212> TYPE: DNA
<213> ORGANISM: Homo sapiens

<400> SEQUENCE: 1238
agcagctcca ggacatcgct ggg                                         23

<210> SEQ ID NO 1239
<211> LENGTH: 23
<212> TYPE: DNA
<213> ORGANISM: Homo sapiens

<400> SEQUENCE: 1239
tcaacgtgac cttgagatgc cgg                                         23

<210> SEQ ID NO 1240
<211> LENGTH: 23
<212> TYPE: DNA
<213> ORGANISM: Homo sapiens

<400> SEQUENCE: 1240
gcttagggtg gtatgaagct ggg                                         23

<210> SEQ ID NO 1241
<211> LENGTH: 23
<212> TYPE: DNA
<213> ORGANISM: Homo sapiens

<400> SEQUENCE: 1241
cttcatacca ccctaagcca tgg                                         23

<210> SEQ ID NO 1242
<211> LENGTH: 23
<212> TYPE: DNA
<213> ORGANISM: Homo sapiens

<400> SEQUENCE: 1242 ccagggtca caactgtagc cgg                                          23

<210> SEQ ID NO 1243
<211> LENGTH: 23
<212> TYPE: DNA
<213> ORGANISM: Homo sapiens

<400> SEQUENCE: 1243
gctgctaccg aaggccagac tgg                                         23

<210> SEQ ID NO 1244
<211> LENGTH: 23
<212> TYPE: DNA
<213> ORGANISM: Homo sapiens

<400> SEQUENCE: 1244
ctgctaccga aggccagact ggg                                         23

<210> SEQ ID NO 1245
```

<211> LENGTH: 23
<212> TYPE: DNA
<213> ORGANISM: Homo sapiens

<400> SEQUENCE: 1245
tcaaggtcac gttgacccca ggg                                              23

<210> SEQ ID NO 1246
<211> LENGTH: 23
<212> TYPE: DNA
<213> ORGANISM: Homo sapiens

<400> SEQUENCE: 1246
ggcttagggt ggtatgaagc tgg                                              23

<210> SEQ ID NO 1247
<211> LENGTH: 23
<212> TYPE: DNA
<213> ORGANISM: Homo sapiens

<400> SEQUENCE: 1247
agaaggggag cgatctctcc agg                                              23

<210> SEQ ID NO 1248
<211> LENGTH: 23
<212> TYPE: DNA
<213> ORGANISM: Homo sapiens

<400> SEQUENCE: 1248
gtcccagccc agcgatgtcc tgg                                              23

<210> SEQ ID NO 1249
<211> LENGTH: 23
<212> TYPE: DNA
<213> ORGANISM: Homo sapiens

<400> SEQUENCE: 1249
ataccaccct aagccatggc tgg                                              23

<210> SEQ ID NO 1250
<211> LENGTH: 23
<212> TYPE: DNA
<213> ORGANISM: Homo sapiens

<400> SEQUENCE: 1250
caacgtgacc ttgagatgcc ggg                                              23

<210> SEQ ID NO 1251
<211> LENGTH: 23
<212> TYPE: DNA
<213> ORGANISM: Homo sapiens

<400> SEQUENCE: 1251
gagctcccag ccatggctta ggg                                              23

<210> SEQ ID NO 1252
<211> LENGTH: 23
<212> TYPE: DNA
<213> ORGANISM: Homo sapiens

<400> SEQUENCE: 1252
tgctaccgaa ggccagactg ggg                                              23

```
<210> SEQ ID NO 1253
<211> LENGTH: 23
<212> TYPE: DNA
<213> ORGANISM: Homo sapiens

<400> SEQUENCE: 1253
gctaccgaag gccagactgg ggg                                          23

<210> SEQ ID NO 1254
<211> LENGTH: 23
<212> TYPE: DNA
<213> ORGANISM: Homo sapiens

<400> SEQUENCE: 1254
caaggtcacg ttgacccag ggg                                           23

<210> SEQ ID NO 1255
<211> LENGTH: 23
<212> TYPE: DNA
<213> ORGANISM: Homo sapiens

<400> SEQUENCE: 1255
taccacccta agccatggct ggg                                          23

<210> SEQ ID NO 1256
<211> LENGTH: 23
<212> TYPE: DNA
<213> ORGANISM: Homo sapiens

<400> SEQUENCE: 1256
tccaagcggg ttggggtgcc cgg                                          23

<210> SEQ ID NO 1257
<211> LENGTH: 23
<212> TYPE: DNA
<213> ORGANISM: Homo sapiens

<400> SEQUENCE: 1257
gctccaggac atcgctgggc tgg                                          23

<210> SEQ ID NO 1258
<211> LENGTH: 23
<212> TYPE: DNA
<213> ORGANISM: Homo sapiens

<400> SEQUENCE: 1258
cttagggtgg tatgaagctg ggg                                          23

<210> SEQ ID NO 1259
<211> LENGTH: 23
<212> TYPE: DNA
<213> ORGANISM: Homo sapiens

<400> SEQUENCE: 1259
ggctacagtt gtgaccctg ggg                                           23

<210> SEQ ID NO 1260
<211> LENGTH: 23
<212> TYPE: DNA
<213> ORGANISM: Homo sapiens

<400> SEQUENCE: 1260
ccagctcgga ggacacatcc cgg                                          23
```

```
<210> SEQ ID NO 1261
<211> LENGTH: 23
<212> TYPE: DNA
<213> ORGANISM: Homo sapiens

<400> SEQUENCE: 1261
agatcgctcc ccttctcttc cgg                                               23

<210> SEQ ID NO 1262
<211> LENGTH: 23
<212> TYPE: DNA
<213> ORGANISM: Homo sapiens

<400> SEQUENCE: 1262
tgagctccca gccatggctt agg                                               23

<210> SEQ ID NO 1263
<211> LENGTH: 23
<212> TYPE: DNA
<213> ORGANISM: Homo sapiens

<400> SEQUENCE: 1263
cagcagctcc aggacatcgc tgg                                               23

<210> SEQ ID NO 1264
<211> LENGTH: 23
<212> TYPE: DNA
<213> ORGANISM: Homo sapiens

<400> SEQUENCE: 1264
agatttggac ttttcaagcc tgg                                               23

<210> SEQ ID NO 1265
<211> LENGTH: 23
<212> TYPE: DNA
<213> ORGANISM: Homo sapiens

<400> SEQUENCE: 1265
aggacacatc ccggaagaga agg                                               23

<210> SEQ ID NO 1266
<211> LENGTH: 23
<212> TYPE: DNA
<213> ORGANISM: Homo sapiens

<400> SEQUENCE: 1266
cagactgggg gccgggtgtc tgg                                               23

<210> SEQ ID NO 1267
<211> LENGTH: 23
<212> TYPE: DNA
<213> ORGANISM: Homo sapiens

<400> SEQUENCE: 1267
actgaataaa cggggctgcc tgg                                               23

<210> SEQ ID NO 1268
<211> LENGTH: 23
<212> TYPE: DNA
<213> ORGANISM: Homo sapiens

<400> SEQUENCE: 1268
ggacacatcc cggaagagaa ggg                                               23
```

```
<210> SEQ ID NO 1269
<211> LENGTH: 23
<212> TYPE: DNA
<213> ORGANISM: Homo sapiens

<400> SEQUENCE: 1269
ctcccagcca tggcttaggg tgg                                              23

<210> SEQ ID NO 1270
<211> LENGTH: 23
<212> TYPE: DNA
<213> ORGANISM: Homo sapiens

<400> SEQUENCE: 1270
cgagctggca gaattctttc tgg                                              23

<210> SEQ ID NO 1271
<211> LENGTH: 23
<212> TYPE: DNA
<213> ORGANISM: Homo sapiens

<400> SEQUENCE: 1271
aggaggtgac tccagcccaa ggg                                              23

<210> SEQ ID NO 1272
<211> LENGTH: 23
<212> TYPE: DNA
<213> ORGANISM: Homo sapiens

<400> SEQUENCE: 1272
cagacacccg gcccccagtc tgg                                              23

<210> SEQ ID NO 1273
<211> LENGTH: 23
<212> TYPE: DNA
<213> ORGANISM: Homo sapiens

<400> SEQUENCE: 1273
tagggtggta tgaagctggg ggg                                              23

<210> SEQ ID NO 1274
<211> LENGTH: 23
<212> TYPE: DNA
<213> ORGANISM: Homo sapiens

<400> SEQUENCE: 1274
ttagggtggt atgaagctgg ggg                                              23

<210> SEQ ID NO 1275
<211> LENGTH: 23
<212> TYPE: DNA
<213> ORGANISM: Homo sapiens

<400> SEQUENCE: 1275
agcagcggta acttcccccct tgg                                             23

<210> SEQ ID NO 1276
<211> LENGTH: 23
<212> TYPE: DNA
<213> ORGANISM: Homo sapiens

<400> SEQUENCE: 1276
```
ctggccttcg gtagcagcag cgg                    23

<210> SEQ ID NO 1277
<211> LENGTH: 23
<212> TYPE: DNA
<213> ORGANISM: Homo sapiens

<400> SEQUENCE: 1277
gaaaagtcca aatctccaag cgg                    23

<210> SEQ ID NO 1278
<211> LENGTH: 23
<212> TYPE: DNA
<213> ORGANISM: Homo sapiens

<400> SEQUENCE: 1278
agctgggggg actgaataaa cgg                    23

<210> SEQ ID NO 1279
<211> LENGTH: 23
<212> TYPE: DNA
<213> ORGANISM: Homo sapiens

<400> SEQUENCE: 1279
gcagcggtaa cttccccctt ggg                    23

<210> SEQ ID NO 1280
<211> LENGTH: 23
<212> TYPE: DNA
<213> ORGANISM: Homo sapiens

<400> SEQUENCE: 1280
agctgggggg actgaataaa cgg                    23

<210> SEQ ID NO 1281
<211> LENGTH: 23
<212> TYPE: DNA
<213> ORGANISM: Homo sapiens

<400> SEQUENCE: 1281
aaaagtccaa atctccaagc ggg                    23

<210> SEQ ID NO 1282
<211> LENGTH: 23
<212> TYPE: DNA
<213> ORGANISM: Homo sapiens

<400> SEQUENCE: 1282
ctccaggaca tcgctgggct ggg                    23

<210> SEQ ID NO 1283
<211> LENGTH: 23
<212> TYPE: DNA
<213> ORGANISM: Homo sapiens

<400> SEQUENCE: 1283 ccggcccca gtctggcctt cgg                    23

<210> SEQ ID NO 1284
<211> LENGTH: 23
<212> TYPE: DNA
<213> ORGANISM: Homo sapiens

<400> SEQUENCE: 1284
gacacatccc ggaagagaag ggg                                     23

<210> SEQ ID NO 1285
<211> LENGTH: 23
<212> TYPE: DNA
<213> ORGANISM: Homo sapiens

<400> SEQUENCE: 1285
ggaggtgact ccagcccaag ggg                                     23

<210> SEQ ID NO 1286
<211> LENGTH: 23
<212> TYPE: DNA
<213> ORGANISM: Homo sapiens

<400> SEQUENCE: 1286
cggtaacttc ccccttgggc tgg                                     23

<210> SEQ ID NO 1287
<211> LENGTH: 23
<212> TYPE: DNA
<213> ORGANISM: Homo sapiens

<400> SEQUENCE: 1287
cagaaagaat tctgccagct cgg                                     23

<210> SEQ ID NO 1288
<211> LENGTH: 23
<212> TYPE: DNA
<213> ORGANISM: Homo sapiens

<400> SEQUENCE: 1288
gatcgctccc cttctcttcc ggg                                     23

<210> SEQ ID NO 1289
<211> LENGTH: 23
<212> TYPE: DNA
<213> ORGANISM: Homo sapiens

<400> SEQUENCE: 1289
tggtgacagg tgaggtcctg ggg                                     23

<210> SEQ ID NO 1290
<211> LENGTH: 23
<212> TYPE: DNA
<213> ORGANISM: Homo sapiens

<400> SEQUENCE: 1290
ctggtgacag gtgaggtcct ggg                                     23

<210> SEQ ID NO 1291
<211> LENGTH: 23
<212> TYPE: DNA
<213> ORGANISM: Homo sapiens

<400> SEQUENCE: 1291
cagcgatgtc ctggagctgc tgg                                     23

<210> SEQ ID NO 1292
<211> LENGTH: 23
<212> TYPE: DNA
<213> ORGANISM: Homo sapiens

```
<400> SEQUENCE: 1292
ctggtgacag gtgaggtcct ggg                                              23

<210> SEQ ID NO 1293
<211> LENGTH: 23
<212> TYPE: DNA
<213> ORGANISM: Homo sapiens

<400> SEQUENCE: 1293
gaggtgactc cagcccaagg ggg                                              23

<210> SEQ ID NO 1294
<211> LENGTH: 23
<212> TYPE: DNA
<213> ORGANISM: Homo sapiens

<400> SEQUENCE: 1294
gctggtgaca ggtgaggtcc tgg                                              23

<210> SEQ ID NO 1295
<211> LENGTH: 23
<212> TYPE: DNA
<213> ORGANISM: Homo sapiens

<400> SEQUENCE: 1295
ctgggctggg accagacacc cgg                                              23

<210> SEQ ID NO 1296
<211> LENGTH: 23
<212> TYPE: DNA
<213> ORGANISM: Homo sapiens

<400> SEQUENCE: 1296
ccgaaggcca gactggggggc cgg                                             23

<210> SEQ ID NO 1297
<211> LENGTH: 23
<212> TYPE: DNA
<213> ORGANISM: Homo sapiens

<400> SEQUENCE: 1297
caggtgaggt cctggggtcg ggg                                              23

<210> SEQ ID NO 1298
<211> LENGTH: 23
<212> TYPE: DNA
<213> ORGANISM: Homo sapiens

<400> SEQUENCE: 1298
gctggcagaa ttctttctgg agg                                              23

<210> SEQ ID NO 1299
<211> LENGTH: 23
<212> TYPE: DNA
<213> ORGANISM: Homo sapiens

<400> SEQUENCE: 1299
gccatggctg ggagctcagc cgg                                              23

<210> SEQ ID NO 1300
<211> LENGTH: 23
<212> TYPE: DNA
<213> ORGANISM: Homo sapiens
```

```
<400> SEQUENCE: 1300
ggcagaattc tttctggagg agg                                              23

<210> SEQ ID NO 1301
<211> LENGTH: 23
<212> TYPE: DNA
<213> ORGANISM: Homo sapiens

<400> SEQUENCE: 1301
gttaccgctg ctgctaccga agg                                              23

<210> SEQ ID NO 1302
<211> LENGTH: 23
<212> TYPE: DNA
<213> ORGANISM: Homo sapiens

<400> SEQUENCE: 1302
cgaaggccag actgggggcc ggg                                              23

<210> SEQ ID NO 1303
<211> LENGTH: 23
<212> TYPE: DNA
<213> ORGANISM: Homo sapiens

<400> SEQUENCE: 1303
gccggctgag ctcccagcca tgg                                              23

<210> SEQ ID NO 1304
<211> LENGTH: 23
<212> TYPE: DNA
<213> ORGANISM: Homo sapiens

<400> SEQUENCE: 1304
acaggtgagg tcctggggtc ggg                                              23

<210> SEQ ID NO 1305
<211> LENGTH: 23
<212> TYPE: DNA
<213> ORGANISM: Homo sapiens

<400> SEQUENCE: 1305
gaggaggtga ctccagccca agg                                              23

<210> SEQ ID NO 1306
<211> LENGTH: 23
<212> TYPE: DNA
<213> ORGANISM: Homo sapiens

<400> SEQUENCE: 1306
ggagctgctg gtgacaggtg agg                                              23

<210> SEQ ID NO 1307
<211> LENGTH: 23
<212> TYPE: DNA
<213> ORGANISM: Homo sapiens

<400> SEQUENCE: 1307
gtcctggagc tgctggtgac agg                                              23

<210> SEQ ID NO 1308
<211> LENGTH: 23
<212> TYPE: DNA
```

<213> ORGANISM: Homo sapiens

<400> SEQUENCE: 1308
cacctgtcac cagcagctcc agg                                              23

<210> SEQ ID NO 1309
<211> LENGTH: 23
<212> TYPE: DNA
<213> ORGANISM: Homo sapiens

<400> SEQUENCE: 1309
gcgagcggaa gacgctcacg cgg                                              23

<210> SEQ ID NO 1310
<211> LENGTH: 23
<212> TYPE: DNA
<213> ORGANISM: Homo sapiens

<400> SEQUENCE: 1310
ggaagacgct cacgcggccc cgg                                              23

<210> SEQ ID NO 1311
<211> LENGTH: 23
<212> TYPE: DNA
<213> ORGANISM: Homo sapiens

<400> SEQUENCE: 1311
agagacgggg tgagagtccg ggg                                              23

<210> SEQ ID NO 1312
<211> LENGTH: 23
<212> TYPE: DNA
<213> ORGANISM: Homo sapiens

<400> SEQUENCE: 1312
agagagagag gtacagtgcg ggg                                              23

<210> SEQ ID NO 1313
<211> LENGTH: 23
<212> TYPE: DNA
<213> ORGANISM: Homo sapiens

<400> SEQUENCE: 1313
agagagaggt acagtgcggg ggg                                              23

<210> SEQ ID NO 1314
<211> LENGTH: 23
<212> TYPE: DNA
<213> ORGANISM: Homo sapiens

<400> SEQUENCE: 1314
cagagacggg gtgagagtcc ggg                                              23

<210> SEQ ID NO 1315
<211> LENGTH: 23
<212> TYPE: DNA
<213> ORGANISM: Homo sapiens

<400> SEQUENCE: 1315
aaacagagcg agcgagcgag cgg                                              23

<210> SEQ ID NO 1316
<211> LENGTH: 23

<212> TYPE: DNA
<213> ORGANISM: Homo sapiens

<400> SEQUENCE: 1316
gtgggtggaa caaggagtt ggg                                                23

<210> SEQ ID NO 1317
<211> LENGTH: 23
<212> TYPE: DNA
<213> ORGANISM: Homo sapiens

<400> SEQUENCE: 1317
gacagataca gagacactag ggg                                               23

<210> SEQ ID NO 1318
<211> LENGTH: 23
<212> TYPE: DNA
<213> ORGANISM: Homo sapiens

<400> SEQUENCE: 1318
gagagagagg tacagtgcgg ggg                                               23

<210> SEQ ID NO 1319
<211> LENGTH: 23
<212> TYPE: DNA
<213> ORGANISM: Homo sapiens

<400> SEQUENCE: 1319
gcagctcctc tgcagagacg ggg                                               23

<210> SEQ ID NO 1320
<211> LENGTH: 23
<212> TYPE: DNA
<213> ORGANISM: Homo sapiens

<400> SEQUENCE: 1320
acagatacag agacactagg ggg                                               23

<210> SEQ ID NO 1321
<211> LENGTH: 23
<212> TYPE: DNA
<213> ORGANISM: Homo sapiens

<400> SEQUENCE: 1321
agtgggtgga acaagggagt tgg                                               23

<210> SEQ ID NO 1322
<211> LENGTH: 23
<212> TYPE: DNA
<213> ORGANISM: Homo sapiens

<400> SEQUENCE: 1322
tggtgacagg tgaggtcctg ggg                                               23

<210> SEQ ID NO 1323
<211> LENGTH: 23
<212> TYPE: DNA
<213> ORGANISM: Homo sapiens

<400> SEQUENCE: 1323
tgggtggaac aagggagttg ggg                                               23

<210> SEQ ID NO 1324

```
<211> LENGTH: 23
<212> TYPE: DNA
<213> ORGANISM: Homo sapiens

<400> SEQUENCE: 1324
tctctgcaga ggagctgccg cgg                                              23

<210> SEQ ID NO 1325
<211> LENGTH: 23
<212> TYPE: DNA
<213> ORGANISM: Homo sapiens

<400> SEQUENCE: 1325
ctggtgacag gtgaggtcct ggg                                              23

<210> SEQ ID NO 1326
<211> LENGTH: 23
<212> TYPE: DNA
<213> ORGANISM: Homo sapiens

<400> SEQUENCE: 1326
gagagagaga ggtacagtgc ggg                                              23

<210> SEQ ID NO 1327
<211> LENGTH: 23
<212> TYPE: DNA
<213> ORGANISM: Homo sapiens

<400> SEQUENCE: 1327
gctggtgaca ggtgaggtcc tgg                                              23

<210> SEQ ID NO 1328
<211> LENGTH: 23
<212> TYPE: DNA
<213> ORGANISM: Homo sapiens

<400> SEQUENCE: 1328
gcagagacgg ggtgagagtc cgg                                              23

<210> SEQ ID NO 1329
<211> LENGTH: 23
<212> TYPE: DNA
<213> ORGANISM: Homo sapiens

<400> SEQUENCE: 1329
caggtgaggt cctggggtcg ggg                                              23

<210> SEQ ID NO 1330
<211> LENGTH: 23
<212> TYPE: DNA
<213> ORGANISM: Homo sapiens

<400> SEQUENCE: 1330
ctctcacccc gtctctgcag agg                                              23

<210> SEQ ID NO 1331
<211> LENGTH: 23
<212> TYPE: DNA
<213> ORGANISM: Homo sapiens

<400> SEQUENCE: 1331
agagagagag aggtacagtg cgg                                              23
```

```
<210> SEQ ID NO 1332
<211> LENGTH: 23
<212> TYPE: DNA
<213> ORGANISM: Homo sapiens

<400> SEQUENCE: 1332
acaggtgagg tcctggggtc ggg                                              23

<210> SEQ ID NO 1333
<211> LENGTH: 23
<212> TYPE: DNA
<213> ORGANISM: Homo sapiens

<400> SEQUENCE: 1333
gggtggaaca agggagttgg ggg                                              23

<210> SEQ ID NO 1334
<211> LENGTH: 23
<212> TYPE: DNA
<213> ORGANISM: Homo sapiens

<400> SEQUENCE: 1334
ggcagctcct ctgcagagac ggg                                              23

<210> SEQ ID NO 1335
<211> LENGTH: 23
<212> TYPE: DNA
<213> ORGANISM: Homo sapiens

<400> SEQUENCE: 1335
gaggagaagt gggtggaaca agg                                              23

<210> SEQ ID NO 1336
<211> LENGTH: 23
<212> TYPE: DNA
<213> ORGANISM: Homo sapiens

<400> SEQUENCE: 1336
cacttctcct ccccgacccc agg                                              23

<210> SEQ ID NO 1337
<211> LENGTH: 23
<212> TYPE: DNA
<213> ORGANISM: Homo sapiens

<400> SEQUENCE: 1337
gggagggaca gagagatata ggg                                              23

<210> SEQ ID NO 1338
<211> LENGTH: 23
<212> TYPE: DNA
<213> ORGANISM: Homo sapiens

<400> SEQUENCE: 1338
ggggagggac agagagatat agg                                              23

<210> SEQ ID NO 1339
<211> LENGTH: 23
<212> TYPE: DNA
<213> ORGANISM: Homo sapiens

<400> SEQUENCE: 1339
gacaggtgag gtcctggggt cgg                                              23
```

```
<210> SEQ ID NO 1340
<211> LENGTH: 23
<212> TYPE: DNA
<213> ORGANISM: Homo sapiens

<400> SEQUENCE: 1340
gtgaggtcct ggggtcgggg agg                                              23

<210> SEQ ID NO 1341
<211> LENGTH: 23
<212> TYPE: DNA
<213> ORGANISM: Homo sapiens

<400> SEQUENCE: 1341
ggagctgctg gtgacaggtg agg                                              23

<210> SEQ ID NO 1342
<211> LENGTH: 23
<212> TYPE: DNA
<213> ORGANISM: Homo sapiens

<400> SEQUENCE: 1342
tggggtcggg gaggagaagt ggg                                              23

<210> SEQ ID NO 1343
<211> LENGTH: 23
<212> TYPE: DNA
<213> ORGANISM: Homo sapiens

<400> SEQUENCE: 1343
gtcctggagc tgctggtgac agg                                              23

<210> SEQ ID NO 1344
<211> LENGTH: 23
<212> TYPE: DNA
<213> ORGANISM: Homo sapiens

<400> SEQUENCE: 1344
tggaacaagg gagttggggg agg                                              23

<210> SEQ ID NO 1345
<211> LENGTH: 23
<212> TYPE: DNA
<213> ORGANISM: Homo sapiens

<400> SEQUENCE: 1345
cggcagctcc tctgcagaga cgg                                              23

<210> SEQ ID NO 1346
<211> LENGTH: 23
<212> TYPE: DNA
<213> ORGANISM: Homo sapiens

<400> SEQUENCE: 1346
aaagagagac agagcgaggc ggg                                              23

<210> SEQ ID NO 1347
<211> LENGTH: 23
<212> TYPE: DNA
<213> ORGANISM: Homo sapiens

<400> SEQUENCE: 1347
ggaacaaggg agttggggga ggg                                              23
```

```
<210> SEQ ID NO 1348
<211> LENGTH: 23
<212> TYPE: DNA
<213> ORGANISM: Homo sapiens

<400> SEQUENCE: 1348
gaaagagaga cagagcgagg cgg                                              23

<210> SEQ ID NO 1349
<211> LENGTH: 23
<212> TYPE: DNA
<213> ORGANISM: Homo sapiens

<400> SEQUENCE: 1349
agggaaagag agacagagcg agg                                              23

<210> SEQ ID NO 1350
<211> LENGTH: 23
<212> TYPE: DNA
<213> ORGANISM: Homo sapiens

<400> SEQUENCE: 1350
ggtcggggag gagaagtggg tgg                                              23

<210> SEQ ID NO 1351
<211> LENGTH: 23
<212> TYPE: DNA
<213> ORGANISM: Homo sapiens

<400> SEQUENCE: 1351
ctggggtcgg ggaggagaag tgg                                              23

<210> SEQ ID NO 1352
<211> LENGTH: 23
<212> TYPE: DNA
<213> ORGANISM: Homo sapiens

<400> SEQUENCE: 1352
aggagaagtg ggtggaacaa ggg                                              23

<210> SEQ ID NO 1353
<211> LENGTH: 23
<212> TYPE: DNA
<213> ORGANISM: Homo sapiens

<400> SEQUENCE: 1353
aagacagata cagagacact agg                                              23

<210> SEQ ID NO 1354
<211> LENGTH: 23
<212> TYPE: DNA
<213> ORGANISM: Homo sapiens

<400> SEQUENCE: 1354
acagagaaag cgagagacag agg                                              23

<210> SEQ ID NO 1355
<211> LENGTH: 23
<212> TYPE: DNA
<213> ORGANISM: Homo sapiens

<400> SEQUENCE: 1355
```
agaggcagaa ggagaaaggg agg                                              23

<210> SEQ ID NO 1356
<211> LENGTH: 23
<212> TYPE: DNA
<213> ORGANISM: Homo sapiens

<400> SEQUENCE: 1356
aaagcgagag acagaggaga agg                                              23

<210> SEQ ID NO 1357
<211> LENGTH: 23
<212> TYPE: DNA
<213> ORGANISM: Homo sapiens

<400> SEQUENCE: 1357 ctaggggag agagagagac agg                                               23

<210> SEQ ID NO 1358
<211> LENGTH: 23
<212> TYPE: DNA
<213> ORGANISM: Homo sapiens

<400> SEQUENCE: 1358
cacctgtcac cagcagctcc agg                                              23

<210> SEQ ID NO 1359
<211> LENGTH: 23
<212> TYPE: DNA
<213> ORGANISM: Homo sapiens

<400> SEQUENCE: 1359
agggaggcag agagagaggc agg                                              23

<210> SEQ ID NO 1360
<211> LENGTH: 23
<212> TYPE: DNA
<213> ORGANISM: Homo sapiens

<400> SEQUENCE: 1360
agagaggcag gcagagagag agg                                              23

<210> SEQ ID NO 1361
<211> LENGTH: 23
<212> TYPE: DNA
<213> ORGANISM: Homo sapiens

<400> SEQUENCE: 1361
agaaagaggc agaaggagaa agg                                              23

<210> SEQ ID NO 1362
<211> LENGTH: 23
<212> TYPE: DNA
<213> ORGANISM: Homo sapiens

<400> SEQUENCE: 1362
agggaggcag agagagaggc agg                                              23

<210> SEQ ID NO 1363
<211> LENGTH: 23
<212> TYPE: DNA
<213> ORGANISM: Homo sapiens

<400> SEQUENCE: 1363
agagggaggc agagagaggg agg    23

<210> SEQ ID NO 1364
<211> LENGTH: 23
<212> TYPE: DNA
<213> ORGANISM: Homo sapiens

<400> SEQUENCE: 1364
aggcaggcag agagagaggc agg    23

<210> SEQ ID NO 1365
<211> LENGTH: 23
<212> TYPE: DNA
<213> ORGANISM: Homo sapiens

<400> SEQUENCE: 1365
gaaagaggca gaaggagaaa ggg    23

<210> SEQ ID NO 1366
<211> LENGTH: 23
<212> TYPE: DNA
<213> ORGANISM: Homo sapiens

<400> SEQUENCE: 1366
aggcaggcag agagagaggg agg    23

<210> SEQ ID NO 1367
<211> LENGTH: 23
<212> TYPE: DNA
<213> ORGANISM: Homo sapiens

<400> SEQUENCE: 1367
agacaggcag agagaaagag agg    23

<210> SEQ ID NO 1368
<211> LENGTH: 23
<212> TYPE: DNA
<213> ORGANISM: Homo sapiens

<400> SEQUENCE: 1368 taggggga gagagagaca ggg    23

<210> SEQ ID NO 1369
<211> LENGTH: 23
<212> TYPE: DNA
<213> ORGANISM: Homo sapiens

<400> SEQUENCE: 1369 aggggagag agagagacag ggg    23

<210> SEQ ID NO 1370
<211> LENGTH: 23
<212> TYPE: DNA
<213> ORGANISM: Homo sapiens

<400> SEQUENCE: 1370
aggggagcag agagagagag agg    23

<210> SEQ ID NO 1371
<211> LENGTH: 23
<212> TYPE: DNA
<213> ORGANISM: Homo sapiens

```
<400> SEQUENCE: 1371
gagaggcagg cagagagaga ggg                                              23

<210> SEQ ID NO 1372
<211> LENGTH: 23
<212> TYPE: DNA
<213> ORGANISM: Homo sapiens

<400> SEQUENCE: 1372
agaaagggag gcagagagag agg                                              23

<210> SEQ ID NO 1373
<211> LENGTH: 23
<212> TYPE: DNA
<213> ORGANISM: Homo sapiens

<400> SEQUENCE: 1373
aggcagacag agagagagac agg                                              23

<210> SEQ ID NO 1374
<211> LENGTH: 23
<212> TYPE: DNA
<213> ORGANISM: Homo sapiens

<400> SEQUENCE: 1374
agagagaggg aggcagagag agg                                              23

<210> SEQ ID NO 1375
<211> LENGTH: 23
<212> TYPE: DNA
<213> ORGANISM: Homo sapiens

<400> SEQUENCE: 1375
agggaggcag agagagaggg agg                                              23

<210> SEQ ID NO 1376
<211> LENGTH: 23
<212> TYPE: DNA
<213> ORGANISM: Homo sapiens

<400> SEQUENCE: 1376
agagagggag gcagagagag agg                                              23

<210> SEQ ID NO 1377
<211> LENGTH: 23
<212> TYPE: DNA
<213> ORGANISM: Homo sapiens

<400> SEQUENCE: 1377
gaaagggagg cagagagaga ggg                                              23

<210> SEQ ID NO 1378
<211> LENGTH: 23
<212> TYPE: DNA
<213> ORGANISM: Homo sapiens

<400> SEQUENCE: 1378
gagagagaga aagaggcaga agg                                              23

<210> SEQ ID NO 1379
<211> LENGTH: 23
<212> TYPE: DNA
<213> ORGANISM: Homo sapiens
```

-continued

<400> SEQUENCE: 1379
gagagaggga ggcagagaga ggg                                              23

<210> SEQ ID NO 1380
<211> LENGTH: 23
<212> TYPE: DNA
<213> ORGANISM: Homo sapiens

<400> SEQUENCE: 1380 gggggagag agagagaaag agg                                               23

<210> SEQ ID NO 1381
<211> LENGTH: 23
<212> TYPE: DNA
<213> ORGANISM: Homo sapiens

<400> SEQUENCE: 1381
gagagggagg cagagagaga ggg                                              23

<210> SEQ ID NO 1382
<211> LENGTH: 23
<212> TYPE: DNA
<213> ORGANISM: Homo sapiens

<400> SEQUENCE: 1382
agaggcagaa agagagagag agg                                              23

<210> SEQ ID NO 1383
<211> LENGTH: 23
<212> TYPE: DNA
<213> ORGANISM: Homo sapiens

<400> SEQUENCE: 1383
gagcttcgtg ctgtaccgcg agg                                              23

<210> SEQ ID NO 1384
<211> LENGTH: 23
<212> TYPE: DNA
<213> ORGANISM: Homo sapiens

<400> SEQUENCE: 1384
cgggggaacc tagtccgcct ggg                                              23

<210> SEQ ID NO 1385
<211> LENGTH: 23
<212> TYPE: DNA
<213> ORGANISM: Homo sapiens

<400> SEQUENCE: 1385
ggggtctaag gaccgttccg cgg                                              23

<210> SEQ ID NO 1386
<211> LENGTH: 23
<212> TYPE: DNA
<213> ORGANISM: Homo sapiens

<400> SEQUENCE: 1386
gttcccccgg gtgtagtcgg agg                                              23

<210> SEQ ID NO 1387
<211> LENGTH: 23
<212> TYPE: DNA

<213> ORGANISM: Homo sapiens

<400> SEQUENCE: 1387
gggggaacct agtccgcctg ggg                                              23

<210> SEQ ID NO 1388
<211> LENGTH: 23
<212> TYPE: DNA
<213> ORGANISM: Homo sapiens

<400> SEQUENCE: 1388
agcttcgtgc tgtaccgcga ggg                                              23

<210> SEQ ID NO 1389
<211> LENGTH: 23
<212> TYPE: DNA
<213> ORGANISM: Homo sapiens

<400> SEQUENCE: 1389
cgtgctgtac cgcgagggcg tgg                                              23

<210> SEQ ID NO 1390
<211> LENGTH: 23
<212> TYPE: DNA
<213> ORGANISM: Homo sapiens

<400> SEQUENCE: 1390
ctgcgctgcg acagcacgta ggg                                              23

<210> SEQ ID NO 1391
<211> LENGTH: 23
<212> TYPE: DNA
<213> ORGANISM: Homo sapiens

<400> SEQUENCE: 1391
taggttcccc cgggtgtagt cgg                                              23

<210> SEQ ID NO 1392
<211> LENGTH: 23
<212> TYPE: DNA
<213> ORGANISM: Homo sapiens

<400> SEQUENCE: 1392
aaaagtgacc agcgcgccca ggg                                              23

<210> SEQ ID NO 1393
<211> LENGTH: 23
<212> TYPE: DNA
<213> ORGANISM: Homo sapiens

<400> SEQUENCE: 1393
gcgcgctggt cactttgac tgg                                               23

<210> SEQ ID NO 1394
<211> LENGTH: 23
<212> TYPE: DNA
<213> ORGANISM: Homo sapiens

<400> SEQUENCE: 1394
gcacgaagct catgttccgc agg                                              23

<210> SEQ ID NO 1395
<211> LENGTH: 23

```
<212> TYPE: DNA
<213> ORGANISM: Homo sapiens

<400> SEQUENCE: 1395
gacagcacgt agggcgcgga ggg                                              23

<210> SEQ ID NO 1396
<211> LENGTH: 23
<212> TYPE: DNA
<213> ORGANISM: Homo sapiens

<400> SEQUENCE: 1396
tgaaaggaag acgcgattag tgg                                              23

<210> SEQ ID NO 1397
<211> LENGTH: 23
<212> TYPE: DNA
<213> ORGANISM: Homo sapiens

<400> SEQUENCE: 1397
tgggccgact tcacgctgct ggg                                              23

<210> SEQ ID NO 1398
<211> LENGTH: 23
<212> TYPE: DNA
<213> ORGANISM: Homo sapiens

<400> SEQUENCE: 1398
agcagcgtga agtcggccca ggg                                              23

<210> SEQ ID NO 1399
<211> LENGTH: 23
<212> TYPE: DNA
<213> ORGANISM: Homo sapiens

<400> SEQUENCE: 1399
gctcaggggc ggataccagc agg                                              23

<210> SEQ ID NO 1400
<211> LENGTH: 23
<212> TYPE: DNA
<213> ORGANISM: Homo sapiens

<400> SEQUENCE: 1400
caaaagtgac cagcgcgccc agg                                              23

<210> SEQ ID NO 1401
<211> LENGTH: 23
<212> TYPE: DNA
<213> ORGANISM: Homo sapiens

<400> SEQUENCE: 1401
ggaataaaag ctggcgagcg cgg                                              23

<210> SEQ ID NO 1402
<211> LENGTH: 23
<212> TYPE: DNA
<213> ORGANISM: Homo sapiens

<400> SEQUENCE: 1402
cgcgcagcgc aggctcacgt tgg                                              23

<210> SEQ ID NO 1403
```

```
<211> LENGTH: 23
<212> TYPE: DNA
<213> ORGANISM: Homo sapiens

<400> SEQUENCE: 1403
agcgccacca gcgacggccg cgg                                              23

<210> SEQ ID NO 1404
<211> LENGTH: 23
<212> TYPE: DNA
<213> ORGANISM: Homo sapiens

<400> SEQUENCE: 1404
ctgcgacagc acgtagggcg cgg                                              23

<210> SEQ ID NO 1405
<211> LENGTH: 23
<212> TYPE: DNA
<213> ORGANISM: Homo sapiens

<400> SEQUENCE: 1405
ccgggggaac ctagtccgcc tgg                                              23

<210> SEQ ID NO 1406
<211> LENGTH: 23
<212> TYPE: DNA
<213> ORGANISM: Homo sapiens

<400> SEQUENCE: 1406
caatcagcag gacacgggcg ggg                                              23

<210> SEQ ID NO 1407
<211> LENGTH: 23
<212> TYPE: DNA
<213> ORGANISM: Homo sapiens

<400> SEQUENCE: 1407
ccattttaca gagcgctgat tgg                                              23

<210> SEQ ID NO 1408
<211> LENGTH: 23
<212> TYPE: DNA
<213> ORGANISM: Homo sapiens

<400> SEQUENCE: 1408
aacgtgagcc tgcgctgcgc ggg                                              23

<210> SEQ ID NO 1409
<211> LENGTH: 23
<212> TYPE: DNA
<213> ORGANISM: Homo sapiens

<400> SEQUENCE: 1409
caacgtgagc ctgcgctgcg cgg                                              23

<210> SEQ ID NO 1410
<211> LENGTH: 23
<212> TYPE: DNA
<213> ORGANISM: Homo sapiens

<400> SEQUENCE: 1410
gctgcgctgc gacagcacgt agg                                              23
```

```
<210> SEQ ID NO 1411
<211> LENGTH: 23
<212> TYPE: DNA
<213> ORGANISM: Homo sapiens

<400> SEQUENCE: 1411
cgacagcacg tagggcgcgg agg                                              23

<210> SEQ ID NO 1412
<211> LENGTH: 23
<212> TYPE: DNA
<213> ORGANISM: Homo sapiens

<400> SEQUENCE: 1412
cgtgctgtcg cagcgcagcg agg                                              23

<210> SEQ ID NO 1413
<211> LENGTH: 23
<212> TYPE: DNA
<213> ORGANISM: Homo sapiens

<400> SEQUENCE: 1413
ctgggccgac ttcacgctgc tgg                                              23

<210> SEQ ID NO 1414
<211> LENGTH: 23
<212> TYPE: DNA
<213> ORGANISM: Homo sapiens

<400> SEQUENCE: 1414
cagcagcgtg aagtcggccc agg                                              23

<210> SEQ ID NO 1415
<211> LENGTH: 23
<212> TYPE: DNA
<213> ORGANISM: Homo sapiens

<400> SEQUENCE: 1415
gctcctccga ctacacccgg ggg                                              23

<210> SEQ ID NO 1416
<211> LENGTH: 23
<212> TYPE: DNA
<213> ORGANISM: Homo sapiens

<400> SEQUENCE: 1416
gctggctgag ctccgcggaa cgg                                              23

<210> SEQ ID NO 1417
<211> LENGTH: 23
<212> TYPE: DNA
<213> ORGANISM: Homo sapiens

<400> SEQUENCE: 1417
gctgtaccgc gagggcgtgg cgg                                              23

<210> SEQ ID NO 1418
<211> LENGTH: 23
<212> TYPE: DNA
<213> ORGANISM: Homo sapiens

<400> SEQUENCE: 1418
cgaagctcat gttccgcagg cgg                                              23
```

```
<210> SEQ ID NO 1419
<211> LENGTH: 23
<212> TYPE: DNA
<213> ORGANISM: Homo sapiens

<400> SEQUENCE: 1419
ggctcctccg actacacccg ggg                                              23

<210> SEQ ID NO 1420
<211> LENGTH: 23
<212> TYPE: DNA
<213> ORGANISM: Homo sapiens

<400> SEQUENCE: 1420
agagtctgct tccacgttgt ggg                                              23

<210> SEQ ID NO 1421
<211> LENGTH: 23
<212> TYPE: DNA
<213> ORGANISM: Homo sapiens

<400> SEQUENCE: 1421
ctggctcctc cgactacacc cgg                                              23

<210> SEQ ID NO 1422
<211> LENGTH: 23
<212> TYPE: DNA
<213> ORGANISM: Homo sapiens

<400> SEQUENCE: 1422
caaagttgag ggggagtcga tgg                                              23

<210> SEQ ID NO 1423
<211> LENGTH: 23
<212> TYPE: DNA
<213> ORGANISM: Homo sapiens

<400> SEQUENCE: 1423
caggcggact aggttccccc ggg                                              23

<210> SEQ ID NO 1424
<211> LENGTH: 23
<212> TYPE: DNA
<213> ORGANISM: Homo sapiens

<400> SEQUENCE: 1424
ggacacgggc ggggacaata agg                                              23

<210> SEQ ID NO 1425
<211> LENGTH: 23
<212> TYPE: DNA
<213> ORGANISM: Homo sapiens

<400> SEQUENCE: 1425
cggagtggcg gtactgcagc ggg                                              23

<210> SEQ ID NO 1426
<211> LENGTH: 23
<212> TYPE: DNA
<213> ORGANISM: Homo sapiens

<400> SEQUENCE: 1426
ggagtggcgg tactgcagcg ggg                                              23
```

<210> SEQ ID NO 1427
<211> LENGTH: 23
<212> TYPE: DNA
<213> ORGANISM: Homo sapiens

<400> SEQUENCE: 1427
agtcagaacc gcgctcctgc tgg                                        23

<210> SEQ ID NO 1428
<211> LENGTH: 23
<212> TYPE: DNA
<213> ORGANISM: Homo sapiens

<400> SEQUENCE: 1428
ccaggcggac taggttcccc cgg                                        23

<210> SEQ ID NO 1429
<211> LENGTH: 23
<212> TYPE: DNA
<213> ORGANISM: Homo sapiens

<400> SEQUENCE: 1429
cctcatctcc ctgggcgcgc tgg                                        23

<210> SEQ ID NO 1430
<211> LENGTH: 23
<212> TYPE: DNA
<213> ORGANISM: Homo sapiens

<400> SEQUENCE: 1430
gcggagtggc ggtactgcag cgg                                        23

<210> SEQ ID NO 1431
<211> LENGTH: 23
<212> TYPE: DNA
<213> ORGANISM: Homo sapiens

<400> SEQUENCE: 1431
tggctcctcc gactacaccc ggg                                        23

<210> SEQ ID NO 1432
<211> LENGTH: 23
<212> TYPE: DNA
<213> ORGANISM: Homo sapiens

<400> SEQUENCE: 1432
tcgatggagg cttcaactcc tgg                                        23

<210> SEQ ID NO 1433
<211> LENGTH: 23
<212> TYPE: DNA
<213> ORGANISM: Homo sapiens

<400> SEQUENCE: 1433
gaacctagtc cgcctggggc tgg                                        23

<210> SEQ ID NO 1434
<211> LENGTH: 23
<212> TYPE: DNA
<213> ORGANISM: Homo sapiens

<400> SEQUENCE: 1434

```
ttgcgccag gacccaccac cgg                                                    23

<210> SEQ ID NO 1435
<211> LENGTH: 23
<212> TYPE: DNA
<213> ORGANISM: Homo sapiens

<400> SEQUENCE: 1435
cgtgtgatag tagcagctgt agg                                                   23

<210> SEQ ID NO 1436
<211> LENGTH: 23
<212> TYPE: DNA
<213> ORGANISM: Homo sapiens

<400> SEQUENCE: 1436
gtcgcagcgc agcgaggtgc tgg                                                   23

<210> SEQ ID NO 1437
<211> LENGTH: 23
<212> TYPE: DNA
<213> ORGANISM: Homo sapiens

<400> SEQUENCE: 1437
ccaatcagca ggacacgggc ggg                                                   23

<210> SEQ ID NO 1438
<211> LENGTH: 23
<212> TYPE: DNA
<213> ORGANISM: Homo sapiens

<400> SEQUENCE: 1438
agaacaaagc tcccacaacg tgg                                                   23

<210> SEQ ID NO 1439
<211> LENGTH: 23
<212> TYPE: DNA
<213> ORGANISM: Homo sapiens

<400> SEQUENCE: 1439
cagagtctgc ttccacgttg tgg                                                   23

<210> SEQ ID NO 1440
<211> LENGTH: 23
<212> TYPE: DNA
<213> ORGANISM: Homo sapiens

<400> SEQUENCE: 1440
ccaatcagcg ctctgtaaaa tgg                                                   23

<210> SEQ ID NO 1441
<211> LENGTH: 23
<212> TYPE: DNA
<213> ORGANISM: Homo sapiens

<400> SEQUENCE: 1441
gacacgggcg gggacaataa ggg                                                   23

<210> SEQ ID NO 1442
<211> LENGTH: 23
<212> TYPE: DNA
<213> ORGANISM: Homo sapiens

<400> SEQUENCE: 1442
```
ccgggcagcg ccaccagcga cgg                                          23

<210> SEQ ID NO 1443
<211> LENGTH: 23
<212> TYPE: DNA
<213> ORGANISM: Homo sapiens

<400> SEQUENCE: 1443
gctgccgcgg ccgtcgctgg tgg                                          23

<210> SEQ ID NO 1444
<211> LENGTH: 23
<212> TYPE: DNA
<213> ORGANISM: Homo sapiens

<400> SEQUENCE: 1444
cgatggaggc ttcaactcct ggg                                          23

<210> SEQ ID NO 1445
<211> LENGTH: 23
<212> TYPE: DNA
<213> ORGANISM: Homo sapiens

<400> SEQUENCE: 1445
agcttctccg ccactcaggt tgg                                          23

<210> SEQ ID NO 1446
<211> LENGTH: 23
<212> TYPE: DNA
<213> ORGANISM: Homo sapiens

<400> SEQUENCE: 1446
cccgagactt ccaacctgag tgg                                          23

<210> SEQ ID NO 1447
<211> LENGTH: 23
<212> TYPE: DNA
<213> ORGANISM: Homo sapiens

<400> SEQUENCE: 1447
ggcgcccagc agcgtgaagt cgg                                          23

<210> SEQ ID NO 1448
<211> LENGTH: 23
<212> TYPE: DNA
<213> ORGANISM: Homo sapiens

<400> SEQUENCE: 1448
gactagactc ctggatctga ggg                                          23

<210> SEQ ID NO 1449
<211> LENGTH: 23
<212> TYPE: DNA
<213> ORGANISM: Homo sapiens

<400> SEQUENCE: 1449
cggccagccc caggcggact agg                                          23

<210> SEQ ID NO 1450
<211> LENGTH: 23
<212> TYPE: DNA
<213> ORGANISM: Homo sapiens

```
<400> SEQUENCE: 1450
gattcgaacc ctctgtcttc tgg                                          23

<210> SEQ ID NO 1451
<211> LENGTH: 23
<212> TYPE: DNA
<213> ORGANISM: Homo sapiens

<400> SEQUENCE: 1451
cacaacgtgg aagcagactc tgg                                          23

<210> SEQ ID NO 1452
<211> LENGTH: 23
<212> TYPE: DNA
<213> ORGANISM: Homo sapiens

<400> SEQUENCE: 1452
gtagcagctg taggtgccgg ggg                                          23

<210> SEQ ID NO 1453
<211> LENGTH: 23
<212> TYPE: DNA
<213> ORGANISM: Homo sapiens

<400> SEQUENCE: 1453
gcgaggtgct ggtcatcagc tgg                                          23

<210> SEQ ID NO 1454
<211> LENGTH: 23
<212> TYPE: DNA
<213> ORGANISM: Homo sapiens

<400> SEQUENCE: 1454
atagtagcag ctgtaggtgc cgg                                          23

<210> SEQ ID NO 1455
<211> LENGTH: 23
<212> TYPE: DNA
<213> ORGANISM: Homo sapiens

<400> SEQUENCE: 1455
gagctggagg actagactcc tgg                                          23

<210> SEQ ID NO 1456
<211> LENGTH: 23
<212> TYPE: DNA
<213> ORGANISM: Homo sapiens

<400> SEQUENCE: 1456
ggctgcagga ctagacccct ggg                                          23

<210> SEQ ID NO 1457
<211> LENGTH: 23
<212> TYPE: DNA
<213> ORGANISM: Homo sapiens

<400> SEQUENCE: 1457
agttgagggg gagtcgatgg agg                                          23

<210> SEQ ID NO 1458
<211> LENGTH: 23
<212> TYPE: DNA
<213> ORGANISM: Homo sapiens
```

```
<400> SEQUENCE: 1458
acagggcaca gcggggtcta agg                                           23

<210> SEQ ID NO 1459
<211> LENGTH: 23
<212> TYPE: DNA
<213> ORGANISM: Homo sapiens

<400> SEQUENCE: 1459
ctactactac agtgagtaga cgg                                           23

<210> SEQ ID NO 1460
<211> LENGTH: 23
<212> TYPE: DNA
<213> ORGANISM: Homo sapiens

<400> SEQUENCE: 1460
accaatcagc aggacacggg cgg                                           23

<210> SEQ ID NO 1461
<211> LENGTH: 23
<212> TYPE: DNA
<213> ORGANISM: Homo sapiens

<400> SEQUENCE: 1461
gctcccggac cccaaagtct ggg                                           23

<210> SEQ ID NO 1462
<211> LENGTH: 23
<212> TYPE: DNA
<213> ORGANISM: Homo sapiens

<400> SEQUENCE: 1462
ccactcaggt tggaagtctc ggg                                           23

<210> SEQ ID NO 1463
<211> LENGTH: 23
<212> TYPE: DNA
<213> ORGANISM: Homo sapiens

<400> SEQUENCE: 1463
gccactcagg ttggaagtct cgg                                           23

<210> SEQ ID NO 1464
<211> LENGTH: 23
<212> TYPE: DNA
<213> ORGANISM: Homo sapiens

<400> SEQUENCE: 1464
acgtggaagc agactctggt ggg                                           23

<210> SEQ ID NO 1465
<211> LENGTH: 23
<212> TYPE: DNA
<213> ORGANISM: Homo sapiens

<400> SEQUENCE: 1465
ggagctgccg cggccgtcgc tgg                                           23

<210> SEQ ID NO 1466
<211> LENGTH: 23
<212> TYPE: DNA
```

<213> ORGANISM: Homo sapiens

<400> SEQUENCE: 1466
agtagcagct gtaggtgccg ggg                                           23

<210> SEQ ID NO 1467
<211> LENGTH: 23
<212> TYPE: DNA
<213> ORGANISM: Homo sapiens

<400> SEQUENCE: 1467
agctcccgga ccccaaagtc tgg                                           23

<210> SEQ ID NO 1468
<211> LENGTH: 23
<212> TYPE: DNA
<213> ORGANISM: Homo sapiens

<400> SEQUENCE: 1468
cagtgagtag acggcagtgc tgg                                           23

<210> SEQ ID NO 1469
<211> LENGTH: 23
<212> TYPE: DNA
<213> ORGANISM: Homo sapiens

<400> SEQUENCE: 1469
ccatcttaca gagtgctgat tgg                                           23

<210> SEQ ID NO 1470
<211> LENGTH: 23
<212> TYPE: DNA
<213> ORGANISM: Homo sapiens

<400> SEQUENCE: 1470
gcgctgcccg ggccggtggt ggg                                           23

<210> SEQ ID NO 1471
<211> LENGTH: 23
<212> TYPE: DNA
<213> ORGANISM: Homo sapiens

<400> SEQUENCE: 1471
ccaatcagca ctctgtaaga tgg                                           23

<210> SEQ ID NO 1472
<211> LENGTH: 23
<212> TYPE: DNA
<213> ORGANISM: Homo sapiens

<400> SEQUENCE: 1472
tagtagcagc tgtaggtgcc ggg                                           23

<210> SEQ ID NO 1473
<211> LENGTH: 23
<212> TYPE: DNA
<213> ORGANISM: Homo sapiens

<400> SEQUENCE: 1473
cgaggtgctg gtcatcagct ggg                                           23

<210> SEQ ID NO 1474
<211> LENGTH: 23

```
<212> TYPE: DNA
<213> ORGANISM: Homo sapiens

<400> SEQUENCE: 1474
gggctgcagg actagacccc tgg                                              23

<210> SEQ ID NO 1475
<211> LENGTH: 23
<212> TYPE: DNA
<213> ORGANISM: Homo sapiens

<400> SEQUENCE: 1475
ggtccctaag tccaccccag ggg                                              23

<210> SEQ ID NO 1476
<211> LENGTH: 23
<212> TYPE: DNA
<213> ORGANISM: Homo sapiens

<400> SEQUENCE: 1476
gagacttcca acctgagtgg cgg                                              23

<210> SEQ ID NO 1477
<211> LENGTH: 23
<212> TYPE: DNA
<213> ORGANISM: Homo sapiens

<400> SEQUENCE: 1477
ttcaacccag gaagtccagc tgg                                              23

<210> SEQ ID NO 1478
<211> LENGTH: 23
<212> TYPE: DNA
<213> ORGANISM: Homo sapiens

<400> SEQUENCE: 1478
tagtgagacg tgaagccagc tgg                                              23

<210> SEQ ID NO 1479
<211> LENGTH: 23
<212> TYPE: DNA
<213> ORGANISM: Homo sapiens

<400> SEQUENCE: 1479
agtgagtaga cggcagtgct ggg                                              23

<210> SEQ ID NO 1480
<211> LENGTH: 23
<212> TYPE: DNA
<213> ORGANISM: Homo sapiens

<400> SEQUENCE: 1480
tgtaaaatgg accaatcagc agg                                              23

<210> SEQ ID NO 1481
<211> LENGTH: 23
<212> TYPE: DNA
<213> ORGANISM: Homo sapiens

<400> SEQUENCE: 1481
tgcgctgcgc gggccgcctg cgg                                              23

<210> SEQ ID NO 1482
```

-continued

<210> SEQ ID NO 1482
<211> LENGTH: 23
<212> TYPE: DNA
<213> ORGANISM: Homo sapiens

<400> SEQUENCE: 1482
gcaggcggcc cgcgcagcgc agg          23

<210> SEQ ID NO 1483
<211> LENGTH: 23
<212> TYPE: DNA
<213> ORGANISM: Homo sapiens

<400> SEQUENCE: 1483
aactttgaga ctgtagagtc agg          23

<210> SEQ ID NO 1484
<211> LENGTH: 23
<212> TYPE: DNA
<213> ORGANISM: Homo sapiens

<400> SEQUENCE: 1484
cagcccctgg ggtggactta ggg          23

<210> SEQ ID NO 1485
<211> LENGTH: 23
<212> TYPE: DNA
<213> ORGANISM: Homo sapiens

<400> SEQUENCE: 1485
actctacagt ctcaaagttg agg          23

<210> SEQ ID NO 1486
<211> LENGTH: 23
<212> TYPE: DNA
<213> ORGANISM: Homo sapiens

<400> SEQUENCE: 1486
ggcggatacc agcaggagcg cgg          23

<210> SEQ ID NO 1487
<211> LENGTH: 23
<212> TYPE: DNA
<213> ORGANISM: Homo sapiens

<400> SEQUENCE: 1487
aacctgagtg gcggagaagc tgg          23

<210> SEQ ID NO 1488
<211> LENGTH: 23
<212> TYPE: DNA
<213> ORGANISM: Homo sapiens

<400> SEQUENCE: 1488
tggacttcct gggttgaatg ggg          23

<210> SEQ ID NO 1489
<211> LENGTH: 23
<212> TYPE: DNA
<213> ORGANISM: Homo sapiens

<400> SEQUENCE: 1489
ggactagact cctggatctg agg          23

```
<210> SEQ ID NO 1490
<211> LENGTH: 23
<212> TYPE: DNA
<213> ORGANISM: Homo sapiens

<400> SEQUENCE: 1490
tccaggtccc cattcaaccc agg                                            23

<210> SEQ ID NO 1491
<211> LENGTH: 23
<212> TYPE: DNA
<213> ORGANISM: Homo sapiens

<400> SEQUENCE: 1491
gcggggccgc cacgccctcg cgg                                            23

<210> SEQ ID NO 1492
<211> LENGTH: 23
<212> TYPE: DNA
<213> ORGANISM: Homo sapiens

<400> SEQUENCE: 1492
gccaggaccc accaccggcc cgg                                            23

<210> SEQ ID NO 1493
<211> LENGTH: 23
<212> TYPE: DNA
<213> ORGANISM: Homo sapiens

<400> SEQUENCE: 1493
gactagaccc ctgggtctga agg                                            23

<210> SEQ ID NO 1494
<211> LENGTH: 23
<212> TYPE: DNA
<213> ORGANISM: Homo sapiens

<400> SEQUENCE: 1494
gtactggggc ccgggaatcc tgg                                            23

<210> SEQ ID NO 1495
<211> LENGTH: 23
<212> TYPE: DNA
<213> ORGANISM: Homo sapiens

<400> SEQUENCE: 1495
ccggctccgc ccgcagactc tgg                                            23

<210> SEQ ID NO 1496
<211> LENGTH: 23
<212> TYPE: DNA
<213> ORGANISM: Homo sapiens

<400> SEQUENCE: 1496
ccagagtctg cgggcggagc cgg                                            23

<210> SEQ ID NO 1497
<211> LENGTH: 23
<212> TYPE: DNA
<213> ORGANISM: Homo sapiens

<400> SEQUENCE: 1497
gtctcgggct gcagtgctcc tgg                                            23
```

```
<210> SEQ ID NO 1498
<211> LENGTH: 23
<212> TYPE: DNA
<213> ORGANISM: Homo sapiens

<400> SEQUENCE: 1498
acctgagtgg cggagaagct ggg                                              23

<210> SEQ ID NO 1499
<211> LENGTH: 23
<212> TYPE: DNA
<213> ORGANISM: Homo sapiens

<400> SEQUENCE: 1499
ctacagtctc aaagttgagg ggg                                              23

<210> SEQ ID NO 1500
<211> LENGTH: 23
<212> TYPE: DNA
<213> ORGANISM: Homo sapiens

<400> SEQUENCE: 1500
gagttcaggg cccagacttt ggg                                              23

<210> SEQ ID NO 1501
<211> LENGTH: 23
<212> TYPE: DNA
<213> ORGANISM: Homo sapiens

<400> SEQUENCE: 1501
gctggacttc ctgggttgaa tgg                                              23

<210> SEQ ID NO 1502
<211> LENGTH: 23
<212> TYPE: DNA
<213> ORGANISM: Homo sapiens

<400> SEQUENCE: 1502
ctggacttcc tgggttgaat ggg                                              23

<210> SEQ ID NO 1503
<211> LENGTH: 23
<212> TYPE: DNA
<213> ORGANISM: Homo sapiens

<400> SEQUENCE: 1503
tggaccaatc agcaggacac ggg                                              23

<210> SEQ ID NO 1504
<211> LENGTH: 23
<212> TYPE: DNA
<213> ORGANISM: Homo sapiens

<400> SEQUENCE: 1504
accgccactc cgcgcagccc tgg                                              23

<210> SEQ ID NO 1505
<211> LENGTH: 23
<212> TYPE: DNA
<213> ORGANISM: Homo sapiens

<400> SEQUENCE: 1505
tactggggcc cgggaatcct ggg                                              23
```

<210> SEQ ID NO 1506
<211> LENGTH: 23
<212> TYPE: DNA
<213> ORGANISM: Homo sapiens

<400> SEQUENCE: 1506
caggtcccta agtccacccc agg                                              23

<210> SEQ ID NO 1507
<211> LENGTH: 23
<212> TYPE: DNA
<213> ORGANISM: Homo sapiens

<400> SEQUENCE: 1507
ttccgcggag ctcagccagc agg                                              23

<210> SEQ ID NO 1508
<211> LENGTH: 23
<212> TYPE: DNA
<213> ORGANISM: Homo sapiens

<400> SEQUENCE: 1508
cgtggaagca gactctggtg ggg                                              23

<210> SEQ ID NO 1509
<211> LENGTH: 23
<212> TYPE: DNA
<213> ORGANISM: Homo sapiens

<400> SEQUENCE: 1509
aacgtggaag cagactctgg tgg                                              23

<210> SEQ ID NO 1510
<211> LENGTH: 23
<212> TYPE: DNA
<213> ORGANISM: Homo sapiens

<400> SEQUENCE: 1510
cgtcgctggt ggcgctgccc ggg                                              23

<210> SEQ ID NO 1511
<211> LENGTH: 23
<212> TYPE: DNA
<213> ORGANISM: Homo sapiens

<400> SEQUENCE: 1511
ccgtcgctgg tggcgctgcc cgg                                              23

<210> SEQ ID NO 1512
<211> LENGTH: 23
<212> TYPE: DNA
<213> ORGANISM: Homo sapiens

<400> SEQUENCE: 1512
cctggactgc tggatcagga agg                                              23

<210> SEQ ID NO 1513
<211> LENGTH: 23
<212> TYPE: DNA
<213> ORGANISM: Homo sapiens

<400> SEQUENCE: 1513
cccgggccgg tggtgggtcc tgg                                                  23

<210> SEQ ID NO 1514
<211> LENGTH: 23
<212> TYPE: DNA
<213> ORGANISM: Homo sapiens

<400> SEQUENCE: 1514
gctgtaggtg ccggggcgc ggg                                                   23

<210> SEQ ID NO 1515
<211> LENGTH: 23
<212> TYPE: DNA
<213> ORGANISM: Homo sapiens

<400> SEQUENCE: 1515
ggtctgaggg cggaggtcct ggg                                                  23

<210> SEQ ID NO 1516
<211> LENGTH: 23
<212> TYPE: DNA
<213> ORGANISM: Homo sapiens

<400> SEQUENCE: 1516
aggtccctaa gtccacccca ggg                                                  23

<210> SEQ ID NO 1517
<211> LENGTH: 23
<212> TYPE: DNA
<213> ORGANISM: Homo sapiens

<400> SEQUENCE: 1517
cagagtctgc gggcggagcc ggg                                                  23

<210> SEQ ID NO 1518
<211> LENGTH: 23
<212> TYPE: DNA
<213> ORGANISM: Homo sapiens

<400> SEQUENCE: 1518
tctcgggctg cagtgctcct ggg                                                  23

<210> SEQ ID NO 1519
<211> LENGTH: 23
<212> TYPE: DNA
<213> ORGANISM: Homo sapiens

<400> SEQUENCE: 1519
gaagtcggcc cagggctgcg cgg                                                  23

<210> SEQ ID NO 1520
<211> LENGTH: 23
<212> TYPE: DNA
<213> ORGANISM: Homo sapiens

<400> SEQUENCE: 1520
cccgggaatc ctgggtctga ggg                                                  23

<210> SEQ ID NO 1521
<211> LENGTH: 23
<212> TYPE: DNA
<213> ORGANISM: Homo sapiens

<400> SEQUENCE: 1521
tcggaggagc cagagtctgc ggg    23

<210> SEQ ID NO 1522
<211> LENGTH: 23
<212> TYPE: DNA
<213> ORGANISM: Homo sapiens

<400> SEQUENCE: 1522
tctacagtct caaagttgag ggg    23

<210> SEQ ID NO 1523
<211> LENGTH: 23
<212> TYPE: DNA
<213> ORGANISM: Homo sapiens

<400> SEQUENCE: 1523
ctctacagtc tcaaagttga ggg    23

<210> SEQ ID NO 1524
<211> LENGTH: 23
<212> TYPE: DNA
<213> ORGANISM: Homo sapiens

<400> SEQUENCE: 1524
agttcagggc ccagactttg ggg    23

<210> SEQ ID NO 1525
<211> LENGTH: 23
<212> TYPE: DNA
<213> ORGANISM: Homo sapiens

<400> SEQUENCE: 1525
tgaagccagc tggacttcct ggg    23

<210> SEQ ID NO 1526
<211> LENGTH: 23
<212> TYPE: DNA
<213> ORGANISM: Homo sapiens

<400> SEQUENCE: 1526
ctggaaagaa gctacagcac agg    23

<210> SEQ ID NO 1527
<211> LENGTH: 23
<212> TYPE: DNA
<213> ORGANISM: Homo sapiens

<400> SEQUENCE: 1527
tagactcctg gatctgaggg agg    23

<210> SEQ ID NO 1528
<211> LENGTH: 23
<212> TYPE: DNA
<213> ORGANISM: Homo sapiens

<400> SEQUENCE: 1528
aagtctgggc cctgaactcc agg    23

<210> SEQ ID NO 1529
<211> LENGTH: 23
<212> TYPE: DNA
<213> ORGANISM: Homo sapiens

<400> SEQUENCE: 1529
atggaccaat cagcaggaca cgg                                              23

<210> SEQ ID NO 1530
<211> LENGTH: 23
<212> TYPE: DNA
<213> ORGANISM: Homo sapiens

<400> SEQUENCE: 1530
ccgccactcc gcgcagccct ggg                                              23

<210> SEQ ID NO 1531
<211> LENGTH: 23
<212> TYPE: DNA
<213> ORGANISM: Homo sapiens

<400> SEQUENCE: 1531
agctgtaggt gccggggcg cgg                                               23

<210> SEQ ID NO 1532
<211> LENGTH: 23
<212> TYPE: DNA
<213> ORGANISM: Homo sapiens

<400> SEQUENCE: 1532
ccttcctgat ccagcagtcc agg                                              23

<210> SEQ ID NO 1533
<211> LENGTH: 23
<212> TYPE: DNA
<213> ORGANISM: Homo sapiens

<400> SEQUENCE: 1533
ctgcattcct ggggcggagg agg                                              23

<210> SEQ ID NO 1534
<211> LENGTH: 23
<212> TYPE: DNA
<213> ORGANISM: Homo sapiens

<400> SEQUENCE: 1534 tagaccctg ggtctgaagg agg                                               23

<210> SEQ ID NO 1535
<211> LENGTH: 23
<212> TYPE: DNA
<213> ORGANISM: Homo sapiens

<400> SEQUENCE: 1535
tcccagcttc tccgccactc agg                                              23

<210> SEQ ID NO 1536
<211> LENGTH: 23
<212> TYPE: DNA
<213> ORGANISM: Homo sapiens

<400> SEQUENCE: 1536
tttcccaagg agtagctgaa agg                                              23

<210> SEQ ID NO 1537
<211> LENGTH: 23
<212> TYPE: DNA
<213> ORGANISM: Homo sapiens

```
<400> SEQUENCE: 1537
gaaccctctg tcttctggct tgg                                            23

<210> SEQ ID NO 1538
<211> LENGTH: 23
<212> TYPE: DNA
<213> ORGANISM: Homo sapiens

<400> SEQUENCE: 1538
cttacaagag gattgtaaaa tgg                                            23

<210> SEQ ID NO 1539
<211> LENGTH: 23
<212> TYPE: DNA
<213> ORGANISM: Homo sapiens

<400> SEQUENCE: 1539
gcagctcctc tgcagagacg ggg                                            23

<210> SEQ ID NO 1540
<211> LENGTH: 23
<212> TYPE: DNA
<213> ORGANISM: Homo sapiens

<400> SEQUENCE: 1540
ctcctccgcc ccaggaatgc agg                                            23

<210> SEQ ID NO 1541
<211> LENGTH: 23
<212> TYPE: DNA
<213> ORGANISM: Homo sapiens

<400> SEQUENCE: 1541
ggtatccgcc cctgagcccc agg                                            23

<210> SEQ ID NO 1542
<211> LENGTH: 23
<212> TYPE: DNA
<213> ORGANISM: Homo sapiens

<400> SEQUENCE: 1542
tagtagtagc agctacagaa agg                                            23

<210> SEQ ID NO 1543
<211> LENGTH: 23
<212> TYPE: DNA
<213> ORGANISM: Homo sapiens

<400> SEQUENCE: 1543
tttcagctac tccttgggaa agg                                            23

<210> SEQ ID NO 1544
<211> LENGTH: 23
<212> TYPE: DNA
<213> ORGANISM: Homo sapiens

<400> SEQUENCE: 1544
ggtggcgctg cccgggccgg tgg                                            23

<210> SEQ ID NO 1545
<211> LENGTH: 23
<212> TYPE: DNA
```

<213> ORGANISM: Homo sapiens

<400> SEQUENCE: 1545
ccaggaccca ccaccggccc ggg                                          23

<210> SEQ ID NO 1546
<211> LENGTH: 23
<212> TYPE: DNA
<213> ORGANISM: Homo sapiens

<400> SEQUENCE: 1546
cccaggaatc ctgggtctga ggg                                          23

<210> SEQ ID NO 1547
<211> LENGTH: 23
<212> TYPE: DNA
<213> ORGANISM: Homo sapiens

<400> SEQUENCE: 1547
ggggcctgga ctgctggatc agg                                          23

<210> SEQ ID NO 1548
<211> LENGTH: 23
<212> TYPE: DNA
<213> ORGANISM: Homo sapiens

<400> SEQUENCE: 1548
ccagcccctg gggtggactt agg                                          23

<210> SEQ ID NO 1549
<211> LENGTH: 23
<212> TYPE: DNA
<213> ORGANISM: Homo sapiens

<400> SEQUENCE: 1549
tagtccgcct ggggctggcc ggg                                          23

<210> SEQ ID NO 1550
<211> LENGTH: 23
<212> TYPE: DNA
<213> ORGANISM: Homo sapiens

<400> SEQUENCE: 1550
cgggctggtc ctcatctccc tgg                                          23

<210> SEQ ID NO 1551
<211> LENGTH: 23
<212> TYPE: DNA
<213> ORGANISM: Homo sapiens

<400> SEQUENCE: 1551
ctagtccgcc tggggctggc cgg                                          23

<210> SEQ ID NO 1552
<211> LENGTH: 23
<212> TYPE: DNA
<213> ORGANISM: Homo sapiens

<400> SEQUENCE: 1552
cttcctttca gctactcctt ggg                                          23

<210> SEQ ID NO 1553
<211> LENGTH: 23

-continued

```
<212> TYPE: DNA
<213> ORGANISM: Homo sapiens

<400> SEQUENCE: 1553
gtaagacaga aaagttctcc agg                                              23

<210> SEQ ID NO 1554
<211> LENGTH: 23
<212> TYPE: DNA
<213> ORGANISM: Homo sapiens

<400> SEQUENCE: 1554
cggcccaggg ctgcgcggag tgg                                              23

<210> SEQ ID NO 1555
<211> LENGTH: 23
<212> TYPE: DNA
<213> ORGANISM: Homo sapiens

<400> SEQUENCE: 1555
ctgctgggcg cccgcgcccc cgg                                              23

<210> SEQ ID NO 1556
<211> LENGTH: 23
<212> TYPE: DNA
<213> ORGANISM: Homo sapiens

<400> SEQUENCE: 1556
ggcctgcatt cctggggcgg agg                                              23

<210> SEQ ID NO 1557
<211> LENGTH: 23
<212> TYPE: DNA
<213> ORGANISM: Homo sapiens

<400> SEQUENCE: 1557
ctcgggctgc agtgctcctg ggg                                              23

<210> SEQ ID NO 1558
<211> LENGTH: 23
<212> TYPE: DNA
<213> ORGANISM: Homo sapiens

<400> SEQUENCE: 1558
agctcagcca gcaggactgt ggg                                              23

<210> SEQ ID NO 1559
<211> LENGTH: 23
<212> TYPE: DNA
<213> ORGANISM: Homo sapiens

<400> SEQUENCE: 1559 gaactttttct gtcttacaag agg                                             23

<210> SEQ ID NO 1560
<211> LENGTH: 23
<212> TYPE: DNA
<213> ORGANISM: Homo sapiens

<400> SEQUENCE: 1560
ggcgctgccc gggccggtgg tgg                                              23

<210> SEQ ID NO 1561
```

```
<210> SEQ ID NO 1561
<211> LENGTH: 23
<212> TYPE: DNA
<213> ORGANISM: Homo sapiens

<400> SEQUENCE: 1561
gtctgagggc ggaggtcctg ggg                                              23

<210> SEQ ID NO 1562
<211> LENGTH: 23
<212> TYPE: DNA
<213> ORGANISM: Homo sapiens

<400> SEQUENCE: 1562
gggtctgagg gcggaggtcc tgg                                              23

<210> SEQ ID NO 1563
<211> LENGTH: 23
<212> TYPE: DNA
<213> ORGANISM: Homo sapiens

<400> SEQUENCE: 1563
cccagggctg cgcggagtgg cgg                                              23

<210> SEQ ID NO 1564
<211> LENGTH: 23
<212> TYPE: DNA
<213> ORGANISM: Homo sapiens

<400> SEQUENCE: 1564
aggaggcggg ccgggcctca ggg                                              23

<210> SEQ ID NO 1565
<211> LENGTH: 23
<212> TYPE: DNA
<213> ORGANISM: Homo sapiens

<400> SEQUENCE: 1565
cctaagtcca ccccaggggc tgg                                              23

<210> SEQ ID NO 1566
<211> LENGTH: 23
<212> TYPE: DNA
<213> ORGANISM: Homo sapiens

<400> SEQUENCE: 1566
gctactcctt gggaaaggcc tgg                                              23

<210> SEQ ID NO 1567
<211> LENGTH: 23
<212> TYPE: DNA
<213> ORGANISM: Homo sapiens

<400> SEQUENCE: 1567
tctctgcaga ggagctgccg cgg                                              23

<210> SEQ ID NO 1568
<211> LENGTH: 23
<212> TYPE: DNA
<213> ORGANISM: Homo sapiens

<400> SEQUENCE: 1568
gtgctggtca tcagctggga agg                                              23
```

```
<210> SEQ ID NO 1569
<211> LENGTH: 23
<212> TYPE: DNA
<213> ORGANISM: Homo sapiens

<400> SEQUENCE: 1569
ggctggaaac ctggagttca ggg                                              23

<210> SEQ ID NO 1570
<211> LENGTH: 23
<212> TYPE: DNA
<213> ORGANISM: Homo sapiens

<400> SEQUENCE: 1570
agggcccaga ctttggggtc cgg                                              23

<210> SEQ ID NO 1571
<211> LENGTH: 23
<212> TYPE: DNA
<213> ORGANISM: Homo sapiens

<400> SEQUENCE: 1571
agctgatggc ccctctctcc cgg                                              23

<210> SEQ ID NO 1572
<211> LENGTH: 23
<212> TYPE: DNA
<213> ORGANISM: Homo sapiens

<400> SEQUENCE: 1572
ccagcgcgcc cagggagatg agg                                              23

<210> SEQ ID NO 1573
<211> LENGTH: 23
<212> TYPE: DNA
<213> ORGANISM: Homo sapiens

<400> SEQUENCE: 1573
ctacagcaca gggcacagcg ggg                                              23

<210> SEQ ID NO 1574
<211> LENGTH: 23
<212> TYPE: DNA
<213> ORGANISM: Homo sapiens

<400> SEQUENCE: 1574
ggagttcagg gcccagactt tgg                                              23

<210> SEQ ID NO 1575
<211> LENGTH: 23
<212> TYPE: DNA
<213> ORGANISM: Homo sapiens

<400> SEQUENCE: 1575
agagaggggc catcagctcc cgg                                              23

<210> SEQ ID NO 1576
<211> LENGTH: 23
<212> TYPE: DNA
<213> ORGANISM: Homo sapiens

<400> SEQUENCE: 1576
gctggtggcg ctgcccgggc cgg                                              23
```

```
<210> SEQ ID NO 1577
<211> LENGTH: 23
<212> TYPE: DNA
<213> ORGANISM: Homo sapiens

<400> SEQUENCE: 1577
ggctgggtcc caggaatcct ggg                                              23

<210> SEQ ID NO 1578
<211> LENGTH: 23
<212> TYPE: DNA
<213> ORGANISM: Homo sapiens

<400> SEQUENCE: 1578
gaggagccag agtctgcggg cgg                                              23

<210> SEQ ID NO 1579
<211> LENGTH: 23
<212> TYPE: DNA
<213> ORGANISM: Homo sapiens

<400> SEQUENCE: 1579
gcgggcggag ccgggagaga ggg                                              23

<210> SEQ ID NO 1580
<211> LENGTH: 23
<212> TYPE: DNA
<213> ORGANISM: Homo sapiens

<400> SEQUENCE: 1580
ggtcctgggg cctgcattcc tgg                                              23

<210> SEQ ID NO 1581
<211> LENGTH: 23
<212> TYPE: DNA
<213> ORGANISM: Homo sapiens

<400> SEQUENCE: 1581
ggtcatcagc tgggaaggtg agg                                              23

<210> SEQ ID NO 1582
<211> LENGTH: 23
<212> TYPE: DNA
<213> ORGANISM: Homo sapiens

<400> SEQUENCE: 1582
gcctggagtc ctgggtctga ggg                                              23

<210> SEQ ID NO 1583
<211> LENGTH: 23
<212> TYPE: DNA
<213> ORGANISM: Homo sapiens

<400> SEQUENCE: 1583
ggtctgaggg aggaggtact ggg                                              23

<210> SEQ ID NO 1584
<211> LENGTH: 23
<212> TYPE: DNA
<213> ORGANISM: Homo sapiens

<400> SEQUENCE: 1584
gtcggaggag ccagagtctg cgg                                              23
```

<210> SEQ ID NO 1585
<211> LENGTH: 23
<212> TYPE: DNA
<213> ORGANISM: Homo sapiens

<400> SEQUENCE: 1585
ctgtgctgta gcttctttcc agg                                          23

<210> SEQ ID NO 1586
<211> LENGTH: 23
<212> TYPE: DNA
<213> ORGANISM: Homo sapiens

<400> SEQUENCE: 1586
tcctgggttg aatggggacc tgg                                          23

<210> SEQ ID NO 1587
<211> LENGTH: 23
<212> TYPE: DNA
<213> ORGANISM: Homo sapiens

<400> SEQUENCE: 1587
gacaataagg gaataaaagc tgg                                          23

<210> SEQ ID NO 1588
<211> LENGTH: 23
<212> TYPE: DNA
<213> ORGANISM: Homo sapiens

<400> SEQUENCE: 1588
ctctcacccc gtctctgcag agg                                          23

<210> SEQ ID NO 1589
<211> LENGTH: 23
<212> TYPE: DNA
<213> ORGANISM: Homo sapiens

<400> SEQUENCE: 1589
gggcccagac tttggggtcc ggg                                          23

<210> SEQ ID NO 1590
<211> LENGTH: 23
<212> TYPE: DNA
<213> ORGANISM: Homo sapiens

<400> SEQUENCE: 1590
tggaaagaag ctacagcaca ggg                                          23

<210> SEQ ID NO 1591
<211> LENGTH: 23
<212> TYPE: DNA
<213> ORGANISM: Homo sapiens

<400> SEQUENCE: 1591
gtcctggggc ctgcattcct ggg                                          23

<210> SEQ ID NO 1592
<211> LENGTH: 23
<212> TYPE: DNA
<213> ORGANISM: Homo sapiens

<400> SEQUENCE: 1592
ccctcagacc caggattccc ggg                                              23

<210> SEQ ID NO 1593
<211> LENGTH: 23
<212> TYPE: DNA
<213> ORGANISM: Homo sapiens

<400> SEQUENCE: 1593
gctcagccag caggactgtg ggg                                              23

<210> SEQ ID NO 1594
<211> LENGTH: 23
<212> TYPE: DNA
<213> ORGANISM: Homo sapiens

<400> SEQUENCE: 1594
ggacctccgc cctcagaccc agg                                              23

<210> SEQ ID NO 1595
<211> LENGTH: 23
<212> TYPE: DNA
<213> ORGANISM: Homo sapiens

<400> SEQUENCE: 1595
aggaatcctg ggtctgaggg agg                                              23

<210> SEQ ID NO 1596
<211> LENGTH: 23
<212> TYPE: DNA
<213> ORGANISM: Homo sapiens

<400> SEQUENCE: 1596
cctctcctcc ttcagaccca ggg                                              23

<210> SEQ ID NO 1597
<211> LENGTH: 23
<212> TYPE: DNA
<213> ORGANISM: Homo sapiens

<400> SEQUENCE: 1597
tcccaggaat cctgggtctg agg                                              23

<210> SEQ ID NO 1598
<211> LENGTH: 23
<212> TYPE: DNA
<213> ORGANISM: Homo sapiens

<400> SEQUENCE: 1598
aactccaggt ttccagcccc tgg                                              23

<210> SEQ ID NO 1599
<211> LENGTH: 23
<212> TYPE: DNA
<213> ORGANISM: Homo sapiens

<400> SEQUENCE: 1599
tgcagtgctc ctggggctca ggg                                              23

<210> SEQ ID NO 1600
<211> LENGTH: 23
<212> TYPE: DNA
<213> ORGANISM: Homo sapiens

<400> SEQUENCE: 1600
aggaaaggac agtccagccc agg                                           23

<210> SEQ ID NO 1601
<211> LENGTH: 23
<212> TYPE: DNA
<213> ORGANISM: Homo sapiens

<400> SEQUENCE: 1601
cccgcccgtg tcctgctgat tgg                                           23

<210> SEQ ID NO 1602
<211> LENGTH: 23
<212> TYPE: DNA
<213> ORGANISM: Homo sapiens

<400> SEQUENCE: 1602
gctcctgggt ctgagggcgg agg                                           23

<210> SEQ ID NO 1603
<211> LENGTH: 23
<212> TYPE: DNA
<213> ORGANISM: Homo sapiens

<400> SEQUENCE: 1603
cttcctggac ccaggactcc agg                                           23

<210> SEQ ID NO 1604
<211> LENGTH: 23
<212> TYPE: DNA
<213> ORGANISM: Homo sapiens

<400> SEQUENCE: 1604
gtctgaggga ggaggtactg ggg                                           23

<210> SEQ ID NO 1605
<211> LENGTH: 23
<212> TYPE: DNA
<213> ORGANISM: Homo sapiens

<400> SEQUENCE: 1605
caccccaggg gctggaaacc tgg                                           23

<210> SEQ ID NO 1606
<211> LENGTH: 23
<212> TYPE: DNA
<213> ORGANISM: Homo sapiens

<400> SEQUENCE: 1606
ggactgctgg atcaggaagg agg                                           23

<210> SEQ ID NO 1607
<211> LENGTH: 23
<212> TYPE: DNA
<213> ORGANISM: Homo sapiens

<400> SEQUENCE: 1607
ctttggggtc cgggagctga tgg                                           23

<210> SEQ ID NO 1608
<211> LENGTH: 23
<212> TYPE: DNA
<213> ORGANISM: Homo sapiens

```
<400> SEQUENCE: 1608
ctgcagcccc acagtcctgc tgg                                           23

<210> SEQ ID NO 1609
<211> LENGTH: 23
<212> TYPE: DNA
<213> ORGANISM: Homo sapiens

<400> SEQUENCE: 1609
ggcggagaag ctgggaccct ggg                                           23

<210> SEQ ID NO 1610
<211> LENGTH: 23
<212> TYPE: DNA
<213> ORGANISM: Homo sapiens

<400> SEQUENCE: 1610
ggcagctcct ctgcagagac ggg                                           23

<210> SEQ ID NO 1611
<211> LENGTH: 23
<212> TYPE: DNA
<213> ORGANISM: Homo sapiens

<400> SEQUENCE: 1611
gcccgggaat cctgggtctg agg                                           23

<210> SEQ ID NO 1612
<211> LENGTH: 23
<212> TYPE: DNA
<213> ORGANISM: Homo sapiens

<400> SEQUENCE: 1612
gactgctgga tcaggaagga ggg                                           23

<210> SEQ ID NO 1613
<211> LENGTH: 23
<212> TYPE: DNA
<213> ORGANISM: Homo sapiens

<400> SEQUENCE: 1613
actcctgggt ccaggaagaa ggg                                           23

<210> SEQ ID NO 1614
<211> LENGTH: 23
<212> TYPE: DNA
<213> ORGANISM: Homo sapiens

<400> SEQUENCE: 1614
acttccaagc cagaagacag agg                                           23

<210> SEQ ID NO 1615
<211> LENGTH: 23
<212> TYPE: DNA
<213> ORGANISM: Homo sapiens

<400> SEQUENCE: 1615
attcctgggg cggaggaggc ggg                                           23

<210> SEQ ID NO 1616
<211> LENGTH: 23
<212> TYPE: DNA
<213> ORGANISM: Homo sapiens
```

```
<400> SEQUENCE: 1616
gccccaggaa tgcaggcccc agg                                              23

<210> SEQ ID NO 1617
<211> LENGTH: 23
<212> TYPE: DNA
<213> ORGANISM: Homo sapiens

<400> SEQUENCE: 1617
tccctcagac ccaggattcc cgg                                              23

<210> SEQ ID NO 1618
<211> LENGTH: 23
<212> TYPE: DNA
<213> ORGANISM: Homo sapiens

<400> SEQUENCE: 1618
tccctcagac ccaggattcc tgg                                              23

<210> SEQ ID NO 1619
<211> LENGTH: 23
<212> TYPE: DNA
<213> ORGANISM: Homo sapiens

<400> SEQUENCE: 1619
gggctgggtc ccaggaatcc tgg                                              23

<210> SEQ ID NO 1620
<211> LENGTH: 23
<212> TYPE: DNA
<213> ORGANISM: Homo sapiens

<400> SEQUENCE: 1620
gcctctcctc cttcagaccc agg                                              23

<210> SEQ ID NO 1621
<211> LENGTH: 23
<212> TYPE: DNA
<213> ORGANISM: Homo sapiens

<400> SEQUENCE: 1621
gggtctgagg gaggaggtac tgg                                              23

<210> SEQ ID NO 1622
<211> LENGTH: 23
<212> TYPE: DNA
<213> ORGANISM: Homo sapiens

<400> SEQUENCE: 1622
gagctcagcc agcaggactg tgg                                              23

<210> SEQ ID NO 1623
<211> LENGTH: 23
<212> TYPE: DNA
<213> ORGANISM: Homo sapiens

<400> SEQUENCE: 1623
gcctgggctc ctgggtctga ggg                                              23

<210> SEQ ID NO 1624
<211> LENGTH: 23
<212> TYPE: DNA
```

```
<213> ORGANISM: Homo sapiens

<400> SEQUENCE: 1624
gaggaggcgg gccgggcctc agg                                         23

<210> SEQ ID NO 1625
<211> LENGTH: 23
<212> TYPE: DNA
<213> ORGANISM: Homo sapiens

<400> SEQUENCE: 1625
ccctcagacc caggattcct ggg                                         23

<210> SEQ ID NO 1626
<211> LENGTH: 23
<212> TYPE: DNA
<213> ORGANISM: Homo sapiens

<400> SEQUENCE: 1626
ctggagtcct gggtccagga agg                                         23

<210> SEQ ID NO 1627
<211> LENGTH: 23
<212> TYPE: DNA
<213> ORGANISM: Homo sapiens

<400> SEQUENCE: 1627
ctctcctcct tcagacccag ggg                                         23

<210> SEQ ID NO 1628
<211> LENGTH: 23
<212> TYPE: DNA
<213> ORGANISM: Homo sapiens

<400> SEQUENCE: 1628
gggaatcctg ggtctgaggg agg                                         23

<210> SEQ ID NO 1629
<211> LENGTH: 23
<212> TYPE: DNA
<213> ORGANISM: Homo sapiens

<400> SEQUENCE: 1629
caggtttcca gccctgggg tgg                                          23

<210> SEQ ID NO 1630
<211> LENGTH: 23
<212> TYPE: DNA
<213> ORGANISM: Homo sapiens

<400> SEQUENCE: 1630
cagggagatg aggaccagcc cgg                                         23

<210> SEQ ID NO 1631
<211> LENGTH: 23
<212> TYPE: DNA
<213> ORGANISM: Homo sapiens

<400> SEQUENCE: 1631
agctacagca cagggcacag cgg                                         23

<210> SEQ ID NO 1632
<211> LENGTH: 23
```

<212> TYPE: DNA
<213> ORGANISM: Homo sapiens

<400> SEQUENCE: 1632
cttccaagcc agaagacaga ggg                                    23

<210> SEQ ID NO 1633
<211> LENGTH: 23
<212> TYPE: DNA
<213> ORGANISM: Homo sapiens

<400> SEQUENCE: 1633
cggcccgcct cctccgcccc agg                                    23

<210> SEQ ID NO 1634
<211> LENGTH: 23
<212> TYPE: DNA
<213> ORGANISM: Homo sapiens

<400> SEQUENCE: 1634
tggagtcctg ggtctgaggg agg                                    23

<210> SEQ ID NO 1635
<211> LENGTH: 23
<212> TYPE: DNA
<213> ORGANISM: Homo sapiens

<400> SEQUENCE: 1635
gggctggaaa cctggagttc agg                                    23

<210> SEQ ID NO 1636
<211> LENGTH: 23
<212> TYPE: DNA
<213> ORGANISM: Homo sapiens

<400> SEQUENCE: 1636
tgcgggcgga gccgggagag agg                                    23

<210> SEQ ID NO 1637
<211> LENGTH: 23
<212> TYPE: DNA
<213> ORGANISM: Homo sapiens

<400> SEQUENCE: 1637
ctccaggttt ccagcccctg ggg                                    23

<210> SEQ ID NO 1638
<211> LENGTH: 23
<212> TYPE: DNA
<213> ORGANISM: Homo sapiens

<400> SEQUENCE: 1638
tggcggagaa gctgggaccc tgg                                    23

<210> SEQ ID NO 1639
<211> LENGTH: 23
<212> TYPE: DNA
<213> ORGANISM: Homo sapiens

<400> SEQUENCE: 1639
ccgcctgggg ctggccgggc tgg                                    23

<210> SEQ ID NO 1640

```
<211> LENGTH: 23
<212> TYPE: DNA
<213> ORGANISM: Homo sapiens

<400> SEQUENCE: 1640
aactcctggg tccaggaaga agg                                            23

<210> SEQ ID NO 1641
<211> LENGTH: 23
<212> TYPE: DNA
<213> ORGANISM: Homo sapiens

<400> SEQUENCE: 1641
cgggcggagc cgggagagag ggg                                            23

<210> SEQ ID NO 1642
<211> LENGTH: 23
<212> TYPE: DNA
<213> ORGANISM: Homo sapiens

<400> SEQUENCE: 1642
gcagtgctcc tggggctcag ggg                                            23

<210> SEQ ID NO 1643
<211> LENGTH: 23
<212> TYPE: DNA
<213> ORGANISM: Homo sapiens

<400> SEQUENCE: 1643
gctacagcac agggcacagc ggg                                            23

<210> SEQ ID NO 1644
<211> LENGTH: 23
<212> TYPE: DNA
<213> ORGANISM: Homo sapiens

<400> SEQUENCE: 1644
tggggcggag gaggcgggcc ggg                                            23

<210> SEQ ID NO 1645
<211> LENGTH: 23
<212> TYPE: DNA
<213> ORGANISM: Homo sapiens

<400> SEQUENCE: 1645
actcctggat ctgagggagg agg                                            23

<210> SEQ ID NO 1646
<211> LENGTH: 23
<212> TYPE: DNA
<213> ORGANISM: Homo sapiens

<400> SEQUENCE: 1646
tccctcagac ccaggactcc agg                                            23

<210> SEQ ID NO 1647
<211> LENGTH: 23
<212> TYPE: DNA
<213> ORGANISM: Homo sapiens

<400> SEQUENCE: 1647
agccccttct tcctggaccc agg                                            23
```

```
<210> SEQ ID NO 1648
<211> LENGTH: 23
<212> TYPE: DNA
<213> ORGANISM: Homo sapiens

<400> SEQUENCE: 1648
ctgcagtgct cctggggctc agg                                              23

<210> SEQ ID NO 1649
<211> LENGTH: 23
<212> TYPE: DNA
<213> ORGANISM: Homo sapiens

<400> SEQUENCE: 1649
gtcctgctgg ctgagctccg cgg                                              23

<210> SEQ ID NO 1650
<211> LENGTH: 23
<212> TYPE: DNA
<213> ORGANISM: Homo sapiens

<400> SEQUENCE: 1650
cggcagctcc tctgcagaga cgg                                              23

<210> SEQ ID NO 1651
<211> LENGTH: 23
<212> TYPE: DNA
<213> ORGANISM: Homo sapiens

<400> SEQUENCE: 1651
gcccctcctc cctcagatcc agg                                              23

<210> SEQ ID NO 1652
<211> LENGTH: 23
<212> TYPE: DNA
<213> ORGANISM: Homo sapiens

<400> SEQUENCE: 1652
actgctggat caggaaggag ggg                                              23

<210> SEQ ID NO 1653
<211> LENGTH: 23
<212> TYPE: DNA
<213> ORGANISM: Homo sapiens

<400> SEQUENCE: 1653
aggcttcaac tcctgggtcc agg                                              23

<210> SEQ ID NO 1654
<211> LENGTH: 23
<212> TYPE: DNA
<213> ORGANISM: Homo sapiens

<400> SEQUENCE: 1654
tcctggggcc tgcattcctg ggg                                              23

<210> SEQ ID NO 1655
<211> LENGTH: 23
<212> TYPE: DNA
<213> ORGANISM: Homo sapiens

<400> SEQUENCE: 1655
tgggctcctg ggtctgaggg cgg                                              23
```

<210> SEQ ID NO 1656
<211> LENGTH: 23
<212> TYPE: DNA
<213> ORGANISM: Homo sapiens

<400> SEQUENCE: 1656
gtacctcctc cctcagaccc agg                                              23

<210> SEQ ID NO 1657
<211> LENGTH: 23
<212> TYPE: DNA
<213> ORGANISM: Homo sapiens

<400> SEQUENCE: 1657
gggctggtcc tcatctccct ggg                                              23

<210> SEQ ID NO 1658
<211> LENGTH: 23
<212> TYPE: DNA
<213> ORGANISM: Homo sapiens

<400> SEQUENCE: 1658
cattcctggg gcggaggagg cgg                                              23

<210> SEQ ID NO 1659
<211> LENGTH: 23
<212> TYPE: DNA
<213> ORGANISM: Homo sapiens

<400> SEQUENCE: 1659
ctcctggatc tgagggagga ggg                                              23

<210> SEQ ID NO 1660
<211> LENGTH: 23
<212> TYPE: DNA
<213> ORGANISM: Homo sapiens

<400> SEQUENCE: 1660
tgggtccagg aagaagggc tgg                                               23

<210> SEQ ID NO 1661
<211> LENGTH: 23
<212> TYPE: DNA
<213> ORGANISM: Homo sapiens

<400> SEQUENCE: 1661
ctggatcagg aaggaggggc tgg                                              23

<210> SEQ ID NO 1662
<211> LENGTH: 23
<212> TYPE: DNA
<213> ORGANISM: Homo sapiens

<400> SEQUENCE: 1662
ctcctgggtc caggaagaag ggg                                              23

<210> SEQ ID NO 1663
<211> LENGTH: 23
<212> TYPE: DNA
<213> ORGANISM: Homo sapiens

<400> SEQUENCE: 1663
ggaccagccc ggccagcccc agg                                              23

<210> SEQ ID NO 1664
<211> LENGTH: 23
<212> TYPE: DNA
<213> ORGANISM: Homo sapiens

<400> SEQUENCE: 1664
ttctttccag gcctttccca agg                                              23

<210> SEQ ID NO 1665
<211> LENGTH: 23
<212> TYPE: DNA
<213> ORGANISM: Homo sapiens

<400> SEQUENCE: 1665
cgcaggctca cgttggcgcc agg                                              23

<210> SEQ ID NO 1666
<211> LENGTH: 23
<212> TYPE: DNA
<213> ORGANISM: Homo sapiens

<400> SEQUENCE: 1666
gtcatcagct gggaaggtga ggg                                              23

<210> SEQ ID NO 1667
<211> LENGTH: 23
<212> TYPE: DNA
<213> ORGANISM: Homo sapiens

<400> SEQUENCE: 1667
ctggggcgga ggaggcgggc cgg                                              23

<210> SEQ ID NO 1668
<211> LENGTH: 23
<212> TYPE: DNA
<213> ORGANISM: Homo sapiens

<400> SEQUENCE: 1668
agggaggagg tactggggcc cgg                                              23

<210> SEQ ID NO 1669
<211> LENGTH: 23
<212> TYPE: DNA
<213> ORGANISM: Homo sapiens

<400> SEQUENCE: 1669
actccaggtt tccagcccct ggg                                              23

<210> SEQ ID NO 1670
<211> LENGTH: 23
<212> TYPE: DNA
<213> ORGANISM: Homo sapiens

<400> SEQUENCE: 1670
cagcaggact gtggggctgc agg                                              23

<210> SEQ ID NO 1671
<211> LENGTH: 23
<212> TYPE: DNA
<213> ORGANISM: Homo sapiens

<400> SEQUENCE: 1671

```
ggactgtggg gctgcaggaa agg                                              23

<210> SEQ ID NO 1672
<211> LENGTH: 23
<212> TYPE: DNA
<213> ORGANISM: Homo sapiens

<400> SEQUENCE: 1672
gccctcagac ccaggagccc agg                                              23

<210> SEQ ID NO 1673
<211> LENGTH: 23
<212> TYPE: DNA
<213> ORGANISM: Homo sapiens

<400> SEQUENCE: 1673
gggaggaggt actggggccc ggg                                              23

<210> SEQ ID NO 1674
<211> LENGTH: 23
<212> TYPE: DNA
<213> ORGANISM: Homo sapiens

<400> SEQUENCE: 1674
agtcctgggt ccaggaagga ggg                                              23

<210> SEQ ID NO 1675
<211> LENGTH: 23
<212> TYPE: DNA
<213> ORGANISM: Homo sapiens

<400> SEQUENCE: 1675
ccctgggtct gaaggaggag agg                                              23

<210> SEQ ID NO 1676
<211> LENGTH: 23
<212> TYPE: DNA
<213> ORGANISM: Homo sapiens

<400> SEQUENCE: 1676
tggatcagga aggaggggct ggg                                              23

<210> SEQ ID NO 1677
<211> LENGTH: 23
<212> TYPE: DNA
<213> ORGANISM: Homo sapiens

<400> SEQUENCE: 1677
ggaaaggaca gtccagccca ggg                                              23

<210> SEQ ID NO 1678
<211> LENGTH: 23
<212> TYPE: DNA
<213> ORGANISM: Homo sapiens

<400> SEQUENCE: 1678
aaggtgaggg ccctgaggcc cgg                                              23

<210> SEQ ID NO 1679
<211> LENGTH: 23
<212> TYPE: DNA
<213> ORGANISM: Homo sapiens

<400> SEQUENCE: 1679
``` agccctcct tcctggaccc agg                                                23

<210> SEQ ID NO 1680
<211> LENGTH: 23
<212> TYPE: DNA
<213> ORGANISM: Homo sapiens

<400> SEQUENCE: 1680
atcctgggtc tgagggagga ggg                                                23

<210> SEQ ID NO 1681
<211> LENGTH: 23
<212> TYPE: DNA
<213> ORGANISM: Homo sapiens

<400> SEQUENCE: 1681
aatcctgggt ctgagggagg agg                                                23

<210> SEQ ID NO 1682
<211> LENGTH: 23
<212> TYPE: DNA
<213> ORGANISM: Homo sapiens

<400> SEQUENCE: 1682
gtcctgggtc caggaaggag ggg                                                23

<210> SEQ ID NO 1683
<211> LENGTH: 23
<212> TYPE: DNA
<213> ORGANISM: Homo sapiens

<400> SEQUENCE: 1683
ggtctgaagg aggagaggct ggg                                                23

<210> SEQ ID NO 1684
<211> LENGTH: 23
<212> TYPE: DNA
<213> ORGANISM: Homo sapiens

<400> SEQUENCE: 1684
gggtccagga agaagggct ggg                                                 23

<210> SEQ ID NO 1685
<211> LENGTH: 23
<212> TYPE: DNA
<213> ORGANISM: Homo sapiens

<400> SEQUENCE: 1685
aggccccagc cccttcttcc tgg                                                23

<210> SEQ ID NO 1686
<211> LENGTH: 23
<212> TYPE: DNA
<213> ORGANISM: Homo sapiens

<400> SEQUENCE: 1686
tcttcctttc agctactcct tgg                                                23

<210> SEQ ID NO 1687
<211> LENGTH: 23
<212> TYPE: DNA
<213> ORGANISM: Homo sapiens

<400> SEQUENCE: 1687
ggctgggggc ctggagtcct ggg                                        23

<210> SEQ ID NO 1688
<211> LENGTH: 23
<212> TYPE: DNA
<213> ORGANISM: Homo sapiens

<400> SEQUENCE: 1688
ggcctggagt cctgggtctg agg                                        23

<210> SEQ ID NO 1689
<211> LENGTH: 23
<212> TYPE: DNA
<213> ORGANISM: Homo sapiens

<400> SEQUENCE: 1689
agtcctgggt ctgagggagg agg                                        23

<210> SEQ ID NO 1690
<211> LENGTH: 23
<212> TYPE: DNA
<213> ORGANISM: Homo sapiens

<400> SEQUENCE: 1690
gtgaagccag ctggacttcc tgg                                        23

<210> SEQ ID NO 1691
<211> LENGTH: 23
<212> TYPE: DNA
<213> ORGANISM: Homo sapiens

<400> SEQUENCE: 1691
ggcctgggct cctgggtctg agg                                        23

<210> SEQ ID NO 1692
<211> LENGTH: 23
<212> TYPE: DNA
<213> ORGANISM: Homo sapiens

<400> SEQUENCE: 1692
tggggcctgc attcctgggg cgg                                        23

<210> SEQ ID NO 1693
<211> LENGTH: 23
<212> TYPE: DNA
<213> ORGANISM: Homo sapiens

<400> SEQUENCE: 1693
gggctggggg cctggagtcc tgg                                        23

<210> SEQ ID NO 1694
<211> LENGTH: 23
<212> TYPE: DNA
<213> ORGANISM: Homo sapiens

<400> SEQUENCE: 1694
tgggtccagg aaggaggggc tgg                                        23

<210> SEQ ID NO 1695
<211> LENGTH: 23
<212> TYPE: DNA
<213> ORGANISM: Homo sapiens

```
<400> SEQUENCE: 1695
ggtccaggaa gaagggctg ggg                                          23

<210> SEQ ID NO 1696
<211> LENGTH: 23
<212> TYPE: DNA
<213> ORGANISM: Homo sapiens

<400> SEQUENCE: 1696
tctgaaggag gagaggctgg ggg                                         23

<210> SEQ ID NO 1697
<211> LENGTH: 23
<212> TYPE: DNA
<213> ORGANISM: Homo sapiens

<400> SEQUENCE: 1697
gatctgaggg aggaggggct ggg                                         23

<210> SEQ ID NO 1698
<211> LENGTH: 23
<212> TYPE: DNA
<213> ORGANISM: Homo sapiens

<400> SEQUENCE: 1698
ggggctgggg cctggactgc tgg                                         23

<210> SEQ ID NO 1699
<211> LENGTH: 23
<212> TYPE: DNA
<213> ORGANISM: Homo sapiens

<400> SEQUENCE: 1699
gtgctcctgg ggctcagggg cgg                                         23

<210> SEQ ID NO 1700
<211> LENGTH: 23
<212> TYPE: DNA
<213> ORGANISM: Homo sapiens

<400> SEQUENCE: 1700 ggctggggc ctgggctcct ggg                                          23

<210> SEQ ID NO 1701
<211> LENGTH: 23
<212> TYPE: DNA
<213> ORGANISM: Homo sapiens

<400> SEQUENCE: 1701
gagtcctggg tccaggaagg agg                                         23

<210> SEQ ID NO 1702
<211> LENGTH: 23
<212> TYPE: DNA
<213> ORGANISM: Homo sapiens

<400> SEQUENCE: 1702
gggcctggag tcctgggtcc agg                                         23

<210> SEQ ID NO 1703
<211> LENGTH: 23
<212> TYPE: DNA
```

```
<213> ORGANISM: Homo sapiens

<400> SEQUENCE: 1703
gtctgaagga ggagaggctg ggg                                        23

<210> SEQ ID NO 1704
<211> LENGTH: 23
<212> TYPE: DNA
<213> ORGANISM: Homo sapiens

<400> SEQUENCE: 1704
gggtctgaag gaggagaggc tgg                                        23

<210> SEQ ID NO 1705
<211> LENGTH: 23
<212> TYPE: DNA
<213> ORGANISM: Homo sapiens

<400> SEQUENCE: 1705
tcctggatct gagggaggag ggg                                        23

<210> SEQ ID NO 1706
<211> LENGTH: 23
<212> TYPE: DNA
<213> ORGANISM: Homo sapiens

<400> SEQUENCE: 1706
gggaggaggg gctgggtccc agg                                        23

<210> SEQ ID NO 1707
<211> LENGTH: 23
<212> TYPE: DNA
<213> ORGANISM: Homo sapiens

<400> SEQUENCE: 1707
gggtccagga aggaggggct ggg                                        23

<210> SEQ ID NO 1708
<211> LENGTH: 23
<212> TYPE: DNA
<213> ORGANISM: Homo sapiens

<400> SEQUENCE: 1708
tctgagggag gaggggctgc agg                                        23

<210> SEQ ID NO 1709
<211> LENGTH: 23
<212> TYPE: DNA
<213> ORGANISM: Homo sapiens

<400> SEQUENCE: 1709
ggaggagagg ctgggggcct ggg                                        23

<210> SEQ ID NO 1710
<211> LENGTH: 23
<212> TYPE: DNA
<213> ORGANISM: Homo sapiens

<400> SEQUENCE: 1710
gatcaggaag gagggctgg ggg                                         23

<210> SEQ ID NO 1711
<211> LENGTH: 23
```

```
<212> TYPE: DNA
<213> ORGANISM: Homo sapiens

<400> SEQUENCE: 1711
ctgggaaggt gagggccctg agg                                              23

<210> SEQ ID NO 1712
<211> LENGTH: 23
<212> TYPE: DNA
<213> ORGANISM: Homo sapiens

<400> SEQUENCE: 1712
aggaggagag gctgggggcc tgg                                              23

<210> SEQ ID NO 1713
<211> LENGTH: 23
<212> TYPE: DNA
<213> ORGANISM: Homo sapiens

<400> SEQUENCE: 1713
aggctggggg cctgggctcc tgg                                              23

<210> SEQ ID NO 1714
<211> LENGTH: 23
<212> TYPE: DNA
<213> ORGANISM: Homo sapiens

<400> SEQUENCE: 1714
ggtccaggaa ggaggggctg ggg                                              23

<210> SEQ ID NO 1715
<211> LENGTH: 23
<212> TYPE: DNA
<213> ORGANISM: Homo sapiens

<400> SEQUENCE: 1715
gagaagctgg gaccctgggc tgg                                              23

<210> SEQ ID NO 1716
<211> LENGTH: 23
<212> TYPE: DNA
<213> ORGANISM: Homo sapiens

<400> SEQUENCE: 1716
ccagcccggc cagccccagg cgg                                              23

<210> SEQ ID NO 1717
<211> LENGTH: 23
<212> TYPE: DNA
<213> ORGANISM: Homo sapiens

<400> SEQUENCE: 1717
gctcctcctc cctcagaccc agg                                              23

<210> SEQ ID NO 1718
<211> LENGTH: 23
<212> TYPE: DNA
<213> ORGANISM: Homo sapiens

<400> SEQUENCE: 1718 ggccccagc ccctccttcc tgg                                               23

<210> SEQ ID NO 1719
```

```
<211> LENGTH: 23
<212> TYPE: DNA
<213> ORGANISM: Homo sapiens

<400> SEQUENCE: 1719
gtccaggaag gagggctgg ggg                                              23

<210> SEQ ID NO 1720
<211> LENGTH: 23
<212> TYPE: DNA
<213> ORGANISM: Homo sapiens

<400> SEQUENCE: 1720
gcccctcctc cctcagaccc agg                                             23

<210> SEQ ID NO 1721
<211> LENGTH: 23
<212> TYPE: DNA
<213> ORGANISM: Homo sapiens

<400> SEQUENCE: 1721
ggaaggaggg gctgggggcc tgg                                             23

<210> SEQ ID NO 1722
<211> LENGTH: 23
<212> TYPE: DNA
<213> ORGANISM: Homo sapiens

<400> SEQUENCE: 1722
tctgagggag gaggagctgg agg                                             23

<210> SEQ ID NO 1723
<211> LENGTH: 23
<212> TYPE: DNA
<213> ORGANISM: Homo sapiens

<400> SEQUENCE: 1723
ggatcaggaa ggagggctg ggg                                              23

<210> SEQ ID NO 1724
<211> LENGTH: 23
<212> TYPE: DNA
<213> ORGANISM: Homo sapiens

<400> SEQUENCE: 1724
tcctgggtct gagggaggag ggg                                             23

<210> SEQ ID NO 1725
<211> LENGTH: 23
<212> TYPE: DNA
<213> ORGANISM: Homo sapiens

<400> SEQUENCE: 1725
gggtctgagg gaggaggagc tgg                                             23

<210> SEQ ID NO 1726
<211> LENGTH: 23
<212> TYPE: DNA
<213> ORGANISM: Homo sapiens

<400> SEQUENCE: 1726
ggatctgagg gaggaggggc tgg                                             23
```

<210> SEQ ID NO 1727
<211> LENGTH: 23
<212> TYPE: DNA
<213> ORGANISM: Homo sapiens

<400> SEQUENCE: 1727
aggaagaagg ggctggggcc tgg                                            23

<210> SEQ ID NO 1728
<211> LENGTH: 23
<212> TYPE: DNA
<213> ORGANISM: Homo sapiens

<400> SEQUENCE: 1728
cgggggaacc tagtccgcct ggg                                            23

<210> SEQ ID NO 1729
<211> LENGTH: 23
<212> TYPE: DNA
<213> ORGANISM: Homo sapiens

<400> SEQUENCE: 1729
ggggtctaag gaccgttccg cgg                                            23

<210> SEQ ID NO 1730
<211> LENGTH: 23
<212> TYPE: DNA
<213> ORGANISM: Homo sapiens

<400> SEQUENCE: 1730
gttcccccgg gtgtagtcgg agg                                            23

<210> SEQ ID NO 1731
<211> LENGTH: 23
<212> TYPE: DNA
<213> ORGANISM: Homo sapiens

<400> SEQUENCE: 1731
gggggaacct agtccgcctg ggg                                            23

<210> SEQ ID NO 1732
<211> LENGTH: 23
<212> TYPE: DNA
<213> ORGANISM: Homo sapiens

<400> SEQUENCE: 1732
taggttcccc cgggtgtagt cgg                                            23

<210> SEQ ID NO 1733
<211> LENGTH: 23
<212> TYPE: DNA
<213> ORGANISM: Homo sapiens

<400> SEQUENCE: 1733
aaaagtgacc agcgcgccca ggg                                            23

<210> SEQ ID NO 1734
<211> LENGTH: 23
<212> TYPE: DNA
<213> ORGANISM: Homo sapiens

<400> SEQUENCE: 1734
gcgcgctggt cactttttgac tgg                                           23

<210> SEQ ID NO 1735
<211> LENGTH: 23
<212> TYPE: DNA
<213> ORGANISM: Homo sapiens

<400> SEQUENCE: 1735
tgaaaggaag acgcgattag tgg                                              23

<210> SEQ ID NO 1736
<211> LENGTH: 23
<212> TYPE: DNA
<213> ORGANISM: Homo sapiens

<400> SEQUENCE: 1736
gctcaggggc ggataccagc agg                                              23

<210> SEQ ID NO 1737
<211> LENGTH: 23
<212> TYPE: DNA
<213> ORGANISM: Homo sapiens

<400> SEQUENCE: 1737
caaaagtgac cagcgcgccc agg                                              23

<210> SEQ ID NO 1738
<211> LENGTH: 23
<212> TYPE: DNA
<213> ORGANISM: Homo sapiens

<400> SEQUENCE: 1738
ggaataaaag ctggcgagcg cgg                                              23

<210> SEQ ID NO 1739
<211> LENGTH: 23
<212> TYPE: DNA
<213> ORGANISM: Homo sapiens

<400> SEQUENCE: 1739
ccgggggaac ctagtccgcc tgg                                              23

<210> SEQ ID NO 1740
<211> LENGTH: 23
<212> TYPE: DNA
<213> ORGANISM: Homo sapiens

<400> SEQUENCE: 1740
caatcagcag gacacgggcg ggg                                              23

<210> SEQ ID NO 1741
<211> LENGTH: 23
<212> TYPE: DNA
<213> ORGANISM: Homo sapiens

<400> SEQUENCE: 1741
ccattttaca gagcgctgat tgg                                              23

<210> SEQ ID NO 1742
<211> LENGTH: 23
<212> TYPE: DNA
<213> ORGANISM: Homo sapiens

<400> SEQUENCE: 1742
gctcctccga ctacacccgg ggg                                              23

<210> SEQ ID NO 1743
<211> LENGTH: 23
<212> TYPE: DNA
<213> ORGANISM: Homo sapiens

<400> SEQUENCE: 1743
gctggctgag ctccgcggaa cgg                                         23

<210> SEQ ID NO 1744
<211> LENGTH: 23
<212> TYPE: DNA
<213> ORGANISM: Homo sapiens

<400> SEQUENCE: 1744
ggctcctccg actacacccg ggg                                         23

<210> SEQ ID NO 1745
<211> LENGTH: 23
<212> TYPE: DNA
<213> ORGANISM: Homo sapiens

<400> SEQUENCE: 1745
agagtctgct tccacgttgt ggg                                         23

<210> SEQ ID NO 1746
<211> LENGTH: 23
<212> TYPE: DNA
<213> ORGANISM: Homo sapiens

<400> SEQUENCE: 1746
caggcggact aggttccccc ggg                                         23

<210> SEQ ID NO 1747
<211> LENGTH: 23
<212> TYPE: DNA
<213> ORGANISM: Homo sapiens

<400> SEQUENCE: 1747
ctggctcctc cgactacacc cgg                                         23

<210> SEQ ID NO 1748
<211> LENGTH: 23
<212> TYPE: DNA
<213> ORGANISM: Homo sapiens

<400> SEQUENCE: 1748
ggacacgggc ggggacaata agg                                         23

<210> SEQ ID NO 1749
<211> LENGTH: 23
<212> TYPE: DNA
<213> ORGANISM: Homo sapiens

<400> SEQUENCE: 1749
agtcagaacc gcgctcctgc tgg                                         23

<210> SEQ ID NO 1750
<211> LENGTH: 23
<212> TYPE: DNA
<213> ORGANISM: Homo sapiens

<400> SEQUENCE: 1750

| | |
|---|---|
| ccaggcggac taggttcccc cgg | 23 |

<210> SEQ ID NO 1751
<211> LENGTH: 23
<212> TYPE: DNA
<213> ORGANISM: Homo sapiens

<400> SEQUENCE: 1751

| | |
|---|---|
| cctcatctcc ctgggcgcgc tgg | 23 |

<210> SEQ ID NO 1752
<211> LENGTH: 23
<212> TYPE: DNA
<213> ORGANISM: Homo sapiens

<400> SEQUENCE: 1752

| | |
|---|---|
| tggctcctcc gactacaccc ggg | 23 |

<210> SEQ ID NO 1753
<211> LENGTH: 23
<212> TYPE: DNA
<213> ORGANISM: Homo sapiens

<400> SEQUENCE: 1753

| | |
|---|---|
| gaacctagtc cgcctggggc tgg | 23 |

<210> SEQ ID NO 1754
<211> LENGTH: 23
<212> TYPE: DNA
<213> ORGANISM: Homo sapiens

<400> SEQUENCE: 1754

| | |
|---|---|
| ccaatcagca ggacacgggc ggg | 23 |

<210> SEQ ID NO 1755
<211> LENGTH: 23
<212> TYPE: DNA
<213> ORGANISM: Homo sapiens

<400> SEQUENCE: 1755

| | |
|---|---|
| agaacaaagc tcccacaacg tgg | 23 |

<210> SEQ ID NO 1756
<211> LENGTH: 23
<212> TYPE: DNA
<213> ORGANISM: Homo sapiens

<400> SEQUENCE: 1756

| | |
|---|---|
| cagagtctgc ttccacgttg tgg | 23 |

<210> SEQ ID NO 1757
<211> LENGTH: 23
<212> TYPE: DNA
<213> ORGANISM: Homo sapiens

<400> SEQUENCE: 1757

| | |
|---|---|
| ccaatcagcg ctctgtaaaa tgg | 23 |

<210> SEQ ID NO 1758
<211> LENGTH: 23
<212> TYPE: DNA
<213> ORGANISM: Homo sapiens

<400> SEQUENCE: 1758
gacacgggcg gggacaataa ggg                                          23

<210> SEQ ID NO 1759
<211> LENGTH: 23
<212> TYPE: DNA
<213> ORGANISM: Homo sapiens

<400> SEQUENCE: 1759
agcttctccg ccactcaggt tgg                                          23

<210> SEQ ID NO 1760
<211> LENGTH: 23
<212> TYPE: DNA
<213> ORGANISM: Homo sapiens

<400> SEQUENCE: 1760
cccgagactt ccaacctgag tgg                                          23

<210> SEQ ID NO 1761
<211> LENGTH: 23
<212> TYPE: DNA
<213> ORGANISM: Homo sapiens

<400> SEQUENCE: 1761
cggccagccc caggcggact agg                                          23

<210> SEQ ID NO 1762
<211> LENGTH: 23
<212> TYPE: DNA
<213> ORGANISM: Homo sapiens

<400> SEQUENCE: 1762
gattcgaacc ctctgtcttc tgg                                          23

<210> SEQ ID NO 1763
<211> LENGTH: 23
<212> TYPE: DNA
<213> ORGANISM: Homo sapiens

<400> SEQUENCE: 1763
cacaacgtgg aagcagactc tgg                                          23

<210> SEQ ID NO 1764
<211> LENGTH: 23
<212> TYPE: DNA
<213> ORGANISM: Homo sapiens

<400> SEQUENCE: 1764
acagggcaca gcgggtcta agg                                           23

<210> SEQ ID NO 1765
<211> LENGTH: 23
<212> TYPE: DNA
<213> ORGANISM: Homo sapiens

<400> SEQUENCE: 1765
ctactactac agtgagtaga cgg                                          23

<210> SEQ ID NO 1766
<211> LENGTH: 23
<212> TYPE: DNA
<213> ORGANISM: Homo sapiens

```
<400> SEQUENCE: 1766
accaatcagc aggacacggg cgg                                              23

<210> SEQ ID NO 1767
<211> LENGTH: 23
<212> TYPE: DNA
<213> ORGANISM: Homo sapiens

<400> SEQUENCE: 1767
ccactcaggt tggaagtctc ggg                                              23

<210> SEQ ID NO 1768
<211> LENGTH: 23
<212> TYPE: DNA
<213> ORGANISM: Homo sapiens

<400> SEQUENCE: 1768
gccactcagg ttggaagtct cgg                                              23

<210> SEQ ID NO 1769
<211> LENGTH: 23
<212> TYPE: DNA
<213> ORGANISM: Homo sapiens

<400> SEQUENCE: 1769
acgtggaagc agactctggt ggg                                              23

<210> SEQ ID NO 1770
<211> LENGTH: 23
<212> TYPE: DNA
<213> ORGANISM: Homo sapiens

<400> SEQUENCE: 1770
cagtgagtag acggcagtgc tgg                                              23

<210> SEQ ID NO 1771
<211> LENGTH: 23
<212> TYPE: DNA
<213> ORGANISM: Homo sapiens

<400> SEQUENCE: 1771
ccatcttaca gagtgctgat tgg                                              23

<210> SEQ ID NO 1772
<211> LENGTH: 23
<212> TYPE: DNA
<213> ORGANISM: Homo sapiens

<400> SEQUENCE: 1772
ccaatcagca ctctgtaaga tgg                                              23

<210> SEQ ID NO 1773
<211> LENGTH: 23
<212> TYPE: DNA
<213> ORGANISM: Homo sapiens

<400> SEQUENCE: 1773
gagacttcca acctgagtgg cgg                                              23

<210> SEQ ID NO 1774
<211> LENGTH: 23
<212> TYPE: DNA
<213> ORGANISM: Homo sapiens
```

-continued

```
<400> SEQUENCE: 1774
tagtgagacg tgaagccagc tgg                                                  23

<210> SEQ ID NO 1775
<211> LENGTH: 23
<212> TYPE: DNA
<213> ORGANISM: Homo sapiens

<400> SEQUENCE: 1775
agtgagtaga cggcagtgct ggg                                                  23

<210> SEQ ID NO 1776
<211> LENGTH: 23
<212> TYPE: DNA
<213> ORGANISM: Homo sapiens

<400> SEQUENCE: 1776
tgtaaaatgg accaatcagc agg                                                  23

<210> SEQ ID NO 1777
<211> LENGTH: 23
<212> TYPE: DNA
<213> ORGANISM: Homo sapiens

<400> SEQUENCE: 1777
ggcggatacc agcaggagcg cgg                                                  23

<210> SEQ ID NO 1778
<211> LENGTH: 23
<212> TYPE: DNA
<213> ORGANISM: Homo sapiens

<400> SEQUENCE: 1778
aacctgagtg gcggagaagc tgg                                                  23

<210> SEQ ID NO 1779
<211> LENGTH: 23
<212> TYPE: DNA
<213> ORGANISM: Homo sapiens

<400> SEQUENCE: 1779
tggacttcct gggttgaatg ggg                                                  23

<210> SEQ ID NO 1780
<211> LENGTH: 23
<212> TYPE: DNA
<213> ORGANISM: Homo sapiens

<400> SEQUENCE: 1780
tccaggtccc cattcaaccc agg                                                  23

<210> SEQ ID NO 1781
<211> LENGTH: 23
<212> TYPE: DNA
<213> ORGANISM: Homo sapiens

<400> SEQUENCE: 1781
ccggctccgc ccgcagactc tgg                                                  23

<210> SEQ ID NO 1782
<211> LENGTH: 23
<212> TYPE: DNA
```

```
<213> ORGANISM: Homo sapiens

<400> SEQUENCE: 1782
ccagagtctg cgggcggagc cgg                                              23

<210> SEQ ID NO 1783
<211> LENGTH: 23
<212> TYPE: DNA
<213> ORGANISM: Homo sapiens

<400> SEQUENCE: 1783
gtctcgggct gcagtgctcc tgg                                              23

<210> SEQ ID NO 1784
<211> LENGTH: 23
<212> TYPE: DNA
<213> ORGANISM: Homo sapiens

<400> SEQUENCE: 1784
acctgagtgg cggagaagct ggg                                              23

<210> SEQ ID NO 1785
<211> LENGTH: 23
<212> TYPE: DNA
<213> ORGANISM: Homo sapiens

<400> SEQUENCE: 1785
gctggacttc ctgggttgaa tgg                                              23

<210> SEQ ID NO 1786
<211> LENGTH: 23
<212> TYPE: DNA
<213> ORGANISM: Homo sapiens

<400> SEQUENCE: 1786
tggaccaatc agcaggacac ggg                                              23

<210> SEQ ID NO 1787
<211> LENGTH: 23
<212> TYPE: DNA
<213> ORGANISM: Homo sapiens

<400> SEQUENCE: 1787
ctggacttcc tgggttgaat ggg                                              23

<210> SEQ ID NO 1788
<211> LENGTH: 23
<212> TYPE: DNA
<213> ORGANISM: Homo sapiens

<400> SEQUENCE: 1788
ttccgcggag ctcagccagc agg                                              23

<210> SEQ ID NO 1789
<211> LENGTH: 23
<212> TYPE: DNA
<213> ORGANISM: Homo sapiens

<400> SEQUENCE: 1789
cgtggaagca gactctggtg ggg                                              23

<210> SEQ ID NO 1790
<211> LENGTH: 23
```

```
<212> TYPE: DNA
<213> ORGANISM: Homo sapiens

<400> SEQUENCE: 1790
aacgtggaag cagactctgg tgg                                              23

<210> SEQ ID NO 1791
<211> LENGTH: 23
<212> TYPE: DNA
<213> ORGANISM: Homo sapiens

<400> SEQUENCE: 1791
cagagtctgc gggcggagcc ggg                                              23

<210> SEQ ID NO 1792
<211> LENGTH: 23
<212> TYPE: DNA
<213> ORGANISM: Homo sapiens

<400> SEQUENCE: 1792
tctcgggctg cagtgctcct ggg                                              23

<210> SEQ ID NO 1793
<211> LENGTH: 23
<212> TYPE: DNA
<213> ORGANISM: Homo sapiens

<400> SEQUENCE: 1793
tcggaggagc cagagtctgc ggg                                              23

<210> SEQ ID NO 1794
<211> LENGTH: 23
<212> TYPE: DNA
<213> ORGANISM: Homo sapiens

<400> SEQUENCE: 1794
tgaagccagc tggacttcct ggg                                              23

<210> SEQ ID NO 1795
<211> LENGTH: 23
<212> TYPE: DNA
<213> ORGANISM: Homo sapiens

<400> SEQUENCE: 1795
ctggaaagaa gctacagcac agg                                              23

<210> SEQ ID NO 1796
<211> LENGTH: 23
<212> TYPE: DNA
<213> ORGANISM: Homo sapiens

<400> SEQUENCE: 1796
atggaccaat cagcaggaca cgg                                              23

<210> SEQ ID NO 1797
<211> LENGTH: 23
<212> TYPE: DNA
<213> ORGANISM: Homo sapiens

<400> SEQUENCE: 1797
tcccagcttc tccgccactc agg                                              23

<210> SEQ ID NO 1798
```

-continued

<210> SEQ ID NO 1798
<211> LENGTH: 23
<212> TYPE: DNA
<213> ORGANISM: Homo sapiens

<400> SEQUENCE: 1798
tttcccaagg agtagctgaa agg                                           23

<210> SEQ ID NO 1799
<211> LENGTH: 23
<212> TYPE: DNA
<213> ORGANISM: Homo sapiens

<400> SEQUENCE: 1799
gaaccctctg tcttctggct tgg                                           23

<210> SEQ ID NO 1800
<211> LENGTH: 23
<212> TYPE: DNA
<213> ORGANISM: Homo sapiens

<400> SEQUENCE: 1800
cttacaagag gattgtaaaa tgg                                           23

<210> SEQ ID NO 1801
<211> LENGTH: 23
<212> TYPE: DNA
<213> ORGANISM: Homo sapiens

<400> SEQUENCE: 1801
ggtatccgcc cctgagcccc agg                                           23

<210> SEQ ID NO 1802
<211> LENGTH: 23
<212> TYPE: DNA
<213> ORGANISM: Homo sapiens

<400> SEQUENCE: 1802
tagtagtagc agctacagaa agg                                           23

<210> SEQ ID NO 1803
<211> LENGTH: 23
<212> TYPE: DNA
<213> ORGANISM: Homo sapiens

<400> SEQUENCE: 1803
tttcagctac tccttgggaa agg                                           23

<210> SEQ ID NO 1804
<211> LENGTH: 23
<212> TYPE: DNA
<213> ORGANISM: Homo sapiens

<400> SEQUENCE: 1804
tagtccgcct ggggctggcc ggg                                           23

<210> SEQ ID NO 1805
<211> LENGTH: 23
<212> TYPE: DNA
<213> ORGANISM: Homo sapiens

<400> SEQUENCE: 1805
cgggctggtc ctcatctccc tgg                                           23

<210> SEQ ID NO 1806
<211> LENGTH: 23
<212> TYPE: DNA
<213> ORGANISM: Homo sapiens

<400> SEQUENCE: 1806
ctagtccgcc tggggctggc cgg                                             23

<210> SEQ ID NO 1807
<211> LENGTH: 23
<212> TYPE: DNA
<213> ORGANISM: Homo sapiens

<400> SEQUENCE: 1807
cttcctttca gctactcctt ggg                                             23

<210> SEQ ID NO 1808
<211> LENGTH: 23
<212> TYPE: DNA
<213> ORGANISM: Homo sapiens

<400> SEQUENCE: 1808
gtaagacaga aaagttctcc agg                                             23

<210> SEQ ID NO 1809
<211> LENGTH: 23
<212> TYPE: DNA
<213> ORGANISM: Homo sapiens

<400> SEQUENCE: 1809
ctcgggctgc agtgctcctg ggg                                             23

<210> SEQ ID NO 1810
<211> LENGTH: 23
<212> TYPE: DNA
<213> ORGANISM: Homo sapiens

<400> SEQUENCE: 1810
agctcagcca gcaggactgt ggg                                             23

<210> SEQ ID NO 1811
<211> LENGTH: 23
<212> TYPE: DNA
<213> ORGANISM: Homo sapiens

<400> SEQUENCE: 1811 gaactttct gtcttacaag agg                                              23

<210> SEQ ID NO 1812
<211> LENGTH: 23
<212> TYPE: DNA
<213> ORGANISM: Homo sapiens

<400> SEQUENCE: 1812
gctactcctt gggaaaggcc tgg                                             23

<210> SEQ ID NO 1813
<211> LENGTH: 23
<212> TYPE: DNA
<213> ORGANISM: Homo sapiens

<400> SEQUENCE: 1813
ccagcgcgcc cagggagatg agg                                             23

-continued

```
<210> SEQ ID NO 1814
<211> LENGTH: 23
<212> TYPE: DNA
<213> ORGANISM: Homo sapiens

<400> SEQUENCE: 1814
ctacagcaca gggcacagcg ggg                                              23

<210> SEQ ID NO 1815
<211> LENGTH: 23
<212> TYPE: DNA
<213> ORGANISM: Homo sapiens

<400> SEQUENCE: 1815
gaggagccag agtctgcggg cgg                                              23

<210> SEQ ID NO 1816
<211> LENGTH: 23
<212> TYPE: DNA
<213> ORGANISM: Homo sapiens

<400> SEQUENCE: 1816
gtcggaggag ccagagtctg cgg                                              23

<210> SEQ ID NO 1817
<211> LENGTH: 23
<212> TYPE: DNA
<213> ORGANISM: Homo sapiens

<400> SEQUENCE: 1817
ctgtgctgta gcttctttcc agg                                              23

<210> SEQ ID NO 1818
<211> LENGTH: 23
<212> TYPE: DNA
<213> ORGANISM: Homo sapiens

<400> SEQUENCE: 1818
gacaataagg gaataaaagc tgg                                              23

<210> SEQ ID NO 1819
<211> LENGTH: 23
<212> TYPE: DNA
<213> ORGANISM: Homo sapiens

<400> SEQUENCE: 1819
tcctgggttg aatggggacc tgg                                              23

<210> SEQ ID NO 1820
<211> LENGTH: 23
<212> TYPE: DNA
<213> ORGANISM: Homo sapiens

<400> SEQUENCE: 1820
tggaaagaag ctacagcaca ggg                                              23

<210> SEQ ID NO 1821
<211> LENGTH: 23
<212> TYPE: DNA
<213> ORGANISM: Homo sapiens

<400> SEQUENCE: 1821
gctcagccag caggactgtg ggg                                              23
```

<210> SEQ ID NO 1822
<211> LENGTH: 23
<212> TYPE: DNA
<213> ORGANISM: Homo sapiens

<400> SEQUENCE: 1822
tgcagtgctc ctggggctca ggg                                          23

<210> SEQ ID NO 1823
<211> LENGTH: 23
<212> TYPE: DNA
<213> ORGANISM: Homo sapiens

<400> SEQUENCE: 1823
aggaaaggac agtccagccc agg                                          23

<210> SEQ ID NO 1824
<211> LENGTH: 23
<212> TYPE: DNA
<213> ORGANISM: Homo sapiens

<400> SEQUENCE: 1824
cccgcccgtg tcctgctgat tgg                                          23

<210> SEQ ID NO 1825
<211> LENGTH: 23
<212> TYPE: DNA
<213> ORGANISM: Homo sapiens

<400> SEQUENCE: 1825
ggcggagaag ctgggaccct ggg                                          23

<210> SEQ ID NO 1826
<211> LENGTH: 23
<212> TYPE: DNA
<213> ORGANISM: Homo sapiens

<400> SEQUENCE: 1826
ctgcagcccc acagtcctgc tgg                                          23

<210> SEQ ID NO 1827
<211> LENGTH: 23
<212> TYPE: DNA
<213> ORGANISM: Homo sapiens

<400> SEQUENCE: 1827
acttccaagc cagaagacag agg                                          23

<210> SEQ ID NO 1828
<211> LENGTH: 23
<212> TYPE: DNA
<213> ORGANISM: Homo sapiens

<400> SEQUENCE: 1828
gagctcagcc agcaggactg tgg                                          23

<210> SEQ ID NO 1829
<211> LENGTH: 23
<212> TYPE: DNA
<213> ORGANISM: Homo sapiens

<400> SEQUENCE: 1829
cagggagatg aggaccagcc cgg                                              23

<210> SEQ ID NO 1830
<211> LENGTH: 23
<212> TYPE: DNA
<213> ORGANISM: Homo sapiens

<400> SEQUENCE: 1830
agctacagca cagggcacag cgg                                              23

<210> SEQ ID NO 1831
<211> LENGTH: 23
<212> TYPE: DNA
<213> ORGANISM: Homo sapiens

<400> SEQUENCE: 1831
cttccaagcc agaagacaga ggg                                              23

<210> SEQ ID NO 1832
<211> LENGTH: 23
<212> TYPE: DNA
<213> ORGANISM: Homo sapiens

<400> SEQUENCE: 1832
tggcggagaa gctgggaccc tgg                                              23

<210> SEQ ID NO 1833
<211> LENGTH: 23
<212> TYPE: DNA
<213> ORGANISM: Homo sapiens

<400> SEQUENCE: 1833
ccgcctgggg ctggccgggc tgg                                              23

<210> SEQ ID NO 1834
<211> LENGTH: 23
<212> TYPE: DNA
<213> ORGANISM: Homo sapiens

<400> SEQUENCE: 1834
gcagtgctcc tggggctcag ggg                                              23

<210> SEQ ID NO 1835
<211> LENGTH: 23
<212> TYPE: DNA
<213> ORGANISM: Homo sapiens

<400> SEQUENCE: 1835
gctacagcac agggcacagc ggg                                              23

<210> SEQ ID NO 1836
<211> LENGTH: 23
<212> TYPE: DNA
<213> ORGANISM: Homo sapiens

<400> SEQUENCE: 1836
ctgcagtgct cctggggctc agg                                              23

<210> SEQ ID NO 1837
<211> LENGTH: 23
<212> TYPE: DNA
<213> ORGANISM: Homo sapiens

<400> SEQUENCE: 1837

```
gtcctgctgg ctgagctccg cgg                                              23

<210> SEQ ID NO 1838
<211> LENGTH: 23
<212> TYPE: DNA
<213> ORGANISM: Homo sapiens

<400> SEQUENCE: 1838
gggctggtcc tcatctccct ggg                                              23

<210> SEQ ID NO 1839
<211> LENGTH: 23
<212> TYPE: DNA
<213> ORGANISM: Homo sapiens

<400> SEQUENCE: 1839
ggaccagccc ggccagcccc agg                                              23

<210> SEQ ID NO 1840
<211> LENGTH: 23
<212> TYPE: DNA
<213> ORGANISM: Homo sapiens

<400> SEQUENCE: 1840
ttctttccag gcctttccca agg                                              23

<210> SEQ ID NO 1841
<211> LENGTH: 23
<212> TYPE: DNA
<213> ORGANISM: Homo sapiens

<400> SEQUENCE: 1841
ggactgtggg gctgcaggaa agg                                              23

<210> SEQ ID NO 1842
<211> LENGTH: 23
<212> TYPE: DNA
<213> ORGANISM: Homo sapiens

<400> SEQUENCE: 1842
cagcaggact gtggggctgc agg                                              23

<210> SEQ ID NO 1843
<211> LENGTH: 23
<212> TYPE: DNA
<213> ORGANISM: Homo sapiens

<400> SEQUENCE: 1843
ggaaaggaca gtccagccca ggg                                              23

<210> SEQ ID NO 1844
<211> LENGTH: 23
<212> TYPE: DNA
<213> ORGANISM: Homo sapiens

<400> SEQUENCE: 1844
tcttcctttc agctactcct tgg                                              23

<210> SEQ ID NO 1845
<211> LENGTH: 23
<212> TYPE: DNA
<213> ORGANISM: Homo sapiens
```

```
<400> SEQUENCE: 1845
gtgaagccag ctggacttcc tgg                                              23

<210> SEQ ID NO 1846
<211> LENGTH: 23
<212> TYPE: DNA
<213> ORGANISM: Homo sapiens

<400> SEQUENCE: 1846
gtgctcctgg ggctcagggg cgg                                              23

<210> SEQ ID NO 1847
<211> LENGTH: 23
<212> TYPE: DNA
<213> ORGANISM: Homo sapiens

<400> SEQUENCE: 1847
gagaagctgg gaccctgggc tgg                                              23

<210> SEQ ID NO 1848
<211> LENGTH: 23
<212> TYPE: DNA
<213> ORGANISM: Homo sapiens

<400> SEQUENCE: 1848
ccagcccggc cagccccagg cgg                                              23

<210> SEQ ID NO 1849
<211> LENGTH: 23
<212> TYPE: DNA
<213> ORGANISM: Homo sapiens

<400> SEQUENCE: 1849
caaagttgag ggggagtcga tgg                                              23

<210> SEQ ID NO 1850
<211> LENGTH: 23
<212> TYPE: DNA
<213> ORGANISM: Homo sapiens

<400> SEQUENCE: 1850
tcgatggagg cttcaactcc tgg                                              23

<210> SEQ ID NO 1851
<211> LENGTH: 23
<212> TYPE: DNA
<213> ORGANISM: Homo sapiens

<400> SEQUENCE: 1851
cgatggaggc ttcaactcct ggg                                              23

<210> SEQ ID NO 1852
<211> LENGTH: 23
<212> TYPE: DNA
<213> ORGANISM: Homo sapiens

<400> SEQUENCE: 1852
gactagactc ctggatctga ggg                                              23

<210> SEQ ID NO 1853
<211> LENGTH: 23
<212> TYPE: DNA
<213> ORGANISM: Homo sapiens
```

<400> SEQUENCE: 1853
ggctgcagga ctagacccct ggg            23

<210> SEQ ID NO 1854
<211> LENGTH: 23
<212> TYPE: DNA
<213> ORGANISM: Homo sapiens

<400> SEQUENCE: 1854
gagctggagg actagactcc tgg            23

<210> SEQ ID NO 1855
<211> LENGTH: 23
<212> TYPE: DNA
<213> ORGANISM: Homo sapiens

<400> SEQUENCE: 1855
agttgagggg gagtcgatgg agg            23

<210> SEQ ID NO 1856
<211> LENGTH: 23
<212> TYPE: DNA
<213> ORGANISM: Homo sapiens

<400> SEQUENCE: 1856
gctcccggac cccaaagtct ggg            23

<210> SEQ ID NO 1857
<211> LENGTH: 23
<212> TYPE: DNA
<213> ORGANISM: Homo sapiens

<400> SEQUENCE: 1857
agctcccgga ccccaaagtc tgg            23

<210> SEQ ID NO 1858
<211> LENGTH: 23
<212> TYPE: DNA
<213> ORGANISM: Homo sapiens

<400> SEQUENCE: 1858
ggtccctaag tccaccccag ggg            23

<210> SEQ ID NO 1859
<211> LENGTH: 23
<212> TYPE: DNA
<213> ORGANISM: Homo sapiens

<400> SEQUENCE: 1859
gggctgcagg actagacccc tgg            23

<210> SEQ ID NO 1860
<211> LENGTH: 23
<212> TYPE: DNA
<213> ORGANISM: Homo sapiens

<400> SEQUENCE: 1860
cagcccctgg ggtggactta ggg            23

<210> SEQ ID NO 1861
<211> LENGTH: 23
<212> TYPE: DNA

-continued

```
<213> ORGANISM: Homo sapiens

<400> SEQUENCE: 1861
actctacagt ctcaaagttg agg                                              23

<210> SEQ ID NO 1862
<211> LENGTH: 23
<212> TYPE: DNA
<213> ORGANISM: Homo sapiens

<400> SEQUENCE: 1862
aactttgaga ctgtagagtc agg                                              23

<210> SEQ ID NO 1863
<211> LENGTH: 23
<212> TYPE: DNA
<213> ORGANISM: Homo sapiens

<400> SEQUENCE: 1863
ggactagact cctggatctg agg                                              23

<210> SEQ ID NO 1864
<211> LENGTH: 23
<212> TYPE: DNA
<213> ORGANISM: Homo sapiens

<400> SEQUENCE: 1864
gtactggggc ccgggaatcc tgg                                              23

<210> SEQ ID NO 1865
<211> LENGTH: 23
<212> TYPE: DNA
<213> ORGANISM: Homo sapiens

<400> SEQUENCE: 1865
gactagaccc ctgggtctga agg                                              23

<210> SEQ ID NO 1866
<211> LENGTH: 23
<212> TYPE: DNA
<213> ORGANISM: Homo sapiens

<400> SEQUENCE: 1866
ccggctccgc ccgcagactc tgg                                              23

<210> SEQ ID NO 1867
<211> LENGTH: 23
<212> TYPE: DNA
<213> ORGANISM: Homo sapiens

<400> SEQUENCE: 1867
ccagagtctg cgggcggagc cgg                                              23

<210> SEQ ID NO 1868
<211> LENGTH: 23
<212> TYPE: DNA
<213> ORGANISM: Homo sapiens

<400> SEQUENCE: 1868
gagttcaggg cccagacttt ggg                                              23

<210> SEQ ID NO 1869
<211> LENGTH: 23
```

<212> TYPE: DNA
<213> ORGANISM: Homo sapiens

<400> SEQUENCE: 1869
ctacagtctc aaagttgagg ggg                                         23

<210> SEQ ID NO 1870
<211> LENGTH: 23
<212> TYPE: DNA
<213> ORGANISM: Homo sapiens

<400> SEQUENCE: 1870
tactggggcc cgggaatcct ggg                                         23

<210> SEQ ID NO 1871
<211> LENGTH: 23
<212> TYPE: DNA
<213> ORGANISM: Homo sapiens

<400> SEQUENCE: 1871
caggtcccta agtccacccc agg                                         23

<210> SEQ ID NO 1872
<211> LENGTH: 23
<212> TYPE: DNA
<213> ORGANISM: Homo sapiens

<400> SEQUENCE: 1872
cctggactgc tggatcagga agg                                         23

<210> SEQ ID NO 1873
<211> LENGTH: 23
<212> TYPE: DNA
<213> ORGANISM: Homo sapiens

<400> SEQUENCE: 1873
ggtctgaggg cggaggtcct ggg                                         23

<210> SEQ ID NO 1874
<211> LENGTH: 23
<212> TYPE: DNA
<213> ORGANISM: Homo sapiens

<400> SEQUENCE: 1874
cagagtctgc gggcggagcc ggg                                         23

<210> SEQ ID NO 1875
<211> LENGTH: 23
<212> TYPE: DNA
<213> ORGANISM: Homo sapiens

<400> SEQUENCE: 1875
aggtccctaa gtccacccca ggg                                         23

<210> SEQ ID NO 1876
<211> LENGTH: 23
<212> TYPE: DNA
<213> ORGANISM: Homo sapiens

<400> SEQUENCE: 1876
tctacagtct caaagttgag ggg                                         23

<210> SEQ ID NO 1877

```
<211> LENGTH: 23
<212> TYPE: DNA
<213> ORGANISM: Homo sapiens

<400> SEQUENCE: 1877
tcggaggagc cagagtctgc ggg                                              23

<210> SEQ ID NO 1878
<211> LENGTH: 23
<212> TYPE: DNA
<213> ORGANISM: Homo sapiens

<400> SEQUENCE: 1878
ctctacagtc tcaaagttga ggg                                              23

<210> SEQ ID NO 1879
<211> LENGTH: 23
<212> TYPE: DNA
<213> ORGANISM: Homo sapiens

<400> SEQUENCE: 1879
cccgggaatc ctgggtctga ggg                                              23

<210> SEQ ID NO 1880
<211> LENGTH: 23
<212> TYPE: DNA
<213> ORGANISM: Homo sapiens

<400> SEQUENCE: 1880
agttcagggc ccagactttg ggg                                              23

<210> SEQ ID NO 1881
<211> LENGTH: 23
<212> TYPE: DNA
<213> ORGANISM: Homo sapiens

<400> SEQUENCE: 1881
tagactcctg gatctgaggg agg                                              23

<210> SEQ ID NO 1882
<211> LENGTH: 23
<212> TYPE: DNA
<213> ORGANISM: Homo sapiens

<400> SEQUENCE: 1882
aagtctgggc cctgaactcc agg                                              23

<210> SEQ ID NO 1883
<211> LENGTH: 23
<212> TYPE: DNA
<213> ORGANISM: Homo sapiens

<400> SEQUENCE: 1883
ccttcctgat ccagcagtcc agg                                              23

<210> SEQ ID NO 1884
<211> LENGTH: 23
<212> TYPE: DNA
<213> ORGANISM: Homo sapiens

<400> SEQUENCE: 1884 tagaccctg ggtctgaagg agg                                               23
```

```
<210> SEQ ID NO 1885
<211> LENGTH: 23
<212> TYPE: DNA
<213> ORGANISM: Homo sapiens

<400> SEQUENCE: 1885
ctgcattcct ggggcggagg agg                                              23

<210> SEQ ID NO 1886
<211> LENGTH: 23
<212> TYPE: DNA
<213> ORGANISM: Homo sapiens

<400> SEQUENCE: 1886
ctcctccgcc ccaggaatgc agg                                              23

<210> SEQ ID NO 1887
<211> LENGTH: 23
<212> TYPE: DNA
<213> ORGANISM: Homo sapiens

<400> SEQUENCE: 1887
ggggcctgga ctgctggatc agg                                              23

<210> SEQ ID NO 1888
<211> LENGTH: 23
<212> TYPE: DNA
<213> ORGANISM: Homo sapiens

<400> SEQUENCE: 1888
cccaggaatc ctgggtctga ggg                                              23

<210> SEQ ID NO 1889
<211> LENGTH: 23
<212> TYPE: DNA
<213> ORGANISM: Homo sapiens

<400> SEQUENCE: 1889
ccagcccctg gggtggactt agg                                              23

<210> SEQ ID NO 1890
<211> LENGTH: 23
<212> TYPE: DNA
<213> ORGANISM: Homo sapiens

<400> SEQUENCE: 1890
ggcctgcatt cctggggcgg agg                                              23

<210> SEQ ID NO 1891
<211> LENGTH: 23
<212> TYPE: DNA
<213> ORGANISM: Homo sapiens

<400> SEQUENCE: 1891
gtctgagggc ggaggtcctg ggg                                              23

<210> SEQ ID NO 1892
<211> LENGTH: 23
<212> TYPE: DNA
<213> ORGANISM: Homo sapiens

<400> SEQUENCE: 1892
gggtctgagg gcggaggtcc tgg                                              23
```

<210> SEQ ID NO 1893
<211> LENGTH: 23
<212> TYPE: DNA
<213> ORGANISM: Homo sapiens

<400> SEQUENCE: 1893
cctaagtcca ccccaggggc tgg                                              23

<210> SEQ ID NO 1894
<211> LENGTH: 23
<212> TYPE: DNA
<213> ORGANISM: Homo sapiens

<400> SEQUENCE: 1894
aggaggcggg ccgggcctca ggg                                              23

<210> SEQ ID NO 1895
<211> LENGTH: 23
<212> TYPE: DNA
<213> ORGANISM: Homo sapiens

<400> SEQUENCE: 1895
gtgctggtca tcagctggga agg                                              23

<210> SEQ ID NO 1896
<211> LENGTH: 23
<212> TYPE: DNA
<213> ORGANISM: Homo sapiens

<400> SEQUENCE: 1896
ggctggaaac ctggagttca ggg                                              23

<210> SEQ ID NO 1897
<211> LENGTH: 23
<212> TYPE: DNA
<213> ORGANISM: Homo sapiens

<400> SEQUENCE: 1897
agggcccaga ctttggggtc cgg                                              23

<210> SEQ ID NO 1898
<211> LENGTH: 23
<212> TYPE: DNA
<213> ORGANISM: Homo sapiens

<400> SEQUENCE: 1898
agctgatggc ccctctctcc cgg                                              23

<210> SEQ ID NO 1899
<211> LENGTH: 23
<212> TYPE: DNA
<213> ORGANISM: Homo sapiens

<400> SEQUENCE: 1899
ggagttcagg gcccagactt tgg                                              23

<210> SEQ ID NO 1900
<211> LENGTH: 23
<212> TYPE: DNA
<213> ORGANISM: Homo sapiens

<400> SEQUENCE: 1900 agagagggc catcagctcc cgg                                               23

<210> SEQ ID NO 1901
<211> LENGTH: 23
<212> TYPE: DNA
<213> ORGANISM: Homo sapiens

<400> SEQUENCE: 1901
ggctgggtcc caggaatcct ggg                                              23

<210> SEQ ID NO 1902
<211> LENGTH: 23
<212> TYPE: DNA
<213> ORGANISM: Homo sapiens

<400> SEQUENCE: 1902
gcgggcggag ccgggagaga ggg                                              23

<210> SEQ ID NO 1903
<211> LENGTH: 23
<212> TYPE: DNA
<213> ORGANISM: Homo sapiens

<400> SEQUENCE: 1903
gaggagccag agtctgcggg cgg                                              23

<210> SEQ ID NO 1904
<211> LENGTH: 23
<212> TYPE: DNA
<213> ORGANISM: Homo sapiens

<400> SEQUENCE: 1904
gtcggaggag ccagagtctg cgg                                              23

<210> SEQ ID NO 1905
<211> LENGTH: 23
<212> TYPE: DNA
<213> ORGANISM: Homo sapiens

<400> SEQUENCE: 1905
ggtctgaggg aggaggtact ggg                                              23

<210> SEQ ID NO 1906
<211> LENGTH: 23
<212> TYPE: DNA
<213> ORGANISM: Homo sapiens

<400> SEQUENCE: 1906
ggtcctgggg cctgcattcc tgg                                              23

<210> SEQ ID NO 1907
<211> LENGTH: 23
<212> TYPE: DNA
<213> ORGANISM: Homo sapiens

<400> SEQUENCE: 1907
ggtcatcagc tgggaaggtg agg                                              23

<210> SEQ ID NO 1908
<211> LENGTH: 23
<212> TYPE: DNA
<213> ORGANISM: Homo sapiens

<400> SEQUENCE: 1908

```
gcctggagtc ctgggtctga ggg                                              23

<210> SEQ ID NO 1909
<211> LENGTH: 23
<212> TYPE: DNA
<213> ORGANISM: Homo sapiens

<400> SEQUENCE: 1909
gggcccagac tttggggtcc ggg                                              23

<210> SEQ ID NO 1910
<211> LENGTH: 23
<212> TYPE: DNA
<213> ORGANISM: Homo sapiens

<400> SEQUENCE: 1910
gtcctggggc ctgcattcct ggg                                              23

<210> SEQ ID NO 1911
<211> LENGTH: 23
<212> TYPE: DNA
<213> ORGANISM: Homo sapiens

<400> SEQUENCE: 1911
ccctcagacc caggattccc ggg                                              23

<210> SEQ ID NO 1912
<211> LENGTH: 23
<212> TYPE: DNA
<213> ORGANISM: Homo sapiens

<400> SEQUENCE: 1912
tcccaggaat cctgggtctg agg                                              23

<210> SEQ ID NO 1913
<211> LENGTH: 23
<212> TYPE: DNA
<213> ORGANISM: Homo sapiens

<400> SEQUENCE: 1913
ggacctccgc cctcagaccc agg                                              23

<210> SEQ ID NO 1914
<211> LENGTH: 23
<212> TYPE: DNA
<213> ORGANISM: Homo sapiens

<400> SEQUENCE: 1914
cctctcctcc ttcagaccca ggg                                              23

<210> SEQ ID NO 1915
<211> LENGTH: 23
<212> TYPE: DNA
<213> ORGANISM: Homo sapiens

<400> SEQUENCE: 1915
aggaatcctg ggtctgaggg agg                                              23

<210> SEQ ID NO 1916
<211> LENGTH: 23
<212> TYPE: DNA
<213> ORGANISM: Homo sapiens

<400> SEQUENCE: 1916
```
aactccaggt ttccagcccc tgg				23

<210> SEQ ID NO 1917
<211> LENGTH: 23
<212> TYPE: DNA
<213> ORGANISM: Homo sapiens

<400> SEQUENCE: 1917
gtctgaggga ggaggtactg ggg				23

<210> SEQ ID NO 1918
<211> LENGTH: 23
<212> TYPE: DNA
<213> ORGANISM: Homo sapiens

<400> SEQUENCE: 1918
ggactgctgg atcaggaagg agg				23

<210> SEQ ID NO 1919
<211> LENGTH: 23
<212> TYPE: DNA
<213> ORGANISM: Homo sapiens

<400> SEQUENCE: 1919
gctcctgggt ctgagggcgg agg				23

<210> SEQ ID NO 1920
<211> LENGTH: 23
<212> TYPE: DNA
<213> ORGANISM: Homo sapiens

<400> SEQUENCE: 1920
ctttggggtc cgggagctga tgg				23

<210> SEQ ID NO 1921
<211> LENGTH: 23
<212> TYPE: DNA
<213> ORGANISM: Homo sapiens

<400> SEQUENCE: 1921
cttcctggac ccaggactcc agg				23

<210> SEQ ID NO 1922
<211> LENGTH: 23
<212> TYPE: DNA
<213> ORGANISM: Homo sapiens

<400> SEQUENCE: 1922
caccccaggg gctggaaacc tgg				23

<210> SEQ ID NO 1923
<211> LENGTH: 23
<212> TYPE: DNA
<213> ORGANISM: Homo sapiens

<400> SEQUENCE: 1923
gcccgggaat cctgggtctg agg				23

<210> SEQ ID NO 1924
<211> LENGTH: 23
<212> TYPE: DNA
<213> ORGANISM: Homo sapiens -continued

```
<400> SEQUENCE: 1924
gactgctgga tcaggaagga ggg                                                23

<210> SEQ ID NO 1925
<211> LENGTH: 23
<212> TYPE: DNA
<213> ORGANISM: Homo sapiens

<400> SEQUENCE: 1925
actcctgggt ccaggaagaa ggg                                                23

<210> SEQ ID NO 1926
<211> LENGTH: 23
<212> TYPE: DNA
<213> ORGANISM: Homo sapiens

<400> SEQUENCE: 1926
tccctcagac ccaggattcc tgg                                                23

<210> SEQ ID NO 1927
<211> LENGTH: 23
<212> TYPE: DNA
<213> ORGANISM: Homo sapiens

<400> SEQUENCE: 1927
tccctcagac ccaggattcc cgg                                                23

<210> SEQ ID NO 1928
<211> LENGTH: 23
<212> TYPE: DNA
<213> ORGANISM: Homo sapiens

<400> SEQUENCE: 1928
gggtctgagg gaggaggtac tgg                                                23

<210> SEQ ID NO 1929
<211> LENGTH: 23
<212> TYPE: DNA
<213> ORGANISM: Homo sapiens

<400> SEQUENCE: 1929
gggctgggtc ccaggaatcc tgg                                                23

<210> SEQ ID NO 1930
<211> LENGTH: 23
<212> TYPE: DNA
<213> ORGANISM: Homo sapiens

<400> SEQUENCE: 1930
gcctctcctc cttcagaccc agg                                                23

<210> SEQ ID NO 1931
<211> LENGTH: 23
<212> TYPE: DNA
<213> ORGANISM: Homo sapiens

<400> SEQUENCE: 1931
gccccaggaa tgcaggcccc agg                                                23

<210> SEQ ID NO 1932
<211> LENGTH: 23
<212> TYPE: DNA
<213> ORGANISM: Homo sapiens
```

-continued

<400> SEQUENCE: 1932
attcctgggg cggaggaggc ggg                                    23

<210> SEQ ID NO 1933
<211> LENGTH: 23
<212> TYPE: DNA
<213> ORGANISM: Homo sapiens

<400> SEQUENCE: 1933
gggaatcctg ggtctgaggg agg                                    23

<210> SEQ ID NO 1934
<211> LENGTH: 23
<212> TYPE: DNA
<213> ORGANISM: Homo sapiens

<400> SEQUENCE: 1934
gcctgggctc ctgggtctga ggg                                    23

<210> SEQ ID NO 1935
<211> LENGTH: 23
<212> TYPE: DNA
<213> ORGANISM: Homo sapiens

<400> SEQUENCE: 1935
gaggaggcgg gccgggcctc agg                                    23

<210> SEQ ID NO 1936
<211> LENGTH: 23
<212> TYPE: DNA
<213> ORGANISM: Homo sapiens

<400> SEQUENCE: 1936
ctggagtcct gggtccagga agg                                    23

<210> SEQ ID NO 1937
<211> LENGTH: 23
<212> TYPE: DNA
<213> ORGANISM: Homo sapiens

<400> SEQUENCE: 1937
ctctcctcct tcagacccag ggg                                    23

<210> SEQ ID NO 1938
<211> LENGTH: 23
<212> TYPE: DNA
<213> ORGANISM: Homo sapiens

<400> SEQUENCE: 1938
ccctcagacc caggattcct ggg                                    23

<210> SEQ ID NO 1939
<211> LENGTH: 23
<212> TYPE: DNA
<213> ORGANISM: Homo sapiens

<400> SEQUENCE: 1939
caggtttcca gccctggggg tgg                                    23

<210> SEQ ID NO 1940
<211> LENGTH: 23
<212> TYPE: DNA

```
<213> ORGANISM: Homo sapiens

<400> SEQUENCE: 1940
tggagtcctg ggtctgaggg agg                                          23

<210> SEQ ID NO 1941
<211> LENGTH: 23
<212> TYPE: DNA
<213> ORGANISM: Homo sapiens

<400> SEQUENCE: 1941
tgcgggcgga gccgggagag agg                                          23

<210> SEQ ID NO 1942
<211> LENGTH: 23
<212> TYPE: DNA
<213> ORGANISM: Homo sapiens

<400> SEQUENCE: 1942
gggctggaaa cctggagttc agg                                          23

<210> SEQ ID NO 1943
<211> LENGTH: 23
<212> TYPE: DNA
<213> ORGANISM: Homo sapiens

<400> SEQUENCE: 1943
ctccaggttt ccagcccctg ggg                                          23

<210> SEQ ID NO 1944
<211> LENGTH: 23
<212> TYPE: DNA
<213> ORGANISM: Homo sapiens

<400> SEQUENCE: 1944
cggcccgcct cctccgcccc agg                                          23

<210> SEQ ID NO 1945
<211> LENGTH: 23
<212> TYPE: DNA
<213> ORGANISM: Homo sapiens

<400> SEQUENCE: 1945
cgggcggagc cgggagagag ggg                                          23

<210> SEQ ID NO 1946
<211> LENGTH: 23
<212> TYPE: DNA
<213> ORGANISM: Homo sapiens

<400> SEQUENCE: 1946
aactcctggg tccaggaaga agg                                          23

<210> SEQ ID NO 1947
<211> LENGTH: 23
<212> TYPE: DNA
<213> ORGANISM: Homo sapiens

<400> SEQUENCE: 1947
tggggcggag gaggcgggcc ggg                                          23

<210> SEQ ID NO 1948
<211> LENGTH: 23
```

-continued

```
<212> TYPE: DNA
<213> ORGANISM: Homo sapiens

<400> SEQUENCE: 1948
tccctcagac ccaggactcc agg                                              23

<210> SEQ ID NO 1949
<211> LENGTH: 23
<212> TYPE: DNA
<213> ORGANISM: Homo sapiens

<400> SEQUENCE: 1949
agccccttct tcctggaccc agg                                              23

<210> SEQ ID NO 1950
<211> LENGTH: 23
<212> TYPE: DNA
<213> ORGANISM: Homo sapiens

<400> SEQUENCE: 1950
actcctggat ctgagggagg agg                                              23

<210> SEQ ID NO 1951
<211> LENGTH: 23
<212> TYPE: DNA
<213> ORGANISM: Homo sapiens

<400> SEQUENCE: 1951 gccctcctc cctcagatcc agg                                               23

<210> SEQ ID NO 1952
<211> LENGTH: 23
<212> TYPE: DNA
<213> ORGANISM: Homo sapiens

<400> SEQUENCE: 1952
aggcttcaac tcctgggtcc agg                                              23

<210> SEQ ID NO 1953
<211> LENGTH: 23
<212> TYPE: DNA
<213> ORGANISM: Homo sapiens

<400> SEQUENCE: 1953
actgctggat caggaaggag ggg                                              23

<210> SEQ ID NO 1954
<211> LENGTH: 23
<212> TYPE: DNA
<213> ORGANISM: Homo sapiens

<400> SEQUENCE: 1954
tgggctcctg ggtctgaggg cgg                                              23

<210> SEQ ID NO 1955
<211> LENGTH: 23
<212> TYPE: DNA
<213> ORGANISM: Homo sapiens

<400> SEQUENCE: 1955
tcctggggcc tgcattcctg ggg                                              23

<210> SEQ ID NO 1956
```

-continued

```
<211> LENGTH: 23
<212> TYPE: DNA
<213> ORGANISM: Homo sapiens

<400> SEQUENCE: 1956
gtacctcctc cctcagaccc agg                                               23

<210> SEQ ID NO 1957
<211> LENGTH: 23
<212> TYPE: DNA
<213> ORGANISM: Homo sapiens

<400> SEQUENCE: 1957
tgggtccagg aagaagggc tgg                                                23

<210> SEQ ID NO 1958
<211> LENGTH: 23
<212> TYPE: DNA
<213> ORGANISM: Homo sapiens

<400> SEQUENCE: 1958
ctggatcagg aaggaggggc tgg                                               23

<210> SEQ ID NO 1959
<211> LENGTH: 23
<212> TYPE: DNA
<213> ORGANISM: Homo sapiens

<400> SEQUENCE: 1959
ctcctgggtc caggaagaag ggg                                               23

<210> SEQ ID NO 1960
<211> LENGTH: 23
<212> TYPE: DNA
<213> ORGANISM: Homo sapiens

<400> SEQUENCE: 1960
ctcctggatc tgagggagga ggg                                               23

<210> SEQ ID NO 1961
<211> LENGTH: 23
<212> TYPE: DNA
<213> ORGANISM: Homo sapiens

<400> SEQUENCE: 1961
cattcctggg gcggaggagg cgg                                               23

<210> SEQ ID NO 1962
<211> LENGTH: 23
<212> TYPE: DNA
<213> ORGANISM: Homo sapiens

<400> SEQUENCE: 1962
gtcatcagct gggaaggtga ggg                                               23

<210> SEQ ID NO 1963
<211> LENGTH: 23
<212> TYPE: DNA
<213> ORGANISM: Homo sapiens

<400> SEQUENCE: 1963
ctggggcgga ggaggcgggc cgg                                               23
```

```
<210> SEQ ID NO 1964
<211> LENGTH: 23
<212> TYPE: DNA
<213> ORGANISM: Homo sapiens

<400> SEQUENCE: 1964
agggaggagg tactggggcc cgg                                           23

<210> SEQ ID NO 1965
<211> LENGTH: 23
<212> TYPE: DNA
<213> ORGANISM: Homo sapiens

<400> SEQUENCE: 1965
actccaggtt tccagcccct ggg                                           23

<210> SEQ ID NO 1966
<211> LENGTH: 23
<212> TYPE: DNA
<213> ORGANISM: Homo sapiens

<400> SEQUENCE: 1966
tggatcagga aggaggggct ggg                                           23

<210> SEQ ID NO 1967
<211> LENGTH: 23
<212> TYPE: DNA
<213> ORGANISM: Homo sapiens

<400> SEQUENCE: 1967
gggaggaggt actggggccc ggg                                           23

<210> SEQ ID NO 1968
<211> LENGTH: 23
<212> TYPE: DNA
<213> ORGANISM: Homo sapiens

<400> SEQUENCE: 1968
gccctcagac ccaggagccc agg                                           23

<210> SEQ ID NO 1969
<211> LENGTH: 23
<212> TYPE: DNA
<213> ORGANISM: Homo sapiens

<400> SEQUENCE: 1969
ccctgggtct gaaggaggag agg                                           23

<210> SEQ ID NO 1970
<211> LENGTH: 23
<212> TYPE: DNA
<213> ORGANISM: Homo sapiens

<400> SEQUENCE: 1970
agtcctgggt ccaggaagga ggg                                           23

<210> SEQ ID NO 1971
<211> LENGTH: 23
<212> TYPE: DNA
<213> ORGANISM: Homo sapiens

<400> SEQUENCE: 1971
atcctgggtc tgagggagga ggg                                           23
```

```
<210> SEQ ID NO 1972
<211> LENGTH: 23
<212> TYPE: DNA
<213> ORGANISM: Homo sapiens

<400> SEQUENCE: 1972
agcccctcct tcctggaccc agg                                              23

<210> SEQ ID NO 1973
<211> LENGTH: 23
<212> TYPE: DNA
<213> ORGANISM: Homo sapiens

<400> SEQUENCE: 1973
aatcctgggt ctgagggagg agg                                              23

<210> SEQ ID NO 1974
<211> LENGTH: 23
<212> TYPE: DNA
<213> ORGANISM: Homo sapiens

<400> SEQUENCE: 1974
aaggtgaggg ccctgaggcc cgg                                              23

<210> SEQ ID NO 1975
<211> LENGTH: 23
<212> TYPE: DNA
<213> ORGANISM: Homo sapiens

<400> SEQUENCE: 1975
gtcctgggtc caggaaggag ggg                                              23

<210> SEQ ID NO 1976
<211> LENGTH: 23
<212> TYPE: DNA
<213> ORGANISM: Homo sapiens

<400> SEQUENCE: 1976
ggtctgaagg aggagaggct ggg                                              23

<210> SEQ ID NO 1977
<211> LENGTH: 23
<212> TYPE: DNA
<213> ORGANISM: Homo sapiens

<400> SEQUENCE: 1977
gggtccagga agaaggggct ggg                                              23

<210> SEQ ID NO 1978
<211> LENGTH: 23
<212> TYPE: DNA
<213> ORGANISM: Homo sapiens

<400> SEQUENCE: 1978
aggccccagc cccttcttcc tgg                                              23

<210> SEQ ID NO 1979
<211> LENGTH: 23
<212> TYPE: DNA
<213> ORGANISM: Homo sapiens

<400> SEQUENCE: 1979
ggctgggggc ctggagtcct ggg                                              23
```

<210> SEQ ID NO 1980
<211> LENGTH: 23
<212> TYPE: DNA
<213> ORGANISM: Homo sapiens

<400> SEQUENCE: 1980
ggcctggagt cctgggtctg agg                  23

<210> SEQ ID NO 1981
<211> LENGTH: 23
<212> TYPE: DNA
<213> ORGANISM: Homo sapiens

<400> SEQUENCE: 1981
agtcctgggt ctgagggagg agg                  23

<210> SEQ ID NO 1982
<211> LENGTH: 23
<212> TYPE: DNA
<213> ORGANISM: Homo sapiens

<400> SEQUENCE: 1982
tgggtccagg aaggaggggc tgg                  23

<210> SEQ ID NO 1983
<211> LENGTH: 23
<212> TYPE: DNA
<213> ORGANISM: Homo sapiens

<400> SEQUENCE: 1983
tggggcctgc attcctgggg cgg                  23

<210> SEQ ID NO 1984
<211> LENGTH: 23
<212> TYPE: DNA
<213> ORGANISM: Homo sapiens

<400> SEQUENCE: 1984
ggtccaggaa gaagggctg ggg                   23

<210> SEQ ID NO 1985
<211> LENGTH: 23
<212> TYPE: DNA
<213> ORGANISM: Homo sapiens

<400> SEQUENCE: 1985
gggctggggg cctggagtcc tgg                  23

<210> SEQ ID NO 1986
<211> LENGTH: 23
<212> TYPE: DNA
<213> ORGANISM: Homo sapiens

<400> SEQUENCE: 1986
ggcctgggct cctgggtctg agg                  23

<210> SEQ ID NO 1987
<211> LENGTH: 23
<212> TYPE: DNA
<213> ORGANISM: Homo sapiens

<400> SEQUENCE: 1987

```
tctgaaggag gagaggctgg ggg                                              23

<210> SEQ ID NO 1988
<211> LENGTH: 23
<212> TYPE: DNA
<213> ORGANISM: Homo sapiens

<400> SEQUENCE: 1988
ggggctgggg cctggactgc tgg                                              23

<210> SEQ ID NO 1989
<211> LENGTH: 23
<212> TYPE: DNA
<213> ORGANISM: Homo sapiens

<400> SEQUENCE: 1989
gatctgaggg aggagggct ggg                                               23

<210> SEQ ID NO 1990
<211> LENGTH: 23
<212> TYPE: DNA
<213> ORGANISM: Homo sapiens

<400> SEQUENCE: 1990
gtctgaagga ggagaggctg ggg                                              23

<210> SEQ ID NO 1991
<211> LENGTH: 23
<212> TYPE: DNA
<213> ORGANISM: Homo sapiens

<400> SEQUENCE: 1991
gggtctgaag gaggagaggc tgg                                              23

<210> SEQ ID NO 1992
<211> LENGTH: 23
<212> TYPE: DNA
<213> ORGANISM: Homo sapiens

<400> SEQUENCE: 1992
gggcctggag tcctgggtcc agg                                              23

<210> SEQ ID NO 1993
<211> LENGTH: 23
<212> TYPE: DNA
<213> ORGANISM: Homo sapiens

<400> SEQUENCE: 1993
ggctgggggc ctgggctcct ggg                                              23

<210> SEQ ID NO 1994
<211> LENGTH: 23
<212> TYPE: DNA
<213> ORGANISM: Homo sapiens

<400> SEQUENCE: 1994
gagtcctggg tccaggaagg agg                                              23

<210> SEQ ID NO 1995
<211> LENGTH: 23
<212> TYPE: DNA
<213> ORGANISM: Homo sapiens

<400> SEQUENCE: 1995
```
tcctggatct gagggaggag ggg                                         23

<210> SEQ ID NO 1996
<211> LENGTH: 23
<212> TYPE: DNA
<213> ORGANISM: Homo sapiens

<400> SEQUENCE: 1996
gggtccagga aggaggggct ggg                                         23

<210> SEQ ID NO 1997
<211> LENGTH: 23
<212> TYPE: DNA
<213> ORGANISM: Homo sapiens

<400> SEQUENCE: 1997
gggaggaggg gctgggtccc agg                                         23

<210> SEQ ID NO 1998
<211> LENGTH: 23
<212> TYPE: DNA
<213> ORGANISM: Homo sapiens

<400> SEQUENCE: 1998
tctgagggag gaggggctgc agg                                         23

<210> SEQ ID NO 1999
<211> LENGTH: 23
<212> TYPE: DNA
<213> ORGANISM: Homo sapiens

<400> SEQUENCE: 1999
ggaggagagg ctgggggcct ggg                                         23

<210> SEQ ID NO 2000
<211> LENGTH: 23
<212> TYPE: DNA
<213> ORGANISM: Homo sapiens

<400> SEQUENCE: 2000
gatcaggaag gaggggctgg ggg                                         23

<210> SEQ ID NO 2001
<211> LENGTH: 23
<212> TYPE: DNA
<213> ORGANISM: Homo sapiens

<400> SEQUENCE: 2001
ctgggaaggt gagggccctg agg                                         23

<210> SEQ ID NO 2002
<211> LENGTH: 23
<212> TYPE: DNA
<213> ORGANISM: Homo sapiens

<400> SEQUENCE: 2002
aggaggagag gctgggggcc tgg                                         23

<210> SEQ ID NO 2003
<211> LENGTH: 23
<212> TYPE: DNA
<213> ORGANISM: Homo sapiens

```
<400> SEQUENCE: 2003
ggtccaggaa ggaggggctg ggg                                            23

<210> SEQ ID NO 2004
<211> LENGTH: 23
<212> TYPE: DNA
<213> ORGANISM: Homo sapiens

<400> SEQUENCE: 2004
aggctggggg cctgggctcc tgg                                            23

<210> SEQ ID NO 2005
<211> LENGTH: 23
<212> TYPE: DNA
<213> ORGANISM: Homo sapiens

<400> SEQUENCE: 2005
gtccaggaag gagggctgg ggg                                             23

<210> SEQ ID NO 2006
<211> LENGTH: 23
<212> TYPE: DNA
<213> ORGANISM: Homo sapiens

<400> SEQUENCE: 2006
ggcccccagc ccctccttcc tgg                                            23

<210> SEQ ID NO 2007
<211> LENGTH: 23
<212> TYPE: DNA
<213> ORGANISM: Homo sapiens

<400> SEQUENCE: 2007
gctcctcctc cctcagaccc agg                                            23

<210> SEQ ID NO 2008
<211> LENGTH: 23
<212> TYPE: DNA
<213> ORGANISM: Homo sapiens

<400> SEQUENCE: 2008
tctgagggag gaggagctgg agg                                            23

<210> SEQ ID NO 2009
<211> LENGTH: 23
<212> TYPE: DNA
<213> ORGANISM: Homo sapiens

<400> SEQUENCE: 2009
ggatcaggaa ggaggggctg ggg                                            23

<210> SEQ ID NO 2010
<211> LENGTH: 23
<212> TYPE: DNA
<213> ORGANISM: Homo sapiens

<400> SEQUENCE: 2010
ggaaggaggg gctgggggcc tgg                                            23

<210> SEQ ID NO 2011
<211> LENGTH: 23
<212> TYPE: DNA
<213> ORGANISM: Homo sapiens
```

-continued

<400> SEQUENCE: 2011
gcccctcctc cctcagaccc agg                                    23

<210> SEQ ID NO 2012
<211> LENGTH: 23
<212> TYPE: DNA
<213> ORGANISM: Homo sapiens

<400> SEQUENCE: 2012
tcctgggtct gagggaggag ggg                                    23

<210> SEQ ID NO 2013
<211> LENGTH: 23
<212> TYPE: DNA
<213> ORGANISM: Homo sapiens

<400> SEQUENCE: 2013
gggtctgagg gaggaggagc tgg                                    23

<210> SEQ ID NO 2014
<211> LENGTH: 23
<212> TYPE: DNA
<213> ORGANISM: Homo sapiens

<400> SEQUENCE: 2014
ggatctgagg gaggaggggc tgg                                    23

<210> SEQ ID NO 2015
<211> LENGTH: 23
<212> TYPE: DNA
<213> ORGANISM: Homo sapiens

<400> SEQUENCE: 2015
aggaagaagg ggctggggcc tgg                                    23

<210> SEQ ID NO 2016
<211> LENGTH: 20
<212> TYPE: DNA
<213> ORGANISM: Artificial Sequence
<220> FEATURE:
<223> OTHER INFORMATION: primer

<400> SEQUENCE: 2016
ctccatcgga gaaggacagc                                        20

<210> SEQ ID NO 2017
<211> LENGTH: 22
<212> TYPE: DNA
<213> ORGANISM: Artificial Sequence
<220> FEATURE:
<223> OTHER INFORMATION: primer

<400> SEQUENCE: 2017
aggtcctgaa agtccattgt cc                                     22

<210> SEQ ID NO 2018
<211> LENGTH: 120
<212> TYPE: DNA
<213> ORGANISM: Mus musculus

<400> SEQUENCE: 2018
aaaaaggcag ggtcaacctt ttcctcagct ccacggagag tgcccaccat ggtcctgtcg    60

```
<210> SEQ ID NO 2019
<211> LENGTH: 120
<212> TYPE: DNA
<213> ORGANISM: Mus musculus

<400> SEQUENCE: 2019
gccaaggatc cacacacagg ggagggacag ctcacagaga gtcgacagct ggagtatcag    60
cgacaggacc atggtgggca ctctccgtgg agctgaggaa aaggttgacc ctgccttttt   120

<210> SEQ ID NO 2020
<211> LENGTH: 146
<212> TYPE: DNA
<213> ORGANISM: Mus musculus

<400> SEQUENCE: 2020
gccaaggatc cacacacagg ggagggacag ctcacagaga gtcgacagct ggagtatcag    60
cctcagaaga actcgtcaag aagtcacgac aggaccatgg tgggcactct ccgtggagct   120
gaggaaaagg ttgaccctgc cttttt                                        146

<210> SEQ ID NO 2021
<211> LENGTH: 120
<212> TYPE: DNA
<213> ORGANISM: Mus musculus

<400> SEQUENCE: 2021 acctttttcct cagctccacg gagagtgccc accatggtcc tgtcgctgat actccagctg   60
tcgactctct gtgagctgtc cctcccctgt gtgtggatcc ttggctgggc tgagggctat   120

<210> SEQ ID NO 2022
<211> LENGTH: 120
<212> TYPE: DNA
<213> ORGANISM: Mus musculus

<400> SEQUENCE: 2022
atagccctca gcccagccaa ggatccacac acaggggagg acagctcac agagagtcga    60 cagctggagt atcagcgaca ggaccatggt gggcactctc cgtggagctg aggaaaaggt   120

<210> SEQ ID NO 2023
<211> LENGTH: 146
<212> TYPE: DNA
<213> ORGANISM: Mus musculus

<400> SEQUENCE: 2023
atagccctca gcccagccaa ggatccacac acaggggagg acagctcac agagagtcga    60 cctcagaaga actcgtcaag aagtcacagc tggagtatca gcgacaggac catggtgggc   120
actctccgtg gagctgagga aaaggt                                        146

<210> SEQ ID NO 2024
<211> LENGTH: 58
<212> TYPE: DNA
<213> ORGANISM: Mus musculus

<400> SEQUENCE: 2024
atggtcctgt cgtgacttct tgagagttct actgaggctg atactccagc tgtcgact     58

<210> SEQ ID NO 2025
<211> LENGTH: 59
```

```
<212> TYPE: DNA
<213> ORGANISM: Mus musculus

<400> SEQUENCE: 2025
atggtcctgt cgctgatact ccagctgtga cttcttgacg agttcttctg aggtcgact      59

<210> SEQ ID NO 2026
<211> LENGTH: 12
<212> TYPE: PRT
<213> ORGANISM: Mus musculus

<400> SEQUENCE: 2026

Met Val Leu Ser Leu Ile Leu Gln Leu Ser Thr Leu
1               5                   10

<210> SEQ ID NO 2027
<211> LENGTH: 4
<212> TYPE: PRT
<213> ORGANISM: Mus musculus

<400> SEQUENCE: 2027

Met Val Leu Ser
1

<210> SEQ ID NO 2028
<211> LENGTH: 9
<212> TYPE: PRT
<213> ORGANISM: Mus musculus

<400> SEQUENCE: 2028

Met Val Leu Ser Leu Ile Leu Gln Leu
1               5
```

PHARMACEUTICAL COMPOSITION OR FOOD COMPOSITION, AND METHOD FOR ASSESSING EFFECT OF ACTIVE INGREDIENT IN VIVO

A sequence listing in electronic (ASCII text file) format is filed with this application and incorporated herein by reference. The name of the ASCII text file is "P17-066US_Seq_Listing_210514.txt"; the file was created on May 18, 2021; the size of the file is 314 kilobytes (KB) or 322,454 bytes (b).

TECHNICAL FIELD

The present invention relates to a pharmaceutical composition or food composition comprising an active ingredient capable of suppressing functional expression of Oscar protein. The present invention also relates to a device, program, and method for evaluating an effect of the active ingredient in the body.

BACKGROUND ART

Diseases include those in a state that can be reversibly treated, and those in a state that cannot, i.e., those in an irreversible state. Early detection and treatment of abnormalities during a reversible state, or preventing such a state from occurring, is essential for health maintenance. Even in a reversible state, early detection of disease directly leads to milder treatment, a shorter treatment period, and better prognostic health. As in heart disease, brain disease, cancer, and diabetes, it is well known that abnormalities in one organ or tissue lead to a disease state in other organs (commonly called a "complication"). In such diseases, it is essential to prevent, at the earliest possible time, abnormalities in one organ or tissue from causing disease in other organs or tissue.

In all animals, including humans, each organ and tissue form a functional network, rather than serving as separate parts, and quality control at the individual level is achieved. Transport of endocrine factors, such as hormones, by the vascular network throughout the entire body and coordinated adjustment of organ functions by the neural network are typical examples of an "inter-organ cross talk system," and systematized as physiology or endocrinology.

Meanwhile, the number of end-stage kidney disease (ESKD) patients in need of dialysis or kidney transplant has been increasing worldwide. The number of ESKD patients increased from 430,000 to 1,065,000 over the decade from 1990 to 2000, and further increased to at least about 1,650,000 in 2008 (Non-patent Literature 1). Chronic kidney disease (CKD) progresses to ESKD. However, in the kidneys, called the "silent organ," even if kidney damage occurs, its condition is less likely to appear in clinical data etc. Thus, early detection of declined kidney function before onset of chronic kidney disease is difficult.

FGF23 is a hormone that lowers the phosphorus concentration in blood, and is known to suppress reabsorption of phosphorus in the renal proximal tubule and absorption of phosphorus from the intestinal tract, to thereby lower the phosphorus concentration in blood. An increase in the concentration of FGF23 is also known to cause chronic kidney disease-mineral and bone disorder (CKD-MBD).

Further, it has been reported that the fibrinogen concentration in urine or blood is increased in patients with chronic kidney disease (CKD), acute kidney injury, renal fibrosis, glomerulonephritis, or like disease; therefore, fibrinogen has the property of a biomarker of kidney function (Non-patent Literature 2 to 5).

CITATION LIST

Non-Patent Literature

NPL 1: Lysaght M J: J Am Soc Nephrol. 2002 January; 13 Suppl 1; S37-40.
NPL 2: Hoffmann, D. et al.; The American Journal of Pathology, 181, 818-828, doi:10.1016/j.ajpath.2012.06.004 (2012).
NPL 3: Prinsen, B. H. et al.; Kidney International, 64, 1495-1504, doi:10.1046/j.1523-1755.2003.00211.x (2003).
NPL 4: Zhang, Q. et al.; Biomarkers in Medicine, 8, 85-94, doi:10.2217/bmm.13.106 (2014).
NPL 5: Craciun, F. L. et al.; American Journal of Physiology—Renal Physiology, 307, F471-484, doi:10.1152/a$_j$prenal.00189.2014 (2014).

SUMMARY OF INVENTION

Technical Problem

CKD develops due to various diseases such as diabetes, hypertension, and like lifestyle-related diseases; and urinary tract infection, urinary tract obstruction, glomerulonephritis, vascular disease in the kidneys (blood flow disorder), drug-induced nephropathy caused by an analgesic, and like urinary system diseases. Thus, after kidney function has declined, treatment of such a primary disease is first performed in order to slow progression of the declined kidney function. In addition, treatment such as blood-pressure control or dietary restriction is conducted to slow progression of CKD. Further, for example, a drug therapy using a phosphate-binding agent etc. is performed for abnormal bone metabolism associated with chronic kidney disease when CKD progresses.

However, there is currently no fundamental therapeutic agent that halts progression of declined kidney function.

An object of the present invention is to provide a pharmaceutical composition or food or drink composition comprising an active ingredient that suppresses functional expression of Oscar protein. Another object of the present invention is to provide a pharmaceutical composition or food composition for use in preventing or treating kidney disease. A further object of the present invention is to provide a pharmaceutical composition or food or drink composition that suppresses functional expression of Oscar in a living organism in order to suppress functional expression of FGF23. A still further object of the present invention is to provide a method for evaluating an effect, in the body, of an active ingredient that suppresses functional expression of Oscar protein.

Solution to Problem

The present inventor conducted extensive research, and found that the expression of Oscar protein is increased in a kidney disease animal model. The inventor also found that progression of declined kidney function can be suppressed, or that declined kidney function can be improved, by suppressing the function of Oscar protein.

Moreover, the inventor conducted extensive research, and found that the expression of Oscar is increased in the bones of unilateral nephrectomy, model mice ingested diet with high phosphorus content compared with that in a sham-operated model. The inventor also found that an increase in the expression of FGF23 is mitigated in Oscar gene mutant mice.

The present invention has been accomplished based on these findings, and includes the following embodiments.

I. Pharmaceutical Composition or Food or Drink Composition

I-1. A pharmaceutical composition or food or drink composition comprising an active ingredient that suppresses functional expression of Oscar protein.

I-2. The pharmaceutical composition or food or drink composition according to Item I-1, wherein the active ingredient is at least one member selected from the group consisting of antagonists of the Oscar protein;
genome editing systems that target Oscar gene;
at least one RNA molecule selected from the group consisting of siRNA, shRNA, and miRNA that target Oscar mRNA, or vectors capable of expressing the RNA molecule; and
antibodies that specifically bind to the Oscar protein and suppress function of the Oscar.

I-3. The pharmaceutical composition or food or drink composition according to Item I-2, wherein the active ingredient is an antagonist of the Oscar protein, and the antagonist is a soluble receptor of the Oscar.

I-4. The pharmaceutical composition or food or drink composition according to Item I-2, wherein the active ingredient is a genome editing system that targets the Oscar gene, and the genome editing system is a CRISPR/Cas9 system comprising a sequence that targets the Oscar gene.

I-5. The pharmaceutical composition or food or drink composition according to any one of Items I-1 to I-4 for use in preventing or treating kidney disease.

I-6. The pharmaceutical composition or food or drink composition according to any one of Items I-1 to I-4 for use in suppressing functional expression of FGF23.

I-7. The pharmaceutical composition or food or drink composition according to any one of Items I-1 to I-4, wherein the pharmaceutical composition or food or drink composition is administered to an individual with a high measurement value relating to at least one protein selected from the group consisting of proline-rich proteins (PRPs) and fibrinogens in a specimen, and/or a high measurement value of mRNA of the protein in a specimen.

I-8. A method of treatment, comprising administering an active ingredient to an individual, the active ingredient being at least one member selected from the group consisting of antagonists of Oscar protein;
genome editing systems that target Oscar gene;
at least one RNA molecule selected from the group consisting of siRNA, shRNA, and miRNA that target Oscar mRNA, or vectors capable of expressing the RNA molecule; and
antibodies that specifically bind to Oscar protein and suppress function of the Oscar.

I-9. Use of at least one member selected from the group consisting of antagonists of Oscar protein; genome editing systems that target Oscar gene; at least one RNA molecule selected from the group consisting of siRNA, shRNA, and miRNA that target Oscar mRNA, or vectors capable of expressing the RNA molecule; and antibodies that specifically bind to Oscar protein and suppress function of the Oscar,
for the production of a composition for preventing or treating kidney disease; or for the production of a composition for suppressing functional expression of FGF23.

I-10. At least one member selected from the group consisting of antagonists of Oscar protein; genome editing systems that target Oscar gene; at least one RNA molecule selected from the group consisting of siRNA, shRNA, and miRNA that target Oscar mRNA, or vectors capable of expressing the RNA molecule; and antibodies that specifically bind to Oscar protein and suppress function of the Oscar,
for use in preventing or treating kidney disease; or for use in suppressing functional expression of FGF23.

Here, Items I-8 to I-10 may have dependent items containing features corresponding to Items I-3 to I-7 described above.

II. Evaluation of Effect of Active Ingredient in Body

II-1. A device for evaluating an effect, in the body, of an active ingredient that suppresses functional expression of Oscar protein, the device comprising the following computation means:
first obtaining means for obtaining a measurement value relating to at least one protein selected from the group consisting of proline-rich proteins (PRPs) and fibrinogens contained in a specimen collected from a subject to which the active ingredient has been administered (a treated specimen), and/or a measurement value of mRNA of the protein contained in a specimen collected from the subject; and
means for evaluating the effect of the active ingredient based on the measurement value(s) obtained by the obtaining means.

II-2. The device according to Item II-1, further comprising:
second obtaining means for obtaining a measurement value relating to the at least one protein selected from the group consisting of proline-rich proteins (PRPs) and fibrinogens, and/or a measurement value of mRNA of the protein in a specimen collected from a subject, test tissue, or test cell that is not treated with the active ingredient (an untreated specimen); and
means for comparing the measurement value(s) of the treated specimen with the measurement value(s) of the untreated specimen,
wherein the evaluation means evaluates the effect of the active ingredient in the body based on the comparison result obtained by the measurement value comparison means.

II-3. The device according to Item II-2, wherein the evaluation means determines that the active ingredient is effective in the body when the measurement value(s) of the treated specimen are lower than the measurement value(s) of the untreated specimen.

II-4. The device according to any one of Items II-1 to II-3, wherein the active ingredient is at least one member selected from the group consisting of
antagonists of the Oscar protein;
genome editing systems that target Oscar gene;
at least one RNA molecule selected from the group consisting of siRNA, snRNA, and miRNA that target Oscar mRNA, or vectors capable of expressing the RNA molecule; and
antibodies that specifically bind to the Oscar protein and suppress function of the Oscar.

II-5. An evaluation program that, when executed by a computer, causes the computer to carry out the following processing to evaluate an effect, in the body, of an active ingredient that suppresses functional expression of Oscar protein:
first obtaining processing of obtaining a measurement value relating to at least one protein selected from the group consisting of proline-rich proteins (PRPs) and fibrinogens contained in a specimen collected from a subject to which the active ingredient has been administered (a treated specimen), and/or a measurement value of mRNA of the protein contained in a specimen collected from the subject; and processing of evaluating the effect of the active ingredient based on the measurement value(s) obtained by the obtaining processing.

II-6. The evaluation program according to Item II-5, wherein the program further causes the computer to carry out second obtaining processing of obtaining a measurement value relating to the at least one protein selected from the group consisting of proline-rich proteins (PRPs) and fibrinogens, and/or a measurement value of mRNA of the protein in a specimen collected from a subject, test tissue, or test cell that is not treated with the active ingredient (an untreated specimen); and processing of comparing the measurement value (s) of the treated specimen with the measurement value(s) of the untreated specimen, and in the evaluation processing, the effect of the active ingredient in the body is evaluated based on the comparison result obtained by the measurement value comparison processing.

II-7. The evaluation program according to Item II-6, wherein in the evaluation processing, it is determined that the active ingredient is effective in the body when the measurement value(s) of the treated specimen are lower than the measurement value(s) of the untreated specimen.

II-8. The evaluation program according to any one of Items II-5 to II-7, wherein the active ingredient is at least one member selected from the group consisting of antagonists of the Oscar protein;

genome editing systems that target Oscar gene;

at least one RNA molecule selected from the group consisting of siRNA, shRNA, and miRNA that target Oscar mRNA, or vectors capable of expressing the RNA molecule; and antibodies that specifically bind to the Oscar protein and suppress function of the Oscar.

II-9. A method for supporting the evaluation of an effect, in the body, of an active ingredient that suppresses functional expression of Oscar protein, the method comprising the following steps:

a first obtaining step of obtaining a measurement value relating to at least one protein selected from the group consisting of proline-rich proteins (PRPs) and fibrinogens contained in a specimen collected from a subject to which the active ingredient has been administered (a treated specimen), and/or a measurement value of mRNA of the protein contained in a specimen collected from the subject; and a step of evaluating the effect of the active ingredient based on the measurement value(s) obtained by the obtaining step.

II-10. The method according to Item II-9, further comprising the following steps:

a second obtaining step of obtaining a measurement value relating to the at least one protein selected from the group consisting of proline-rich proteins (PRPs) and fibrinogens, and/or a measurement value of mRNA of the protein in a specimen collected from a subject, test tissue, or test cell that is not treated with the active ingredient (an untreated specimen); and a step of comparing the measurement value(s) of the treated specimen with the measurement value(s) of the untreated specimen, wherein in the evaluation step, the effect of the active ingredient in the body is evaluated based on the comparison result obtained by the measurement value comparison step.

II-11. The method according to Item II-10, wherein in the evaluation step, it is determined that the active ingredient is effective in the body when the measurement value(s) of the treated specimen are lower than the measurement value(s) of the untreated specimen.

II-12. The method according to any one of Items II-9 to II-11, wherein the active ingredient is at least one member selected from the group consisting of antagonists of the Oscar protein;

genome editing systems that target Oscar gene;

at least one RNA molecule selected from the group consisting of siRNA, shRNA, and miRNA that target Oscar mRNA, or vectors capable of expressing the RNA molecule; and antibodies that specifically bind to the Oscar protein and suppress function of the Oscar.

III. Genome Editing System and gRNA

III-1. A genome editing system comprising a sequence that targets Oscar gene.

III-2. The genome editing system according to Item III-1, which is a CRISPR/Cas9 system comprising a sequence that targets the Oscar gene.

III-3. gRNA comprising a sequence that targets Oscar gene.

Advantageous Effects of Invention

The present invention makes it possible to provide a pharmaceutical composition or food or drink composition that suppresses the function of Oscar protein. The present invention also makes it possible to provide a pharmaceutical composition or food or drink composition for suppressing progression of declined kidney function or improving declined kidney function, and preventing or treating a disease selected from the group consisting of declined kidney function, chronic kidney disease, and renal failure. The present invention further makes it possible to provide a pharmaceutical composition or food or drink composition for suppressing functional expression of FGF23. Furthermore, the present invention makes it possible to evaluate an effect, in the body, of an active ingredient that suppresses functional expression of Oscar protein.

BRIEF DESCRIPTION OF DRAWINGS

FIG. 8A shows a mutation site of Oscar-gRNA1 and a sequence of ssODNs. FIG. 8B shows a mutation site of Oscar-gRNA2 and a sequence of ssODNs. FIG. 8C indicates genotypes of Oscar in obtained mutant mice. In FIG. 8A, the amino acid sequence vertically between SEQ ID NO: 2018 and SEQ ID NO: 2019 is SEQ ID NO: 2026. In FIG. 8B, the amino acid sequence vertically between SEQ ID NO: 2021 and SEQ ID NO: 2022 is also SEQ ID NO: 2026. In FIG. 8C, the amino acid sequence directly below SEQ ID NO: 2024 is SEQ ID NO: 2027, and the amino acid sequence directly below SEQ ID NO: 2025 is SEQ ID NO: 2028.

FIG. 18 shows the concentrations of proline in saliva in a group that ingested a diet with high phosphorus content (group A: High Pi), and a group that ingested a diet with low phosphorus content (group B: Low Pi).

FIG. 19 shows qRT-PCR results of Fgg gene in the kidneys. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein.

FIG. 20 shows the sequences of gRNA. FIG. 20 is a multi-page figure which is divided into FIGS. 20-1 to 20-34.

DESCRIPTION OF EMBODIMENTS

1. Explanation of terms

Figure 1:
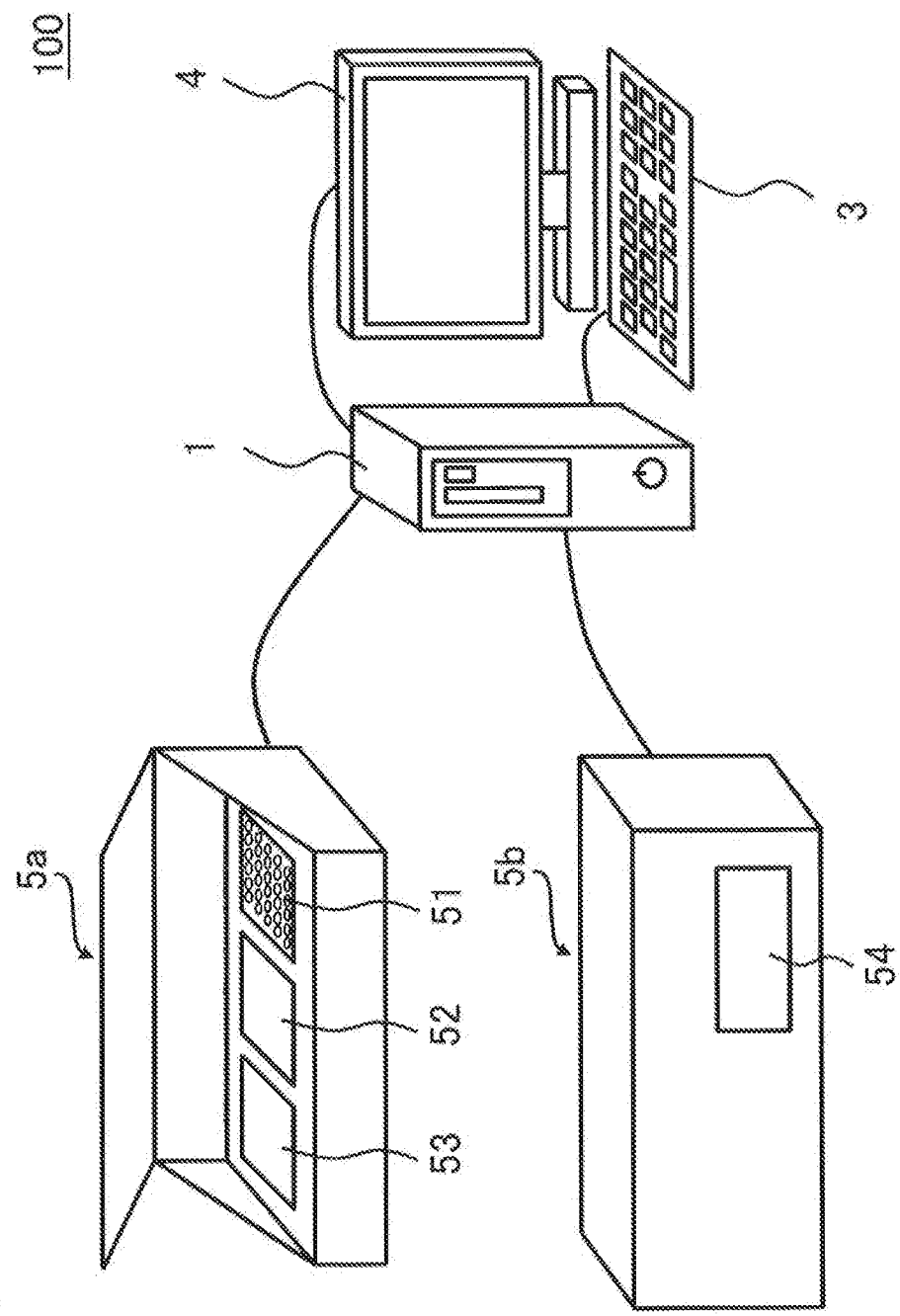
FIG. 1 is an overview of a system 100 according to a first embodiment of the present invention.

First, terms used in the present specification, claims, and abstract are explained. Unless otherwise stated, terms used in the present specification, claims, and abstract are in accordance with the definitions in this section.

"Oscar mRNA" as used herein includes, for example, RNA shown in Table 1, splicing variants of the RNA, and the RNA having SNPs. "Oscar protein" includes, for example, proteins translated from RNA shown in Table 1, splicing variants of the RNA, and the RNA having SNPs. "Oscar gene" includes, for example, genes indicated by the Gene IDs of Table 1.

TABLE 1

| Animal species | Ref. Seq. No.* | Gene ID |
|---|---|---|
| Mouse | NM_001290377.1 | 232790 |
|  | NM_175632.3 |  |
| Rat | NM_001184973.1 | 292537 |
|  | XM_006228020.3 |  |
| Human | NM_206818.2 | 126014 |
|  | NM_130771.4 |  |
|  | NM_133169.4 |  |
|  | NM_133168.4 |  |
|  | NM_001282349.1 |  |
|  | NM_001282350.1 |  |

*NCBI Reference Sequence Number

"Functional expression" means that original functions of Oscar proteins or FGF23 proteins are exhibited. For example, the functional expression of Oscar protein is a function to increase the expression of FGF23 mRNA; a function to activate osteoclasts via NFATc1; a function to activate immune cells via calcium release, immune cell maturation, inhibition of apoptosis, and antigen transport and antigen presentation by an MHC class II antigen; or a function to enhance a pro-inflammatory response via IL-8.

Such a function of Oscar can be evaluated by a method described in the section "3. Evaluation of function of Oscar protein" described later.

The functional expression of FGF23 protein is a function to suppress the expression of NaPi-2a and NaPi-2c in the kidneys, and suppress phosphorus reabsorption in the kidneys; a function to induce the expression of CYP24A1 while suppressing the expression of CYP27B1 in the kidneys and inhibit synthesis of 1,25-dihydroxyvitamin D, thereby suppressing phosphorus absorption in the intestinal tract; a function to suppress secretion of PTH from the parathyroid glands; or a function to induce the expression of Klotho in the kidneys and/or activate the function of Klotho.

Such a function of FGF23 protein is suppressed by suppressing the functional expression of Oscar protein.

"Suppressing the functional expression" refers to suppressing or decreasing exhibition of an aforementioned function of Oscar protein or FGF23 protein, and suppressing the expression of Oscar protein or FGF23 protein.

"Active ingredient" as used herein is not limited, as long as it can suppress the functional expression of Oscar protein in the body of an individual. Examples include antagonists of Oscar protein; genome editing systems that target Oscar gene; at least one RNA molecule selected from the group consisting of siRNA, shRNA, and miRNA that targets Oscar mRNA or vectors capable of expressing the RNA molecule; at least one member selected from antibodies that specifically bind to Oscar protein and suppress function of the Oscar protein; and inhibitors of Oscar protein.

In the present invention, the antagonist may be a type that competitively inhibits a target (competitive inhibitory-type), or a type that non-competitively inhibits a target (non-competitive inhibitory-type). The antagonist is preferably a competitive inhibitory-type.

Examples of competitive inhibitory-type antagonists include substances that compete with a molecule for binding to Oscar protein as a target (hereinafter also referred to as "competitive substances").

The antagonist is preferably, for example, a soluble receptor of Oscar protein. The soluble receptor comprises an amino acid sequence of a ligand-binding region in the Oscar protein. The soluble receptor may also comprise, for example, the Fc portion of an immunoglobulin or synthetic polymer polyethylene glycol (PEG) as a molecule other than the amino acid sequence of the ligand-binding region in the Oscar protein. In the case of humans, an example of the soluble receptor is the soluble receptor set forth in NP_996554.2 (SEQ ID NO: 1), which is capable of inhibiting activation of Oscar protein. In the case of humans, the soluble receptor comprises, among the sequence of the 1st to 228th amino acids of the amino acid sequence set forth in SEQ ID NO: 1, at least the sequence of the 1st to 220th amino acids, preferably the sequence of the 1st to 228th amino acids. The soluble receptor may comprise an amino acid sequence with at least 70%, preferably at least 80%, more preferably at least 85%, even more preferably at least 90%, still even more preferably at least 95% homology to the sequence of the 1st to 228th amino acids of the amino acid sequence set forth in SEQ ID NO: 1, in place of the amino acid sequence set forth in SEQ ID NO: 1. The soluble receptor is preferably, for example, a soluble receptor comprising a peptide comprising the amino acid sequence set forth in SEQ ID NO: 2 or a peptide having the same amino acid sequence as the amino acid sequence of the peptide, except that one to three amino acids are substituted, deleted, or inserted, the amino acid sequence being capable of inhibiting activation of human Oscar. In the case of mice, an example of the soluble receptor is the soluble receptor set forth in NP_783440.1 (SEQ ID NO: 3), which is capable of inhibiting activation of Oscar. The soluble receptor comprises, among the sequence of the 1st to 235th amino acids of the amino acid sequence set forth in SEQ ID NO: 3, at least the sequence of the 1st to 225th amino acids, and preferably the sequence of the 1st to 235th amino acids. The soluble receptor may comprise an amino acid sequence with at least 70%, preferably at least 80%, more preferably at least 85%, even more preferably at least 90%, still even more preferably at least 95% homology to the sequence of the 1st to 235th amino acids of the amino acid sequence set forth in SEQ ID NO: 3, in place of the amino acid sequence set forth in SEQ ID NO: 3. The soluble receptor is preferably a soluble receptor comprising a peptide comprising the amino acid sequence set forth in SEQ ID NO: 4 or a peptide having the same amino acid sequence as the amino acid sequence of the peptide, except that one to three amino acids are substituted, deleted, or inserted, the amino acid sequence being capable of inhibiting activation of mouse Oscar.

When the antagonist is systemically administered, it can be administered in an amount of 0.01 to 1,000 mg/day per kg of body weight of an adult.

When the antagonist is locally administered, it can be administered in an amount of 0.01 to 100 mg per $cm^2$ of target tissue.

"Genome editing systems that target Oscar gene" as used herein are not particularly limited, as long as they are systems that enable recombination to take place in the Oscar gene in the body of an individual. Examples include a CompoZr Zinc Finger Nuclease (ZFN) system, TAL effector nuclease (TALEN) system, Clustered regularly interspaced short palindromic repeats/CRISPR associated protein 9 (CRISPR/Cas9) system, and the like. A CRISPR/Cas9 system is preferable. A CRISPR/Cas9 system using a vector is preferable. In the CRISPR/Cas9 system using a vector, a nucleic acid encoding CRISPR and a nucleic acid encoding Cas9 may be located on different vectors, or one vector. The promoter for allowing CRISPR to function is not particularly limited, and is preferably a U6 promoter. The promoter for allowing Cas9 to function is not particularly limited, and is preferably a promoter that is expressed in mammalian cells, such as a cytomegalovirus promoter. As the CRISPR/Cas9 system, a commercially available vector such as pX330-U6-Chimeric BB-CBh-hSpCas9 vector can be preferably used.

The sequence that targets Oscar gene (hereinafter also referred to as "Oscar gene target sequence") to be incorporated into the CRISPR sequence is not limited, as long as it is a sequence that can be incorporated into guide RNA (also called gRNA or crRNA) by the CRISPR/Cas9 system, and transcribed to achieve recombination of the Oscar gene. It is generally said that a sequence of about 20 nucleotides in the 5' upstream region of nucleotide sequence "NGG" present in the Oscar gene can be selected as the Oscar gene target sequence. The Oscar gene target sequence can be designed using a known publicly available design tool, such as Optimized CRISPR design tool (website of Massachusetts Institute of Technology, Zhang Lab (http://crispr.mit.edu/)), E-CRISP (http://www.e-crisp.org/E-CRISP/(German Cancer Research Center)), ZiFiT Targeter (http://zifit.partners.org/ZiFit/(Zing Finger Consortium)), Cas9 design (http://cas9.cbi.pku.edu.cn (Peking University)), CRISPRdirect (http://crispr.dbcls.jp (University of Tokyo)), or CRISPR-P (http://cbi.hzau.edu.cn/crispr/(Huazhong Agricultural University)).

Examples of sequences that target human Oscar gene include the sequences shown in FIGS. 20-1 to 20-32. The sequences shown in FIGS. 20-1 to 20-32 are sequences designed by using the Optimized CRISPR design tool. gRNA having a sequence designed using this tool enables efficient recombination; therefore, any of such sequences may be used as the target sequence. Preferable examples include sequences in which the score shown in FIGS. 20-1 to 20-32 exceeds 70%, more preferably 80%, and even more preferably 90°. The sequence that targets human Oscar gene is preferably a sequence present in exon 2, 3, or 4, more preferably a sequence present in exon 2 or 3, even more preferably a sequence present in exon 2.

Moreover, when single nucleotide polymorphisms (SNPs) are present in a PAM sequence, it is preferable to avoid such a sequence. When SNPs of an individual are known, it is preferable to optimize the target sequence according to each SNP.

The selected sequence of 20 nucleotides may be 1, 2, 3, or 4 nucleotides shorter, preferably 1, 2, or 3 nucleotides shorter, in the 5' end region of the Oscar gene target sequence. The 5' end region of the Oscar gene target sequence may include a sequence of one or two nucleotides upstream of a sequence shown in FIG. 20.

The CRISPR/Cas9 system may be transfected into cells as a vector. Alternatively, a combination of gRNA, trans-activating crRNA (tracrRNA), and RNA encoding Cas9 artificially synthesized or synthesized by in vitro transcription may be introduced into cells.

Further, in the genome editing system, donor oligo DNA, such as single-stranded oligodeoxynucleotides (ssODNs), may be co-introduced. The ssODNs can be designed by a known method.

When the genome editing system that targets Oscar gene is administered to an individual, it may be administered systemically or locally. In the case of systemic administration, it is preferably administered intravenously. When the genome editing system is a system in which a nucleic acid based on DNA, for example, a lentivirus-derived or adenovirus-derived vector that can be expressed in an individual may be used as a vector. In addition, the vector may be administered to an individual with a nucleic acid delivery reagent, such as a liposome. When the genome editing system is a system in which a nucleic acid based on RNA, a vector may be administered with a liposome. Such a vector is preferably linearized as necessary.

When the genome editing system is administered systemically, it can be administered in an amount of $10^{10}$ to $10^{18}$ vg/day per kg of body weight of an adult.

When the genome editing system is administered locally, a vector or RNA can be injected into target tissue using a syringe or a catheter. In this case, a nucleic acid delivery reagent, such as a liposome, may also be used. In the case of local administration, the genome editing system can be administered in an amount of $10^9$ to $10^{16}$ vg/day per $cm^2$ of target tissue.

In both systemic administration and local administration, the genome editing system can be administered in a single dose, or multiple doses. When the genome editing system is administered in multiple doses, the administration can be repeated every three days, every five days, or every other week. When the genome editing system is administered in multiple doses, it can be administered twice, 5 times, 10 times, 15 times, 20 times, or 24 times.

In this embodiment, "RNA molecule that targets Oscar mRNA" is not particularly limited, as long as it can target Oscar mRNA and suppress expression of the Oscar protein. Examples include RNA molecules that have an action to degrade target mRNA, such as siRNA, siRNA, dsRNA, or miRNA; and/or RNA molecules that suppress translation of target mRNA. The sequences of these RNA molecules can be appropriately designed by a person skilled in the art according to a known method on the basis of information regarding the nucleotide sequence of the target gene described above. The RNA molecules may be prepared based on a known method, or commercially available RNA molecules may be used. As the RNA molecules, siRNA, shRNA, and miRNA are preferable, and siRNA and shRNA are particularly preferable.

The vector capable of expressing the RNA molecule that targets Oscar mRNA is not particularly limited, as long as it is capable of expressing the RNA molecule that suppresses the expression of the Oscar protein, in the body of an individual or in cells. An example of the vector is a vector expressing hairpin RNA. The vector expressing hairpin RNA comprises, for example, at least a sense strand DNA nucleotide sequence having the same sequence as the sense strand of target mRNA (note that uracil in mRNA is replaced by thymine); a loop nucleotide sequence that forms a loop structure after transcription; an antisense strand DNA nucleotide sequence capable of complementarily binding to all or a portion of the sense strand DNA nucleotide sequence; and a terminator sequence, downstream of a promoter nucleotide sequence suitable for expression of short RNA, such as a U6 promoter. Examples of vectors include plasmid vectors, adenovirus vectors, retrovirus vectors, lentivirus vectors, and the like.

When at least one RNA molecule selected from the group consisting of siRNA, shRNA, and miRNA that target Oscar mRNA or a vector capable of expressing the RNA molecule is administered systemically, it can be administered in an amount of 0.1 to 1,000 mg/day per kg of body weight of an adult. The vector can be linearized as necessary.

When at least one RNA molecule selected from the group consisting of siRNA, shRNA, and miRNA that target Oscar mRNA or a vector capable of expressing the RNA molecule is administered locally, the vector or RNA can be injected into target tissue using a syringe or a catheter. In this case, a nucleic acid delivery reagent, such as a liposome, may also be used. In the case of local administration, the RNA or vector can be administered in an amount of 0.01 to 100 mg/day per $cm^2$ of target tissue.

In both systemic administration and local administration, at least one RNA molecule selected from the group consisting of siRNA, shRNA, and miRNA that target Oscar mRNA or a vector capable of expressing the RNA molecule can be administered in a single dose, or multiple doses. When the RNA or vector is administered in multiple doses, the administration can be repeated every three days, every five days, or every other week. When the RNA or vector is administered in multiple doses, it can be administered twice, 5 times, 10 times, 15 times, 20 times, or 24 times.

In the present invention, "antibodies that bind to the Oscar protein" are not limited, as long as they can specifically bind to the Oscar protein, and suppress the functional expression of the protein. The antibodies may be polyclonal antibodies or monoclonal antibodies. The polyclonal antibodies and monoclonal antibodies can be suitably prepared by a person skilled in the art according to a known method. When the antibodies are monoclonal antibodies, they may be chimeric antibodies, humanized antibodies, or human antibodies prepared by a known method. The antibodies may also be antibody fragments, such as Fab, $F(ab)_2$, a diabody, scFv, a minibody, a peptibody, or a mimetibody. Examples of antibodies that bind to the Oscar protein include antibodies described in WO2013/011059A1.

When an antibody that binds to the Oscar protein is administered systemically, it can be administered in an amount of 0.01 to 1,000 mg/day per kg of body weight of an adult.

When an antibody that binds to the Oscar protein is administered locally, it can be administered in an amount of 0.01 to 100 mg per $cm^2$ of target tissue.

"Kidney disease" as used herein refers to any abnormality or disease of the kidneys that causes declined kidney function, and is not particularly limited as long as there is some impairment in the kidneys functionally or physically. Specific examples include acute kidney disease such as acute renal failure, acute pyelonephritis, acute glomerulonephritis (e.g., glomerulonephritis accompanied by hemolytic streptococcal infection, and rapidly progressive glomerulonephritis), and acute disease (e.g., cardiorenal syndrome type 1) among kidney disease accompanied by heart disease; chronic kidney disease such as chronic pyelonephritis, reflux nephropathy, interstitial nephritis, polycystic kidney disease, chronic glomerulonephritis (e.g., IgA nephropathy and glomerulonephritis due to systemic lupus erythematosus (lupus nephritis)), chronic disease (e.g., cardiorenal syndrome type 2) among kidney disease accompanied by heart disease, diabetic nephropathy, kidney glomerular fibrosis, and like chronic nephritis; nephrotic syndrome; and kidney tumor; and like. The kidney disease is preferably acute kidney disease. As another embodiment, the kidney disease is preferably kidney disease accompanied by ischemic heart disease, particularly acute kidney disease accompanied by ischemic heart disease (e.g., cardiorenal syndrome type 1). The kidney disease is preferably at least one disease selected from the group consisting of declined kidney function, chronic kidney disease, and renal failure.

"Declined kidney function" as used herein refers to, in the case of humans, a condition in which, for example, at least one kidney disease marker (preferably other than urinary proteins) shown in Tables 2-1 to 2-3 below, which are generally measured in clinical examination, falls outside a threshold range. More preferably, the kidney disease marker is at least one member selected from the group consisting of serum urea nitrogen, serum creatinine, serum inorganic phosphorus, fibrinogen in urine, creatinine clearance, 24-hour creatinine clearance estimated glomerular filtration rate (eGFR), urea clearance, inulin clearance, sodium thiosulfate clearance, renal plasma flow, filtration fraction, fractional excretion of sodium, fractional excretion of lithium, phenolsulfonphthalein test, concentration test, dilution test, free water clearance, free water reabsorption, maximal tubular excretory capacity, maximal tubular reabsorption capacity, rate of phosphate reabsorption, β2-microglobulin, and al-microglobulin.

"Declined kidney function" as used herein refers to, in the case of humans, a condition in which, for example, at least one kidney disease marker shown in Tables 2-1 to 2-3 below falls outside a threshold range.

TABLE 2-1

| | Item | Threshold | Unit | Measurement method |
|---|---|---|---|---|
| Serum | Total protein | 6.7 to 7.8 | g/dl | Biuret method |
| | Albumin | 3.8 to 5.3 | mg/dl | BCG method |
| | Urea nitrogen | 8 to 20 | mg/dl | Urease-GLDH method |
| | Creatinine | Male: 0.6 to 1.0 Female: 0 4 to 0.8 | mg/dl | Enzymatic method |
| | Uric add | Male: 3 to 7.7 Female: 2 to 7.7 | mg/dl | Uricase-POD method |
| | Ammonia | 12 to 66 | μg/dl | GLDH method |
| | Sodium | 136 to 145 | mEq/l | ISE |
| | Potassium | 3.4 to 4.5 | mEq/l | ISE |
| | Chlorine | 100 to 108 | mEq/l | ISE |
| | Total calcium | 8.6 to 10.1 | mg/dl | OCPC method |
| | Magnesium | 1.8 to 2.3 | mg/dl | Enzymatic method |
| | Inorganic phosphorus | Adult: 2.2 to 4.1 Child: 4.0 to 7.0 | mg/dl | Enzymatic method |
| | Copper | 71 to 132 | μg/dl | Chelate colorimetric method |
| | Amylase | 40 to 126 | IU/l | JSCC standardization corresponding method |
| | FGF23 | Full-length assay threshold: 10 to 50 C-terminal assay threshold: 150 | pg/ml RU/ml | ELISA |
| Whole blood | Red blood cell count | Male: 414 to 563 Female: 373 to 495 | $\times 10^4/\mu l$ | Electrical resistance-type automatic blood cell counter |
| | Hemoglobin | Male: 12.9 to 17.4 Female: 10.7 to 15.3 | g/dl | Oxyhemoglobin method |
| | Pyruvic acid | 0.30 to 0.94 | mg/dl | Enzymatic method |

TABLE 2-2

| | Item | Threshold | Unit | Measurement method |
|---|---|---|---|---|
| Arterial blood gas analysis/acid-base | $O_2$ saturation $SaO_2$ | 94 to 99 | % | |
| | $O_2$ partial pressure $PaO_2$ | 80 to 100 | Torr | |
| | $CO_2$ partial pressure $PaCO_2$ | 35 to 45 | Torr | |
| | pH | 7.35 to 7.45 | | |

TABLE 2-2-continued

|  | Item | Threshold | Unit | Measurement method |
|---|---|---|---|---|
| equilibrium | $HCO_3^-$ | 22 to 26 | mEq/l |  |
|  | Base excess (BE) | −2.2 to +2.2 | mEq/l |  |
|  | Buffer base (BB) | 46 to 52 | mEq/l |  |
|  | Standard bicarbonate (SB) | 21 to 25 | mEq/l |  |
| Urine | Urinary output | 600 to 1,600 | ml/day |  |
|  | Specific gravity (spot urine) | 1.006 to 1.030 |  |  |
|  | pH | 4.5 to 7.5 |  |  |
|  | Urinary protein | 20 to 120 | mg/day | Pyrogallol red-Mo coloring method |
|  | Albumin | 5.7 ± 2.6 | mg/day |  |
|  | Glucose | 2 to 20 | mg/dl |  |
| Urinary sediment | Red blood cell count | <5 | /400× field |  |
|  | Leukocyte count | <5 |  |  |
|  | Epithelial cell count | Less than 1 (excluding squamous epithelium) |  |  |
|  | Cast count | <1 |  |  |

TABLE 2-3

|  | Item | Threshold | Unit | Measurement method |
|---|---|---|---|---|
| Kidney function | Creatinine clearance (Ccr) | 70 to 130 | ml/min |  |
|  | 24-Hour creatinine clearance | Male: 62 to 108<br>Female: 57 to 78 | ml/min |  |
|  | Glomerular filtration rate (GFR) | Male: 129 ± 26<br>Female: 97 ± 13 | ml/min |  |
|  | Urea clearance | Maximum clearance: 62 to 77<br>Standard clearance: 45 to 55 | ml/min |  |
|  | Inulin clearance (GFR) | Male: 72 to 176<br>Female: 81 to 137 | $ml/min/1.73\ m^2$<br>$ml/min/1.73\ m^2$ |  |
|  | Sodium thiosulfate clearance | Male: 90 to 138<br>Female: 86 to 120 | ml/min |  |
|  | Renal plasma flow (RPF) | 350 to 650 | ml/min | $C_{PAH}$ |
|  | Filtration fraction (FF) | 0.18 to 0.22 |  | GRF/RPF |
|  | Fractional excretion of sodium | 1≤ | % |  |
|  | Fractional excretion of lithium | 20 to 30 | % |  |
|  | Phendsulfonphthalein (PSP) test | ≤100<br>15 min value: ≥25<br>120 min value: ≥55 | mOsm/kg<br>%<br>% |  |
|  | Concentration test | ≥1.025 | (Specific gravity) | Fishberg |
|  | Dilution test | ≤ 1.006 | (Specific gravity) | Fishberg |
|  | Free water clearance | At the time of water diuresis: 13 to 15 | ml/min |  |
|  | Free water reabsorption | At the time of concentration: 1.5 to 2.0 | ml/min |  |
|  | Maximal tubular excretory capacity | 81 ± 11 | $mg/min/1.48\ m^2$ | $T_{mPAH}$ |
|  | Maximal tubular reabsorption capacity | 340 ± 18 | $mg/min/1.48\ m^2$ | $T_{mPAH}$ |
|  | Rate of phosphate reabsorption | 80 to 96 | % | %TRP |
|  | $\beta_2$- Microglobulin | Serum: 0.8 to 0.2<br>Urine: 11 to 253<br>(30 to 340) | mg/l<br>µg/day<br>(µg/l) | LPIA<br>LPIA |
|  | $\alpha_1$- Microglobulin | Serum: 10 to 30<br>Urine: 1.8 ± 0.9 | mg/l<br>mg/l | EIA<br>EIA |

The kidney disease markers described above can be measured according to known methods described in, for example, Kanai's Manual of Clinical Laboratory Medicine, Revised 32nd Edition (edited by Masamitsu Kanai; Kanehara & Co., Ltd.).

"Acute renal failure" as used herein is a disease in which kidney function is rapidly declined. For example, acute renal failure is a disease in which the serum creatinine value is rapidly increased to 2.0 to 2.5 mg/dl or more (a disease in which the serum creatinine value is increased by 50% or more compared to the previous value when there is underlying declined kidney failure), or a disease in which the serum creatinine value is increased at a rate of 0.5 mg/dl/day or more and urea nitrogen is increased at a rate of 10 mg/dl/day or more. Acute renal failure includes (1) prerenal acute renal failure, caused by a decrease in renal blood flow; (2) renal acute renal failure, in which there is damage in the renal parenchyma; and (3) postrenal acute renal failure, caused by urine flow disorder downstream of the kidneys. Acute renal function to which the present invention is preferably applied is prerenal acute renal failure and renal acute renal failure, and preferably prerenal acute renal failure.

Kidney disease accompanied by heart disease is also called cardiorenal syndrome. Cardiorenal syndrome includes acute and chronic clinical states, and is categorized into multiple types. Among these, type 1 and type 2 are triggered by heart disease. Type 1 is acute cardiorenal syndrome, and type 2 is chronic cardiorenal syndrome. Type 1 may be triggered by ischemic heart disease or the like.

Cardiorenal syndrome type 1 is a condition that falls under any of the following stages 1 to 3 due to some sort of heart disease:

Stage 1: The serum creatinine value is increased to about 1.5 to 1.9 times the threshold, or the serum creatinine value is increased by 0.3 mg/dl or more compared to the previous value in the same individual, and the urinary output is about 0.5 ml/kg/hour over a period of 6 to 12 hours.

Stage 2: The serum creatinine value is increased to about 2.0 to 2.9 times the threshold, and urinary output of less than 0.5 mL/kg/hour persists for 12 hours or more.

Stage 3: The serum creatinine value is increased to about 3 times the threshold, the serum creatinine value is increased by 4.0 mg/dL or more compared to the previous value in the same individual, renal replacement therapy is started, or eGFR is decreased to less than 35 mL/min/1.73 m² in a patient under the age of 18; and, in addition to any of the above four conditions, urinary output of less than 0.3 mL/kg/hour persists for 24 hours or more, or anuria persists for 12 hours or more.

"Chronic kidney disease" as used herein refers to, when the subject is a human, a condition in which kidney damage (for example, urine abnormalities such as proteinuria including microalbuminuria, abnormal urinary sediment, imaging abnormalities such as a single kidney and polycystic kidney disease, declined kidney function such as increased serum creatinine, electrolyte abnormalities such as hypokalemia due to tubular damage, abnormalities in histopathological examination such as renal biopsy), or declined kidney function, i.e., an estimated GFR (glomerular filtration rate) of less than 60 mL/min/1.73 m², persists for 3 months or more, according to the Clinical Practice Guidebook for Diagnosis and Treatment of Chronic Kidney Disease 2012 (edited by the Japanese Society of Nephrology).

Here, the estimated GFR (eGFR) can be calculated using the estimation formulas (eGFRcreat) from a serum creatinine value shown in Table 3 below. The estimation formulas (eGFRcys) based on serum cystatin C can be applied to those who have extremely low muscle mass, such as lower-extremity amputees.

TABLE 3

| Male | eGFRcreat (mL/min/1.73 m²) = 194 × Cr$^{-1.094}$ × age$^{-0.287}$ |
| --- | --- |
| | eGFRcys (mL/min/1.73 m²) = (104 × Cys-C$^{-1.019}$ × 0.996$^{age}$) − 8 |
| Female | eGFRcreat (mL/min/1.73 m²) = 194 × Cr$^{-1.094}$ × age$^{-0.287}$ × 0.739 |
| | eGFRcys (mL/min/1.73 m²) = (104 × Cys-C$^{-1.019}$ × 0.996$^{age}$ × 0.929) − 8 |

*This evaluation of kidney function is performed for persons aged 18 or older.

For example, in the case in which protein is used as an index, when the results of a urine test 3 months or more prior and a recent urine test show that the subject has a persistent urinary protein level of 0.15 g/gCr or more, such a condition can be diagnosed as chronic kidney disease. When the subject has diabetes and the results of an albuminuria test 3 months or more prior and a recent albuminuria test show that the subject has a persistent urinary albumin level of 30 mg/gCr or more, such a condition can be diagnosed as chronic kidney disease.

For children, a threshold of serum creatinine (Cr) can be determined by using an enzymatic method for Japanese children, and used to evaluate children with kidney function abnormalities. For example, the eGFR in % for children aged 2 or older but 11 or younger can be represented by equation 1 below.

$$\text{eGFR (\%)} = (0.3 \times \text{body height (m)} / \text{serum Cr value in subject}) \times 100 \quad \text{Equation 1}$$

In the case of non-human mammals, such as cats and dogs, it can be predicted whether a non-human mammal has chronic kidney disease from, for example, average daily water intake or urine specific gravity.

The severity of chronic kidney disease can be determined based on, for example, Table 4 below in the case of humans (Table 4 is Table 2 in the Clinical Practice Guidebook for Diagnosis and Treatment of Chronic Kidney Disease, 2012).

TABLE 4

| Primary disease | proteinuria category | | A1 | A2 | A3 |
|---|---|---|---|---|---|
| Diabetes | Urinary albumin quantification (mg/day) Urinary albumin/Cr ratio (mg/gCr) | | Normal Less than 30 | Microalbuminuria 30~299 | Macroalbuminuria 300 or more |
| High blood pressure Nephritis Polycystic kidney Renal graft Unknown Others | Urinary protein quantification (g/day) Urinary protein/Cr ratio (g/gCr) | | Normal Less than 0.15 | Mild proteinuria 0.15~0.49 | High proteinuria 0.50 or more |
| GFR Category (Ml/MIN/ 1.73M2) | G1 | Normal or elevated value | ≥90 | A | B | C |
| | G2 | Normal or mild reduction | 60~89 | A | B | C |
| | G3a | Mild to moderate reduction | 45~59 | B | C | D |
| | G3b | Moderate to severe reduction | 30~44 | C | D | D |
| | G4 | Severe reduction | 15~29 | D | D | D |
| | G5 | End-stage kidney disease (ESKD) | <15 | D | D | D |

The severity is evaluated by a stage in which the primary disease, the GFR category, and the proteinuria category are combined.
Regarding the severity of CKD, the risks of mortality, end-stage kidney disease, and cardiovascular mortality increase as the stage increases in the order of B, C, and D with reference to the stage A.

"Renal failure" as used herein is included in the "chronic kidney disease" described above. For example, in the case of humans, "renal failure" refers to a condition in which eGFR is less than 45 ml/min/1.73 m$^2$, preferably less than 30 ml/min/1.73 m$^2$, and more preferably less than 15 ml/min/1.73 m$^2$ in chronic kidney disease.

The disease associated with FGF23 is not limited, as long as it is a disease that develops in association with overexpression of FGF23. Examples include hypophosphatemic rickets/osteomalacia, autosomal dominant hypophosphatemic rickets/osteomalacia, autosomal recessive hypophosphatemic rickets/osteomalacia, X-linked hypophosphatemic rickets/osteomalacia, tumor-induced rickets/osteomalacia, secondary hyperparathyroidism, abnormal phosphorous metabolism in acute kidney disease or chronic kidney disease, chronic kidney disease-mineral and bone disorder (CKD-MBD), McCune-Albright syndrome, Osteoglophonic dysplasia, epidermal nevus syndrome, familial tumoral calcinosis, X-linked hypophosphatemia, and the like.

"Individual" as used herein is not particularly limited, and includes humans and non-human mammals. Examples of non-human mammals include bovines, horses, sheep, goats, pigs, dogs, cats, rabbits, monkeys, and the like. Humans, cats, and dogs are preferable. There is no limitation on the age or sex of the individual.

"Subject" is an individual to which an active ingredient is to be administered. The subject is preferably an individual with a history of declined kidney function or other kidney disease. Individuals that may be the subject preferably have symptoms, such as polyuria, thirst, increased water intake, excessive gastric juice, vomiting, bloody urine, and general malaise. Further, individuals that may be the subject include individuals suspected of having kidney damage or chronic kidney disease according to a known diagnostic method, such as a medical interview, a urine test, a biochemical test of blood, kidney diagnostic imaging, or a renal biopsy, disease animal models, and the like.

"Test tissue" as used herein refers to tissue from which a measurement value described later is to be obtained. For example, the test tissue is living tissue in vitro, for example, collected from an individual that may be the subject, and cultured in vitro. The tissue may be an entire organ or a portion of an organ.

"Test cell" as used herein refers to a cell from which a measurement value described later is to be obtained. For example, the test cell is a living cell in vitro, for example, collected from an individual that may be the subject, and cultured in vitro. The cell may be a cell whose passage capability is limited, such as a primary cultured cell; or may be a so-called cultured cell whose passage capability is maintained. Such cells may be cells prepared by genetic engineering.

"Specimen" as used herein includes cells, tissue (the adrenal glands, aorta, brain, lungs, pancreas, pituitary gland, skin, skull, skeletal muscle, spleen, testes, thyroid gland, kidneys, colon, eyeballs, heart, liver, submandibular glands, thymus, adipose tissue, stomach, jejunum, ileum, and the like), body fluids (sweat, secretions from skin, lacrimal fluid, saliva, spinal fluid, ascites fluid, and pleural effusion), urine, blood samples, and the like, derived from a subject described above. As specimens, adipose tissue, skin, hair roots, salivary glands (parotid glands, submandibular glands, and sublingual glands, and preferably parotid glands), sweat, secretions from skin, lacrimal fluid, saliva, urine, and blood samples are preferable; and saliva, salivary glands (particularly preferably parotid glands), adipose tissue, hair roots, skin, secretions from skin, and sweat are more preferable.

Moreover, "specimen" may include test tissue itself, a portion of test tissue, a test cell itself, a portion of a test cell, and a culture supernatant of test tissue or a test cell.

In the section "2. Method for obtaining each measurement value" described later, when a measurement value relating to at least one protein selected from the group consisting of proline-rich proteins (PRPs) and/or a measurement value of mRNA of the protein is obtained, the specimen is preferably saliva, salivary glands (particularly preferably parotid glands), blood sample, saliva, or like body fluid. In the same section, when a measurement value of mRNA of a kidney function prediction marker protein is obtained, the specimen is preferably the parotid glands or saliva. When a measurement value relating to at least one protein selected from the group consisting of fibrinogens and/or a measurement value of mRNA of the protein is obtained, the specimen is preferably the kidneys; or a body fluid such as a blood sample or urine. In the same section, when a measurement value of mRNA of a kidney function prediction marker protein is obtained, the specimen is preferably the kidneys.

"Blood sample" as used herein includes blood (whole blood) collected from a subject, or serum, plasma, or the like prepared from the blood. The blood sample is preferably serum or plasma, and more preferably serum. When the measurement value of mRNA is obtained, it is preferable to use whole blood. The type of anticoagulant used for collecting plasma is not particularly limited. The type of blood sample of a subject used for measurement and the type of blood sample used for determining a predetermined threshold may be the same or different, and are preferably the same. When plasma is used as a blood sample, it is preferable that plasma for determining a predetermined threshold is prepared from blood collected using the same anticoagulant as used for plasma of the subject.

Further, the specimen may be a fresh specimen, or may be a preserved specimen. When the specimen is preserved, it can be preserved in a room-temperature environment, a refrigerated environment, or a frozen environment; and cryopreservation is preferable.

Further, a specimen collected from a subject, test tissue, or test cell treated with an active ingredient may be referred to as "active-ingredient-treated specimen" in the present specification. In addition, a specimen collected from a subject, test tissue, or test cell that is not treated with an active ingredient may be referred to as "untreated specimen" in the present specification.

"Healthy individual" is not particularly limited. Preferably, the healthy individual is a human or non-human mammal that is described in the explanation of the term "individual" and that does not show abnormal data in biochemical tests, blood tests, urine tests, serum tests, physiological tests, etc. The age and sex of the healthy individual are not particularly limited.

"Proline-rich proteins (PRPs)" as used herein include acidic PRPs (aPRPs) including PRH1 and PRH2; basic PRPs (bPRPs) including PRB1, PRB2, and PRB4; glycosylated PRPs (GPRPs) including PRB3; PRPMP5; PRP2; splicing variants thereof; post-translationally modified variants thereof; and the like.

PRPs expressed from a group of genes that cluster around 132055403 to 132601236 of chromosome 6 (mm10 database: GRCm38/mm10: December 2011) in the case of mice, PRPs expressed from a group of genes that cluster around 10824960 to 11395565 of chromosome 12 (hg38 database: GRCh38/hg38: December, 2013) in the case of humans, splicing variants thereof, post-translationally modified variants thereof, and the like are preferable. At least one member selected from the group consisting of PRH1, PRP2, PRB1, and PRPMP5, splicing variants thereof, and post-translationally modified variants thereof is more preferable.

The PRH1 protein is preferably NCBI Reference sequence ID: NP_035304.4 in the case of mice, and a protein expressed from the gene shown in NCBI Gene ID: 5554 (updated on Nov. 22, 2015) in the case of humans. The PRH1 protein may also include splicing variants thereof, post-translationally modified variants thereof, and the like.

The PRP2 protein is preferably NCBI Reference sequence ID: NP_113687.2 in the case of mice, and may also include splicing variants thereof, post-translationally modified variants thereof, and the like.

The PRB1 protein is preferably NCBI Reference sequence ID: NP_941071.1 in the case of mice, and a protein expressed from the gene shown in NCBI Gene ID: 5542 (updated on Jan. 3, 2016) in the case of humans. The PRB1 protein may also include splicing variants thereof, post-translationally modified variants thereof, and the like.

The PRPMP5 protein is preferably NCBI Reference sequence ID: NP_001019876.2 in the case of mice, and may also include splicing variants thereof, post-translationally modified variants thereof, and the like.

The PRH1 mRNA is preferably NCBI Reference sequence ID: NM_011174.4 in the case of mice, and mRNA expressed from the gene shown in NCBI Gene ID: 5554 (updated on Nov. 22, 2015) in the case of humans. The PRH1 mRNA may also include splicing variants thereof and the like.

The PRP2 mRNA is preferably NCBI Reference sequence ID: NM_031499.2 in the case of mice, and may also include splicing variants thereof and the like.

The PRB1 mRNA is preferably NCBI Reference sequence ID: NM_198669.1 in the case of mice, and mRNA expressed from the gene shown in NCBI Gene ID: 5542 (updated on Jan. 3, 2016) in the case of humans. The PRB1 mRNA may also include splicing variants thereof and the like.

The PRPMP5 mRNA is preferably NCBI Reference sequence ID: NM_001024705.2 in the case of mice, and may also include splicing variants thereof and the like.

Fibrinogen (Fg) is a homodimer in which two polypeptide chains are linked by disulfide bonds, and each of the two polypeptide chains contains an A$\alpha$ chain, a B$\beta$, chain, and a $\gamma$ chain. The A$\alpha$ chain, chain, and $\gamma$ chain are individually encoded by three independent genes (FGA, FGB, FGG). Fibrinogens include FGA, FGB, FGG, and splicing variants thereof. In the case of humans, for example, FGA protein is NCBI Reference sequence ID: NP_000499.1 or NP_068657.1; FGB protein is NCBI Reference sequence ID: NP_005132.2 or NP_005132.2; FGG protein is NCBI Reference sequence ID: NP_068656.2 or NP_000500.2. In the case of humans, for example, FGA mRNA is NCBI Reference sequence ID: NM_000508.4 or NM_021871.3; FGB mRNA is NCBI Reference sequence ID: NM_005141.4 or NM_001184741.1; and FGG mRNA is NCBI Reference sequence ID: NM_021870.2 or NM_000509.5.

In the case of mice, for example, FGA protein is NCBI Reference sequence ID: NP_034326.1 or NP_001104518.1; FGB protein is NCBI Reference sequence ID: NP_862897.1; and FGG protein is NCBI Reference sequence ID: NP_598623.1 or NP_001304034.1. In the case of mice, for example, FGA mRNA is NCBI Reference sequence ID: NM_0NM_001111048.2.4 or NM_010196.4; FGB mRNA is NCBI Reference sequence ID: NM_181849.3; and FGG mRNA is NCBI Reference sequence ID: NM_133862.2 or NM_001317105.1. "Measurement value relating to at least one protein selected from the group consisting of proline-rich proteins (PRPs)" or "measurement value relating to at least one protein selected from the group consisting of fibrinogens" refers to a value reflecting the amount or concentration of at least one protein selected from the group consisting of PRPs, or at least one protein selected from the group consisting of fibrinogens. When the measurement value is indicated by "amount," it may be expressed on either a mole basis or a mass basis; however, it is preferable to indicate the amount on a mass basis. When the value is expressed in terms of "concentration," it may be a molar concentration or a ratio of a mass per constant volume of a specimen (mass/volume), preferably a mass/volume ratio. The value reflecting the amount or concentration may be the above, or the intensity of a signal such as fluorescence or luminescence. The measurement value relating to at least one protein selected from the group consisting of PRPs may be the measurement value of at least one protein itself selected from the group consisting of PRPs, or a value measured as the amount of proline after treating at least one protein selected from the group consisting of PRPs with an enzyme or the like. Proline can be measured by, for example, the method shown in Reference Example 3.

"Measurement value of at least one mRNA selected from the group consisting of proline-rich proteins (PRPs)" or "measurement value of at least one mRNA selected from the group consisting of fibrinogens" may be represented by the number of copies (absolute amount) of each mRNA present in a certain amount of a specimen; or may be a value reflecting the relative expression level to that of a housekeeping gene, such as β2-microglobulin mRNA, GAPDH mRNA, Maea mRNA, or β-actin mRNA. The measurement value may also be represented by the intensity of a signal such as fluorescence or luminescence.

"Anti-PRP antibody" or "anti-fibrinogen antibody" is not limited, as long as the antibody specifically binds to at least one protein selected from the group consisting of PRPs, or at least one protein selected from the group consisting of fibrinogens. For example, any of polyclonal antibodies, monoclonal antibodies, and fragments thereof (for example, Fab, F(ab)$_2$, etc.) obtained by immunizing a non-human animal with at least one protein selected from the group consisting of PRPs or a part thereof, or at least one protein selected from the group consisting of fibrinogens or a part thereof, as an antigen can be used. Additionally, immunoglobulin classes and subclasses are not particularly limited. Moreover, the anti-PRP antibody or anti-fibrinogen antibody may be a chimeric antibody. Further, the anti-PRP antibody or anti-fibrinogen antibody may be scFv or the like.

Examples of proteins used as an antigen for preparing an anti-PRP antibody or an anti-fibrinogen antibody include the entirety or a part of at least one protein selected from the group consisting of PRPs, or the entirety or a part of at least one protein selected from the group consisting of fibrinogens.

"Nucleic acid for PRP mRNA detection" as used herein is not limited, as long as it contains a sequence that specifically hybridizes to at least one mRNA selected from the group consisting of PRPs, or to a reverse transcription product of the mRNA. "Nucleic acid for fibrinogen mRNA detection" is not limited, as long as it contains a sequence that specifically hybridizes to at least one mRNA selected from the group consisting of fibrinogens, or to a reverse transcription product of the mRNA. The nucleic acid for detection may be DNA or RNA, and the nucleotides contained in the nucleic acid for detection may be naturally occurring nucleotides or artificially synthesized nucleotides.

The length of the nucleic acid for detection is not particularly limited. When the nucleic acid for detection is used as a capture probe in, for example, a microarray, the length of sequence that hybridizes to a target nucleic acid is preferably about 100 mer, more preferably about 60 mer, and even more preferably about 20 to 30 mer. The capture probe can be produced with, for example, a known oligonucleotide synthesizer. The capture probe may contain a sequence that does not hybridize to the target nucleic acid.

When the nucleic acid for detection is a primer used for PCR reactions, the length of sequence that hybridizes to a target nucleic acid is preferably about 50 mer, more preferably about 30 mer, and even more preferably about 15 to 25 mer. The primer can be produced with, for example, a known oligonucleotide synthesizer. The primer may contain a sequence that does not hybridize to the target nucleic acid. The primer may be labeled with a fluorescent dye or the like.

A probe for quantification that is decomposed during a PCR reaction may also be used for real-time quantification of a PCR product in RT-PCR, in addition to primers. The probe for quantification is not limited as long as it hybridizes to a target nucleic acid. The probe for quantification is preferably a nucleic acid with a length of about 5 to 20 mer that contains a sequence that hybridizes to a target nucleic acid. Further, it is preferred that the probe for quantification is labeled at one end with a fluorescent dye, and at the other end with a quencher of the fluorescent dye.

When the measurement value relating to at least one protein selected from the group consisting of proline-rich proteins (PRPs) (hereinafter may be abbreviated as "measurement value of a PRP protein" in the present specification) is measured, a measurement method using an anti-PRP antibody described above can be used in the process in order to obtain the measurement value. A known ELISA method or the like can be used as the measurement method for obtaining the measurement value of a PRP protein.

When the measurement value relating to at least one protein selected from the group consisting of fibrinogens (hereinafter may be abbreviated as "measurement value of a fibrinogen protein" in the present specification) is measured, a measurement method using an anti-fibrinogen antibody described above can be used in the process in order to obtain the measurement value. A known ELISA method or the like can be used as the measurement method for obtaining the measurement value of a fibrinogen protein.

In this embodiment, an anti-PRP antibody for antigen capture or an anti-fibrinogen antibody for antigen capture can be immobilized on a solid phase such as a microplate, fluorescent beads, or magnetic beads in advance, and a complex between the immobilized anti-PRP antibody or anti-fibrinogen antibody and an antigen in a specimen can be formed. The amount or concentration of the PRP protein or fibrinogen protein contained in the specimen can be measured by detecting the complex immobilized on the solid phase or the complex formed on the solid phase by a method known in the art. In this embodiment, a complex between an anti-PRP antibody for antigen capture or an anti-fibrinogen antibody for antigen capture and an antigen in a specimen may be formed in advance, and then immobilized on a solid phase.

The method for immobilizing an antibody for antigen capture on a solid phase is not particularly limited. An antibody may be directly immobilized or indirectly immobilized with another substance interposed therebetween by using a known method. Examples of direct binding include physical adsorption and the like. Preferably, for example, an immunoplate may be used to directly physically bind an antibody to the microplate.

The shape of the solid phase is not particularly limited. Examples include microplates, microtubes, test tubes, beads, and the like. The material of the solid phase is not particularly limited. For example, polystyrene, polypropylene, and the like can be used for microplates, microtubes, test tubes, etc. In the case of beads, Polystyrene xMAP (registered trademark) Beads (Luminex), MagPlex (registered trademark) Microspheres (Luminex), and the like can be used.

This method may comprise, following the formation of the complex, an operation of washing the solid phase. In washing, for example, PBS containing a surfactant or the like may be used.

In this method, the complex can be detected by using an anti-PRP antibody for detection labeled with a labeling substance or an anti-fibrinogen antibody for detection labeled with a labeling substance; or using an unlabeled anti-PRP antibody or anti-fibrinogen antibody, an anti-immunoglobulin antibody labeled with a labeling substance and capable of binding to the unlabeled anti-PRP antibody or anti-fibrinogen antibody, etc. It is preferable to use a labeled anti-PRP antibody for detection, or a labeled anti-fibrinogen antibody for detection. It is also preferable that the epitope in the antigen of the antibody for detection is different from the epitope in the antigen of the antibody for antigen capture.

The labeling substance used for the antibody for detection or the labeled anti-immunoglobulin antibody is not particularly limited, as long as the labeling substance generates a detectable signal. Examples include fluorescent substances, radioactive isotopes, enzymes, and the like. Examples of enzymes include alkaline phosphatase, peroxidase, and the like. Examples of fluorescent substances include fluorescent dyes such as fluorescein isothiocyanate (FITC), rhodamine, and Alexa Fluor (registered trademark), fluorescent proteins such as GFP, and the like. Examples of radioactive isotopes include 125I, 14C, 32P and the like. Among them, alkaline phosphatase or peroxidase is preferable as the labeling substance.

The antibody for detection is obtained by labeling an antibody with the above-mentioned labeling substance by a labeling method known in the art. Alternatively, such labeling may be performed using a commercially available labeling kit or the like. For the labeled immunoglobulin antibody, the same method as the labeling of the antibody for detection may be used, or a commercially available product may be used.

In this method, the measurement value of the kidney function prediction marker contained in the specimen can be obtained by detecting a signal generated by the labeling substance of the labeled antibody contained in the complex. Here, "detecting a signal" includes qualitatively detecting the presence or absence of a signal, quantifying the signal intensity, and semi-quantitatively detecting the signal intensity. Such semi-quantitative detection refers to indicating the signal intensity in stages such as "no signal generation," "weak," "medium," and "strong." In this step, it is preferable to detect the signal intensity quantitatively or semi-quantitatively.

As the method for detecting a signal, a known method may be used. In this method, a measurement method according to the type of signal derived from the above-mentioned labeling substance may be appropriately selected. For example, when the labeling substance is an enzyme, detection of a signal may be performed by measuring a signal such as light or color generated by the reaction of the enzyme with a substrate using a known device such as a luminometer or a spectrophotometer.

The substrate of an enzyme can be appropriately selected from known substrates depending on the type of enzyme. For example, when alkaline phosphatase is used as an enzyme, examples of substrates include chemiluminescent substrates such as CDP-Star (registered trademark) (disodium 4-chloro-3-(methoxyspiro[1,2-dioxetane-3,2'-(5'-chloro)tricyclo[3.3.1.1$^{3,7}$]decan]-4-yl)phenyl phosphate), and chromogenic substrates such as 5-bromo-4-chloro-3-indolyl phosphate (BCIP), disodium 5-bromo-6-chloro-3-indolyl phosphate, and p-nitrophenyl phosphate. When the labeling substance is peroxidase, examples of substrates include tetramethylbenzidine (TMB) and the like.

When the labeling substance is a radioactive isotope, a signal, i.e., radiation, can be measured using a known device such as a scintillation counter. When the labeling substance is a fluorescent substance, a signal, i.e., fluorescence, can be measured using a known device such as a fluorescence microplate reader or Luminex (registered trademark) system (Luminex). The excitation wavelength and the fluorescence wavelength can be appropriately determined according to the type of fluorescent substance used.

The detection results of the signal can be used as the measurement value of the PRP protein, or the measurement value of the fibrinogen protein. For example, when the signal intensity is quantitatively detected, the measurement value itself of the signal intensity or a value calculated from the measurement value of the signal intensity can be used as the measurement value of the kidney function prediction marker protein.

2. Method for Measuring PRP mRNA or Fibrinogen mRNA

The methods for obtaining a measurement value relating to at least one protein selected from the group consisting of proline-rich proteins (PRPs) and fibrinogens, and a measurement value of mRNA of the protein in the present specification are not limited, as long as the measurement values can be obtained. For example, they can be obtained according to the methods described below.

A known measurement method, such as a microarray method, an RNA-Seq analysis method, or a quantitative RT-PCR method, can be used to obtain the measurement value of at least one mRNA selected from the group consisting of proline-rich proteins (PRPs) (hereinafter may be abbreviated as "measurement value of PRP mRNA" in the present specification), or the measurement value of at least one mRNA selected from the group consisting of fibrinogens (hereinafter may be abbreviated as "measurement value of fibrinogen mRNA" in the present specification). As probes used for the microarray method, probes of one's choosing, or known probes, may be synthesized and used; or a commercially available microarray chip may be used.

In this method, any of total RNA and mRNA extracted from a specimen may be used. It is preferred that the specimen used for total RNA and mRNA extraction is subjected to RNA extraction immediately after being collected from an individual; or is frozen (preferably under an atmosphere at −196° C. or less (rapidly cooled in liquid nitrogen)) immediately after being collected from an individual, and stored at −80° C. or less until RNA extraction.

The method for extracting total RNA and mRNA from a specimen is not particularly limited, and a known extraction method may be used.

Quantification by the microarray method may be performed according to a known method. The expression level of each mRNA may be expressed as the relative expression level to that of a housekeeping gene; or expressed as the measurement value of the signal intensity of, for example, a fluorescent dye.

Quantification by RT-PCR may be performed by conducting a reverse transcription reaction using total RNA or mRNA extracted from a specimen as a template, and performing analysis by a real-time PCR method or the like with the obtained cDNA as a template by using specific primers for each mRNA. In this case, the expression level of each mRNA may be expressed as the relative expression level to that of a housekeeping gene; or expressed as the measurement value of the signal intensity of, for example, a fluorescent dye.

In the RNA-Seq analysis method, mRNA extracted from a specimen is fragmented, cDNA is synthesized by reverse transcription reaction using these fragments as a template, and libraries are prepared. The nucleotide sequence of each fragment contained in each library is determined by using a next-generation sequencer, the obtained information is mapped to a reference gene sequence, and the expression level of mRNA is represented as RPKM (Reads Per Kilobase per Million). RPKM may be represented as the intensity of a signal in, for example, a heat map.

The detection results of the signal can be used as the expression level of each mRNA. For example, when the signal intensity is quantitatively detected, the measurement value itself of the signal intensity, or a value calculated from the measurement value of the signal intensity, can be used as the expression level of each mRNA.

Examples of the value calculated from the measurement value of the signal intensity include a value obtained by subtracting, from the measurement value of the signal intensity, the measurement value of the signal intensity of a negative control sample; a value obtained by dividing the measurement value of the signal intensity by the measurement value of the signal intensity of a positive control sample; a combination thereof; and the like. Examples of negative control samples include specimens of healthy subjects and the like. Examples of positive control samples include specimens containing individual mRNAs at a predetermined expression level.

The detection results obtained by using the ELISA method, Western blotting method, quantitative RT-PCR method, RNA-Seq method, and reporter assay, and the measurement results of a chemical mediator can be used as evaluation results of function of Oscar protein. The evaluation results may be quantitative data, semi-quantitative information such as "high" and "low," or qualitative data such as "present" and "not present."

A situation in which the measurement value relating to at least one protein selected from the group consisting of proline-rich proteins (PRPs) in a specimen and/or the measurement value of mRNA of the protein in a specimen is high includes at least a case in which the measurement value derived from the specimen is higher than the measurement value of a healthy individual. This situation also includes a case in which the measurement value is higher when compared with a past measurement value in the same individual. Further, a situation in which the measurement value relating to at least one protein selected from the group consisting of fibrinogens in a specimen and/or the measurement value of mRNA of the protein in a specimen is high includes at least a case in which the measurement value derived from the specimen is higher than the measurement value of a healthy individual. This situation also includes a case in which the measurement value is higher when compared with a past measurement value in the same individual.

3. Evaluation of Function of Oscar Protein

In the present invention, the method for evaluating the function of Oscar protein is not particularly limited, as long as the function of Oscar protein can be evaluated. "Function of Oscar protein" as used herein is the original function of Oscar protein.

An example of the method for evaluating the function of Oscar protein is a method in which the presence or absence of, for example, phosphorylation or dephosphorylation of a protein downstream in the signaling pathway to which Oscar protein belongs; an increase or decrease in the expression level of a protein located downstream; activation or inactivation of the transcriptional regulatory region of a protein located downstream; or the like is detected. More specifically, when the measurement value of FGF23 protein, which is considered to be a protein downstream of Oscar protein, and/or the measurement value of mRNA of the protein in a specimen treated with a test substance is decreased, it can be determined that the test substance is a candidate substance for an active ingredient. When the measurement value of a fibrinogen protein, which is considered to be a protein downstream of Oscar protein, and/or the measurement value of mRNA of the protein in a specimen treated with a test substance is decreased, it can be determined that the test substance is a candidate substance for an active ingredient. When the measurement value of a proline-rich protein (PRP), which is considered to be a protein downstream of Oscar protein, and/or the measurement value of mRNA of the protein in a specimen treated with a test substance is decreased, it can be determined that the test substance is a candidate substance for an active ingredient. Further, when the activity of lipoprotein lipase in a specimen treated with a test substance is enhanced, it can be determined that the test substance is a candidate substance for an active ingredient.

For example, the presence or absence of phosphorylation of a protein can be detected by a known method, such as Western blotting. For example, an increase or decrease in the expression level of a protein can be detected by a known method, such as the ELISA method, Western blotting method, quantitative RT-PCR method, or RNA-Seq method. Further, activation or inactivation of the transcriptional regulatory region can be detected by a reporter assay. Examples of reporters include firefly luciferase, *Renilla* luciferase, GFP (Green Fluorescent Protein), β-galactosidase, and the like. The reporter assay can be performed according to a known method.

An example of another method for evaluating the function of Oscar protein is a method in which the binding activity of NFATc1 is observed by a reporter assay. More specifically, the binding activity can be observed by the method described in, for example, JCI 2011; 121: 3505/J Immunol 2015; 194: 3317. The function of Oscar protein can be measured by, for example, a method in which an Oscar ligand is added to NFAT-GFP reporter cells expressing a protein in which the Oscar extracellular domain is fused to the TCR CD3 signal chain, and then downstream signaling by binding of Oscar to the Oscar ligand is quantified using the amount of GFP fluorescence.

Moreover, an example of another method for evaluating the function of Oscar protein is a method in which the concentration of calcium in monocytes or dendritic cells is measured. The concentration of calcium in the cells can be measured by a known method.

Examples of another method for evaluating the function of Oscar protein include a method in which the expression level of Bcl-2 is measured by the Western blotting method or the like; and a method in which apoptosis inhibitory action is evaluated by the TUNEL method.

4. Pharmaceutical Composition and Food or Drink Composition

The present invention includes, as an embodiment, a pharmaceutical composition or a food or drink composition. Moreover, the present invention includes, as an embodiment, a pharmaceutical composition or food or drink composition for preventing or treating kidney disease. The pharmaceutical composition or food or drink composition comprises, as an active ingredient, a substance capable of regulating the functional expression of Oscar protein.

As shown in Example 1 and Experimental Example 1 described later, a substance capable of regulating the functional expression of Oscar protein can be used for suppressing the functional expression of FGF23. Moreover, as shown in Non-patent Literature 2 to 5, it has been reported that the fibrinogen concentration in urine or blood is increased in patients with chronic kidney disease (CKD), acute kidney injury, renal fibrosis, glomerulonephritis, or like disease. Furthermore, as shown in Example 2 described later, a substance capable of regulating the functional expression of Oscar protein can be used for suppressing the expression of a fibrinogen gene in model mice ingested a diet with high phosphorus content; therefore, a substance capable of regulating the functional expression of Oscar protein is believed to improve kidney function. In the model mice ingested a diet with high phosphorus content, the mRNA expression of PRPs in the parotid glands and the amount of secretion of PRPs in saliva are increased before creatinine, which is a kidney function marker, shows changes. On the other hand, this increased expression is mitigated by a substance capable of regulating the functional expression of Oscar protein, as shown in Example 2.

The present invention thus includes, as another embodiment, a pharmaceutical composition or food or drink composition for use in suppressing the functional expression of FGF23. The present invention includes, as another further embodiment, a pharmaceutical composition or food or drink composition for being administered to an individual with a high measurement value relating to at least one protein selected from the group consisting of proline-rich proteins (PRPs) and fibrinogens in a specimen, and/or a high measurement value of mRNA of the protein in a specimen.

"Preventing kidney disease" as used herein includes preventing the onset of kidney disease; and includes suppressing a shift from normal state to declined kidney function, a shift from declined kidney function to chronic kidney disease, or a shift from a state of a lower category to a state of a higher category in the GFR categories shown in Table 4 in chronic kidney disease. "Treating kidney disease" includes improving or curing kidney disease. Here, improving means that data about at least one of the items shown in Tables 2-1 to 2-3 is shifted toward the threshold.

The pharmaceutical composition according to a first embodiment of the present invention can be prepared by combining the active ingredient described above with suitable carriers or additives. As carriers and additives that can be used for preparing the pharmaceutical composition, carriers and additives widely used in typical drugs can be used according to the dosage form of the pharmaceutical composition. Examples of carriers and additives include excipients, binders, disintegrators, lubricants, coloring agents, taste enhancers, flavor enhancers, surfactants, and the like.

When the active ingredient is a peptide, an antibody, an antibody fragment, an RNA molecule, a plasmid vector, or the like, a transfection reagent containing a polymer, a lipid, magnetism, etc., may be used as a carrier.

The dosage form of the pharmaceutical composition for oral administration is not particularly limited, and examples include tablets, powders, granules, capsules (including hard capsules and soft capsules), fluids, pills, suspensions, emulsions, and the like. The dosage form of the pharmaceutical composition for parenteral administration include injections, drops, suppositories, nasal drops, preparations for transpulmonary administration, and the like.

When the pharmaceutical composition is prepared in the form of a solid oral composition, such as tablets, powders, granules, pills, and capsules, examples of usable carriers include excipients such as lactose, saccharose, sodium chloride, glucose, urea, starch, calcium carbonate, kaolin, crystalline cellulose, silicic acid, methylcellulose, glycerol, sodium alginate, and gum arabic; binders such as simple syrups, liquid glucose, liquid starch, gelatin solutions, polyvinyl alcohol, polyvinyl ether, polyvinylpyrrolidone, carboxymethylcellulose, shellac, methylcellulose, ethylcellulose, water, ethanol, and potassium phosphate; disintegrators such as dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, and lactose; disintegration inhibitors such as saccharose, stearic acid, cocoa butter, and hydrogenated oils; absorption enhancers such as sodium lauryl sulfate; humectants such as glycerol and starch; adsorbents such as starch, lactose, kaolin, bentonite, and colloidal silicic acid; lubricants such as purified talc, stearic acid salts, powdered boric acid, and polyethylene glycol; and the like. Tablets may be optionally provided with general coatings to provide sugar-coated tablets, gelatin-coated tablets, enteric-coated tablets, film-coated tablets, double-layer tablets, multi-layer tablets, and the like.

When the pharmaceutical composition is prepared in the form of a pill, which is a solid oral composition, examples of usable carriers include excipients such as glucose, lactose, starch, cacao butter, hydrogenated vegetable oils, kaolin, and talc; binders such as powdered gum arabic, powdered tragacanth, and gelatin; disintegrators such as laminaran and agar; and the like.

When the pharmaceutical composition is prepared in the form of a capsule, which is a solid oral composition, it is prepared by mixing the active ingredient with carriers mentioned above, and filling a hard capsule, a soft capsule, or the like with the mixture.

When the preparation is a liquid preparation, it may take the form of a water-based or oil-based suspension, solution, syrup, or elixir; and can be prepared according to a common method, using generally used additives.

When the pharmaceutical composition is prepared in the form of an injection, examples of usable carriers include diluents such as water, ethyl alcohol, macrogol, propylene glycol, ethoxylated isostearyl alcohol, polyoxylated isostearyl alcohol, and polyoxyethylene sorbitan fatty acid esters; pH-adjusters such as sodium citrate, sodium acetate, and sodium phosphate; buffers such as dipotassium phosphate, trisodium phosphate, sodium hydrogen phosphate, and sodium citrate; stabilizers such as sodium pyrosulfite, EDTA, thioglycolic acid, and thiolactic acid; saccharides such as mannitol, inositol, maltose, sucrose, and lactose for use as binders in freeze-drying; and the like. In this case, glucose or glycerol may be incorporated in the pharmaceutical preparation in an amount sufficient to prepare an isotonic solution. General solubilizing agents, soothing agents, topical anesthetics, etc., may also be added to the solution. Subcutaneous, intramuscular, and intravenous injections can be prepared according to common methods by adding these carriers.

When the preparation is prepared in the form of a drop, it can be prepared by dissolving the compound to be administered in an isotonic electrolyte infusion preparation, such as physiological saline or Ringer's solution.

The dose of the pharmaceutical composition of the present invention is not particularly limited as long as the effects of the present invention are achieved, and can be suitably determined according to the dosage form; the age, sex, and condition of a patient; etc. For example, the daily dose is about 0.1 to 1,000 mg/kg, and preferably about 0.5 to 500 mg/kg, in terms of the amount of the active ingredient in an adult (15 years of age or older) (calculated based on the assumption that the body weight is about 60 kg).

The food or drink composition according to the present embodiment includes general food and food with health claims (foods with function claims, food with nutrient function claims, food for specified health uses). The definition and classification of food with health claims are in accordance with those prescribed by the Health Promotion Act and the Food Sanitation Act in Japan.

The food or drink composition according to a second embodiment of the present invention includes food and drink (pet food) for pets (e.g., dogs, cats, hamsters, rabbits, and birds), and food and drink (feed compositions) for livestock (cattle, pigs, poultry).

The food or drink composition according to the present embodiment is not particularly limited. Examples include drinks (e.g., milk beverages, lactic acid bacteria beverages, fruit-juice-containing soft drinks, carbonated drinks, fruit juice drinks, vegetable drinks, vegetable and fruit drinks, alcohol, sports drinks, powder drinks, and tea drinks), chilled desserts (e.g., jelly, bavarois, and custard pudding), iced desserts (e.g., ice cream, ice milk, lacto ice (ice cream with a milk solids content of 3% or more), and sherbet), confectioneries (e.g., cookies, biscuits, rice crackers, candies, chocolates, and gum), bread, noodles (e.g., Chinese noodles, pasta, wheat-flour noodles, buckwheat noodles, and somen (thin noodles)), soups (including powdered soup and soup cubes), seasonings (e.g., dressings, jellied seasonings, sauces, mayonnaise-like sauces, and sauces for dipping, basting, etc.), and the like.

Moreover, the food or drink composition according to the present invention includes not only food and drink in the forms described above, but also food or drink compositions in the form of a supplement and food for the sick (including food for persons in need of nursing care and food for persons with dysphagia). When the food or drink composition is prepared as a composition in the form of a supplement or as food for the sick, preferable forms thereof are, for example, fluids (drinkable preparations), syrups, dry syrups, jelly preparations (including jelly preparations prepared at the time of use; the same applies hereinafter), granules, powders, pills, tablets, capsules (hard capsules, soft capsules), lozenges, and chewables, in view of ease of continuous intake. Fluids (drinkable preparations), jelly preparations, granules, tablets, and capsules (hard capsules, soft capsules) are preferable, and fluids (drinkable preparations) and jelly preparations are more preferable. The composition in such a form can be prepared by an ordinary method for producing preparations using pharmaceutically acceptable carriers or additives according to the form of each preparation, as explained in the section of the phaLmaceutical composition described above.

If the domestic laws of a country prohibit the use, for the food or drink composition, of a statement concerning the relationship between the composition and a disease, the statement concerning the relationship with the disease can be changed so as not to violate the domestic laws. For example, an expression, such as "for keeping the kidneys in a good state (in a healthy state)," may be indicated as a use of the food or drink composition.

The dose of the food or drink composition according to the present invention is not particularly limited as long as the effects of the present invention are achieved, and can be suitably determined according to the dosage form; the age, sex, and condition of a patient; etc. For example, the daily dose is about 0.1 to 1,000 mg/kg, and preferably about 0.5 to 500 mg/kg, in terms of the amount of the active ingredient in an adult (15 years of age or older) (calculated based on the assumption that the body weight is about 60 kg).

5. Evaluation of Effect of Active Ingredient in Body 5-1. Method for Supporting Evaluation of Effect of Active Ingredient in Body The present invention includes, as a third embodiment, a method for supporting the evaluation of an effect, in the body, of an active ingredient that suppresses functional expression of Oscar protein. Specifically, the third embodiment comprises a step of obtaining a measurement value relating to at least one protein selected from the group consisting of proline-rich proteins (PRPs) and fibrinogens contained in a specimen collected from a subject to which the active ingredient has been administered (a treated specimen), and/or a measurement value of mRNA of the protein contained in a specimen collected from the subject; and a step of evaluating the effect of the active ingredient based on the measurement value(s) obtained by the obtaining step. The method may also comprise a second obtaining step of obtaining a measurement value relating to the at least one protein selected from the group consisting of proline-rich proteins (PRPs) and fibrinogens, and/or a measurement value of mRNA of the protein in a specimen collected from a subject, test tissue, or test cell that is not treated with the active ingredient (an untreated specimen). The method may further comprise a step of comparing the measurement value(s) of the treated specimen with the measurement value(s) of the untreated specimen. Moreover, in the evaluation step, the effect of the active ingredient in the body can be evaluated based on the comparison result obtained by the measurement value comparison step. Specifically, when the measurement value(s) of the treated specimen are lower than the measurement value(s) of the untreated specimen, it can be determined that the active ingredient is effective in the body.

Here, the subject, test tissue, or test cell that is not treated with the active ingredient is a subject, test tissue, or test cell that has never been treated with the test substance. Instead of using this, a comparison may be made with a measurement value relating to the at least one protein selected from the group consisting of proline-rich proteins (PRPs) and fibrinogens, and/or a measurement value of mRNA relating to the protein. Hereinafter, the same applies to the fourth and fifth embodiments.

5-2. System Configuration

Figure 2:
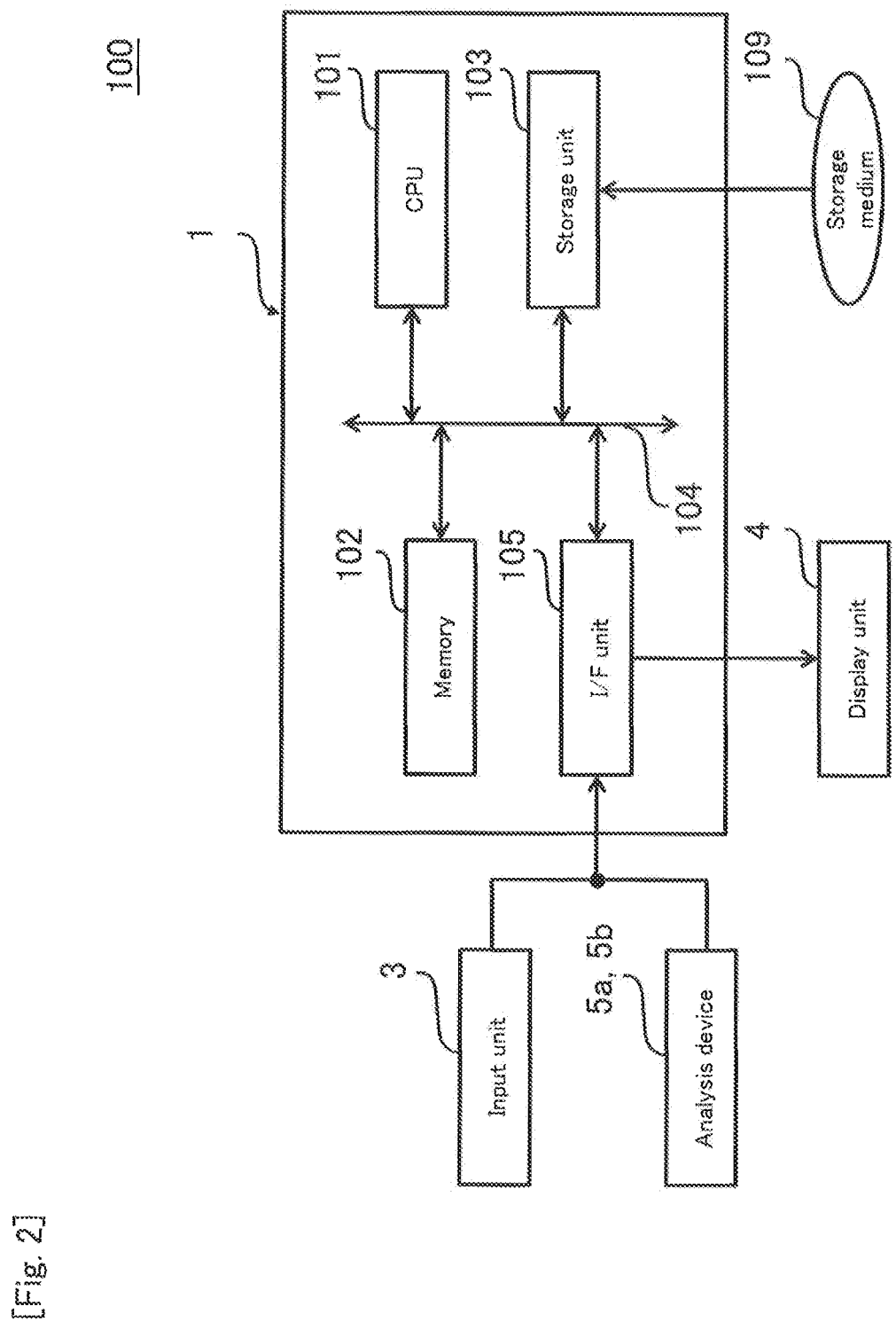
FIG. 2 is a block diagram illustrating a hardware configuration of the system 100 according to the fourth embodiment of the present invention.

FIG. 1 is an overview of a system 100 according to a fourth embodiment of the present invention, and FIG. 2 is a block diagram illustrating a hardware configuration of the system 100. As an embodiment, the system 100 comprises an evaluation device 1, an input unit 3, a display unit 4, and an analysis device 5a or an analysis device 5b.

The evaluation device 1 includes, for example, a general-purpose personal computer; and comprises a CPU 101 for performing data processing described later, a memory 102 serving as a work area for data processing, a storage unit 103 for storing processed data, a bus 104 for transmitting data between the units, and an interface unit 105 (hereinafter referred to as "I/F unit") for performing data input and output between the evaluation device and external devices. The input unit 3 and the display unit 4 are connected to the evaluation device 1. The input unit 3 includes, for example, a keyboard; and the display unit 4 includes, for example, a liquid crystal display. The input unit 3 and the display unit 4 may be integrated and implemented as a display with a touch panel. The evaluation device 1 need not be a single device; and the CPU 101, the memory 102, the storage unit 103, and the like may be located in separate places, and connected via a network. The evaluation device may also be a device that omits the input unit 3 and the display unit 4, and that does not require an operator.

The evaluation device 1 and the analysis device 5a or the analysis device 5b are also not necessarily located in one place, and may be configured such that the devices located in separate places are communicatively connected to each other via a network.

In the explanation below, a process performed by the evaluation device 1 means a process performed by the CPU 101 of the evaluation device 1 based on an evaluation program stored in the storage unit 103 or the memory 102 shown in FIG. 2, unless otherwise specified. The CPU 101 temporarily stores necessary data (such as intermediate data being processed) in the memory 102 that serves as a work area, and suitably stores data that is stored for a long period of time, such as computation results, in the storage unit 103.

The analysis device 5a is a device for measuring the amount or concentration of a protein, and comprises a sample placement area 51, a reaction unit 52, and a detection unit 53. A specimen, collected from a subject, set in the sample placement area 51 is dispensed into and incubated in a microplate that is placed in the reaction unit 52 and on which an antibody against an kidney function prediction marker for antibody capture is immobilized. The unreacted antigen is removed, if necessary. Thereafter, a detection antibody is dispensed into the microplate, followed by incubation. The unreacted antigen is removed if necessary, and a substrate for detecting the detection antibody is dispensed into the microplate. The microplate is transferred to the detection unit 53, and a signal generated by reaction with the substrate is measured. Another embodiment of the analysis device 5a is a device for measuring the expression level of mRNA by microarray analysis. A reverse transcription reaction product set in the sample placement area 51 is dispensed into a microarray chip set in the reaction unit 52, followed by hybridization. After the microarray chip is washed, it is transferred to the detection unit 53, and a signal is detected.

Further, another embodiment of the analysis device 5a is a device for measuring the expression level of mRNA by RT-PCR. A reverse transcription reaction product set in the sample placement area 51 is dispensed into a microtube set in the reaction unit 52, and a reagent for quantitative PCR is subsequently dispensed into the microtube. A signal in the tube is detected by the detection unit 53 while performing a PCR reaction in the reaction unit 52.

The analysis device 5b is a device for measuring the expression level of mRNA by the RNA-Seq method, and comprises a sequence analysis unit 54. A sample subjected to a reaction for RNA-Seq is set in the sequence analysis unit 54, and analysis of nucleotide sequences is performed in the sequence analysis unit 54.

The analysis devices 5a or 5b are connected to the evaluation device 1 by a wired or wireless connection. The analysis device 5a A/D converts the measurement value of a protein or the measurement value of mRNA and transmits it as digital data to the evaluation device 1. Similarly, the analysis device 5b A/D converts the measurement value of mRNA, and transmits it as digital data to the evaluation device 1. Therefore, the evaluation device 1 can obtain, as digital data that can be computed, the measurement value of a protein or the measurement value of mRNA.

5-3. Evaluation Device

The present invention includes, as the fourth embodiment, a device for evaluating an effect, in the body, of an active ingredient that suppresses functional expression of Oscar protein, the device comprising the following computation means:

means for obtaining a measurement value relating to at least one protein selected from the group consisting of proline-rich proteins (PRPs) and fibrinogens contained in a specimen collected from a subject to which the active ingredient has been administered (a treated specimen), and/or a measurement value of mRNA of the protein contained in a specimen collected from the subject; and means for evaluating the effect of the active ingredient based on the measurement value(s) obtained by the obtaining means.

The fourth embodiment may further comprises:

second obtaining means for obtaining a measurement value relating to the at least one protein selected from the group consisting of proline-rich proteins (PRPs) and fibrinogens, and/or a measurement value of mRNA relating to the protein in a specimen collected from a subject, test tissue, or test cell that is not treated with the active ingredient (an untreated specimen); and means for comparing the measurement value(s) of the treated specimen with the measurement value(s) of the untreated specimen. Further, the evaluation means may evaluate the effect of the active ingredient in the body based on the comparison result obtained by the measurement value comparison means. The evaluation means can determine that the active ingredient is effective in the body when the measurement value(s) of the treated specimen are lower than the measurement value(s) of the untreated specimen.

In this embodiment, an effect, in the body, of an active ingredient that suppresses functional expression of Oscar protein can be evaluated by the system 100 (FIG. 1) comprising the evaluation device 1 as the evaluation device described above.

Figure 3:
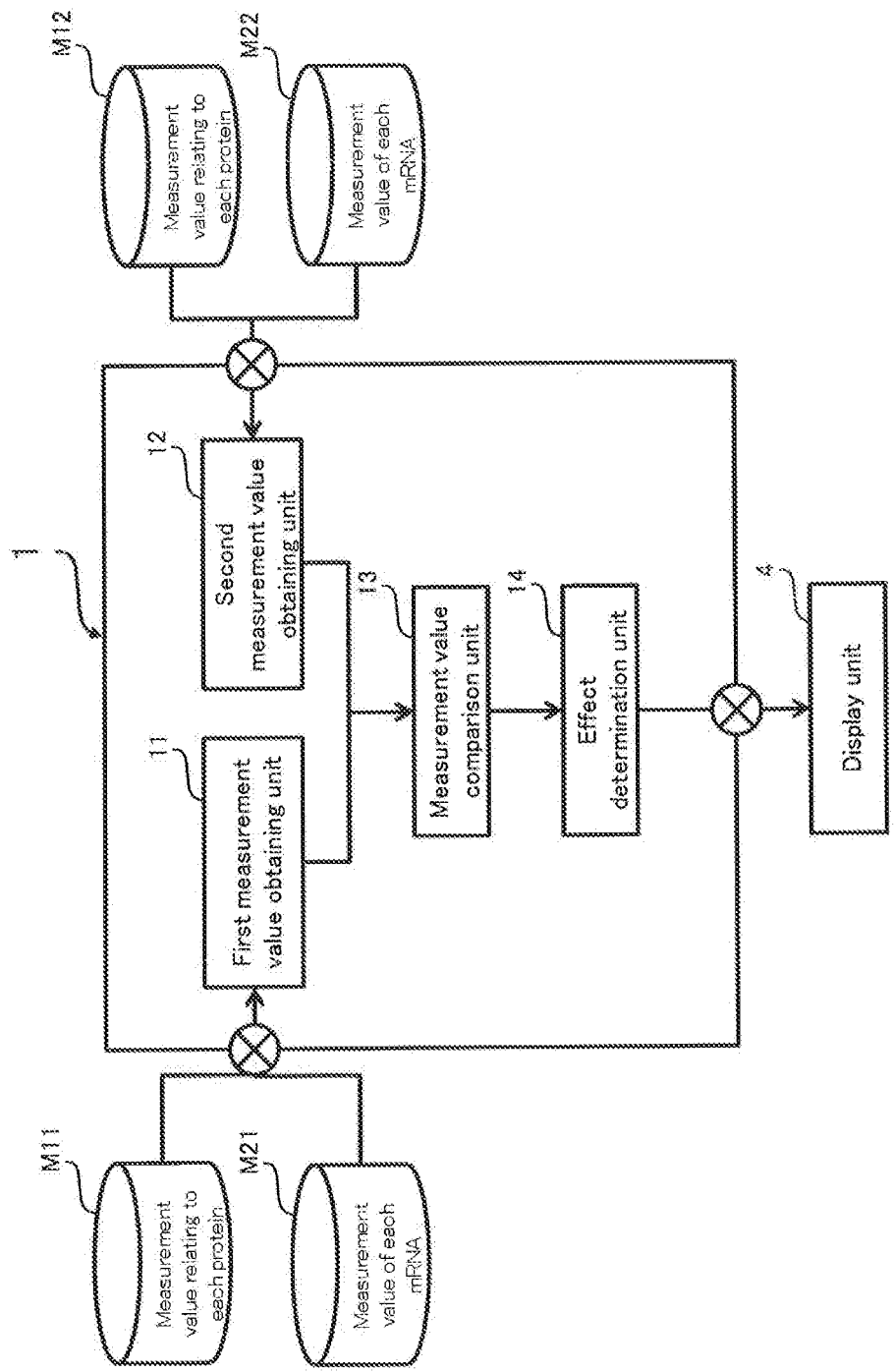
FIG. 3 is a block diagram illustrating functions of an evaluation device 1 according to the fourth embodiment of the present invention.

FIG. 3 is a block diagram illustrating functions of the evaluation device 1 according to this embodiment. The evaluation device 1 comprises a first measurement value obtaining unit 11, a second measurement value obtaining unit 12, a measurement value comparison unit 13, and a candidate substance determination unit 14. The second measurement value obtaining unit 12 may be optional. These functional blocks are implemented by installing the evaluation program according to the present invention in the storage unit 103 or the memory 102 of the evaluation device 1 shown in FIG. 2, and causing the CPU 101 to execute the evaluation program. Thereby, the evaluation device 1 carries out the method in the section "5-5. Evaluation method" described later. The first obtaining means, second obtaining means, measurement value comparison means, and determination means recited in the claims correspond to the first measurement value obtaining unit 11, second measurement value obtaining unit 12, measurement value comparison unit 13, and effect determination unit 14 shown in FIG. 3, respectively.

In other words, the evaluation device 1 is a device for evaluating an effect, in the body, of an active ingredient that suppresses functional expression of Oscar protein, the device executing the following computation functions by the CPU 101:

a first obtaining function for obtaining a measurement value relating to at least one protein selected from the group consisting of proline-rich proteins (PRPs) and fibrinogens contained in a specimen collected from a subject to which the active ingredient has been administered (a treated specimen), and/or a measurement value of mRNA of the protein contained in a specimen collected from the subject; and a function for evaluating the effect of the active ingredient based on the measurement value(s) obtained by the obtaining function.

Preferably, the evaluation device 1 further executes the following functions by the CPU 101:

a second obtaining function for obtaining a measurement value relating to the at least one protein selected from the group consisting of proline-rich proteins (PRPs) and fibrinogens, and/or a measurement value of mRNA of the protein in a specimen collected from a subject, test tissue, or test cell that is not treated with the active ingredient (an untreated specimen); and a function for comparing the measurement value(s) of the treated specimen with the measurement value(s) of the untreated specimen, wherein the evaluation function evaluates the effect of the active ingredient in the body based on the comparison result obtained by the measurement value comparison function, and the evaluation function determines that the active ingredient is effective in the body when the measurement value(s) of the treated specimen are lower than the measurement value(s) of the untreated specimen.

In this embodiment, a measurement value M11 relating to each protein is put into the evaluation device 1 from the analysis device 5a, and a measurement value M21 of mRNA of the protein is put into the evolution device 1 from the analysis device 5a or 5b. Similarly, a measurement value M12 relating to the protein in an untreated specimen is also put into the evaluation device 1 from the analysis device 5a, and a measurement value M22 of mRNA of the protein is also put into the evaluation device 1 from the analysis device 5a or 5b.

The measurement values M11 and M12 relating to the protein and the measurement values M21 and M22 of mRNA of the protein in the treated specimen and the untreated specimen may also be put into the evaluation device 1 from a third-party organization (not shown) via a network.

Moreover, the functional blocks, i.e., the first measurement value obtaining unit 11, the second measurement value obtaining unit 12, the measurement value comparison unit 13, and the effect determination unit 14, are not necessarily executed by a single CPU, and may be processed by multiple CPUs in a distributed manner. For example, these functional blocks may be configured such that the functions of the first measurement value obtaining unit 11 and the second measurement value obtaining unit 12 are executed by a CPU of a first computer, and such that the functions of the measurement value comparison unit 13 and the effect determination unit 14 are executed by a CPU of a second computer, i.e., another computer.

5-4. Evaluation Program

In order to carry out the processing for steps S11 to S17 in FIG. 4 below, the evaluation device 1 according to the fourth embodiment of the present invention stores the evaluation program according to this embodiment in the storage unit 103 beforehand, for example, in an executable format (for example, a form in which the program can be produced by conversion from a programming language using a compiler). The evaluation device 1 carries out the processing using the evaluation program stored in the storage unit 103.

Specifically, the evaluation program according to the fourth embodiment of the present invention is an evaluation program that, when executed by a computer, causes the computer to carry out the following processing to evaluate an effect, in the body, of an active ingredient that suppresses functional expression of Oscar protein:

first obtaining processing of obtaining a measurement value relating to at least one protein selected from the group consisting of proline-rich proteins (PRPs) and fibrinogens contained in a specimen collected from a subject to which the active ingredient has been administered (a treated specimen), and/or a measurement value of mRNA of the protein contained in a specimen collected from the subject; and processing of evaluating the effect of the active ingredient based on the measurement value(s) obtained by the obtaining processing.

The evaluation program may further cause the computer to carry out second obtaining processing of obtaining a measurement value relating to the at least one protein selected from the group consisting of proline-rich proteins (PRPs) and fibrinogens, and/or a measurement value of mRNA of the protein in a specimen collected from a subject, test tissue, or test cell that is not treated with the active ingredient (an untreated specimen); and processing of comparing the measurement value(s) of the treated specimen with the measurement value(s) of the untreated specimen. In the evaluation processing, the effect of the active ingredient in the body may be evaluated based on the comparison result obtained by the measurement value comparison processing. In the evaluation processing, it can be determined that the active ingredient is effective in the body when the measurement value(s) of the treated specimen are lower than the measurement value(s) of the untreated specimen.

In this embodiment, as shown in FIG. 2, the evaluation program is stored in a computer-readable non-transitory tangible storage medium 109, such as a CD-ROM, and is installed in the evaluation device 1 from the storage medium 109; alternatively, the evaluation device 1 may be connected to the internet (not shown) to download the program code of the evaluation program via the internet.

5-5. Evaluation Method

Figure 4:
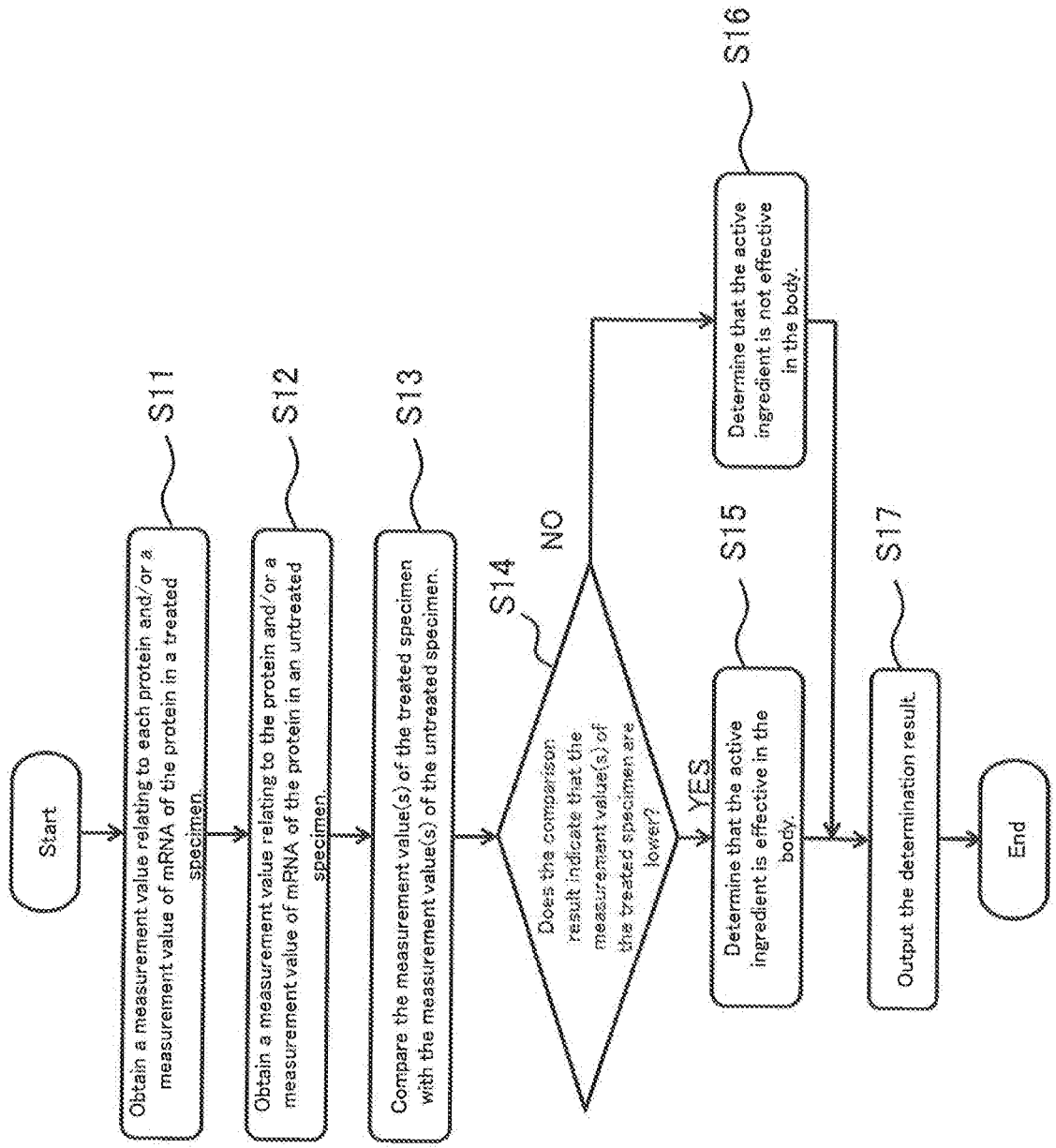
FIG. 4 is a flow chart illustrating a flow of data processing performed by the evaluation device 1 according to the fourth embodiment of the present invention to carry out an evaluation method.

FIG. 4 is a flow chart illustrating a flow of data processing performed by the evaluation device 1 according to the fourth embodiment of the present invention to carry out the evaluation method. Steps S11, S12, and S13 are performed by the first measurement value obtaining unit 11, second measurement value obtaining unit 12, and measurement value comparison unit 13 shown in FIG. 3, respectively. Steps S14 to S17 are performed by the effect determination unit 14 shown in FIG. 3.

In step S11, the first measurement value obtaining unit 11 obtains a measurement value M11 relating to each protein and/or a measurement value M21 of mRNA of the protein in a treated specimen.

In step S12, the second measurement value obtaining unit 12 obtains a measurement value M12 relating to the protein and/or a measurement value M22 of mRNA of the protein in an untreated specimen.

In step S13, the measurement value comparison unit 13 compares the measurement value(s) of the treated specimen obtained in step S11 with the measurement value(s) of the untreated specimen obtained in step S12. The comparison result is output to the effect determination unit 14.

The effect determination unit 14 determines that the active ingredient is effective in the body based on the comparison result obtained by the measurement value comparison unit 13. More specifically, when the comparison result indicates that the measurement value(s) of the treated specimen are lower (YES in step S14), the effect determination unit 14 determines, in step S15, that the active ingredient is effective in the body.

More specifically, when a value obtained by dividing M11 by M12 or a value obtained by dividing M21 by M22 is, for example, 0.85 or less, preferably 0.7 or less, and more preferably 0.5 or less, the measurement value comparison unit 13 determines that the active ingredient is effective in the body, and outputs the comparison result such that the active ingredient is effective.

In step S17, the effect determination unit 14 outputs the result determined in step S15. In this embodiment, whether the active ingredient is effective in the body is displayed on the display unit 4, and the determination result is stored in the storage unit 103 in the evaluation device 1. The determination result may be displayed on a display unit of an external computer terminal connected to the evaluation device 1 via the internet, for example, a display unit of a computer terminal in a third-party organization (not shown), instead of displaying the determination result on the display unit 4.

When the comparison result indicates that the measurement value(s) of the treated specimen are not lower in step S14, the processing proceeds to step S16, and the effect determination unit 14 determines that the active ingredient is not effective in the body. In this case, the result such that the active ingredient is not effective may be displayed on the display unit 4.

6. Genome Editing System and Kit Comprising the System

The present invention includes a genome editing system comprising a sequence that targets Oscar gene described in the above section "1. Explanation of terms." The genome editing system is preferably a CRISPR/Cas9 system comprising a sequence that targets Oscar gene. The CRISPR/Cas9 system comprising a sequence that targets Oscar gene may be a combination of gRNA, tracrRNA, and RNA encoding Cas9. In this case, the gRNA, tracrRNA, and RNA encoding Cas9 may be provided in the same package, or in separate packages.

The genome editing system comprising a sequence that targets Oscar gene according to the present invention may be provided in the form of a kit.

For example, when the genome editing system is a vector, the kit may comprise, in addition to the vector, a package insert, a transfection reagent such as a liposome, a buffer for dissolving the vector, a sequestering agent, and the like.

When the genome editing system is RNA, the kit may comprise, in addition to the RNA, a package insert, a transfection reagent such as a liposome, a buffer for dissolving the RNA, an RNase inhibitor, a sequestering agent, and the like. Moreover, the kit may comprise both gRNA and RNA encoding Cas9, or may comprise only gRNA.

The kit can be used for preventing, improving, or treating kidney disease.

EXAMPLES

The present invention is described in more detail below with reference to examples. The present invention, however, should not be construed as limited to the examples.

Example 1: Preparation of Soluble Human Oscar-Fc Fusion Protein

An expression plasmid containing a nucleotide sequence encoding a soluble human Oscar-Fc fusion protein was expressed in animal cells, thereby preparing the soluble human Oscar-Fc fusion protein shown in SEQ ID NO: 2. The preparation of the protein was outsourced to Protein-Express Co., Ltd. (Chiba, Japan).

```
<Amino acid sequence of humanOscar-humanIgG1>
                                        (SEQ ID NO: 2)
MALVLILQLLTLWPLCHTDITPSVAIIVPPASYHPKPWLGAQPATVVTPG

VNVTLRCRAPQPAWRFGLFKPGEIAPLLFRDVSSELAEFFLEEVTPAQGG

SYRCCYRRPDWGPGVWSQPSDVLELLVTEELPRPSLVALPGPVVGPGANV

SLRCAGRLRNMSFVLYREGVAAPLQYRHSAQPWADFTLLGARAPGTYSCY

YHTPSAPYVLSQRSEVLVISWEGEGPEARPASDKTHTCPPCRAPELLGGP

SVFLFPPKPKDTLMISRTPEVTCVVVDVSHEDPEVKFNWYVDGVEVHNAK

TKPREEQYNSTYRVVSVLTVLRQDWLNGKEYKCKVSNKALPAPIEKTISK

AKGQPREPQVYTLPPSREEMTKNQVSLTCLVKGFYPSDIAVEWESNGQPE

NNYKTTPPVLDSDGSFFLYSKLTVDKSRWQQGNVFSCSVMHEALHNHYTQ

KSLSLSPGK*
```

(The underline indicates a hinge region. The upstream from the hinge region indicates the sequence of human Oscar, and the downstream from the hinge region indicates the human IgG1 sequence.)

1. Preparation of Cells

FreeStyle 293-F cells were subcultured in FreeStyle 293 Expression Medium (Invitrogen). The subculture was performed using a 500 ml flask at the following conditions: a shaking speed of 120 r.p.m., a carbon dioxide concentration of 8%, and a temperature of 37° C. (170 mL of medium). The cells were diluted at $6\times10^5$ cells/mL to a total amount of 1 L the day before transfection, and cultured for 24 hours. After the culture, the number of cells was adjusted to $1\times10^6$ cells/mL, and the cells were used for transfection.

2. Expression Test 2.1 mL of 293fectin Transfection Reagent (Invitrogen) was added to 30 mL of OptiPRO SFM (Invitrogen) prewarmed to 37° C., thereby preparing a reagent solution. Similarly, 1 mg of pcDNA3 (Invitrogen) containing kozak-hOscar-hIgG1-intronXbaI having the following sequence was added to 30 mL of OptiPRO SFM, thereby preparing a DNA solution. The prepared reagent solution and DNA solution were incubated at room temperature for 5 minutes.

The reagent solution and DNA solution after the 5 minutes were mixed to prepare a transfection solution. The transfection solution was incubated at room temperature for 20 minutes and added to the culture medium adjusted for transfection, followed by sampling on day 1, day 2, and day 3 after the start of the transfection. The culture was then terminated on day 4. The obtained samples were centrifuged to separate into a supernatant and a precipitate. The protein expression was confirmed by SDS-PAGE and Western blotting.

<kozak-hOscar-hIgG1-intronXbaI>
(SEQ ID NO: 5)
aagcttgccaccATGGCCCTCGTGCTTATCCTCCAACTTCTCACGCTT

TGGCCTCTGTGCCACACCGACATTACTCCGTCTGTTGCGATAATTGTC

CCTCCCGCCTCTTATCACCCTAAACCTTGGCTGGGCGCACAGCCAGCT

ACTGTGGTTACTCCTGGGGTGAACGTAACACTGCGCTGCCGTGCTCCT

CAGCCCGCCTGGAGATTTGGGTTGTTTAAGCCGGAGAGATAGCACCA

CTGCTGTTTCGGGATGTGTCCTCAGAGCTGGCTGAGTTCTTCCTGGAA

GAGGTCACTCCTGCCCAAGGAGGCAGCTATCGGTGCTGTTATAGGCGG

CCGGATTGGGGACCCGGCGTTTGGTCCCAACCATCTGATGTGCTCGAA

CTGCTTGTGACAGAAGAGCTGCCCAGACCTAGCTTGGTAGCCTTGCCC

GGTCCTGTCGTCGGACCTGGTGCCAATGTTTCTCTTCGATGTGCCGGA

AGGCTGCGCAATATGTCCTTTGTACTGTATAGGGAGGGAGTAGCCGCA

CCTCTGCAGTATAGGCATAGCGCTCAGCCCTGGGCGGATTTTACTCTG

CTTGGTGCCAGAGCACCCGGGACCTATTCCTGCTACTACCACACTCCT

TCCGCACCCTACGTCCTGTCACAGAGATCAGAAGTGCTCGTGATCTCC

TGGGAGGGAGAAGGCCCAGAAGCCGACAAAACTCACACATGCCCACCG

TGCCCAGgtaagccagcccaggcctcgccctccagctcaaggcgggac aggtgccctagagtagcctgcatccagggacaggccccagccgggtgc tgacacgtccacctccatctcttcctcagCACCTGAACTCCTGGGGGG

ACCGTCAGTCTTCCTCTTCCCCCCAAAACCCAAGGACACCCTCATGAT

CTCCCGGACCCCTGAGGTCACATGCGTGGTGGTGGACGTGAGCCACGA

AGACCCTGAGGTCAAGTTCAACTGGTACGTGGACGGCGTGGAGGTGCA

TAATGCCAAGACAAAGCCGCGGGAGGAGCAGTACAACAGCACGTACCG

TGTGGTCAGCGTCCTCACCGTCCTGCACCAGGACTGGCTGAATGGCAA

GGAGTACAAGTGCAAGGTCTCCAACAAAGCCCTCCCAGCCCCCATCGA

GAAAACCATCTCCAAAGCCAAAGtgggacccgtggggtgcgagggcc acatggacagaggccggctcggcccaccctctgccctgagagtgactg ctgtaccaacctctgtccctacagGGCAGCCCCGAGAACCACAGGTGT

ACACCCTGCCCCCATCCCGGGATGAGCTGACCAAGAACCAGGTCAGCC

TGACCTGCCTGGTCAAAGGCTTCTATCCCAGCGACATCGCCGTGGAGT

GGGAGAGCAATGGGCAGCCGGAGAACAACTACAAGACCACGCCTCCCG

TGCTGGACTCCGACGGCTCCTTCTTCCTCTACAGCAAGCTCACCGTGG

ACAAGAGCAGGTGGCAGCAGGGGAACGTCTTCTCATGCTCCGTGATGC

ATGAGGCTCTGCACAACCACTACACGCAGAAGAGCCTCTCCCTGTCTC

CGGGTAAATGAtctaga

3. Purification Using Bipo Resin Protein A

The culture supernatant (1 L) was loaded on Bipo Resin Protein A (10 mL) to purify a target protein. After washing with PBS, elution of the target protein was performed using 100 mM citric acid buffer (pH 2.5) (5 mL×5). The eluate was neutralized with 1M Tris-HCl (pH 9.0). After the purification, protein purification was confirmed in each fraction by SDS-PAGE and Western blotting. The results confirmed a band of the target protein in the elution fraction. The fraction containing the target protein was collected, followed by a buffer exchange into PBS (total amount: 50 mL). Thereby, 1 mg/mL of a soluble human Oscar-Fc fusion protein was obtained.

Example 2: Experiment of Administration of Soluble Human Oscar-Fc Fusion Protein to HP Model Mice HP mice (mice ingested a diet with high phosphorus content) were obtained by feeding mice a diet with high phosphorus content. The soluble human Oscar-Fc fusion protein was administered to this model every week.

1. Phosphorus Overload

Mice ingested a diet with high phosphorus content (HP) were obtained by feeding mice (C57BL/6N, 8 weeks old, male) a diet containing 2% inorganic phosphorus (TD.10662, OrientalBioService, Inc.) as a special phosphorus diet. Mice ingested a diet with low phosphorus content (LP) were fed a diet containing 0.35% inorganic phosphorus (TD.10662 modified type, OrientalBioService, Inc.).

2. Administration of Soluble Human Oscar-Fc Fusion Protein and Collection of Tissue The soluble human Oscar-Fc fusion protein (10 mg/kg) was intraperitoneally administered weekly from the start date of the diet with high phosphorus content (week 0) to week 4, i.e., a total of five times. In this experiment, physiological saline was administered to a control group. Tissue was collected the day after completion of the intraperitoneal administration on week 4, i.e., the fifth intraperitoneal administration. The animals from which the tissue was to be collected were euthanized by cervical dislocation after blood was collected in an EDTA-supplemented tube from the orbit under tribromoethanol anesthesia (250 mg/kg), and the organs and tissue (the skull, brain, pituitary gland, parotid glands, thyroid gland, heart, lung, pancreas, kidney, adrenal glands, liver, spleen, thymus, aorta, femoral muscle, skin, testis, adipose tissue, stomach, jejunum, ileum, colon, and bone marrow cells) were collected. After the wet weights of the collected organs and tissue were measured, the organs and tissue were rapidly frozen in liquid nitrogen and stored at −80° C. The collected blood was centrifuged at 1200 g for 10 minutes at room temperature. After the centrifugation, the supernatant plasma was collected and stored at −80° C.

3. Analysis of Gene Expression in Each Tissue 3-1. RNA Extraction from Each Tissue Each cryopreserved tissue was individually homogenized in TRIzol Reagent (Thermo Fisher Scientific, MA, USA) with a PT10-35 GT Polytron homogenizer (KINEMATICA, Luzern, Switzerland) at 15,000 r.p.m. for 10 minutes, or homogenized using zirconia beads of different sizes (1.5 mm diameter×50, 3 mm diameter×5, 5 mm diameter×2) with a Cell Destroyer PS1000 or PS2000 (Bio Medical Science Inc., Tokyo, Japan) at 4,260 r.p.m. for 45 seconds at 4° C. After incubation at room temperature for 5 minutes to separate proteins, 0.2 ml of chloroform was added per 1 mL of TRIzol, and the tube was capped. Subsequently, the mixture was vortexed vigorously for 15 seconds. After the vortexing, the mixture was incubated at room temperature for 3 minutes and centrifuged at 12,000 g for 15 minutes at 4° C., and the RNA-containing aqueous layer was collected in a fresh tube. An equal amount of 70% ethanol was added to the collected aqueous layer, and mixed. Then, 700 μL of the mixture was applied to each RNeasy Mini column (Qiagen), and purified RNAs were collected according to the RNeasy Mini kit (Qiagen) standard protocol. The quality and concentration of each of the collected RNAs was evaluated by using NanoDrop (Thermo Fisher Scientific, MA, USA).

3-2. qRT-PCR 0.5 to 1 μg of total RNA obtained from each tissue was used as a template for cDNA synthesis, and cDNA was synthesized using Oligo dT20 primer according to the standard protocol of SuperScript III First-Strand Synthesis SuperMix (Life Technologies). After the synthesized cDNA was diluted 20-fold with TE buffer (10 mM Tris-HCl, pH 8.0, 0.1 mM EDTA), real-time PCR was performed with a LightCycler 480 II (Roche) according to the standard protocol of LightCycler 480 SYBR Green I Master (Roche, Basel, Switzerland), and Cp values were measured. The relative expression level of each gene to a reference gene was quantified by comparing the Cp value obtained for each gene with the Cp value for Maea as the reference gene. The primer pairs used in the real-time PCR are as shown in Table 5. All of the primers were designed by using Primer-BLAST (NCBI).

added to each well, and the wash solution was removed. This operation was performed four times. After the wash solution was thoroughly removed, 100 μl of an enzyme-labeled antibody solution (FGF-23 Conjugate) supplied with the kit was added to each well, and the plate was sealed, followed by stirring and incubating at room temperature for 1 hour. After the 1 hour, the sample in each well was aspirated and discarded. 300 μl of the wash solution supplied with the kit was then added to each well, and the wash solution was removed. This operation was performed four times. After the wash solution was thoroughly removed, 100 μl of a substrate solution (Substrate) supplied with the kit was added to each well, and the plate was allowed to stand at room temperature for 30 minutes in the shade. Thereafter, 100 μl of a reaction stop solution (Stop Solution) supplied with the kit was added to each well, followed by gentle shaking. Absorbance at 450 nm was then measured with an absorbance microplate reader (Multiskan GO, Thermo Fisher Scientific Inc.). The concentration of FGF23 in plasma was calculated by making a calibration curve from the measurement result of recombinant FGF23 supplied with the kit.

5. Statistical Analysis

In statistical analysis, Student's t-test or one-way analysis of variance was performed, and then significant differences were determined by the Tukey-Kramer test. The case in which the p-value is less than 0.05 was defined as being significant.

6. Results

Hereinafter, in the drawings, HP4W indicates mice 4 weeks after the start of the diet with high phosphorus content, and LP4W indicates mice 4 weeks after the start of the diet with low phosphorus content (control group). sOscar indicates mice to which the soluble human Oscar-Fc fusion

TABLE 5

| | Gene | Forward | SEQ ID NO. | Reverse | SEQ ID NO. |
|---|---|---|---|---|---|
| 1 | Maea | AAGACCTTGAGTAGTTGCCCA | (6) | TGCTCGATCCTACGTTTGCAG | (7) |
| 2 | Fgf23 | AGGAGCCATGACTCGAAGGT | (8) | GCTCACCAGGTAGTGATGCTT | (9) |
| 3 | Prb1 | ACCCCAGCATGGAAACAAAG | (10) | AAGAATGGTATTGAAGTCATCTGTC | (11) |
| 4 | Prh1 | ACCCCGTGAAGAAAATCAGAA | (12) | TAACAGGCGGTCTTGGTTGG | (13) |
| 5 | Prp2 | TGGTGGTCCTGTTTACAGTGG | (14) | TTCTGAAGTTCTTCACGGGGT | (15) |
| 6 | Prpmp5 | CCTACGAAGACTCAAATTCTCAGC | (16) | GAGGACCATGGTGGTGTCC | (17) |
| 7 | B2m | GCTCGGTGACCCTGGTCTTT | (18) | AATGTGAGGCGGGTGGAACT | (19) |
| 8 | Fgg | CTCCATCGGAGAAGGACAGC | (2016) | AGGTCCTGAAAGTCCATTGTCC | (2017) |

4. Measurement of Concentration of FGF23 in Plasma by ELISA Method

The concentration of FGF23 in plasma was measured using an ELISA kit sold by KAINOS Laboratories, Inc. (TCY4000). A plasma sample cryopreserved in a freezer was thawed on ice, and the sample undiluted or the sample diluted 5-fold with standard solution 1 (FGF-23 concentration, 0 pg/ml) supplied with the kit was used for measurement.

50 μl of the diluted sample or a sample for a calibration curve was added to each well of an ELISA plate supplied with the kit. The plate was sealed, followed by stirring and incubating at room temperature for 2 hours. After the 2 hours, the sample in each well was aspirated and discarded. 300 μl of a wash solution supplied with the kit was then protein was administered, and NS indicates mice to which physiological saline was administered in place of the soluble human Oscar-Fc fusion protein. WT (12W) indicates 12-week-old male wild-type mice fed a normal diet.

Figure 5:
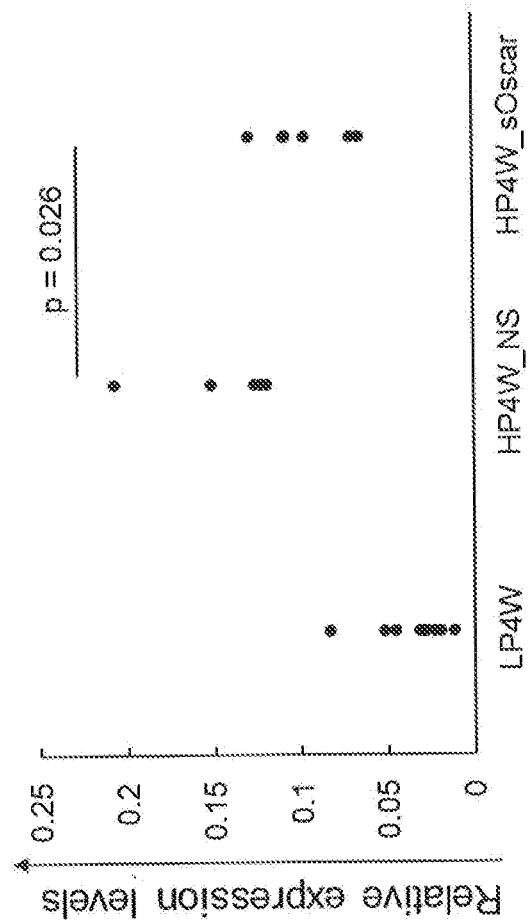
FIG. 5 shows qRT-PCR results of FGF23 in the skull. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein.
Figure 6:
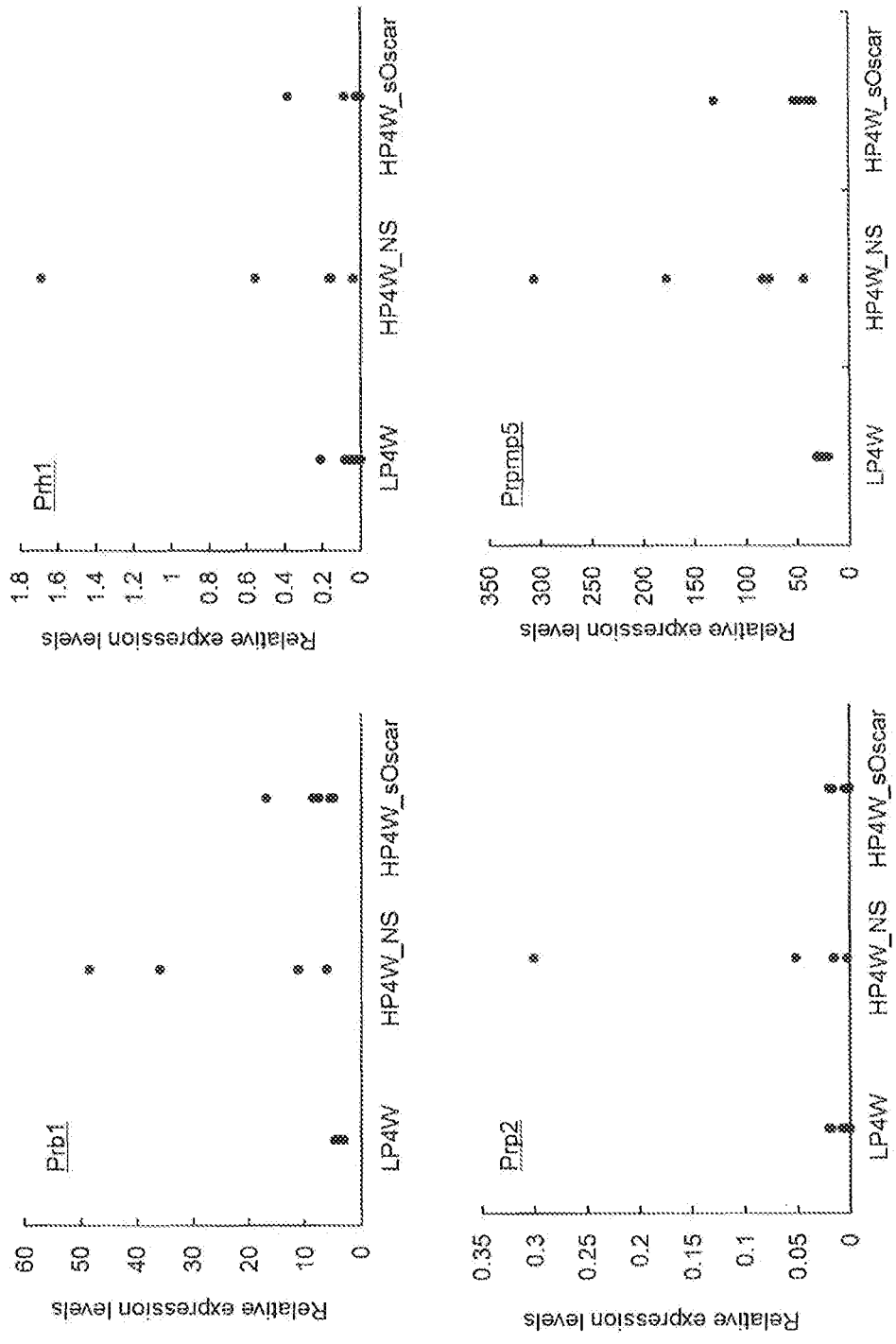
FIG. 6 shows qRT-PCR results of PRP genes in the parotid gland. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein.

FIG. 5 shows qRT-PCR results of FGF23 in the skull. FIG. 6 shows qRT-PCR results of PRP genes in the parotid glands. FGF23 is a master regulator of inter-organ cross talk between the parathyroid glands, bones, and kidneys in kidney disease. The expression of FGF23 was induced by the diet with high phosphorus content in the skulls. However, the expression of FGF23 was suppressed by administration of the soluble human Oscar-Fc fusion protein (FIG. 5) (n=5 to 6). The expression was normalized by by the expression of the Maea gene, and a significance test was performed. The results showed a significant difference (p=0.026) between HP to which sOscar was administered and HP to which sOscar was not administered. The expression of PRP genes (Prb1, Prh1, Prp2, and Prpmp5) whose expression is induced by the diet with high phosphorus content was suppressed by administration of the soluble human Oscar-Fc fusion protein in the parotid glands (FIG. 6) (n=5 to 6). From the above, it was indicated that the expression of renal failure early markers FGF23 gene (the skull) and PRP genes (the parotid glands) was suppressed by administration of the soluble human Oscar-Fc fusion protein to the model mouse of phosphorus overload for 4 weeks.

Figure 7:
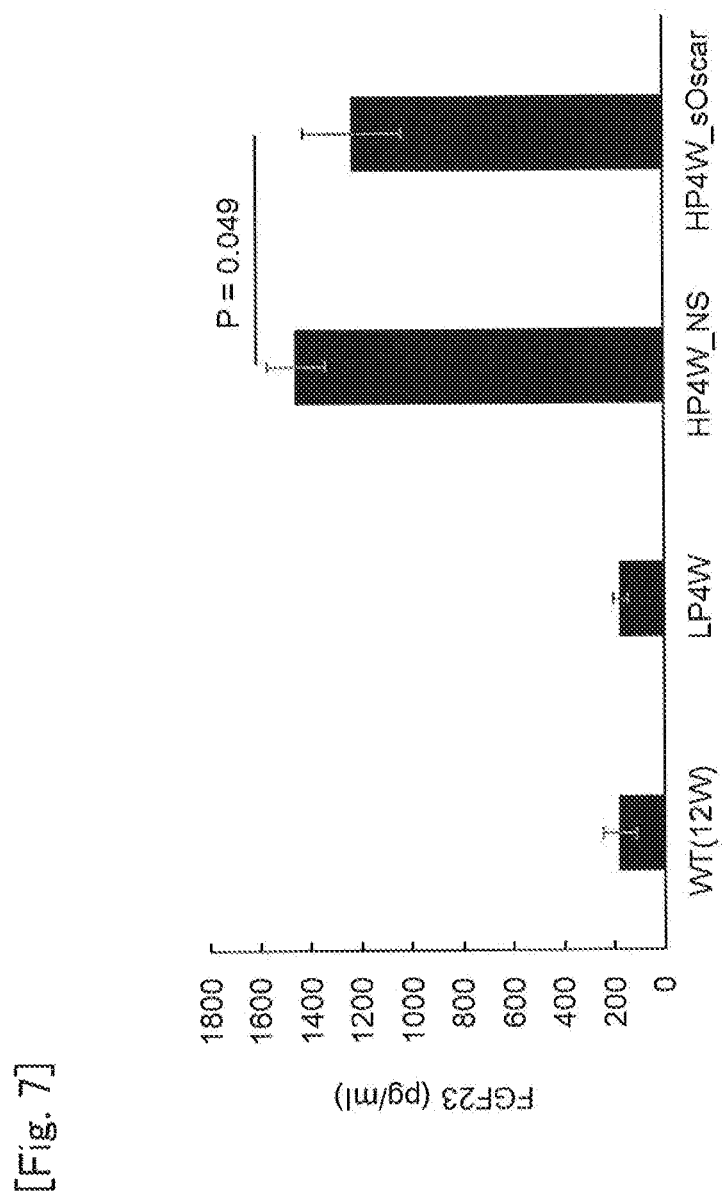
FIG. 7 shows ELISA measurement results of FGF23 in plasma. HP4W indicates mice 4 weeks after the start of a diet with high phosphorus content, and LP4W indicates mice 4 weeks after the start of a diet with low phosphorus content (a control group). sOscar indicates mice to which a soluble human Oscar-Fc fusion protein was administered, and NS indicates mice to which physiological saline was administered in place of the soluble human Oscar-Fc fusion protein. WT (12W) indicates 12-week-old male wild-type mice fed a normal diet.

FIG. 7 shows ELISA measurement results of FGF23 in plasma. In HP, the concentration of FGF23 in plasma was higher than that in LP4W and WT (12W). The increase in the concentration of FGF23, which is a renal failure early marker in blood, was statistically significantly suppressed by administration of the soluble human Oscar-Fc fusion protein to HP (p=0.049).

As described later, qRT-PCR analysis in the bones of the 1-week model of Oscar gene mutant mice fed the diet with high phosphorus content showed that the increase in the expression of renal failure early marker FGF23 gene was significantly suppressed. In this experiment, administering the soluble human Oscar-Fc fusion protein, which has an effect of inhibiting ligand binding to Oscar, from the early stage of phosphorus overload suppressed the expression of the FGF23 gene, which is deeply involved in clinical states such as chronic kidney disease, in the bones; and further suppressed the increase in the concentration of FGF23 in plasma. This showed the potential of administering the soluble human Oscar-Fc fusion protein as a novel treatment method for improving a clinical state caused by an excess phosphorus state, such as kidney damage.

To evaluate the effect of the soluble Oscar-Fc fusion protein on kidney function, the expression of a kidney function marker was confirmed in the kidneys of HP4W NS, HP4W sOscar, and LP4W.

In the kidneys, the expression of the Fgg gene, which is a fibrinogen gene whose expression is induced by a diet with high phosphorus content, was significantly suppressed by administration of the soluble Oscar-Fc fusion protein (FIG. 19) (p=0.00071; n=5 to 6). Fibrinogen genes have been reported as kidney function markers and therapeutic targets. Thus, the results suggest that at least one disease selected from the group consisting of declined kidney function, chronic kidney disease, and renal failure, which are associated with a high-phosphorus state, can be prevented or treated by administering the soluble Oscar-Fc fusion protein.

Experimental Example I. Establishment of Oscar Gene Mutant Mice

Figure 8:
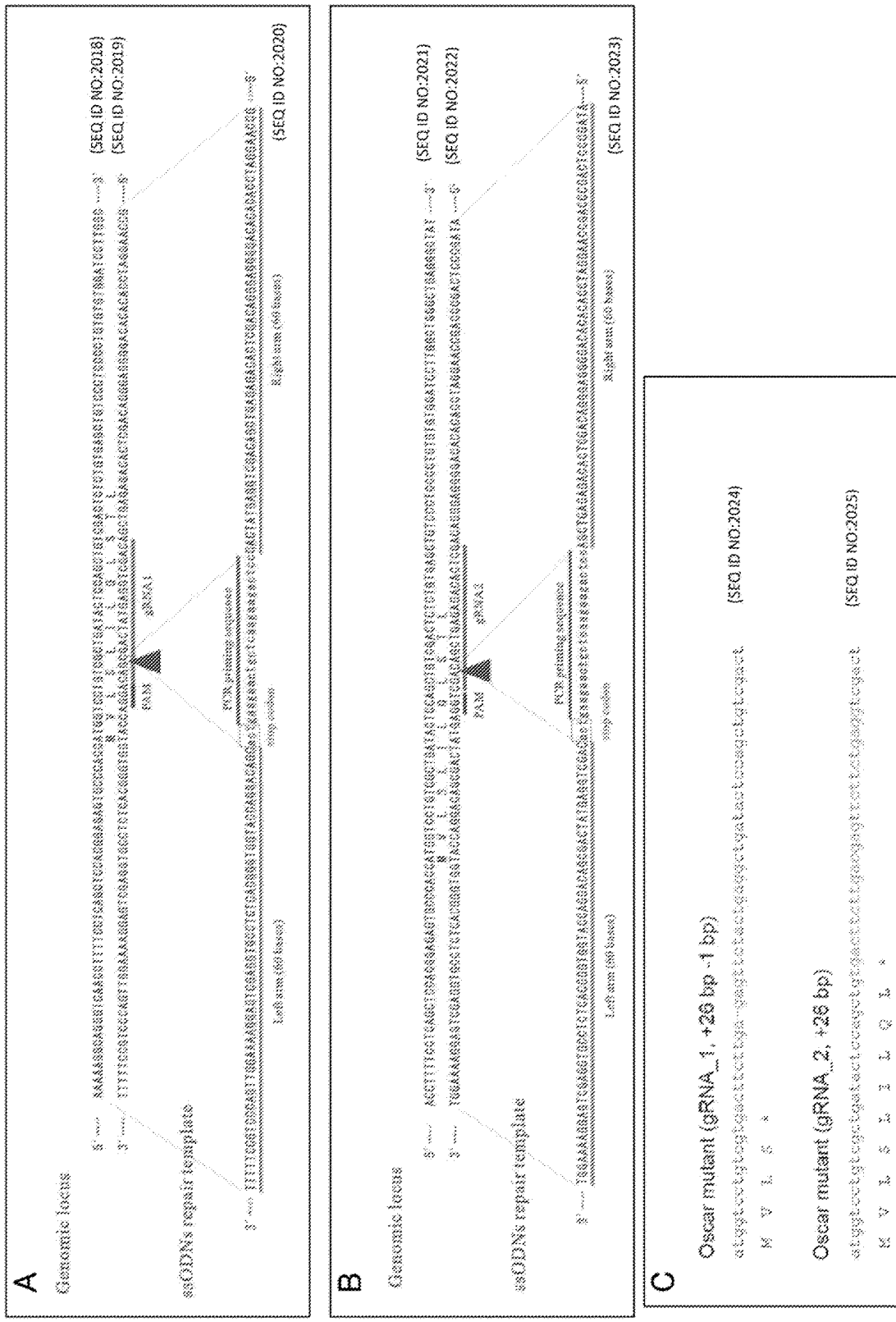
FIG. 8 shows mutation sites by CRISPR/Cas9 and sequences of ssODNs for obtaining Oscar gene mutant mice.

1. Construction of gRNA and Cas9 Expression Vector gRNA sequences (Oscar-gRNA1 and Oscar-gRNA2) were designed, and oligo DNA encoding the gRNA sequences was synthesized using an Optimized CRISPR design tool (publicly available on the website of Massachusetts Institute of Technology, Zhang Lab (http://crispr.mit.edu/)). The Oscar gene target sequences contained in these sequences are the following sequences: ACAGCTGGAGTATCAGCGAC (SEQ ID NO: 20) in Oscar-gRNA1 and GCTCACAGAGAGTCGACAGC (SEQ ID NO: 21) in Oscar-gRNA2, which are present in exon 1 of the Oscar gene. These were individually inserted into pX330-U6-Chimeric_BB-CBh-hSpCas9, which is a Cas9 expression vector (pX330-Oscar-gRNA1 and pX330-Oscar-gRNA2). The nucleotide sequences of the gRNA insertion sites in the obtained vectors were determined to confirm that gRNA was inserted as designed. In addition, single-stranded oligodeoxynucleotides (ssODNs) were individually synthesized so as to include the respective Oscar gene target sequences. The donor oligo DNA region was designed so that a stop codon is placed immediately downstream of the Serine coding sequence of the predetermined Oscar-gRNA1 cleavage site, and immediately downstream of the Leucine coding sequence of the predetermined Oscar-gRNA2 cleavage site (FIG. 8A and FIG. 8B).

ssODNs for Oscar-gRNA1:
(SEQ ID NO: 22)
GCCAAGGATCCACACACAGGGGAGGGGACAGCTCACAGAGAGTCGACA GCTGGAGTATCAGcctcagaagaactcgtcaagaagtcaCGACAGGAC

CATGGTGGGCACTCTCCGTGGAGCTGAGGAAAAGGTTGACCCTGCCTT

TTT ssODNs for Oscar-gRNA2:
(SEQ ID NO: 23)
ATAGCCCTCAGCCCAGCCAAGGATCCACACACAGGGGAGGGACAGCTC ACAGAGAGTCGAcctcagaagaactcgtcaagaagtcaCAGCTGGAGT

ATCAGCGACAGGACCATGGTGGGCACTCTCCGTGGAGCTGAGGAAAAG

GT

2. Establishment of Oscar Gene Mutant Mice pX330-Oscar-gRNA1 and pX330-Oscar-gRNA2 were individually injected into C57BL/6N Slc fertilized eggs together with the corresponding ssODNs. The fertilized eggs after the injection were injected into the oviducts of pseudopregnant ICR female mice. The genotype of the F0 mice was confirmed by PCR (for the primers, see Table 5) and direct sequencing. F1 mice were obtained by mating the F0 mice.

The genotype of each mouse was determined by direct sequencing and high-resolution melting (HRM) analyses using the primers shown in Table 5.

FIG. 8C shows the sequences of the genotypes of the obtained mutant mice.

Experimental Example II. Establishment of Disease Model Mice

1. Establishment of UNx/HPi Model Mice

UNx/HPi mice (unilateral nephrectomy—a diet with high phosphorus content-ingested mice) were obtained by feeding mice a diet with high phosphorus content after unilateral nephrectomy. As a control, mice were obtained by feeding them a diet with low phosphorus content after a sham operation.

1-1. Unilateral Nephrectomy

After mice (C57BL/6J, 8 weeks old, male) were anesthetized by intraperitoneal administration of Avertin (250 mg/kg), the skin was incised from the back. The right renal artery and vein, and ureter were ligated. After cutting on the distal side of the ligation, the right kidney was removed, and the incision was closed. The control mice were subjected to a sham operation. In the sham operation, the right renal artery and vein, and ureter were exposed, and the incision was closed without ligation. In order to wait for the mice to completely recover from operative stress, the mice were fed a 0.54% inorganic phosphorus-containing normal diet (CE-2, CLEA Japan, Inc.) for 4 weeks.

1-2. Phosphorus Overload and Collection of Tissue

From 4 weeks after the completion of the operation (12 weeks old), the unilaterally nephrectomized mice were given a diet with high phosphorus content in which contains 2% inorganic phosphorus (TD.10662, OrientalBioService, Inc.) (hereinafter also referred to as the "kidney disease group"). The sham-operated mice were given a diet with low phosphorus content in which contains 0.35% inorganic phosphorus (TD.10662 modified type, OrientalBioService, Inc.) (hereinafter also referred to as the "Sham group").

The model mice of chronic kidney disease were obtained by a modification of the method described in Hu M. C. et al. (J Am Soc Nephrol 22, 124-136, 2011). In Hu M. C. et al., the remaining kidney (left kidney) is subjected to ischemia-reperfusion injury at the time of unilateral nephrectomy in Item 1 above. However, in this modification, ischemia-reperfusion was not performed. Tissue was collected 1 week (E), 4 weeks (M), and 8 weeks (L) after the start of the a diet with high phosphorus content (the diet with low phosphorus content in the Sham group).

The animals from which the tissue was to be collected were euthanized by cervical dislocation after blood was collected from the orbit under anesthesia, and the organs and tissue (bone marrow, brain, skin, heart, kidney, liver, lung, pancreas, skeletal muscle, spleen, testis, thymus, adipose, colon, stomach, adrenal glands, aorta, eyes, ileum, jejunum, pituitary gland, skull, salivary glands, and thyroid gland) were collected. After the wet weights of the collected organs and tissue were measured, the organs and tissue were rapidly frozen in liquid nitrogen and stored at −80° C.

2. Establishment of Model of Phosphorus-Overloaded Mice 2-1. Phosphorus Overload WT mice (C57BL/6N, 7 weeks old, male) or Oscar gene mutant mice (7-16 weeks old, male/female) were fed a 0.54° inorganic phosphorus-containing normal diet (CE-2, CLEA Japan, Inc.) for 1 week. Thereafter, the mice were given a diet with high phosphorus content in which contains 2% inorganic phosphorus (TD.10662, OrientalBioService, Inc.) or a diet with low phosphorus content in which contains 0.35% inorganic phosphorus (TD.10662 modified type, OrientalBioService, Inc.) as a special phosphorus diet.

2-2. Collection of Tissue

The skull was collected at the time of the start of the special phosphorus diet fed to the WT mice (8 weeks old), 1 day, 3 days, 1 week (9 weeks old), and 4 weeks (12 weeks old) after the start. In the Oscar gene mutant mice, the skull was collected 1 week after the start of the special phosphorus diet. The animals from which the tissue was to be collected were euthanized by cervical dislocation after being anesthetized by intraperitoneal administration of Avertin (250 mg/kg), and the tissue was collected. After the weight of the collected tissue was measured, the tissue was rapidly frozen in liquid nitrogen, and stored at −80° C.

Experimental Example III. Analysis of Gene Expression in Each Tissue

1. Extraction of RNA from Each Tissue

Each cryopreserved tissue was individually homogenized in TRIzol Reagent (Thermo Fisher Scientific, MA, USA) with a PT10-35 GT Polytron homogenizer (KINEMATICA, Luzern, Switzerland) at 15,000 r.p.m. for 10 minutes; or ground with a mortar and pestle in liquid nitrogen, dried, and then homogenized in TRIzol Reagent (Thermo Fisher Scientific, MA, USA) with a PT10-35 GT Polytron homogenizer (KINEMATICA, Luzern, Switzerland) at 15,000 r.p.m. for 10 minutes; or homogenized using zirconia beads of different sizes (1.5 mm diameter×50, 3 mm diameter×5, 5 mm diameter×2) with Cell Destroyer PS1000 or PS2000 (Bio Medical Science Inc., Tokyo, Japan) at 4,260 r.p.m. for 45 seconds at 4° C. After incubation at room temperature for 5 minutes to separate proteins, 0.2 mL of chloroform was added per mL of TRIzol, and the tube was capped. Subsequently, the mixture was vortexed vigorously for 15 seconds. After the vortexing, the mixture was incubated at room temperature for 3 minutes and centrifuged at 12,000 g for 15 minutes at 4° C., and the RNA-containing aqueous layer was collected in a fresh tube. An equal amount of 70% ethanol was added to the collected aqueous layer, and mixed. Then, 700 μL of the mixture was applied to each RNeasy Mini column (Qiagen), and purified RNAs were collected according to the RNeasy Mini kit (Qiagen) standard protocol. The quality and concentration of each of the collected RNAs was evaluated by using NanoDrop (Thermo Fisher Scientific, MA, USA).

2. Analysis of RNA Expression (RNA-Seq)

(1) Obtaining RNA-Seq Data

RNA-Seq data was obtained using the samples described above by the following procedure.

a. Quality Check

Quality testing of the samples was performed based on the following items.

Concentration measurement using NanoDrop (spectrophotometer)

Concentration measurement and quality check using Agilent 2100 Bioanalyzer b. Preparation of sample A library for a HiSeq next-generation sequencer was prepared with a SureSelect Strand-Specific RNA library preparation kit in the following manner.

i. Collection of poly (A)+RNA (mRNA) from total RNA using Oligo (dT) magnetic beads
ii. Fragmentation of RNA
iii. cDNA synthesis
iv. Double-stranded cDNA synthesis
v. Terminus repair, phosphorylation, A tail addition
vi. Ligation of adapters with indices
vii. 13-cycle PCR
viii. Purification with magnetic beads c. Obtaining Data Using Next-Generation Sequencer Sequencing was performed using a HiSeq 2500 or 4000 next-generation sequencer (Illumina) in the following manner.

i. Addition of Sequencing Reagent
Reagent: TruSeq PE Cluster Kit v3-cBot-HS (1 flowcell) <PE-401-3001> (Illumina)
Reagent: TruSeq SBS Kit v3-HS (200 cycle)<FC-401-3001>
(Illumina)
ii. Single-base extension reaction
iii. Removal of unreacted bases
iv. Incorporation of fluorescent signal
v. Removal of protecting groups and fluorescence The cycle was repeated (e.g., cycle 2, cycle 3 . . . ) and these steps were carried out to 100 cycles.

vi. For the opposite strand (Read 2), i to v were carried out to 100 cycles.

(2) Analysis of RNA-Seq Data (2)-1. Analysis of Output Data Obtained Using Next-Generation Sequencer The following information processing was carried out for the output data.

i. Base calling: text data of nucleotide sequences was obtained from the output raw data of analysis (image data).

ii. Filtering: selection of read data by predetermined filtering was performed.
iii. Sorting based on index sequences: sample data was sorted based on index information.

(2)-2. Secondary Analysis of Output Data

The data file (Fastq format) obtained using an Illumina HiSeq 2500 or 4000 was uploaded on Galaxy (https://usegalaxy.org/) downloaded to a local server. Thereafter, analysis was carried out using Bowtie2 (http://bowtie-bio.sourceforge.net/bowtie2/index.shtml) to map each sequence to mouse genome map information mm10. The BAM file obtained using Bowtie2 was analyzed using Cufflinks (http://cole-trapnell-lab.github.io/cufflinks/) to calculate the FPKM (RPKM) of genes. That is, in this analysis, all RNAs expressed in each tissue were analyzed.

3. qRT-PCR

1 μg of total RNA obtained from each tissue was used as a template for cDNA synthesis, and cDNA was synthesized using Oligo dT20 primer according to the standard protocol of SuperScript III First-Strand Synthesis SuperMix (Life Technologies). After the synthesized cDNA was diluted 20-fold with TE buffer (10 mM Tris-HCl, pH 8.0, 0.1 mM EDTA), real-time PCR was performed with a LightCycler 480 II (Roche) according to the standard protocol of LightCycler 480 SYBR Green I Master (Roche, Basel, Switzerland), and Cp values were measured. The relative expression level of each gene to a reference gene was quantified by comparing the Cp value obtained for each gene with the Cp value for 32-microglobulin (B2m) as the reference gene. The primer pairs used in the real-time PCR are as shown in Table 6. All of the primers were designed by using Primer-BLAST (NCBI).

TABLE 6

| Target | Sequence | SEQ ID NO. |
| --- | --- | --- |
| Forward primer for Direct-sequence analysis | CTACTTAGCGACAACGTCCT | 24 |
| Reverse primer for Direct-sequence analysis | GCCTTGGGGTTTGAAGGTTT | 25 |
| Sequence primer for Direct-sequence analysis | CAGAGGCTATGACTGTTCCA | 26 |
| Forward primer for HRM analysis | GGCAGGGTCAACCTTTTCCT | 27 |
| Reverse primer for HRM analysis | AGGGACAGCTCACAGAGACT | 28 |
| Forward primer: B2m | GCTCGGTGACCCTGGTCTTT | 29 |
| Reverse primer: B2m | AATGTGAGGCGGGTGGAACT | 30 |
| Forward primer: Oscar | CGGGCATGAGTTTTGCACTG | 31 |
| Reverse primer: Oscar | TGGGTATAGTCCAAGGAGCCA | 32 |
| Forward primer: Fgf23 | AGGAGCCATGACTCGAAGGT | 33 |
| Reverse primer: Fgf23 | GCTCACCAGGTAGTGATGCTT | 34 |

4. Analysis of Differentially Expressed Genes

To extract differentially expressed genes, the number of annotation reads of each transcript in sequence data mapped by Bowtie2 was counted by using HTSeq-count (parameter: -r was pos, and -s was no). The obtained results were analyzed by DESeq2 (Love, M. I., Huber, W. & Anders, S.; Genome biology 15, 550, doi:10.1186/s13059-014-0550-8 (2014)) with default settings. Expression differences were compared in E-UNx/HPi vs. E-/M-/L-Sham (n=3), M-UNx/HPi vs. E-/M-/L-Sham (n=3), and L-UNx/HPi vs. E-/M-/L-Sham (n=3). Gene ontology (GO) enrichment analysis was performed using R package "topGO." In the gene ontology (GO) enrichment analysis, the case in which the result of the DESeq2 analysis is 1 or more and the p-value is less than 0.05 was defined as "$\log_2$ (fold-change)."

5. Statistical Analysis

In statistical analysis, Student's t-test or one-way analysis of variance was performed, and then significant differences were determined by the Tukey-Kramer test. The case in which the p-value is less than 0.05 was defined as being significant (* $p<0.05$,  $p<0.01$, and * $p<0.001$). In the scatter plots, the average value is indicated by a horizontal line.

6. Results

Figure 9:
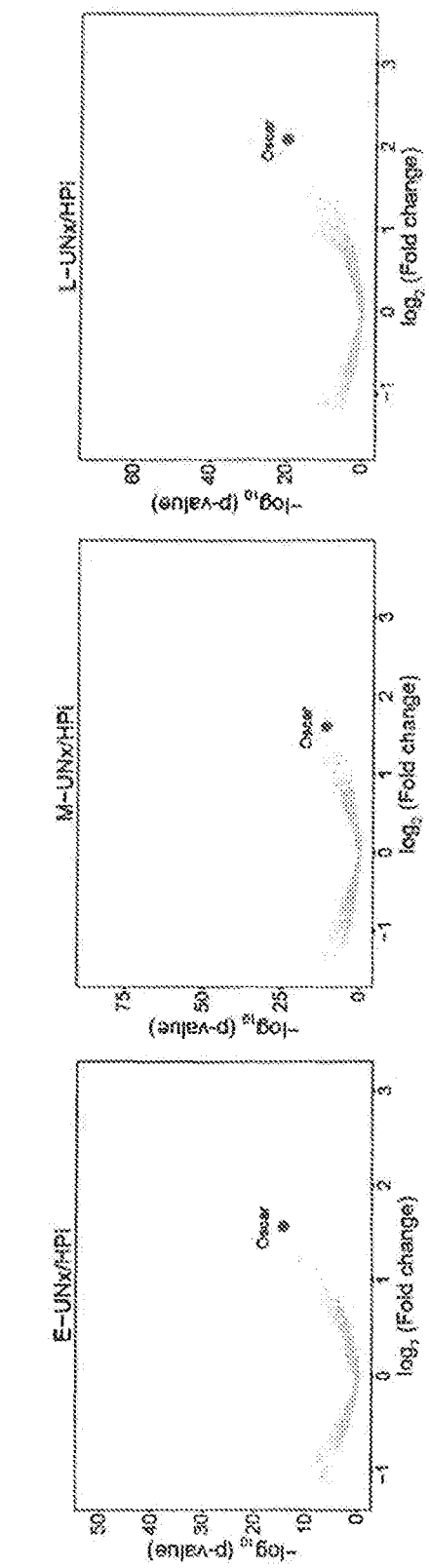
FIG. 9 shows volcano plots in the skull 1 week (E), 4 weeks (M), and 8 weeks (L) after the start of a diet with high phosphorus content in UNx/HPi model mice (a diet with low phosphorus content in a Sham group).
Figure 10:
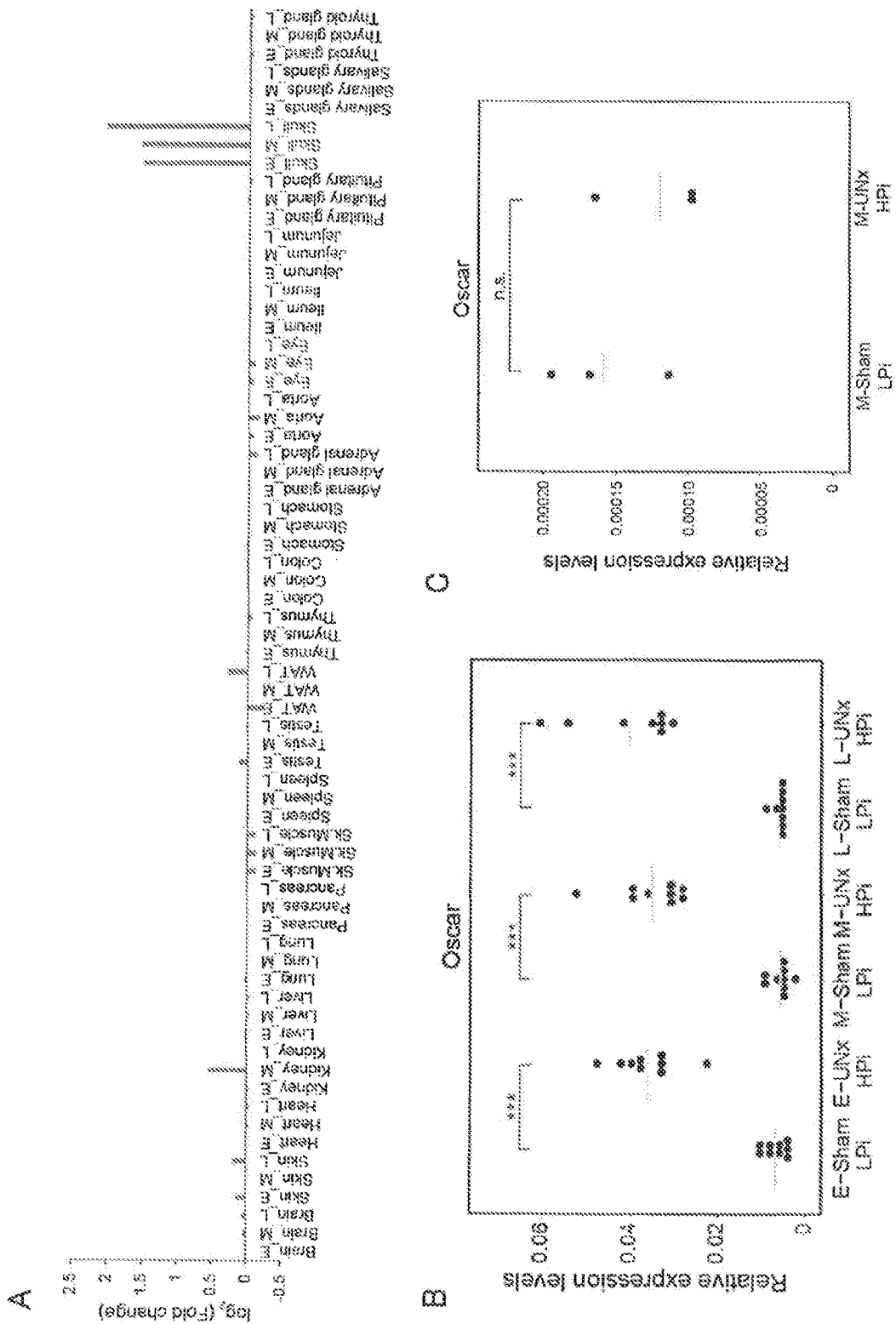
FIG. 10A shows DESeq analysis results of expression of Oscar gene in each tissue.
FIG. 10B shows results of expression of Oscar mRNA in the UNx/HPi model mice and sham mice at E, M, and L examined by qRT-PCR.
FIG. 10C shows results of the expression of Oscar gene in the kidneys confirmed by qRT-PCR. In the graphs, *** indicates $p<0.001$, and n.s. indicates no significant difference.

FIG. 9 shows volcano plots in the skull 1 week (E-UNx/HPi), 4 weeks (M-UNx/HPi), and 8 weeks (L-UNx/HPi) after the start of the diet with high phosphorus content. Each mRNA after DESeq analysis was plotted as a small dot, and Oscar was indicated by a large dot. The expression of the Oscar gene increased in the UNx/HPi model mice (HPi) at E-UNx/HPi, M-UNx/HPi, and L-UNx/HPi compared with that in the sham-operated mice (LPi). FIG. 10A shows DESeq analysis results of expression of the Oscar gene in each tissue. The Oscar gene showed high expression in the skull of the UNx/HPi model at E-, M-, and L-. This result was confirmed by qRT-PCR (n=8 to 9). As a result, it was revealed that the expression of the Oscar gene increased in the skull in the UNx/HPi model mice (HPi) at E-UNx/HPi, M-UNx/HPi, and L-UNx/HPi compared with that in the sham-operated mice (LPi) (FIG. 10B). The expression of the Oscar gene slightly increased in the kidney in the DESeq analysis; however, no significant difference was observed in confirmation by qRT-PCR (FIG. 10C).

Figure 11:
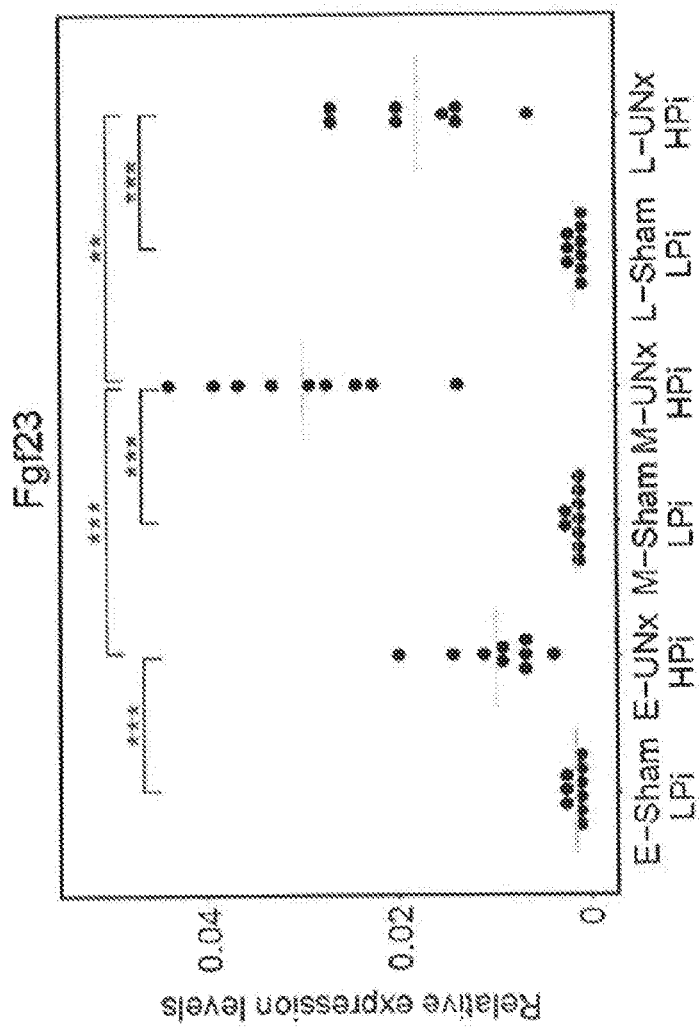
FIG. 11 shows results of expression of FGF23 gene in the skull confirmed by qRT-PCR. In the graph,  indicates $p<0.01$, and * indicates $p<0.001$.

FGF23 is a master regulator of inter-organ cross talk between the parathyroid glands, bones, and kidneys in kidney disease. The expression of the FGF23 gene in the skull increased in the UNx/HPi model mice (HPi) at E-UNx/HPi, M-UNx/HPi, and L-UNx/HPi, compared with that in the sham-operated mice (LPi) (FIG. 11).

Figure 12:
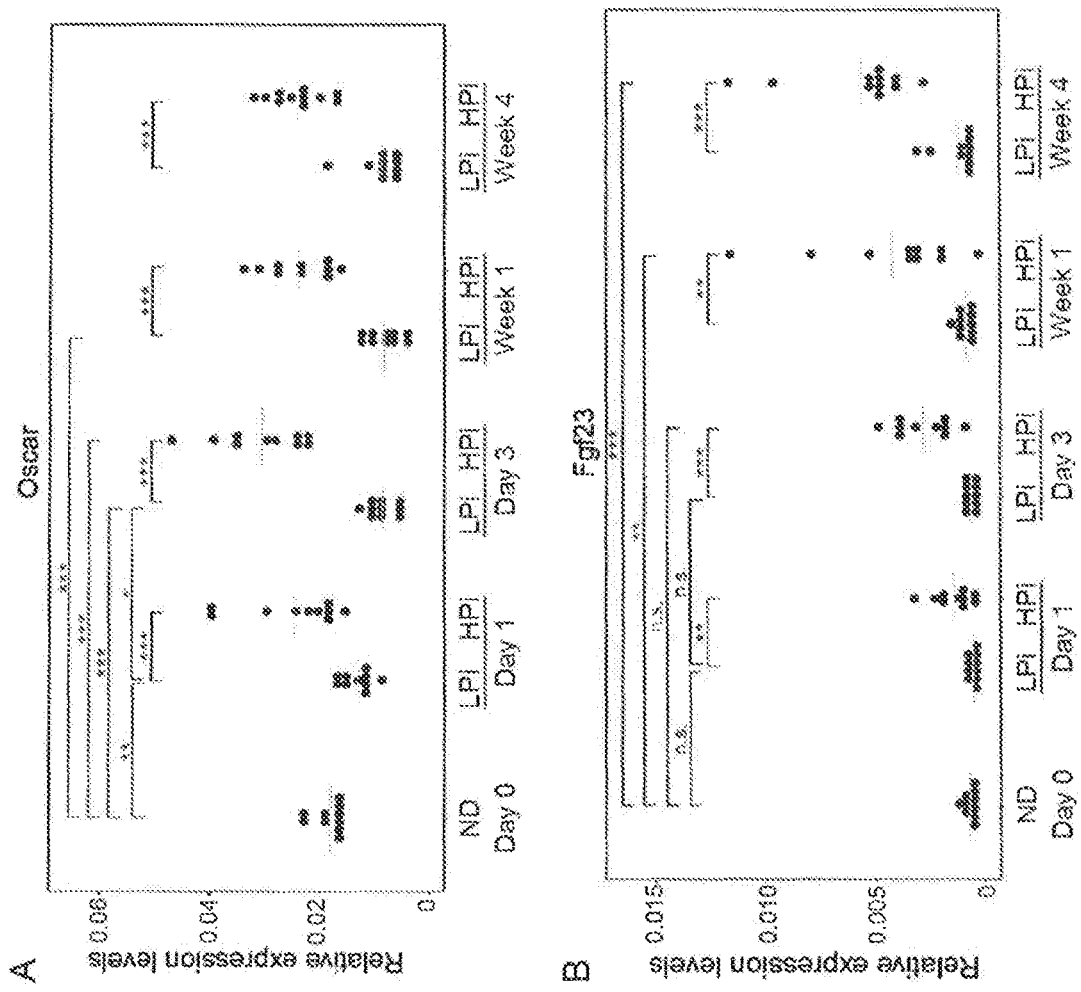
FIG. 12A shows the expression of Oscar gene in the skull 1 day, 3 days, 1 week, and 4 weeks after switching from a normal diet to a diet with low phosphorus content or a diet with high phosphorus content.
FIG. 12B shows the expression of FGF23 gene in the skull 1 day, 3 days, 1 week, and 4 weeks after switching from a normal diet to a diet with low phosphorus content or a diet with high phosphorus content. In the graphs, indicates $p<0.05$,  indicates $p<0.01$, * indicates $p<0.001$, and n.s. indicates no significant difference.

Next, the expression of the Oscar gene and the FGF23 gene over time after the feed of the mice was switched from the noLnLal diet to the diet with low phosphorus content or the diet with high phosphorus content was examined in the skull. FIG. 12A shows the expression of the Oscar gene in the skull 1 day, 3 days, 1 week, and 4 weeks after switching to the diet with low phosphorus content or the diet with high phosphorus content. FIG. 12B shows the expression of the FGF23 gene 1 day, 3 days, 1 week, and 4 weeks after switching to the diet with low phosphorus content or the diet with high phosphorus content. The expression of the Oscar gene and the FGF23 gene already increased in the skull on day 1 after switching to the diet with high phosphorus content. Because the p-value was lower in Student's t-test, the expression of the Oscar gene increased more robustly than the expression of the FGF23 gene. After the feed was switched from the normal diet to the diet with low phosphorus content, the expression level of the Oscar gene significantly decreased, whereas the expression level of the FGF23 gene was unchanged. After peaking 3 days following the switch to the diet with high phosphorus content, the expression of the Oscar gene showed a tendency to gradually cease to increase. In contrast, the expression of the FGF23 gene gradually increased as the period of the diet with high phosphorus content lengthened. These results showed that the expression of the Oscar gene reflects phosphorus intake more strongly and more sensitively than the expression of FGF23.

Figure 13:
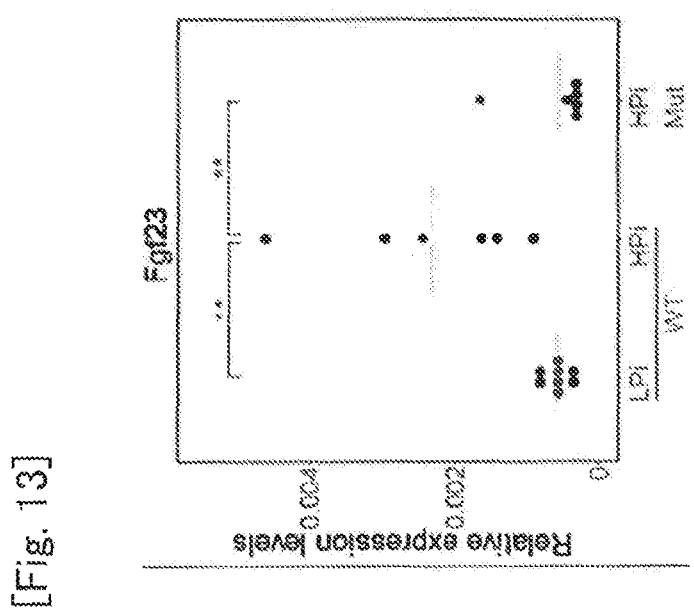
FIG. 13 shows the expression of FGF23 in the bones of normal mice and Oscar gene mutant mice fed a diet with high phosphorus content. ** indicates $p<0.01$.

Further, what effect an increase in the expression of Oscar in the bones has on the expression of FGF23 in the bones was examined. The Oscar gene mutant mice obtained in Item I. above were fed a diet with high phosphorus content, and the expression of FGF23 in the bones was examined by qRT-PCR. The results revealed that the expression of FGF23 did not increase in the bones of the Oscar gene mutant mice even if they were fed the diet with high phosphorus content, as shown in FIG. 13.

The above results showed that Oscar up-regulates the expression pathway of FGF23. This indicated that suppressing the functional expression of Oscar enables suppression of the functional expression of FGF23, and further that suppressing the functional expression of Oscar enables control of disease associated with FGF23.

Experimental Example IV: Measurement of Creatinine in Plasma

Mice (C57BL/6N, 8 weeks old, male) were fed a diet with high phosphorus content in which contains 2% inorganic phosphorus (TD.10662, OrientalBioService, Inc.) or a diet with low phosphorus content in which contains 0.35% inorganic phosphorus (TD.10662 modified type, OrientalBioService, Inc.) as a special phosphorus diet for 4 weeks. Thereafter, plasma samples (LP4W, HP4W) were collected and cryopreserved. A plasma sample (WT (12W)) was collected from 12-week-old male mice (C57BL/6N) fed a normal diet, and cryopreserved. 8-week-old male mice (C57BL/6N) were subjected to unilateral nephrectomy, and after being adapted for 4 weeks, the mice were fed a diet with high phosphorus content for 4 weeks. Thereafter, a plasma sample (UNx/HP4W) was collected and cryopreserved. Creatinine values in plasma were measured using 100 μl of each sample by an enzymatic method.

Figure 14:
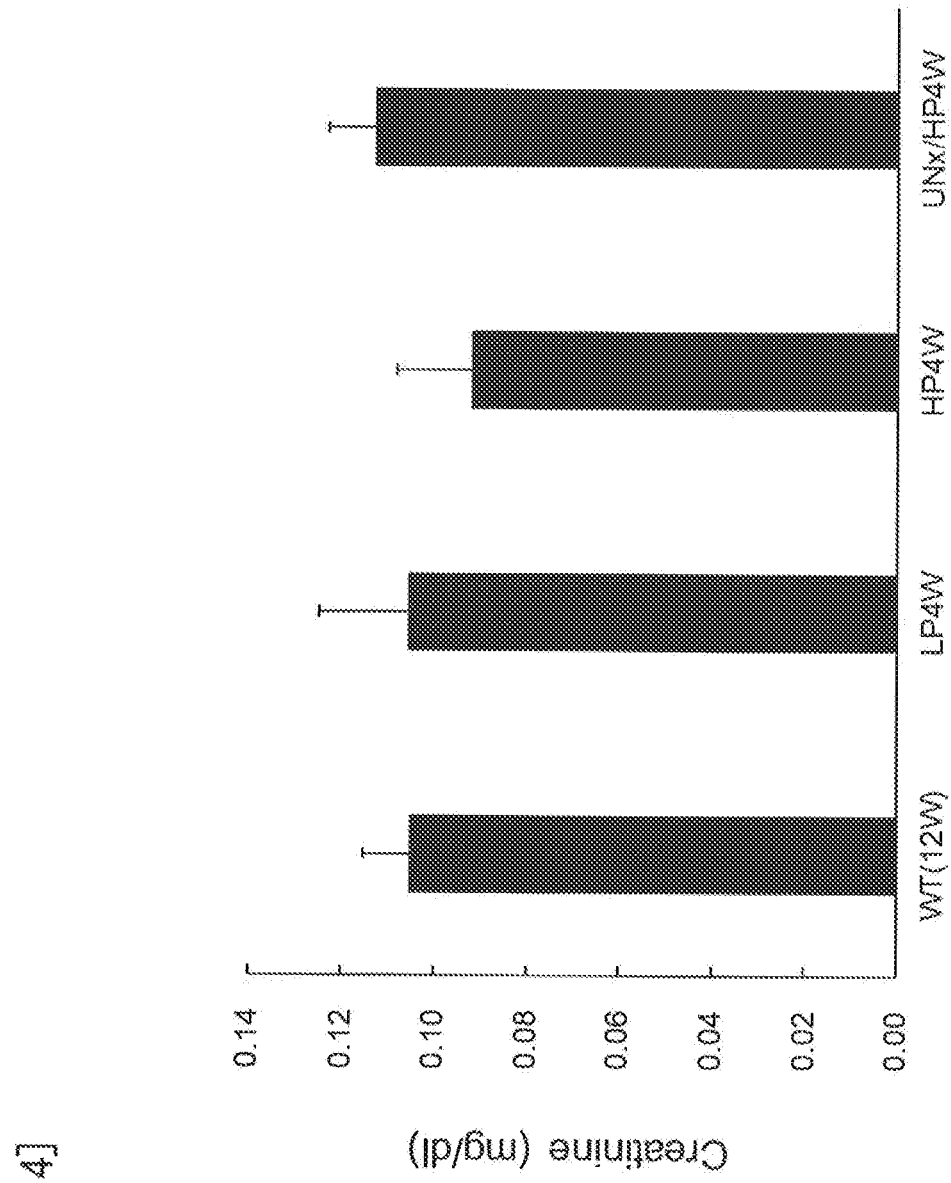
FIG. 14 shows the concentration of creatinine in plasma. HP4W indicates mice 4 weeks after the start of a diet with high phosphorus content, and LP4W indicates mice 4 weeks after the start of a diet with low phosphorus content (a control group). WT (12W) indicates 12-week-old male wild-type mice fed a normal diet. UNx/HP4W indicates UNx/HPi model mice 4 weeks after the start of a diet with high phosphorus content.

FIG. 14 shows a creatinine value in plasma in each model of phosphorus overload. In the HP4W model and the UNx/HP4W model, the amount of creatinine, which is a blood marker of renal failure, did not increase.

From the fact that the expression of PRPs and Fgg increased in the HP4W model and the UNx/HP4W model, it was believed that measuring PRPs and Fgg enables detection of declined kidney function earlier than the amount of creatinine in blood increases. Therefore, it was believed that a decline in kidney function can be suppressed in an early stage by administering the soluble human Oscar-Fc fusion protein at a stage when the amount of creatinine has not yet increased, and when PRPs and Fgg are increased.

Reference Example 1: Expression of PRPs in Model of Phosphorus-Overloaded Mice

1. Establishment of Model of Phosphorus-Overloaded Mice

Mice (C57BL/6, 7 weeks old, male) that had not been subjected to unilateral nephrectomy were fed a 0.54% inorganic phosphorus-containing normal diet (CE-2, CLEA Japan, Inc.) for 1 week. Thereafter, the mice were given a diet which contains 2% inorganic phosphorus (TD.10662, OrientalBioService, Inc.) as a diet with high phosphorus content or a diet which contains 0.35% inorganic phosphorus (TD.10662 modified type, OrientalBioService, Inc.) as a diet with low phosphorus content. In each group, n=10.

2. Analysis of Proline-Rich Protein (PRP) Gene Expression in Salivary Glands (1) Collection of Tissue The salivary glands and skull were collected 1 week (9 weeks old) and 4 weeks (12 weeks old) after the start of the diet with high phosphorus content or the diet with low phosphorus content in the mice. Regarding the salivary glands, the submandibular glands, sublingual glands, parotid glands, and surrounding connective tissue (including lymph nodes) were separately collected individually. The animals from which the tissue was to be collected were euthanized by cervical dislocation after being anesthetized by intraperitoneal administration of Avertin (250 mg/kg), and the tissue was collected. After the weight of the collected tissue was measured, the tissue was rapidly frozen in liquid nitrogen, and stored at −80° C.

(2) Analysis of RNA i. Extraction of RNA from Each Tissue

Each cryopreserved tissue was individually homogenized in TRIzol Reagent (Life Technologies) with a Cell Destroyer PS1000 (Bio Medical Science Inc.). After incubation at room temperature for 5 minutes to separate proteins, 0.2 mL of chloroform was added per mL of TRIzol, and the tube was capped. Subsequently, the mixture was vortexed vigorously for 15 seconds. After the vortexing, the mixture was incubated at room temperature for 3 minutes and centrifuged at 12,000 g for 15 minutes at 4° C., and the RNA-containing aqueous layer was collected in a fresh tube. An equal amount of 70% ethanol was added to the collected aqueous layer, and mixed. Then, the mixture was applied to an RNeasy Mini column (Qiagen), and purified RNAs were collected according to the RNeasy Mini kit (Qiagen) standard protocol. The quality and concentration of each of the collected RNAs was evaluated by 1% agarose electrophoresis and NanoDrop.

ii. cDNA Synthesis and Quantifying Relative Expression Level by Real-Time PCR

1 μg of total RNA obtained from each tissue was used as a template for cDNA synthesis, and cDNA was synthesized using Oligo dT20 primer according to the standard protocol of SuperScript III First-Strand Synthesis SuperMix (Life Technologies). After the synthesized cDNA was diluted 20-fold with TE buffer (10 mM Tris-HCl, pH 8.0, 0.1 mM EDTA), real-time PCR was performed with a LightCycler 480 II (Roche) according to the standard protocol of Light-Cycler 480 SYBR Green I Master (Roche), and Cp values were measured. The relative expression level ($2^{-\Delta Cp}$) of each gene to a reference gene was quantified by comparing the Cp value obtained for each gene with the Cp value for β2-microglobulin (B2m) or Maea as the reference gene. The expression of PRP genes (PRPs: Prb1, Prh1, Prp2, Prpmp5) was examined in each salivary gland tissue, and the expression of FGF23 was examined in the skull. The primer pairs used in the real-time PCR are as shown in Table 5.

(3) Results

Figure 15:
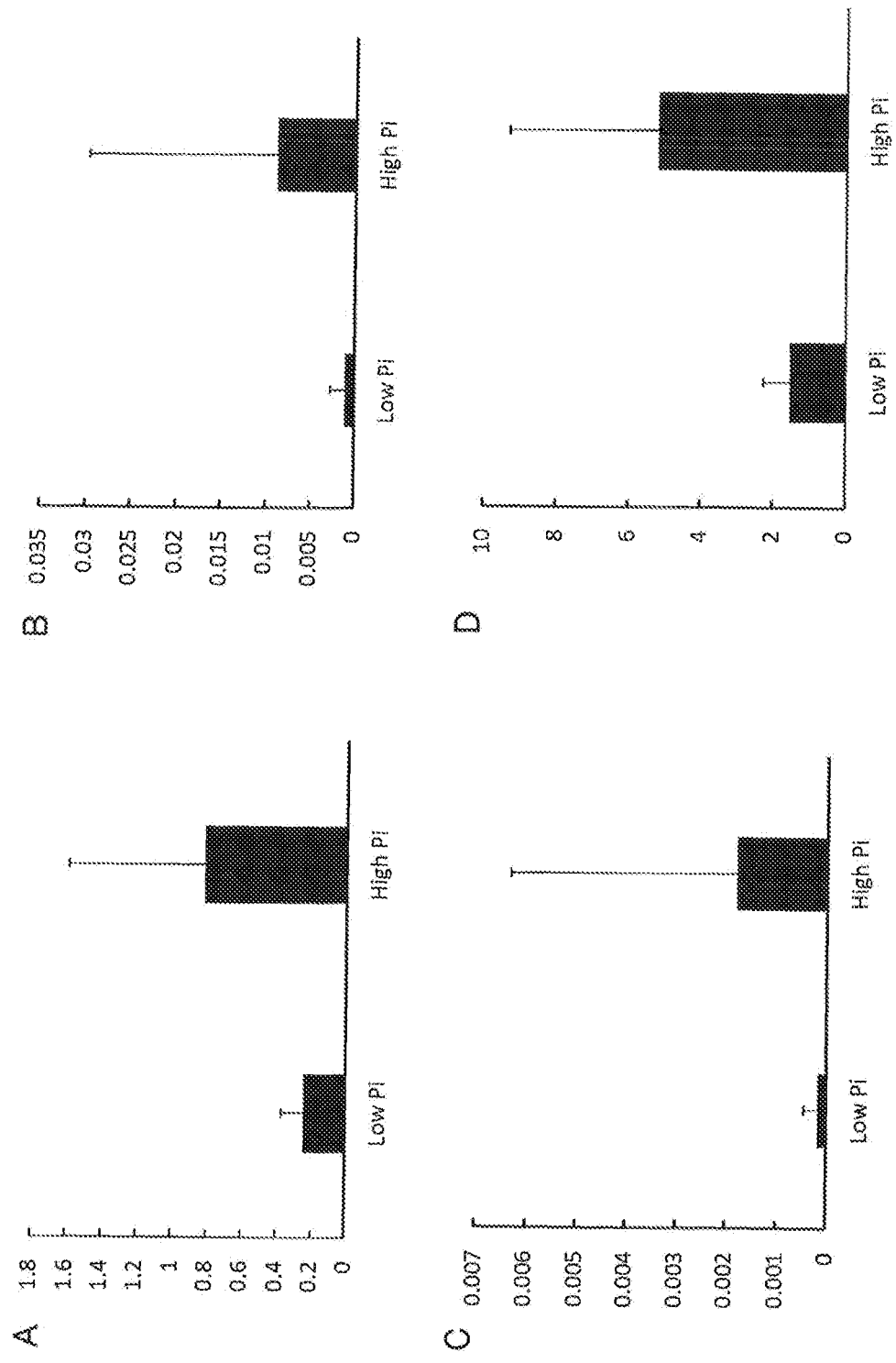
FIG. 15 shows the expression levels of PRPs in the salivary glands of a group that ingested a diet with high phosphorus content (High Pi) and a group that ingested a diet with low phosphorus content (Low Pi). A: Prb1, B: Prh1, C: Prp2, and D: Prpmp5.

As shown in FIG. 15, the expression levels of Prb1 (FIG. 15A), Prh1 (FIG. 15B), Prp2 (FIG. 15C), and Prpmp5 (FIG. 15D) were increased in the parotid glands in the group ingested the diet with high phosphorus content (High Pi) compared with those in the group ingested the diet with low phosphorus content (Low Pi).

Example 3: Expression of PRPs in Subject Who Ingested Diet with High Phosphorus Content (1) Subject Subjects were selected according to the following inclusion criteria.

i. Person who is able to fully understand this study plan, and is able to give consent by themselves
ii. Person aged 20 years or older at the time of obtaining consent However, persons who meet any of the following criteria were excluded from the subjects.

i. Person with a history of kidney disease to date
ii. Person having a cardiovascular risk factor (obesity, high blood pressure, diabetes, smoking)
iii. Person who is deemed unsuitable as a subject by a researcher (2) Diet with High Phosphorus Content Ingestion A diet with high phosphorus content group (group A) was asked to ingest a diet with high phosphorus content in addition to a normal diet. A normal diet group (group B) was a subject group that ingests a normal diet; the normal diet group was, however, asked to ingest as few phosphorus-rich foods as possible.

Both group A and group B were asked to refrain from ingesting phosphorus-rich foods (foods listed in Table 7) as much as possible from Day −7. Group A was asked to select one of the dietary patterns shown in Table 8, and ingest the diet from Day 1 for 7 days. Group B was asked to ingest a normal diet (refrain from ingesting phosphorus-rich foods as much as possible). Table 9 shows the diet and saliva collection schedule.

TABLE 7

| |
| --- |
| Fish and shellfish |
| dried whitebait, dried small sardine, sardine, sand lance, splendid alfonsino, ayu (sweetfish), smelt, eel, dried squid, dried shrimp, salmon roe, cod roe, sea urchin, etc. |
| Pulses |
| freeze-dried tofu, soybean, soybean flour, pea, fermented soybean, etc. |
| Dairy products |
| processed cheese, skim milk powder, milk, etc. |
| Flesh |
| egg yolk, beef jerky, liver, etc. |
| Nuts |
| sesame, pine nut, cashew nut, almond, pistachio, peanut, walnut, etc. |
| Processed foods rich in inorganic phosphorus as a food additive |
| pastry, instant noodles, Chinese noodles, confectionery (biscuit, cookie)/seasoning for sprinkling over rice, rice ball containing solid ingredients, take-out meal in a box, savory bread, instant Chinese noodles, ham/sausage, bacon, frozen food, hamburger steak, fish meat/fish-paste product, food boiled in soy sauce, pastry, biscuit, cookie, carbonated drink, etc. |
| Processed foods in which the following are indicated as ingredients |
| lye water (potassium phosphate, sodium phosphate) |
| yeast food (phosphoric acid salt) |
| emulsifier etc. |
| leavening agent (calcium phosphate) |
| binding agent (phosphoric acid salt, potassium polyphosphate) |
| agent for quality improvement (sodium polyphosphate) |

TABLE 8

| Pattern A | Drink | Skim milk (Megmilk Snow Brand Mainichi Honebuto*) | 1 L (powder: 96 g) | 960 mg |
| --- | --- | --- | --- | --- |
| Pattern B | Side dish | 6P cheese (Megmilk Snow Brand*) | 18 g × 6 pieces | 800 mg |
| | Snack between meals | One of snacks a to c | | 200 mg |
| Pattern C | Staple food | Cup Noodles* (Nissin*) | 1 | 120 mg |
| | Drink | Skim mik (Megmilk Snow Brand Mainichi Honebuto*) | 500 ml (powder: 48 g) | 480 mg |
| | Side dish | 6P cheese (Megmilk Snow Brand*) | 18 g × 3 pieces | 400 mg |
| Pattern D | Drink | Skim milk (Megmilk Snow Brand Mainichi Honebuto*) | 500 ml (powder: 48 g) | 480 mg |
| | Side dish | 6P cheese (Megmilk Snow Brand*) | 18 g × 3 pieces | 400 mg |
| | Snack between meals | One of snacks a to c | | 200 mg |

Snack a: popcorn (Seven & i), one bag (90 g)
Snack b: chocolate bar (Meiji Milk Chocolate), two bars (116 g)
Snack c: Glico Pucchin Purin* (pudding), 67 g × 3 (201 g)
The asterisk (*) indicates a registered trademark.

TABLE 9

| | Day −7 | Day −6 | Day −5 | Day −4 | Day −3 | Day −2 | Day −1 | Day 1 | Day 2 | Day 3 | Day 4 | Day 5 | Day 6 | Day 7 |
|---|---|---|---|---|---|---|---|---|---|---|---|---|---|---|
| Group A (high-phosphorus diet group) | ⇐ Ingest as few phosphorus-rich foods as possible ⇒ | | | | | | | ⇐ normal diet + high-phosphorus diet ⇒ | | | | | | |
| Group B (normal diet group) | ⇐ Ingest as few phosphorus-rich foods as possible ⇒ | | | | | | | ⇐ Ingest as few phosphorus-rich foods as possible ⇒ | | | | | | |
| Saliva collection | — | — | — | — | — | — | ○ | ○ | — | ○ | — | ○ | — | ○ |
| Diet record | ○ | ○ | ○ | ○ | ○ | ○ | ○ | ○ | ○ | ○ | ○ | ○ | ○ | ○ |

(3) Preparation of saliva sample

Saliva was collected with a Saliva Collection Aid (SCA) (Salimetrics LLC, Carlsbad, Calif.) on Days −1, 1, 3, 5, and 7. The collected saliva was stored in a freezer before measurement.

The saliva was stored in the freezer until measurement after collection from the subjects. At the time of measurement, the cryopreserved saliva was thawed, and part of the saliva was transferred to a 1.5-mL tube, followed by centrifugation at 1,000 g for 15 minutes at 4° C. After the centrifugation, the supernatant was collected, and PRPs in saliva samples obtained by diluting the supernatant 100- to 800-fold (hPRH2) or 10,000- to 80,000-fold (hPRB1, hPRB2) in phosphate buffer (PBS) were quantified by ELISA.

(4) ELISA Protocol

The concentrations of human PRPs in each saliva sample were measured by using ELISA kits sold by Cloud-Clone Corp. (SED810Hu (for detection of hPRB1), SED809Hu (for detection of hPRB2), SED812Hu (for detection of hPRH2)).

100 µl of the saliva sample or a sample for a calibration curve containing a recombinant protein in a predetermined amount, which is supplied with each kit, was added to each well of an ELISA plate supplied with the kit. The plate containing the sample was sealed, followed by incubation at 37° C. for 2 hours. After the incubation, the sample in each well was aspirated and discarded, and 100 µl of Detection Reagent A containing a biotin-labeled antibody prepared according to the kit protocol was added to each well. The plate was sealed, followed by incubation at 37° C. for 1 hour. After the incubation, the solution in each well was aspirated and discarded, and each well was washed three times with a wash solution. After the wash solution was thoroughly removed, 100 µl of Detection Reagent B containing enzyme-labeled avidin prepared according to the kit protocol was added to each well. The plate was sealed, followed by incubation at 37° C. for 30 minutes. After the 30 minutes, the solution in each well was aspirated and discarded, and each well was washed five times with a wash solution. After the wash solution was thoroughly removed, 90 µl of a substrate solution supplied with the kit was added to each well. The plate was sealed, followed by incubation at 37° C. for 20 minutes (hPRB1, hPRB2) or 40 minutes (PRH2). Thereafter, 50 µl of a reaction stop solution supplied with the kit was added to each well, and absorbance at 450 nm was measured with an absorbance microplate reader (Multiskan GO, Thermo Fisher Scientific Inc.). The concentration of each protein, i.e., the concentration of each of PRPs in the saliva, was calculated by making a calibration curve using each recombinant protein supplied with the kit.

(5) Results

Figure 16:
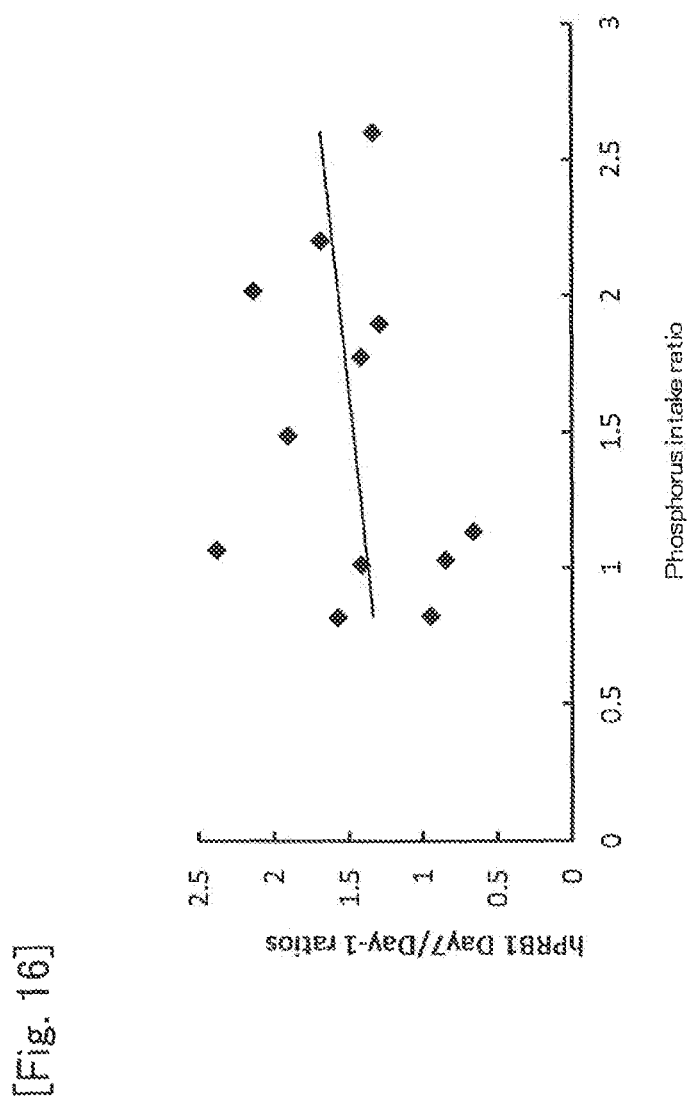
FIG. 16 shows the ratios of the concentrations of hPRB1 in saliva on the final day of a test (Day 7) divided by the concentrations of hPRB1 in saliva one day before the start of the test (Day −1) in group A and group B (hPRB1 Day 7/Day −1 ratios). "Phosphorus intake ratio" is a ratio of the total phosphorus intake for 7 days after the start of the diet with high phosphorus content (or normal diet) ingestion test divided by the total phosphorus intake for 7 days before the start of the diet with high phosphorus content (or normal diet) ingestion test.

FIG. 16 shows the ratios of the concentrations of hPRB1 in saliva on the final day of the test (Day 7) divided by the concentrations of hPRB1 in saliva on one day before the start of the test (Day −1) in group A and group B (hPRB1 Day7/Day−1 ratios).

Phosphorus intake was calculated from the ingested diets. "Phosphorus intake ratio" in FIG. 16 is a ratio of the total phosphorus intake for 7 days after the start of the diet with high phosphorus content (or normal diet) ingestion test divided by the total phosphorus intake for 7 days before the start of the diet with high phosphorus content (or normal diet) ingestion test. In subjects showing a high phosphorus intake ratio (subjects who ingested the diet with high phosphorus content), the amount of hPRB1 in saliva increased. This indicates that PRPs reflect kidney function and phosphorus intake.

Reference Example 2: Expression of PRPs in Patient with Kidney Disease (1) Subject Subjects were selected according to the following inclusion criteria.

i. Patient diagnosed with chronic kidney disease or diabetic nephropathy
  Regarding chronic kidney disease, patient in GFR category G3 to G5
  Regarding diabetic nephropathy, patient in clinical stage 1 to 3
  Patient with multiple myeloma and at risk for kidney disease Alternatively, healthy subject (including subject at risk for lifestyle-related disease)
ii. Person who is able to fully understand this study plan, and is able to give consent by themselves
iii. Person aged 20 years or older at the time of obtaining consent However, persons who meet any of the following criteria were excluded from the subjects.

i. Person who is deemed unsuitable as a subject by a researcher
ii. HBs antigen-positive person, HCV antibody-positive person
iii. Subject undergoing dialysis Table 10 shows clinical data of subjects diagnosed with chronic kidney disease or diabetic nephropathy.

TABLE 10

| | Subject No. | | | | | | Reference value | Unit |
|---|---|---|---|---|---|---|---|---|
| | 1 | 2 | 3 | 4 | 5 | 6 | | |
| Underlying disease | CKD | MM | MM | CKD | CKD | CKD | | |
| Notes | MDS, ML | | | ML | MDS | MDS | | |
| Body height | 166.8 | 147.7 | 167.8 | 156.3 | 152.2 | 160.7 | | |
| Body weight | 61.6 | 55.2 | 65.4 | 55.2 | 53.2 | 60.8 | | |
| BMI | 22.14 | 25.3 | 23.28 | 22.6 | 26.67 | 23.16 | | |
| Age | 72 | 77 | 72 | 81 | 85 | 75 | | |
| Sex | M | M | M | M | M | M | | |
| Blood pressure | 106/52 | 122/64 | 120/82 | 125/80 | 138/75 | 113/59 | | |
| Blood cell count | | | | | | | | |
| WBC | 1500 | 3100 | 5600 | 6300 | 2900 | 1300 | 3400-8600 | /µl |
| RBC | 262 | 242 | 302 | 351 | 328 | 237 | 429-571(M), 369-491(F) | ×10^4/µl |
| Hb | 9 | 7.6 | 9.6 | 10.9 | 9 | 7.4 | 13.4-17.1(M), 11.4-15.1(F) | g/dl |
| Ht | 26.5 | 23.7 | 29.9 | 33.5 | 29.7 | 23.2 | 39.9-50.1(M), 34.9-45.1(F) | % |
| Plt | 0.4 | 0.8 | 21.7 | 22.8 | 3.1 | 1.8 | 14.9-35.1 | ×10^4/µl |
| Biochemical data | | | | | | | | |
| GOT | 16 | 10 | 19 | 20 | 23 | 19 | 13-33 | U/L |
| GPT | 13 | 15 | 32 | 24 | 12 | 14 | 6.0-27 | U/L |
| γGTP | 15 | 35 | 16 | 49 | 18 | 30 | 10-47 | U/L |
| Neutral fat | 186 | 96 | 157 | 165 | 101 | 199 | 30-149 | mg/dl |
| HDL-Chol | 39.5 | 50.8 | 52.4 | 50.4 | 47 | 24 | 40-96 | mg/dl |
| LDL-Chol | 93 | 63 | 70 | 104 | 90 | 86 | 70-139 | mg/dl |
| Creatinine | 2.05 | 0.85 | 1.19 | 1.27 | 1.31 | 1.12 | 0.4-0.7 | mg/dl |
| eGFR | 25.9 | 66.6 | 47 | 42.3 | 40.3 | 49.6 | | |
| Inorganic P | 3.8 | 3.5 | 4.5 | 3.1 | 3.6 | 2.6 | 2.5-4.7 | mg/dl |
| BUN | 23.9 | 23.1 | 22.3 | 19.7 | 37.6 | 12.3 | 8.0-22 | mg/dl |
| Albumin | 3.3 | 3.4 | 3 | 3.7 | 3.8 | 2.7 | 4.0-5.0 | mg/dl |
| FGF23 (serum) | 162 | 33 | 122 | 12 | 69 | 46 | ?? | pg/ml |
| Fasting blood sugar | 89 | 79 | 102 | 77 | 109 | 89 | 70-109 | mg/dl |
| HbA1c (NGSP) | 5.8 | 5.7 | 6.2 | 6 | 5.4 | 6.2 | 4.6-6.2 | % |
| Urinary protein | — | 2+ | — | — | — | — | | |
| Urinary sugar | — | — | — | — | — | — | | |
| L-FABP (urine) concentration | 9.26 | 106.82 | 1.77 | 4.42 | 2.84 | 9.76 | ?? | ng/ml |
| L-FABP in terms of creatinine | 13.35 | 177.41 | 2.37 | 7.93 | 4.94 | 19.06 | 8.4 or less | µg/gCr |
| hPrb1 in saliva | 145.9 | 472.8 | 1018.1 | 904.1 | 602.2 | 1013.6 | | µg/ml |

CKD: chronic kidney disease,
MM: multiple myeloma,
MDS: myelodysplastic syndrome,
ML: malignant lymphoma (2) Measurement of hPRB1

The concentration of hPRB1 in saliva of each subject was measured according to the methods of Example 3 (3) and (4).

Statistical Analysis was Performed by Using Student's t-Test.

(3) Results

Figure 17:
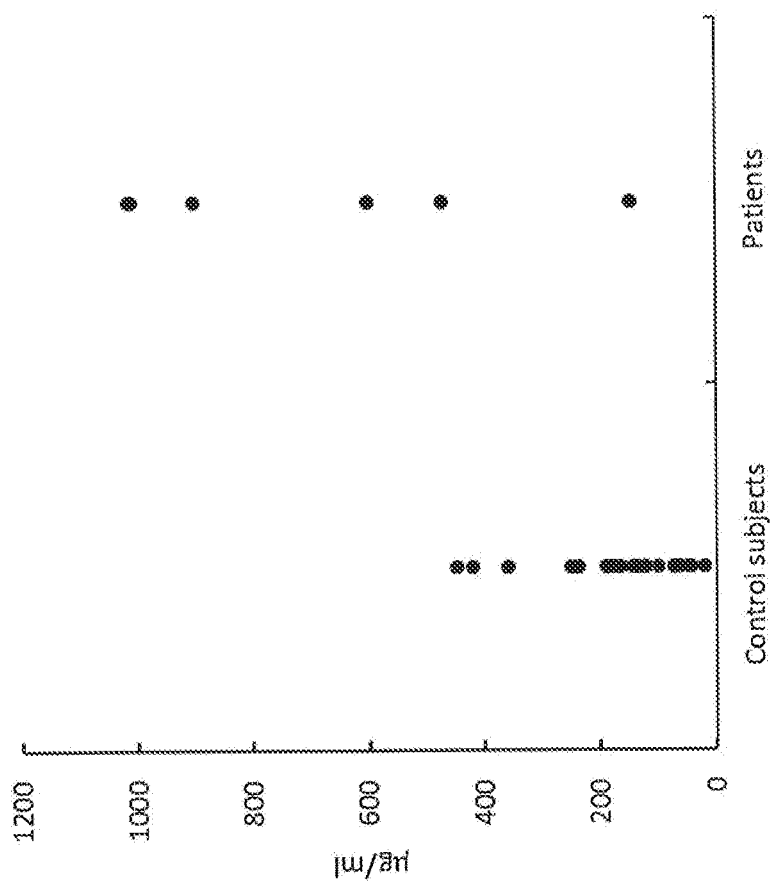
FIG. 17 shows the concentrations of hPRB1 in saliva in subjects diagnosed with chronic kidney disease, or diagnosed as having multiple myeloma and being at risk for kidney disease (Patients); and healthy subjects (Control Subjects).

As shown in FIG. 17, the concentration of hPRB1 in saliva of the subjects diagnosed with chronic kidney disease or diagnosed as having multiple myeloma and being at risk for kidney disease (Patients) was higher than that in the healthy subjects (Control Subjects) ($p=1.3 \times 10^{-6}$). This indicates that PRPs can be used as kidney function prediction markers.

Reference Example 3: Expression of PRPs in Subject Who Ingested Diet with High Phosphorus Content (2)

The proteins in saliva collected from the subjects of Reference Example 2(1) were decomposed with a proteolytic enzyme, and the concentration of proline was measured to examine whether the proline concentration correlates with the diet with high phosphorus content.

(1) Decomposition of Protein in Saliva and Derivatization of Decomposition Product After cryopreserved saliva was thawed, 700 µL of the saliva was transferred to a 1.5-mL tube and centrifuged at 1,000×g for 15 minutes at 4° C., and the supernatant was collected. 10.5 µL of the saliva supernatant was diluted 20-fold with 199.5 µL of Digestion Buffer (0.1 M Tris-HCl (pH 7.5), 0.5% SDS). 100 µL of the diluted saliva supernatant was transferred to a 1.5-mL tube. 20 µL of Pronase (10 µg/mL) was added to 100 µL of the diluted saliva supernatant, and the tube was wrapped with aluminum foil, followed by reacting at room temperature for 1 hour.

1.5 µL of 2-isopropylmalic acid (internal standard) was added per mL of chromatography grade methanol, and a requisite amount of the resulting solution was prepared. Subsequently, 500 µL of the methanol solution containing 2-isopropylmalic acid was added to the Pronase reaction mixture, and the mixture was stirred by vortexing for 30 seconds for spin-down. After the mixture was allowed to stand at room temperature for 5 minutes, 200 µL of ultrapure water was added, and the mixture was stirred by vortexing for 30 seconds and centrifuged at 4600×g for 5 minutes at 4° C. 400 µL of the first supernatant was transferred from the centrifuge tube to another 1.5-mL tube. 200 µL of ultrapure water was added to the first supernatant, and the mixture was stirred by vortexing for 30 seconds and centrifuged at 4600×g for 5 minutes at 4° C. 400 µL of the second supernatant was transferred from the centrifuge tube to an ultrafiltration unit cup (Hydrophilic PTFE membrane, 0.2 µm; Millipore) and centrifuged at 9100×g for 15 minutes at 4° C. The filtrate was dried under reduced pressure at 65° C.

for one hour and 30 minutes. 50 μL of a pyridine solution containing 20 mg/mL methoxyamine hydrochloride was added to the residue after drying, and the mixture was shaken with a shaker at 37° C. for 90 minutes. Thereafter, 50 μL of N-methyl-N-trimethylsilyltrifluoroacetamide (MSTFA) was further added, and the mixture was shaken with a shaker at 37° C. for 30 minutes, and trimethylsilylated.

(2) GCMS Measurement

GCMS-TQ8030 (Shimadzu Corporation) was used for GCMS, and DB-5 (30 m×0.25 mm (inner diameter)×1.00 um (film thickness)) (Agilent Technologies) was used as a capillary column for GC. GC was performed under the following temperature increase conditions: the temperature was increased at a rate of 4° C./rain from 100° C. to 320° C. The injector port temperature was 280° C. Helium was used as a carrier gas, and made to flow at a rate of 39.0 cm/sec. The energy of the electron ionization was 150 eV, the ion source temperature was 200° C., and proline-2TMS {142.10/73.0} and 2-isopropylmalic acid {216.10/147.10} were measured in MRM mode. 1 μL of the sample was injected, the splitless mode was used, and measurement was performed at a detector voltage of 1.50 kV.

(3) Analysis of GCMS Data

Analysis was performed by using GCMS Solution Ver. 4.2 data analysis software and the GCMS Metabolites Database (Shimadzu Corporation). A dilution series of purified proline at the following six points: 0.02, 0.01, 0.005, 0.0005, 0.00005, and 0.000005 (nmol/μL) was prepared, and a calibration curve was prepared by using known concentrations of proline.

The concentration of proline was determined by dividing the peak area of proline by the peak area of the internal standard (2-isopropylmalic acid) to obtain a ratio, and applying the ratio to the calibration curve.

(4) Quantification Results

As shown in FIG. 18, the concentration of proline increased in the group that had ingested the diet with high phosphorus content for 7 days (High Pi) compared with that in the group that had ingested the diet with low phosphorus content (Low Pi). This indicates that kidney function and phosphorus intake can be predicted by decomposing the proteins in saliva, and measuring the concentration of proline in the decomposition liquid.

DESCRIPTION OF REFERENCE NUMERALS

1 Evaluation device
3 Input unit
4 Display unit
5a Analysis device
5b Analysis device
11 First measurement value obtaining unit
12 Second measurement value obtaining unit
13 Measurement value comparison unit
14 Effect determination unit
52 Reaction/electrophoresis unit
53 Detection unit
100 System
101 CPU
102 Memory
103 Storage unit
104 Bus
105 Interface unit
109 Storage medium

The invention claimed is:

1. A method of suppressing expression of FGF23 induced by phosphorus overload, comprising:

administering a therapeutically-effective amount of (i) a soluble human Oscar-Fc fusion protein comprising the amino acid sequence of SEQ ID NO:2, or (ii) a soluble human Oscar-Fc fusion protein comprising the amino acid sequence of SEQ ID NO: 2 except that one to three amino acids are substituted, deleted, or inserted, to a human during phosphorus overload, wherein expression of FGF23 is suppressed.

* * * * *